US012049482B2

(12) United States Patent
Jan et al.

(10) Patent No.: US 12,049,482 B2
(45) Date of Patent: Jul. 30, 2024

(54) MOLECULAR SWITCH-MEDIATED CONTROL OF ENGINEERED CELLS

(71) Applicants: THE GENERAL HOSPITAL CORPORATION, Boston, MA (US); THE BRIGHAM & WOMEN'S HOSPITAL, INC., Boston, MA (US); PRESIDENT AND FELLOWS OF HARVARD COLLEGE, Cambridge, MA (US)

(72) Inventors: Max Jan, Boston, MA (US); Quinlan L. Sievers, Boston, MA (US); Benjamin Ebert, Boston, MA (US); Marcela Maus, Boston, MA (US)

(73) Assignees: The Brigham and Women's Hospital, Inc., Boston, MA (US); The General Hospital Corporation, Boston, MA (US); President and Fellows of Harvard College, Cambridge, MA (US)

(*) Notice: Subject to any disclaimer, the term of this patent is extended or adjusted under 35 U.S.C. 154(b) by 664 days.

(21) Appl. No.: 16/759,490

(22) PCT Filed: Oct. 30, 2018

(86) PCT No.: PCT/US2018/058210

§ 371 (c)(1),
(2) Date: Apr. 27, 2020

(87) PCT Pub. No.: WO2019/089592

PCT Pub. Date: May 9, 2019

(65) Prior Publication Data

US 2021/0040166 A1 Feb. 11, 2021

Related U.S. Application Data

(60) Provisional application No. 62/633,725, filed on Feb. 22, 2018, provisional application No. 62/579,454, filed on Oct. 31, 2017.

(51) Int. Cl.

| | |
|---|---|
| ***C07K 14/47*** | (2006.01) |
| ***C07K 14/705*** | (2006.01) |
| ***C07K 14/725*** | (2006.01) |
| ***C07K 16/00*** | (2006.01) |

(52) U.S. Cl.

CPC ...... *C07K 14/4702* (2013.01); *C07K 14/7051* (2013.01); *C07K 14/70521* (2013.01); *C07K 14/70578* (2013.01); *C07K 16/00* (2013.01); *C07K 2317/622* (2013.01); *C07K 2319/02* (2013.01); *C07K 2319/03* (2013.01)

(58) Field of Classification Search

CPC ...... C07K 14/7051; C07K 2319/00-03; C07K 14/4702

See application file for complete search history.

(56) References Cited

U.S. PATENT DOCUMENTS

| | | | | |
|---|---|---|---|---|
| 10,683,360 | B2 * | 6/2020 | Brayshaw | C07K 16/2878 |
| 2015/0232826 | A1 | 8/2015 | Handa et al. | |
| 2016/0282354 | A1 | 9/2016 | Ebert et al. | |
| 2016/0311907 | A1 | 10/2016 | Brogdon et al. | |
| 2020/0339704 | A1 | 10/2020 | Bradner et al. | |
| 2022/0098251 | A1 * | 3/2022 | Fischer | C07K 7/08 |

FOREIGN PATENT DOCUMENTS

| | | | |
|---|---|---|---|
| WO | 2014004990 | A2 | 1/2014 |
| WO | 2017024318 | A1 | 2/2017 |
| WO | 2017044801 | A2 | 3/2017 |

OTHER PUBLICATIONS

Ito & Handa, Int J Hematol. 104:293-299 (Year: 2016).*
Extended European Search Report in corresponding application No. 18873975.9 dated Aug. 3, 2021.
International Preliminary Report on Patentability dated May 14, 2020 for related Application No. PCT/US2018/058210.
International Search Report dated Mar. 14, 2019 for related Application No. PCT/US2018/058210.

* cited by examiner

*Primary Examiner* — Jessica H Roark
(74) *Attorney, Agent, or Firm* — Withers Bergman LLP; Christopher R. Cowles

(57) ABSTRACT

The present disclosure relates to therapeutic methods and clinically useful molecular switches, for which activity or degradation of a switch-presenting polypeptide can be precisely induced via administration or withdrawal of an FDA-approved drug. Certain aspects of the disclosure relate to an engineered drug-inducible heterodimeric system including a first polypeptide presenting a CRBN polypeptide disrupted for or lacking a DDB 1-interacting domain and a second polypeptide presenting a CRBN polypeptide substrate, where binding between the CRBN polypeptide and the CRBN polypeptide substrate are inducible via administration of an CFDA-approved thalidomide analog immunomodulatory drug (IMiD). Another aspect of the disclosure relates to a chimeric antigen receptor (CAR) that presents a minimal fragment of the CRBN polypeptide substrate IKZF3 capable of triggering proteasomal degradation of CAR upon administration of an FDA-approved IMiD.

16 Claims, 35 Drawing Sheets

Specification includes a Sequence Listing.

MOLECULAR SWITCH-MEDIATED CONTROL OF ENGINEERED CELLS

CROSS-REFERENCE TO RELATED APPLICATIONS

The present application is a national stage application, filed under 35 U.S.C. § 371, of International Application No. PCT/US2018/058210, filed Oct. 30, 2018 and published in English on May 9, 2019 as publication WO 2019/089592, which is related to and claims priority under 35 U.S.C. § 119(e) to U.S. provisional patent application No. 62/579,454, entitled "Molecular Switch-Mediated Control of Engineered Cells," filed Oct. 31, 2017, and to U.S. provisional patent application No. 62/633,725, entitled "Molecular Switch-Mediated Control of Engineered Cells," filed Feb. 22, 2018. The entire content of the aforementioned patent applications is incorporated herein by this reference.

STATEMENT REGARDING FEDERALLY SPONSORED RESEARCH

This invention was made with government support under Grant No. CA066996 awarded by the National Institutes of Health. The government has certain rights in the invention.

FIELD OF THE INVENTION

The invention relates generally to small molecule-responsive molecular switches.

BACKGROUND OF THE INVENTION

With recent FDA approval of the first chimeric antigen receptor (CAR) T-cell therapy (Wall Street Journal, Aug. 30, 2017), certain cell-based immunotherapeutics have begun to realize their clinical potential. However, current cellular therapies are constitutively active and lack user-control, meaning that if/when a cell-based immunotherapy elicits a negative reaction in a subject, little can be done (at least with any molecular precision) to halt such a negative reaction. A need therefore exists for clinically applicable systems that enable precise and ideally small molecule-mediated modulation of molecular pathways within engineered cells, particularly CAR-T cells.

BRIEF SUMMARY OF THE INVENTION

The current disclosure relates, at least in part, to discovery and development of engineered, clinically useful control systems gated by FDA-approved small molecules, that can be employed in engineered cells, particularly therapeutic engineered cells including, e.g., chimeric antigen receptor (CAR) T-cells.

In one aspect, the disclosure provides a method for treating a subject with a chimeric antigen receptor (CAR) cellular therapy, the method including administering to the subject a mammalian cell harboring a drug-responsive CAR that includes: an extracellular antigen-binding domain; a transmembrane domain (TMD); a co-stimulatory domain; a signaling domain; and a CRBN polypeptide substrate domain capable of binding CRBN in response to drug, thereby promoting ubiquitin pathway-mediated degradation of the drug-responsive CAR, where administration of the CAR cellular therapy thereby treats the subject.

In some embodiments, the mammalian cell overexpresses a CRBN polypeptide. Optionally, the overexpressed CRBN polypeptide is targeted to the plasma membrane with a targeting sequence derived from LAT, PAG, LCK, FYN, LAX, CD2, CD3, CD4, CD5, CD7, CD8a, PD1, SRC, or LYN. Optionally, the local concentration of the ubiquitin ligase $CRL4^{CRBN}$ is increased at the plasma membrane via inclusion of such targeting sequence, as compared to an appropriate control polypeptide.

In one embodiment, the method further includes administering the drug.

In another embodiment, the method further includes identifying a CAR cellular therapy-related side effect in the subject. In a related embodiment, the method further includes administering the drug to the subject after the CAR cellular therapy-related side effect is identified in the subject.

In certain embodiments, the subject has or is at risk of developing cancer.

In certain embodiments, the CRBN polypeptide substrate is IKZF1, IKZF3, CK1α, ZFP91, GSPT1, MEIS2, GSS, E4F1, ZN276, ZN517, ZN582, ZN653, ZN654, ZN692, ZN787, ZN827 or a fragment thereof that is capable of drug-inducible binding the CRBN polypeptide disrupted for or lacking a DDB1-interacting domain, or where the CRBN polypeptide substrate is a chimeric fusion product of native CRBN polypeptide substrate sequences, optionally the IKZF3/ZFP91/IKZF3 polypeptide SEQ ID NO: 95.

In some embodiments, the CRBN polypeptide substrate domain includes a hybrid fusion polypeptide that includes ten or more residues of a non-IKZF3 C2H2 zinc finger degron sequence that are flanked by an N-terminal IKZF3 degron sequence and a C-terminal IKZF3 degron sequence. Optionally, the N-terminal IKZF3 degron sequence includes or is amino acids 130-145 (SEQ ID NO: 97) of IKZF3 or a K0 from thereof (SEQ ID NO: 100) and/or the C-terminal IKZF3 degron sequence includes or is amino acids 169-189 (SEQ ID NO: 102) of IKZF3 or a K0 form thereof (SEQ ID NO: 103). Optionally, the non-IKZF3 C2H2 zinc finger degron sequence is a ZFP91 sequence.

Another aspect of the disclosure provides a drug-responsive chimeric antigen receptor (CAR) that includes: an extracellular antigen-binding domain; a transmembrane domain (TMD); a co-stimulatory domain; a signaling domain; and a CRBN polypeptide substrate domain capable of binding CRBN in response to drug, thereby promoting ubiquitin pathway-mediated degradation of the drug-responsive CAR.

In an additional aspect, the disclosure provides a mammalian cell harboring a drug-responsive CAR of the instant disclosure.

In one embodiment, the mammalian cell is a T cell.

In another embodiment, the mammalian cell is a B cell, a plasma cell, a NK cell, a NKT cell, an innate lymphoid cell, a macrophage, a dendritic cell, a monocyte, a neutrophil, a basophil, an eosinophil, a mast cell, a hematopoietic progenitor cell, a hematopoietic stem cell, or another adult stem cell such as neural, cornea, muscle, skin, small intestine, colon, bone, mesenchyme, embryonic stem cell or an induced pluripotent stem cell.

Another aspect of the disclosure provides a polypeptide that includes SEQ ID NO: 95.

A further aspect of the disclosure provides a nucleic acid sequence that includes SEQ ID NO: 84, SEQ ID NO: 85, SEQ ID NO: 86, SEQ ID NO: 87 or SEQ ID NO: 88.

In one aspect, the disclosure provides a method for treating a subject with a chimeric antigen receptor (CAR) cellular therapy, the method involving administering to the subject a mammalian cell having a split chimeric antigen receptor (CAR) system suitable for clinical application that includes a drug-inducible heterodimer, where the split CAR system includes a first polypeptide and a second polypeptide having the following: the first polypeptide includes an extracellular antigen-binding domain, a transmembrane domain (TMD), a co-stimulatory domain and a first domain of a drug-inducible heterodimer; and the second polypeptide includes a second domain of the drug-inducible heterodimer and a signaling domain, where administration of the mammalian cell/CAR cellular therapy thereby treats the subject.

In one embodiment, the first and second domains of the drug-inducible heterodimer bind one another in the presence of the drug. In a related embodiment, the drug-inducible heterodimer is an IMiD-inducible CRBN/CRBN polypeptide substrate heterodimer. In certain embodiments, the IMiD-inducible CRBN/CRBN polypeptide substrate heterodimer includes a CRBN polypeptide disrupted for or lacking a DDB1-interacting domain, optionally the CRBN polypeptide is selected from SEQ ID NOs: 1-4.

In certain embodiments, the IMiD-inducible CRBN/CRBN polypeptide substrate heterodimer includes a CRBN polypeptide disrupted for or lacking a DDB1-interacting domain further including a residue substitution at one or more of positions 371 and 388, optionally where the CRBN polypeptide disrupted for or lacking a DDB1-interacting domain includes a residue substitution selected from 1371A, 1371G, V388A, and V388G.

In one embodiment, the IMiD-inducible CRBN/CRBN polypeptide substrate heterodimer includes a CRBN polypeptide substrate that is IKZF3, IKZF1, ZFP91, GSPT1, GSS, or a fragment thereof that is capable of drug-inducible binding to CRBN polypeptide, optionally where the CRBN polypeptide substrate is SEQ ID NO: 5.

In another embodiment, the IMiD-inducible CRBN/CRBN polypeptide substrate heterodimer includes a CRBN polypeptide substrate including a substituted form of IKZF3 aa130-189 that includes K→R residue substitutions at positions 137, 158, 166, 172 and 175 of the IKZF3 aa130-189 polypeptide sequence.

In one embodiment, the IMiD-inducible CRBN/CRBN polypeptide substrate heterodimer includes a CRBN polypeptide substrate having a substituted form of IKZF3 aa130-189 that includes a residue substitution at position 153, optionally where the residue substitution at position 153 is selected from A153I, A153M, A153T, A153N, A153Q, A153R, A153H, A153K, A153D, A153E and A153C.

In another embodiment, the method further includes administering the drug to the subject. In a related embodiment, induction of the CAR cellular therapy occurs upon administration of the drug to the subject.

In one embodiment, the drug is an FDA-approved drug, optionally an FDA-approved small molecule drug. Optionally, the drug is a thalidomide analog immunomodulatory drug (IMiD).

In a related embodiment, the drug is thalidomide, lenalidomide or pomalidomide.

In one embodiment, the signaling domain is selected from a CD3ζ domain, a CD3 gamma domain, a CD3 delta domain, a CD3 epsilon domain, a FcR gamma domain, a FcR beta domain, a CD5 domain, a CD79a domain, a CD79b domain, a CD66d domain, a CD4 domain, a CD8 domain, a Dap10 domain and a Dap-12 domain.

In another embodiment, the second polypeptide having the signaling domain further includes one or more domains that is a transmembrane domain (TMD) and/or a co-stimulatory domain.

In one embodiment, the co-stimulatory domain is selected from a CD28 co-stimulatory domain, a 4-1BB co-stimulatory domain, or additional co-stimulatory domains from CD27, OX40, CD30, CD40, ICOS, LFA-1, CD2, CD7, NKG2C, or B7-H3, optionally where the co-stimulatory domain includes K→R residue substitutions at positions 182 and 204 of a CD28 co-stimulatory domain sequence, or where the co-stimulatory domain includes K→R residue substitutions at positions 214, 218, 219, and 225 of a 4-1BB co-stimulatory domain sequence, or where the co-stimulatory domain includes K→R residue substitutions as shown in any of SEQ ID NOs: 46-69.

In another embodiment, the extracellular antigen-binding domain includes a scFv.

Optionally, the extracellular antigen-binding domain includes an anti-CD19/BCMA scFv or a scFv targeting CD19, CD20, CD22, BCMA, CD138, CD38, SLAMF7, kappa light chain, lambda light chain, CD123, CD33, CD45, CD30, CD40, CD70, ErbB2, EGFR, EpCAM, EGFRvIII, mesothelin, ROR1, LeY, PSMA, PSCA, CD34, CD90, TIM3, CD99, CD3, CD4, CD8, CD52 or TCR recognizing WT1.

In one embodiment, the method further includes identifying a CAR cellular therapy-related side effect in the subject. In a related embodiment, the method further includes halting administration of the drug after the CAR cellular therapy-related side effect is identified in the subject.

In another embodiment, the heterodimer is constitutively paired in the absence of the drug. In a related embodiment, the heterodimer is capable of being destabilized by administration of the drug (e.g., a small molecule). Optionally, the drug-destabilized heterodimer is an IMiD-destabilized CRBN/CRBN polypeptide substrate heterodimer, optionally where the heterodimer is CRBN/MEIS2, a MDM2/P53 polypeptide heterodimer inhibited by RG7112, a VHL/HIF-1α or VHL/HIF-2a polypeptide heterodimer inhibited by VH298, or a cIAP/SMAC heterodimer inhibited by birinapant.

Another aspect of the disclosure provides a method for treating a subject with a cellular therapy, the method involving administering to the subject a mammalian cell harboring a drug-inducible heterodimer composition that includes: (i) a first polypeptide having an N-terminus and a C-terminus and including a CRBN polypeptide disrupted for or lacking a DDB1-interacting domain and (ii) a second polypeptide having an N-terminus and a C-terminus and including a CRBN polypeptide substrate, where the CRBN polypeptide and the CRBN polypeptide substrate associate with one another upon administration of the drug, where administering the mammalian cell/cellular therapy thereby treats the subject.

In one embodiment, the cellular therapy is a CAR T cellular therapy.

In certain embodiments, the drug is a small molecule.

In one embodiment, the drug can be administered to a human subject in a clinical setting.

Optionally, the drug is an IMiD, e.g., thalidomide, lenalidomide or pomalidomide.

In one embodiment, the CRBN polypeptide disrupted for or lacking a DDB1-interacting domain is one of SEQ ID NOs: 1-4.

In one embodiment, the CRBN polypeptide substrate is IKZF3 or a fragment thereof that is capable of drug-inducible binding of the CRBN polypeptide disrupted for or lacking a DDB1-interacting domain. Optionally, the CRBN polypeptide substrate is SEQ ID NO: 5.

In certain embodiments, the first and second polypeptides form a system that is a drug-gated split chimeric antigen receptor (CAR) system or a drug-gated heterodimeric cytokine receptor, including class I cytokine receptors, class II cytokine receptors, TNF receptors, IL-1 receptors, tyrosine kinase receptors, and chemokine receptors, drug-gated heterodimeric TGF-beta receptors, drug-gated split genome editing proteins such as CAS9, drug-gated split transcription factors, optionally where a first component ("component A") encodes a DNA binding motif and a second component ("component B") encodes an effector motif such as transactivation, repression, or recruitment of an epigenetic reader, writer, or eraser protein.

In one embodiment, the drug-inducible heterodimer incorporates any of the components recited immediately above (receptors, kinases, transcription factors, epigenetic modifiers, genome editing proteins), where the second component serves as a tether to a particular subcellular localization, such that the drug-dependent heterodimerization serves as a location-based gain-, loss- or change-of function switch.

In another embodiment, the first or second polypeptide includes one or more domains that are an extracellular antigen-binding domain, a transmembrane domain (TMD) or a co-stimulatory domain.

In one embodiment, the first or second polypeptide includes a signaling domain. In a related embodiment, the signaling domain is a CD3ζ domain, a CD3 gamma domain, a CD3 delta domain, a CD3 epsilon domain, a FcR gamma domain, a FcR beta domain, a CD5 domain, a CD79a domain, a CD79b domain, a CD66d domain, a CD4 domain, a CD8 domain, a Dap10 domain or a Dap-12 domain. Optionally, the first or second polypeptide including the signaling domain further includes one or more of a transmembrane domain (TMD) and/or a co-stimulatory domain.

In certain embodiments, the co-stimulatory domain is a CD28 co-stimulatory domain, a 4-1BB co-stimulatory domain, and/or includes a co-stimulatory domains from CD27, OX40, CD30, CD40, ICOS, LFA-1, CD2, CD7, NKG2C and/or B7-H3.

In one embodiment, the co-stimulatory domain includes K→R residue substitutions at positions 182 and 204 of a CD28 (*Homo sapiens* CD28 isoform 1 Uniprot identifier P10747-1) co-stimulatory domain sequence.

In another embodiment, the CRBN polypeptide substrate includes a substituted form of IKZF3 aa130-189 that includes a residue substitution at position 153, optionally where the residue substitution at position 153 is selected from among A153I, A153M, A153T, A153N, A153Q, A153R, A153H, A153K, A153D, A153E and A153C.

In one embodiment, the CRBN polypeptide disrupted for or lacking a DDB1-interacting domain, such as the min-CRBN variants 1-4 described in SEQ ID NOs: 1-4, additionally includes a residue substitution at one or more of positions 371 and 388, optionally where the CRBN polypeptide disrupted for or lacking a DDB1-interacting domain includes a residue substitution selected from I371A, I371G, V388A and V388G.

In another embodiment, the CRBN polypeptide substrate includes a substituted form of IKZF3 aa130-189 that includes K→R residue substitutions at positions 137, 158, 166, 172 and 175 of the IKZF3 aa130-189 polypeptide sequence.

In one embodiment, the subject has or is at risk of developing cancer.

In another embodiment, the cellular therapy is administered in a therapeutically effective amount.

In an additional embodiment, the method further includes identifying a cellular therapy-related side effect in the subject. In a related embodiment, the method additionally includes halting administration of the drug after the cellular therapy-related side effect is identified in the subject.

Another aspect of the disclosure provides a drug-inducible heterodimer composition that includes: (i) a first polypeptide having an N-terminus and a C-terminus and including a CRBN polypeptide disrupted for or lacking a DDB1-interacting domain and (ii) a second polypeptide having an N-terminus and a C-terminus and including a CRBN polypeptide substrate, where the CRBN polypeptide and the CRBN polypeptide substrate associate upon administration of the drug.

In one embodiment, the drug-inducible heterodimer composition further includes the drug.

In certain embodiments, the drug is a small molecule. In a related embodiment, the drug is an FDA-approved drug. Optionally, the drug can be administered to a human subject in a clinical setting.

In some embodiments, the drug is an IMiD. Optionally, the drug is thalidomide, lenalidomide or pomalidomide.

In one embodiment, the CRBN polypeptide disrupted for or lacking a DDB1-interacting domain is selected from SEQ ID NOs: 1-4.

In certain embodiments, the extracellular antigen-binding domain includes a scFv. In a related embodiment, the extracellular antigen-binding domain includes a scFv targeting CD19, CD20, CD22, BCMA, CD138, CD38, SLAMF7, kappa light chain, lambda light chain, CD123, CD33, CD45, CD30, CD40, CD70, ErbB2, EGFR, EpCAM, EGFRvIII, mesothelin, ROR1, LeY, PSMA, PSCA, CD34, CD90, TIM3, CD99, CD3, CD4, CD8, CD52, or TCR recognizing WT1.

In another aspect, the disclosure provides a mammalian cell harboring a drug-inducible heterodimer composition of the instant disclosure.

In one embodiment, the mammalian cell is a T cell. In another embodiment, the mammalian cell is a B cell, plasma cell, NK cell, NKT cell, innate lymphoid cell, macrophage, dendritic cell, monocyte, neutrophil, basophil, eosinophil, mast cell, hematopoietic progenitor cell, hematopoietic stem cell, other adult stem cell such as neural, cornea, muscle, skin, small intestine, colon, bone, mesenchyme, embryonic stem cell, or induced pluripotent stem cell.

In certain embodiments, the mammalian cell includes a genomic disruption of native CRBN, optionally a biallelic disruption of native CRBN. In a related embodiment, the mammalian cell includes a genomic disruption of CRBN exon 5, optionally a CRBNΔe5 disruption.

Another aspect of the disclosure provides a split chimeric antigen receptor (CAR) system suitable for clinical application including a drug-inducible heterodimer, where the split CAR system includes a first polypeptide and a second polypeptide, where: the first polypeptide includes an extracellular antigen-binding domain, a transmembrane domain (TMD), a co-stimulatory domain and a first domain of a drug-inducible heterodimer; and the second polypeptide includes a second domain of the drug-inducible heterodimer and a signaling domain, where the first and second domains of the drug-inducible heterodimer bind one another in the presence of the drug.

In one embodiment, the drug-inducible heterodimer is an IMiD-inducible CRBN/CRBN polypeptide substrate heterodimer.

In another embodiment, the heterodimer is constitutively paired. In a related embodiment, the heterodimer is capable of being destabilized with the addition of a small molecule, optionally where the drug-destabilized heterodimer is an IMiD-destabilized CRBN/CRBN polypeptide substrate heterodimer such as CRBN/MEIS2, a MDM2/P53 polypeptide heterodimer inhibited by RG7112, a VHL/HIF-1α or VHL/HIF-2a polypeptide heterodimer inhibited by VH298, or a cIAP/SMAC heterodimer inhibited by birinapant.

In certain embodiments, the IMiD-inducible CRBN/CRBN polypeptide substrate heterodimer includes a CRBN polypeptide disrupted for or lacking a DDB1-interacting domain, optionally where the CRBN polypeptide is selected from SEQ ID NOs: 1-4.

In one embodiment, the IMiD-inducible CRBN/CRBN polypeptide substrate heterodimer includes a CRBN polypeptide disrupted for or lacking a DDB1-interacting domain further including a residue substitution at one or more of positions 371 and 388, optionally where the CRBN polypeptide disrupted for or lacking a DDB1-interacting domain includes a residue substitution selected from 1371A, 1371G, V388A and V388G.

In another embodiment, the IMiD-inducible CRBN/CRBN polypeptide substrate heterodimer includes a CRBN polypeptide substrate selected from IKZF3, IKZF1, ZFP91, GSPT1, GSS, or a fragment thereof that is capable of drug-inducible binding to CRBN polypeptide, optionally where the CRBN polypeptide substrate is SEQ ID NO: 5.

In certain embodiments, the IMiD-inducible CRBN/CRBN polypeptide substrate heterodimer includes a CRBN polypeptide substrate including a substituted form of IKZF3 aa130-189 that includes K→R residue substitutions at positions 137, 158, 166, 172 and 175 of the IKZF3 aa130-189 polypeptide sequence.

In another embodiment, the IMiD-inducible CRBN/CRBN polypeptide substrate heterodimer includes a CRBN polypeptide substrate including a substituted form of IKZF3 aa130-189 that includes a residue substitution at position 153, optionally where the residue substitution at position 153 is selected from A153I, A153M, A153T, A153N, A153Q, A153R, A153H, A153K, A153D, A153E and A153C.

Another aspect of the disclosure provides a mammalian cell including a split CAR system of the instant disclosure.

A further aspect of the disclosure provides a CRBN polypeptide disrupted for or lacking a DDB1-interacting domain and including one or more domains selected from a CRBN thalidomide binding domain (TBD), a CRBN LLP1-C domain, a CRBN LLP1-N domain and a CRBN N-terminal domain, where the CRBN polypeptide is not SEQ ID NO: 1 or SEQ ID NO: 4.

Another aspect of the disclosure provides a polypeptide including SEQ ID NO: 3.

An additional aspect of the disclosure provides polypeptide including SEQ ID NO: 2 in the absence of any other CRBN sequence.

An additional aspect of the disclosure provides a drug-responsive polypeptide that includes an inhibitor of CAR signaling and a CRBN polypeptide substrate domain capable of binding CRBN in response to drug, and which thereby promotes ubiquitin pathway-mediated degradation of the drug-responsive polypeptide, thereby activating CAR signaling.

In one embodiment, the inhibitor of CAR signaling is a proximal, pan-CAR/TCR signal transduction inhibitor, optionally the inhibitor of CAR signaling is Carboxy-terminal Src Kinase (CSK).

In another embodiment, the inhibitor of CAR signaling selectively abrogates a CAR signal transduction pathway and/or a CAR effector function, optionally the inhibitor of CAR signaling selectively abrogates a pathway or function that is Ras signaling, PKC, calcium-dependent signaling, NF-kappaB, NFAT, actin and cytoskeletal responses, cytokine secretion, cell proliferation, degranulation, and/or tumor cell killing, differentiation, or exhaustion.

In some embodiments, the inhibitor of CAR signaling is a ubiquitin ligase involved in TCR/CAR signal transduction. Optionally, the inhibitor of CAR signaling is c-CBL, CBL-B, ITCH, RNF125, RNF128 or WWP2.

In other embodiments, the inhibitor of CAR signaling is a TCR/CAR negative regulatory enzyme. Optionally, the inhibitor of CAR signaling is SHP1, SHP2, SHIP1, SHIP2, CD45, CSK, CD148, PTPN22, DGKalpha, DGKzeta, DRAK2, HPK1, HPK1, STS1, STS2 or SLAT.

In certain embodiments, the inhibitor of CAR signaling is a TCR/CAR negative regulatory scaffold/adapter protein. Optionally, the inhibitor of CAR signaling is PAG, LIME, NTAL, LAX31, SIT, GAB2, GRAP, ALX, SLAP, SLAP2, DOK1 or DOK2.

In another embodiment, the inhibitor of CAR signaling is a dominant negative version of an activating TCR signaling component. Optionally, the inhibitor of CAR signaling is ZAP70, LCK, FYN, NCK, VAV1, SLP76, ITK, ADAP, GADS, PLCgamma1, LAT, p85, SOS, GRB2, NFAT, p50, p65, AP1, RAP1, CRKII, C3G, WAVE2, ARP2/3, ABL, ADAP, RIAM or SKAP55.

In other embodiments, the inhibitor of CAR signaling includes the cytoplasmic tail of a TCR/CAR negative co-regulatory receptor. Optionally, the inhibitor of CAR signaling includes the cytoplasmic tail of a CD5, PD1, CTLA4, BTLA, LAG3, B7-H1, B7-1, CD160, TIM3, 2B4 or TIGIT TCR/CAR negative co-regulatory receptor.

In certain embodiments, the inhibitor of CAR signaling is targeted to the plasma membrane. Optionally, the inhibitor of CAR signaling possesses a targeting sequence derived from LAT, PAG, LCK, FYN, LAX, CD2, CD3, CD4, CD5, CD7, CD8a, PD1, SRC, or LYN.

In one embodiment, the drug-responsive polypeptide is cytosolic.

In another embodiment, the drug-responsive polypeptide possesses a membrane tether and/or transmembrane domain.

Another aspect of the disclosure provides a method for treating a subject with a chimeric antigen receptor (CAR) cellular therapy, the method involving administering to the subject a mammalian cell harboring a CAR and a drug-responsive polypeptide that includes an inhibitor of CAR signaling and a CRBN polypeptide substrate domain capable of binding CRBN in response to drug, the CRBN polypeptide substrate domain thereby promoting ubiquitin pathway-mediated degradation of the drug-responsive polypeptide, which activates CAR signaling (as the inhibitory element is released/degraded).

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

"Activation", as used herein, refers to the state of a T-cell that has been sufficiently stimulated to induce detectable cellular proliferation. Activation can also be associated with induced cytokine production, and detectable effector functions. The term "activated T-cells" refers to, among other things, T-cells that are undergoing cell division.

The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

By "agent" is meant any small compound (e.g., small molecule), antibody, nucleic acid molecule, or polypeptide, or fragments thereof.

The term "antigen" or "Ag" as used herein is defined as a molecule that can be targeted by an antibody or antibody fragment thereof.

As used herein, a "tumor antigen" means a biological molecule having antigenicity, expression of which is associated with a neoplastic cell. The tumor antigens targeted in the present disclosure include a tumor specific antigen (an antigen which is present only in tumor cells and is not found in other normal cells), and a tumor-associated antigen (an antigen which is also present in other organs and tissues or heterogeneous and allogeneic normal cells, or an antigen which is expressed on the way of development and differentiation).

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, bi-specific antibodies, multi-specific antibodies, and fusion proteins comprising an antigen-binding (also referred to herein as antigen binding) portion of an antibody and a non-antibody protein. The antibodies can be detectably labeled, e.g., with a radioisotope, an enzyme that generates a detectable product, a fluorescent protein, and the like. The antibodies can be further conjugated to other moieties, such as members of specific binding pairs, e.g., biotin (member of biotin-avidin specific binding pair), and the like. The antibodies can also be bound to a solid support, including, but not limited to, polystyrene plates or beads, and the like. Also encompassed by the term are Fab', Fv, $F(ab')_2$, and or other antibody fragments that retain specific binding to antigen, and monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "humanized immunoglobulin" as used herein refers to an immunoglobulin comprising portions of immunoglobulins of different origin, wherein at least one portion comprises amino acid sequences of human origin. For example, the humanized antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes).

Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B 1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519, 596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies.

The term "nanobody" (Nb), as used herein, refers to the smallest antigen binding fragment or single variable domain ($V_{HH}$) derived from naturally occurring heavy chain antibody and is known to the person skilled in the art. They are derived from heavy chain only antibodies, seen in camelids (Hamers-Casterman et al., 1993; Desmyter et al., 1996). In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama, Llama guanicoe* and *Llama vicugna*). A single variable domain heavy chain antibody is referred to herein as a nanobody or a $V_{HH}$ antibody.

"Antibody fragments" comprise a portion of an intact antibody, for example, the antigen binding or variable region of the intact antibody. Examples of antibody fragments include Fab, Fab', $F(ab')_2$, and Fv fragments; diabodies; linear antibodies (Zapata et al., Protein Eng. 8(10): 1057-1062 (1995)); domain antibodies (dAb; Holt et al. (2003) Trends Biotechnol. 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen.

"Fv" is the minimum antibody fragment that contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CHj) of the heavy chain. Fab fragments differ from Fab' fragments by the addition of a few residues at the carboxyl terminus of the heavy chain CHj domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

As used herein, the term "autologous" is meant to refer to any material derived from the same individual to which it is later to be re-introduced into the individual.

As used herein "endogenous" refers to any material from or produced inside an organism, cell, tissue or system.

As used herein, the term "exogenous" refers to any material introduced from or produced outside an organism, cell, tissue, or system.

A "co-stimulatory molecule" refers to the cognate binding partner on a T-cell that specifically binds with a co-stimulatory ligand, thereby mediating a co-stimulatory response by the T-cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T-cell proliferation, activation, and/or upregulation or downregulation of key molecules.

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

The term "cancer" refers to a malignant neoplasm (Stedman's Medical Dictionary, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term "CAR" is not limited specifically to CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled. CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application No. US2014/016527; Fedorov et al. 5c/Transl Med (2013); 5(215):215ral72; Glienke et al. Front Pharmacol (2015) 6:21; Kakarla & Gottschalk 52 Cancer J (2014) 20(2): 151-5; Riddell et al. Cancer J (2014) 20(2): 141-4; Pegram et al. Cancer J (2014) 20(2): 127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety.

The terms "domain" and "motif, used interchangeably herein, refer to both structured domains having one or more particular functions and unstructured segments of a polypeptide that, although unstructured, retain one or more particular functions. For example, a structured domain may encompass but is not limited to a continuous or discontinuous plurality of amino acids, or portions thereof, in a folded polypeptide that comprise a three-dimensional structure which contributes to a particular function of the polypeptide. In other instances, a domain may include an unstructured segment of a polypeptide comprising a plurality of two or more amino acids, or portions thereof, that maintains a particular function of the polypeptide unfolded or disordered. Also encompassed within this definition are domains that may be disordered or unstructured but become structured or ordered upon association with a target or binding partner. Non-limiting examples of intrinsically unstructured domains and domains of intrinsically unstructured proteins are described, e.g., in Dyson & Wright. Nature Reviews Molecular Cell Biology 6: 191-208.

By "fragment" is meant a portion, e.g., a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the disclosure also comprises polypeptides and nucleic acid fragments, so long as they exhibit the desired/indicated biological activity/activities of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this disclosure. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this disclosure.

"Heterologous," as used herein, means a nucleotide or polypeptide sequence that is not found in the native (e.g., naturally-occurring) nucleic acid or protein, respectively.

As used herein, the term "immune cells" generally includes white blood cells (leukocytes) which are derived from hematopoietic stem cells (HSC) produced in the bone marrow. "Immune cells" includes, e.g., lymphocytes (T cells, B cells, natural killer (NK) cells) and myeloid-derived cells (neutrophil, eosinophil, basophil, monocyte, macrophage, dendritic cells).

"T cell" includes all types of immune cells expressing CD3 including T-helper cells (CD4+ cells), cytotoxic T-cells ($CD8^+$ cells), T-regulatory cells (Treg) and gamma-delta T cells.

A "cytotoxic cell" includes $CD8^+$ T cells, natural-killer (NK) cells, and neutrophils, which cells are capable of mediating cytotoxicity responses.

As used herein, the term "stem cell" generally includes pluripotent or multipotent stem cells. "Stem cells" includes, e.g., embryonic stem cells (ES); mesenchymal stem cells (MSC); induced-pluripotent stem cells (iPS); and committed progenitor cells (hematopoietic stem cells (HSC); bone marrow derived cells, neural progenitor cells, etc.).

As used herein, the term "heteromeric" refers to a polypeptide or protein that contains more than one kind of subunit. Such heteromeric polypeptides may, in some instances, be referred to as "a heteromer". Heteromeric polypeptides may contain two or more different polypeptides, wherein different polypeptides are defined at least as two polypeptides that are not identical, however, such different polypeptides may or may not include one or more portions of similar and/or identical amino acid sequence. In some instances, the two or more polypeptides of a heteromer share no identical amino acid sequence or share no identical domains. A heteromer may, in some instances, consist of two different polypeptides or two different types of polypeptides and may be referred to as a heterodimer. In some instances, a heteromer may consist of three different polypeptides or three different types of polypeptides and may be referred to as a heterotrimer. In some instances, a heteromer may consist of two or more different polypeptides or two or more different types of polypeptides, including but not limited to, e.g., three or more different polypeptides, four or more different polypeptides, five or more different polypeptides, six or more different polypeptides, seven or more different polypeptides, eight or more different polypeptides, etc.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

By "marker" is meant any protein or polynucleotide having an alteration in expression level or activity that is associated with a disease or disorder.

As used herein, "neoplasia" means a disease state of a human or an animal in which there are cells and/or tissues which proliferate abnormally. Neoplastic conditions include, but are not limited to, cancers, sarcomas, tumors, leukemias, lymphomas, and the like. A neoplastic condition refers to the disease state associated with the neoplasia. Hepatocellular carcinoma, colon cancer (e.g., colorectal cancer), lung cancer and ovarian cancer are examples (non-limiting) of a neoplastic condition. A "cancer" in a subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a subject, or may be a non-tumorigenic cancer cell, such as a leukemia cell. Examples of cancer include but are not limited to hepatic carcinoma, colon cancer, colorectal cancer, breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, esophageal cancer, gastrointestinal cancer, glioblastoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

"Operably linked" refers to a juxtaposition wherein the components so described are in a relationship permitting them to function in their intended manner. For instance, a promoter is operably linked to a coding sequence if the promoter affects its transcription or expression.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In some embodiments, the polypeptide will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated polypeptide includes the polypeptide in situ within recombinant cells since at least one component of the polypeptide's natural environment will not be present. In some instances, isolated polypeptide will be prepared by at least one purification step.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the term "tumor" means a mass of transformed cells that are characterized by neoplastic uncontrolled cell multiplication and at least in part, by containing angiogenic vasculature. The abnormal neoplastic cell growth is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e., a metastatic tumor), a tumor also can be nonmalignant (i.e., non-metastatic tumor). Tumors are hallmarks of cancer, a neoplastic disease the natural course of which is fatal. Cancer cells exhibit the properties of invasion and metastasis and are highly anaplastic.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease or condition in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

A "vector" or "expression vector" is a replicon, such as plasmid, phage, virus, or cosmid, to which another DNA segment, i.e. an "insert", may be attached so as to bring about the replication of the attached segment in a cell.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

A "therapeutically effective amount" of an agent described herein is an amount sufficient to provide a therapeutic benefit in the treatment of a condition or to delay or minimize one or more symptoms associated with the condition. A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which.

Figure 2:
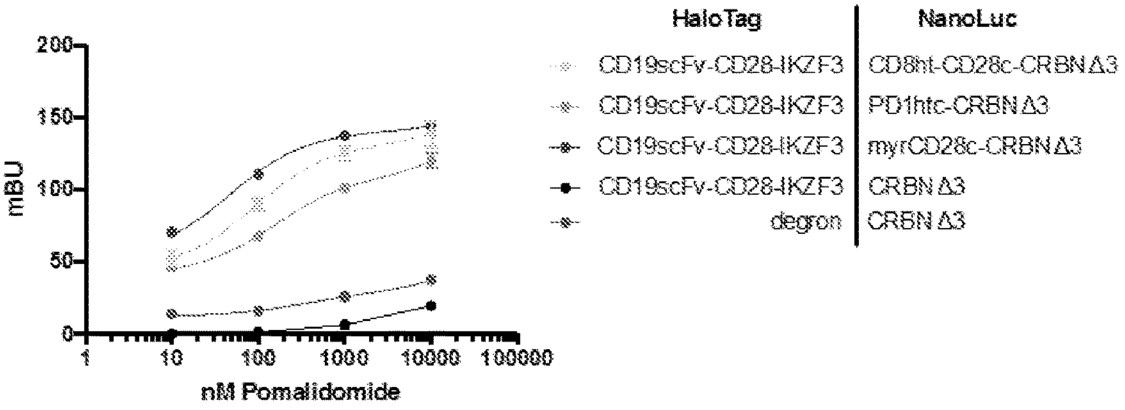

FIG. 2 shows that cell surface localization in a split receptor configuration augmented heterodimerization of IKZF3 degron and minCRBN (minCRBN3, aka CRBNΔ3). Dimerization of indicated pairs of molecules (CD19scFv-CD28-IKZF3 respectively paired with CD8ht-CD28c-CRBNΔ3, PD1htc-CRBNΔ3, myrCD28c-CRBNΔ3 or CRBNΔ3; or degron paired with CRBNΔ3) was assessed by BRET in 293T cells with 10 μM MG132 (a proteasome inhibitor) after 2 hours of drug treatment.

Figure 3:
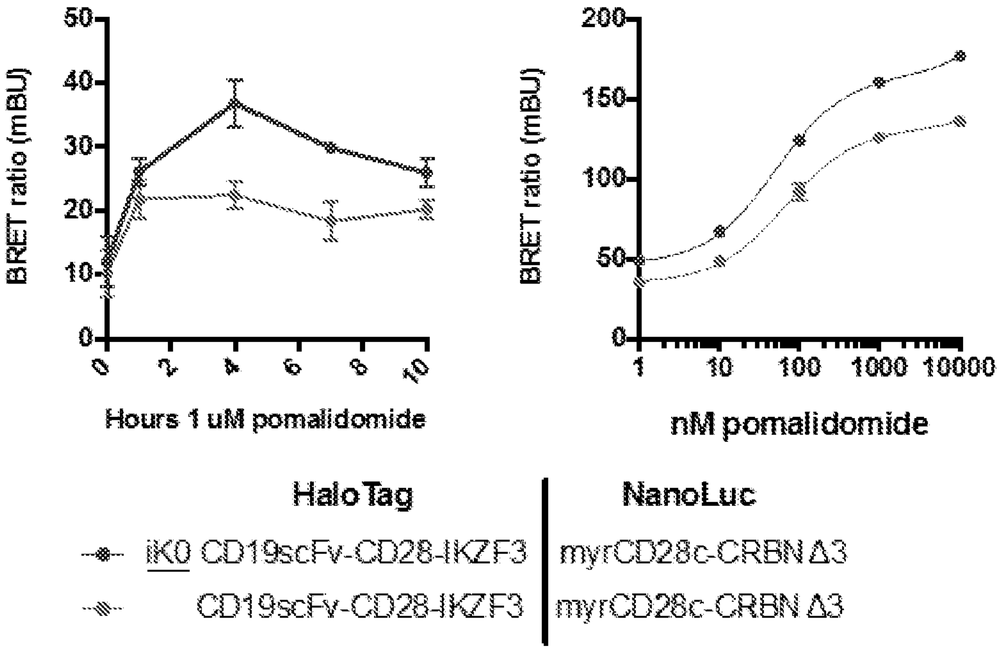

FIG. 3 shows that an IKZF3 degron engineered to remove ubiquitination sites ("iK0") produced enhanced IKZF3 degron-minCRBN3 split receptor dimerization, in the presence of endogenous CRBN. Specifically, intracellular lysine-to-arginine substitutions enhanced the duration and amplitude of IKZF3 degron—minCRBN3 split receptor dimerization in the presence of endogenous CRBN. From the position of the lysines in the IKZF3 zinc finger degron in an IKZF3 ZF2—CRBN crystal structure (not shown), it was hypothesized that substituting arginines for all lysines would not disrupt protein-protein binding between the IKZF3 degron and CRBN. Because the CD28 intracellular domain contains three signaling adapter motifs that do not contain conserved lysine residues, it was further hypothesized that it would be possible to substitute arginines for both lysines in the CD28 intracellular tail without altering the functional properties of this domain. With these seven lysine-to-arginine substitutions, a split receptor was generated that contained no lysine residues in the intracellular compartment (iK0). It was further hypothesized that extracellular lysines would not need to be modified to avoid ubiquitination by $CRL4^{CRBN}$, because these residues would be separated from the ubiquitin ligase by the plasma membrane. At left, dimerization was assessed in 293T cells after varying hours of exposure to 1 μM pomalidomide. At right, dimerization between the specified anti-CD19-CD28-IKZF3 protein and myrCD28-minCRBN3 (CRBNΔ3) was assessed in 293T cells 2 hours after addition of various concentrations of pomalidomide and 10 mM MG132. Wild type (wt) and iK0 Kd (SE) values were 53.4 (6.7) and 46.3 (6.3), respectively. Bmax 17.5 (0.5) and 22.5 (0.7).

Figure 4:
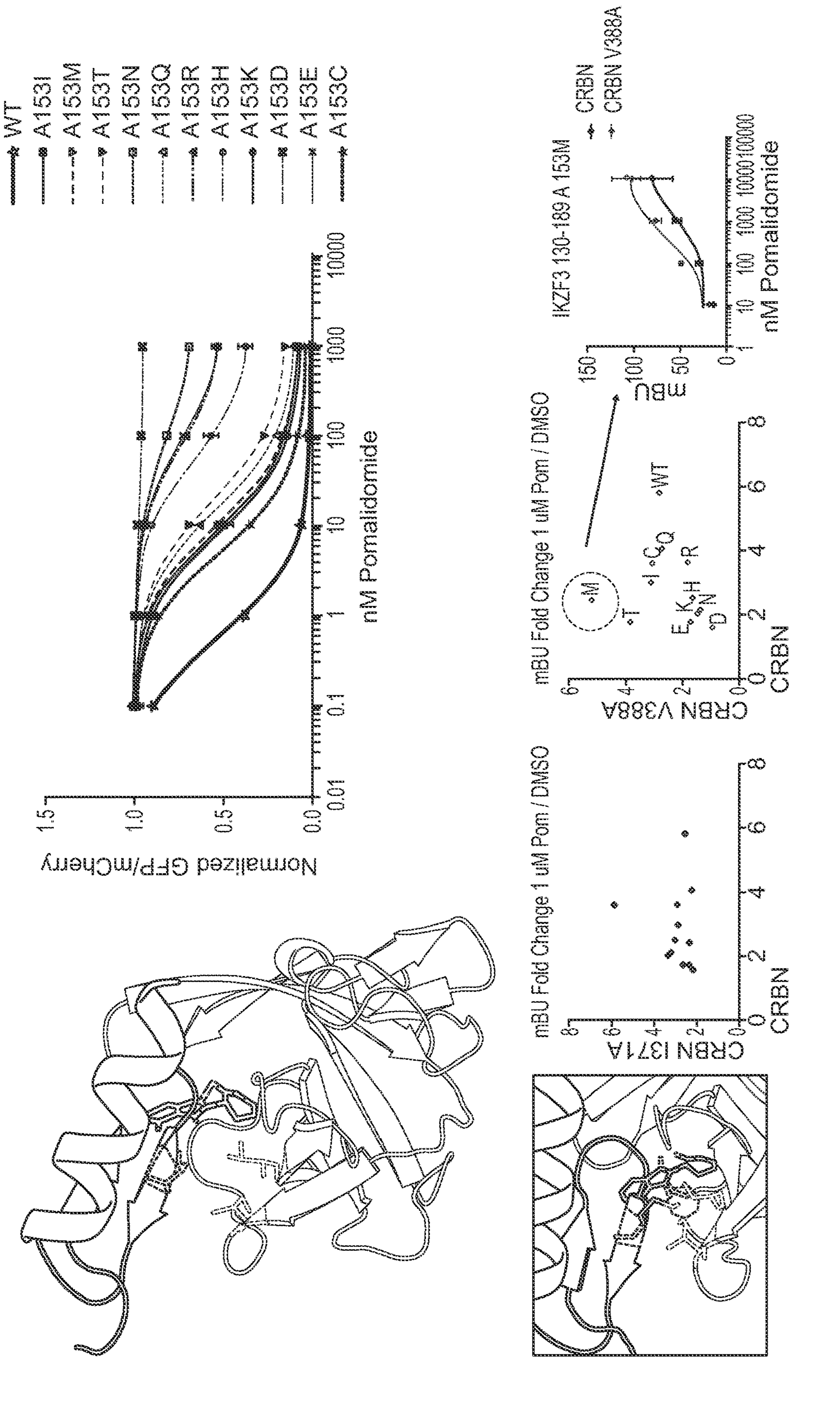

FIG. 4 shows that strategic residue substitutions, made respectively within the IMiD (pomalidomide) binding pocket of the IKZF3 degron and the CRBN polypeptide could be used (a) to make the IKZF3 degron less responsive/effectively non-responsive to pomalidomide-dependent degradation by native forms of CRBN polypeptide, while (b) "offsetting" substituted forms of CRBN polypeptide could also be identified that restored pomalidomide-dependent association to the substituted IKZF3 degron-substituted CRBN interaction (thereby effectively freeing this substituted IKZF3 degron-substituted CRBN dimerization from the potential degradative impacts of wild-type CRBN, where present, thus reducing or eliminating the need for genomic disruption of native CRBN in candidate therapeutic cells that employ such a substituted IKZF3 degron-substituted CRBN dimer system). In particular, the top plot demonstrates that substitutions at IKZF3 residue A153 increased the observed EC50 of pomalidomide-dependent degradation. Notably, the IKZF3 A153M substitution disrupted binding and degradation by CRBN (among the various substituted forms tested—in the topplot, wild-type is the left-hand trace, while various substituted forms as indicated provide the traces to the right of the wild-type trace). As shown in the bottom row of plots, a CRBN V388A substitution restored binding affinity with IKZF3 A153M, thereby generating a preferential knob-in-hole binding pair (see structure schematic at left). The bottom row of charts shows that in 293T cells exposed for 2 hours to 10 μM MG132 and either 1 μM Pomalidomide or DMSO, the mBU fold change at 1 μM Pomalidomide/DMSO treatment was calculated for IKZF3 A153 substitutions and CRBN, CRBN V388A, or CRBN 1371A. mBU fold change was plotted for mutant versus wild type CRBN. The CRBN V388A mutation increased the mBU fold change versus wild type CRBN (FIG. 4 at bottom right).

Figure 5:
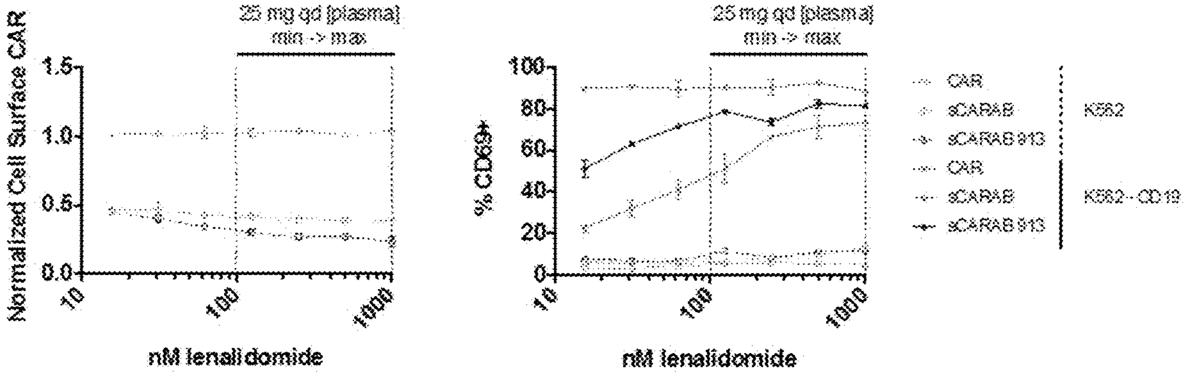

FIG. 5 demonstrates that the "ON"-switch was further improved using a "d913" degron for dimerization. Specifically, an engineered hybrid degron, d913, enabled more robust control than the endogenous IKZF3 degron for tumor antigen-dependent activation marker expression and IL2 release. As for the IKZF3 degron described above, a "K0" form of the "d913" degron was produced, and the chemically-induced dimerization system employing a "K0" d913 super-degron-derived dimerization domain (sCARAB 913) was identified to enable more robust drug-dependent activation than the corresponding IKZF3-CRBN dimerization system (sCARAB). To generate figure plots, T cells were transduced with lentivirus generated with the lentivectors BigSur and Eureka driving the expression of the indicated split CAR constructs (sCARAB, sCARAB 913 and a CAR control). 100,000 Jurkat cells were co-cultured with 20,000 K562 or K562-CD19 cells for 18 hours. Via flow cytometry analysis, cell surface split CAR expression (myc tag) and activation marker expression (CD69) were assessed in eGFP+/mCherry+Jurkat cells transduced with both components of the split receptor. At left, observed cell surface CAR expression (as assessed by flow cytometry using anti-Myc-tag antibody) is shown. At right, activation (% CD69+) by flow cytometry of Jurkat CAR-T cells is shown. IL2 secretion from Jurkat CAR-T cells was also assessed (data not shown), with IL2 ELISA performed upon cell culture supernatant.

Figure 6:
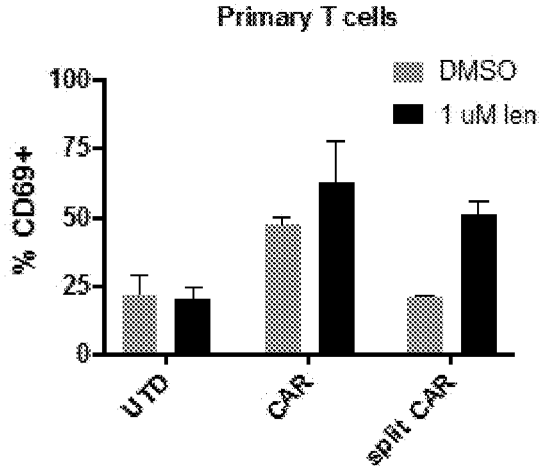

FIG. 6 shows primary T cell activation data obtained for the split CAR system. In particular, lenalidomide-dependent activation of the split CAR was successfully observed in primary T cells. In such experiments, co-culture of NALM6 B cells with primary human T cells transduced with BigSur_sCARA and Eureka_sCARB or BigSur_1928z and subsequently expanded in vitro. mCherry+ (CAR) or mCherry+/eGFP+ (split CAR) cells were sorted by FACS and subsequently co-cultured for 24 hours with NALM6-CBG-eGFP target cells. CD69 expressed was assessed by flow cytometry. UTD=untransduced. CAR=BigSur_19-28z. "split CAR"=cells transduced both with BigSur_sCARA and Eureka_sCARB, as demonstrated by co-expression of mCherry and eGFP.

Figure 7:
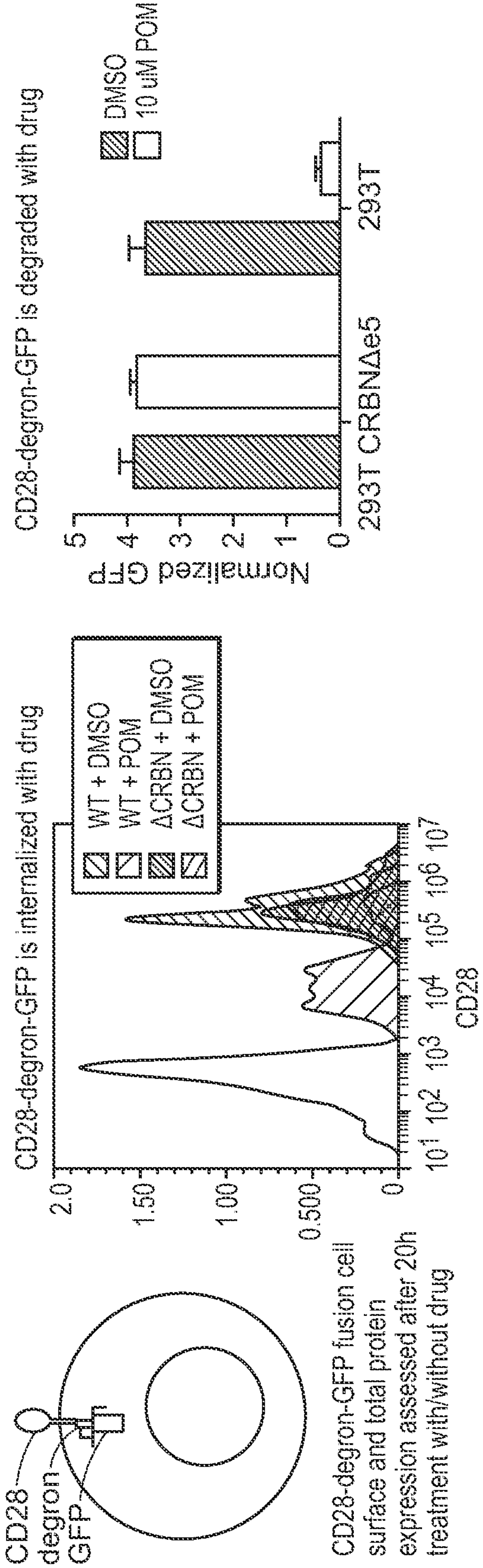

FIG. 7 demonstrates the effect of IKZF3 degron inclusion within a GFP-tagged CD28 fusion protein. Specifically, a minimal IKZF3 degron polypeptide conferred IMiD-dependent internalization and degradation to a CAR-like transmembrane protein.

Figure 8:
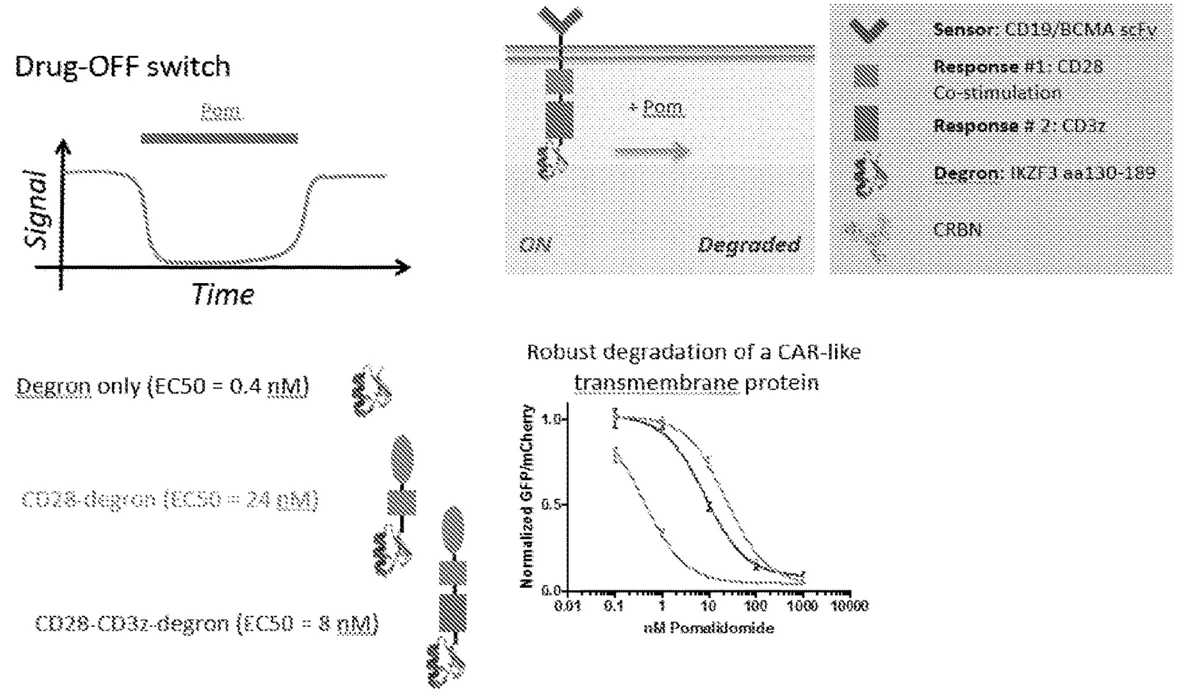

FIG. 8 shows that the IKZF3 degron (comprising amino acids 130-189 of IKZF3) functioned as a highly pomalidomide-responsive OFF-switch when integrated into the context of a CAR construct. In particular, CAR-like CRL4$^{CRBN}$ degron-tagged transmembrane proteins were confirmed as degraded with pomalidomide. The instant CD28-CD3ζ-degron protein differed from an anti-CD19 CAR sequence published previously (PMID 19561539) in two ways. First, the FMC63 anti-CD19 scFv was exchanged for the CD28 Ig-like V-type extracellular domain. Second, the protein was fused in-frame at its C-terminus with the degron IKZF3aa130-189, which was previously shown to mediate lenalidomide-dependent degradation by CRL4$^{CRBN}$ (PMID 24292625). Jurkat T cells were transduced with lentivirus encoding the three degron-eGFP fusion proteins (pSFFV-insert-linker-eGFP-IRES-mCherry). mCherry expression served as an internal control for transgene expression. Degradation of the degron-GFP fusion protein at varying concentrations of pomalidomide was quantified as the eGFP/mCherry ratio normalized to the DMSO treatment control. Experiments were performed in triplicate. EC50 and standard error values for degron, CD28-degron, and CD28-CD3ζ-degron, respectively were 0.42+/−0.03, 23.5+/−2.7, and 8.2+/−0.9. Anti-BCMA-CD28-CD3ζ-degron CAR is also assessed for tumor killing, cytokine release, and cell surface co-receptor expression in primary human T cells, both in vitro and in vivo.

Figure 9:
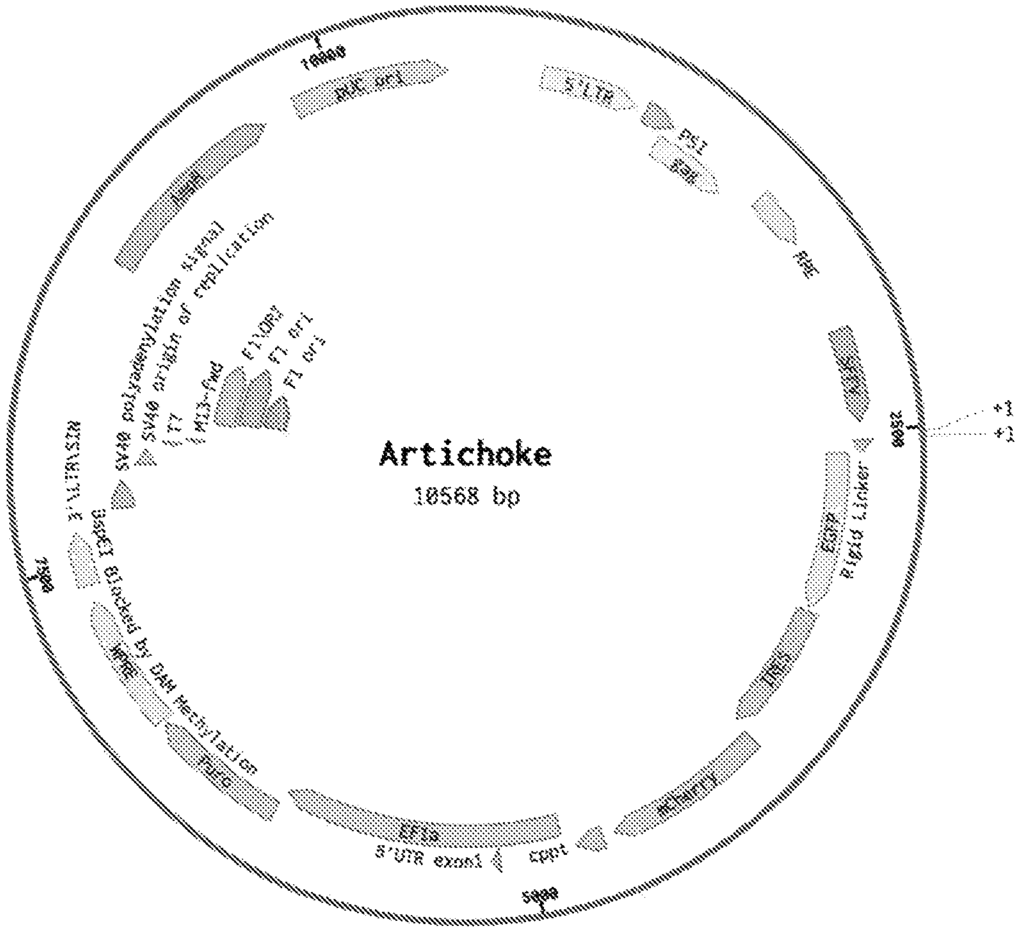

FIG. 9 shows a plasmid map for the "Artichoke" expression plasmid of the instant disclosure, where the "+1" sites mark the BsmBI restriction endonuclease cloning sites that were used to insert genes of interest.

Figure 10:
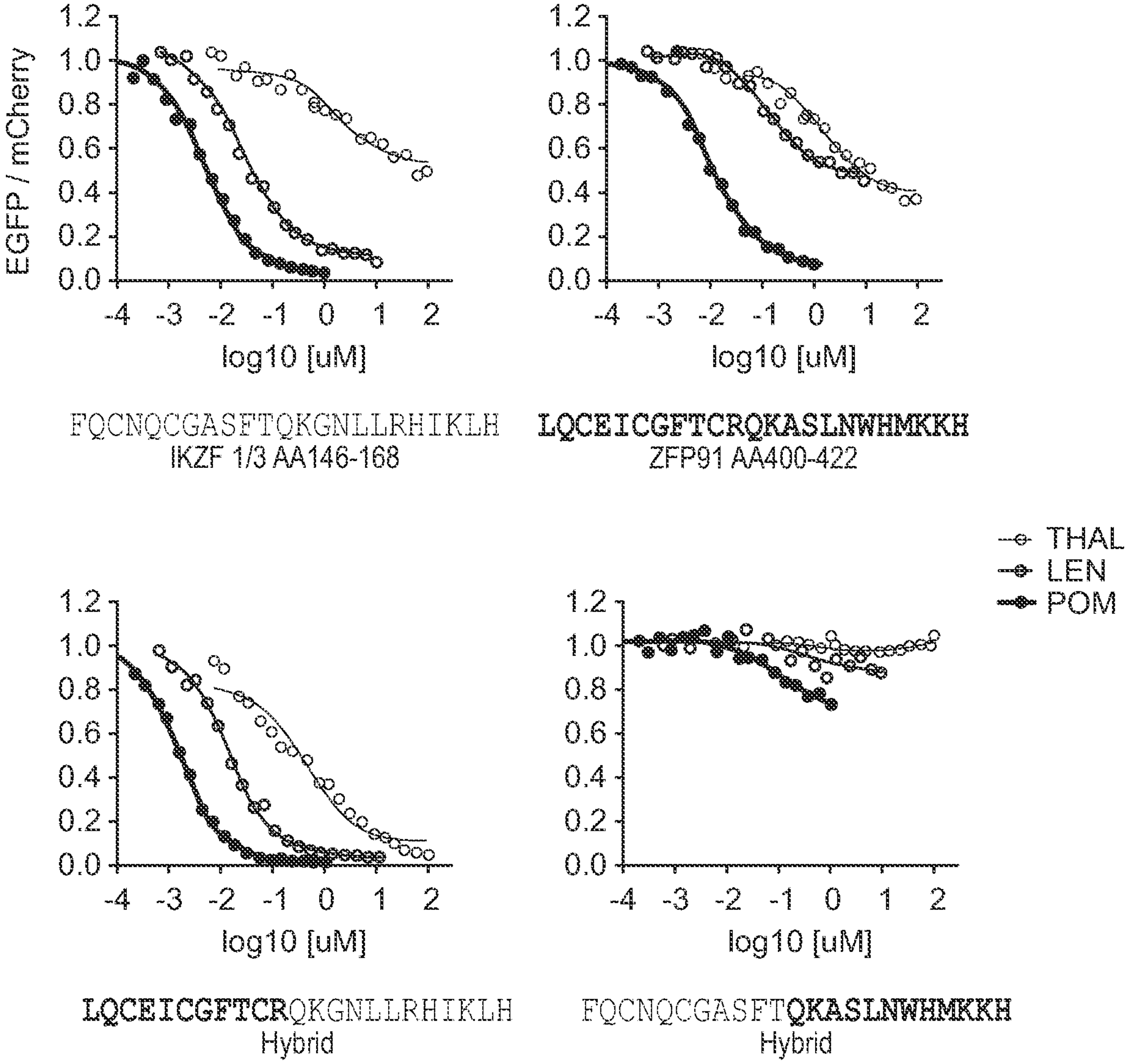

FIG. 10 shows that a ZFP91/IKZF3 hybrid degron polypeptide was a degron polypeptide that was more sensitive than either the ZFP91 degron sequence alone or the IKZF3 degron sequence alone (sequences from which the hybrid degron derives).

Figure 11:
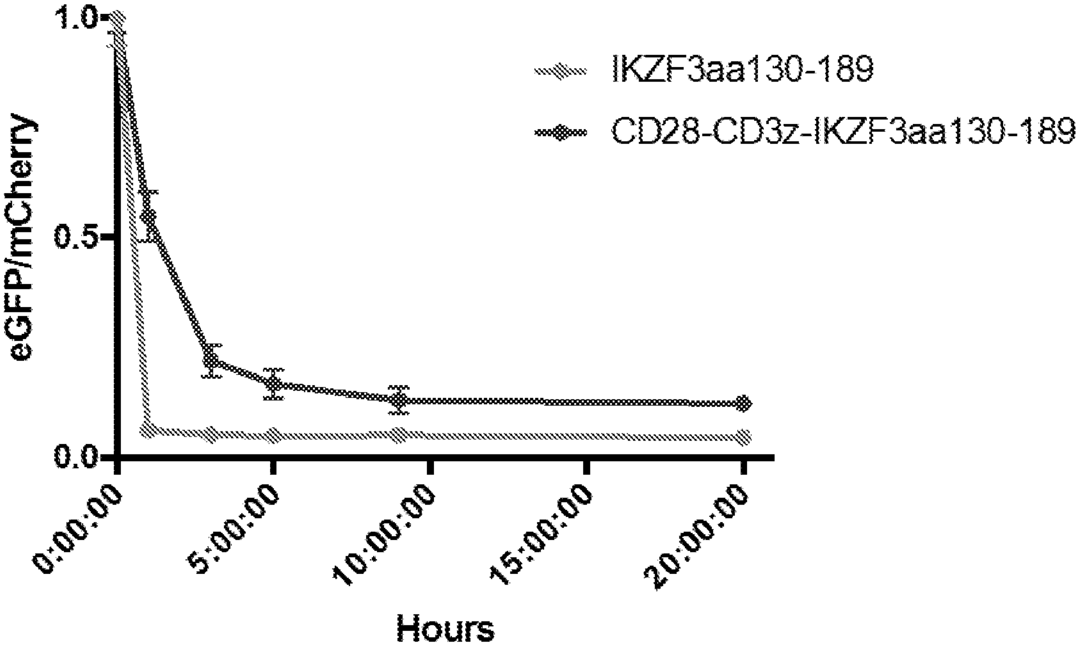

FIG. 11 shows a plot demonstrating the dynamics of transmembrane protein internalization upon addition of pomalidomide for the OFF-switch CAR design.

Figure 12:
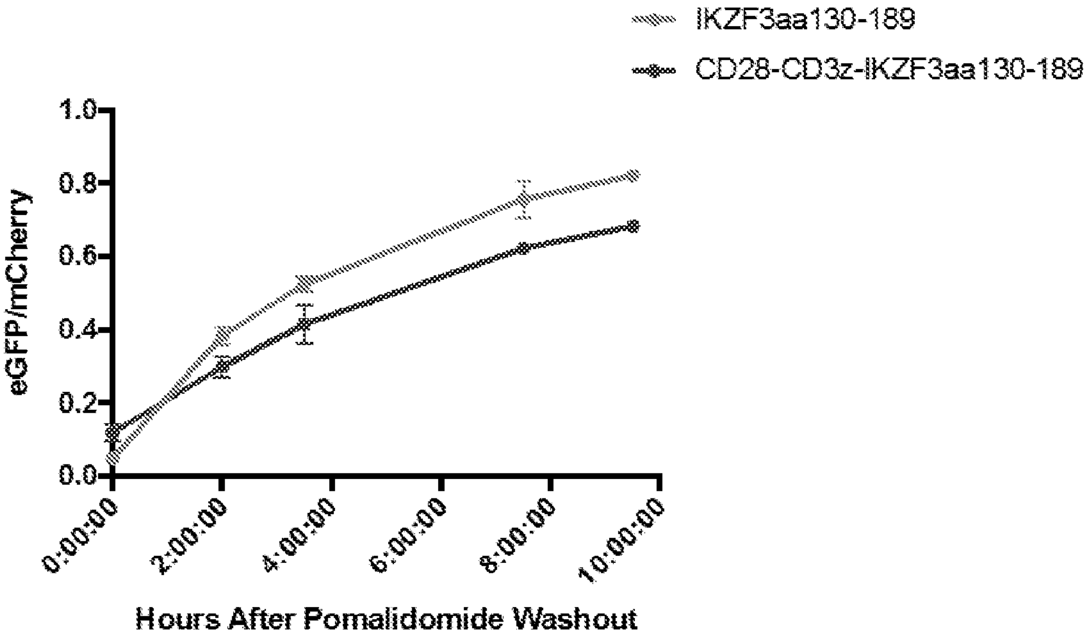

FIG. 12 shows a plot demonstrating the dynamics of re-synthesis of transmembrane degron-tagged protein after washout of pomalidomide.

Figure 13:
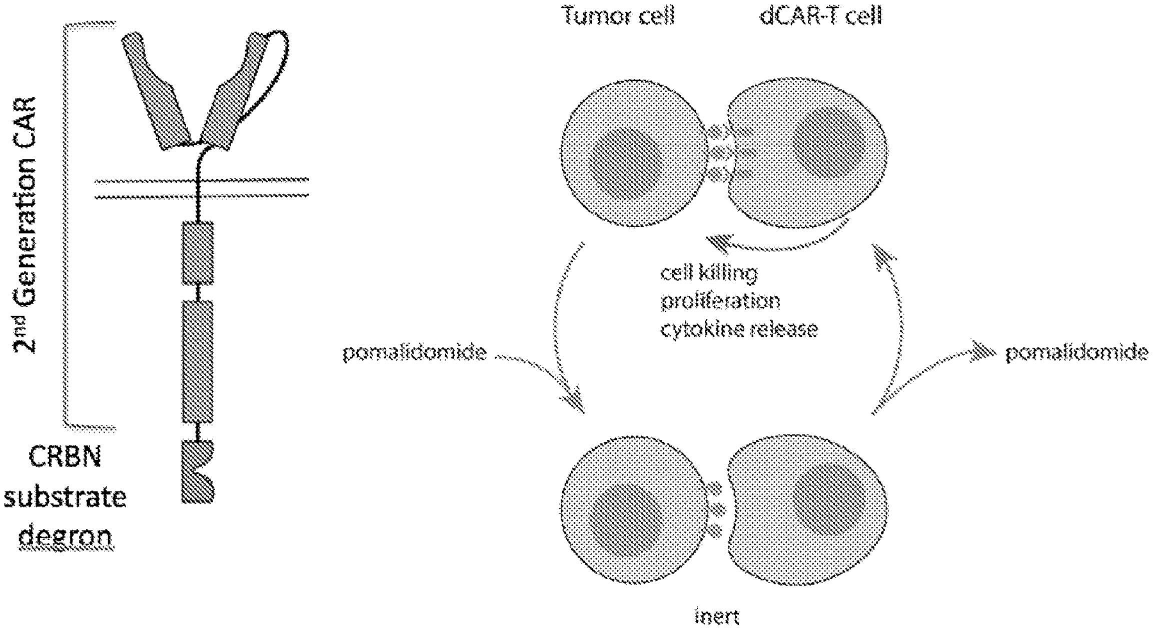

FIG. 13 depicts a degron-tagged CAR (dCAR) reversible drug-OFF switch design. At left, a CRBN substrate degron has been appended to the cytoplasmic C-terminus of a second generation CAR. At right, a schematic of the drug-OFF switch design is shown: dCAR-T cells are able to respond to antigen-positive tumor cells. With the addition of pomalidomide, lenalidomide, or another small molecule controller, the dCAR-T cell degrades the dCAR, thereby reducing or eliminating the capacity of these cells to respond to tumor cells. With cessation of the controller drug, the dCAR-T cell can reactivate as the protein concentration of the dCAR increases.

Figure 14:
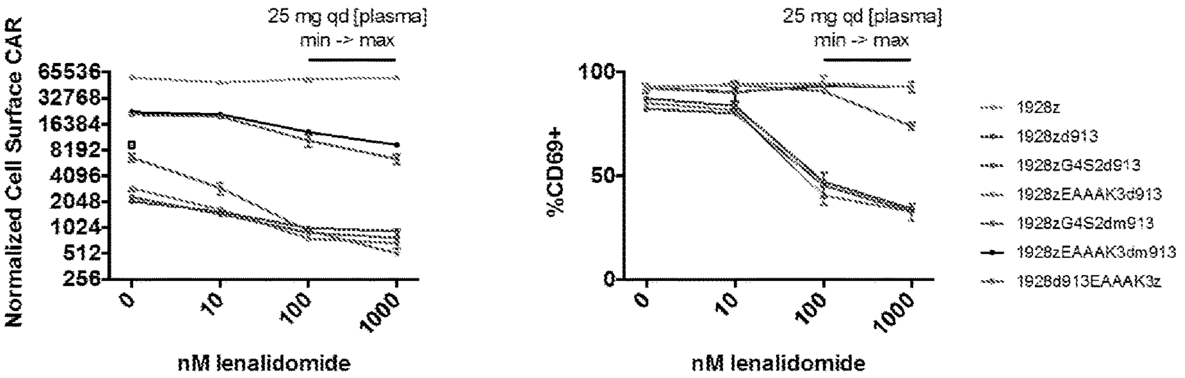

FIG. 14 shows results of experiments that demonstrated degron position, length, and linker sequences to impact CAR protein abundance and chemical control. In particular, a relationship was discovered between degron position, length, and linker for CAR expression and functional control. The left panel shows observed mean fluorescence intensity (MFI) of Jurkat CAR-T cells incubated with lenalidomide for 18 hours, with cells stained with anti-Myc-tag antibody that detected cell surface CAR expression. The right panel shows observed levels of activation (% CD69+) as assessed by flow cytometry of Jurkat T cells transduced with the indicated degron-tagged CAR constructs and incubated with K562-CD19 cells for 18 hours. To produce these data, Jurkat T cells were transduced with lentivirus generated with the lentivector BigSur driving the expression of the indicated CAR construct. mCherry+ cells were then analyzed for surface Myc-tag and CD69 expression. In the panels, 19=anti-CD19 scFv FMC63; 28z=CD28 hinge, transmembrane, and costimulatory domain and CD3zeta intracellular signaling domain; G4S2=polypeptide linker with the sequence GGGGSGGGGS (SEQ ID NO: 93); EAAAK3=polypeptide linker with the sequence AEAAAKEAAAKEAAAKA (SEQ ID NO: 94); dm913=seq.:32; d913=IKZF3 aa 130-145+ZFP91 aa 400-410+IKZF3 aa 157-189 (FNVLMVHKRSHTGERPLQCEICGFTCRQKGNLLRHIKLHTGEKPFKCHLCNYACQRRDA L; SEQ ID NO: 95).

Figure 15:
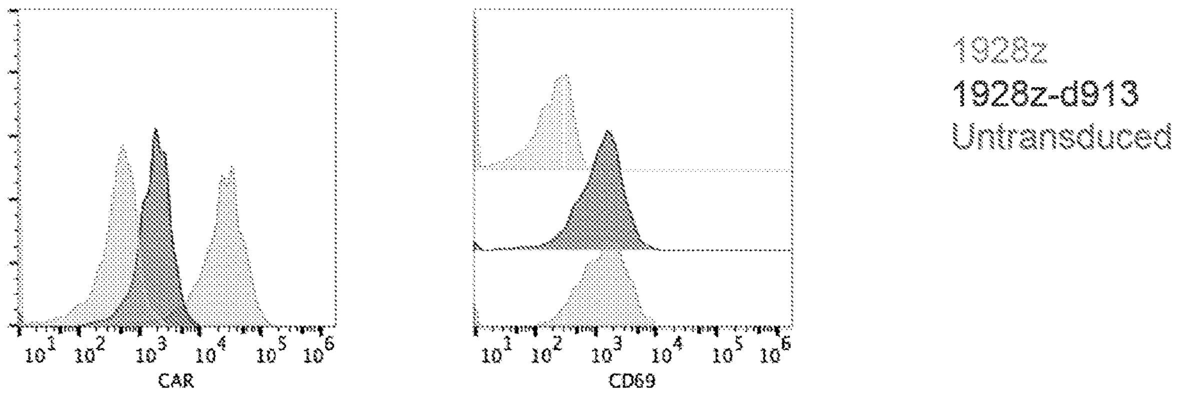

FIG. 15 demonstrates that a degron tag (here, the d913 degron tag) reduced tonic cell surface CAR expression without altering the ability of CARs to express activation markers in response to target antigen presentation. The left panel shows observed expression of cell surface CAR (anti-Myc tag) on Jurkat T cells. To obtain these results, Jurkat T cells were transduced with lentivirus generated with the lentivector BigSur driving the expression of the indicated CAR construct. mCherry+ cells were analyzed for surface Myc-tag and CD69 expression. Addition of the degron (d913) resulted in lower tonic CAR cell surface protein abundance versus the control CAR. The right panel demonstrates the activation observed for Jurkat T cells transduced with the indicated CAR, or untransduced, after 18 hour co-culture with K562-CD19 cells. Although the degron-tagged CAR was expressed at lower protein abundance, activation marker expression was indistinguishable between it and the non-degron-tagged form.

Figure 16:
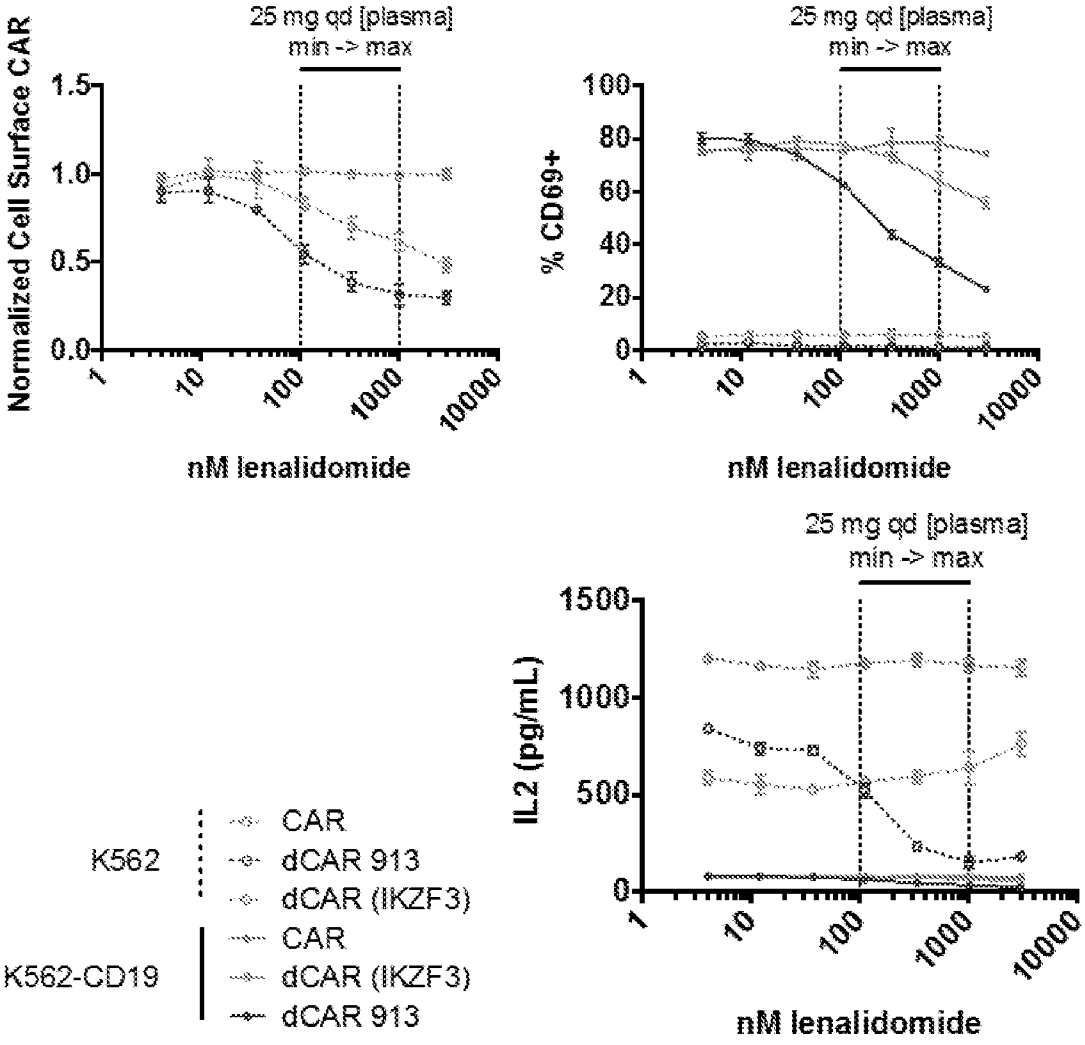

FIG. 16 demonstrates that degron sequence determined the efficacy of the drug OFF-switch. In particular, the engineered hybrid degron (d913) was observed to enable more robust control over CAR protein expression, activation, and cytokine secretion than the endogenous IKZF3 degron for tumor antigen-dependent activation marker expression and IL2 release. To obtain the displayed results, T cells were transduced with lentivirus generated with the lentivector BigSur driving the expression of the indicated CAR construct. mCherry+ cells were purified by fluorescence-activated cell sorting. 100,000 CAR-T Jurkat cells were co-cultured with 20,000 K562 or K562-CD19 cells for 18 hours. The top left panel shows observed cell surface CAR expression (as assessed by flow cytometry using anti-Myc-tag antibody). The top right panel shows observed activation (% CD69+) by flow cytometry of Jurkat CAR-T cells. The bottom panel shows IL2 secretion results obtained from Jurkat CAR-T cells—IL2 ELISA was performed on cell culture supernatant for each of the indicated constructs.

Figure 17:
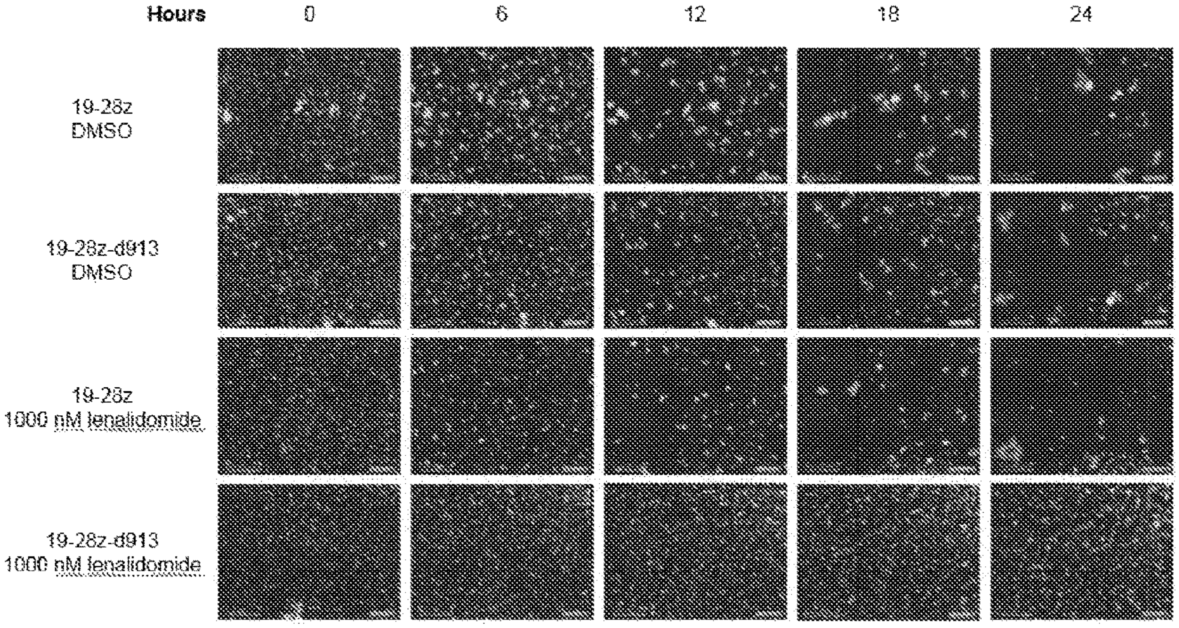

FIG. 17 demonstrates degron-tagged construct-mediated control of U87-CD19 tumor cell killing in primary T cells. In particular, control of target cell killing (U87 human cell line engineered to express CD19) with lenalidomide was observed in primary human degron-tagged CAR-T cells. Displayed images are the result of co-culture of U87-CD19-eGFP cells with primary human T cells transduced with lentivirus generated with the lentivector BigSur driving the expression of the indicated CAR construct and subsequently expanded in vitro. Equal numbers of U87-CD19-eGFP cells and the indicated CAR-T cells were co-cultured with 1000 nM lenalidomide or DMSO control for 24 hours. Fluorescence live cell microscopy was then performed throughout the 24 hour timecourse, yielding the displayed images.

Figure 18:
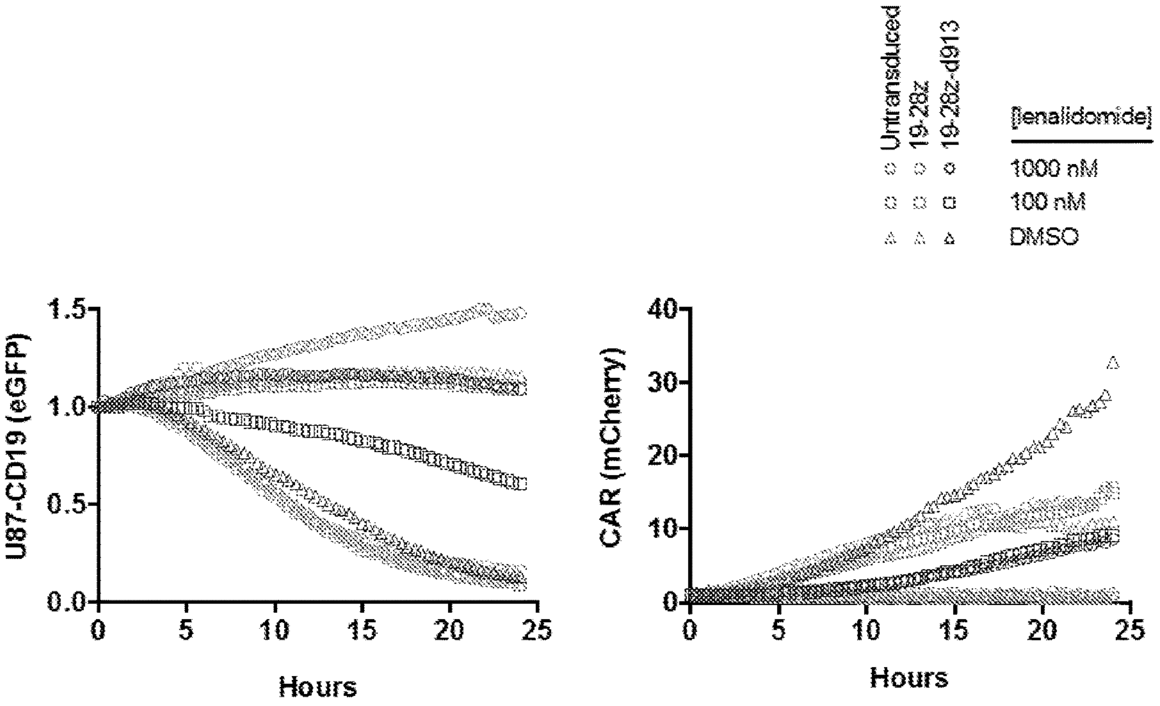

FIG. 18 shows plots that further demonstrate degron-tagged construct-mediated control of U87-CD19 tumor cell killing in primary T cells. In particular, control of target cell killing (U87 human cell line engineered to express CD19) with lenalidomide was observed in primary human degron-tagged CAR-T cells, as above. Plots were generated following co-culture of U87-CD19-eGFP cells with primary human T cells transduced with lentivirus generated with the lentivector BigSur driving the expression of the indicated CAR construct and subsequently expanded in vitro. Equal numbers of U87-CD19-eGFP cells and the indicated CAR-T cells were co-cultured with 1000 nM or 100 nM lenalidomide or DMSO control for 24 hours. Fluorescence live cell microscopy was performed throughout the 24 hour timecourse. GFP (left plot) or mCherry (right plot) fluorescence intensity was depicted for each condition, normalized to the fluorescence at T=0 hours for each well.

Figure 19:
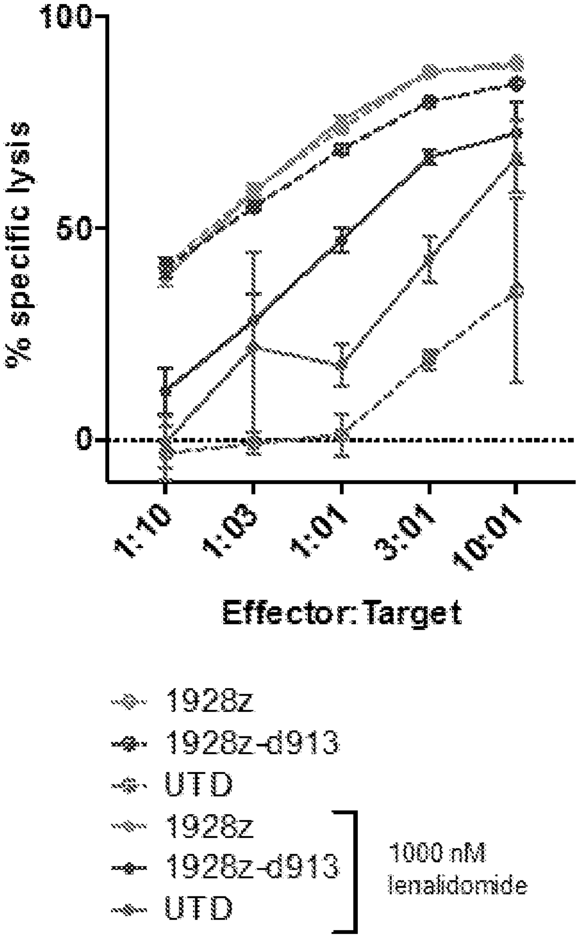

FIG. 19 demonstrates partial control of CAR-T cell killing of NALM6 target cells (human B-ALL cell line; ND33) in primary T cells, with lenalidomide in primary human degron-tagged CAR-T cells. The displayed graph shows observed levels of killing of NALM6-CBG-GFP cells after 18 hour co-culture at the specified ratios. To generate the displayed results, primary human T cells were transduced with lentivirus generated with the lentivector BigSur driving the expression of the indicated CAR construct and subsequently expanded in vitro. NALM6-CBG-GFP cells and CAR-T cells were mixed at the indicated ratios and incubated in culture for 18 hours with DMSO or 1000 nM lenalidomide. Experiments were performed in triplicate from a single normal donor (ND33). Killing from 1928z-d913 without lenalidomide approximated killing from 1928z (with or without lenalidomide). 1928z-d913 killing was blunted with 1000 nM but not 100 nM lenalidomide.

Figure 20:
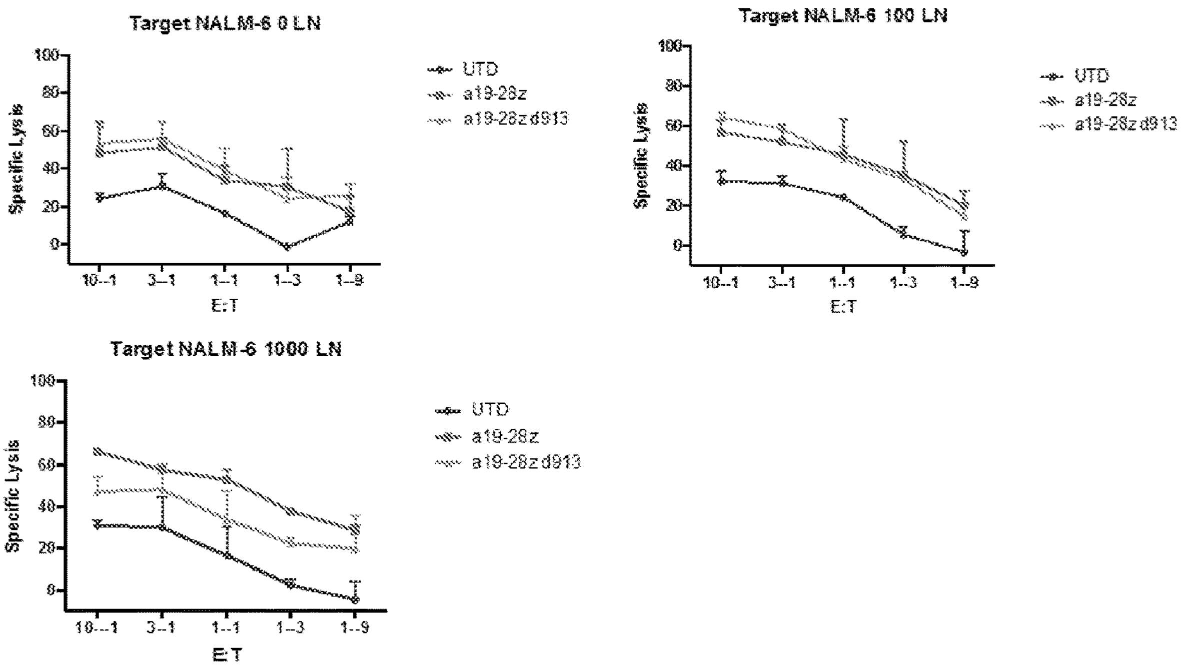

FIG. 20 further demonstrates partial control of CAR-T cell killing of NALM6 target cells (human B-ALL cell line; ND34) in primary T cells, with lenalidomide in primary human degron-tagged CAR-T cells. Plots show killing of NALM6-CBG-GFP cells after 18 hour co-culture at the specified ratios. Primary human T cells were transduced with lentivirus generated with the lentivector BigSur driving the expression of the indicated CAR construct and subsequently expanded in vitro. NALM6-CBG-GFP cells and CAR-T cells were mixed at the indicated ratios and incubated in culture for 18 hours with DMSO, 100 nM lenalidomide, or 1000 nM lenalidomide. Experiments were performed in triplicate from a single normal donor (ND34). As above, killing from 1928z-d913 without lenalidomide approximated killing from 1928z (with or without lenalidomide). Meanwhile 1928z-d913 killing was blunted with 1000 nM but not 100 nM lenalidomide.

Figure 21:
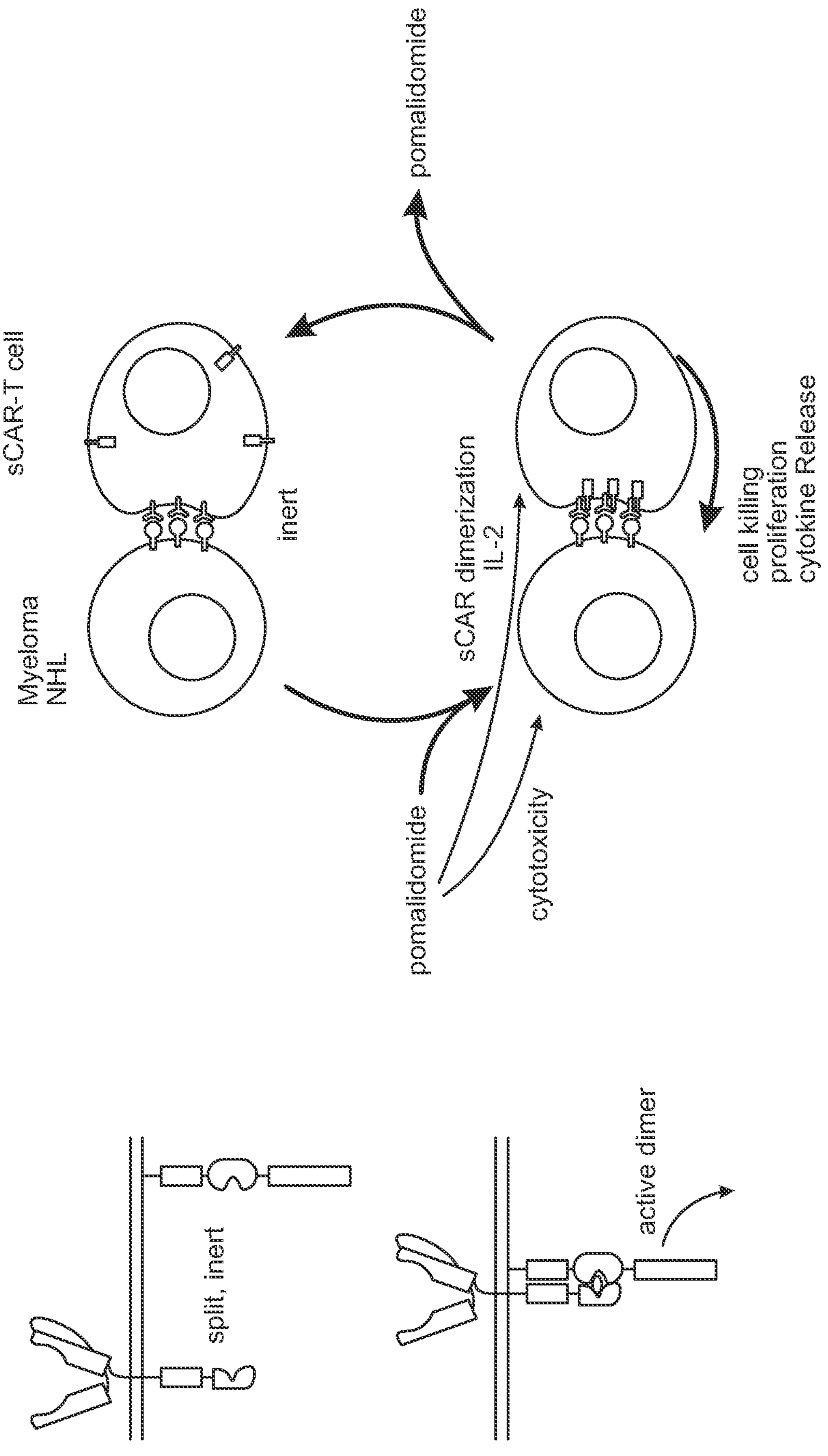

FIG. 21 exemplifies a split CAR reversible drug-ON switch design. Top left: components A (antigen-binding, co-stimulatory domain, and IKZF3-derived dimerization domain) and B (transmembrane domain, co-stimulatory domain, CD3z intracellular domain, and CRBN-derived dimerization domain) are split and inactive without drug. Bottom left: upon addition of the controller drug, e.g. lenalidomide or pomalidomide, the split components dimerize and are licensed to activate in the presence of the target antigen. Top right: the split CAR is designed to be inactive in the absence of drug. Bottom right: upon addition of the controller drug, the CAR-T cell can activate when interacting with a cell expressing the target antigen. In Multiple Myeloma, Non-Hodgkin's Lymphoma, and other indications, synergy occurs between the on-target effect of the controller drug on the tumor cells, activation of the split CAR, and derepression of IL2 via degradation of IKZF1/3 in the CAR-T cells.

Figure 22:
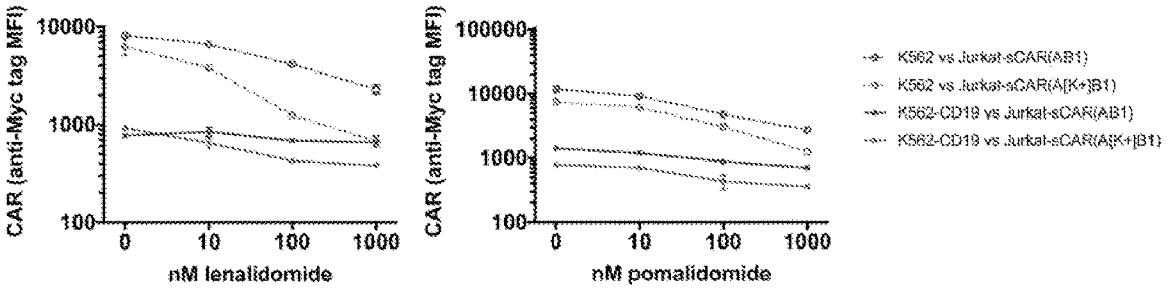

FIG. 22 demonstrates the increased protein concentration with increasing drug concentration of the intracellular K0 versus the unmodified variant of the split CAR component A. Split CAR component A variants, either (A) FMC63-CD28-IKZF3 iK0 or (A[K+]) FMC63-CD28-IKZF3, were delivered via the lentiviral expression vector Jenner and bear a N-terminal myc tag and a C-terminal 2A sequence followed by the coding sequence for mCherry. Component B1 (CD8-CD28-mCRBN3-IKZF3) of the split CAR were delivered via the lentiviral expression vector Eureka and bear a C-terminal eGFP tag. Cells were analyzed by flow cytometry after co-culture for 24 hours with K562 or K562-CD19 target cells and the indicated concentration of lenalidomide, pomalidomide, or DMSO control.

Figure 23:
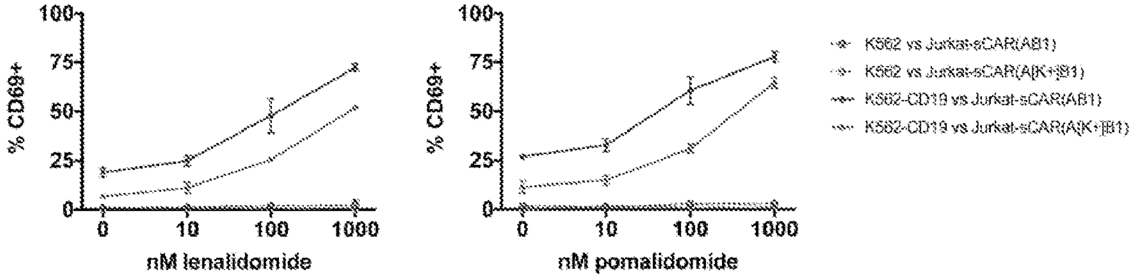

FIG. 23 demonstrates the increased drug-dependent T cell activation, as assessed by CD69 marker expression, of the intracellular K0 versus the unmodified variant of the split CAR component A. Split CAR component A variants, either (A) FMC63-CD28-IKZF3 iK0 or (A[K+]) FMC63-CD28-IKZF3, were delivered via the lentiviral expression vector Jenner. Component B1 (CD8-CD28-mCRBN3-IKZF3) of the split CAR were delivered via the lentiviral expression vector Eureka. Cells were analyzed by flow cytometry after co-culture for 24 hours with K562 or K562-CD19 target cells and the indicated concentration of lenalidomide, pomalidomide, or DMSO control.

Figure 24:
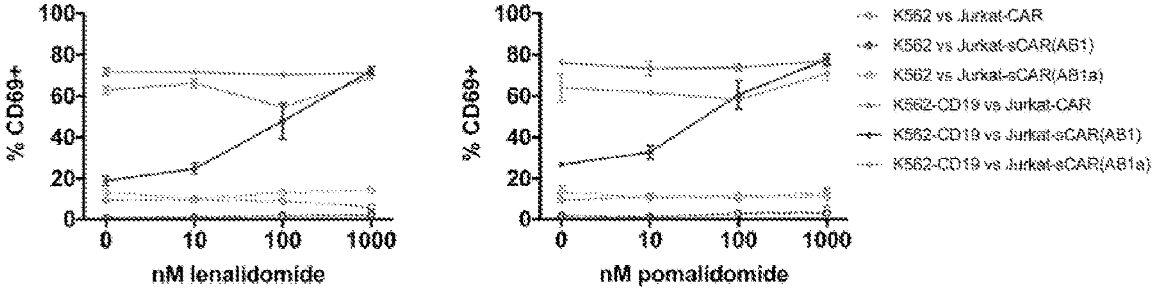

FIG. 24 demonstrates drug- and antigen-dependent activation, as assessed by CD69 marker expression, for Jurkat cells expressing the split CAR A/B1 versus the split CAR A/B1a and a control CAR (FMC63-CD28-CD3z). Cells were analyzed by flow cytometry after co-culture for 24 hours with K562 or K562-CD19 target cells and the indicated concentration of lenalidomide, pomalidomide, or DMSO control. Split CAR A=FMC63-CD28-IKZF3 iK0. Split CAR B1=CD8-CD28-mCRBN3-CD3z. Split CAR B1a=CD8-CD28-mCRBN2-CD3z.

Figure 25:
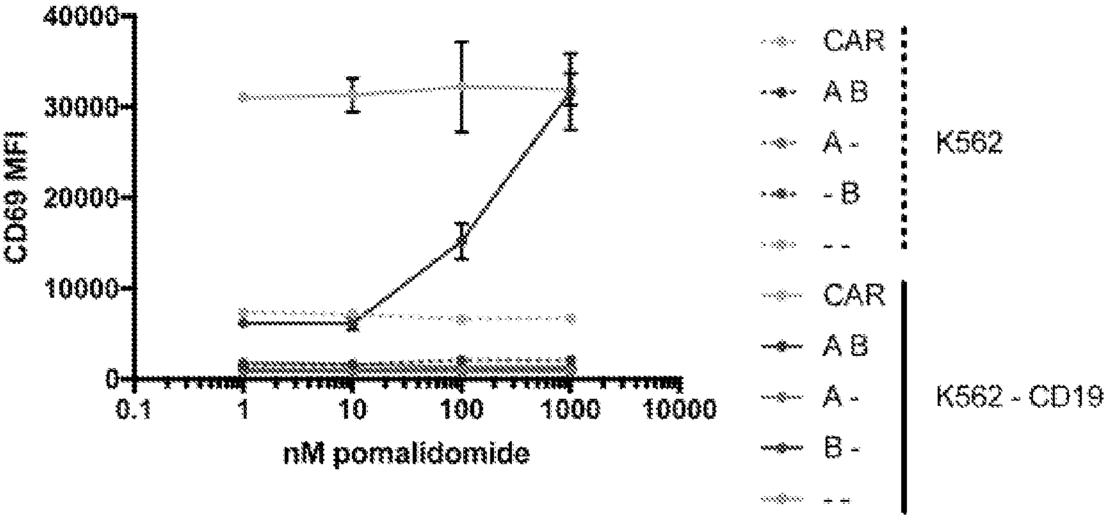

FIG. 25 shows the requirement of antigen, drug, and both split CAR components A and B1 for Jurkat T cell activation, as assessed by CD69 marker expression. Jurkat cells expressing single split CAR components A (FMC63-CD28-IKZF3 iK0) or B1 (CD8-CD28-mCRBN3-IKZF3), both split CAR components A and B1, a control CAR (FMC63-CD28-CD3z), or untransduced cells were analyzed. Cells were analyzed by flow cytometry after co-culture for 24 hours with K562 or K562-CD19 target cells and the indicated concentration of lenalidomide, pomalidomide, or DMSO control.

Figure 26:
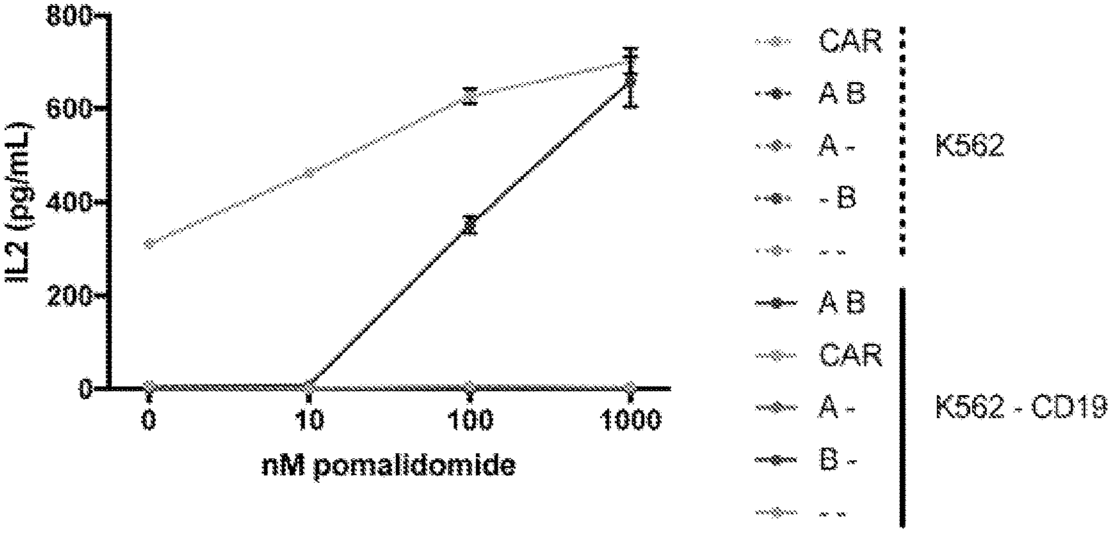

FIG. 26 shows the requirement of antigen, drug, and both split CAR components A and B1 for Jurkat cell IL2 secretion, as assessed by IL2 ELISA. Jurkat cells expressing single split CAR components A (FMC63-CD28-IKZF3 iK0) or B1 (CD8-CD28-mCRBN3-IKZF3), both split CAR components A and B1, a control CAR (FMC63-CD28-CD3z), or untransduced cells were analyzed. Cell culture supernatant was collected after 24 hours of co-culture with K562 or K562-CD19 target cells and the indicated concentration of lenalidomide, pomalidomide, or DMSO control.

Figure 27:
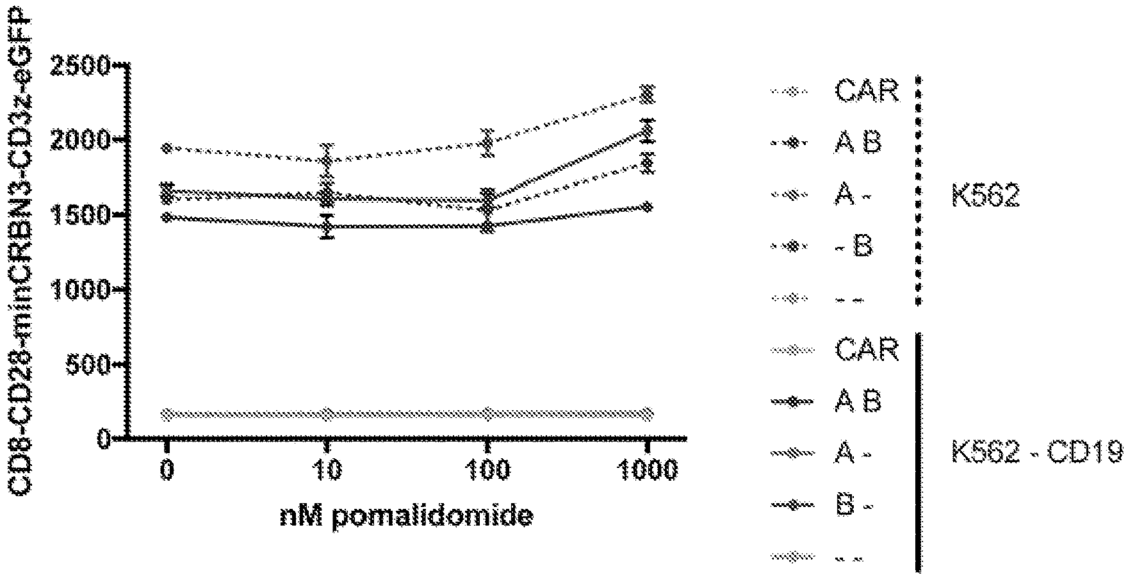

FIG. 27 shows that the expression of eGFP-tagged split CAR component B1 (CD8-CD28-mCRBN3-IKZF3) was stable across concentrations of pomalidomide and with either K562 or K562-CD19 target cells. Cells were analyzed by flow cytometry after co-culture for 24 hours with K562 or K562-CD19 target cells and the indicated concentration of lenalidomide, pomalidomide, or DMSO control.

Figure 28:
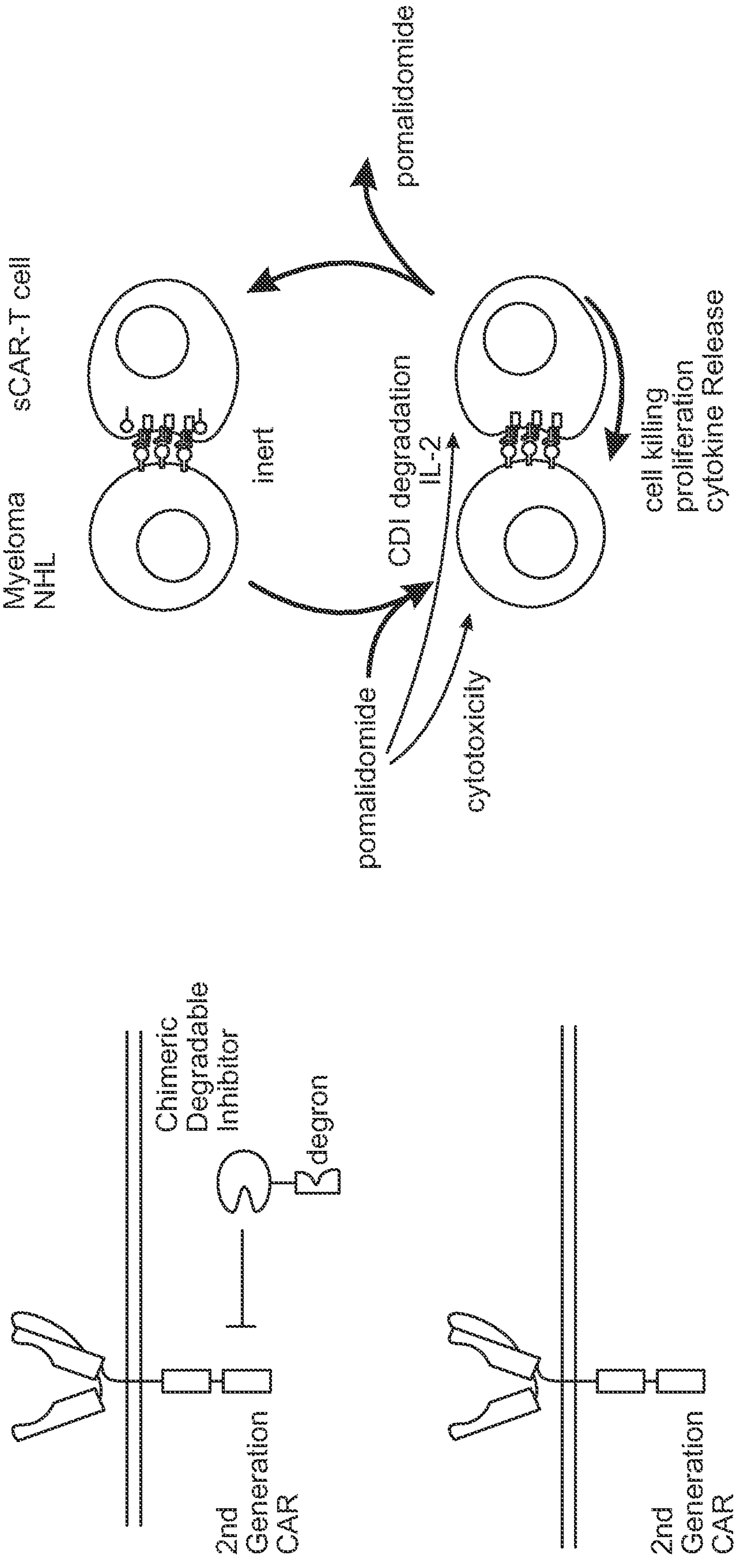

FIG. 28 demonstrates the drug-ON switch design combining a CAR and a Chimeric Degradable Inhibitor (CDI). Top left: The CDI tonically inhibits some or all effects of CAR signal transduction. Bottom left: with addition of the controller drug, degradation of the CDI results in unopposed CAR signaling, allowing for full activation. Top right: the CAR+CDI system is designed to be inactive in the absence of drug. Bottom right: upon addition of the controller drug, the CAR+CDI system is unmasked and licensed for activation. In Multiple Myeloma, Non-Hodgkin's Lymphoma, and other indications, synergy between the on-target effect of the controller drug on the tumor cells, de-repression of the CAR, and de-repression of IL2 via degradation of IKZF1/3 in the CAR-T cells is envisioned.

Figure 29:
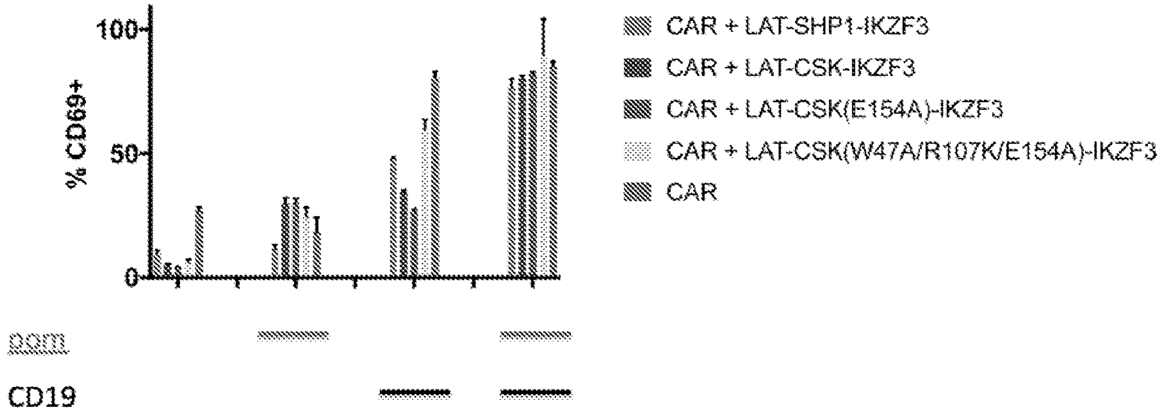

FIG. 29 demonstrates that various CDIs are able to inhibit antigen-dependent Jurkat T cell activation, as assessed by CD69 marker expression, with de-repression of antigen-independent activation with 1 uM pomalidomide. Jurkat cells were transduced with Bolinas lentiviral expression vector encoding a CAR (FMC63-CD28-CD3z) and also transduced with Eureka lentiviral expression vector encoding a CDI targeted to the plasma membrane with a N-terminal LAT transmembrane anchor and C-terminal tagged with the IKZF3 degron. The CDI constructs tested here are CSK, CSK E154A, CSK W47A/R107K/E154A and SHP1 (amino acids 203-595). Cells were analyzed by flow cytometry after co-culture for 24 hours with K562 or K562-CD19 target cells and 1 uM pomalidomide or DMSO control.

Figure 30:
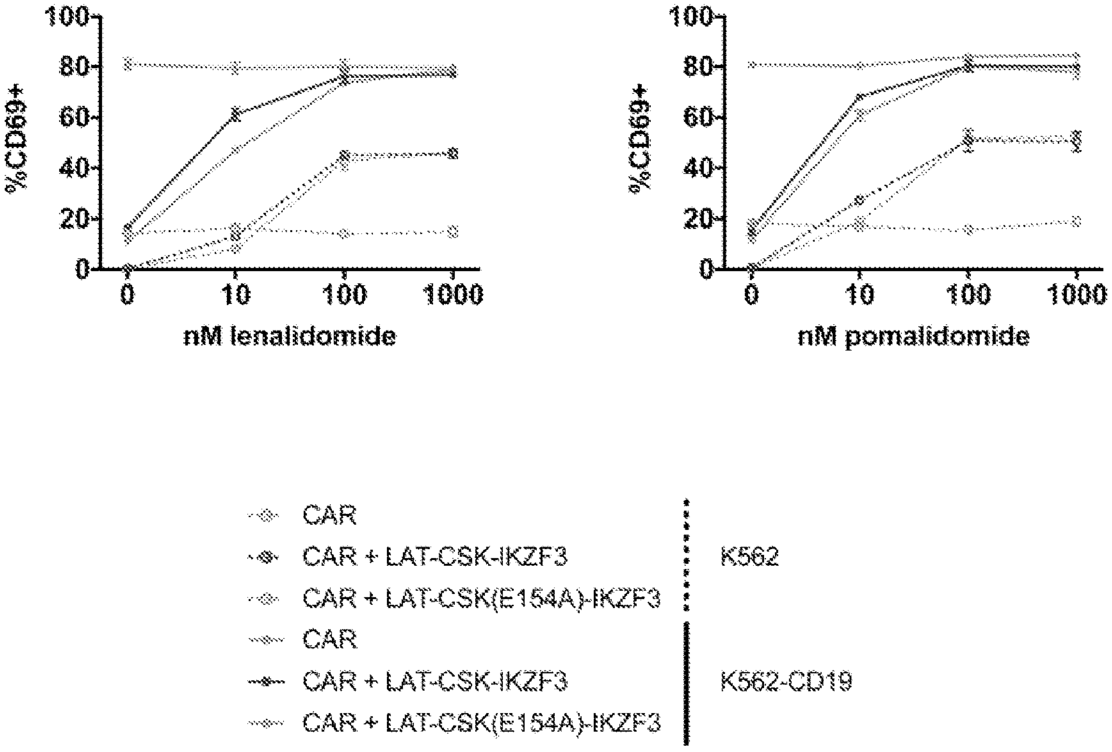

FIG. 30 demonstrates that various CDIs are able to inhibit antigen-dependent Jurkat T cell activation, as assessed by CD69 marker expression, and lenalidomide or pomalidomide results in full activation in the presence of antigen and partial antigen-independent activation. Jurkat cells were transduced with Bolinas lentiviral expression vector encoding a CAR (FMC63-CD28-CD3z) and also transduced with Eureka lentiviral expression vector encoding a CDI targeted to the plasma membrane with a N-terminal LAT transmembrane anchor and C-terminal tagged with the IKZF3 degron. The CDI constructs tested here are CSK and CSK E154A. Cells were analyzed by flow cytometry after co-culture for 24 hours with K562 or K562-CD19 target cells and the indicated concentration of lenalidomide, pomalidomide, or DMSO control.

Figure 31:
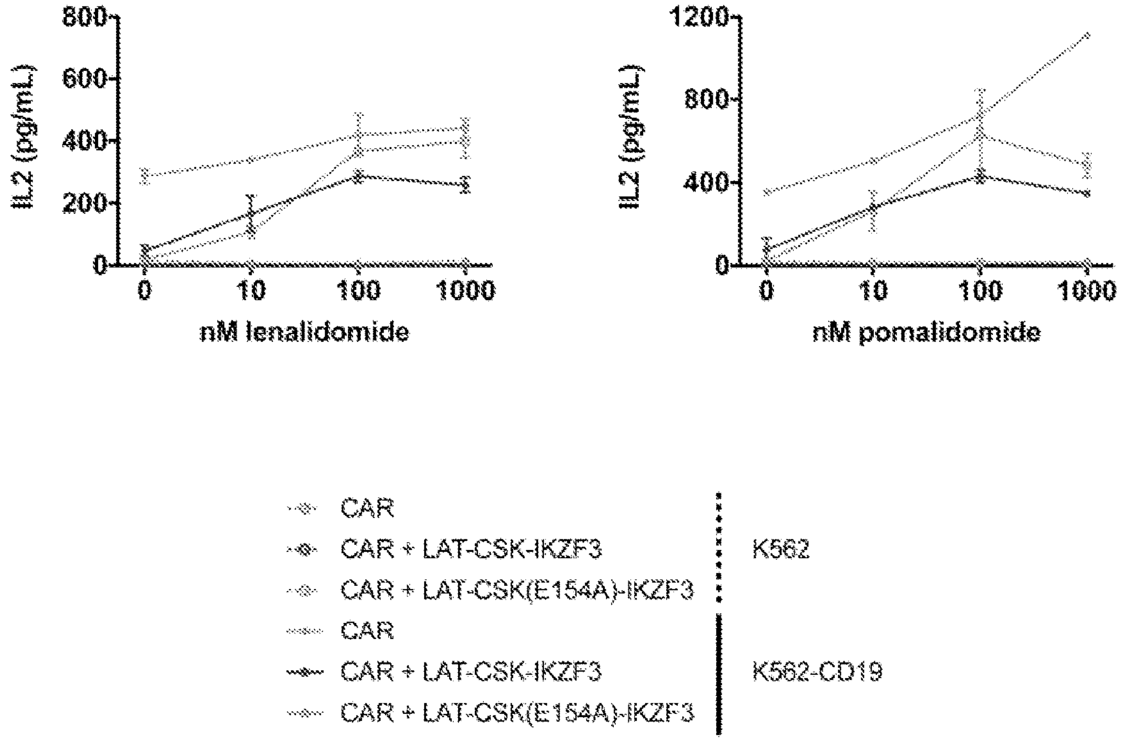

FIG. 31 demonstrates that various CDIs are able to inhibit Jurkat IL2 secretion, and lenalidomide or pomalidomide licenses antigen-dependent activation. Jurkat cells were transduced with Bolinas lentiviral expression vector encoding a CAR (FMC63-CD28-CD3z) and also transduced with Eureka lentiviral expression vector encoding a Chimeric Degradable Inhibitor (CDI) targeted to the plasma membrane with a N-terminal LAT transmembrane anchor and C-terminal tagged with the IKZF3 degron. The CDI constructs tested here are CSK and CSK E154A. Cell culture supernatant was collected after co-culture for 24 hours with K562 or K562-CD19 target cells and the indicated concentration of lenalidomide, pomalidomide, or DMSO control.

Figure 32:
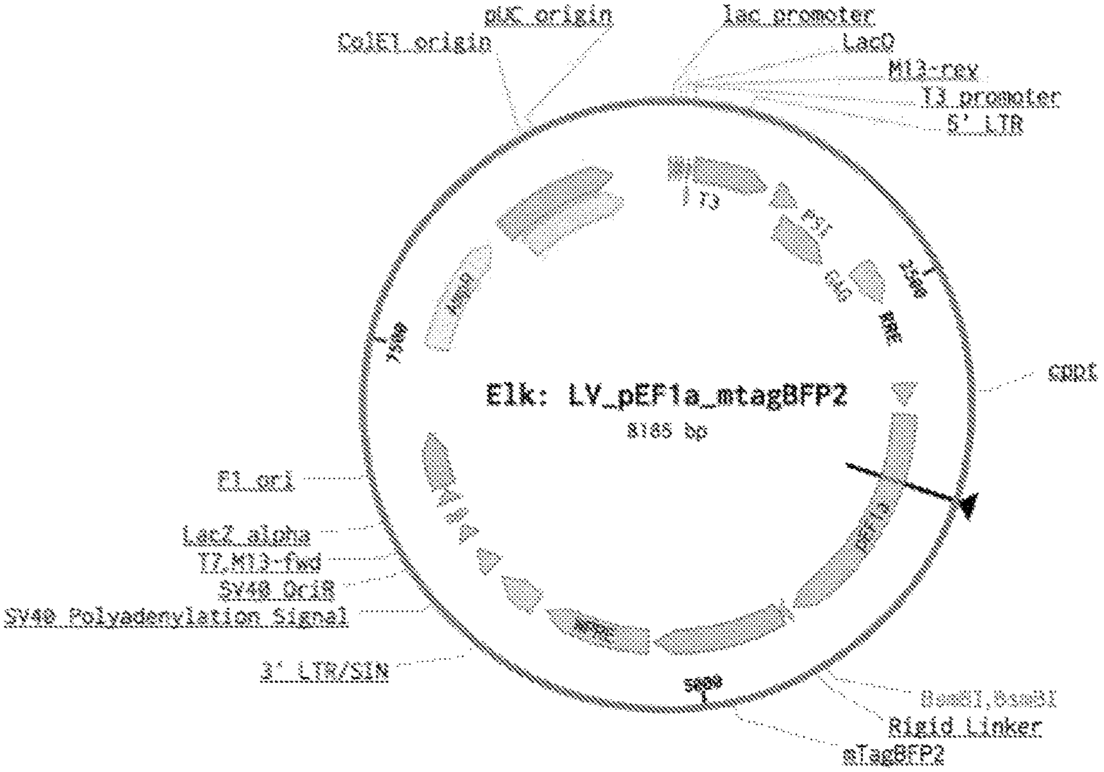

FIG. 32 shows a plasmid map for the "Elk" expression plasmid of the instant disclosure, where the BsmBI restriction endonuclease cloning sites were used to insert genes of interest.

Figure 33:
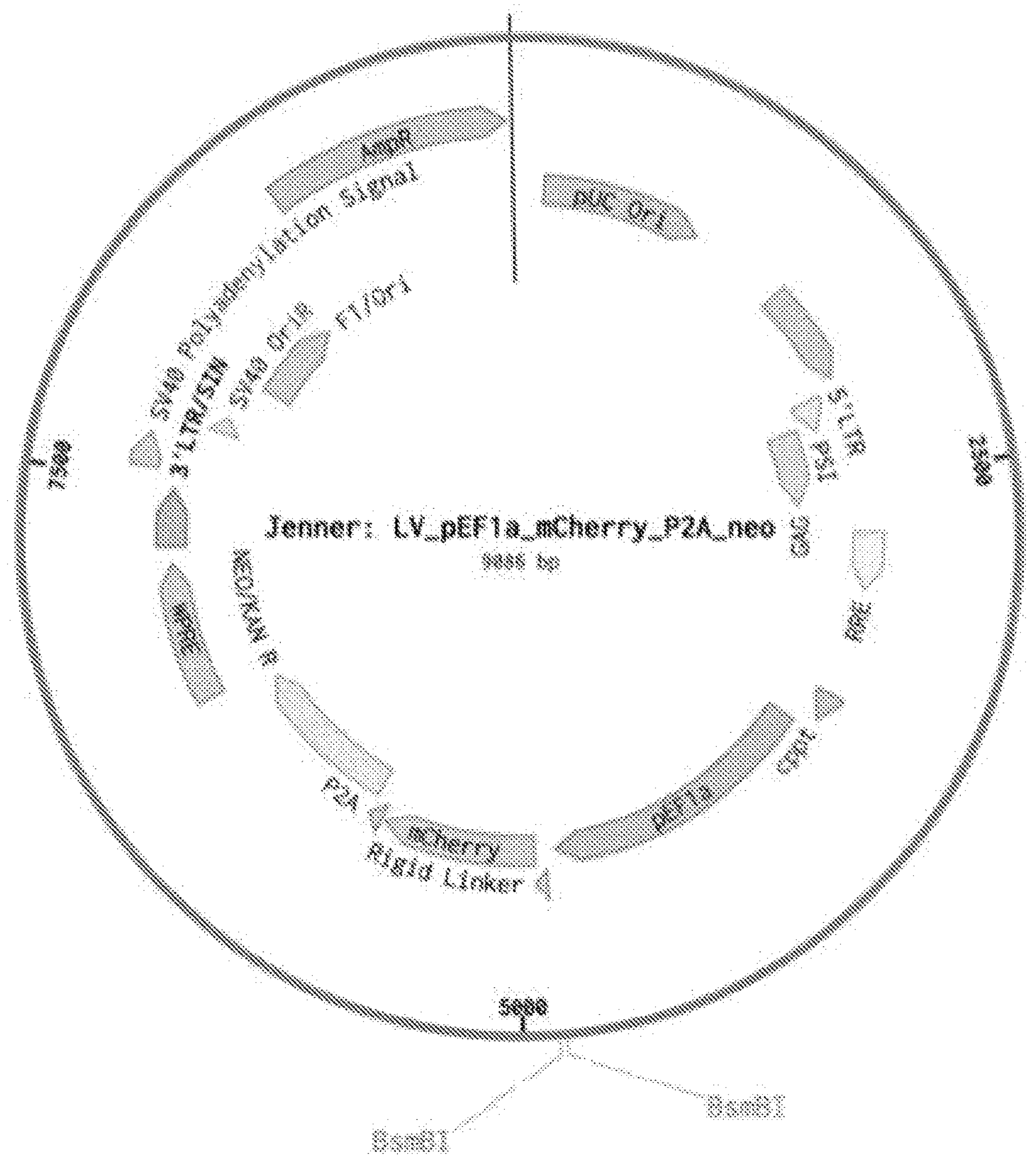

FIG. 33 shows a plasmid map for the "Jenner" expression plasmid of the instant disclosure, where the BsmBI restriction endonuclease cloning sites were used to insert genes of interest.

Figure 34:
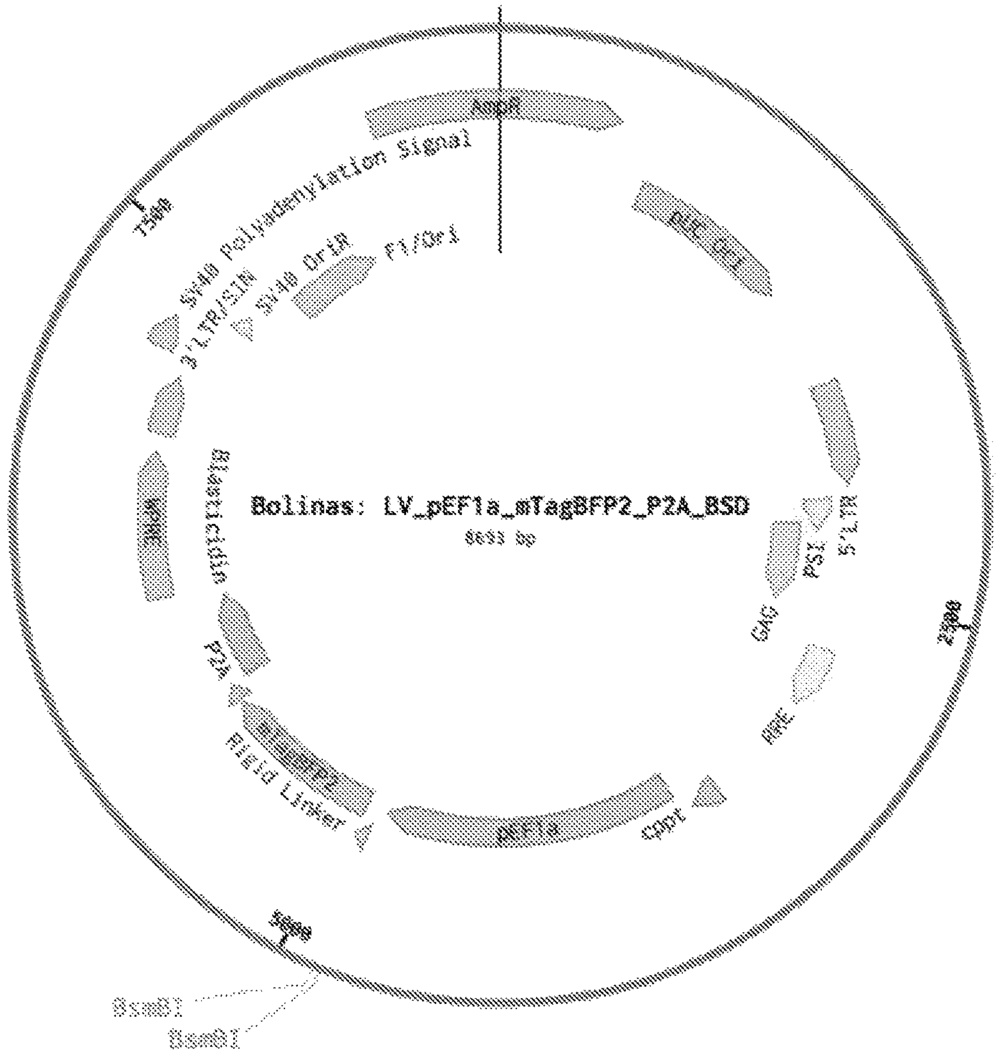

FIG. 34 shows a plasmid map for the "Bolinas" expression plasmid of the instant disclosure, where the BsmBI restriction endonuclease cloning sites were used to insert genes of interest.

Figure 35:
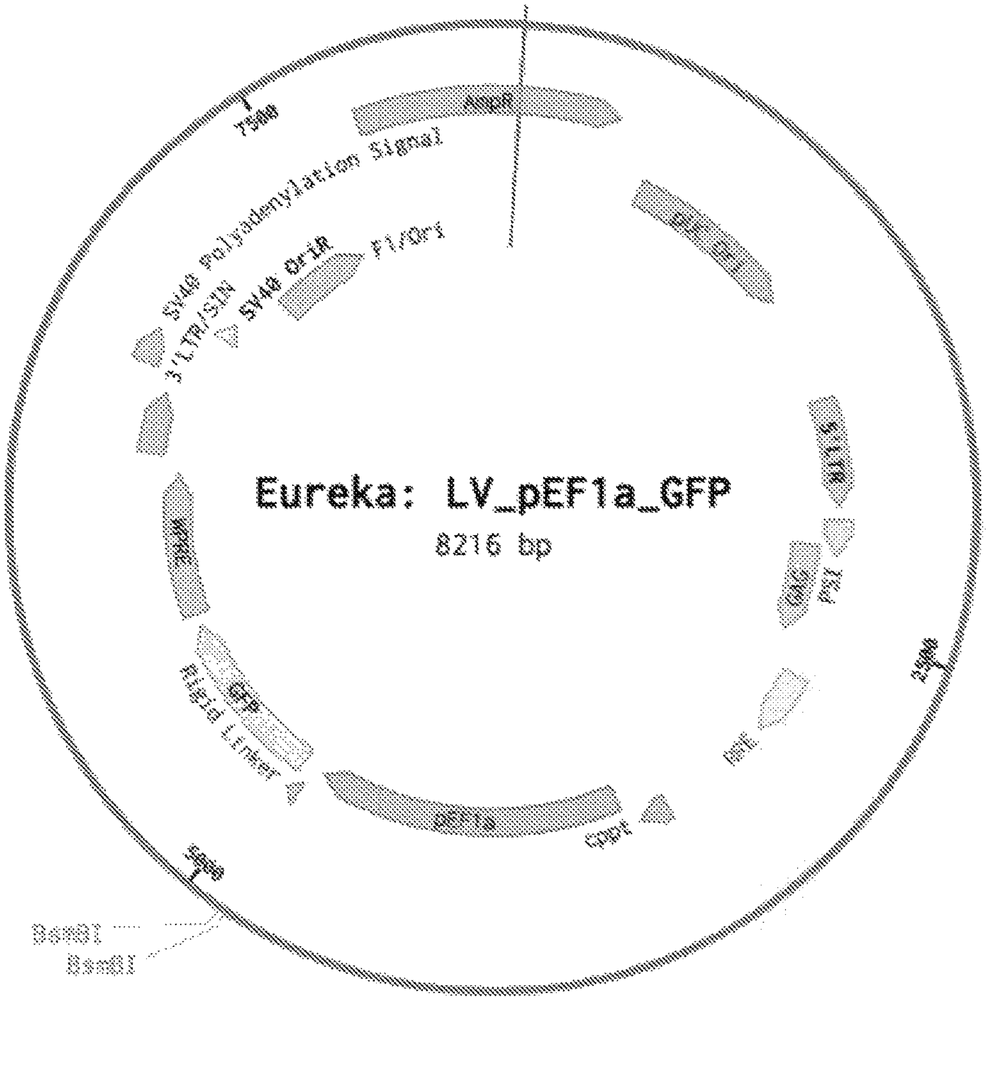

FIG. 35 shows a plasmid map for the "Eureka" expression plasmid of the instant disclosure, where the BsmBI restriction endonuclease cloning sites were used to insert genes of interest.

Figure 36:
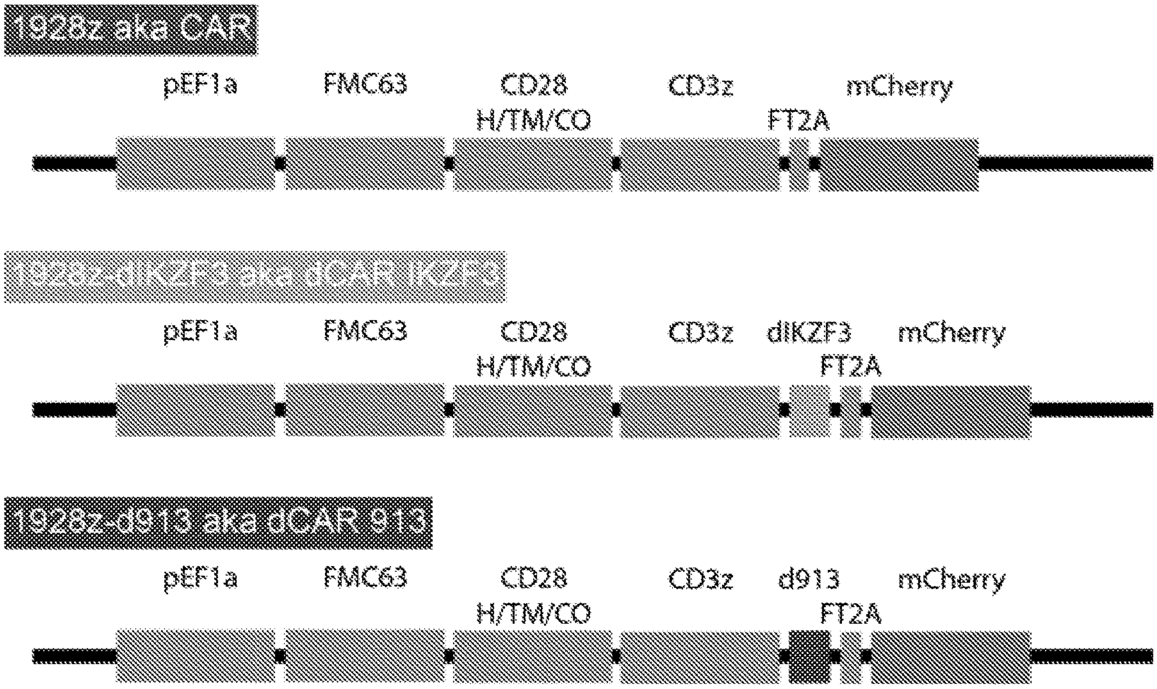

FIG. 36 shows schematic diagrams of additional CAR degron constructs that were made in the current study, including 1928z-dIKZF3 aka dCAR IKZF3 and 1928z-d913 aka dCAR 913. In the schematics, CD28 H/TM/CO=hinge/transmembrane/costimulatory domain. 1928z-d913=DCAR 913. d913=degron derived from the fusion of ZFP91 and IKZF3 zinc finger degrons. FT2A=furin cleavage site+T2A.

DETAILED DESCRIPTION OF THE INVENTION

The present disclosure is directed, at least in part, to discovery and engineering of switch systems that are responsive at the molecular level to small molecules approved for human use, which renders such engineered switch systems applicable for a variety of clinical uses (e.g., CAR T-cell use, precision control of gene therapies for other immune and stem cell therapies, etc.), in contrast to previously described molecular switch systems.

Negative reactions to cell-based immunotherapies can be fatal, as seen in certain CAR-T therapy clinical trials ("In staggering setback, toxic reaction kills Cellectis' first CAR-T patient, forcing trial halt," *Endpoints News, Sep.* 5, 2017; see also Juno Therapeutics, in which an altered preconditioning regimen was used to enhance efficacy and persistence of CAR-T cell product, but five deaths attributable to cerebral edema occurred, as well as high rates of grade 3-4 cytokine release syndrome (71%) and grade 3 neurotoxicity (25%) occurred—the JCAR015 phase II Rocket clinical trial was therefore placed on clinical hold (Turtle et al. "Biomarkers of Cytokine Release Syndrome and Neurotoxicity after CD19 CAR-T Cells and Mitigation of Toxicity By Cell Dose" ASH Annual Meeting Abstract (2016) 1852)).

Cytokine release syndrome (CRS) is an inflammatory response clinically manifesting with fever, nausea, headache, tachycardia, hypotension, hypoxia, as well as cardiac and/or neurologic manifestations. Severe cytokine release syndrome is described as a cytokine storm, and can be fatal. CRS is believed to be a result of the sustained activation of a variety of cell types such as monocytes and macrophages, T-cells and B cells, and is generally characterized by an increase in levels of TNFα and IFNγ within 1 to 2 hours of stimulus exposure, followed by increases in interleukin (IL)-6 and IL-10 and, in some cases, IL-2 and IL-8

(Doessegger et al., "Clinical development methodology for infusion-related reactions with monoclonal antibodies." Nat. Clin. Transl. Immuno.4 (2015): e39).

Tumor lysis syndrome (TLS) is a metabolic syndrome that is caused by the sudden killing of tumor cells with chemotherapy, and subsequent release of cellular contents with the release of large amounts of potassium, phosphate, and nucleic acids into the systemic circulation. Catabolism of the nucleic acids to uric acid leads to hyperuricemia; the marked increase in uric acid excretion can result in the precipitation of uric acid in the renal tubules and renal vasoconstriction, impaired autoregulation, decreased renal flow, oxidation, and inflammation, resulting in acute kidney injury. Hyperphosphatemia with calcium phosphate deposition in the renal tubules can also cause acute kidney injury. High concentrations of both uric acid and phosphate potentiate the risk of acute kidney injury because uric acid precipitates more readily in the presence of calcium phosphate and vice versa that results in hyperkalemia, hyperphosphatemia, hypocalcemia, remia, and acute renal failure. It usually occurs in patients with bulky, rapidly proliferating, treatment-responsive tumors (Wintrobe M M, et al., "Complications of hematopoietic neoplasms." Wintrobe's Clinical Hematology, 11th ed. Philadelphia, Pa: Lippincott Williams & Wilkins; Vol II (2003):1919-1944).

The dramatic clinical activity of CAR T-cell therapy has provoked design of additional "safety" strategies to rapidly reverse or abort the T-cell responses in patients that are undergoing CRS or associated adverse events. Metabolic approaches including co-expression of Herpes simplex virus-thymidine kinase (HSV-TK) induce apoptosis of CAR T-cells upon treatment with ganciclovir. This approach is limited by the delayed kinetics of response and the potential for immunogenic reaction to HSV. Apoptosis promoting strategies have been developed in which a drug binding domain is expressed in frame with components of the apoptotic machinery, including Caspase 9 and FAS. This system allows for conditional activation of apoptosis upon administration of a small molecule inducer of dimerization. The effect is rapid, non-immunogenic, and reduces payload of transduced cells by 90%. Both approaches are currently being evaluated in clinical trials. While expression of "suicide" genes provides a mechanism to reverse the unwanted toxicities, both approaches are considered irreversible, effectively limiting any further therapeutic benefit to the patient.

Other strategies for controlling CAR T-cell activation include certain systems of separating dual costimulatory domains from the antigen-recognition domain, wherein stimulation of the CAR T-cell is controlled by the small-molecule drug rimiducid. These T-cells, known as GoCAR-Ts, can only be fully activated when they are exposed to both cancer cells and the drug. In addition, strategies incorporating bispecific CARs which includes a second binding domain on the CAR T-cell that can lead to either an inhibitory or amplifying signal, allows for decreased off-target effects, wherein the presence of one target protein leads to activation of the CAR T-cell while the presence of a second protein leads to inhibition.

WO2016/115177 to Juno Therapeutics, Inc. titled "Modified Hepatitis Post-Transcriptional Regulatory Elements" describes the inclusion of post-transcriptional regulatory elements (PREs) in administered proteins to hasten degradation by encouraging natural ubiquitination of the protein and shorten half-life, including for example chimeric antigen receptors. The employed strategy, however, is not regulatable.

True precision control of CAR-T cells (including effective and clinically useful reversible treatments for modulating the activity of CAR T-cells) is therefore and unmet need, at least in view of the fact that CAR-T cell hyperactivation is common, life-threatening and impedes clinical development. Reversible user control of gene and cellular therapies, such as disclosed herein, can therefore increase safety and unlock new therapeutic opportunities. Precision control of gene therapies can therefore open new designs for immune and stem cell therapies. In exemplified embodiments, precision control of CAR-T cell activation is a pivotal unmet need for safer clinical development and use of CAR-T cell therapies.

Three distinct systems for IMiD-gated control of CARs and other proteins have been described herein: (1) an ON-switch IMiD-dependent heterodimer forming system, (2) an OFF-switch that employs a CRBN substrate ("degron") as an IMiD-responsive target that induces degradation, and (3) an ON-switch that employs a fusion polypeptide having a degron joined to a CAR inhibitor, where the drug-responsive fusion polypeptide is degraded upon drug administration, thereby releasing the CAR from inhibition. Structure-guided engineering of CRBN and the $CRL4^{CRBN}$ substrate IKZF3 was initially performed to generate minimal protein domains that functioned as drug-inducible ON- and OFF-switch peptide logic gates. For the OFF-switch, such studies were further extended to incorporate sequences of additional CRBN substrate ZFP91 (an E3 ubiquitin-protein ligase) into hybrid degron sequences (in various configurations as described herein), some of which demonstrated improved functionality as an OFF-switch. As shown in the below Examples, these control systems were functionally tested in human cell lines.

ON-Switch—Chemically Inducible Dimerization (CID)-Mediated

Chemically inducible dimerization (CID) is an ideal molecular control system. However, no current CID system is broadly clinically tractable. Conserved design features of CID systems include: (1) specific drug-dependent interaction; (2) modular domain structures; (3) minimal dimerization domains; and (4) minimal interaction with endogenous proteins. Requirements for clinical use include: (1) non-toxicity, including non-immunosuppressive and non-immunogenic; (2) availability, including both pharmacodynamics and pharmacokinetic availability; and (3) free of regulatory impediment, i.e., modulatory agent(s) must be FDA-approved. Rapamycin-induced dimerization of FRB and FKBP is the canonical example of chemically-induced dimerization. However, potent immunosuppression severely limits the clinical scenarios where rapamycin or related compounds may be beneficial (Hubbard, Paul A., Colleen L. Moody, and Ramachandran Murali. "Allosteric modulation of Ras and the PI3K/AKT/mTOR pathway: emerging therapeutic opportunities." Frontiers in physiology 5 (2014)).

CRBN-CRBN Substrate Dimerization

In certain aspects, the instant disclosure relates to repurposing the thalidomide analog immunomodulatory drug (IMiD)-dependent heterodimer that forms between cereblon and a cereblon substrate (Krönke et al. Oncoimmunology 3: e941742), such heterodimer which in native forms promotes E3 ubiquitin-mediated degradation, into a drug-dependent heterodimer capable of activating heterodimerized polypeptides when brought together, while removing E3 ubiquitin-mediated degradation from the engineered system (see also Krönke et al. Science 343.6168: 301-305; Krönke et al. Nature 523.7559: 183-188; Petzold et al. Nature 532: 127-130). CRBN and CRBN substrates have therefore been reengineered to arrive at the ON-switch of the instant disclosure. Individual components of such heterodimers are considered in greater detail below.

An exemplified IMiD-responsive ON-switch of the disclosure brings together the following split receptor elements upon IMiD-induced binding between IKZF3 degron and minimal CRBN polypeptide (in certain embodiments described herein, minimal CRBN is a CRBN deleted for DDB1/CUL4 interaction domain but retaining IMiD/IKZF3 interacting domains): an antigen-responsive scFV, CD28 co-stimulatory domain(s) and a CD3ζ domain. As described herein, multiple protein engineering steps were undertaken to turn the IKZF3-CRBN protein-protein interaction into a chemically-inducible dimerization system as exemplified herein.

Cereblon (CRBN)

Cereblon (CRBN) is a 442 amino acid protein that forms an E3 ubiquitin ligase complex with damaged DNA binding protein 1 (DDB1), Cullin-4A (CUL4A) and regulator of cullins 1 (ROC1; Angers et al. *Nature* 443: 590-593). This complex ubiquitinates a number of other proteins. Preclinical studies identified CRBN as a direct molecular target for the teratogenecity of thalidomide. CRBN binds directly to thalidomide analog affinity beads and is linked to the teratogenic effects of thalidomide in zebrafish and chicks (Ito et al. *Science* 327: 1345-1350). It was also shown that thalidomide, lenalidomide and pomalidomide each binds to CRBN in vitro (Lopez-Girona et al. Leukemia 26: 2326-2335).

Native *Homo sapiens* CRBN polypeptide has the following sequence (GenBank Accession No. AAH17419.1):

(SEQ ID NO: 6)
MAGEGDQQDAAHNMGNHLPLLPAESEEEDEMEVEDQDSKEAKKPNIINFD
TSLPTSHTYLGADMEEFHGRTLHDDDSCQVIPVLPQVMMILIPGQTLPLQ
LFHPQEVSMVRNLIQKDRTFAVLAYSNVQEREAQFGTTAEIYAYREEQDF
GIEIVKVKAIGRQRFKVLELRTQSDGIQQAKVQILPECVLPSTMSAVQLE
SLNKCQIFPSKPVSREDQCSYKWWQKYQKRKFHCANLTSWPRWLYSLYDA
ETLMDRIKKQLREWDENLKDDSLPSNPIDFSYRVAACLPIDDVLRIQLLK
IGSAIQRLRCELDIMNKCTSLCCKQCQETEITTKNEIFSLSLCGPMAAYV
NPHGYVHETLTVYKACNLNLIGRPSTEHSWFPGYAWTVAQCKICASHIGW
KFTATKKDMSPQKFWGLTRSALLPTIPDTEDEISPDKVILCL

Minimal forms of CRBN described herein have the following sequences:

minCRBN1:
(SEQ ID NO: 1)
SLSLCGPMAAYVNPHGYVHETLTVYKACNLNLIGRPSTEHSWFPGYAWTV
AQCKICASHIGWKFTATKKDMSPQKFWGLTRSALLPTIPDTEDEISPDKV
ILCL minCRBN2:
(SEQ ID NO: 2)
CTSLCCKQCQETEITTKNEIFSLSLCGPMAAYVNPHGYVHETLTVYKACN
LNLIGRPSTEHSWFPGYAWTVAQCKICASHIGWKFTATKKDMSPQKFWGL
TRSALLPTIPDTEDEISPDKVILCL -continued minCRBN3:
(SEQ ID NO: 3)
AGEGDQQDAAHNMGNHLPLLPESEEEDEMEVEDQDSKEAKKPNIINFDTS
LPTSHTYLGADMEEFHGRTLHDDDSCQVIPVLPQVMMILIPGQTLPLQLF
HPQEVSMVRNLIQKDRTFAVLAYSNVQEREAQFGTTAEIYAYREEQDFGI
EIVKVKAIGRQRFKVLELRTQSDGIQQAKVQILPECVLPSTYDAETLMDR
IKKQLREWDENLKDDSLPSNPIDFSYRVAACLPIDDVLRIQLLKIGSAIQ
RLRCELDIMNKCTSLCCKQCQETEITTKNEIFSLSLCGPMAAYVNPHGYV
HETLTVYKACNLNLIGRPSTEHSWFPGYAWTVAQCKICASHIGWKFTATK
KDMSPQKFWGLTRSALLPTIPDTEDEISPDKVILCL minCRBN4:
(SEQ ID NO: 4)
MAGEGDQQDAAHNMGNHLPLLPESEEEDEMEVEDQDSKEAKKPNIINFDT
SLPTSHTYLGADMEEFHGRTLHDDDSCQVIPVLPQVMMILIPGQTLPLQL
FHPQEVSMVRNLIQKDRTFAVLAYSNVQEREAQFGTTAEIYAYREEQDFG
IEIVKVKAIGRQRFKVLELRTQSDGIQQAKVQILPLREWDENLKDDSLPS
NPIDFSYRVAACLPIDDVLRIQLLKIGSAIQRLRCELDIMNKCTSLCCKQ
CQETEITTKNEIFSLSLCGPMAAYVNPHGYVHETLTVYKACNLNLIGRPS
TEHSWFPGYAWTVAQCKICASHIGWKFTATKKDMSPQKFWGLTRSALLPT
IPDTEDEISPDKVILCL Variant/residue-substituted forms of CRBN as described herein have the following sequences:

minCRBN3 I371A:
(SEQ ID NO: 7)
AGEGDQQDAAHNMGNHLPLLPESEEEDEMEVEDQDSKEAKKPNIINFDTS
LPTSHTYLGADMEEFHGRTLHDDDSCQVIPVLPQVMMILIPGQTLPLQLF
HPQEVSMVRNLIQKDRTFAVLAYSNVQEREAQFGTTAEIYAYREEQDFGI
EIVKVKAIGRQRFKVLELRTQSDGIQQAKVQILPECVLPSTYDAETLMDR
IKKQLREWDENLKDDSLPSNPIDFSYRVAACLPIDDVLRIQLLKIGSAIQ
RLRCELDIMNKCTSLCCKQCQETEITTKNEIFSLSLCGPMAAYVNPHGYV
HETLTVYKACNLNLAGRPSTEHSWFPGYAWTVAQCKICASHIGWKFTATK
KDMSPQKFWGLTRSALLPTIPDTEDEISPDKVILCL minCRBN3 I371G:
(SEQ ID NO: 8)
AGEGDQQDAAHNMGNHLPLLPESEEEDEMEVEDQDSKEAKKPNIINFDTS
LPTSHTYLGADMEEFHGRTLHDDDSCQVIPVLPQVMMILIPGQTLPLQLF
HPQEVSMVRNLIQKDRTFAVLAYSNVQEREAQFGTTAEIYAYREEQDFGI
EIVKVKAIGRQRFKVLELRTQSDGIQQAKVQILPECVLPSTYDAETLMDR
IKKQLREWDENLKDDSLPSNPIDFSYRVAACLPIDDVLRIQLLKIGSAIQ
RLRCELDIMNKCTSLCCKQCQETEITTKNEIFSLSLCGPMAAYVNPHGYV
HETLTVYKACNLNLGGRPSTEHSWFPGYAWTVAQCKICASHIGWKFTATK
KDMSPQKFWGLTRSALLPTIPDTEDEISPDKVILCL minCRBN3 V388A:

(SEQ ID NO: 9)

AGEGDQQDAAHNMGNHLPLLPESEEEDEMEVEDQDSKEAKKPNIINFDTS

LPTSHTYLGADMEEFHGRTLHDDDSCQVIPVLPQVMMILIPGQTLPLQLF

HPQEVSMVRNLIQKDRTFAVLAYSNVQEREAQFGTTAEIYAYREEQDFGI

EIVKVKAIGRQRFKVLELRTQSDGIQQAKVQILPECVLPSTYDAETLMDR

IKKQLREWDENLKDDSLPSNPIDFSYRVAACLPIDDVLRIQLLKIGSAIQ

RLRCELDIMNKCTSLCCKQCQETEITTKNEIFSLSLCGPMAAYVNPHGYV

HETLTVYKACNLNLIGRPSTEHSWFPGYAWTAAQCKICASHIGWKFTATK

KDMSPQKFWGLTRSALLPTIPDTEDEISPDKVILCL minCRBN3 V388G:

(SEQ ID NO: 10)

AGEGDQQDAAHNMGNHLPLLPESEEEDEMEVEDQDSKEAKKPNIINFDTS

LPTSHTYLGADMEEFHGRTLHDDDSCQVIPVLPQVMMILIPGQTLPLQLF

HPQEVSMVRNLIQKDRTFAVLAYSNVQEREAQFGTTAEIYAYREEQDFGI

EIVKVKAIGRQRFKVLELRTQSDGIQQAKVQILPECVLPSTYDAETLMDR

IKKQLREWDENLKDDSLPSNPIDFSYRVAACLPIDDVLRIQLLKIGSAIQ

RLRCELDIMNKCTSLCCKQCQETEITTKNEIFSLSLCGPMAAYVNPHGYV

HETLTVYKACNLNLIGRPSTEHSWFPGYAWTGAQCKICASHIGWKFTATK

KDMSPQKFWGLTRSALLPTIPDTEDEISPDKVILCL

CRBN Substrates

Known CRBN substrates include: Ikaros (IKZF1), Aiolos (IKZF3; Krönke et al. *Science* 343.6168: 301-305; Lu et al. *Science* 343: 305-309) casein kinase Ia (CkIa; Krönke et al. *Nature* 523: 183-188), Homeobox protein Meis2 (MEIS2; Fischer et al. *Nature* 512: 49-53), E3 ubiquitin-protein ligase (ZFP91; 28530236), Eukaryotic peptide chain release factor GTP-binding subunit ERF3A (GSPT1; 27338790), and Glutathione synthetase (GSS; 26990986).

Native *Homo sapiens* IKZF1 polypeptide has the following sequence (GenBank Accession No. AAH18349.1):

(SEQ ID NO: 11)

MDADEGQDMSQVSGKESPPVSDTPDEGDEPMPIPEDLSTTSGGQQSSKSD

RVVASNVKVETQSDEENGRACEMNGEECAEDLRMLDASGEKMNGSHRDQG

SSALSGVGGIRLPNGKLKCDICGIICIGPNVLMVHKRSHTGERPFQCNQC

GASFTQKGNLLRHIKLHSGEKPFKCHLCNYACRRRDALTGHLRTHSVIKE

ETNHSEMAEDLCKIGSERSLVLDRLASNVAKRKSSMPQKFLGDKGLSDTP

YDSSASYEKENEMMKSHVMDQAINNAINYLGAESLRPLVQTPPGGSEVVP

VISPMYQLHKPLAEGTPRSNHSAQDSAVENLLLLSKAKLVPSEREASPSN

SCQDSTDTESNNEEQRSGLIYLTNHIAPHARNGLSLKEEHRAYDLLRAAS

ENSQDALRVVSTSGEQMKVYKCEHCRVLFLDHVMYTIHMGCHGFRDPFEC

NMCGYHSQDRYEFSSHITRGEHRFHMS

Native *Homo sapiens* IKZF3 polypeptide has the following sequence (GenBank Accession No. NP_001271445.1):

(SEQ ID NO: 12)

MGSERALVLDRLASNVAKRKSSMPQKFIGEKRHCFDVNYNSSYMYEKESE

LIQTRMMDQAINNAISYLGAEALRPLVQTPPAPTSEMVPVISSMYPIALT

RAEMSNGAPQELEKKSIHLPEKSVPSERGLSPNNSGHDSTDTDSNHEERQ

NHIYQQNHMVLSRARNGMPLLKEVPRSYELLKPPPICPRDSVKVINKEGE

VMDVYRCDHCRVLFLDYVMFTIHMGCHGFRDPFECNMCGYRSHDRYEFSS

HIARGEHRALLK

Native *Homo sapiens* CK1α polypeptide has the following sequence (GenBank Accession No. NP_001020276.1):

(SEQ ID NO: 13)

MASSSGSKAEFIVGGKYKLVRKIGSGSFGDIYLAINITNGEEVAVKLESQ

KARHPQLLYESKLYKILQGGVGIPHIRWYGQEKDYNVLVMDLLGPSLEDL

FNFCSRRFTMKTVLMLADQMISRIEYVHTKNFIHRDIKPDNFLMGIGRHC

NKLFLIDFGLAKKYRDNRTRQHIPYREDKNLTGTARYASINAHLGIEQSR

RDDMESLGYVLMYFNRTSLPWQGLKAATKKQKYEKISEKKMSTPVEVLCK

GFPAEFAMYLNYCRGLRFEEAPDYMYLRQLFRILFRTLNHQYDYTFDWTM

LKQKAAQQAASSSGQGQQAQTPTGKQTDKTKSNMKGF

Native *Homo sapiens* ZFP91 polypeptide has the following sequence (GenBank Accession No. NP_444251.1):

(SEQ ID NO: 14)

MPGETEEPRPPEQQDQEGGEAAKAAPEEPQQRPPEAVAAAPAGTTSSRVL

RGGRDRGRAAAAAAAAAVSRRRKAEYPRRRRSSPSARPPDVPGQPQAAK

SPSPVQGKKSPRLLCIEKVTTDKDPKEEKEEEDDSALPQEVSIAASRPSR

GWRSSRTSVSRHRDTENTRSSRSKTGSLQLICKSEPNTDQLDYDVGEEHQ

SPGGISSEEEEEEEEEMLISEEEIPFKDDPRDETYKPHLERETPKPRRKS

GKVKEEKEKKEIKVEVEVEVKEEENEIREDEEPPRKRGRRRKDDKSPRLP

KRRKKPPIQYVRCEMEGCGTVLAHPRYLQHHIKYQHLLKKKYVCPHPSCG

RLFRLQKQLLRHAKHHTDQRDYICEYCARAFKSSHNLAVHRMIHTGEKPL

QCEICGFTCRQKASLNWHMKKHDADSFYQFSCNICGKKFEKKDSVVAHKA

KSHPEVLIAEALAANAGALITSTDILGTNPESLTQPSDGQGLPLLPEPLG

NSTSGECLLLEAEGMSKSYCSGTERVSLMADGKIFVGSGSSGGTEGLVMN

SDILGATTEVLIEDSDSAGP

Native *Homo sapiens* GSPT1 polypeptide has the following sequence (GenBank Accession No. AAH09503.2):

(SEQ ID NO: 15)

MDPGSGGGGGGGGSSSGSSSSDSAPDCWDQADMEAPGPGPCGGGGSLAAA

AEAQRENLSAAFSRQLNVNAKPFVPNVHAAEFVPSFLRCPAAPPPPAGGA

ANNHGAGSGAGGRAAPVESSQEEQSLCEGSNSAVSMELSEPIENGETEMS

PEESWEHKEEISEAEPGGGSLGDGRPPEESAHEMMEEEEEIPKPKSVVAP

PGAPKKEHVNVVFIGHVDAGKSTIGGQIMYLTGMVDKRTLEKYEREAKEK

NRETWYLSWALDTNQEERDKGKTVEVGRAYFETEKKHFTILDAPGHKSFV

PNMIGGASQADLAVLVISARKGEFETGFEKGGQTREHAMLAKTAGVKHLI

VLINKMDDPTVNWSNERYEECKEKLVPFLKKVGFNPKKDIHFMPCSGLTG

ANLKEQSDFCPWYIGLPFIPYLDNLPNFNRSVDGPIRLPIVDKYKDMGTV

VLGKLESGSICKGQQLVMMPNKHNVEVLGILSDDVETDTVAPGENLKIRL

KGIEEEEILPGFILCDPNNLCHSGRTFDAQIVIIEHKSIICPGYNAVLHI

-continued

HTCIEEVEITALICLVDKKSGEKSKTRPRFVKQDQVCIARLRTAGTICLE

TFKDFPQMGRFTLRDEGKTIAIGKVLKLVPEKD

Native *Homo sapiens* Glutamine Synthetase polypeptide has the following sequence (GenBank Accession No. NP_001309423.1):

(SEQ ID NO: 16)

MATNWGSLLQDKQQLEELARQAVDRALAEGVLLRTSQEPTSSEVVSYAPF

TLFPSLVPSALLEQAYAVQMDFNLLVDAVSQNAAFLEQTLSSTIKQDDFT

ARLFDIHKQVLKEGIAQTVFLGLNRSDYMFQRSADGSPALKQIEINTISA

SFGGLASRTPAVHRHVLSVLSKTKEAGKILSNNPSKGLALGIAKAWELYG

SPNALVLLIAQEKERNIFDQRAIENELLARNIHVIRRTFEDISEKGSLDQ

DRRLFVDGQEIAVVYFRDGYMPRQYSLQNWEARLLLERSHAAKCPDIATQ

LAGTKKVQQELSRPGMLEMLLPGQPEAVARLRATFAGLYSLDVGEEGDQA

IAEALAAPSRFVLKPQREGGGNNLYGEEMVQALKQLKDSEERASYILMEK

IEPEPFENCLLRPGSPARVVQCISELGIFGVYVRQEKTLVMNKHVGHLLR

TKAIEHADGGVAAGVAVLDNPYPV

Native *Homo sapiens* MEIS2 polypeptide has the following sequence (GenBank Accession No. NP_733777.1):

(SEQ ID NO: 17)

MAQRYDELPHYGGMDGVGVPASMYGDPHAPRPIPPVHHLNHGPPLHATQH

YGAHAPHPNVMPASMGSAVNDALKRDKDAIYGHPLFPLLALVFEKCELAT

CTPREPGVAGGDVCSSDSFNEDIAVFAKQVRAEKPLFSSNPELDNLMIQA

IQVLRFHLLELEKVHELCDNFCHRYISCLKGKMPIDLVIDERDGSSKSDH

EELSGSSTNLADHNPSSWRDHDDATSTHSAGTPGPSSGGHASQSGDNSSE

QGDGLDNSVASPGTGDDDDPDKDKKRQKKRGIFPKVATNIMRAWLFQHLT

HPYPSEEQKKQLAQDTGLTILQVNNWFINARRRIVQPMIDQSNRAGFLLD

PSVSQGAAYSPEGQPMGSFVLDGQQHMGIRPAGPMSGMGMNMGMDGQWHY

M

Meis2 is noted as an endogenous substrate of CRBN (PMID: 25043012). IMiDs and IMiD-dependent substrates compete with Meis2. Therefore, it is contemplated herein that Meis2 can be stabilized by the addition of IMiDs, generating the inverse switch-behavior when using Meis2 as the degron or dimerization partner.

Other IMiD-dependent CRBN targets include E4F1, ZN276, ZN517, ZN582, ZN653, ZN654, ZN692, ZN787 and ZN827.

Native *Homo sapiens* ZNF692 polypeptide has the following sequence (GenBank Accession No. NP_001129508.1):

(SEQ ID NO: 18)

MPLVHMASSPAVDVSCRRREKRRQLDARRSKCRIRLGGHMEQWCLLKERL

GFSLHSQLAKFLLDRYTSSGCVLCAGPEPLPPKGLQYLVLLSHAHSRECS

LVPGLRGPGGQDGGLVWECSAGHTFSWGPSLSPTPSEAPKPASLPHTTRR

SWCSEATSGQELADLESEHDERTQEARLPRRVGPPPETFPPPGEEEGEEE

EDNDEDEEEMLSDASLWTYSSSPDDSEPDAPRLLPSPVTCTPKEGETPPA

PAALSSPLAVPALSASSLSSRAPPPAEVRVQPQLSRTPQAAQQTEALAST

GSQAQSAPTPAWDEDTAQIGPKRIRKAAKRELMPCDFPGCGRIFSNRQYL

-continued

NHHKKYQHIHQKSFSCPEPACGKSFNFKKHLKEHMKLHSDTRDYICEFCA

RSFRTSSNLVIHRRIHTGEKPLQCEICGFTCRQKASLNWHQRKHAETVAA

LRFPCEFCGKRFEKPDSVAAHRSKSHPALLLAPQESPSGPLEPCPSISAP

GPLGSSEGSRPSASPQAPTLLPQQ

IKZF3 degron polypeptide, amino acids 130-189:

(SEQ ID NO: 5)

FNVLMVHKRSHTGERPFQCNQCGASFTQKGNLLRHIKLHTGEKPFKCHLC

NYACQRRDAL

IKZF3 degron polypeptide, amino acids 146-168:

(SEQ ID NO: 19)

FQCNQCGASFTQKGNLLRHIKLH

In certain embodiments, a C2H2 zinc finger degron can be produced by adding IKZF3 flanking sequences to core sequences of a non-IKZF3 C2H2 degron. For example, as specifically described below for the IKZF3/ZFP91/IKZF3 "d913" hybrid degron polypeptide, a C2H2 zinc finger degron that includes IKZF3 amino acids 130-145 (FNVLMVHKRSHTGERP; SEQ ID NO: 97) positioned N-terminal to amino acids 400-410 of ZFP91 (LQCEICGFTCR; SEQ ID NO: 98), and IKZF3 amino acids 157-189 (QKGNLLRHIKLHTGEKPFKCHLCNYACQRRDAL; SEQ ID NO: 99) positioned C-terminal to the ZFP91 sequence has been demonstrated herein to be a particularly effective degron sequence. Corresponding "K0" forms of such sequences can also be employed, as demonstrated elsewhere herein—e.g., "K0" forms of IKZF3 amino acids 130-145 (FNVLMVHRRSHTGERP; SEQ ID NO: 100) and 157-189 (QRGNLLRHIRLHTGERPFRCHLCNYACQRRDAL; SEQ ID NO: 101) can also be used to flank a non-IKZF3-C2H2 zinc finger degron sequence.

More generally, in certain embodiments, improved degron performance can be imparted by modifying a given non-IKZF3 C2H2 zinc finger degron via addition of IKZF3 amino acids 130-145 (FNVLMVHKRSHTGERP; SEQ ID NO: 97) to the N-terminus and IKZF3 amino acids 169-189 (TGEKPFKCHLCNYACQRRDAL; SEQ ID NO: 102) to the C-terminus of the non-IKZF3 C2H2 zinc finger degron sequence, in order to generate an approximately 60 amino acid hybrid zinc finger. Experiments described elsewhere herein have demonstrated that such longer hybrid degrons result in lower protein abundance, and more sensitive/deep drug-induced protein degradation. Optionally, "K0" forms of such flanking sequences (e.g., SEQ ID NO: 100 and TGERPFRCHLCNYACQRRDAL; SEQ ID NO: 103) can be used, as described above. Exemplary such embodiments include IKZF3 sequence-flanked forms of the E4F1 amino acids 220-242 sequence (HECKLCGASFRTKGSLIRHHRRH; SEQ ID NO: 104); ZN276 amino acids 524-546 sequence (LQCEVCGFQCRQRASLKYHMTKH; SEQ ID NO: 105); ZN517 amino acids 452-474 (YRCRACGRACSRLSTLIQHQKVH; SEQ ID NO: 106); ZN582 amino acids 395-417 (YQCKVCGRAFKRVSHLTVHYRIH; SEQ ID NO: 107); ZN653 amino acids 556-578 (LQCEICGYQCRQRASLNWHMKKH; SEQ ID NO: 108); ZN654 amino acids 25-47 (FACVICGRKFRNRGLMQKHLKNH; SEQ ID NO: 109); ZN692 amino acids 417-439 (LQCEICGFTCRQKASLNWHQRKH; SEQ ID NO: 110); ZN787 amino acids 178-200 (FVCPRCGRGFSQPKSLARHLRLH; SEQ ID NO: 111); ZN827 amino acids 374-396 (FQCPICGLVIKRKSYWKRHMVIH; SEQ ID NO: 112); and ZFP91 amino acids 400-422 (LQCEICGFTCRQKASLN-WHMKKH; SEQ ID NO: 113). The following table (Table 1) presents these exemplary non-IKZF3 C2H2 zinc finger degrons modified via addition of IKZF3 amino acids 130-145 (FNVLMVHKRSHTGERP; SEQ ID NO: 97) to the N-terminus and IKZF3 amino acids 169-189 (TGEKPFKCHLCNYACQRRDAL; SEQ ID NO: 102) to the C-terminus of the non-IKZF3 C2H2 zinc finger degron sequence:

TABLE 1

| Component 1 | X | Component 2 | X | Component 3 |
|---|---|---|---|---|
| FNVLMVHKRSHTGERP (IKZF3 aa130-145; SEQ ID NO: 97) | | HECKLCGASFRTKGSLIRHHRRH (SEQ ID NO: 104) | | TGEKPFKCHLCNYACQRRDAL (IKZF3 aa169-189; SEQ ID NO: 102) |
| SEQ ID NO: 97 | | LQCEVCGFQCRQRASLKYHMTKH (SEQ ID NO: 105) | | SEQ ID NO: 102 |
| SEQ ID NO: 97 | | YRCRACGRACSRLSTLIQHQKVH (SEQ ID NO: 106) | | SEQ ID NO: 102 |
| SEQ ID NO: 97 | | YQCKVCGRAFKRVSHLTVHYRIH (SEQ ID NO: 107) | | SEQ ID NO: 102 |
| SEQ ID NO: 97 | | LQCEICGYQCRQRASLNWHMKKH (SEQ ID NO: 108) | | SEQ ID NO: 102 |
| SEQ ID NO: 97 | | FACVICGRKFRNRGLMQKHLKNH (SEQ ID NO: 109) | | SEQ ID NO: 102 |
| SEQ ID NO: 97 | | LQCEICGFTCRQKASLNWHQRKH (SEQ ID NO: 110) | | SEQ ID NO: 102 |
| SEQ ID NO: 97 | | FVCPRCGRGFSQPKSLARHLRLH (SEQ ID NO: 111) | | SEQ ID NO: 102 |
| SEQ ID NO: 97 | | FQCPICGLVIKRKSYWKRHMVIH (SEQ ID NO: 112) | | SEQ ID NO: 102 |
| SEQ ID NO: 97 | | LQCEICGFTCRQKASLNWHMKKH (SEQ ID NO: 113) | | SEQ ID NO: 102 |

ZFP91 degron polypeptide, amino acids 400-422:
(SEQ ID NO: 20)
LQCEICGFTCRQKASLNWHMKKH IKZF1 degron polypeptide, amino acids 145-167 (which are identical to IKZF3 amino acids 146-168):
(SEQ ID NO: 21)
FQCNQCGASFTQKGNLLRHIKLH IKZF1 degron polypeptide, amino acids 129-188:
(SEQ ID NO: 22)
PNVLMVHKRSHTGERPFQCNQCGASFTQKGNLLRHIKLHSGEKPFKCHLC

NYACRRRDAL

The following specific zinc finger sequences of Table 2 have also been identified as IMiD-dependent CRBN targets.

TABLE 2

| Gene | AA. Start | AA. Stop | AA. Length | AA. Sequence |
|---|---|---|---|---|
| E4F1 | 220 | 242 | 23 | HECKLCGASFRTKGS LIRHHRRH (SEQ ID NO: 23) |
| ZN276 | 524 | 546 | 23 | LQCEVCGFQCRQRAS LKYHMTKH (SEQ ID NO: 24) |

TABLE 2-continued

| Gene | AA. Start | AA. Stop | AA. Length | AA. Sequence |
|---|---|---|---|---|
| ZN517 | 452 | 474 | 23 | YRCRACGRACSRLST LIQHQKVH (SEQ ID NO: 25) |

TABLE 2-continued

| Gene | AA. Start | AA. Stop | AA. Length | AA. Sequence |
|---|---|---|---|---|
| ZN582 | 395 | 417 | 23 | YQCKVCGRAFKRVSH LTVHYRIH (SEQ ID NO: 26) |
| ZN653 | 556 | 578 | 23 | LQCEICGYQCRQRAS LNWHMKKH (SEQ ID NO: 27) |
| ZN654 | 25 | 47 | 23 | FACVICGRKFRNRGL MQKHLKNH (SEQ ID NO: 28) |
| ZN692 | 417 | 439 | 23 | LQCEICGFTCRQKAS LNWHQRKH (SEQ ID NO: 29) |
| ZN787 | 178 | 200 | 23 | FVCPRCGRGFSQPKS LARHLRLH (SEQ ID NO: 30) |
| ZN827 | 374 | 396 | 23 | FQCPICGLVIKRKSY WKRHMVIH (SEQ ID NO: 31) |

ZFP91/IKZF3 hybrid degron polypeptide, ZFP91 amino acids 400-410 + IKZF3 amino acids 157-168:
(SEQ ID NO: 32)
LQCEICGFTCRQKGNLLRHIKLH IKZF3/ZFP91 hybrid degron polypeptide, IKZF3 amino acids 146-156 + ZFP91 amino acids 411-422:
(SEQ ID NO: 33)
FQCNQCGASFTQKASLNWHMKKH ZFP91/IKZF3 hybrid degron in IKZF3 context polypeptide, IKZF3 amino acids 130-145 + ZFP91 amino acids 400-410 + IKZF3 amino acids 157-189:
(SEQ ID NO: 34)
FNVLMVHKRSHTGERPLQCEICGFTCRQKGNLLRHIKLHTGEKPFKCHLC
NYACQRRDAL IKZF3 degron polypeptide, amino acids 130-189 A153I:
(SEQ ID NO: 35)
FNVLMVHKRSHTGERPFQCNQCGISFTQKGNLLRHIKLHTGEKPFKCHLC
NYACQRRDAL IKZF3 degron polypeptide, amino acids 130-189 A153M:
(SEQ ID NO: 36)
FNVLMVHKRSHTGERPFQCNQCGMSFTQKGNLLRHIKLHTGEKPFKCHLC
NYACQRRDAL IKZF3 degron polypeptide, amino acids 130-189 A153T:
(SEQ ID NO: 37)
FNVLMVHKRSHTGERPFQCNQCGTSFTQKGNLLRHIKLHTGEKPFKCHLC
NYACQRRDAL IKZF3 degron polypeptide, amino acids 130-189 A153N:
(SEQ ID NO: 38)
FNVLMVHKRSHTGERPFQCNQCGNSFTQKGNLLRHIKLHTGEKPFKCHLC
NYACQRRDAL IKZF3 degron polypeptide, amino acids 130-189 A153Q:
(SEQ ID NO: 39)
FNVLMVHKRSHTGERPFQCNQCGQSFTQKGNLLRHIKLHTGEKPFKCHLC
NYACQRRDAL IKZF3 degron polypeptide, amino acids 130-189 A153R:
(SEQ ID NO: 40)
FNVLMVHKRSHTGERPFQCNQCGRSFTQKGNLLRHIKLHTGEKPFKCHLC
NYACQRRDAL IKZF3 degron polypeptide, amino acids 130-189 A153H:
(SEQ ID NO: 41)
FNVLMVHKRSHTGERPFQCNQCGHSFTQKGNLLRHIKLHTGEKPFKCHLC
NYACQRRDAL IKZF3 degron polypeptide, amino acids 130-189 A153K:
(SEQ ID NO: 42)
FNVLMVHKRSHTGERPFQCNQCGKSFTQKGNLLRHIKLHTGEKPFKCHLC
NYACQRRDAL IKZF3 degron polypeptide, amino acids 130-189 A153D:
(SEQ ID NO: 43)
FNVLMVHKRSHTGERPFQCNQCGDSFTQKGNLLRHIKLHTGEKPFKCHLC
NYACQRRDAL -continued IKZF3 degron polypeptide, amino acids 130-189 A153E:
(SEQ ID NO: 44)
FNVLMVHKRSHTGERPFQCNQCGESFTQKGNLLRHIKLHTGEKPFKCHLC
NYACQRRDAL IKZF3 degron polypeptide, amino acids 130-189 A153C:
(SEQ ID NO: 45)
FNVLMVHKRSHTGERPFQCNQCGCSFTQKGNLLRHIKLHTGEKPFKCHLC
NYACQRRDAL IKZF3-derived polypeptide, amino acids 130-189, with all lysine residues substituted to arginines (aka "K0"), thus generating a CRBN substrate polypeptide that can be bound but not ubiquitinated:

(SEQ ID NO: 46)
FNVLMVHRRSHTGERPFQCNQCGASFTQRGNLLRHIRLHTGERPFRCHLC
NYACQRRDAL

IKZF3/ZFP91/IKZF3 "d913" hybrid degron polypeptide, IKZF3 amino acids 130-145+ZFP91 amino acids 400-410+IKZF3 amino acids 157-189: FNVLMVHKRSHTGERPLQCEICGFTCRQKGNLLRHIKLHTGEKPFKCHLCNYACQRRDAL (SEQ ID NO: 95) (use of this sequence yielded successful generation of an OFF-switch CAR)

IKZF3/ZFP91/IKZF3 "d913" hybrid degron polypeptide, IKZF3 amino acids 130-145+ZFP91 amino acids 400-410+IKZF3 amino acids 157-189, with all lysine residues substituted to arginines (aka "KG"), thus generating a CRBN substrate polypeptide that can be bound but not ubiquitinated: FNVLMVHRRSHTGERPLQCEICGFTCRQRGNLLRHIRLHTGERPFRCHLCNYACQRRDAL (SEQ ID NO: 96) (this derivative "KG" d913 improved the performance of the chemically-induced proximity system described elsewhere herein)

Corresponding "K0" forms of all above-referenced CRBN substrates and degron sequences can also be generated, to produce CRBN substrate polypeptides that can be bound but not ubiquitinated, as listed below.

IKZF3 "K0" degron polypeptide, amino acids 146-168:
(SEQ ID NO: 47)
FQCNQCGASFTQRGNLLRHIRLH ZFP91 "K0" degron polypeptide, amino acids 400-422:
(SEQ ID NO: 48)
LQCEICGFTCRQRASLNWHMRRH IKZF1 "K0" degron polypeptide, amino acids 145-167 (which are identical to IKZF3 amino acids 146-168):
(SEQ ID NO: 49)
FQCNQCGASFTQRGNLLRHIRLH IKZF1 "K0" degron polypeptide, amino acids 129-188:
(SEQ ID NO: 50)
PNVLMVHRRSHTGERPFQCNQCGASFTQRGNLLRHIRLHSGERPFRCHLCN
YACRRRDAL "K0" zinc finger sequences of Table 2 are found in Table 3 below.

TABLE 3

| Gene | AA. Start | AA. Stop | AA. Length | AA. Sequence |
|---|---|---|---|---|
| E4F1 | 220 | 242 | 23 | HECRLCGASFRTRGS LIRHHRRH (SEQ ID NO: 51) |
| ZN276 | 524 | 546 | 23 | LQCEVCGFQCRQRAS LRYHMTRH (SEQ ID NO: 52) |
| ZN517 | 452 | 474 | 23 | YRCRACGRACSRLST LIQHQRVH (SEQ ID NO: 53) |
| ZN582 | 395 | 417 | 23 | YQCRVCGRAFRRVSH LTVHYRIH (SEQ ID NO: 54) |
| ZN653 | 556 | 578 | 23 | LQCEICGYQCRQRAS LNWHMRRH (SEQ ID NO: 55) |
| ZN654 | 25 | 47 | 23 | FACVICGRRFRNRGL MQRHLRNH (SEQ ID NO: 56) |
| ZN692 | 417 | 439 | 23 | LQCEICGFTCRQRAS LNWHQRRH (SEQ ID NO: 57) |
| ZN787 | 178 | 200 | 23 | FVCPRCGRGFSQPRS LARHLRLH (SEQ ID NO: 58) |
| ZN827 | 374 | 396 | 23 | FQCPICGLVIRRRSY WRRHMVIH (SEQ ID NO: 59) |

ZFP91/IKZF3 hybrid "K0" degron polypeptide, ZFP91 amino acids 400-410 + IKZF3 amino acids 157-168:
(SEQ ID NO: 60)
LQCEICGFTCRQRGNLLRHIRLH IKZF3/ZFP91 hybrid "K0" degron polypeptide, IKZF3 amino acids 146-156 + ZFP91 amino acids 411-422:
(SEQ ID NO: 61)
FQCNQCGASFTQRASLNWHMRRH ZFP91/IKZF3 hybrid "K0" degron in IKZF3 context polypeptide, IKZF3 amino acids 130-145 + ZFP91 amino acids 400-410 + IKZF3 amino acids 157-189:
(SEQ ID NO: 62)
FNVLMVHRRSHTGERPLQCEICGFTCRQRGNLLRHIRLHTGERPFRCHLCN
YACQRRDAL "K0" form of native *Homo sapiens* IKZF1 polypeptide:
(SEQ ID NO: 63)
MDADEGQDMSQVSGRESPPVSDTPDEGDEPMPIPEDLSTTSGGQQSSRSDR
VVASNVRVETQSDEENGRACEMNGEECAEDLRMLDASGERMNGSHRDQGSS
ALSGVGGIRLPNGRLRCDICGIICIGPNVLMVHRRSHTGERPFQCNQCGAS
FTQRGNLLRHIRLHSGERPFRCHLCNYACRRRDALTGHLRTHSVIREETNH
SEMAEDLCRIGSERSLVLDRLASNVARRRSSMPQRFLGDRGLSDTPYDSSA
SYERENEMMRSHVMDQAINNAINYLGAESLRPLVQTPPGGSEVVPVISPMY
QLHRPLAEGTPRSNHSAQDSAVENLLLLSRARLVPSEREASPSNSCQDSTD -continued
TESNNEEQRSGLIYLTNHIAPHARNGLSLREEHRAYDLLRAASENSQDALR
VVSTSGEQMRVYRCEHCRVLFLDHVMYTIHMGCHGFRDPFECNMCGYHSQD
RYEFSSHITRGEHRFHMS "K0" form of native *Homo sapiens* IKZF3 polypeptide:
(SEQ ID NO: 64)
MGSERALVLDRLASNVARRRSSMPQRFIGERRHCFDVNYNSSYMYERESEL
IQTRMMDQAINNAISYLGAEALRPLVQTPPAPTSEMVPVISSMYPIALTRA
EMSNGAPQELERRSIHLPERSVPSERGLSPNNSGHDSTDTDSNHEERQNHI
YQQNHMVLSRARNGMPLLREVPRSYELLRPPPICPRDSVRVINREGEVMDV
YRCDHCRVLFLDYVMFTIHMGCHGFRDPFECNMCGYRSHDRYEFSSHIARG
EHRALLR "K0" form of native *Homo sapiens* CK1α polypeptide
(SEQ ID NO: 65)
MASSSGSRAEFIVGGRYRLVRRIGSGSFGDIYLAINITNGEEVAVRLESQR
ARHPQLLYESRLYRILQGGVGIPHIRWYGQERDYNVLVMDLLGPSLEDLFN
FCSRRFTMRTVLMLADQMISRIEYVHTRNFIHRDIRPDNFLMGIGRHCNRC
LESPVGRRRRSMTVSTSQDPSFSGLNQLFLIDFGLARRYRDNRTRQHIPYR
EDRNLTGTARYASINAHLGIEQSRRDDMESLGYVLMYFNRTSLPWQGLRAA
TRRQRYERISERRMSTPVEVLCRGFPAEFAMYLNYCRGLRFEEAPDYMYLR
QLFRILFRTLNHQYDYTFDWTMLRQRAAQQAASSSGQGQQAQTPTGRQTDR
TRSNMRGF "K0" form of native *Homo sapiens* ZFP91 polypeptide:
(SEQ ID NO: 66)
MPGETEEPRPPEQQDQEGGEAARAAPEEPQQRPPEAVAAAPAGTTSSRVLR
GGRDRGRAAAAAAAAAVSRRRRAEYPRRRRSSPSARPPDVPGQQPQAARSP
SPVQGRRSPRLLCIERVTTDRDPREEREEEDDSALPQEVSIAASRPSRGWR
SSRTSVSRHRDTENTRSSRSRTGSLQLICRSEPNTDQLDYDVGEEHQSPGG
ISSEEEEEEEEEMLISEEEIPFRDDPRDETYRPHLERETPRPRRRSGRVRE
ERERREIRVEVEVEVREEENEIREDEEPPRRRGRRRRDDRSPRLPRRRRRP
PIQYVRCEMEGCGTVLAHPRYLQHHIRYQHLLRRRYVCPHPSCGRLFRLQR
QLLRHARHHTDQRDYICEYCARAFRSSHNLAVHRMIHTGERPLQCEICGFT
CRQRASLNWHMRRHDADSFYQFSCNICGRRFERRDSVVAHRARSHPEVLIA
EALAANAGALITSTDILGTNPESLTQPSDGQGLPLLPEPLGNSTSGECLLL
EAEGMSRSYCSGTERVSLMADGRIFVGSGSSGGTEGLVMNSDILGATTEVL
IEDSDSAGP "K0" form of native *Homo sapiens* GSPT1 polypeptide:
(SEQ ID NO: 67)
MDPGSGGGGGGGGSSSGSSSSDSAPDCWDQADMEAPGPGPCGGGGSLAAAA
EAQRENLSAAFSRQLNVNARPFVPNVHAAEFVPSFLRCPAAPPPPAGGAAN
NHGAGSGAGGRAAPVESSQEEQSLCEGSNSAVSMELSEPIENGETEMSPEE
SWEHREEISEAEPGGGSLGDGRPPEESAHEMMEEEEEIPRPRSVVAPPGAP
RREHVNVVFIGHVDAGRSTIGGQIMYLTGMVDRRTLERYEREARERNRETW
YLSWALDTNQEERDRGRTVEVGRAYFETERRHFTILDAPGHRSFVPNMIGG
ASQADLAVLVISARRGEFETGFERGGQTREHAMLARTAGVRHLIVLINRMD
DPTVNWSNERYEECRERLVPFLRRVGFNPRRDIHFMPCSGLTGANLREQSD -continued

FCPWYIGLPFIPYLDNLPNFNRSVDGPIRLPIVDRYRDMGTVVLGRLESGS

ICRGQQLVMMPNRHNVEVLGILSDDVETDTVAPGENLRIRLRGIEEEEILP

GFILCDPNNLCHSGRTFDAQIVIIEHRSIICPGYNAVLHIHTCIEEVEITA

LICLVDRRSGERSRTRPRFVRQDQVCIARLRTAGTICLETFRDFPQMGRFT

LRDEGRTIAIGRVLRLVPERD

"K0" form of native *Homo sapiens* Glutamine Synthetase polypeptide:

(SEQ ID NO: 68)

MATNWGSLLQDRQQLEELARQAVDRALAEGVLLRTSQEPTSSEVVSYAPFT

LFPSLVPSALLEQAYAVQMDFNLLVDAVSQNAAFLEQTLSSTIRQDDFTAR

LFDIHRQVLREGIAQTVFLGLNRSDYMFQRSADGSPALRQIEINTISASFG

GLASRTPAVHRHVLSVLSRTREAGRILSNNPSRGLALGIARAWELYGSPNA

LVLLIAQERERNIFDQRAIENELLARNIHVIRRTFEDISERGSLDQDRRLF

VDGQEIAVVYFRDGYMPRQYSLQNWEARLLLERSHAARCPDIATQLAGTRR

VQQELSRPGMLEMLLPGQPEAVARLRATFAGLYSLDVGEEGDQAIAEALAA

PSRFVLRPQREGGGNNLYGEEMVQALRQLRDSEERASYILMERIEPEPFEN

CLLRPGSPARVVQCISELGIFGVYVRQERTLVMNRHVGHLLRTRAIEHADG

GVAAGVAVLDNPYPV

"K0" form of native *Homo sapiens* MEIS2 polypeptide:

(SEQ ID NO: 69)

MAQRYDELPHYGGMDGVGVPASMYGDPHAPRPIPPVHHLNHGPPLHATQHY

GAHAPHPNVMPASMGSAVNDALRRDRDAIYGHPLFPLLALVFERCELATCT

PREPGVAGGDVCSSDSFNEDIAVFARQVRAERPLFSSNPELDNLMIQAIQV

LRFHLLELERVHELCDNFCHRYISCLRGRMPIDLVIDERDGSSRSDHEELS

GSSTNLADHNPSSWRDHDDATSTHSAGTPGPSSGGHASQSGDNSSEQGDGL

DNSVASPGTGDDDDPDRDRRRQRRRGIFPRVATNIMRAWLFQHLTHPYPSE

EQRRQLAQDTGLTILQVNNWFINARRRIVQPMIDQSNRAGFLLDPSVSQGA

AYSPEGQPMGSFVLDGQQHMGIRPAGPMSGMGMNMGMDGQWHYM

C2H2 Zinc Finger Polypeptides

The Cys2His2-like fold group (C2H2) is by far the best-characterized class of zinc fingers and are extremely common in mammalian transcription factors. These domains adopt a simple Ppa fold and have the amino acid Sequence motif (Pabo et al. Annual Review of Biochemistry. 70: 313-40):

X2-Cys-X2,4-Cys-X12-His-X3,4,5-His

This class of zinc fingers can have a variety of functions such as binding RNA and mediating protein-protein interactions, but is best known for its role in sequence-specific DNA-binding proteins such as Zif268 (Egr1). In such proteins, individual zinc finger domains typically occur as tandem repeats with two, three, or more fingers comprising the DNA-binding domain of the protein. These tandem arrays can bind in the major groove of DNA and are typically spaced at 3-bp intervals. The α-helix of each domain (often called the "recognition helix") can make sequence-specific contacts to DNA bases; residues from a single recognition helix can contact 4 or more bases to yield an overlapping pattern of contacts with adjacent zinc fingers.

Exemplary known C2H2 zinc finger polypeptides include: BNC1, BNC2, CTCF, CTCFL, EGR2, EGR3, EGR4, E4F1, GFI1B, GLIS1, GLIS2, GLI1, GLI2, GLI3, GTF3A, IKZF1, IKZF2, IKZF3, IKZF4, IKZF5, INSM2, KLF1, KLF2, KLF3, KLF4, KLF5, KLF6, KLF7, KLF9, KLF10, KLF11, KLF12, KLF13, KLF14, KLF15, KLF16, MECOM, OSR1, OSR2, OVOL1, PLAGL1, PRDM1, PRDM4, PRDM5, PRDM6, PRDM10, PRDM12, PRDM14, PRDM16, PRKRIP1, RLF, RREB1, SNAI1, SNAI2, SP1, SP2, SP3, SP4, SP5, SP6, SP7, SP8, SUZ12, TRPS1, TSHZ1, WT1, YY1, ZBTB3, ZBTB5, ZBTB10, ZBTB12, ZEB1, ZEB2, ZFP28, ZHX1, ZHX2, ZHX3, ZIC2, ZIC4, ZIC5, ZNF2, ZNF3, ZNF7, ZNF8, ZNF10, ZNF12, ZNF14, ZNF16, ZNF17, ZNF18, ZNF19, ZNF20, ZNF22, ZNF23, ZNF24, ZNF25, ZNF26, ZNF28, ZNF30, ZNF32, ZNF33A, ZNF33B, ZNF34, ZNF35, ZKSCAN1, ZNF37A, ZSCAN21, HIVEP1, HIVEP2, HIVEP3, ZNF41, MZF1, ZNF43, ZNF44, ZNF45, ZBTB25, ZNF48, ZSCAN22, BCL6, ZNF56, ZNF57, ZBTB17, BCL6B, ZKSCAN7, ZNF69, ZNF70, ZNF71, ZNF73, ZNF74, ZNF75A, ZNF75D, ZNF76, ZNF77, ZNF79, ZNF80, ZNF81, ZNF83, ZNF84, ZNF85, ZFPM1, ZFPM2, ZNF90, ZNF91, ZNF92, ZNF93, ZSCAN12, ZNF98, ZNF99, ZNF100, ZNF101, ZNF106, ZNF107, ZNF112, ZNF114, ZNF117, ZNF121, ZNF124, ZNF131, ZNF132, ZNF133, ZNF134, ZNF135, ZNF136, ZNF138, ZNF140, ZNF141, ZNF142, ZNF143, ZBTB16, ZNF146, ZNF148, ZNF154, ZNF155, ZNF157, ZNF160, VEZF1, GFI1, ZNF165, ZNF169, ZNF174, ZNF175, ZNF177, ZNF180, ZNF181, ZNF182, ZNF184, ZSCAN26, ZNF189, ZKSCAN8, ZSCAN9, ZNF195, ZNF197, ZNF200, ZIC1, ZNF202, ZIC3, ZNF205, ZSCAN10, ZNF207, ZNF208, ZNF211, ZNF212, ZNF213, ZNF214, ZNF215, ZNF217, TSHZ2, ZNF219, ZNF221, ZNF222, ZNF223, ZNF224, EGR1, ZNF225, ZNF226, ZNF227, ZNF229, ZNF230, ZNF232, ZNF233, ZNF234, ZNF235, ZNF236, ZBTB18, ZNF239, ZNF248, ZNF250, ZNF251, ZNF253, ZNF254, ZNF256, ZNF257, ZNF260, ZNF263, ZNF264, ZNF266, ZNF267, ZNF268, ZNF271P, ZNF273, ZNF274, ZNF275, ZNF276, PATZ1, ZNF281, ZNF282, ZNF283, ZNF284, ZNF285, ZNF286A, ZNF286B, ZNF287, ZBTB20, SCAPER, ZNF292, SNAI3, ZBTB21, ZNF296, ZBTB22, ZBTB43, PRDM15, ZNF300, ZNF302, ZNF304, ZKSCAN3, ZKSCAN4, ZNF311, FEZF2, FEZF1, ZNF316, ZNF317, ZNF318, ZNF319, ZNF320, ZNF322, ZSCAN31, ZNF324, ZNF324B, ZNF326, ZNF329, ZNF330, ZNF331, ZNF333, ZNF334, ZNF335, GZF1, ZNF337, ZFP64, OVOL2, ZBTB46, ZNF341, ZNF343, ZNF345, ZNF347, ZBTB33, ZNF350, ZNF354A, ZNF354B, ZNF354C, ZNF358, ZSCAN20, ZNF362, ZNF365, ZNF366, ZNF367, ZNF382, ZNF383, ZNF384, ZSCAN23, ZNF391, ZSCAN16, KLF17, ZNF394, ZNF395, ZNF396, ZNF397, ZNF398, ZNF404, ZFAT, ZNF407, ZNF408, ZFHX2, ZNF410, ZNF414, ZNF415, ZNF416, ZNF417, ZNF418, ZNF419, ZNF420, ZNF423, ZNF425, ZNF426, ZNF428, ZNF429, ZNF430, ZNF431, ZNF432, ZNF433, ZSCAN32, ZNF436, ZBTB2, ZNF438, ZNF439, ZNF440, ZNF441, ZNF442, ZNF443, ZNF444, ZNF445, ZNF446, ZSCAN18, ZNF449, ZBTB24, ZNF451, ZNF454, ZNF460, ZNF461, ZNF462, REPIN1, ZNF467, ZNF468, ZNF469, ZNF470, ZNF471, ZNF473, ZNF474, ZFP1, ZBTB14, ZNF479, ZNF480, ZBTB26, ZBTB6, ZNF483, ZNF484, ZNF485, ZNF486, ZNF487, ZNF488, ZNF490, ZNF491, ZNF492, ZNF493, ZSCAN4, ZSCAN5A, ZSCAN5B, ZSCAN5C, ZSCAN5DP, ZNF496, ZNF497, ZSCAN25, ZBTB45, ZNF500, ZNF501, ZNF502, ZNF503, ZNF506, ZNF507, ADNP2, ZBTB49, ZNF510, ZNF511, ZNF512, ZNF513, ZNF514, GLIS3, ZNF516, ZNF517, ZNF518A, ZNF518B, ZNF519, ZNF521, ZNF524, ZNF525, ZNF526, ZNF527, ZNF528, ZNF529, ZNF530, ZFP14, ZNF532, ZNF534, ZNF536, TSHZ3, ZBTB32, ZNF540, ZNF541, ZNF542P, ZNF543, ZNF544, ZFP82, ZNF546, ZNF547, ZNF548, ZNF549, ZNF550, ZNF551, ZNF552, ZNF554, ZNF555, ZNF556, ZNF557, ZNF558, ZNF559, ZNF560, ZNF561, ZNF562, ZNF563, ZNF564, ZNF565, ZNF566, ZNF567, ZNF568, ZNF569, ZNF570, ZNF571, ZNF572, ZNF573, ZNF574, ZNF575, ZNF576, ZNF577, ZNF578, ZNF579, ZNF580, ZNF581, ZNF582, ZNF583, ZNF584, ZNF585A, ZNF585B, ZNF586, ZNF587, ZNF587B, ZNF589, ZNF592, ZNF594, ZNF595, ZNF596, ZNF597, ZNF598, ZNF599, ZNF600, ZNF605, ZNF606, ZNF607, ZNF608, ZNF609, ZNF610, ZNF611, ZNF613, ZNF614, ZNF615, ZNF616, ZNF618, ZNF619, ZNF620, ZNF621, ZNF623, ZNF624, ZNF625, ZNF626, ZNF627, ZNF628, ZNF629, ZNF630, YY2, ZNF639, ZNF641, ZFP69, ZFP69B, ZNF646, ZNF648, ZNF649, ZBTB47, ZNF652, ZNF653, ZNF655, ZIM2, ZIM3, ZNF658, ZNF660, ZNF662, ZNF663P, ZNF664, ZNF665, ZNF667, ZNF668, ZNF669, ZNF670, ZNF671, ZNF672, ZNF674, ZNF675, ZNF676, ZNF677, ZNF678, ZNF679, ZNF680, ZNF681, ZNF682, ZNF683, ZNF684, ZNF688, ZNF689, ZSCAN29, ZNF691, ZNF692, CASZ1, ZKSCAN2, ZNF695, ZNF696, ZNF697, ZFP57, ZNF699, ZNF700, ZNF701, ZNF705A, ZNF705B, ZNF705D, ZNF705F, ZNF705G, ZNF707, ZNF708, ZNF709, ZNF710, ZNF711, ZNF713, ZNF714, ZNF716, ZNF717, ZNF718, ZNF720, ZNF721, ZNF726, ZNF727, ZNF728, ZNF729, ZNF730, ZNF732, ZNF735, ZNF736, ZNF737, ZNF740, KLF8, HINFP, ANKZF1, ZFP30, ZNF746, ZNF747, ZNF749, ZFP2, ZFP3, ZFP41, ZFP42, ZFP62, ZFP90, ZFP91, ZNF761, ZIK1, ZNF763, ZNF764, ZNF765, ZNF766, ZNF767P, ZNF768, RBAK, ZNF770, ZNF771, ZNF772, ZNF773, ZNF774, ZNF775, ZNF776, ZNF777, ZNF778, ZNF780A, ZNF780B, ZNF781, ZNF782, ZNF783, ZNF784, ZNF785, ZNF786, ZNF787, ZNF788P, ZNF789, ZNF790, ZNF791, ZNF792, ZNF793, SALL1, SALL2, SALL3, SALL4, FIZ1, ZNF799, ZNF800, MAZ, JAZF1, WIZ, ZNF805, ZNF806, ZNF807, ZNF808, ZNF812P, ZNF813, ZNF814, ZNF816, ZNF821, ATMIN, ZNF823, ZNF827, CHAMP1, ZNF829, ZNF835, ZNF836, ZNF837, ZNF841, ZNF843, ZNF844, ZNF845, ZNF846, ZNF850, ZBTB44, ZNF852, ZNF853, ZSCAN2, ZBTB48, BCL11A, BCL11B, ZBTB7A, ZBTB7B, ZBTB7C, ZNF860, ZNF862, ZNF865, HKR1, ZNF878, ZNF879, ZNF880, ZNF883, ZNF888, ZNF891, ZXDA, ZFP92, SCRT1, SCRT2, PRDM9, PLAGL2, HIC1, MYNN, ZBTB4, PEG3, ZXDB, ZFP37, HIC2, ZBTB37, ZBTB1, PRDM7, ZFY, PLAG1, ZBTB11, ZKSCAN5, ZSCAN1, ZBTB8A, ZBTB8B, ZSCAN30, ZBTB34, ZBTB9, ZBTB38, ZBTB39, ZBTB40, ZBTB41, ZBTB42, ZFX, ZFHX3, GLI4, SP9, ZUP1 and ZXDC.

Thalidomide Analog Immunomodulatory Drugs (IMiDs)

Immunomodulatory drugs (IMiDs) include thalidomide and a recently developed class of anti-cancer drug derived from thalidomide, which have been developed and exert potent anti-cancer effects. Exemplary IMiDs include:

Thalidomide:

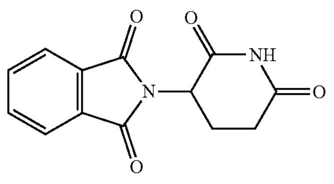

Phthalimide Glutarimide

Thalidomide can be administered orally and is available in 50 mg, 100 mg, 150 mg, and 200 mg dose capsules. An exemplary on-label dose of thalidomide is 200 mg per day to a human subject.

Lenalidomide:

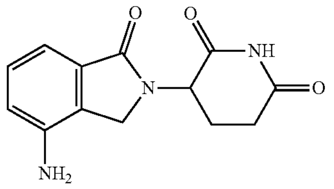 [SMILES: Nc1cccc2c1CN(C1CCC(=O)NC1=O)C2=O]

Common adult human oral lenalidomide dosages include: 2.5 mg once a day, 5 mg once a day, 10 mg once a day, 15 mg once a day, 15 mg every other day, 25 mg once a day and 25 mg every other day.

Pomalidomide:

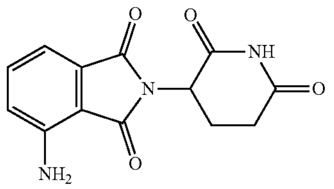 [SMILES: Nc1cccc2c1C(=O)N(C1CCC(=O)NC1=O)C2=O]

Common adult human oral pomalidomide dosages include: 1-5 mg once a day, including 3 mg once a day and 4 mg once a day.

CC-122:

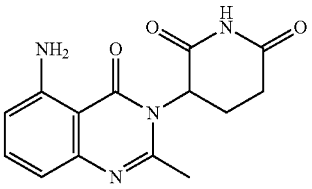 [SMILES: Cc1nc2cccc(N)c2c(=O)n1C1CCC(=O)NC1=O]

Exemplary adult human oral CC-122 dosages include: 0.5-5 mg once a day, including 0.5, 1, 1.5, 2, 2.5, 3 and 3.5 mg once a day.

CC-885 targets GSPT1 to CRBN (Nature, 2016 vol. 535 (7611) pp. 252-257).

As shown above, thalidomide is composed of a glutarimide ring and a pthalimide ring. Lenalidomide and pomalidomide are very similar to thalidomide. Lenalidomide is a 4-amino analog of thalidomide lacking a carbonyl group of pthalidmide. Pomalidomide is a 4-amino analog of thalidomide. Although CC-122 possesses a glutarimide ring, the structure is quite different from other IMiDs.

The thalidomide analog immunomodulatory drugs (IMiDs) lenalidomide and pomalidomide are well-tolerated, FDA-approved drugs for hematologic malignancies that induce the degradation of proteins required for myeloma and MDS cell survival via binding to CRBN, the substrate adapter for the $CRL^{CRBN}$ E3 ubiquitin ligase (Krönke et al. *Science* 343.6168: 301-305; Krönke et al. *Nature* 523.7559: 183-188).

Controlled, reversible CAR-T activation with pomalidomide (Pom)-gated control switches can help prevent or suppress CAR-T cell hyperactivation syndromes. Disclosed herein is an engineered, chemically induced dimerization domain from the IKZF3-Pom-CRBN interaction with application to medical uses, including IMiD-gated split CARs as schematically demonstrated in, e.g., FIGS. 1-4, and as exemplified herein. It is expressly contemplated that a range of IMiD compounds can be used in such systems, in addition to the specifically exemplified pomalidomide, with similar effect.

OFF-Switch—CRBN Substrate Degron-Mediated

Certain aspects of the instant disclosure employ the polypeptide sequence of a CRBN substrate or fragment thereof as a IMiD-inducible element that promotes ubiquitination and degradation of the polypeptide to which the CRBN substrate sequence (thereby termed a "degron") is attached. Exemplary CRBN substrate polypeptide sequences used and/or contemplated for use in such OFF-switches of the instant disclosure include those recited above (e.g., IKZF1, IKZF3, and Ck1α polypeptide sequences, including fragments and variants thereof).

In certain OFF-switch configurations, multiple degron elements (e.g., CRBN polypeptide substrate domains capable of binding CRBN in response to drug, thereby promoting ubiquitin pathway-mediated degradation of a drug-responsive CAR) can be employed, and optionally can be joined to each other in series or array configuration, e.g., joined to one another via polypeptide linkers. A range of polypeptide linkers are known in the art and can be employed within fusion polypeptides of the instant disclosure, including synthetic and natural polypeptide linkers, e.g., synthetic flexible polypeptide sequences such as $(G4S)_n$, synthetic rigid polypeptide sequences such as $A(EAAAK)_3A$, and/or natural linkers such as those that join zinc fingers in IKZF3, such as TGEKP or TGERP.

Examples of specific linkers include those set forth in Klein et al. (Protein Engineering, Design & Selection. 27: 325-30), e.g., linkers L1-L24 below (SEQ ID NOs: 114-137):

Other exemplary linker polypeptides include @2-microglobulin, Zn-(2-glycoprotein and tetratricopeptide repeats, among many other forms of polypeptide linkers known in the art.

For degron-mediated switch configurations (whether a degron-mediated OFF-switch or a degron-mediated ON-switch, as described below) it is expressly contemplated that the depth and/or speed of CRBN-mediated ubiquitylation and degradation of a degron-tagged CAR or CAR inhibitory polypeptide can be enhanced by overexpressing CRBN in a mammalian cell harboring such degron-tagged fusion polypeptide, thereby increasing the concentration of the ubiquitin ligase $CRL4^{CRBN}$.

| Linker | Name | Complete sequence |
|---|---|---|
| L1 | GPcPcPc | AGSGGSGGSGGSPVPSTPPTNSSSTPPTPSPSPVPSTPPTNSSSTPPTPSPSPVPSTPPTNSS STPPTPSPSAS |
| L2 | GPPcP | AGSGGSGGSGGSPVPSTPPTPSPSTPPTPSPSPVPSTPPTNSSSTPPTPSPSPVPSTPPTPSP STPPTPSPSAS |
| L3 | GPGcP | AGSGGSGGSGGSPVPSTPPTPSPSTPPTPSPSGGSGNSSGSGGSPVPSTPPTPSPSTPPTPSP SAS |
| L4 | GPPP | AGSGGSGGSGGSPVPSTPPTPSPSTPPTPSPSPVPSTPPTPSPSTPPTPSPSPVPSTPPTPSP STPPTPSPSAS |
| L5 | GPbP | AGSGGSGGSGGSPVPSTPPTPSPSTPPTPSPSIQRTPKIQVYSRHPAENGKSNFLNCYVSGFH PSDIEVDLLKNGERIEKVEHSDLSFSKDWSFYLLYYTEFTPTEKDEYACRVNHVTLSQPKIVK WDRDPVPSTPPTPSPSTPPTPSPSAS |
| L6 | GPbG | AGSGGSGGSGGSPVPSTPPTPSPSTPPTPSPSIQRTPKIQVYSRHPAENGKSNFLNCYVSGFH PSDIEVDLLKNGERIEKVEHSDLSFSKDWSFYLLYYTEFTPTEKDEYACRVNHVTLSQPKIVK WDRDGGSGGSGGSGGSAS |
| L7 | PbGbG | AGPVPSTPPTPSPSTPPTPSPSIQRTPKIQVYSRHPAENGKSNFLNCYVSGFHPSDIEVDLLK NGERIEKVEHSDLSFSKDWSFYLLYYTEFTPTEKDEYACRVNHVTLSQPKIVKWDRDGGSGGS GGSGGSIQRTPKIQVYSRHPAENGKSNFLNCYVSGFHPSDIEVDLLKNGERIEKVEHSDLSFS KDWSFYLLYYTEFTPTEKDEYACRVNHVTLSQPKIVKWDRDGGSGGSGGSGAS |
| L8 | GPbGbP | AGSGGSGGSGGSPVPSTPPTPSPSTPPTPSPSIQRTPKIQVYSRHPAENGKSNFLNCYVSGFH PSDIEVDLLKNGERIEKVEHSDLSFSKDWSFYLLYYTEFTPTEKDEYACRVNHVTLSQPKIVK WDRDGGSGGSGGSGGSIQRTPKIQVYSRHPAENGKSNFLNCYVSGFHPSDIEVDLLKNGERIE KVEHSDLSFSKDWSFYLLYYTEFTPTEKDEYACRVNHVTLSQPKIVKWDRDPVPSTPPTPSPS TPPTPSPSAS |
| L9 | GPUG | AGSGGSGGSGGSPVPSTPPTPSPSTPPTPSPSQIFVKTLTGKTITLEVEPSDTIENVKAKIQD KEGIPPDQQRLIFAGKQLEDGRTLSDYNIQKESTLHLVLRLRGGGGSGGSGGSGGSAS |
| L10 | GPZP | AGSGGSGGSGGSPVPSTPPTPSPSTPPTPSPSDGRYSLTYIYTGLSKHVEDVPAFQALGSLND LQFFRYNSKDRKSQPMGLWRQVEGMEDWKQDSQLQKAREDIFMETLKDIVEYYNDSNGSHVLQ GRFGCEIENNRSSGAFWKYYYDGKDYIEFNKEIPAWVPFDPAAQITKQKWEAEPVYVQRAKAY LEEECPATLRKYLKYSKNILDRQDPPSVVVTSHQAPGEKKKLKCLAYDFYPGKIDVHWTRAGE VQEPELRGDVLHNGNGTYQSWVVVAVPPQDTAPYSCHVQHSSLAQPLVVPWEASPVPSTPPTP SPSTPPTPSAS |
| L11 | GGZGZP | AGSGGSGGSGGSGGSGGSGGSGGSDGRYSLTYIYTGLSKHVEDVPAFQALGSLNDLQFFRYNS KDRKSQPMGLWRQVEGMEDWKQDSQLQKAREDIFMETLKDIVEYYNDSNGSHVLQGRFGCEIE NNRSSGAFWKYYYDGKDYIEFNKEIPAWVPFDPAAQITKQKWEAEPVYVQRAKAYLEEECPAT LRKYLKYSKNILDRQDPPSVVVTSHQAPGEKKKLKCLAYDFYPGKIDVHWTRAGEVQEPELRG DVLHNGNGTYQSWVVVAVPPQDTAPYSCHVQHSSLAQPLVVPWEASGGSGGSGGSGGSDGRYS |

-continued

| Linker | Name | Complete sequence |
|---|---|---|
| | | LTYIYTGLSKHVEDVPAFQALGSLNDLQFFRYNSKDRKSQPMGLWRQVEGMEDWKQDSQLQKA<br>REDIFMETLKDIVEYYNDSNGSHVLQGRFGCEIENNRSSGAFWKYYYDGKDYIEFNKEIPAWV<br>PFDPAAQITKQKWEAEPVYVQRAKAYLEEECPATLRKYLKYSKNILDRQDPPSVVVTSHQAPG<br>EKKKLKCLAYDFYPGKIDVHWTRAGEVQEPELRGDVLHNGNGTYQSWVVVAVPPQDTAPYSCH<br>VQHSSLAQPLVVPWEASPVPSTPPTPSPSTPPTPSPSAS |
| L12 | GcGcP | AGSGNSSGSGGSGGSGNSSGSGGSPVPSTPPTPSPSTPPTPSPSAS |
| L13 | cTPR3 | KLSGGGGSGGGGSGGGGSAEAWYNLGNAYYKQGDYQKAIEYYQKALELDPNNAEAWYNLGNAY<br>YKQGDYQKAIEYYQKALELDPNNAEAWYNLGNAYYKQGDYQKAIEDYQKALELDPNNLQRSAG<br>GGGSGGGGSGGGGAS |
| L14 | cTPR6 | KLSGGGGSGGGGSGGGGSAEAWYNLGNAYYKQGDYQKAIEYYQKALELDPNNAEAWYNLGNAY<br>YKQGDYQKAIEYYQKALELDPNNAEAWYNLGNAYYKQGDYQKAIEDYQKALELDPNNLQAEAW<br>KNLGNAYYKQGDYQKAIEYYQKALELDPNNASAWYNLGNAYYKQGDYQKAIEYYQKALELDPN<br>NAKAWYRRGNAYYKQGDYQKAIEDYQKALELDPNNRSRSAGGGGSGGGGSGGGGAS |
| L15 | cTPR9 | KLSGGGGSGGGGSGGGGSAEAWYNLGNAYYKQGDYQKAIEYYQKALELDPNNAEAWYNLGNAY<br>YKQGDYQKAIEYYQKALELDPNNAEAWYNLGNAYYKQGDYQKAIEDYQKALELDPNNLQAEAW<br>KNLGNAYYKQGDYQKAIEYYQKALELDPNNASAWYNLGNAYYKQGDYQKAIEYYQKALELDPN<br>NAKAWYRRGNAYYKQGDYQKAIEDYQKALELDPNNRSAEAWYNLGNAYYKQGDYQKAIEYYQK<br>ALELDPNNAEAWYNLGNAYYKQGDYQKAIEYYQKALELDPNNAEAWYNLGNAYYKQGDYQKAI<br>EDYQKALELDPNNLQRSAGGGGSGGGGSGGGGAS |
| L16 | cTPR12 | KLSGGGGSGGGGSGGGGSAEAWYNLGNAYYKQGDYQKAIEYYQKALELDPNNAEAWYNLGNAY<br>YKQGDYQKAIEYYQKALELDPNNAEAWYNLGNAYYKQGDYQKAIEDYQKALELDPNNLQAEAW<br>KNLGNAYYKQGDYQKAIEYYQKALELDPNNASAWYNLGNAYYKQGDYQKAIEYYQKALELDPN<br>NAKAWYRRGNAYYKQGDYQKAIEDYQKALELDPNNRSAEAWYNLGNAYYKQGDYQKAIEYYQK<br>ALELDPNNAEAWYNLGNAYYKQGDYQKAIEYYQKALELDPNNAEAWYNLGNAYYKQGDYQKAI<br>EDYQKALELDPNNLQAEAWKNLGNAYYKQGDYQKAIEYYQKALELDPNNASAWYNLGNAYYKQ<br>GDYQKAIEYYQKALELDPNNAKAWYRRGNAYYKQGDYQKAIEDYQKALELDPNNRSAGGGGSG<br>GGGSGGGGAS |
| L17 | GS1 | GGGGSAS |
| L18 | GS2 | GGGGSGGGGSAS |
| L19 | GS3 | GGGGSGGGGSGGGGSAS |
| L20 | GS5 | GGGGSGGGGSGGGGSGGGGSGGGGSAS |
| L21 | GS6 | GGGGSGGGGSGGGGSGGGGSGGGGSGGGGSAS |
| L22 | GS7 | AGGGSGGGGSGGGGSGGGGSGGGGSGGGGSGGGGSAS |
| L23 | GS8 | AGGGSGGGGSGGGGSGGGGSGGGGSGGGGSGGGGSGGGGSAS |
| L24 | GS9 | AGGGSGGGGSGGGGSGGGGSGGGGSGGGGSGGGGSGGGGSGGGGSAS |

It is further contemplated for degron-mediated switch configurations that the depth and/or speed of CRBN-mediated ubiquitylation and degradation of a degron-tagged CAR or CAR inhibitory polypeptide can be enhanced by overexpressing a CRBN-containing polypeptide that is targeted to the plasma membrane via a targeting sequence of or derived from LAT, PAG, LCK, FYN, LAX, CD2, CD3, CD4, CD5, CD7, CD8a, PD1, SRC and/or LYN, thereby increasing the local concentration of the ubiquitin ligase CRL4C$^{RBN}$ at the plasma membrane.

Degron-Mediated ON-Switch Configuration

In certain aspects of the instant disclosure, one or more degrons (e.g., a CRBN polypeptide substrate domain capable of binding CRBN in response to drug, thereby promoting ubiquitin pathway-mediated degradation of a drug-responsive CAR) is fused to a CAR inhibitor, such that a degron-mediated, drug-responsive ON-switch is formed. As for other degron-presenting fusion polypeptides, degron polypeptide domains can be included as single degron polypeptide domains or as multiple degron polypeptide domains, optionally where multiple degron polypeptide domains are joined in a series or an array, optionally using polypeptide linkers, such as those known in the art and/or described above.

The fusion polypeptide that includes a CAR inhibitory domain and a degron can also be referred to as a chimeric degradable inhibitor (CDI). In certain embodiments that CDI is a constitutive inhibitor of CAR signaling absent administration of a degron-targeting drug. Upon administration of the drug, degradation of the inhibitor licenses the CAR for antigen-dependent signal transduction.

In such degron-mediated ON-switch configurations, it is contemplated that the inhibitor may be a proximal, pan-CAR/TCR signal transduction inhibitor, such as CSK. The inhibitor may also selectively abrogate specific signal transduction pathways and/or effector functions, such as Ras signaling, PKC, calcium-dependent signaling, NF-kappaB, NFAT, actin and cytoskeletal responses, cytokine secretion, cell proliferation, degranulation, tumor cell killing, differentiation, or exhaustion.

The inhibitor may be a ubiquitin ligase involved in TCR/CAR signal transduction, such as c-CBL, CBL-B, ITCH, RNF125, RNF128, or WWP2.

The inhibitor may be a TCR/CAR negative regulatory enzyme such as SHP1, SHP2, SHIP1, SHIP2, CD45, CSK, CD148, PTPN22, DGKalpha, DGKzeta, DRAK2, HPK1, HPK1, STS1, STS2, or SLAT.

The inhibitor may be a TCR/CAR negative regulatory scaffold/adapter protein such as PAG, LIME, NTAL, LAX31, SIT, GAB2, GRAP, ALX, SLAP, SLAP2, DOK1, or DOK2.

The inhibitor may be a dominant negative version of an activating TCR signaling component, such ZAP70, LCK, FYN, NCK, VAV1, SLP76, ITK, ADAP, GADS, PLCgamma1, LAT, p85, SOS, GRB2, NFAT, p50, p65, AP1, RAP1, CRKII, C3G, WAVE2, ARP2/3, ABL, ADAP, RIAM, or SKAP55.

The inhibitor may contain the cytoplasmic tail of TCR/CAR negative co-regulatory receptors such as CD5, PD1, CTLA4, BTLA, LAG3, B7-H1, B7-1, CD160, TIM3, 2B4, or TIGIT.

The inhibitor may be targeted to the plasma membrane with a targeting sequence derived from LAT, PAG, LCK, FYN, LAX, CD2, CD3, CD4, CD5, CD7, CD8a, PD1, SRC, or LYN.

Both OFF-switch and ON-switch compositions of the instant disclosure can be readily applied in pre-clinical models of immune and stem cell therapy, as a prelude to clinical application.

More generally, FDA-approved drug-controllable activation and/or degradation of engineered proteins in cellular therapies can have broad applications, including the immunotherapeutic and stem cell therapies expressly presented herein.

Chimeric Antigen Receptors (CARs)

CAR-T cells can act to kill targeted tumor cells, but can also elicit negative effects capable of propagating in an unchecked manner. Conventional CAR-T design uses a single polypeptide that includes tumor antigen-binding domains (e.g., an scFv), a transmembrane domain, a costimulatory domain and a CD3ζ domain (TCR ITAMs), with this single polypeptide therefore capable of specifically binding a tumor antigen and propagating an activated T cell response. (see, e.g., Wu et al. *Science* 350: aab4077.)

As contemplated herein, the CARs (including split CAR systems) of the present disclosure include an extracellular ligand binding domain capable of binding a targeted protein, typically an antigen, for example a tumor antigen. In one embodiment, the extracellular ligand binding domain is an antigen binding domain, for example, an antibody or an antigen binding fragment thereof. In particular embodiments, the antigen-binding fragment is a Fab or scFv. In one embodiment, the extracellular ligand binding domain is a ligand for a tumor marker, for example, a ligand that binds a marker expressed on the cell surface of a tumor, for example IL13 which binds to the IL13 receptor (IL13R) on glioma cells or heregulin which binds to erb B2, B3, and B4 on breast cancer cells. In one embodiment, the extracellular ligand binding domain targets a labeled or tagged protein or molecule, for example biotin or fluorescein isothiocyanate, which is bound to an antibody targeting a tumor expressed protein. For example, the extracellular ligand binding domain can target a label on a tumor-specific antibody, for example biotin, so that when the antibody-label binds to the tumor cell, the extracellular binding ligand of the CAR T-cell binds the label, activating the T-cell, and killing the tumor cell. In this regard, a "universal CAR" can be generated capable of binding any tagged or labeled antibody. See, e.g., Abate Daga et al., "CAR models: next generation CAR modifications for enhanced T-cell function," Molecular Therapy-Oncolytics (2016)3:1-7.

In certain embodiments, the antigen binding domain in the CAR binds to a tumor antigen, for example, a tumor antigen associated with a hematological malignancy or a solid tumor. Tumor antigens capable of being targeted by CAR T-cells are known, and include, for example, but are not limited to, CD19, CD20, CD22, CD30, CD40, CD70, CD123, ErbB2 (HER2/neu), epithelial cell adhesion molecule (EpCAM), Epidermal growth factor receptor (EGFR), epidermal growth factor receptor variant III (EGFRvIII). Disialoganglioside GD2, disialoganglioside GD3, mesothelian, ROR1, mesothelin, CD33/IL3Ra, C-Met, PSMA, Glycolipid, F77, EGFRvIII, GD-2, NY-ESO-1 TCR, melanoma-associated antigen (MAGE) A3 TCR, melanoma-associated antigen (MAGE) A1 TCR, alphafetapotein (AFP), carcinoembryonic antigen (CEA), CA-125, MUC-1, epithelial tumor antigen (ETA), tyrosinase, CA15-3, CA27-29, CA19-9, calcitonin, calretinin CD34, CD99MIC2, CD7, chromogranin, cytokeratin, desmin, CD31 FLI, glial fibrillary acidic protein, gross cystid disease fluid protein, HMB-45, human chorionic gonadotropin inhibin, MART-1, Myo D1, neuron-specific enolast, placental alkaline phosphatase, prostate specific antigens, PSCA. PTPRC, S100 protein, synaptophysin, thyroglobulin, thyroid transcription factor 1, tumor M2-PK, vimentin, human telomerase reverse transcriptase (hTERT), surviving, mouse double minute 2 homolog (MDM2), kappa-light chain, LeY, L1 cell adhesion molecule, oncofetal antigen (h5T4), TAG-72, VEGF-R2, and combinations thereof, as well as others described herein. Other antigens to which the antigen binding domain of the CAR can be directed include, but are not limited to, tissue or cell lineage specific antigens including, but not limited to, CD3, CD4, CD8, CD24, CD25, CD33, CD34, CD133, CD138, or a combination thereof.

In certain embodiments, a CAR (or split CAR system) of the disclosure includes an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. In one embodiment, the transmembrane domain is the CD8α hinge domain.

With respect to the cytoplasmic domain, the CAR (or split CAR system) of the disclosure is designed to include at least one signaling domain, at least one co-stimulatory domain and either a FDA-approved drug-responsive heterodimer or a FDA-approved drug-inducible degron moiety. The heterodimer components and/or degron of the CAR or CAR system are amino acid sequences to which the FDA-approved drug can be bound, leading to activation in the presence of both drug and an antigen in the ON-switch split CAR system of the disclosure or to the degradation of the CAR when in contact with the drug in the OFF-switch aspects of the disclosure.

In OFF-switch aspects, the degron should not interfere with the function of the CAR. In certain embodiments, the OFF-switch degron and/or ON-switch heterodimer components are amino acid sequences derived from an endogenous protein which has been modified so that the FDA-approved compound selectively binds to modified degron and/or modified heterodimer components, relative to endogenously expressed proteins.

As contemplated herein, the CARs (including split CAR systems) of the present disclosure include a transmembrane domain spanning the extracellular ligand binding domain and the at least one intracellular co-stimulatory and/or signaling domain. Transmembrane domains useful in the construction of CARs are known in the art, and can be derived from natural or synthetic sources.

For example, transmembrane regions contemplated herein include, but are not limited to, those derived from (i.e. comprise at least the transmembrane region(s) of) the alpha, beta or zeta chain of the T-cell receptor, CD28, CD3 epsilon, CD8, CD45, CD4, CD5, CDS, CD9, CD 16, CD22, CD33, CD37, CD64, CD80, CD86, CD 134, CD137, CD 154, or KIR2DS2. Alternatively the transmembrane domain in some embodiments is synthetic, for example, comprising predominantly hydrophobic residues such as leucine and valine. In some aspects, a triplet of phenylalanine, tryptophan and valine will be found at each end of a synthetic transmembrane domain.

As further contemplated herein, the CARs (or split CAR systems) of the present disclosure include at least one intracellular (or cytoplasmic) signaling domain. The intracellular signaling domain of the CAR activates at least one of the normal effector functions or responses of the immune cell. For example, upon binding of the extracellular ligand domain to a target antigen, the signaling domain may act to activate the CAR T-cell, for example, by inducing a function of a T-cell such as cytolytic activity or T-helper activity, including the secretion of cytokines or other factors. In some embodiments, the CAR includes an intracellular component of the TCR complex, such as a TCR CD3+ chain that mediates T-cell activation and cytotoxicity, e.g., the immunoreceptor tyrosine-based activation motif (ITAM) domain CD3 zeta chain (CD3ζ). Thus, in some aspects as contemplated herein, the antigen binding molecule is linked to one or more cell signaling domains. In some embodiments, cell signaling domains include CD3 transmembrane domain, CD3 intracellular signaling domains, and/or other CD transmembrane domains. In some embodiments, the CAR further includes a portion of one or more additional molecules such as Fc receptor γ, for example FcεRIγ, CD8, CD4, CD25, or CD16. For example, in some aspects, the CAR includes a chimeric molecule between CD3-zeta (CD3-ζ) or Fc receptor γ and CD8, CD4, CD25 or CD16. In one embodiment, the intracellular signaling domain is a Dap-12 derived signaling domain.

The intracellular signaling domain, or cytoplasmic signaling domain, used interchangeably herein, of the CAR (or split CAR system) of the disclosure is responsible for activation of at least one of the normal effector functions of the immune cell in which the CAR has been placed. The term "effector function" refers to a specialized function of a cell. Effector function of a T-cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the CAR (and/or split CAR system) of the disclosure include the cytoplasmic sequences of the T-cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone may not be sufficient for full activation of the T-cell and that a secondary or co-stimulatory signal may also be required. Thus, T-cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences that are of particular use in the disclosure include those derived from TCR zeta, FcR gamma, FcR beta, CD3 gamma, CD3 delta, CD3 epsilon, CD5, CD22, CD79a, CD79b, and CD66d. In one embodiment, the cytoplasmic signaling molecule in the CAR of the disclosure comprises a cytoplasmic signaling sequence derived from CD3 zeta.

The cytoplasmic domain of the CAR (and/or split CAR system) can be designed to comprise the CD3-zeta signaling domain by itself or combined with any other desired cytoplasmic domain(s) useful in the context of the CAR of the disclosure. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, any of the costimulatory elements known in the art as useful in the construction of CARs are within the scope of the disclosure.

The cytoplasmic signaling sequences within the cytoplasmic signaling portion of the CAR of the disclosure may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain (optionally including cytoplasmic domains in a split CAR system) is designed to comprise the signaling domain of CD3-zeta and the signaling domain of CD28. In another embodiment, the cytoplasmic domain (optionally including cytoplasmic domains in a split CAR system) is designed to comprise the signaling domain of CD3-zeta and the signaling domain of 4-1BB. In yet another embodiment, the cytoplasmic domain (optionally including cytoplasmic domains in a split CAR system) is designed to comprise the signaling domain of CD3-zeta and the signaling domain of CD28 and 4-1BB. In some embodiments, the intracellular signaling domain comprises a chimeric CD28 and OX40 co-stimulatory domain. In some embodiments, the intracellular signaling domain comprises a chimeric CD27 co-stimulatory domain. In some embodiments, the intracellular signaling domain comprises a chimeric CD27 and DAP10 co-stimulatory domain.

In some embodiments, the intracellular signaling domain or domains include the cytoplasmic sequences of the T-cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability. In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal. In some aspects, the cell comprises a first CAR which contains signaling domains to induce the primary signal and a second CAR which binds to a second antigen and contains the component for generating a costimulatory signal. For example, a first CAR can be an activating CAR and the second CAR can be a costimulatory CAR. In some aspects, both CARs must be ligated in order to induce a particular effector function in the cell, which can provide specificity and selectivity for the cell type being targeted. In one embodiment, the cell comprises a first CAR which contains signaling domains to induce the primary signal and a costimulatory ligand molecule to stimulate other immune cells. See, e.g., Abate Daga et al., "CAR models: next generation CAR modifications for enhanced T-cell function," Molecular Therapy-Oncolytics (2016)3:1-7. In certain split CAR systems, such as exemplified herein, one or more co-stimulatory domains might be presented upon a first polypeptide that is distinct from a second polypeptide comprising antigen binding domains and/or signaling domains, pending drug-induced heterodimeric association between the first and second polypeptides.

In some embodiments, the CAR (or split CAR system) includes a signaling domain and/or transmembrane portion of a costimulatory receptor, such as CD28, 4-1BB, OX40, DAP10, and ICOS. In some aspects, the same CAR includes both the activating and costimulatory components; in other aspects, the activating domain is provided by one polypeptide (e.g., a CAR) whereas the costimulatory component is provided by another polypeptide (e.g., a CAR or ligand recognizing another antigen).

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD 137 (4-1BB, TNFRSF9) co-stimulatory domain, linked to a CD3 zeta intracellular domain. In some embodiments, the intracellular signaling domain comprises a chimeric CD28 or CD 137 (4-1BB, TNFRSF9) co-stimulatory domain. In some embodiments, the intracellular signaling domain comprises a chimeric CD28 and OX40 co-stimulatory domain. In some embodiments, the intracellular signaling domain comprises a chimeric CD27 co-stimulatory domain. In some embodiments, the intracellular signaling domain comprises a chimeric CD27 and DAP10 co-stimulatory domain.

In some embodiments, the CAR (or split CAR system) encompasses two or more costimulatory domain combined with an activation domain, e.g., primary activation domain, in the cytoplasmic portion. One example is a receptor including intracellular components of CD3-zeta, CD28, and 4-1BB. Other examples include a receptor including intracellular components of CD3-zeta, CD28, and OX40.

While the instant disclosure exemplifies ON-switch and OFF-switch drug-inducible modalities as integral components of cellular polypeptides, molecular formats in which the drug-responsive ON-switch or OFF-switch polypeptides of the instant disclosure are joined to receptor- and/or signaling domain-presenting polypeptides using any of an array of art-recognized linkers (e.g., linker sequences, linker compounds, etc., e.g., as described in WO 2017/024318) while retaining switch functionality are also expressly envisioned herein.

Immune Effector Cells

As contemplated herein, the CARs (including split CAR systems) of the present disclosure are expressed by an immune effector cell, for example a T-cell, and administered to a subject in order to treat a disease or disorder, for example, a cancer. Among the cell types that may be used to express the CARs of the present disclosure include, but are not limited to, T-cells, NK cells, CD4+ T-cells, CD8+ cells, and stem cells, such as an induced pluripotent stem cell (iPS cell). In one embodiment, the cell is an autologous T-cell. In one embodiment, the cell shows anti-tumor activity when cross-reacted with a tumor cell containing an antigen capable of being bound by the extracellular ligand binding domain.

Further contemplated herein is the use of an FDA-approved compound capable of binding to a degron presented by a CAR of the present disclosure to induce degradation through ubiquitination. By administering to a subject an FDA-approved compound directed to the degron polypeptide, the immune effector cell response can be modulated in a subject who has previously received an immune effector cell expressing the CARs of the present disclosure. The FDA-approved compounds for use in the present disclosure tend to be small molecules, in certain aspects capable of disabling the biological function of the CAR through binding to the degron polypeptide. The FDA-approved compounds for use in the present disclosure in certain aspects therefore provide prompt ligand-dependent target protein degradation via chemical conjugation with a degron moiety that recruits the function of the Cereblon E3 ubiquitin ligase complex. Using this "OFF"-switch approach, certain CARs of the present disclosure can be degraded rapidly with a high specificity and efficiency.

Moreover, in such OFF-switch aspects, by combining the chemical strategy of protein degradation via the FDA-approved molecules of the present application with the effectiveness of CAR T-cell therapy, the activity of the CAR T-cell, and thus the side effects, can be regulated in a precise, temporal manner by rapidly turning on and off ubiquitination, and proteasomal degradation of the CAR.

Similarly, in "ON"-switch aspects of the disclosure, signaling is only activated upon administration of an FDA-approved agent that promotes formation of a heterodimer, thereby activating, e.g., a split CAR system of the disclosure and effecting CAR T-cell therapy. In such a system, any side effects of CAR T-cell therapy can be regulated in a precise, temporal manner by rapidly removing and/or (re-)administering the FDA-approved agent that induces CAR T-cell activation.

The generation of CAR T-cells is known in the art. For example, see Wang et al, "Clinical manufacturing of CAR T cells: foundation of a promising therapy," Oncolytics (2016) 3:1-7 (and incorporated herein). In general, the CAR T-cells of the disclosure can be generated by introducing a lentiviral vector including a desired CAR and/or CAR system, for example a CAR comprising anti-CD19, CD8α hinge and transmembrane domain, human CD28 and CD3zeta signaling domains, and degron OFF-switch into the cells. The CAR T-cells of the disclosure are able to replicate in vivo resulting in long-term persistence that can lead to sustained tumor control, and are subject to modulation of activation via administration of a FDA-approved drug to which the degron (OFF-switch) or heterodimer (ON-switch) is responsive.

In certain embodiments, genetically modified T-cells expressing a CAR or split CAR system of the disclosure for the treatment of a patient having cancer or at risk of having cancer are administered using lymphocyte infusion. Autologous lymphocyte infusion is used in the treatment. Autologous PBMCs are collected from a patient in need of treatment and T-cells are activated and expanded using the methods described herein and known in the art and then infused back into the patient.

In yet another embodiment, the treatment of a patient at risk of developing CLL is provided. The disclosure also includes treating a malignancy or an autoimmune disease in which chemotherapy and/or immunotherapy in a patient results in significant immunosuppression in the patient, thereby increasing the risk of the patient of developing CLL.

The disclosure includes using CAR T-cells that express a CAR or split CAR system of the disclosure. The CAR T-cells of the disclosure can undergo robust in vivo CAR T-cell expansion and can establish targeted antigen-specific memory cells that persist at high levels for an extended amount of time in blood and bone marrow. In some instances, the CAR T-cells of the disclosure infused into a patient can be modulated by administering to the subject an FDA-approved compound that is capable of activating the CAR (ON-switch split CAR system aspects), thereby activating the CAR T-cell, or provoking degradation of the CAR (OFF-switch aspects) and down regulation of the CAR T-cell activation without destroying the CAR T-cell.

In one aspect, a nucleic acid is provided that encodes a CAR having an extracellular ligand binding domain, a transmembrane domain, and a cytoplasmic domain having at least one intracellular signaling domain and a degron capable of being bound by an FDA-approved agent and a component of the E3 ubiquitin/proteasome degradation system, e.g., cereblon (CRBN).

Specific sequences of certain aspects of the instant disclosure include the following: "Artichoke" (SFFV.BsmBI-CloneSite-17AARigidLinker-EGFP.IRES.mCherry.cppt.EF1a.PuroR; see FIG. 9):

(SEQ ID NO: 70)

CGAACGACCGAGCGCAGCGAGTCAGTGAGCGAGGAAGCGGAAGAGCGCCCAATACG

CAAACCGCCTCTCCCCGCGCGTTGGCCGATTCATTAATGCAGCTGGCACGACAGGTTT

CCCGACTGGAAAGCGGGCAGTGAGCGCAACGCAATTAATGTGAGTTAGCTCACTCAT

TAGGCACCCCAGGCTTTACACTTTATGCTTCCGGCTCGTATGTTGTGTGGAATTGTGAG

CGGATAACAATTTCACACAGGAAACAGCTATGACCATGATTACGCCAAGCGCGCAAT

TAACCCTCACTAAAGGGAACAAAAGCTGGAGCTGCAAGCTTAATGTAGTCTTATGCA

ATACTCTTGTAGTCTTGCAACATGGTAACGATGAGTTAGCAACATGCCTTACAAGGAG

AGAAAAAGCACCGTGCATGCCGATTGGTGGAAGTAAGGTGGTACGATCGTGCCTTAT

TAGGAAGGCAACAGACGGGTCTGACATGGATTGGACGAACCACTGAATTGCCGCATT

GCAGAGATATTGTATTTAAGTGCCTAGCTCGATACATAAACGGGTCTCTCTGGTTAGA

CCAGATCTGAGCCTGGGAGCTCTCTGGCTAACTAGGGAACCCACTGCTTAAGCCTCAA

TAAAGCTTGCCTTGAGTGCTTCAAGTAGTGTGTGCCCGTCTGTTGTGTGACTCTGGTAA

CTAGAGATCCCTCAGACCCTTTTAGTCAGTGTGGAAAATCTCTAGCAGTGGCGCCCGA

ACAGGGACTTGAAAGCGAAAGGGAAACCAGAGGAGCTCTCTCGACGCAGGACTCGG

CTTGCTGAAGCGCGCACGGCAAGAGGCGAGGGGCGGCGACTGGTGAGTACGCCAAA

AATTTTGACTAGCGGAGGCTAGAAGGAGAGAGATGGGTGCGAGAGCGTCAGTATTAA

GCGGGGGAGAATTAGATCGCGATGGGAAAAAATTCGGTTAAGGCCAGGGGGAAAGA

AAAAATATAAATTAAAACATATAGTATGGGCAAGCAGGGAGCTAGAACGATTCGCAG

TTAATCCTGGCCTGTTAGAAACATCAGAAGGCTGTAGACAAATACTGGGACAGCTAC

AACCATCCCTTCAGACAGGATCAGAAGAACTTAGATCATTATATAATACAGTAGCAA

CCCTCTATTGTGTGCATCAAAGGATAGAGATAAAAGACACCAAGGAAGCTTTAGACA

AGATAGAGGAAGAGCAAAACAAAAGTAAGACCACCGCACAGCAAGCGGCCGCTGAT

CTTCAGACCTGGAGGAGGAGATATGAGGGACAATTGGAGAAGTGAATTATATAAATA

-continued

TAAAGTAGTAAAAATTGAACCATTAGGAGTAGCACCCACCAAGGCAAAGAGAAGAGT
GGTGCAGAGAGAAAAAAGAGCAGTGGGAATAGGAGCTTTGTTCCTTGGGTTCTTGGG
AGCAGCAGGAAGCACTATGGGCGCAGCGTCAATGACGCTGACGGTACAGGCCAGACA
ATTATTGTCTGGTATAGTGCAGCAGCAGAACAATTTGCTGAGGGCTATTGAGGCGCAA
CAGCATCTGTTGCAACTCACAGTCTGGGGCATCAAGCAGCTCCAGGCAAGAATCCTG
GCTGTGGAAAGATACCTAAAGGATCAACAGCTCCTGGGGATTTGGGGTTGCTCTGGA
AAACTCATTTGCACCACTGCTGTGCCTTGGAATGCTAGTTGGAGTAATAAATCTCTGG
AACAGATTTGGAATCACACGACCTGGATGGAGTGGGACAGAGAAATTAACAATTACA
CAAGCTTAATACACTCCTTAATTGAAGAATCGCAAAACCAGCAAGAAAAGAATGAAC
AAGAATTATTGGAATTAGATAAATGGGCAAGTTTGTGGAATTGGTTTAACATAACAAA
TTGGCTGTGGTATATAAAATTATTCATAATGATAGTAGGAGGCTTGGTAGGTTTAAGA
ATAGTTTTTGCTGTACTTTCTATAGTGAATAGAGTTAGGCAGGGATATTCACCATTATC
GTTTCAGACCCACCTCCCAACCCCGAGGGGACCCTATTCCAGCACATATGAGCTAGCT
GCAGTAACGCCATTTTGCAAGGCATGGAAAAATACCAAACCAAGAATAGAGAAGTTC
AGATCAAGGGCGGGTACATGAAAATAGCTAACGTTGGGCCAAACAGGATATCTGCGG
TGAGCAGTTTCGGCCCCGGCCCGGGGCCAAGAACAGATGGTCACCGCAGTTTCGGCC
CCGGCCCGAGGCCAAGAACAGATGGTCCCCAGATATGGCCCAACCCTCAGCAGTTTC
TTAAGACCCATCAGATGTTTCCAGGCTCCCCCAAGGACCTGAAATGACCCTGCGCCTT
ATTTGAATTAACCAATCAGCCTGCTTCTCGCTTCTGTTCGCGCGCTTCTGCTTCCCGAG
CTCTATAAAAGAGCTCACAACCCCTCACTCGGCGCGCCAGTCCTCCGACAGACTGAGT
CGGCCGGTCGAATCAAGCTTATCGATACCGTCGACTCCGGAATAGCCACCATGGAGA
CGGACGTCTCAgctgaagctgctgcaAAGgaagctgcagctAAGgaggctgcagctA
AGgctGTGAGCAAGGGCGAGGAGCTGTTCACCGGGGTGGTGCCCATCCTGGTCGAGCTG
GACGGCGACGTAAACGGCCACAAGTTCAGCGTGTCCGGCGAGGGCGAGGGCGATGCCAC
CTACGGCAAGCTGACCCTGAAGTTCATCTGCACCACCGGCAAGCTGCCCGTGCCCTGGC
CCACCCTCGTGACCACCCTGACCTACGGCGTGCAGTGCTTCAGCCGCTACCCCGACCAC
ATGAAGCAGCACGACTTCTTCAAGTCCGCCATGCCCGAAGGCTACGTCCAGGAGCGCAC
CATCTTCTTCAAGGACGACGGCAACTACAAGACCCGCGCCGAGGTGAAGTTCGAGGGCG
ACACCCTGGTGAACCGCATCGAGCTGAAGGGCATCGACTTCAAGGAGGACGGCAACATC
CTGGGGCACAAGCTGGAGTACAACTACAACAGCCACAACGTCTATATCATGGCCGACAA
GCAGAAGAACGGCATCAAGGTGAACTTCAAGATCCGCCACAACATCGAGGACGGCAGC
GTGCAGCTCGCCGACCACTACCAGCAGAACACCCCCATCGGCGACGGCCCCGTGCTG
CTGCCCGACAACCACTACCTGAGCACCCAGTCCGCCCTGAGCAAAGACCCCAACGAG
AAGCGCGATCACATGGTCCTGCTGGAGTTCGTGACCGCCGCCGGGATCACTCTCGGCA
TGGACGAGCTGTACAAGTAAATGCATGAGTAACTGAGGATCCGCCCCTCTCCCTCCCC
CCCCCCTAACGTTACTGGCCGAAGCCGCTTGGAATAAGGCCGGTGTGCGTTTGTCTAT
ATGTTATTTTCCACCATATTGCCGTCTTTTGGCAATGTGAGGGCCCGGAAACCTGGCC
CTGTCTTCTTGACGAGCATTCCTAGGGGTCTTTCCCCTCTCGCCAAAGGAATGCAAGG
TCTGTTGAATGTCGTGAAGGAAGCAGTTCCTCTGGAAGCTTCTTGAAGACAAACAACG
TCTGTAGCGACCCTTTGCAGGCAGCGGAACCCCCCACCTGGCGACAGGTGCCTCTGCG -continued

GCCAAAAGCCACGTGTATAAGATACACCTGCAAAGGCGGCACAACCCCAGTGCCACG

TTGTGAGTTGGATAGTTGTGGAAAGAGTCAAATGGCTCTCCTCAAGCGTATTCAACAA

GGGGCTGAAGGATGCCCAGAAGGTACCCCATTGTATGGGATCTGATCTGGGGCCTCG

GTACACATGCTTTACATGTGTTTAGTCGAGGTTAAAAAAACGTCTAGGCCCCCCGAAC

CACGGGGACGTGGTTTTCCTTTGAAAAACACGATGATAATATGGCCACAACCCTGGA

ATTCGCCACCATGGTGAGCAAGGGCGAGGAGGATAACATGGCCATCATCAAGGAGTT

CATGCGCTTCAAGGTGCACATGGAGGGCTCCGTGAACGGCCACGAGTTCGAGATCGA

GGGCGAGGGCGAGGGCCGCCCCTACGAGGGCACCCAGACCGCCAAGCTGAAGGTGA

CCAAGGGTGGCCCCCTGCCCTTCGCCTGGGACATCCTGTCCCCTCAGTTCATGTACGG

CTCCAAGGCCTACGTGAAGCACCCCGCCGACATCCCCGACTACTTGAAGCTGTCCTTC

CCCGAGGGCTTCAAGTGGGAGCGCGTGATGAACTTCGAGGACGGCGGCGTGGTGACC

GTGACCCAGGACTCCTCCCTGCAGGACGGCGAGTTCATCTACAAGGTGAAGCTGCGC

GGCACCAACTTCCCCTCCGACGGCCCCGTAATGCAGAAGAAGACCATGGGCTGGGAG

GCCTCCTCCGAGCGGATGTACCCCGAGGACGGCGCCCTGAAGGGCGAGATCAAGCAG

AGGCTGAAGCTGAAGGACGGCGGCCACTACGACGCTGAGGTCAAGACCACCTACAAG

GCCAAGAAGCCCGTGCAGCTGCCCGGCGCCTACAACGTCAACATCAAGTTGGACATC

ACCTCCCACAACGAGGACTACACCATCGTGGAACAGTACGAACGCGCCGAGGGCCGC

CACTCCACCGGCGGCATGGACGAGCTGTACAAGTAAACTAGTAAGCTTGGCGTAACT

AGATCTTGAGACAAATGGCAGTATTCATCCACAATTTTAAAAGAAAAGGGGGGATTG

GGGGGTACAGTGCAGGGGAAAGAATAGTAGACATAATAGCAACAGACATACAAACT

AAAGAATTACAAAAACAAATTACAAAAATTCAAAATTTTCGGGTTTATTACAGGGAC

AGCAGAGATCCACTTTGGGCTCGAGGGGGCCCGGGTGCAAAGATGGATAAAGTTTTA

AACAGAGAGGAATCTTTGCAGCTAATGGACCTTCTAGGTCTTGAAAGGAGTGGGAAT

TGGCTCCGGTGCCCGTCAGTGGGCAGAGCGCACATCGCCCACAGTCCCCGAGAAGTT

GGGGGGAGGGGTCGGCAATTGATCCGGTGCCTAGAGAAGGTGGCGCGGGGTAAACTG

GGAAAGTGATGTCGTGTACTGGCTCCGCCTTTTTCCCGAGGGTGGGGGAGAACCGTAT

ATAAGTGCAGTAGTCGCCGTGAACGTTCTTTTTCGCAACGGGTTTGCCGCCAGAACAC

AGGTAAGTGCCGTGTGTGGTTCCCGCGGGCCTGGCCTCTTTACGGGTTATGGCCCTTG

CGTGCCTTGAATTACTTCCACCTGGCTGCAGTACGTGATTCTTGATCCCGAGCTTCGGG

TTGGAAGTGGGTGGGAGAGTTCGAGGCCTTGCGCTTAAGGAGCCCCTTCGCCTCGTGC

TTGAGTTGAGGCCTGGCCTGGGCGCTGGGGCCGCCGCGTGCGAATCTGGTGGCACCTT

CGCGCCTGTCTCGCTGCTTTCGATAAGTCTCTAGCCATTTAAAATTTTTGATGACCTGC

TGCGACGCTTTTTTTCTGGCAAGATAGTCTTGTAAATGCGGGCCAAGATCTGCACACT

GGTATTTCGGTTTTTGGGGCCGCGGGCGGCGACGGGGCCCGTGCGTCCCAGCGCACAT

GTTCGGCGAGGCGGGGCCTGCGAGCGCGGCCACCGAGAATCGGACGGGGGTAGTCTC

AAGCTGGCCGGCCTGCTCTGGTGCCTGGCCTCGCGCCGCCGTGTATCGCCCCGCCCTG

GGCGGCAAGGCTGGCCCGGTCGGCACCAGTTGCGTGAGCGGAAAGATGGCCGCTTCC

CGGCCCTGCTGCAGGGAGCTCAAAATGGAGGACGCGGCGCTCGGGAGAGCGGGCGG

GTGAGTCACCCACACAAAGGAAAAGGGCCTTTCCGTCCTCAGCCGTCGCTTCATGTGA

CTCCACGGAGTACCGGGCGCCGTCCAGGCACCTCGATTAGTTCTCGAGCTTTTGGAGT

ACGTCGTCTTTAGGTTGGGGGGAGGGGTTTTATGCGATGGAGTTTCCCCACACTGAGT

-continued

GGGTGGAGACTGAAGTTAGGCCAGCTTGGCACTTGATGTAATTCTCCTTGGAATTTGC

CCTTTTTGAGTTTGGATCTTGGTTCATTCTCAAGCCTCAGACAGTGGTTCAAAGTTTTT

TTCTTCCATTTCAGGTGTCGTGACGTACGGCCACCATGACCGAGTACAAGCCCACGGT

GCGCCTCGCCACCCGCGACGACGTCCCCAGGGCCGTACGCACCCTCGCCGCCGCGTTC

GCCGACTACCCCGCCACGCGCCACACCGTCGATCCGGACCGCCACATCGAGCGGGTC

ACCGAGCTGCAAGAACTCTTCCTCACGCGCGTCGGGCTCGACATCGGCAAGGTGTGG

GTCGCGGACGACGGCGCCGCCGTGGCGGTCTGGACCACGCCGGAGAGCGTCGAAGCG

GGGGCGGTGTTCGCCGAGATCGGCCCGCGCATGGCCGAGTTGAGCGGTTCCCGGCTG

GCCGCGCAGCAACAGATGGAAGGCCTCCTGGCGCCGCACCGGCCCAAGGAGCCCGCG

TGGTTCCTGGCCACCGTCGGAGTCTCGCCCGACCACCAGGGCAAGGGTCTGGGCAGC

GCCGTCGTGCTCCCCGGAGTGGAGGCGGCCGAGCGCGCCGGGGTGCCCGCCTTCCTG

GAGACCTCCGCGCCCCGCAACCTCCCCTTCTACGAGCGGCTCGGCTTCACCGTCACCG

CCGACGTCGAGGTGCCCGAAGGACCGCGCACCTGGTGCATGACCCGCAAGCCCGGTG

CCTGAACGCGTTAAGTCGACAATCAACCTCTGGATTACAAAATTTGTGAAAGATTGAC

TGGTATTCTTAACTATGTTGCTCCTTTTACGCTATGTGGATACGCTGCTTTAATGCCTTT

GTATCATGCTATTGCTTCCCGTATGGCTTTCATTTTCTCCTCCTTGTATAAATCCTGGTT

GCTGTCTCTTTATGAGGAGTTGTGGCCCGTTGTCAGGCAACGTGGCGTGGTGTGCACT

GTGTTTGCTGACGCAACCCCCACTGGTTGGGGCATTGCCACCACCTGTCAGCTCCTTTC

CGGGACTTTCGCTTTCCCCCTCCCTATTGCCACGGCGGAACTCATCGCCGCCTGCCTTG

CCCGCTGCTGGACAGGGGCTCGGCTGTTGGGCACTGACAATTCCGTGGTGTTGTCGGG

GAAATCATCGTCCTTTCCTTGGCTGCTCGCCTGTGTTGCCACCTGGATTCTGCGCGGGA

CGTCCTTCTGCTACGTCCCTTCGGCCCTCAATCCAGCGGACCTTCCTTCCCGCGGCCTG

CTGCCGGCTCTGCGGCCTCTTCCGCGTCTTCGCCTTCGCCCTCAGACGAGTCGGATCTC

CCTTTGGGCCGCCTCCCCGCGTCGACTTTAAGACCAATGACTTACAAGGCAGCTGTAG

ATCTTAGCCACTTTTTAAAAGAAAAGGGGGGACTGGAAGGGCTAATTCACTCCCAAC

GAAGACAAGATCTGCTTTTTGCTTGTACTGGGTCTCTCTGGTTAGACCAGATCTGAGC

CTGGGAGCTCTCTGGCTAACTAGGGAACCCACTGCTTAAGCCTCAATAAAGCTTGCCT

TGAGTGCTTCAAGTAGTGTGTGCCCGTCTGTTGTGTGACTCTGGTAACTAGAGATCCC

TCAGACCCTTTTAGTCAGTGTGGAAAATCTCTAGCAGTACGTATAGTAGTTCATGTCA

TCTTATTATTCAGTATTTATAACTTGCAAAGAAATGAATATCAGAGAGTGAGAGGAAC

TTGTTTATTGCAGCTTATAATGGTTACAAATAAAGCAATAGCATCACAAATTTCACAA

ATAAAGCATTTTTTTCACTGCATTCTAGTTGTGGTTTGTCCAAACTCATCAATGTATCT

TATCATGTCTGGCTCTAGCTATCCCGCCCCTAACTCCGCCCATCCCGCCCCTAACTCCG

CCCAGTTCCGCCCATTCTCCGCCCCATGGCTGACTAATTTTTTTTATTTATGCAGAGGC

CGAGGCCGCCTCGGCCTCTGAGCTATTCCAGAAGTAGTGAGGAGGCTTTTTTGGAGGC

CTAGGGACGTACCCAATTCGCCCTATAGTGAGTCGTATTACGCGCGCTCACTGGCCGT

CGTTTTACAACGTCGTGACTGGGAAAACCCTGGCGTTACCCAACTTAATCGCCTTGCA

GCACATCCCCCTTTCGCCAGCTGGCGTAATAGCGAAGAGGCCCGCACCGATCGCCCTT

CCCAACAGTTGCGCAGCCTGAATGGCGAATGGGACGCGCCCTGTAGCGGCGCATTAA

GCGCGGCGGGTGTGGTGGTTACGCGCAGCGTGACCGCTACACTTGCCAGCGCCCTAG

-continued

CGCCCGCTCCTTTCGCTTTCTTCCCTTCCTTTCTCGCCACGTTCGCCGGCTTTCCCCGTC

AAGCTCTAAATCGGGGGCTCCCTTTAGGGTTCCGATTTAGTGCTTTACGGCACCTCGA

CCCCAAAAAACTTGATTAGGGTGATGGTTCACGTAGTGGGCCATCGCCCTGATAGACG

GTTTTTCGCCCTTTGACGTTGGAGTCCACGTTCTTTAATAGTGGACTCTTGTTCCAAAC

TGGAACAACACTCAACCCTATCTCGGTCTATTCTTTTGATTTATAAGGGATTTTGCCGA

TTTCGGCCTATTGGTTAAAAAATGAGCTGATTTAACAAAAATTTAACGCGAATTTTAA

CAAAATATTAACGCTTACAATTTAGGTGGCACTTTTCGGGGAAATGTGCGCGGAACCC

CTATTTGTTTATTTTTCTAAATACATTCAAATATGTATCCGCTCATGAGACAATAACCC

TGATAAATGCTTCAATAATATTGAAAAAGGAAGAGTATGAGTATTCAACATTTCCGTG

TCGCCCTTATTCCCTTTTTTGCGGCATTTTGCCTTCCTGTTTTTGCTCACCCAGAAACGC

TGGTGAAAGTAAAAGATGCTGAAGATCAGTTGGGTGCACGAGTGGGTTACATCGAAC

TGGATCTCAACAGCGGTAAGATCCTTGAGAGTTTTCGCCCCGAAGAACGTTTTCCAAT

GATGAGCACTTTTAAAGTTCTGCTATGTGGCGCGGTATTATCCCGTATTGACGCCGGG

CAAGAGCAACTCGGTCGCCGCATACACTATTCTCAGAATGACTTGGTTGAGTACTCAC

CAGTCACAGAAAAGCATCTTACGGATGGCATGACAGTAAGAGAATTATGCAGTGCTG

CCATAACCATGAGTGATAACACTGCGGCCAACTTACTTCTGACAACGATCGGAGGAC

CGAAGGAGCTAACCGCTTTTTTGCACAACATGGGGGATCATGTAACTCGCCTTGATCG

TTGGGAACCGGAGCTGAATGAAGCCATACCAAACGACGAGCGTGACACCACGATGCC

TGTAGCAATGGCAACAACGTTGCGCAAACTATTAACTGGCGAACTACTTACTCTAGCT

TCCCGGCAACAATTAATAGACTGGATGGAGGCGGATAAAGTTGCAGGACCACTTCTG

CGCTCGGCCCTTCCGGCTGGCTGGTTTATTGCTGATAAATCTGGAGCCGGTGAGCGTG

GGTCTCGCGGTATCATTGCAGCACTGGGGCCAGATGGTAAGCCCTCCCGTATCGTAGT

TATCTACACGACGGGGAGTCAGGCAACTATGGATGAACGAAATAGACAGATCGCTGA

GATAGGTGCCTCACTGATTAAGCATTGGTAACTGTCAGACCAAGTTTACTCATATATA

CTTTAGATTGATTTAAAACTTCATTTTTAATTTAAAAGGATCTAGGTGAAGATCCTTTT

TGATAATCTCATGACCAAAATCCCTTAACGTGAGTTTTCGTTCCACTGAGCGTCAGAC

CCCGTAGAAAAGATCAAAGGATCTTCTTGAGATCCTTTTTTTCTGCGCGTAATCTGCTG

CTTGCAAACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAAATACTGTT

CTTCTAGTGTAGCCGTAGTTAGGCCACCACTTCAAGAACTCTGTAGCACCGCCTACAT

ACCTCGCTCTGCTAATCCTGTTACCAGTGGCTGCTGCCAGTGGCGATAAGTCGTGTCTT

ACCGGGTTGGACTCAAGACGATAGTTACCGGATAAGGCGCAGCGGTCGGGCTGAACG

GGGGGTTCGTGCACACAGCCCAGCTTGGAGCGAACGACCTACACCGAACTGAGATAC

CTACAGCGTGAGCTATGAGAAAGCGCCACGCTTCCCGAAGGGAGAAAGGCGGACAG

GTATCCGGTAAGCGGCAGGGTCGGAACAGGAGAGCGCACGAGGGAGCTTCCAGGGG

GAAACGCCTGGTATCTTTATAGTCCTGTCGGGTTTCGCCACCTCTGACTTGAGCGTCG

ATTTTTGTGATGCTCGTCAGGGGGGCGGAGCCTATGGAAAAACGCCAGCAACGCGGC

CTTTTTACGGTTCCTGGCCTTTTGCTGGCCTTTTGCTCACATGTTCTTTCCTGCGTTATC

CCCTGATTCTGTGGATAACCGTATTACCGCCTTTGAGTGAGCTGATACCGCTCGCCGC

AGC

-continued pFC14K (Promega)

(SEQ ID NO: 71)

TCAATATTGGCCATTAGCCATATTATTCATTGGTTATATAGCATAAATCAATATTGGCT

ATTGGCCATTGCATACGTTGTATCTATATCATAATATGTACATTTATATTGGCTCATGT

CCAATATGACCGCCATGTTGGCATTGATTATTGACTAGTTATTAATAGTAATCAATTA

CGGGGTCATTAGTTCATAGCCCATATATGGAGTTCCGCGTTACATAACTTACGGTAAA

TGGCCCGCCTGGCTGACCGCCCAACGACCCCCGCCCATTGACGTCAATAATGACGTAT

GTTCCCATAGTAACGCCAATAGGGACTTTCCATTGACGTCAATGGGTGGAGTATTTAC

GGTAAACTGCCCACTTGGCAGTACATCAAGTGTATCATATGCCAAGTCCGCCCCCTAT

TGACGTCAATGACGGTAAATGGCCCGCCTGGCATTATGCCCAGTACATGACCTTACGG

GACTTTCCTACTTGGCAGTACATCTACGTATTAGTCATCGCTATTACCATGGTGATGCG

GTTTTGGCAGTACACCAATGGGCGTGGATAGCGGTTTGACTCACGGGGATTTCCAAGT

CTCCACCCCATTGACGTCAATGGGAGTTTGTTTTGGCACCAAAATCAACGGGACTTTC

CAAAATGTCGTAATAACCCCGCCCCGTTGACGCAAATGGGCGGTAGGCGTGTACGGT

GGGAGGTCTATATAAGCAGAGCTGGTTTAGTGAACCGTCAGATCACTAGAAGCTTTAT

TGCGGTAGTTTATCACAGTTAAATTGCTAACGCAGTCAGTGCTTCTGACACAACAGTC

TCGAACTTAAGCTGCAGAAGTTGGTCGTGAGGCACTGGGCAGGTAAGTATCAAGGTT

ACAAGACAGGTTTAAGGAGACCAATAGAAACTGGGCTTGTCGAGACAGAGAAGACTC

TTGCGTTTCTGATAGGCACCTATTGGTCTTACTGACATCCACTTTGCCTTTCTCTCCAC

AGGTGTCCACTCCCAGTTCAATTACAGCTCTTAAGGCTAGAGTATTAATACGACTCAC

TATAGGGCTAGCGATCGCCATGGAATAAGTAAGGAATCCACATGGCACAGGTTATCA

ACACGTTTGACGGGGTTGCGGATTATCTTCAGACATATCATAAGCTACCTGATAATTA

CATTACAAAATCAGAAGCACAAGCCCTCGGCTGGGTGGCATCAAAAGGGAACCTTGC

AGACGTCGCTCCGGGGAAAAGCATCGGCGGAGACATCTTCTCAAACAGGGAAGGCAA

ACTCCCGGGCAAAAGCGGACGAACATGGCGTGAAGCGGATATTAACTATACATCAGG

CTTCAGAAATTCAGACCGGATTCTTTACTCAAGCGACTGGCTGATTTACAAAACAACG

GACCATTATCAGACCTTTACAAAAATCAGATAATGTTTAATGACCCCGTGTCGAGCTC

TCGAGCCAACCACTGAGGATCTGTACTTTCAGAGCGATAACGATGGATCCGAAATCG

GTACTGGCTTTCCATTCGACCCCCATTATGTGGAAGTCCTGGGCGAGCGCATGCACTA

CGTCGATGTTGGTCCGCGCGATGGCACCCCTGTGCTGTTCCTGCACGGTAACCCGACC

TCCTCCTACGTGTGGCGCAACATCATCCCGCATGTTGCACCGACCCATCGCTGCATTG

CTCCAGACCTGATCGGTATGGGCAAATCCGACAAACCAGACCTGGGTTATTTCTTCGA

CGACCACGTCCGCTTCATGGATGCCTTCATCGAAGCCCTGGGTCTGGAAGAGGTCGTC

CTGGTCATTCACGACTGGGGCTCCGCTCTGGGTTTCCACTGGGCCAAGCGCAATCCAG

AGCGCGTCAAAGGTATTGCATTTATGGAGTTCATCCGCCCTATCCCGACCTGGGACGA

ATGGCCAGAATTTGCCCGCGAGACCTTCCAGGCCTTCCGCACCACCGACGTCGGCCGC

AAGCTGATCATCGATCAGAACGTTTTTATCGAGGGTACGCTGCCGATGGGTGTCGTCC

GCCCGCTGACTGAAGTCGAGATGGACCATTACCGCGAGCCGTTCCTGAATCCTGTTGA

CCGCGAGCCACTGTGGCGCTTCCCAAACGAGCTGCCAATCGCCGGTGAGCCAGCGAA

CATCGTCGCGCTGGTCGAAGAATACATGGACTGGCTGCACCAGTCCCCTGTCCCGAAG

CTGCTGTTCTGGGGCACCCCAGGCGTTCTGATCCCACCGGCCGAAGCCGCTCGCCTGG

-continued

CCAAAAGCCTGCCTAACTGCAAGGCTGTGGACATCGGCCCGGGTCTGAATCTGCTGCA

AGAAGACAACCCGGACCTGATCGGCAGCGAGATCGCGCGCTGGCTGTCTACTCTGGA

GATTTCCGGTTAATAGAATTCTAGAGTCGACCTGCAGGCATGCAAGCTGATCCGGCTG

CTAACAAAGCCCGAAAGGAAGCTGAGTTGGCTGCTGCCACCGCTGAGCAATAACTAG

CATAACCCCTTGGGGCGGCCGCTTCGAGCAGACATGATAAGATACATTGATGAGTTTG

GACAAACCACAACTAGAATGCAGTGAAAAAAATGCTTTATTTGTGAAATTTGTGATGC

TATTGCTTTATTTGTAACCATTATAAGCTGCAATAAACAAGTTAACAACAACAATTGC

ATTCATTTTATGTTTCAGGTTCAGGGGGAGATGTGGGAGGTTTTTTAAAGCAAGTAAA

ACCTCTACAAATGTGGTAAAATCGAATTCTAATGGATCCTCTTTGCGCTTGCGTTTTCC

CTTGTCCAGATAGCCCAGTAGCTGACATTCATCCGGGGTCAGCACCGTTTCTGCGGAC

TGGCTTTCTACGTGTTCCGCTTCCTTTAGCAGCCCTTGCGCCCTGAGTGCTTGCGGCAG

CGTGAGCTTCAAAAGAATTGCCAGCTGGGGCGCCCTCTGGTAAGGTTGGGAAGCCCT

GCAAAGTAAACTGGATGGCTTTCTTGCCGCCAAGGATCTGATGGCGCAGGGGATCAA

GATCTGATCAAGAGACAGGATGACGGTCGTTTCGCATGCTTGAACAAGATGGATTGC

ACGCAGGTTCTCCGGCCGCTTGGGTGGAGAGGCTATTCGGCTATGACTGGGCACAAC

AGACAATCGGCTGCTCTGATGCCGCCGTGTTCCGGCTGTCAGCGCAGGGGCGCCCGGT

TCTTTTTGTCAAGACCGACCTGTCCGGTGCCCTGAATGAACTGCAGGACGAGGCAGCG

CGGCTATCGTGGCTGGCCACGACGGGCGTTCCTTGCGCAGCTGTGCTCGACGTTGTCA

CTGAAGCGGGAAGGGACTGGCTGCTATTGGGCGAAGTGCCGGGGCAGGATCTCCTGT

CATCTCACCTTGCTCCTGCCGAGAAAGTATCCATCATGGCTGATGCAATGCGGCGGCT

GCATACGCTTGATCCGGCTACCTGCCCATTCGACCACCAAGCGAAACATCGCATCGAG

CGAGCACGCACTCGGATGGAAGCCGGTCTTGTCGATCAGGATGATCTGGACGAAGAG

CATCAGGGGCTCGCGCCAGCCGAACTGTTCGCCAGGCTCAAGGCGCGTATGCCGGAT

GGTGAGGATCTCGTCGTGACTCATGGCGATGCCTGCTTGCCGAATATCATGGTGGAAA

ATGGCCGCTTTTCTGGATTCATCGACTGTGGCCGGCTGGGTGTGGCGGACCGCTATCA

GGACATAGCGTTGGCTACCCGTGATATTGCTGAAGAGCTTGGCGGCGAATGGGCTGA

CCGCTTCCTCGTGCTTTACGGTATCGCCGCTCCCGATTCGCAGCGCATCGCCTTCTATC

GCCTTCTTGACGAGTTCTTCTGAGCGGGACTCTGGGGTTCGAAATGACCGACCAAGCG

ACGCCCAACCGGTATCAGCTCACTCAAAGGCGGTAATACGGTTATCCACAGAATCAG

GGGATAACGCAGGAAAGAACATGTGAGCAAAAGGCCAGCAAAAGGCCAGGAACCGT

AAAAAGGCCGCGTTGCTGGCGTTTTTCCATAGGCTCCGCCCCCCTGACGAGCATCACA

AAAATCGACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCGCTTACCGGA

TACCTGTCCGCCTTTCTCCCTTCGGGAAGCGTGGCGCTTTCTCATAGCTCACGCTGTAG

GTATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTAA

GACACGACTTATCGCCACTGGCAGCAGCCACTGGTAACAGGATTAGCAGAGCGAGGT

ATGTAGGCGGTGCTACAGAGTTCTTGAAGTGGTGGCCTAACTACGGCTACACTAGAA

GGACAGTATTTGGTATCTGCGCTCTGCTGAAGCCAGTTACCTTCGGAAAAAGAGTTGG

TAGCTCTTGATCCGGCAAACAAACCACCGCTGGTAGCGGTGGTTTTTTTGTTTGCAAG

CAGCAGATTACGCGCAGAAAAAAAGGATTTCAAGAAGATCCTTTGATCTTTTCTACGG

-continued

GGTCTGACGCTCAGTGGAACGAAAACTCACGTTAAGGGATTTTGGTCATGAGATTATC

AAAAAGGATCTTCACCTAGATCCTTTTATAGTCCGGAAATACAGGAACGCACGCTGG

ATGGCCCTTCGCTGGGATGGTGAAACCATGAAAAATGGCAGCTTCAGTGGATTAAGT

GGGGGTAATGTGGCCTGTACCCTCTGGTTGCATAGGTATTCATACGGTTAAAATTTAT

CAGGCGCGATTGCGGCAGTTTTTCGGGTGGTTTGTTGCCATTTTTACCTGTCTGCTGCC

GTGATCGCGCTGAACGCGTTTTAGCGGTGCGTACAATTAAGGGATTATGGTAAATCCA

CTTACTGTCTGCCCTCGTAGCCATCGAGATAAACCGCAGTACTCCGGCCACGATGCGT

CCGGCGTAGAGGATCGAGATCT pFC32K (Promega)

(SEQ ID NO: 72)

TCAATATTGGCCATTAGCCATATTATTCATTGGTTATATAGCATAAATCAATATTGGCT

ATTGGCCATTGCATACGTTGTATCTATATCATAATATGTACATTTATATTGGCTCATGT

CCAATATGACCGCCATGTTGGCATTGATTATTGACTAGTTATTAATAGTAATCAATTA

CGGGGTCATTAGTTCATAGCCCATATATGGAGTTCCGCGTTACATAACTTACGGTAAA

TGGCCCGCCTGGCTGACCGCCCAACGACCCCCGCCCATTGACGTCAATAATGACGTAT

GTTCCCATAGTAACGCCAATAGGGACTTTCCATTGACGTCAATGGGTGGAGTATTTAC

GGTAAACTGCCCACTTGGCAGTACATCAAGTGTATCATATGCCAAGTCCGCCCCCTAT

TGACGTCAATGACGGTAAATGGCCCGCCTGGCATTATGCCCAGTACATGACCTTACGG

GACTTTCCTACTTGGCAGTACATCTACGTATTAGTCATCGCTATTACCATGGTGATGCG

GTTTTGGCAGTACACCAATGGGCGTGGATAGCGGTTTGACTCACGGGGATTTCCAAGT

CTCCACCCCATTGACGTCAATGGGAGTTTGTTTTGGCACCAAAATCAACGGGACTTTC

CAAAATGTCGTAATAACCCCGCCCCGTTGACGCAAATGGGCGGTAGGCGTGTACGGT

GGGAGGTCTATATAAGCAGAGCTGGTTTAGTGAACCGTCAGATCACTAGAAGCTTTAT

TGCGGTAGTTTATCACAGTTAAATTGCTAACGCAGTCAGTGCTTCTGACACAACAGTC

TCGAACTTAAGCTGCAGAAGTTGGTCGTGAGGCACTGGGCAGGTAAGTATCAAGGTT

ACAAGACAGGTTTAAGGAGACCAATAGAAACTGGGCTTGTCGAGACAGAGAAGACTC

TTGCGTTTCTGATAGGCACCTATTGGTCTTACTGACATCCACTTTGCCTTTCTCTCCAC

AGGTGTCCACTCCCAGTTCAATTACAGCTCTTAAGGCTAGAGTATTAATACGACTCAC

TATAGGGCTAGCGATCGCCATGGAATAAGTAAGGAATCCACATGGCACAGGTTATCA

ACACGTTTGACGGGGTTGCGGATTATCTTCAGACATATCATAAGCTACCTGATAATTA

CATTACAAAATCAGAAGCACAAGCCCTCGGCTGGGTGGCATCAAAAGGGAACCTTGC

AGACGTCGCTCCGGGGAAAAGCATCGGCGGAGACATCTTCTCAAACAGGGAAGGCAA

ACTCCCGGGCAAAAGCGGACGAACATGGCGTGAAGCGGATATTAACTATACATCAGG

CTTCAGAAATTCAGACCGGATTCTTTACTCAAGCGACTGGCTGATTTACAAAACAACG

GACCATTATCAGACCTTTACAAAAATCAGATAATGTTTAATGACCCCGTGTCGAGCTC

TCGGCTCGAGCGGCGTCTTCACACTCGAAGATTTCGTTGGGGACTGGCGACAGACAGC

CGGCTACAACCTGGACCAAGTCCTTGAACAGGGAGGTGTGTCCAGTTTGTTTCAGAAT

CTCGGGGTGTCCGTAACTCCGATCCAAAGGATTGTCCTGAGCGGTGAAAATGGGCTG

AAGATCGACATCCATGTCATCATCCCGTATGAAGGTCTGAGCGGCGACCAAATGGGC

CAGATCGAAAAAATTTTTAAGGTGGTGTACCCTGTGGATGATCATCACTTTAAGGTGA

TCCTGCACTATGGCACACTGGTAATCGACGGGGTTACGCCGAACATGATCGACTATTT

-continued

CGGACGGCCGTATGAAGGCATCGCCGTGTTCGACGGCAAAAAGATCACTGTAACAGG

GACCCTGTGGAACGGCAACAAAATTATCGACGAGCGCCTGATCAACCCCGACGGCTC

CCTGCTGTTCCGAGTAACCATCAACGGAGTGACCGGCTGGCGGCTGTGCGAACGCATT

CTGGCGTAAGGCCGCGACTCTAGAGTCGACCTGCAGGCATGCAAGCTGATCCGGCTG

CTAACAAAGCCCGAAAGGAAGCTGAGTTGGCTGCTGCCACCGCTGAGCAATAACTAG

CATAACCCCTTGGGGCGGCCGCTTCGAGCAGACATGATAAGATACATTGATGAGTTTG

GACAAACCACAACTAGAATGCAGTGAAAAAAATGCTTTATTTGTGAAATTTGTGATGC

TATTGCTTTATTTGTAACCATTATAAGCTGCAATAAACAAGTTAACAACAACAATTGC

ATTCATTTTATGTTTCAGGTTCAGGGGGAGATGTGGGAGGTTTTTTAAGCAAGTAAA

ACCTCTACAAATGTGGTAAAATCGAATTTTAACAAAATATTAACGCTTACAATTTCCT

GATGCGGTATTTTCTCCTTACGCATCTGTGCGGTATTTCACACCGCATACGCGGATCTG

CGCAGCACCATGGCCTGAAATAACCTCTGAAAGAGGAACTTGGTTAGGTACCTTCTGA

GGCGGAAAGAACCAGCTGTGGAATGTGTGTCAGTTAGGGTGTGGAAAGTCCCCAGGC

TCCCCAGCAGGCAGAAGTATGCAAAGCATGCATCTCAATTAGTCAGCAACCAGGTGT

GGAAAGTCCCCAGGCTCCCCAGCAGGCAGAAGTATGCAAAGCATGCATCTCAATTAG

TCAGCAACCATAGTCCCGCCCCTAACTCCGCCCATCCCGCCCCTAACTCCGCCCAGTT

CCGCCCATTCTCCGCCCCATGGCTGACTAATTTTTTTTATTTATGCAGAGGCCGAGGCC

GCCTCGGCCTCTGAGCTATTCCAGAAGTAGTGAGGAGGCTTTTTTGGAGGCCTAGGCT

TTTGCAAAAAGCTTAATTAACTGTTGACAATTAATCATCGGCATAGTATATCGGCATA

GTATAATACGACAAGGTGAGGAACTAAACCCAGGAGGCAGATCATGATTGAACAAGA

TGGATTGCACGCAGGTTCTCCGGCCGCTTGGGTGGAGAGGCTATTCGGCTATGACTGG

GCACAACAGACAATCGGCTGCTCTGATGCCGCCGTGTTCCGGCTGTCAGCGCAGGGG

CGCCCGGTTCTTTTTGTCAAGACCGACCTGTCCGGTGCCCTGAATGAACTGCAGGACG

AGGCAGCGCGGCTATCGTGGCTGGCCACGACGGGCGTTCCTTGCGCAGCTGTGCTCGA

CGTTGTCACTGAAGCGGGAAGGGACTGGCTGCTATTGGGCGAAGTGCCGGGGCAGGA

TCTCCTGTCATCTCACCTTGCTCCTGCCGAGAAAGTATCCATCATGGCTGATGCAATGC

GGCGGCTGCATACGCTTGATCCGGCTACCTGCCCATTCGACCACCAAGCGAAACATCG

CATCGAGCGAGCACGTACTCGGATGGAAGCCGGTCTTGTCGATCAGGATGATCTGGA

CGAAGAGCATCAGGGGCTCGCGCCAGCCGAACTGTTCGCCAGGCTCAAGGCGCGCAT

GCCCGACGGCGAGGATCTCGTCGTGACCCATGGCGATGCCTGCTTGCCGAATATCATG

GTGGAAAATGGCCGCTTTTCTGGATTCATCGACTGTGGCCGGCTGGGTGTGGCGGACC

GCTATCAGGACATAGCGTTGGCTACCCGTGATATTGCTGAAGAGCTTGGCGGCGAATG

GGCTGACCGCTTCCTCGTGCTTTACGGTATCGCCGCTCCCGATTCGCAGCGCATCGCCT

TCTATCGCCTTCTTGACGAGTTCTTCTGAGCGGGACTCTGGGGTTCGAAATGACCGAC

CAAGCGACGCCCAACCTGCCATCACGATGGCCGCAATAAAATATCTTTATTTTCATTA

CATCTGTGTGTTGGTTTTTTGTGTGAATCGATAGCGATAAGGATCCTCTTTGCGCTTGC

GTTTTCCCTTGTCCAGATAGCCCAGTAGCTGACATTCATCCGGGGTCAGCACCGTTTCT

GCGGACTGGCTTTCTACCCGGTATCAGCTCACTCAAAGGCGGTAATACGGTTATCCAC

AGAATCAGGGGATAACGCAGGAAAGAACATGTGAGCAAAAGGCCAGCAAAAGGCCA

GGAACCGTAAAAAGGCCGCGTTGCTGGCGTTTTTCCATAGGCTCCGCCCCCCTGACGA

GCATCACAAAAATCGACGCTCAAGTCAGAGGTGGCGAAACCCGACAGGACTATAAAG

-continued

ATACCAGGCGTTTCCCCCTGGAAGCTCCCTCGTGCGCTCTCCTGTTCCGACCCTGCCGC

TTACCGGATACCTGTCCGCCTTTCTCCCTTCGGGAAGCGTGGCGCTTTCTCATAGCTCA

CGCTGTAGGTATCTCAGTTCGGTGTAGGTCGTTCGCTCCAAGCTGGGCTGTGTGCACG

AACCCCCCGTTCAGCCCGACCGCTGCGCCTTATCCGGTAACTATCGTCTTGAGTCCAA

CCCGGTAAGACACGACTTATCGCCACTGGCAGCAGCCACTGGTAACAGGATTAGCAG

AGCGAGGTATGTAGGCGGTGCTACAGAGTTCTTGAAGTGGTGGCCTAACTACGGCTA

CACTAGAAGGACAGTATTTGGTATCTGCGCTCTGCTGAAGCCAGTTACCTTCGGAAAA

AGAGTTGGTAGCTCTTGATCCGGCAAACAAACCACCGCTGGTAGCGGTGGTTTTTTTG

TTTGCAAGCAGCAGATTACGCGCAGAAAAAAAGGATTTCAAGAAGATCCTTTGATCTT

TTCTACGGGGTCTGACGCTCAGTGGAACGAAAACTCACGTTAAGGGATTTTGGTCATG

AGATTATCAAAAAGGATCTTCACCTAGATCCTTTTATAGTCCGGAAATACAGGAACGC

ACGCTGGATGGCCCTTCGCTGGGATGGTGAAACCATGAAAAATGGCAGCTTCAGTGG

ATTAAGTGGGGGTAATGTGGCCTGTACCCTCTGGTTGCATAGGTATTCATACGGTTAA

AATTTATCAGGCGCGATTGCGGCAGTTTTTCGGGTGGTTTGTTGCCATTTTTACCTGTC

TGCTGCCGTGATCGCGCTGAACGCGTTTTAGCGGTGCGTACAATTAAGGGATTATGGT

AAATCCACTTACTGTCTGCCCTCGTAGCCATCGAGATAAACCGCAGTACTCCGGCCAC

GATGCGTCCGGCGTAGAGGATCGAGATCT

For BRET dimerization experiments, genes were cloned into pFC14K or pFC32K vectors at Sgf1/EcoICRI restriction sites per manufacturer directions (Promega). For degradation eGFP/mCherry reporter experiments, genes were cloned into the Artichoke vector at BsmBI restriction sites (see FIG. 9).

FMC63-CD28-IKZF3: This sequence corresponds to the anti-CD19 scFv FMC63 (www.ebi.ac.uk/ena/data/view/ADM64594), the CD28 hinge, transmembrane, and cytoplasmic domains (amino acids 114-220), and IKZF3 amino acids 130-189.

(SEQ ID NO: 73)
MLLLVTSLLLCELPHPAFLLIPDIQMTQTTSSLSASLGDRVTISCRASQD

ISKYLNWYQQKPDGTVKLLIYHTSRLHSGVPSRFSGSGSGTDYSLTISNL

EQEDIATYFCQQGNTLPYTFGGGTKLEITGSTSGSGKPGSGEGSTKGEVK

LQESGPGLVAPSQSLSVTCTVSGVSLPDYGVSWIRQPPRKGLEWLGVIWG

SETTYYNSALKSRLTIIKDNSKSQVFLKMNSLQTDDTAIYYCAKHYYYGG

SYAMDYWGQGTSVTVSSAAAIEVMYPPPYLDNEKSNGTIIHVKGKHLCPS

PLFPGPSKPFWVLVVVGGVLACYSLLVTVAFIIFWVRSKRSRLLHSDYMN

MTPRRPGPTRKHYQPYAPPRDFAAYRSSGFNVLMVHKRSHTGERPFQCNQ

CGASFTQKGNLLRHIKLHTGEKPFKCHLCNYACQRRDAL

FMC63-CD28-IKZF3 intracellular K0 (iK0): This sequence corresponds to the anti-CD19 scFv FMC63 (www.ebi.ac.uk/ena/data/view/ADM64594), the CD28 hinge, transmembrane, and cytoplasmic domains (amino acids 114-220), and IKZF3 amino acids 130-189, wherein all intracellular lysines are substituted to arginine.

(SEQ ID NO: 74)
MLLLVTSLLLCELPHPAFLLIPDIQMTQTTSSLSASLGDRVTISCRASQD

ISKYLNWYQQKPDGTVKLLIYHTSRLHSGVPSRFSGSGSGTDYSLTISNL

EQEDIATYFCQQGNTLPYTFGGGTKLEITGSTSGSGKPGSGEGSTKGEVK

LQESGPGLVAPSQSLSVTCTVSGVSLPDYGVSWIRQPPRKGLEWLGVIWG

SETTYYNSALKSRLTIIKDNSKSQVFLKMNSLQTDDTAIYYCAKHYYYGG

SYAMDYWGQGTSVTVSSAAAIEVMYPPPYLDNEKSNGTIIHVKGKHLCPS

PLFPGPSKPFWVLVVVGGVLACYSLLVTVAFIIFWVRSRRSRLLHSDYMN

MTPRRPGPTRRHYQPYAPPRDFAAYRSSGFNVLMVHRRSHTGERPFQCNQ

CGASFTQRGNLLRHIRLHTGERPFRCHLCNYACQRRDAL

The following 3 constructs were the polypeptide sequences used in FIG. 2 and FIG. 3. They differed from other split CAR designs in that they lacked a CD3ζ chain (and have been confirmed to dimerize).

Split CAR component B1 (BRET): The sequence corresponds to the fusion of the CD8 alpha signal sequence (amino acids 1-21), hinge and transmembrane domains (amino acids 138-206), CD28 co-stimulatory domain (amino acids 180-220), a G4S linker, and minCRBN3 (see SEQ ID NO: 3).

(SEQ ID NO: 75)
MALPVTALLLPLALLLHAARPTTTPAPRPPTPAPTIASQPLSLRPEACRP

AAGGAVHTRGLDFACDIYIWAPLAGTCGVLLLSLVITLYCRSKRSRLLHS

DYMNMTPRRPGPTRKHYQPYAPPRDFAAYRSGGGGSAGEGDQQDAAHNMG

-continued

NHLPLLPESEEEDEMEVEDQDSKEAKKPNIINFDTSLPTSHTYLGADMEE
FHGRTLHDDDSCQVIPVLPQVMMILIPGQTLPLQLFHPQEVSMVRNLIQK
DRTFAVLAYSNVQEREAQFGTTAEIYAYREEQDFGIEIVKVKAIGRQRFK
VLELRTQSDGIQQAKVQILPECVLPSTYDAETLMDRIKKQLREWDENLKD
DSLPSNPIDFSYRVAACLPIDDVLRIQLLKIGSAIQRLRCELDIMNKCTS
LCCKQCQETEITTKNEIFSLSLCGPMAAYVNPHGYVHETLTVYKACNLNL
IGRPSTEHSWFPGYAWTVAQCKICASHIGWKFTATKKDMSPQKFWGLTRS
ALLPTIPDTEDEISPDKVILCL

Split CAR component B2 (BRET): The sequence corresponds to the fusion of the LYN palmitoylation/myristoylation domain, CD28 co-stimulatory domain (amino acids 180-220), a G4S linker, and minCRBN3 (see SEQ ID NO: 3).

(SEQ ID NO: 76)
MGCIKSKRKDNLNDDGVDMKTRSKRSRLLHSDYMNMTPRRPGPTRKHYQP
YAPPRDFAAYRSGGGGSAGEGDQQDAAHNMGNHLPLLPESEEEDEMEVED
QDSKEAKKPNIINFDTSLPTSHTYLGADMEEFHGRTLHDDDSCQVIPVLP
QVMMILIPGQTLPLQLFHPQEVSMVRNLIQKDRTFAVLAYSNVQEREAQF
GTTAEIYAYREEQDFGIEIVKVKAIGRQRFKVLELRTQSDGIQQAKVQIL
PECVLPSTYDAETLMDRIKKQLREWDENLKDDSLPSNPIDFSYRVAACLP
IDDVLRIQLLKIGSAIQRLRCELDIMNKCTSLCCKQCQETEITTKNEIFS
LSLCGPMAAYVNPHGYVHETLTVYKACNLNLIGRPSTEHSWFPGYAWTVA
QCKICASHIGWKFTATKKDMSPQKFWGLTRSALLPTIPDTEDEISPDKVI
LCL

Split CAR component 3 (BRET): The sequence corresponds to the fusion of the CD8 alpha signal sequence (amino acids 1-21), PD1 hinge, transmembrane, and intracellular domains, with the substitutions Y223F and Y248F (amino acids 146-288), and minCRBN3 (see SEQ ID NO: 3).

(SEQ ID NO: 77)
MALPVTALLLPLALLLHAARPERRAEVPTAHPSPSPRPAGQFQTLVVGVV
GGLLGSLVLLVWVLAVICSRAARGTIGARRTGQPLKEDPSAVPVFSVDFG
ELDFQWREKTPEPPVPCVPEQTEFATIVFPSGMGTSSPARRGSADGPRSA
QPLRPEDGHCSWPLGGGGSAGEGDQQDAAHNMGNHLPLLPESEEEDEMEV
EDQDSKEAKKPNIINFDTSLPTSHTYLGADMEEFHGRTLHDDDSCQVIPV
LPQVMMILIPGQTLPLQLFHPQEVSMVRNLIQKDRTFAVLAYSNVQEREA
QFGTTAEIYAYREEQDFGIEIVKVKAIGRQRFKVLELRTQSDGIQQAKVQ
ILPECVLPSTYDAETLMDRIKKQLREWDENLKDDSLPSNPIDFSYRVAAC
LPIDDVLRIQLLKIGSAIQRLRCELDIMNKCTSLCCKQCQETEITTKNEI
FSLSLCGPMAAYVNPHGYVHETLTVYKACNLNLIGRPSTEHSWFPGYAWT
VAQCKICASHIGWKFTATKKDMSPQKFWGLTRSALLPTIPDTEDEISPDK
VILCL

Split CAR component B1 (complete): The sequence corresponds to the fusion of the CD8 alpha signal sequence (amino acids 1-21), hinge and transmembrane domains (amino acids 138-206), CD28 co-stimulatory domain (amino acids 180-220), a G4S linker, minCRBN3 (see SEQ ID NO: 3), and the intracellular portion of CD3z (amino acids 55-164).

(SEQ ID NO: 78)
MALPVTALLLPLALLLHAARPTTTPAPRPPTPAPTIASQPLSLRPEACRP
AAGGAVHTRGLDFACDIYIWAPLAGTCGVLLLSLVITLYCRSKRSRLLHS
DYMNMTPRRPGPTRKHYQPYAPPRDFAAYRSGGGGSAGEGDQQDAAHNMG
NHLPLLPESEEEDEMEVEDQDSKEAKKPNIINFDTSLPTSHTYLGADMEE
FHGRTLHDDDSCQVIPVLPQVMMILIPGQTLPLQLFHPQEVSMVRNLIQK
DRTFAVLAYSNVQEREAQFGTTAEIYAYREEQDFGIEIVKVKAIGRQRFK
VLELRTQSDGIQQAKVQILPECVLPSTYDAETLMDRIKKQLREWDENLKD
DSLPSNPIDFSYRVAACLPIDDVLRIQLLKIGSAIQRLRCELDIMNKCTS
LCCKQCQETEITTKNEIFSLSLCGPMAAYVNPHGYVHETLTVYKACNLNL
IGRPSTEHSWFPGYAWTVAQCKICASHIGWKFTATKKDMSPQKFWGLTRS
ALLPTIPDTEDEISPDKVILCLSLGFSRSADAPAYQQGQNQLYNELNLGR
REEYDVLDKRRGRDPEMGGKPQRRKNPQEGLYNELQKDKMAEAYSEIGMK
GERRRGKGHDGLYQGLSTATKDTYDALHMQALPPR

Split CAR component B2 (complete): The sequence corresponds to the fusion of the LYN palmitoylation/myristoylation domain, CD28 co-stimulatory domain (amino acids 180-220), a G4S linker, minCRBN3 (see SEQ ID NO: 3), and the intracellular portion of CD3z (amino acids 55-164).

(SEQ ID NO: 79)
MGCIKSKRKDNLNDDGVDMKTRSKRSRLLHSDYMNMTPRRPGPTRKHYQP
YAPPRDFAAYRSGGGGSAGEGDQQDAAHNMGNHLPLLPESEEEDEMEVED
QDSKEAKKPNIINFDTSLPTSHTYLGADMEEFHGRTLHDDDSCQVIPVLP
QVMMILIPGQTLPLQLFHPQEVSMVRNLIQKDRTFAVLAYSNVQEREAQF
GTTAEIYAYREEQDFGIEIVKVKAIGRQRFKVLELRTQSDGIQQAKVQIL
PECVLPSTYDAETLMDRIKKQLREWDENLKDDSLPSNPIDFSYRVAACLP
IDDVLRIQLLKIGSAIQRLRCELDIMNKCTSLCCKQCQETEITTKNEIFS
LSLCGPMAAYVNPHGYVHETLTVYKACNLNLIGRPSTEHSWFPGYAWTVA
QCKICASHIGWKFTATKKDMSPQKFWGLTRSALLPTIPDTEDEISPDKVI
LCLSLGFSRSADAPAYQQGQNQLYNELNLGRREEYDVLDKRRGRDPEMGG
KPQRRKNPQEGLYNELQKDKMAEAYSEIGMKGERRRGKGHDGLYQGLSTA
TKDTYDALHMQALPPR

Split CAR component 3 (complete): The sequence corresponds to the fusion of the CD8 alpha signal sequence (amino acids 1-21), PD1 hinge, transmembrane, and intracellular domains, with the substitutions Y223F and Y248F (amino acids 146-288), minCRBN3 (see SEQ ID NO: 3), and the intracellular portion of CD3z (amino acids 55-164).

(SEQ ID NO: 80)
MALPVTALLLPLALLLHAARPERRAEVPTARPSPSPRPAGQFQTLVVGVV
GGLLGSLVLLVWVLAVICSRAARGTIGARRTGQPLKEDPSAVPVFSVDFG
ELDFQWREKTPEPPVPCVPEQTEFATIVFPSGMGTSSPARRGSADGPRSA
QPLRPEDGHCSWPLGGGGSAGEGDQQDAAHNMGNHLPLLPESEEEDEMEV
EDQDSKEAKKPNIINFDTSLPTSHTYLGADMEEFHGRTLHDDDSCQVIPV
LPQVMMILIPGQTLPLQLFHPQEVSMVRNLIQKDRTFAVLAYSNVQEREA
QFGTTAEIYAYREEQDFGIEIVKVKAIGRQRFKVLELRTQSDGIQQAKVQ
ILPECVLPSTYDAETLMDRIKKQLREWDENLKDDSLPSNPIDFSYRVAAC
LPIDDVLRIQLLKIGSAIQRLRCELDIMNKCTSLCCKQCQETEITTKNEI
FSLSLCGPMAAYVNPHGYVHETLTVYKACNLNLIGRPSTEHSWFPGYAWT
VAQCKICASHIGWKFTATKKDMSPQKFWGLTRSALLPTIPDTEDEISPDK
VILCLSLGFSRSADAPAYQQGQNQLYNELNLGRREEYDVLDKRRGRDPEM
GGKPQRRKNPQEGLYNELQKDKMAEAYSEIGMKGERRRGKGHDGLYQGLS
TATKDTYDALHMQALPPR

FMC63-CD28-CD3z-IKZF3: This sequence corresponds to the in frame fusion of the CSF2RA signal sequence (amino acids 1-22), anti-CD19 scFv FMC63 (www.ebi-.ac.uk/ena/data/view/ADM64594), the CD28 hinge, transmembrane, and cytoplasmic domains (amino acids 114-220), the CD3z intracellular ITAM domains (amino acids 55-164), a SG linker, and IKZF3 amino acids 130-189.

(SEQ ID NO: 81)
MLLLVTSLLLCELPHPAFLLIPEQKLISEEDLDIQMTQTTSSLSASLGDR
VTISCRASQDISKYLNWYQQKPDGTVKLLIYHTSRLHSGVPSRFSGSGSG
TDYSLTISNLEQEDIATYFCQQGNTLPYTFGGGTKLEITGSTSGSGKPGS
GEGSTKGEVKLQESGPGLVAPSQSLSVTCTVSGVSLPDYGVSWIRQPPRK
GLEWLGVIWGSETTYYNSALKSRLTIIKDNSKSQVFLKMNSLQTDDTAIY
YCAKHYYYGGSYAMDYWGQGTSVTVSSAAAIEVMYPPPYLDNEKSNGTII
HVKGKHLCPSPLFPGPSKPFWVLVVVGGVLACYSLLVTVAFIIFWVRSKR
SRLLHSDYMNMTPRRPGPTRKHYQPYAPPRDFAAYRSRVKFSRSADAPAY
QQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPRS
GFNVLMVHKRSHTGERPFQCNQCGASFTQKGNLLRHIKLHTGEKPFKCHL
CNYACQRRDAL

Proof of concept fusion polypeptides of the IKZF3 degron (amino acids 130-189) that retained IMiD-dependent degradation when fused to the C termini of CD28 and CD3z are included below:

CD28-IKZF3: This sequence corresponds to the in frame fusion of full length CD28, a SG linker, and IKZF3 (amino acids 130-189), relating to FIG. 8:

(SEQ ID NO: 82)
MLRLLLALNLFPSIQVTGNKILVKQSPMLVAYDNAVNLSCKYSYNLFSRE
FRASLHKGLDSAVEVCVVYGNYSQQLQVYSKTGFNCDGKLGNESVTFYLQ

-continued
NLYVNQTDIYFCKIEVMYPPPYLDNEKSNGTIIHVKGKHLCPSPLFPGPS
KPFWVLVVVGGVLACYSLLVTVAFIIFWVRSKRSRLLHSDYMNMTPRRPG
PTRKHYQPYAPPRDFAAYRSSGFNVLMVHKRSHTGERPFQCNQCGASFTQ
KGNLLRHIKLHTGEKPFKCHLCNYACQRRDAL CD28-CD3z-IKZF3: This sequence corresponds to the in frame fusion of full length CD28, the intracellular domain of CD3z (amino acids 55-164), and IKZF3 (amino acids 130-189), relating to FIG. 8:

(SEQ ID NO: 83)
MLRLLLALNLFPSIQVTGNKILVKQSPMLVAYDNAVNLSCKYSYNLFSRE
FRASLHKGLDSAVEVCVVYGNYSQQLQVYSKTGFNCDGKLGNESVTFYLQ
NLYVNQTDIYFCKIEVMYPPPYLDNEKSNGTIIHVKGKHLCPSPLFPGPS
KPFWVLVVVGGVLACYSLLVTVAFIIFWVRSKRSRLLHSDYMNMTPRRPG
PTRKHYQPYAPPRDFAAYRSFSRSADAPAYQQGQNQLYNELNLGRREEYD
VLDKRRGRDPEMGGKPQRRKNPQEGLYNELQKDKMAEAYSEIGMKGERRR
GKGHDGLYQGLSTATKDTYDALHMQALPPRSGFNVLMVHKRSHTGERPFQ
CNQCGASFTQKGNLLRHIKLHTGEKPFKCHLCNYACQRRDAL

Other exemplary sequences include:

Chimeric Degradable Inhibitor LAT-CSK-IKZF3: The sequence corresponds to the fusion of the LAT Signal-Anchor (amino acids 1-33), CSK (full length, amino acids 1-450), and IKZF3 degron (amino acids 130-189).

(SEQ ID NO: 84)
ATGGAGGAGGCCATCCTGGTCCCCTGCGTGCTGGGGCTCCTGCTGCTGC
CCATCCTGGCCATGTTGATGGCACTGTGTGTGCACTGCCACAGACTGCC
AATGTCAGCAATACAGGCCGCCTGGCCATCCGGTACAGAATGTATTGCC
AAGTACAACTTCCACGGCACTGCCGAGCAGGACCTGCCCTTCTGCAAAG
GgGACGTGCTCACCATTGTGGCCGTCACCAAGGACCCCAACTGGTACAA
AGCCAAAAACAAGGTGGGCCGTGAGGGCATCATCCCAGCCAACTACGTC
CAGAAGCGGGAGGGCGTGAAGGCGGGTACCAAACTCAGCCTCATGCCTT
GGTTCCACGGCAAGATCACACGGGAGCAGGCTGAGCGGCTTCTGTACCC
GCCGGAGACAGGCCTGTTCCTGGTGCGGGAGAGCACCAACTACCCCGGA
GACTACACGCTGTGCGTGAGCTGCGACGGCAAGGTGGAGCACTACCGCA
TCATGTACCATGCCAGCAAGCTCAGCATCGACGAGGAGGTGTACTTTGA
GAACCTCATGCAGCTGGTGGAGCACTACACCTCAGACGCAGATGGACTC
TGTACGCGCCTCATTAAACCAAAGGTCATGGAGGGCACAGTGGCGGCCC
AGGATGAGTTCTACCGCAGCGGCTGGGCCCTGAACATGAAGGAGCTGAA
GCTGCTGCAGACCATCGGGAAGGGGGAGTTCGGgGACGTGATGCTGGGC
GATTACCGAGGGAACAAAGTCGCCGTCAAGTGCATTAAGAACGACGCCA
CTGCCCAGGCCTTCCTGGCTGAAGCCTCAGTCATGACGCAACTGCGGCA
TAGCAACCTGGTGCAGCTCCTGGGCGTGATCGTGGAGGAGAAGGGCGGG
CTCTACATCGTCACTGAGTACATGGCCAAGGGGAGCCTTGTGGACTACC
TGCGGTCTAGGGGTCGGTCAGTGCTGGGCGGAGACTGTCTCCTCAAGTT

-continued

CTCGCTAGATGTCTGCGAGGCCATGGAATACCTGGAGGGCAACAATTTC
GTGCATCGAGACCTGGCTGCCCGCAATGTGCTGGTGTCTGAGGACAACG
TGGCCAAGGTCAGCGACTTTGGTCTCACCAAGGAGGCGTCCAGCACCCA
GGACACGGGCAAGCTGCCAGTCAAGTGGACAGCCCCTGAGGCCCTGAGA
GAGAAGAAATTCTCCACTAAGTCTGACGTGTGGAGTTTCGGAATCCTTC
TCTGGGAAATCTACTCCTTTGGGCGAGTGCCTTATCCAAGAATTCCCCT
GAAGGACGTCGTCCCTCGGGTGGAGAAGGGCTACAAGATGGATGCCCCC
GACGGCTGCCCGCCCGCAGTCTATGAAGTCATGAAGAACTGCTGGCACC
TGGACGCCGCCATGCGGCCCTCCTTCCTACAGCTCCGAGAGCAGCTTGA
GCACATCAAAACCCACGAGCTGCACCTGTCCGGATTCAATGTCTTAATG
GTTCATAAGCGAAGCCATACTGGTGAACGCCCATTCCAGTGTAATCAGT
GTGGGGCATCTTTTACTCAGAAAGGTAACCTCCTCCGCCACATTAAACT
GCACACAGGGGAAAAACCTTTTAAGTGTCACCTCTGCAACTATGCATGC
CAAAGAAGAGATGCGCTC

Chimeric Degradable Inhibitor LAT-CSK(E154A)-IKZF3: The sequence corresponds to the fusion of the LAT Signal-Anchor (amino acids 1-33), CSK (full length, amino acids 1-450, substitution E154A), and IKZF3 degron (amino acids 130-189).

(SEQ ID NO: 85)
ATGGAGGAGGCCATCCTGGTCCCCTGCGTGCTGGGGCTCCTGCTGCTGC
CCATCCTGGCCATGTTGATGGCACTGTGTGTGCACTGCCACAGACTGCC
AATGTCAGCAATACAGGCCGCCTGGCCATCCGGTACAGAATGTATTGCC
AAGTACAACTTCCACGGCACTGCCGAGCAGGACCTGCCCTTCTGCAAAG
GgGACGTGCTCACCATTGTGGCCGTCACCAAGGACCCCAACTGGTACAA
AGCCAAAAACAAGGTGGGCCGTGAGGGCATCATCCCAGCCAACTACGTC
CAGAAGCGGGAGGGCGTGAAGGCGGGTACCAAACTCAGCCTCATGCCTT
GGTTCCACGGCAAGATCACACGGGAGCAGGCTGAGCGGCTTCTGTACCC
GCCGGAGACAGGCCTGTTCCTGGTGCGGGAGAGCACCAACTACCCCGGA
GACTACACGCTGTGCGTGAGCTGCGACGGCAAGGTGGAGCACTACCGCA
TCATGTACCATGCCAGCAAGCTCAGCATCGACGAGGAGGTGTACTTTGA
GAACCTCATGCAGCTGGTGGcGCACTACACCTCAGACGCAGATGGACTC
TGTACGCGCCTCATTAAACCAAAGGTCATGGAGGGCACAGTGGCGGCCC
AGGATGAGTTCTACCGCAGCGGCTGGGCCCTGAACATGAAGGAGCTGAA
GCTGCTGCAGACCATCGGGAAGGGGGAGTTCGGgGACGTGATGCTGGGC
GATTACCGAGGGAACAAAGTCGCCGTCAAGTGCATTAAGAACGACGCCA
CTGCCCAGGCCTTCCTGGCTGAAGCCTCAGTCATGACGCAACTGCGGCA
TAGCAACCTGGTGCAGCTCCTGGGCGTGATCGTGGAGGAGAAGGGCGGG
CTCTACATCGTCACTGAGTACATGGCCAAGGGGAGCCTTGTGGACTACC
TGCGGTCTAGGGGTCGGTCAGTGCTGGGCGGAGACTGTCTCCTCAAGTT
CTCGCTAGATGTCTGCGAGGCCATGGAATACCTGGAGGGCAACAATTTC

-continued

GTGCATCGAGACCTGGCTGCCCGCAATGTGCTGGTGTCTGAGGACAACG
TGGCCAAGGTCAGCGACTTTGGTCTCACCAAGGAGGCGTCCAGCACCCA
GGACACGGGCAAGCTGCCAGTCAAGTGGACAGCCCCTGAGGCCCTGAGA
GAGAAGAAATTCTCCACTAAGTCTGACGTGTGGAGTTTCGGAATCCTTC
TCTGGGAAATCTACTCCTTTGGGCGAGTGCCTTATCCAAGAATTCCCCT
GAAGGACGTCGTCCCTCGGGTGGAGAAGGGCTACAAGATGGATGCCCCC
GACGGCTGCCCGCCCGCAGTCTATGAAGTCATGAAGAACTGCTGGCACC
TGGACGCCGCCATGCGGCCCTCCTTCCTACAGCTCCGAGAGCAGCTTGA
GCACATCAAAACCCACGAGCTGCACCTGTCCGGATTCAATGTCTTAATG
GTTCATAAGCGAAGCCATACTGGTGAACGCCCATTCCAGTGTAATCAGT
GTGGGGCATCTTTTACTCAGAAAGGTAACCTCCTCCGCCACATTAAACT
GCACACAGGGGAAAAACCTTTTAAGTGTCACCTCTGCAACTATGCATGC
CAAAGAAGAGATGCGCTC

Chimeric Degradable Inhibitor LAT-CSK(W47A/R107K/E154A)-IKZF3: The sequence corresponds to the fusion of the LAT Signal-Anchor (amino acids 1-33), CSK (full length, amino acids 1-450, substitutions W47A, R107K, and E154A), and IKZF3 degron (amino acids 130-189).

(SEQ ID NO: 86)
ATGGAGGAGGCCATCCTGGTCCCCTGCGTGCTGGGGCTCCTGCTGCTGC
CCATCCTGGCCATGTTGATGGCACTGTGTGTGCACTGCCACAGACTGCC
AATGTCAGCAATACAGGCCGCCTGGCCATCCGGTACAGAATGTATTGCC
AAGTACAACTTCCACGGCACTGCCGAGCAGGACCTGCCCTTCTGCAAAG
GgGACGTGCTCACCATTGTGGCCGTCACCAAGGACCCCAACgcGTACAA
AGCCAAAAACAAGGTGGGCCGTGAGGGCATCATCCCAGCCAACTACGTC
CAGAAGCGGGAGGGCGTGAAGGCGGGTACCAAACTCAGCCTCATGCCTT
GGTTCCACGGCAAGATCACACGGGAGCAGGCTGAGCGGCTTCTGTACCC
GCCGGAGACAGGCCTGTTCCTGGTGaaGGAGAGCACCAACTACCCCGGA
GACTACACGCTGTGCGTGAGCTGCGACGGCAAGGTGGAGCACTACCGCA
TCATGTACCATGCCAGCAAGCTCAGCATCGACGAGGAGGTGTACTTTGA
GAACCTCATGCAGCTGGTGGcGCACTACACCTCAGACGCAGATGGACTC
TGTACGCGCCTCATTAAACCAAAGGTCATGGAGGGCACAGTGGCGGCCC
AGGATGAGTTCTACCGCAGCGGCTGGGCCCTGAACATGAAGGAGCTGAA
GCTGCTGCAGACCATCGGGAAGGGGGAGTTCGGgGACGTGATGCTGGGC
GATTACCGAGGGAACAAAGTCGCCGTCAAGTGCATTAAGAACGACGCCA
CTGCCCAGGCCTTCCTGGCTGAAGCCTCAGTCATGACGCAACTGCGGCA
TAGCAACCTGGTGCAGCTCCTGGGCGTGATCGTGGAGGAGAAGGGCGGG
CTCTACATCGTCACTGAGTACATGGCCAAGGGGAGCCTTGTGGACTACC
TGCGGTCTAGGGGTCGGTCAGTGCTGGGCGGAGACTGTCTCCTCAAGTT
CTCGCTAGATGTCTGCGAGGCCATGGAATACCTGGAGGGCAACAATTTC
GTGCATCGAGACCTGGCTGCCCGCAATGTGCTGGTGTCTGAGGACAACG
TGGCCAAGGTCAGCGACTTTGGTCTCACCAAGGAGGCGTCCAGCACCCA

-continued

GGACACGGGCAAGCTGCCAGTCAAGTGGACAGCCCCTGAGGCCCTGAGA

GAGAAGAAATTCTCCACTAAGTCTGACGTGTGGAGTTTCGGAATCCTTC

TCTGGGAAATCTACTCCTTTGGGCGAGTGCCTTATCCAAGAATTCCCCT

GAAGGACGTCGTCCCTCGGGTGGAGAAGGGCTACAAGATGGATGCCCCC

GACGGCTGCCCGCCCGCAGTCTATGAAGTCATGAAGAACTGCTGGCACC

TGGACGCCGCCATGCGGCCCTCCTTCCTACAGCTCCGAGAGCAGCTTGA

GCACATCAAAACCCACGAGCTGCACCTGTCCGGATTCAATGTCTTAATG

GTTCATAAGCGAAGCCATACTGGTGAACGCCCATTCCAGTGTAATCAGT

GTGGGGCATCTTTTACTCAGAAAGGTAACCTCCTCCGCCACATTAAACT

GCACACAGGGGAAAAACCTTTTAAGTGTCACCTCTGCAACTATGCATGC

CAAAGAAGAGATGCGCTC

Chimeric Degradable Inhibitor LAT-SHP1-IKZF3: The sequence corresponds to the fusion of the LAT Signal-Anchor (amino acids 1-33), SHP1 (amino acids 203-595), and IKZF3 degron (amino acids 130-189). IDC-57 DNA M (SEQ ID NO: 87)

ATGGAGGAGGCCATCCTGGTCCCCTGCGTGCTGGGGCTCCTGCTGCTGC

CCATCCTGGCCATGTTGATGGCACTGTGTGTGCACTGCCACAGACTGCC

ATCAGGCGCCTTTGTCTACCTGCGGCAGCCGTACTATGCCACGAGGGTG

AATGCGGCTGACATTGAGAACCGAGTGTTGGAACTGAACAAGAAGCAGG

AGTCCGAGGATACAGCCAAGGCTGGCTTCTGGGAGGAGTTTGAGAGTTT

GCAGAAGCAGGAGGTGAAGAACTTGCACCAGCGTCTGGAAGGGCAGCGG

CCAGAGAACAAGGGCAAGAACCGCTACAAGAACATTCTCCCCTTTGACC

ACAGCCGAGTGATCCTGCAGGGACGGGACAGTAACATCCCCGGGTCCGA

CTACATCAATGCCAACTACATCAAGAACCAGCTGCTAGGCCCTGATGAG

-continued

AACGCTAAGACCTACATCGCCAGCCAGGGCTGTCTGGAGGCCACGGTCA

ATGACTTCTGGCAGATGGCGTGGCAGGAGAACAGCCGTGTCATCGTCAT

GACCACCCGAGAGGTGGAGAAAGGCCGGAACAAATGCGTCCCATACTGG

CCCGAGGTGGGCATGCAGCGTGCTTATGGGCCCTACTCTGTGACCAACT

GCGGGGAGCATGACACAACCGAATACAAACTCCGTACCTTACAGGTCTC

CCCGCTGGACAATGGAGACCTGATTCGGGAGATCTGGCATTACCAGTAC

CTGAGCTGGCCCGACCATGGGGTCCCCAGTGAGCCTGGGGGTGTCCTCA

GCTTCCTGGACCAGATCAACCAGCGGCAGGAAAGTCTGCCTCACGCAGG

GCCCATCATCGTGCACTGCAGCGCCGGCATCGGCCGCACAGGCACCATC

ATTGTCATCGACATGCTCATGGAGAACATCTCCACCAAGGGCCTGGACT

GTGACATTGACATCCAGAAGACCATCCAGATGGTGCGGGCGCAGCGCTC

GGGCATGGTGCAGACGGAGGCGCAGTACAAGTTCATCTACGTGGCCATC

GCCCAGTTCATTGAAACCACTAAGAAGAAGCTGGAGGTCCTGCAGTCGC

AGAAGGGCCAGGAGTCGGAGTACGGGAACATCACCTATCCCCCAGCCAT

GAAGAATGCCCATGCCAAGGCCTCCCGCACCTCGTCCAAACACAAGGAG

GATGTGTATGAGAACCTGCACACTAAGAACAAGAGGGAGGAGAAAGTGA

AGAAGCAGCGGTCAGCAGACAAGGAGAAGAGCAAGGGTTCCCTCAAGAG

GAAGTCCGGATTCAATGTCTTAATGGTTCATAAGCGAAGCCATACTGGT

GAACGCCCATTCCAGTGTAATCAGTGTGGGGCATCTTTTACTCAGAAAG

GTAACCTCCTCCGCCACATTAAACTGCACACAGGGGAAAAACCTTTTAA

GTGTCACCTCTGCAACTATGCATGCCAAAGAAGAGATGCGCTC

Split CAR component B1a (complete): The sequence corresponds to the fusion of the CD8 alpha signal sequence (amino acids 1-21), hinge and transmembrane domains (amino acids 138-206), CD28 co-stimulatory domain (amino acids 180-220), a G4S linker, minCRBN2 (see SEQ ID NO: 2), and the intracellular portion of CD3z (amino acids 55-164).

(SEQ ID NO: 88)

ATGGCGCTCCCAGTCACTGCCCTGCTTTTGCCCCTGGCACTTCTTCTTCACGCTGCCAG

ACCCACAACGACCCCAGCTCCACGCCCGCCGACTCCCGCGCCAACTATAGCCAGTCAGC

CCCTGTCACTGCGGCCGGAGGCGTGTCGCCCTGCAGCGGGGGGAGCCGTCCACACACGA

GGTCTTGACTTCGCCTGTGACATCTATATCTGGGCGCCTCTGGCCGGTACATGCGGCGT

GTTGTTGCTTAGCCTCGTGATAACACTCTATTGCAGGAGTAAGAGGAGCAGGCTCCTGC

ACAGTGACTACATGAACATGACTCCTAGAAGGCCTGGACCCACCCGCAAGCATTACCAG

CCCTATGCCCCACCACGCGACTTCGCAGCCTATCGCTCCGGAGGGGGTGGTTCTTGTAC

TTCCCTTTGCTGTAAACAATGTCAAGAAACAGAAATAACAACCAAAAATGAAATATTCA

GTTTATCCTTATGTGGGCCGATGGCAGCTTATGTGAATCCTCATGGATATGTGCATGAG

ACACTTACTGTGTATAAGGCTTGCAACTTGAATCTGATAGGCCGGCCTTCTACAGAACA

CAGCTGGTTTCCTGGGTATGCCTGGACTGTTGCCCAGTGTAAGATCTGTGCAAGCCATA

TTGGATGGAAGTTTACGGCCACCAAAAAAGACATGTCACCTCAAAAATTTTGGGGCTTA

ACGCGATCTGCTCTGTTGCCCACGATCCCAGACACTGAAGATGAAATAAGTCCAGACAA

AGTAATACTTTGCTTGTCTCTCGGCTTCAGTCGATCAGCAGATGCTCCAGCGTACCAGC

-continued

AAGGCCAGAACCAACTTTATAATGAACTGAATTTGGGCCGACGCGAGGAATACGACGTT

CTTGACAAGCGGAGGGGCCGCGATCCAGAAATGGGGGGGAAACCGCAACGAAGAAAGAA

TCCCCAGGAGGGGCTCTACAATGAACTTCAAAAGGATAAAATGGCAGAGGCCTATAGCG

AAATCGGTATGAAGGGGGAGCGAAGGCGAGGTAAGGGGCATGATGGGTTGTATCAAGGC

CTGTCCACGGCGACCAAGGATACCTATGACGCTCTTCACATGCAAGCATTGCCTCCTAG

A

“Eureka”: pEF1α-BsmBI cloning
site-17aaRigidLinker-eGFP (SEQ ID NO: 89)

TTTTGCACAACATGGGGGATCATGTAACTCGCCTTGATCGTTGGGAACCGGAGCTGAAT

GAAGCCATACCAAACGACGAGCGTGACACCACGATGCCTGTAGCAATGGCAACAACGTT

GCGCAAACTATTAACTGGCGAACTACTTACTCTAGCTTCCCGGCAACAATTAATAGACT

GGATGGAGGCGGATAAAGTTGCAGGACCACTTCTGCGCTCGGCCCTTCCGGCTGGCTGG

TTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAA

CTATGGATGAACGAAATAGACAGATCGCTGAGATAGGTGCCTCACTGATTAAGCATTGG

TAACTGTCAGACCAAGTTTACTCATATATACTTTAGATTGATTTAAAACTTCATTTTTA

ATTTAAAAGGATCTAGGTGAAGATCCTTTTTGATAATCTCATGACCAAAATCCCTTAAC

GTGAGTTTTCGTTCCACTGAGCGTCAGACCCCGTAGAAAAGATCAAAGGATCTTCTTGA

GATCCTTTTTTTCTGCGCGTAATCTGCTGCTTGCAAACAAAAAAACCACCGCTACCAGC

GGTGGTTTGTTTGCCGGATCAAGAGCTACCAACTCTTTTTCCGAAGGTAACTGGCTTCA

GCAGAGCGCAGATACCAAATACTGTTCTTCTAGTGTAGCCGTAGTTAGGCCACCACTTC

AAGAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGATA

AGGCGCAGCGGTCGGGCTGAACGGGGGGTTCGTGCACACAGCCCAGCTTGGAGCGAACG

ACCTACACCGAACTGAGATACCTACAGCGTGAGCTATGAGAAAGCGCCACGCTTCCCGA

AGGGAGAAAGGCGGACAGGTATCCGGTAAGCGGCAGGGTCGGAACAGGAGAGCGCACGA

GGGAGCTTCCAGGGGGAAACGCCTGGTATCTTTATAGTCCTGTCGGGTTTCGCCACCTC

TGACTTGAGCGTCGATTTTTGTGATGCTCGTCAGGGGGGCGGAGCCTATGGAAAAACGC

CAGCAACGCGGCCTTTTTACGGTTCCTGGCCTTTTGCTGGCCTTTTGCTCACATGTTCT

TTCCTGCGTTATCCCCTGATTCTGTGGATAACCGTATTACCGCCTTTGAGTGAGCTGAT

ACCGCTCGCCGCAGCCGAACGACCGAGCGCAGCGAGTCAGTGAGCGAGGAAGCGGAAGA

GCGCCCAATACGCAAACCGCCTCTCCCCGCGCGTTGGCCGATTCATTAATGCAGCTGGC

ACGACAGGTTTCCCGACTGGAAAGCGGGCAGTGAGCGCAACGCAATTAATGTGAGTTAG

CTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGC

GCGCAATTAACCCTCACTAAAGGGAACAAAAGCTGGAGCTGCAAGCTTAATGTAGTCTT

ATGCAATACTCTTGTAGTCTTGCAACATGGTAACGATGAGTTAGCAACATGCCTTACAA

GGAGAGAAAAAGCACCGTGCATGCCGATTGGTGGAAGTAAGGTGGTACGATCGTGCCTT

ATTAGGAAGGCAACAGACGGGTCTGACATGGATTGGACGAACCACTGAATTGCCGCATT

GCAGAGATATTGTATTTAAGTGCCTAGCTCGATACATAAACGGGTCTCTCTGGTTAGAC

CAGATCTGAGCCTGGGAGCTCTCTGGCTAACTAGGGAACCCACTGCTTAAGCCTCAATA

-continued

AAGCTTGCCTTGAGTGCTTCAAGTAGTGTGTGCCCGTCTGTTGTGTGACTCTGGTAACT

AGAGATCCCTCAGACCCTTTTAGTCAGTGTGGAAAATCTCTAGCAGTGGCGCCCGAACA

GGGACTTGAAAGCGAAAGGGAAACCAGAGGAGCTCTCTCGACGCAGGACTCGGCTTGCT

GAAGCGCGCACGGCAAGAGGCGAGGGGCGGCGACTGGTGAGTACGCCAAAAATTTTGAC

TAGCGGAGGCTAGAAGGAGAGAGATGGGTGCGAGAGCGTCAGTATTAAGCGGGGGAGAA

TTAGATCGCGATGGGAAAAAATTCGGTTAAGGCCAGGGGGAAAGAAAAAATATAAATTA

AAACATATAGTATGGGCAAGCAGGGAGCTAGAACGATTCGCAGTTAATCCTGGCCTGTT

AGAAACATCAGAAGGCTGTAGACAAATACTGGGACAGCTACAACCATCCCTTCAGACAG

GATCAGAAGAACTTAGATCATTATATAATACAGTAGCAACCCTCTATTGTGTGCATCAA

AGGATAGAGATAAAAGACACCAAGGAAGCTTTAGACAAGATAGAGGAAGAGCAAAACAA

AAGTAAGACCACCGCACAGCAAGCGGCCGCTGATCTTCAGACCTGGAGGAGGAGATATG

AGGGACAATTGGAGAAGTGAATTATATAAATATAAAGTAGTAAAAATTGAACCATTAGG

AGTAGCACCCACCAAGGCAAAGAGAAGAGTGGTGCAGAGAGAAAAAAGAGCAGTGGGAA

TAGGAGCTTTGTTCCTTGGGTTCTTGGGAGCAGCAGGAAGCACTATGGGCGCAGCGTCA

ATGACGCTGACGGTACAGGCCAGACAATTATTGTCTGGTATAGTGCAGCAGCAGAACAA

TTTGCTGAGGGCTATTGAGGCGCAACAGCATCTGTTGCAACTCACAGTCTGGGGCATCA

AGCAGCTCCAGGCAAGAATCCTGGCTGTGGAAAGATACCTAAAGGATCAACAGCTCCTG

GGGATTTGGGGTTGCTCTGGAAAACTCATTTGCACCACTGCTGTGCCTTGGAATGCTAG

TTGGAGTAATAAATCTCTGGAACAGATTTGGAATCACACGACCTGGATGGAGTGGGACA

GAGAAATTAACAATTACACAAGCTTAATACACTCCTTAATTGAAGAATCGCAAAACCAG

CAAGAAAAGAATGAACAAGAATTATTGGAATTAGATAAATGGGCAAGTTTGTGGAATTG

GTTTAACATAACAAATTGGCTGTGGTATATAAAATTATTCATAATGATAGTAGGAGGCT

TGGTAGGTTTAAGAATAGTTTTTGCTGTACTTTCTATAGTGAATAGAGTTAGGCAGGGA

TATTCACCATTATCGTTTCAGACCCACCTCCCAACCCCGAGGGGACCCTATTCCAGCAC

ATATGAGGCTTGGCGTAACTAGATCTTGAGACAAATGGCAGTATTCATCCACAATTTTA

AAAGAAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTCGGGT

TTATTACAGGGACAGCAGAGATCCACTTTGGGCTCGAGGGGGCCCGGGTGCAAAGATGG

ATAAAGTTTTAAACAGAGAGGAATCTTTGCAGCTAATGGACCTTCTAGGTCTTGAAAGG

AGTGGGAATTGGCTCCGGTGCCCGTCAGTGGGCAGAGCGCACATCGCCCACAGTCCCCG

AGAAGTTGGGGGGAGGGGTCGGCAATTGATCCGGTGCCTAGAGAAGGTGGCGCGGGGTA

AACTGGGAAAGTGATGTCGTGTACTGGCTCCGCCTTTTTCCCGAGGGTGGGGGAGAACC

GTATATAAGTGCAGTAGTCGCCGTGAACGTTCTTTTTCGCAACGGGTTTGCCGCCAGAA

CACAGGTAAGTGCCGTGTGTGGTTCCCGCGGGCCTGGCCTCTTTACGGGTTATGGCCCT

TGCGTGCCTTGAATTACTTCCACCTGGCTGCAGTACGTGATTCTTGATCCCGAGCTTCG

GGTTGGAAGTGGGTGGGAGAGTTCGAGGCCTTGCGCTTAAGGAGCCCCTTCGCCTCGTG

CTTGAGTTGAGGCCTGGCCTGGGCGCTGGGGCCGCCGCGTGCGAATCTGGTGGCACCTT

CGCGCCTGTCTCGCTGCTTTCGATAAGTCTCTAGCCATTTAAAATTTTTGATGACCTGC

TGCGACGCTTTTTTTCTGGCAAGATAGTCTTGTAAATGCGGGCCAAGATCTGCACACTG

GTATTTCGGTTTTTGGGGCCGCGGGCGGCGACGGGGCCCGTGCGTCCCAGCGCACATGT

-continued

TCGGCGAGGCGGGGCCTGCGAGCGCGGCCACCGAGAATCGGACGGGGGTAGTCTCAAGC

TGGCCGGCCTGCTCTGGTGCCTGGCCTCGCGCCGCCGTGTATCGCCCCGCCCTGGGCGG

CAAGGCTGGCCCGGTCGGCACCAGTTGCGTGAGCGGAAAGATGGCCGCTTCCCGGCCCT

GCTGCAGGGAGCTCAAAATGGAGGACGCGGCGCTCGGGAGAGCGGGCGGGTGAGTCACC

CACACAAAGGAAAAGGGCCTTTCCGTCCTCAGCCGTCGCTTCATGTGACTCCACGGAGT

ACCGGGCGCCGTCCAGGCACCTCGATTAGTTCTCGAGCTTTTGGAGTACGTCGTCTTTA

GGTTGGGGGGAGGGGTTTTATGCGATGGAGTTTCCCCACACTGAGTGGGTGGAGACTGA

AGTTAGGCCAGCTTGGCACTTGATGTAATTCTCCTTGGAATTTGCCCTTTTTGAGTTTG

GATCTTGGTTCATTCTCAAGCCTCAGACAGTGGTTCAAAGTTTTTTTCTTCCATTTCAG

GTGTCGTGAATACCGTCGACTCCGGAATAGCCACCATGGAGACGGACGTCTCAGCTGAA

GCTGCTGCAAAGGAAGCTGCAGCTAAGGAGGCTGCAGCTAAGGCTGTGAGCAAGGGCGA

GGAGCTGTTCACCGGGGTGGTGCCCATCCTGGTCGAGCTGGACGGCGACGTAAACGGCC

ACAAGTTCAGCGTGTCCGGCGAGGGCGAGGGCGATGCCACCTACGGCAAGCTGACCCTG

AAGTTCATCTGCACCACCGGCAAGCTGCCCGTGCCCTGGCCCACCCTCGTGACCACCCT

GACCTACGGCGTGCAGTGCTTCAGCCGCTACCCCGACCACATGAAGCAGCACGACTTCT

TCAAGTCCGCCATGCCCGAAGGCTACGTCCAGGAGCGCACCATCTTCTTCAAGGACGAC

GGCAACTACAAGACCCGCGCCGAGGTGAAGTTCGAGGGCGACACCCTGGTGAACCGCAT

CGAGCTGAAGGGCATCGACTTCAAGGAGGACGGCAACATCCTGGGGCACAAGCTGGAGT

ACAACTACAACAGCCACAACGTCTATATCATGGCCGACAAGCAGAAGAACGGCATCAAG

GTGAACTTCAAGATCCGCCACAACATCGAGGACGGCAGCGTGCAGCTCGCCGACCACTA

CCAGCAGAACACCCCCATCGGCGACGGCCCCGTGCTGCTGCCCGACAACCACTACCTGA

GCACCCAGTCCGCCCTGAGCAAAGACCCCAACGAGAAGCGCGATCACATGGTCCTGCTG

GAGTTCGTGACCGCCGCCGGGATCACTCTCGGCATGGACGAGCTGTACAAGTAAATGCA

TGAGTAACTGAGGATCCAGGGACAGCAGAGATACGCGTTAAGTCGACAATCAACCTCTG

GATTACAAAATTTGTGAAAGATTGACTGGTATTCTTAACTATGTTGCTCCTTTTACGCT

ATGTGGATACGCTGCTTTAATGCCTTTGTATCATGCTATTGCTTCCCGTATGGCTTTCA

TTTTCTCCTCCTTGTATAAATCCTGGTTGCTGTCTCTTTATGAGGAGTTGTGGCCCGTT

GTCAGGCAACGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCCCTATTGCCA

CGGCGGAACTCATCGCCGCCTGCCTTGCCCGCTGCTGGACAGGGGCTCGGCTGTTGGGC

ACTGACAATTCCGTGGTGTTGTCGGGGAAATCATCGTCCTTTCCTTGGCTGCTCGCCTG

TGTTGCCACCTGGATTCTGCGCGGGACGTCCTTCTGCTACGTCCCTTCGGCCCTCAATC

CAGCGGACCTTCCTTCCCGCGGCCTGCTGCCGGCTCTGCGGCCTCTTCCGCGTCTTCGC

CTTCGCCCTCAGACGAGTCGGATCTCCCTTTGGGCCGCCTCCCCGCGTCGACTTTAAGA

CCAATGACTTACAAGGCAGCTGTAGATCTTAGCCACTTTTTAAAAGAAAAGGGGGGACT

GGAAGGGCTAATTCACTCCCAACGAAGACAAGATCTGCTTTTTGCTTGTACTGGGTCTC

TCTGGTTAGACCAGATCTGAGCCTGGGAGCTCTCTGGCTAACTAGGGAACCCACTGCTT

AAGCCTCAATAAAGCTTGCCTTGAGTGCTTCAAGTAGTGTGTGCCCGTCTGTTGTGTGA

CTCTGGTAACTAGAGATCCCTCAGACCCTTTTAGTCAGTGTGGAAAATCTCTAGCAGTA

CGTATAGTAGTTCATGTCATCTTATTATTCAGTATTTATAACTTGCAAAGAAATGAATA

TCAGAGAGTGAGAGGAACTTGTTTATTGCAGCTTATAATGGTTACAAATAAAGCAATAG

-continued

CATCACAAATTTCACAAATAAAGCATTTTTTTCACTGCATTCTAGTTGTGGTTTGTCCA

AACTCATCAATGTATCTTATCATGTCTGGCTCTAGCTATCCCGCCCCTAACTCCGCCCA

TCCCGCCCCTAACTCCGCCCAGTTCCGCCCATTCTCCGCCCCATGGCTGACTAATTTTT

TTTATTTATGCAGAGGCCGAGGCCGCCTCGGCCTCTGAGCTATTCCAGAAGTAGTGAGG

AGGCTTTTTTGGAGGCCTAGGGACGTACCCAATTCGCCCTATAGTGAGTCGTATTACGC

GCGCTCACTGGCCGTCGTTTTACAACGTCGTGACTGGGAAAACCCTGGCGTTACCCAAC

TTAATCGCCTTGCAGCACATCCCCCTTTCGCCAGCTGGCGTAATAGCGAAGAGGCCCGC

ACCGATCGCCCTTCCCAACAGTTGCGCAGCCTGAATGGCGAATGGGACGCGCCCTGTAG

CGGCGCATTAAGCGCGGCGGGTGTGGTGGTTACGCGCAGCGTGACCGCTACACTTGCCA

GCGCCCTAGCGCCCGCTCCTTTCGCTTTCTTCCCTTCCTTTCTCGCCACGTTCGCCGGC

TTTCCCCGTCAAGCTCTAAATCGGGGGCTCCCTTTAGGGTTCCGATTTAGTGCTTTACG

GCACCTCGACCCCAAAAAACTTGATTAGGGTGATGGTTCACGTAGTGGGCCATCGCCCT

GATAGACGGTTTTTCGCCCTTTGACGTTGGAGTCCACGTTCTTTAATAGTGGACTCTTG

TTCCAAACTGGAACAACACTCAACCCTATCTCGGTCTATTCTTTTGATTTATAAGGGAT

TTTGCCGATTTCGGCCTATTGGTTAAAAAATGAGCTGATTTAACAAAAATTTAACGCGA

ATTTTAACAAAATATTAACGCTTACAATTTAGGTGGCACTTTTCGGGGAAATGTGCGCG

GAACCCCTATTTGTTTATTTTTCTAAATACATTCAAATATGTATCCGCTCATGAGACAA

TAACCCTGATAAATGCTTCAATAATATTGAAAAAGGAAGAGTATGAGTATTCAACATTT

CCGTGTCGCCCTTATTCCCTTTTTTGCGGCATTTTGCCTTCCTGTTTTTGCTCACCCAG

AAACGCTGGTGAAAGTAAAAGATGCTGAAGATCAGTTGGGTGCACGAGTGGGTTACATC

GAACTGGATCTCAACAGCGGTAAGATCCTTGAGAGTTTTCGCCCCGAAGAACGTTTTCC

AATGATGAGCACTTTTAAAGTTCTGCTATGTGGCGCGGTATTATCCCGTATTGACGCCG

GGCAAGAGCAACTCGGTCGCCGCATACACTATTCTCAGAATGACTTGGTTGAGTACTCA

CCAGTCACAGAAAAGCATCTTACGGATGGCATGACAGTAAGAGAATTATGCAGTGCTGC

CATAACCATGAGTGATAACACTGCGGCCAACTTACTTCTGACAACGATCGGAGGACCGA

AGGAGCTAACCGCTT

“Elk”: pEF1α-BsmBI cloning
site-17aaRigidLinker-mTagBFP2

(SEQ ID NO: 90)

CTGTCAGACCAAGTTTACTCATATATACTTTAGATTGATTTAAAACTTCATTTTTAATT

TAAAAGGATCTAGGTGAAGATCCTTTTTGATAATCTCATGACCAAAATCCCTTAACGTG

AGTTTTCGTTCCACTGAGCGTCAGACCCCGTAGAAAAGATCAAAGGATCTTCTTGAGAT

CCTTTTTTTCTGCGCGTAATCTGCTGCTTGCAAACAAAAAAACCACCGCTACCAGCGGT

GGTTTGTTTGCCGGATCAAGAGCTACCAACTCTTTTTCCGAAGGTAACTGGCTTCAGCA

GAGCGCAGATACCAAATACTGTTCTTCTAGTGTAGCCGTAGTTAGGCCACCACTTCAAG

AACTCTGTAGCACCGCCTACATACCTCGCTCTGCTAATCCTGTTACCAGTGGCTGCTGC

CAGTGGCGATAAGTCGTGTCTTACCGGGTTGGACTCAAGACGATAGTTACCGGATAAGG

CGCAGCGGTCGGGCTGAACGGGGGGTTCGTGCACACAGCCCAGCTTGGAGCGAACGACC

TACACCGAACTGAGATACCTACAGCGTGAGCTATGAGAAAGCGCCACGCTTCCCGAAGG

GAGAAAGGCGGACAGGTATCCGGTAAGCGGCAGGGTCGGAACAGGAGAGCGCACGAGGG

AGCTTCCAGGGGGAAACGCCTGGTATCTTTATAGTCCTGTCGGGTTTCGCCACCTCTGA

CTTGAGCGTCGATTTTTGTGATGCTCGTCAGGGGGGCGGAGCCTATGGAAAAACGCCAG

-continued

CAACGCGGCCTTTTTACGGTTCCTGGCCTTTTGCTGGCCTTTTGCTCACATGTTCTTTC
CTGCGTTATCCCCTGATTCTGTGGATAACCGTATTACCGCCTTTGAGTGAGCTGATACC
GCTCGCCGCAGCCGAACGACCGAGCGCAGCGAGTCAGTGAGCGAGGAAGCGGAAGAGCG
CCCAATACGCAAACCGCCTCTCCCCGCGCGTTGGCCGATTCATTAATGCAGCTGGCACG
ACAGGTTTCCCGACTGGAAAGCGGGCAGTGAGCGCAACGCAATTAATGTGAGTTAGCTC
ACTCATTAGGCACCCCAGGCTTTACACTTTATGCTTCCGGCTCGTATGTTGTGTGGAAT
TGTGAGCGGATAACAATTTCACACAGGAAACAGCTATGACCATGATTACGCCAAGCGCG
CAATTAACCCTCACTAAAGGGAACAAAAGCTGGAGCTGCAAGCTTAATGTAGTCTTATG
CAATACTCTTGTAGTCTTGCAACATGGTAACGATGAGTTAGCAACATGCCTTACAAGGA
GAGAAAAAGCACCGTGCATGCCGATTGGTGGAAGTAAGGTGGTACGATCGTGCCTTATT
AGGAAGGCAACAGACGGGTCTGACATGGATTGGACGAACCACTGAATTGCCGCATTGCA
GAGATATTGTATTTAAGTGCCTAGCTCGATACATAAACGGGTCTCTCTGGTTAGACCAG
ATCTGAGCCTGGGAGCTCTCTGGCTAACTAGGGAACCCACTGCTTAAGCCTCAATAAAG
CTTGCCTTGAGTGCTTCAAGTAGTGTGTGCCCGTCTGTTGTGTGACTCTGGTAACTAGA
GATCCCTCAGACCCTTTTAGTCAGTGTGGAAAATCTCTAGCAGTGGCGCCCGAACAGGG
ACTTGAAAGCGAAAGGGAAACCAGAGGAGCTCTCTCGACGCAGGACTCGGCTTGCTGAA
GCGCGCACGGCAAGAGGCGAGGGGCGGCGACTGGTGAGTACGCCAAAAATTTTGACTAG
CGGAGGCTAGAAGGAGAGAGATGGGTGCGAGAGCGTCAGTATTAAGCGGGGGAGAATTA
GATCGCGATGGGAAAAAATTCGGTTAAGGCCAGGGGGAAAGAAAAAATATAAATTAAAA
CATATAGTATGGGCAAGCAGGGAGCTAGAACGATTCGCAGTTAATCCTGGCCTGTTAGA
AACATCAGAAGGCTGTAGACAAATACTGGGACAGCTACAACCATCCCTTCAGACAGGAT
CAGAAGAACTTAGATCATTATATAATACAGTAGCAACCCTCTATTGTGTGCATCAAAGG
ATAGAGATAAAAGACACCAAGGAAGCTTTAGACAAGATAGAGGAAGAGCAAAACAAAAG
TAAGACCACCGCACAGCAAGCGGCCGCTGATCTTCAGACCTGGAGGAGGAGATATGAGG
GACAATTGGAGAAGTGAATTATATAAATATAAAGTAGTAAAAATTGAACCATTAGGAGT
AGCACCCACCAAGGCAAAGAGAAGAGTGGTGCAGAGAGAAAAAAGAGCAGTGGGAATAG
GAGCTTTGTTCCTTGGGTTCTTGGGAGCAGCAGGAAGCACTATGGGCGCAGCGTCAATG
ACGCTGACGGTACAGGCCAGACAATTATTGTCTGGTATAGTGCAGCAGCAGAACAATTT
GCTGAGGGCTATTGAGGCGCAACAGCATCTGTTGCAACTCACAGTCTGGGGCATCAAGC
AGCTCCAGGCAAGAATCCTGGCTGTGGAAAGATACCTAAAGGATCAACAGCTCCTGGGG
ATTTGGGGTTGCTCTGGAAAACTCATTTGCACCACTGCTGTGCCTTGGAATGCTAGTTG
GAGTAATAAATCTCTGGAACAGATTTGGAATCACACGACCTGGATGGAGTGGGACAGAG
AAATTAACAATTACACAAGCTTAATACACTCCTTAATTGAAGAATCGCAAAACCAGCAA
GAAAAGAATGAACAAGAATTATTGGAATTAGATAAATGGGCAAGTTTGTGGAATTGGTT
TAACATAACAAATTGGCTGTGGTATATAAAATTATTCATAATGATAGTAGGAGGCTTGG
TAGGTTTAAGAATAGTTTTTGCTGTACTTTCTATAGTGAATAGAGTTAGGCAGGGATAT
TCACCATTATCGTTTCAGACCCACCTCCCAACCCCGAGGGGACCCTATTCCAGCACATA
TGAGGCTTGGCGTAACTAGATCTTGAGACAAATGGCAGTATTCATCCACAATTTTAAAA
GAAAAGGGGGGATTGGGGGGTACAGTGCAGGGGAAAGAATAGTAGACATAATAGCAACA
GACATACAAACTAAAGAATTACAAAAACAAATTACAAAAATTCAAAATTTTCGGGTTTA

-continued

TTACAGGGACAGCAGAGATCCACTTTGGGCTCGAGGGGGCCCGGGTGCAAAGATGGATA

AAGTTTTAAACAGAGAGGAATCTTTGCAGCTAATGGACCTTCTAGGTCTTGAAAGGAGT

GGGAATTGGCTCCGGTGCCCGTCAGTGGGCAGAGCGCACATCGCCCACAGTCCCCGAGA

AGTTGGGGGGAGGGGTCGGCAATTGATCCGGTGCCTAGAGAAGGTGGCGCGGGGTAAAC

TGGGAAAGTGATGTCGTGTACTGGCTCCGCCTTTTTCCCGAGGGTGGGGGAGAACCGTA

TATAAGTGCAGTAGTCGCCGTGAACGTTCTTTTTCGCAACGGGTTTGCCGCCAGAACAC

AGGTAAGTGCCGTGTGTGGTTCCCGCGGGCCTGGCCTCTTTACGGGTTATGGCCCTTGC

GTGCCTTGAATTACTTCCACCTGGCTGCAGTACGTGATTCTTGATCCCGAGCTTCGGGT

TGGAAGTGGGTGGGAGAGTTCGAGGCCTTGCGCTTAAGGAGCCCCTTCGCCTCGTGCTT

GAGTTGAGGCCTGGCCTGGGCGCTGGGGCCGCCGCGTGCGAATCTGGTGGCACCTTCGC

GCCTGTCTCGCTGCTTTCGATAAGTCTCTAGCCATTTAAAATTTTTGATGACCTGCTGC

GACGCTTTTTTTCTGGCAAGATAGTCTTGTAAATGCGGGCCAAGATCTGCACACTGGTA

TTTCGGTTTTTGGGGCCGCGGGCGGCGACGGGGCCCGTGCGTCCCAGCGCACATGTTCG

GCGAGGCGGGGCCTGCGAGCGCGGCCACCGAGAATCGGACGGGGGTAGTCTCAAGCTGG

CCGGCCTGCTCTGGTGCCTGGCCTCGCGCCGCCGTGTATCGCCCCGCCCTGGGCGGCAA

GGCTGGCCCGGTCGGCACCAGTTGCGTGAGCGGAAAGATGGCCGCTTCCCGGCCCTGCT

GCAGGGAGCTCAAAATGGAGGACGCGGCGCTCGGGAGAGCGGGCGGGTGAGTCACCCAC

ACAAAGGAAAAGGGCCTTTCCGTCCTCAGCCGTCGCTTCATGTGACTCCACGGAGTACC

GGGCGCCGTCCAGGCACCTCGATTAGTTCTCGAGCTTTTGGAGTACGTCGTCTTTAGGT

TGGGGGGAGGGGTTTTATGCGATGGAGTTTCCCCACACTGAGTGGGTGGAGACTGAAGT

TAGGCCAGCTTGGCACTTGATGTAATTCTCCTTGGAATTTGCCCTTTTTGAGTTTGGAT

CTTGGTTCATTCTCAAGCCTCAGACAGTGGTTCAAAGTTTTTTTCTTCCATTTCAGGTG

TCGTGAGGATCTACCGGTCGCCACCATGGAGACGGACGTCTCAgctgaagctgctgcaA

AGgaagctgcagctAAGgaggctgcagctAAGgctATGGTGTCTAAGGGCGAAGAGCTG

ATTAAGGAGAACATGCACATGAAGCTGTACATGGAGGGCACCGTGGACAACCATCACTT

CAAGTGCACATCCGAGGGCGAAGGCAAGCCCTACGAGGGCACCCAGACCATGAGAATCA

AGGTGGTCGAGGGCGGCCCTCTCCCCTTCGCCTTCGACATCCTGGCTACTAGCTTCCTC

TACGGCAGCAAGACCTTCATCAACCACACCCAGGGCATCCCCGACTTCTTCAAGCAGTC

CTTCCCTGAGGGCTTCACATGGGAGAGAGTCACCACATACGAAGACGGGGGCGTGCTGA

CCGCTACCCAGGACACCAGCCTCCAGGACGGCTGCCTCATCTACAACGTCAAGATCAGA

GGGGTGAACTTCACATCCAACGGCCCTGTGATGCAGAAGAAAACACTCGGCTGGGAGGC

CTTCACCGAGACcCTGTACCCCGCTGACGGCGGCCTGGAAGGCAGAAACGACATGGCCC

TGAAGCTCGTGGGCGGGAGCCATCTGATCGCAAACGCCAAGACCACATATAGATCCAAG

AAACCCGCTAAGAACCTCAAGATGCCTGGCGTCTACTATGTGGACTACAGACTGGAAAG

AATCAAGGAGGCCAACAACGAGACCTACGTCGAGCAGCACGAGGTGGCAGTGGCCAGAT

ACTGCGACCTCCCTAGCAAACTGGGGCACAAGCTTAATtaaCAGGGACAGCAGAGATAC

GCGTTAAGTCGACAATCAACCTCTGGATTACAAAATTTGTGAAAGATTGACTGGTATTC

TTAACTATGTTGCTCCTTTTACGCTATGTGGATACGCTGCTTTAATGCCTTTGTATCAT

GCTATTGCTTCCCGTATGGCTTTCATTTTCTCCTCCTTGTATAAATCCTGGTTGCTGTC

TCTTTATGAGGAGTTGTGGCCCGTTGTCAGGCAACGTGGCGTGGTGTGCACTGTGTTTG

CTGACGCAACCCCCACTGGTTGGGGCATTGCCACCACCTGTCAGCTCCTTTCCGGGACT

-continued

TTCGCTTTCCCCCTCCCTATTGCCACGGCGGAACTCATCGCCGCCTGCCTTGCCCGCTG

CTGGACAGGGGCTCGGCTGTTGGGCACTGACAATTCCGTGGTGTTGTCGGGGAAATCAT

CGTCCTTTCCTTGGCTGCTCGCCTGTGTTGCCACCTGGATTCTGCGCGGGACGTCCTTC

TGCTACGTCCCTTCGGCCCTCAATCCAGCGGACCTTCCTTCCCGCGGCCTGCTGCCGGC

TCTGCGGCCTCTTCCGCGTCTTCGCCTTCGCCCTCAGACGAGTCGGATCTCCCTTTGGG

CCGCCTCCCCGCGTCGACTTTAAGACCAATGACTTACAAGGCAGCTGTAGATCTTAGCC

ACTTTTTAAAAGAAAAGGGGGGACTGGAAGGGCTAATTCACTCCCAACGAAGACAAGAT

CTGCTTTTTGCTTGTACTGGGTCTCTCTGGTTAGACCAGATCTGAGCCTGGGAGCTCTC

TGGCTAACTAGGGAACCCACTGCTTAAGCCTCAATAAAGCTTGCCTTGAGTGCTTCAAG

TAGTGTGTGCCCGTCTGTTGTGTGACTCTGGTAACTAGAGATCCCTCAGACCCTTTTAG

TCAGTGTGGAAAATCTCTAGCAGTACGTATAGTAGTTCATGTCATCTTATTATTCAGTA

TTTATAACTTGCAAAGAAATGAATATCAGAGAGTGAGAGGAACTTGTTTATTGCAGCTT

ATAATGGTTACAAATAAAGCAATAGCATCACAAATTTCACAAATAAAGCATTTTTTTCA

CTGCATTCTAGTTGTGGTTTGTCCAAACTCATCAATGTATCTTATCATGTCTGGCTCTA

GCTATCCCGCCCCTAACTCCGCCCATCCCGCCCCTAACTCCGCCCAGTTCCGCCCATTC

TCCGCCCCATGGCTGACTAATTTTTTTTATTTATGCAGAGGCCGAGGCCGCCTCGGCCT

CTGAGCTATTCCAGAAGTAGTGAGGAGGCTTTTTTGGAGGCCTAGGGACGTACCCAATT

CGCCCTATAGTGAGTCGTATTACGCGCGCTCACTGGCCGTCGTTTTACAACGTCGTGAC

TGGGAAAACCCTGGCGTTACCCAACTTAATCGCCTTGCAGCACATCCCCCTTTCGCCAG

CTGGCGTAATAGCGAAGAGGCCCGCACCGATCGCCCTTCCCAACAGTTGCGCAGCCTGA

ATGGCGAATGGGACGCGCCCTGTAGCGGCGCATTAAGCGCGGCGGGTGTGGTGGTTACG

CGCAGCGTGACCGCTACACTTGCCAGCGCCCTAGCGCCCGCTCCTTTCGCTTTCTTCCC

TTCCTTTCTCGCCACGTTCGCCGGCTTTCCCCGTCAAGCTCTAAATCGGGGGCTCCCTT

TAGGGTTCCGATTTAGTGCTTTACGGCACCTCGACCCCAAAAAACTTGATTAGGGTGAT

GGTTCACGTAGTGGGCCATCGCCCTGATAGACGGTTTTTCGCCCTTTGACGTTGGAGTC

CACGTTCTTTAATAGTGGACTCTTGTTCCAAACTGGAACAACACTCAACCCTATCTCGG

TCTATTCTTTTGATTTATAAGGGATTTTGCCGATTTCGGCCTATTGGTTAAAAAATGAG

CTGATTTAACAAAAATTTAACGCGAATTTTAACAAAATATTAACGCTTACAATTTAGGT

GGCACTTTTCGGGGAAATGTGCGCGGAACCCCTATTTGTTTATTTTTCTAAATACATTC

AAATATGTATCCGCTCATGAGACAATAACCCTGATAAATGCTTCAATAATATTGAAAAA

GGAAGAGTATGAGTATTCAACATTTCCGTGTCGCCCTTATTCCCTTTTTTGCGGCATTT

TGCCTTCCTGTTTTTGCTCACCCAGAAACGCTGGTGAAAGTAAAAGATGCTGAAGATCA

GTTGGGTGCACGAGTGGGTTACATCGAACTGGATCTCAACAGCGGTAAGATCCTTGAGA

GTTTTCGCCCCGAAGAACGTTTTCCAATGATGAGCACTTTTAAAGTTCTGCTATGTGGC

GCGGTATTATCCCGTATTGACGCCGGGCAAGAGCAACTCGGTCGCCGCATACACTATTC

TCAGAATGACTTGGTTGAGTACTCACCAGTCACAGAAAAGCATCTTACGGATGGCATGA

CAGTAAGAGAATTATGCAGTGCTGCCATAACCATGAGTGATAACACTGCGGCCAACTTA

CTTCTGACAACGATCGGAGGACCGAAGGAGCTAACCGCTTTTTTGCACAACATGGGGGA

TCATGTAACTCGCCTTGATCGTTGGGAACCGGAGCTGAATGAAGCCATACCAAACGACG

AGCGTGACACCACGATGCCTGTAGCAATGGCAACAACGTTGCGCAAACTATTAACTGGC

-continued

GAACTACTTACTCTAGCTTCCCGGCAACAATTAATAGACTGGATGGAGGCGGATAAAGT

TGCAGGACCACTTCTGCGCTCGGCCCTTCCGGCTGGCTGGTTTATTGCTGATAAATCTG

GAGCCGGTGAGCGTGGGTCTCGCGGTATCATTGCAGCACTGGGGCCAGATGGTAAGCCC

TCCCGTATCGTAGTTATCTACACGACGGGGAGTCAGGCAACTATGGATGAACGAAATAG

ACAGATCGCTGAGATAGGTGCCTCACTGATTAAGCATTGGTAA

"Bolinas": pEF1α-BsmBI cloning site-17aaRigidLinker-mTagBFP2-P2A-Blasticidin (SEQ ID NO: 91)

TTTTGCACAACATGGGGGATCATGTAACTCGCCTTGATCGTTGGGAACCGGAGCTGAAT

GAAGCCATACCAAACGACGAGCGTGACACCACGATGCCTGTAGCAATGGCAACAACGTT

GCGCAAACTATTAACTGGCGAACTACTTACTCTAGCTTCCCGGCAACAATTAATAGACT

GGATGGAGGCGGATAAAGTTGCAGGACCACTTCTGCGCTCGGCCCTTCCGGCTGGCTGG

TTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAA

CTATGGATGAACGAAATAGACAGATCGCTGAGATAGGTGCCTCACTGATTAAGCATTGG

TAACTGTCAGACCAAGTTTACTCATATATACTTTAGATTGATTTAAAACTTCATTTTTA

ATTTAAAAGGATCTAGGTGAAGATCCTTTTTGATAATCTCATGACCAAAATCCCTTAAC

GTGAGTTTTCGTTCCACTGAGCGTCAGACCCCGTAGAAAAGATCAAAGGATCTTCTTGA

GATCCTTTTTTTCTGCGCGTAATCTGCTGCTTGCAAACAAAAAAACCACCGCTACCAGC

GGTGGTTTGTTTGCCGGATCAAGAGCTACCAACTCTTTTTCCGAAGGTAACTGGCTTCA

GCAGAGCGCAGATACCAAATACTGTTCTTCTAGTGTAGCCGTAGTTAGGCCACCACTTC

AAGAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGATA

AGGCGCAGCGGTCGGGCTGAACGGGGGGTTCGTGCACACAGCCCAGCTTGGAGCGAACG

ACCTACACCGAACTGAGATACCTACAGCGTGAGCTATGAGAAAGCGCCACGCTTCCCGA

AGGGAGAAAGGCGGACAGGTATCCGGTAAGCGGCAGGGTCGGAACAGGAGAGCGCACGA

GGGAGCTTCCAGGGGGAAACGCCTGGTATCTTTATAGTCCTGTCGGGTTTCGCCACCTC

TGACTTGAGCGTCGATTTTTGTGATGCTCGTCAGGGGGGCGGAGCCTATGGAAAAACGC

CAGCAACGCGGCCTTTTTACGGTTCCTGGCCTTTTGCTGGCCTTTTGCTCACATGTTCT

TTCCTGCGTTATCCCCTGATTCTGTGGATAACCGTATTACCGCCTTTGAGTGAGCTGAT

ACCGCTCGCCGCAGCCGAACGACCGAGCGCAGCGAGTCAGTGAGCGAGGAAGCGGAAGA

GCGCCCAATACGCAAACCGCCTCTCCCCGCGCGTTGGCCGATTCATTAATGCAGCTGGC

ACGACAGGTTTCCCGACTGGAAAGCGGGCAGTGAGCGCAACGCAATTAATGTGAGTTAG

CTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGC

GCGCAATTAACCCTCACTAAAGGGAACAAAAGCTGGAGCTGCAAGCTTAATGTAGTCTT

ATGCAATACTCTTGTAGTCTTGCAACATGGTAACGATGAGTTAGCAACATGCCTTACAA

GGAGAGAAAAAGCACCGTGCATGCCGATTGGTGGAAGTAAGGTGGTACGATCGTGCCTT

ATTAGGAAGGCAACAGACGGGTCTGACATGGATTGGACGAACCACTGAATTGCCGCATT

GCAGAGATATTGTATTTAAGTGCCTAGCTCGATACATAAACGGGTCTCTCTGGTTAGAC

CAGATCTGAGCCTGGGAGCTCTCTGGCTAACTAGGGAACCCACTGCTTAAGCCTCAATA

AAGCTTGCCTTGAGTGCTTCAAGTAGTGTGTGCCCGTCTGTTGTGTGACTCTGGTAACT

-continued

AGAGATCCCTCAGACCCTTTTAGTCAGTGTGGAAAATCTCTAGCAGTGGCGCCCGAACA

GGGACTTGAAAGCGAAAGGGAAACCAGAGGAGCTCTCTCGACGCAGGACTCGGCTTGCT

GAAGCGCGCACGGCAAGAGGCGAGGGGCGGCGACTGGTGAGTACGCCAAAAATTTTGAC

TAGCGGAGGCTAGAAGGAGAGAGATGGGTGCGAGAGCGTCAGTATTAAGCGGGGGAGAA

TTAGATCGCGATGGGAAAAAATTCGGTTAAGGCCAGGGGGAAAGAAAAAATATAAATTA

AAACATATAGTATGGGCAAGCAGGGAGCTAGAACGATTCGCAGTTAATCCTGGCCTGTT

AGAAACATCAGAAGGCTGTAGACAAATACTGGGACAGCTACAACCATCCCTTCAGACAG

GATCAGAAGAACTTAGATCATTATATAATACAGTAGCAACCCTCTATTGTGTGCATCAA

AGGATAGAGATAAAAGACACCAAGGAAGCTTTAGACAAGATAGAGGAAGAGCAAAACAA

AAGTAAGACCACCGCACAGCAAGCGGCCGCTGATCTTCAGACCTGGAGGAGGAGATATG

AGGGACAATTGGAGAAGTGAATTATATAAATATAAAGTAGTAAAAATTGAACCATTAGG

AGTAGCACCCACCAAGGCAAAGAGAAGAGTGGTGCAGAGAGAAAAAAGAGCAGTGGGAA

TAGGAGCTTTGTTCCTTGGGTTCTTGGGAGCAGCAGGAAGCACTATGGGCGCAGCGTCA

ATGACGCTGACGGTACAGGCCAGACAATTATTGTCTGGTATAGTGCAGCAGCAGAACAA

TTTGCTGAGGGCTATTGAGGCGCAACAGCATCTGTTGCAACTCACAGTCTGGGGCATCA

AGCAGCTCCAGGCAAGAATCCTGGCTGTGGAAAGATACCTAAAGGATCAACAGCTCCTG

GGGATTTGGGGTTGCTCTGGAAAACTCATTTGCACCACTGCTGTGCCTTGGAATGCTAG

TTGGAGTAATAAATCTCTGGAACAGATTTGGAATCACACGACCTGGATGGAGTGGGACA

GAGAAATTAACAATTACACAAGCTTAATACACTCCTTAATTGAAGAATCGCAAAACCAG

CAAGAAAAGAATGAACAAGAATTATTGGAATTAGATAAATGGGCAAGTTTGTGGAATTG

GTTTAACATAACAAATTGGCTGTGGTATATAAAATTATTCATAATGATAGTAGGAGGCT

TGGTAGGTTTAAGAATAGTTTTTGCTGTACTTTCTATAGTGAATAGAGTTAGGCAGGGA

TATTCACCATTATCGTTTCAGACCCACCTCCCAACCCCGAGGGGACCCTATTCCAGCAC

ATATGAGGCTTGGCGTAACTAGATCTTGAGACAAATGGCAGTATTCATCCACAATTTTA

AAAGAAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTCGGGT

TTATTACAGGGACAGCAGAGATCCACTTTGGGCTCGAGGGGGCCCGGGTGCAAAGATGG

ATAAAGTTTTAAACAGAGAGGAATCTTTGCAGCTAATGGACCTTCTAGGTCTTGAAAGG

AGTGGGAATTGGCTCCGGTGCCCGTCAGTGGGCAGAGCGCACATCGCCCACAGTCCCCG

AGAAGTTGGGGGGAGGGGTCGGCAATTGATCCGGTGCCTAGAGAAGGTGGCGCGGGGTA

AACTGGGAAAGTGATGTCGTGTACTGGCTCCGCCTTTTTCCCGAGGGTGGGGGAGAACC

GTATATAAGTGCAGTAGTCGCCGTGAACGTTCTTTTTCGCAACGGGTTTGCCGCCAGAA

CACAGGTAAGTGCCGTGTGTGGTTCCCGCGGGCCTGGCCTCTTTACGGGTTATGGCCCT

TGCGTGCCTTGAATTACTTCCACCTGGCTGCAGTACGTGATTCTTGATCCCGAGCTTCG

GGTTGGAAGTGGGTGGGAGAGTTCGAGGCCTTGCGCTTAAGGAGCCCCTTCGCCTCGTG

CTTGAGTTGAGGCCTGGCCTGGGCGCTGGGGCCGCCGCGTGCGAATCTGGTGGCACCTT

CGCGCCTGTCTCGCTGCTTTCGATAAGTCTCTAGCCATTTAAAATTTTTGATGACCTGC

TGCGACGCTTTTTTTCTGGCAAGATAGTCTTGTAAATGCGGGCCAAGATCTGCACACTG

GTATTTCGGTTTTTGGGGCCGCGGGCGGCGACGGGGCCCGTGCGTCCCAGCGCACATGT

TCGGCGAGGCGGGGCCTGCGAGCGCGGCCACCGAGAATCGGACGGGGGTAGTCTCAAGC

TGGCCGGCCTGCTCTGGTGCCTGGCCTCGCGCCGCCGTGTATCGCCCCGCCCTGGGCGG

-continued

CAAGGCTGGCCCGGTCGGCACCAGTTGCGTGAGCGGAAAGATGGCCGCTTCCCGGCCCT

GCTGCAGGGAGCTCAAAATGGAGGACGCGGCGCTCGGGAGAGCGGGCGGGTGAGTCACC

CACACAAAGGAAAAGGGCCTTTCCGTCCTCAGCCGTCGCTTCATGTGACTCCACGGAGT

ACCGGGCGCCGTCCAGGCACCTCGATTAGTTCTCGAGCTTTTGGAGTACGTCGTCTTTA

GGTTGGGGGGAGGGGTTTTATGCGATGGAGTTTCCCCACACTGAGTGGGTGGAGACTGA

AGTTAGGCCAGCTTGGCACTTGATGTAATTCTCCTTGGAATTTGCCCTTTTTGAGTTTG

GATCTTGGTTCATTCTCAAGCCTCAGACAGTGGTTCAAAGTTTTTTTCTTCCATTTCAG

GTGTCGTGAATACCGTCGACTCCGGAATAGCCACCATGGAGACGGACGTCTCAGCTGAA

GCTGCTGCAAAGGAAGCTGCAGCTAAGGAGGCTGCAGCTAAGGCTATGGTGTCTAAGGG

CGAAGAGCTGATTAAGGAGAACATGCACATGAAGCTGTACATGGAGGGCACCGTGGACA

ACCATCACTTCAAGTGCACATCCGAGGGCGAAGGCAAGCCCTACGAGGGCACCCAGACC

ATGAGAATCAAGGTGGTCGAGGGCGGCCCTCTCCCCTTCGCCTTCGACATCCTGGCTAC

TAGCTTCCTCTACGGCAGCAAGACCTTCATCAACCACACCCAGGGCATCCCCGACTTCT

TCAAGCAGTCCTTCCCTGAGGGCTTCACATGGGAGAGAGTCACCACATACGAAGACGGG

GGCGTGCTGACCGCTACCCAGGACACCAGCCTCCAGGACGGCTGCCTCATCTACAACGT

CAAGATCAGAGGGGTGAACTTCACATCCAACGGCCCTGTGATGCAGAAGAAAACACTCG

GCTGGGAGGCCTTCACCGAGACcCTGTACCCCGCTGACGGCGGCCTGGAAGGCAGAAAC

GACATGGCCCTGAAGCTCGTGGGCGGGAGCCATCTGATCGCAAACGCCAAGACCACATA

TAGATCCAAGAAACCCGCTAAGAACCTCAAGATGCCTGGCGTCTACTATGTGGACTACA

GACTGGAAAGAATCAAGGAGGCCAACAACGAGACCTACGTCGAGCAGCACGAGGTGGCA

GTGGCCAGATACTGCGACCTCCCTAGCAAACTGGGGCACAAGCTTAATGGACTCAGAGT

TTGGGTAGGAAGCGGAGCTACTAACTTCAGCCTGCTGAAGCAGGCTGGAGAtGTGGAGG

AGAACCCTGGACCTATGGCCAAGCCTTTGTCTCAAGAAGAATCCACCCTCATTGAAAGA

GCAACGGCTACAATCAACAGCATCCCCATCTCTGAAGACTACAGCGTCGCCAGCGCAGC

TCTCTCTAGCGACGGCCGCATCTTCACTGGTGTCAATGTATATCATTTTACTGGGGGAC

CTTGTGCAGAACTCGTGGTGCTGGGCACTGCTGCTGCTGCGGCAGCTGGCAACCTGACT

TGTATCGTCGCGATCGGAAATGAGAACAGGGGCATCTTGAGCCCCTGCGGACGGTGCCG

ACAGGTGCTTCTCGATCTGCATCCTGGGATCAAAGCCATAGTGAAGGACAGTGATGGAC

AGCCGACGGCAGTTGGGATTCGTGAATTGCTGCCCTCTGGTTATGTGTGGGAGGGCTAA

ATGCATGAGTAACTGAGGATCCAGGGACAGCAGAGATACGCGTTAAGTCGACAATCAAC

CTCTGGATTACAAAATTTGTGAAAGATTGACTGGTATTCTTAACTATGTTGCTCCTTTT

ACGCTATGTGGATACGCTGCTTTAATGCCTTTGTATCATGCTATTGCTTCCCGTATGGC

TTTCATTTTCTCCTCCTTGTATAAATCCTGGTTGCTGTCTCTTTATGAGGAGTTGTGGC

CCGTTGTCAGGCAACGTGGCGTGGTGTGCACTGTGTTTGCTGACGCAACCCCCACTGGT

TGGGGCATTGCCACCACCTGTCAGCTCCTTTCCGGGACTTTCGCTTTCCCCCTCCCTAT

TGCCACGGCGGAACTCATCGCCGCCTGCCTTGCCCGCTGCTGGACAGGGGCTCGGCTGT

TGGGCACTGACAATTCCGTGGTGTTGTCGGGGAAATCATCGTCCTTTCCTTGGCTGCTC

GCCTGTGTTGCCACCTGGATTCTGCGCGGGACGTCCTTCTGCTACGTCCCTTCGGCCCT

CAATCCAGCGGACCTTCCTTCCCGCGGCCTGCTGCCGGCTCTGCGGCCTCTTCCGCGTC

TTCGCCTTCGCCCTCAGACGAGTCGGATCTCCCTTTGGGCCGCCTCCCCGCGTCGACTT

-continued

TAAGACCAATGACTTACAAGGCAGCTGTAGATCTTAGCCACTTTTTAAAAGAAAAGGGG

GGACTGGAAGGGCTAATTCACTCCCAACGAAGACAAGATCTGCTTTTTGCTTGTACTGG

GTCTCTCTGGTTAGACCAGATCTGAGCCTGGGAGCTCTCTGGCTAACTAGGGAACCCAC

TGCTTAAGCCTCAATAAAGCTTGCCTTGAGTGCTTCAAGTAGTGTGTGCCCGTCTGTTG

TGTGACTCTGGTAACTAGAGATCCCTCAGACCCTTTTAGTCAGTGTGGAAAATCTCTAG

CAGTACGTATAGTAGTTCATGTCATCTTATTATTCAGTATTTATAACTTGCAAAGAAAT

GAATATCAGAGAGTGAGAGGAACTTGTTTATTGCAGCTTATAATGGTTACAAATAAAGC

AATAGCATCACAAATTTCACAAATAAAGCATTTTTTTCACTGCATTCTAGTTGTGGTTT

GTCCAAACTCATCAATGTATCTTATCATGTCTGGCTCTAGCTATCCCGCCCCTAACTCC

GCCCATCCCGCCCCTAACTCCGCCCAGTTCCGCCCATTCTCCGCCCCATGGCTGACTAA

TTTTTTTTATTTATGCAGAGGCCGAGGCCGCCTCGGCCTCTGAGCTATTCCAGAAGTAG

TGAGGAGGCTTTTTTGGAGGCCTAGGGACGTACCCAATTCGCCCTATAGTGAGTCGTAT

TACGCGCGCTCACTGGCCGTCGTTTTACAACGTCGTGACTGGGAAAACCCTGGCGTTAC

CCAACTTAATCGCCTTGCAGCACATCCCCCTTTCGCCAGCTGGCGTAATAGCGAAGAGG

CCCGCACCGATCGCCCTTCCCAACAGTTGCGCAGCCTGAATGGCGAATGGGACGCGCCC

TGTAGCGGCGCATTAAGCGCGGCGGGTGTGGTGGTTACGCGCAGCGTGACCGCTACACT

TGCCAGCGCCCTAGCGCCCGCTCCTTTCGCTTTCTTCCCTTCCTTTCTCGCCACGTTCG

CCGGCTTTCCCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAGTGGGCCATC

GCCCTGATAGACGGTTTTTCGCCCTTTGACGTTGGAGTCCACGTTCTTTAATAGTGGAC

TCTTGTTCCAAACTGGAACAACACTCAACCCTATCTCGGTCTATTCTTTTGATTTATAA

GGGATTTTGCCGATTTCGGCCTATTGGTTAAAAAATGAGCTGATTTAACAAAAATTTAA

CGCGAATTTTAACAAAATATTAACGCTTACAATTTAGGTGGCACTTTTCGGGGAAATGT

GCGCGGAACCCCTATTTGTTTATTTTTCTAAATACATTCAAATATGTATCCGCTCATGA

GACAATAACCCTGATAAATGCTTCAATAATATTGAAAAAGGAAGAGTATGAGTATTCAA

CATTTCCGTGTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCACGAGTGGGTT

ACATCGAACTGGATCTCAACAGCGGTAAGATCCTTGAGAGTTTTCGCCCCGAAGAACGT

TTTCCAATGATGAGCACTTTTAAAGTTCTGCTATGTGGCGCGGTATTATCCCGTATTGA

CGCCGGGCAAGAGCAACTCGGTCGCCGCATACACTATTCTCAGAATGACTTGGTTGAGT

ACTCACCAGTCACAGAAAAGCATCTTACGGATGGCATGACAGTAAGAGAATTATGCAGT

GCTGCCATAACCATGAGTGATAACACTGCGGCCAACTTACTTCTGACAACGATCGGAGG

ACCGAAGGAGCTAACCGCTT

"Jenner": pEF1α-BsmBI cloning site-17aaRigidLinker-mCherry-P2A-neo (SEQ ID NO: 92)

TTTTGCACAACATGGGGGATCATGTAACTCGCCTTGATCGTTGGGAACCGGAGCTGAAT

GAAGCCATACCAAACGACGAGCGTGACACCACGATGCCTGTAGCAATGGCAACAACGTT

GCGCAAACTATTAACTGGCGAACTACTTACTCTAGCTTCCCGGCAACAATTAATAGACT

GGATGGAGGCGGATAAAGTTGCAGGACCACTTCTGCGCTCGGCCCTTCCGGCTGGCTGG

TTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAA

-continued

CTATGGATGAACGAAATAGACAGATCGCTGAGATAGGTGCCTCACTGATTAAGCATTGG

TAACTGTCAGACCAAGTTTACTCATATATACTTTAGATTGATTTAAAACTTCATTTTTA

ATTTAAAAGGATCTAGGTGAAGATCCTTTTTGATAATCTCATGACCAAAATCCCTTAAC

GTGAGTTTTCGTTCCACTGAGCGTCAGACCCCGTAGAAAAGATCAAAGGATCTTCTTGA

GATCCTTTTTTTCTGCGCGTAATCTGCTGCTTGCAAACAAAAAAACCACCGCTACCAGC

GGTGGTTTGTTTGCCGGATCAAGAGCTACCAACTCTTTTTCCGAAGGTAACTGGCTTCA

GCAGAGCGCAGATACCAAATACTGTTCTTCTAGTGTAGCCGTAGTTAGGCCACCACTTC

AAGAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGATA

AGGCGCAGCGGTCGGGCTGAACGGGGGGTTCGTGCACACAGCCCAGCTTGGAGCGAACG

ACCTACACCGAACTGAGATACCTACAGCGTGAGCTATGAGAAAGCGCCACGCTTCCCGA

AGGGAGAAAGGCGGACAGGTATCCGGTAAGCGGCAGGGTCGGAACAGGAGAGCGCACGA

GGGAGCTTCCAGGGGGAAACGCCTGGTATCTTTATAGTCCTGTCGGGTTTCGCCACCTC

TGACTTGAGCGTCGATTTTTGTGATGCTCGTCAGGGGGGCGGAGCCTATGGAAAAACGC

CAGCAACGCGGCCTTTTTACGGTTCCTGGCCTTTTGCTGGCCTTTTGCTCACATGTTCT

TTCCTGCGTTATCCCCTGATTCTGTGGATAACCGTATTACCGCCTTTGAGTGAGCTGAT

ACCGCTCGCCGCAGCCGAACGACCGAGCGCAGCGAGTCAGTGAGCGAGGAAGCGGAAGA

GCGCCCAATACGCAAACCGCCTCTCCCCGCGCGTTGGCCGATTCATTAATGCAGCTGGC

ACGACAGGTTTCCCGACTGGAAAGCGGGCAGTGAGCGCAACGCAATTAATGTGAGTTAG

CTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGC

GCGCAATTAACCCTCACTAAAGGGAACAAAAGCTGGAGCTGCAAGCTTAATGTAGTCTT

ATGCAATACTCTTGTAGTCTTGCAACATGGTAACGATGAGTTAGCAACATGCCTTACAA

GGAGAGAAAAAGCACCGTGCATGCCGATTGGTGGAAGTAAGGTGGTACGATCGTGCCTT

ATTAGGAAGGCAACAGACGGGTCTGACATGGATTGGACGAACCACTGAATTGCCGCATT

GCAGAGATATTGTATTTAAGTGCCTAGCTCGATACATAAACGGGTCTCTCTGGTTAGAC

CAGATCTGAGCCTGGGAGCTCTCTGGCTAACTAGGGAACCCACTGCTTAAGCCTCAATA

AAGCTTGCCTTGAGTGCTTCAAGTAGTGTGTGCCCGTCTGTTGTGTGACTCTGGTAACT

AGAGATCCCTCAGACCCTTTTAGTCAGTGTGGAAAATCTCTAGCAGTGGCGCCCGAACA

GGGACTTGAAAGCGAAAGGGAAACCAGAGGAGCTCTCTCGACGCAGGACTCGGCTTGCT

GAAGCGCGCACGGCAAGAGGCGAGGGGCGGCGACTGGTGAGTACGCCAAAAATTTTGAC

TAGCGGAGGCTAGAAGGAGAGAGATGGGTGCGAGAGCGTCAGTATTAAGCGGGGGAGAA

TTAGATCGCGATGGGAAAAAATTCGGTTAAGGCCAGGGGGAAAGAAAAAATATAAATTA

AAACATATAGTATGGGCAAGCAGGGAGCTAGAACGATTCGCAGTTAATCCTGGCCTGTT

AGAAACATCAGAAGGCTGTAGACAAATACTGGGACAGCTACAACCATCCCTTCAGACAG

GATCAGAAGAACTTAGATCATTATATAATACAGTAGCAACCCTCTATTGTGTGCATCAA

AGGATAGAGATAAAAGACACCAAGGAAGCTTTAGACAAGATAGAGGAAGAGCAAAACAA

AAGTAAGACCACCGCACAGCAAGCGGCCGCTGATCTTCAGACCTGGAGGAGGAGATATG

AGGGACAATTGGAGAAGTGAATTATATAAATATAAAGTAGTAAAAATTGAACCATTAGG

AGTAGCACCCACCAAGGCAAAGAGAAGAGTGGTGCAGAGAGAAAAAAGAGCAGTGGGAA

TAGGAGCTTTGTTCCTTGGGTTCTTGGGAGCAGCAGGAAGCACTATGGGCGCAGCGTCA

-continued

ATGACGCTGACGGTACAGGCCAGACAATTATTGTCTGGTATAGTGCAGCAGCAGAACAA

TTTGCTGAGGGCTATTGAGGCGCAACAGCATCTGTTGCAACTCACAGTCTGGGGCATCA

AGCAGCTCCAGGCAAGAATCCTGGCTGTGGAAAGATACCTAAAGGATCAACAGCTCCTG

GGGATTTGGGGTTGCTCTGGAAAACTCATTTGCACCACTGCTGTGCCTTGGAATGCTAG

TTGGAGTAATAAATCTCTGGAACAGATTTGGAATCACACGACCTGGATGGAGTGGGACA

GAGAAATTAACAATTACACAAGCTTAATACACTCCTTAATTGAAGAATCGCAAAACCAG

CAAGAAAAGAATGAACAAGAATTATTGGAATTAGATAAATGGGCAAGTTTGTGGAATTG

GTTTAACATAACAAATTGGCTGTGGTATATAAAATTATTCATAATGATAGTAGGAGGCT

TGGTAGGTTTAAGAATAGTTTTTGCTGTACTTTCTATAGTGAATAGAGTTAGGCAGGGA

TATTCACCATTATCGTTTCAGACCCACCTCCCAACCCCGAGGGGACCCTATTCCAGCAC

ATATGAGGCTTGGCGTAACTAGATCTTGAGACAAATGGCAGTATTCATCCACAATTTTA

AAAGAAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTCGGGT

TTATTACAGGGACAGCAGAGATCCACTTTGGGCTCGAGGGGGCCCGGGTGCAAAGATGG

ATAAAGTTTTAAACAGAGAGGAATCTTTGCAGCTAATGGACCTTCTAGGTCTTGAAAGG

AGTGGGAATTGGCTCCGGTGCCCGTCAGTGGGCAGAGCGCACATCGCCCACAGTCCCCG

AGAAGTTGGGGGGAGGGGTCGGCAATTGATCCGGTGCCTAGAGAAGGTGGCGCGGGGTA

AACTGGGAAAGTGATGTCGTGTACTGGCTCCGCCTTTTTCCCGAGGGTGGGGGAGAACC

GTATATAAGTGCAGTAGTCGCCGTGAACGTTCTTTTTCGCAACGGGTTTGCCGCCAGAA

CACAGGTAAGTGCCGTGTGTGGTTCCCGCGGGCCTGGCCTCTTTACGGGTTATGGCCCT

TGCGTGCCTTGAATTACTTCCACCTGGCTGCAGTACGTGATTCTTGATCCCGAGCTTCG

GGTTGGAAGTGGGTGGGAGAGTTCGAGGCCTTGCGCTTAAGGAGCCCCTTCGCCTCGTG

CTTGAGTTGAGGCCTGGCCTGGGCGCTGGGGCCGCCGCGTGCGAATCTGGTGGCACCTT

CGCGCCTGTCTCGCTGCTTTCGATAAGTCTCTAGCCATTTAAAATTTTTGATGACCTGC

TGCGACGCTTTTTTTCTGGCAAGATAGTCTTGTAAATGCGGGCCAAGATCTGCACACTG

GTATTTCGGTTTTTGGGGCCGCGGGCGGCGACGGGGCCCGTGCGTCCCAGCGCACATGT

TCGGCGAGGCGGGGCCTGCGAGCGCGGCCACCGAGAATCGGACGGGGGTAGTCTCAAGC

TGGCCGGCCTGCTCTGGTGCCTGGCCTCGCGCCGCCGTGTATCGCCCCGCCCTGGGCGG

CAAGGCTGGCCCGGTCGGCACCAGTTGCGTGAGCGGAAAGATGGCCGCTTCCCGGCCCT

GCTGCAGGGAGCTCAAAATGGAGGACGCGGCGCTCGGGAGAGCGGGCGGGTGAGTCACC

CACACAAAGGAAAAGGGCCTTTCCGTCCTCAGCCGTCGCTTCATGTGACTCCACGGAGT

ACCGGGCGCCGTCCAGGCACCTCGATTAGTTCTCGAGCTTTTGGAGTACGTCGTCTTTA

GGTTGGGGGGAGGGGTTTTATGCGATGGAGTTTCCCCACACTGAGTGGGTGGAGACTGA

AGTTAGGCCAGCTTGGCACTTGATGTAATTCTCCTTGGAATTTGCCCTTTTTGAGTTTG

GATCTTGGTTCATTCTCAAGCCTCAGACAGTGGTTCAAAGTTTTTTTCTTCCATTTCAG

GTGTCGTGAATACCGTCGACTCCGGAATAGCCACCATGGAGACGGACGTCTCAGCTGAA

GCTGCTGCAAAGGAAGCTGCAGCTAAGGAGGCTGCAGCTAAGGCTATGGTGAGCAAGGG

CGAGGAGGATAACATGGCCATCATCAAGGAGTTCATGCGCTTCAAGGTGCACATGGAGG

GCTCCGTGAACGGCCACGAGTTCGAGATCGAGGGCGAGGGCGAGGGCCGCCCCTACGAG

GGCACCCAGACCGCCAAGCTGAAGGTGACCAAGGGTGGCCCCCTGCCCTTCGCCTGGGA

-continued

CATCCTGTCCCCTCAGTTCATGTACGGCTCCAAGGCCTACGTGAAGCACCCCGCCGACA

TCCCCGACTACTTGAAGCTGTCCTTCCCCGAGGGCTTCAAGTGGGAGCGCGTGATGAAC

TTCGAGGACGGCGGCGTGGTGACCGTGACCCAGGACTCCTCCCTGCAGGACGGCGAGTT

CATCTACAAGGTGAAGCTGCGCGGCACCAACTTCCCCTCCGACGGCCCCGTAATGCAGA

AGAAGACCATGGGCTGGGAGGCCTCCTCCGAGCGGATGTACCCCGAGGACGGCGCCCTG

AAGGGCGAGATCAAGCAGAGGCTGAAGCTGAAGGACGGCGGCCACTACGACGCTGAGGT

CAAGACCACCTACAAGGCCAAGAAGCCCGTGCAGCTGCCCGGCGCCTACAACGTCAACA

TCAAGTTGGACATCACCTCCCACAACGAGGACTACACCATCGTGGAACAGTACGAACGC

GCCGAGGGCCGCCACTCCACCGGCGGCATGGACGAGCTGTACAAGGGACTCAGAGTTTG

GGTAGGAAGCGGAGCTACTAACTTCAGCCTGCTGAAGCAGGCTGGAGAtGTGGAGGAGA

ACCCTGGACCTATGATTGAACAAGATGGATTGCACGCAGGTTCTCCGGCCGCTTGGGTG

GAGAGGCTATTCGGCTATGACTGGGCACAACAGACAATCGGCTGCTCTGATGCCGCCGT

GTTCCGGCTGTCAGCGCAGGGGCGCCCGGTTCTTTTTGTCAAGACCGACCTGTCCGGTG

CCCTGAATGAACTGCAGGACGAGGCAGCGCGGCTATCGTGGCTGGCCACGACGGGCGTT

CCTTGCGCAGCTGTGCTCGACGTTGTCACTGAAGCGGGAAGGGACTGGCTGCTATTGGG

CGAAGTGCCGGGGCAGGATCTCCTGTCATCTCACCTTGCTCCTGCCGAGAAAGTATCCA

TCATGGCTGATGCAATGCGGCGGCTGCATACGCTTGATCCGGCTACCTGCCCATTCGAC

CACCAAGCGAAACATCGCATCGAGCGAGCACGTACTCGGATGGAAGCCGGTCTTGTCGA

TCAGGATGATCTGGACGAAGAGCATCAGGGGCTCGCGCCAGCCGAACTGTTCGCCAGGC

TCAAGGCGCGCATGCCCGACGGCGAGGATCTCGTCGTGACCCATGGCGATGCCTGCTTG

CCGAATATCATGGTGGAAAATGGCCGCTTTTCTGGATTCATCGACTGTGGCCGGCTGGG

TGTGGCCGACCGCTATCAGGACATAGCGTTGGCTACCCGTGATATTGCTGAAGAGCTTG

GCGGCGAATGGGCTGACCGCTTCCTCGTGCTTTACGGTATCGCCGCTCCCGATTCGCAG

CGCATCGCCTTCTATCGCCTTCTTGACGAGTTCTTCTGAATGCATGAGTAACTGAGGAT

CCAGGGACAGCAGAGATACGCGTTAAGTCGACAATCAACCTCTGGATTACAAAATTTGT

GAAAGATTGACTGGTATTCTTAACTATGTTGCTCCTTTTACGCTATGTGGATACGCTGC

TTTAATGCCTTTGTATCATGCTATTGCTTCCCGTATGGCTTTCATTTTCTCCTCCTTGT

ATAAATCCTGGTTGCTGTCTCTTTATGAGGAGTTGTGGCCCGTTGTCAGGCAACGTGGC

GTGGTGTGCACTGTGTTTGCTGACGCAACCCCCACTGGTTGGGGCATTGCCACCACCTG

TCAGCTCCTTTCCGGGACTTTCGCTTTCCCCCTCCCTATTGCCACGGCGGAACTCATCG

CCGCCTGCCTTGCCCGCTGCTGGACAGGGGCTCGGCTGTTGGGCACTGACAATTCCGTG

GTGTTGTCGGGGAAATCATCGTCCTTTCCTTGGCTGCTCGCCTGTGTTGCCACCTGGAT

TCTGCGCGGGACGTCCTTCTGCTACGTCCCTTCGGCCCTCAATCCAGCGGACCTTCCTT

CCCGCGGCCTGCTGCCGGCTCTGCGGCCTCTTCCGCGTCTTCGCCTTCGCCCTCAGACG

AGTCGGATCTCCCTTTGGGCCGCCTCCCCGCGTCGACTTTAAGACCAATGACTTACAAG

GCAGCTGTAGATCTTAGCCACTTTTTAAAAGAAAAGGGGGGACTGGAAGGGCTAATTCA

CTCCCAACGAAGACAAGATCTGCTTTTTGCTTGTACTGGGTCTCTCTGGTTAGACCAGA

TCTGAGCCTGGGAGCTCTCTGGCTAACTAGGGAACCCACTGCTTAAGCCTCAATAAAGC

TTGCCTTGAGTGCTTCAAGTAGTGTGTGCCCGTCTGTTGTGTGACTCTGGTAACTAGAG

ATCCCTCAGACCCTTTTAGTCAGTGTGGAAAATCTCTAGCAGTACGTATAGTAGTTCAT

GTCATCTTATTATTCAGTATTTATAACTTGCAAAGAAATGAATATCAGAGAGTGAGAGG

-continued

AACTTGTTTATTGCAGCTTATAATGGTTACAAATAAAGCAATAGCATCACAAATTTCAC

AAATAAAGCATTTTTTTCACTGCATTCTAGTTGTGGTTTGTCCAAACTCATCAATGTAT

CTTATCATGTCTGGCTCTAGCTATCCCGCCCCTAACTCCGCCCATCCCGCCCCTAACTC

CGCCCAGTTCCGCCCATTCTCCGCCCCATGGCTGACTAATTTTTTTTATTTATGCAGAG

GCCGAGGCCGCCTCGGCCTCTGAGCTATTCCAGAAGTAGTGAGGAGGCTTTTTTGGAGG

CCTAGGGACGTACCCAATTCGCCCTATAGTGAGTCGTATTACGCGCGCTCACTGGCCGT

CGTTTTACAACGTCGTGACTGGGAAAACCCTGGCGTTACCCAACTTAATCGCCTTGCAG

CACATCCCCCTTTCGCCAGCTGGCGTAATAGCGAAGAGGCCCGCACCGATCGCCCTTCC

CAACAGTTGCGCAGCCTGAATGGCGAATGGGACGCGCCCTGTAGCGGCGCATTAAGCGC

GGCGGGTGTGGTGGTTACGCGCAGCGTGACCGCTACACTTGCCAGCGCCCTAGCGCCCG

CTCCTTTCGCTTTCTTCCCTTCCTTTCTCGCCACGTTCGCCGGCTTTCCCCGTCAAGCT

CTAAATCGGGGGCTCCCTTTAGGGTTCCGATTTAGTGCTTTACGGCACCTCGACCCCAA

AAAACTTGATTAGGGTGATGGTTCACGTAGTGGGCCATCGCCCTGATAGACGGTTTTTC

GCCCTTTGACGTTGGAGTCCACGTTCTTTAATAGTGGACTCTTGTTCCAAACTGGAACA

ACACTCAACCCTATCTCGGTCTATTCTTTTGATTTATAAGGGATTTTGCCGATTTCGGC

CTATTGGTTAAAAAATGAGCTGATTTAACAAAAATTTAACGCGAATTTTAACAAAATAT

TAACGCTTACAATTTAGGTGGCACTTTTCGGGGAAATGTGCGCGGAACCCCTATTTGTT

TATTTTTCTAAATACATTCAAATATGTATCCGCTCATGAGACAATAACCCTGATAAATG

CTTCAATAATATTGAAAAAGGAAGAGTATGAGTATTCAACATTTCCGTGTCGCCCTTAT

TCCCTTTTTTGCGGCATTTTGCCTTCCTGTTTTTGCTCACCCAGAAACGCTGGTGAAAG

TAAAAGATGCTGAAGATCAGTTGGGTGCACGAGTGGGTTACATCGAACTGGATCTCAAC

AGCGGTAAGATCCTTGAGAGTTTTCGCCCCGAAGAACGTTTTCCAATGATGAGCACTTT

TAAAGTTCTGCTATGTGGCGCGGTATTATCCCGTATTGACGCCGGGCAAGAGCAACTCG

GTCGCCGCATACACTATTCTCAGAATGACTTGGTTGAGTACTCACCAGTCACAGAAAAG

CATCTTACGGATGGCATGACAGTAAGAGAATTATGCAGTGCTGCCATAACCATGAGTGA

TAACACTGCGGCCAACTTACTTCTGACAACGATCGGAGGACCGAAGGAGCTAACCGCTT

D913 degron proteins and vectors comprised the following sequences:

1928z-d913, aka FMC63-CD28-CD3z-d913: This sequence corresponds to the in frame fusion of the CSF2RA signal sequence (amino acids 1-22), anti-CD19 scFv FMC63 (www.ebi.ac.uk/ena/data/view/ADM64594), the CD28 hinge, transmembrane, and cytoplasmic domains (amino acids 114-220), the CD3z intracellular ITAM domains (amino acids 55-164), a SG linker, and the d913 degron sequence.

(SEQ ID NO: 138)
MLLLVTSLLLCELPHPAFLLIPEQKLISEEDLDIQMTQTTSSLSASLGDR

VTISCRASQDISKYLNWYQQKPDGTVKLLIYHTSRLHSGVPSRFSGSGSG

TDYSLTISNLEQEDIATYFCQQGNTLPYTFGGGTKLEITGSTSGSGKPGS

GEGSTKGEVKLQESGPGLVAPSQSLSVTCTVSGVSLPDYGVSWIRQPPRK

GLEWLGVIWGSETTYYNSALKSRLTIIKDNSKSQVFLKMNSLQTDDTAIY

YCAKHYYYGGSYAMDYWGQGTSVTVSSAAAIEVMYPPPYLDNEKSNGTII

-continued

HVKGKHLCPSPLFPGPSKPFWVLVVVGGVLACYSLLVTVAFIIFWVRSKR

SRLLHSDYMNMTPRRPGPTRKHYQPYAPPRDFAAYRSRVKFSRSADAPAY

QQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPRS

GFNVLMVHKRSHTGERPLQCEICGFTCRQKGNLLRHIKLHTGEKPFKCHL

CNYACQRRDAL sCARA913 aka FMC63-CD28-d913 intracellular K0 (iK0): This sequence corresponds to the anti-CD19 scFv FMC63 (www.ebi.ac.uk/ena/data/view/ADM64594), the CD28 hinge, transmembrane, and cytoplasmic domains (amino acids 114-220), and d913 degron sequence, wherein all intracellular lysines are substituted to arginine.

(SEQ ID NO: 139)
MLLLVTSLLLCELPHPAFLLIPEQKLISEEDLDIQMTQTTSSLSASLGDRVTISCRASQ

DISKYLNWYQQKPDGTVKLLIYHTSRLHSGVPSRFSGSGSGTDYSLTISNLEQEDIATY

FCQQGNTLPYTFGGGTKLEITGSTSGSGKPGSGEGSTKGEVKLQESGPGLVAPSQSLSV

TCTVSGVSLPDYGVSWIRQPPRKGLEWLGVIWGSETTYYNSALKSRLTIIKDNSKSQVF

LKMNSLQTDDTAIYYCAKHYYYGGSYAMDYWGQGTSVTVSSAAAIEVIVIYPPPYLDNE

KSNGTIIHVKGKHLCPSPLFPGPSKPFWVLVVVGGVLACYSLLVTVAFIIFWVRSRRSR

LLHSDYMNMTPRRPGPTRRHYQPYAPPRDFAAYRSSGFNVLMVHRRSHTGERPLQCEIC

GFTCRQRGNLLRHIRLHTGERPFRCHLCNYACQRRDAL

BigSur-1928z-d913

(SEQ ID NO: 140)
TTTTGCACAACATGGGGGATCATGTAACTCGCCTTGATCGTTGGGAACCGGAGCTGAAT

GAAGCCATACCAAACGACGAGCGTGACACCACGATGCCTGTAGCAATGGCAACAACGTT

GCGCAAACTATTAACTGGCGAACTACTTACTCTAGCTTCCCGGCAACAATTAATAGACT

GGATGGAGGCGGATAAAGTTGCAGGACCACTTCTGCGCTCGGCCCTTCCGGCTGGCTGG

TTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAA

CTATGGATGAACGAAATAGACAGATCGCTGAGATAGGTGCCTCACTGATTAAGCATTGG

TAACTGTCAGACCAAGTTTACTCATATATACTTTAGATTGATTTAAAACTTCATTTTTA

ATTTAAAAGGATCTAGGTGAAGATCCTTTTTGATAATCTCATGACCAAAATCCCTTAAC

GTGAGTTTTCGTTCCACTGAGCGTCAGACCCCGTAGAAAAGATCAAAGGATCTTCTTGA

GATCCTTTTTTTCTGCGCGTAATCTGCTGCTTGCAAACAAAAAAACCACCGCTACCAGC

GGTGGTTTGTTTGCCGGATCAAGAGCTACCAACTCTTTTTCCGAAGGTAACTGGCTTCA

GCAGAGCGCAGATACCAAATACTGTTCTTCTAGTGTAGCCGTAGTTAGGCCACCACTTC

AAGAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGATA

AGGCGCAGCGGTCGGGCTGAACGGGGGGTTCGTGCACACAGCCCAGCTTGGAGCGAACG

ACCTACACCGAACTGAGATACCTACAGCGTGAGCTATGAGAAAGCGCCACGCTTCCCGA

AGGGAGAAAGGCGGACAGGTATCCGGTAAGCGGCAGGGTCGGAACAGGAGAGCGCACGA

GGGAGCTTCCAGGGGGAAACGCCTGGTATCTTTATAGTCCTGTCGGGTTTCGCCACCTC

TGACTTGAGCGTCGATTTTTGTGATGCTCGTCAGGGGGGCGGAGCCTATGGAAAAACGC

CAGCAACGCGGCCTTTTTACGGTTCCTGGCCTTTTGCTGGCCTTTTGCTCACATGTTCT

TTCCTGCGTTATCCCCTGATTCTGTGGATAACCGTATTACCGCCTTTGAGTGAGCTGAT

ACCGCTCGCCGCAGCCGAACGACCGAGCGCAGCGAGTCAGTGAGCGAGGAAGCGGAAGA

GCGCCCAATACGCAAACCGCCTCTCCCCGCGCGTTGGCCGATTCATTAATGCAGCTGGC

ACGACAGGTTTCCCGACTGGAAAGCGGGCAGTGAGCGCAACGCAATTAATGTGAGTTAG

CTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGC

GCGCAATTAACCCTCACTAAAGGGAACAAAAGCTGGAGCTGCAAGCTTAATGTAGTCTT

ATGCAATACTCTTGTAGTCTTGCAACATGGTAACGATGAGTTAGCAACATGCCTTACAA

GGAGAGAAAAAGCACCGTGCATGCCGATTGGTGGAAGTAAGGTGGTACGATCGTGCCTT

ATTAGGAAGGCAACAGACGGGTCTGACATGGATTGGACGAACCACTGAATTGCCGCATT

-continued

```
GCAGAGATATTGTATTTAAGTGCCTAGCTCGATACATAAACGGGTCTCTCTGGTTAGAC

CAGATCTGAGCCTGGGAGCTCTCTGGCTAACTAGGGAACCCACTGCTTAAGCCTCAATA

AAGCTTGCCTTGAGTGCTTCAAGTAGTGTGTGCCCGTCTGTTGTGTGACTCTGGTAACT

AGAGATCCCTCAGACCCTTTTAGTCAGTGTGGAAAATCTCTAGCAGTGGCGCCCGAACA

GGGACTTGAAAGCGAAAGGGAAACCAGAGGAGCTCTCTCGACGCAGGACTCGGCTTGCT

GAAGCGCGCACGGCAAGAGGCGAGGGGCGGCGACTGGTGAGTACGCCAAAAATTTTGAC

TAGCGGAGGCTAGAAGGAGAGAGATGGGTGCGAGAGCGTCAGTATTAAGCGGGGGAGAA

TTAGATCGCGATGGGAAAAAATTCGGTTAAGGCCAGGGGGAAAGAAAAAATATAAATTA

AAACATATAGTATGGGCAAGCAGGGAGCTAGAACGATTCGCAGTTAATCCTGGCCTGTT

AGAAACATCAGAAGGCTGTAGACAAATACTGGGACAGCTACAACCATCCCTTCAGACAG

GATCAGAAGAACTTAGATCATTATATAATACAGTAGCAACCCTCTATTGTGTGCATCAA

AGGATAGAGATAAAAGACACCAAGGAAGCTTTAGACAAGATAGAGGAAGAGCAAAACAA

AAGTAAGACCACCGCACAGCAAGCGGCCGCTGATCTTCAGACCTGGAGGAGGAGATATG

AGGGACAATTGGAGAAGTGAATTATATAAATATAAAGTAGTAAAAATTGAACCATTAGG

AGTAGCACCCACCAAGGCAAAGAGAAGAGTGGTGCAGAGAGAAAAAAGAGCAGTGGGAA

TAGGAGCTTTGTTCCTTGGGTTCTTGGGAGCAGCAGGAAGCACTATGGGCGCAGCGTCA

ATGACGCTGACGGTACAGGCCAGACAATTATTGTCTGGTATAGTGCAGCAGCAGAACAA

TTTGCTGAGGGCTATTGAGGCGCAACAGCATCTGTTGCAACTCACAGTCTGGGGCATCA

AGCAGCTCCAGGCAAGAATCCTGGCTGTGGAAAGATACCTAAAGGATCAACAGCTCCTG

GGGATTTGGGGTTGCTCTGGAAAACTCATTTGCACCACTGCTGTGCCTTGGAATGCTAG

TTGGAGTAATAAATCTCTGGAACAGATTTGGAATCACACGACCTGGATGGAGTGGGACA

GAGAAATTAACAATTACACAAGCTTAATACACTCCTTAATTGAAGAATCGCAAAACCAG

CAAGAAAAGAATGAACAAGAATTATTGGAATTAGATAAATGGGCAAGTTTGTGGAATTG

GTTTAACATAACAAATTGGCTGTGGTATATAAAATTATTCATAATGATAGTAGGAGGCT

TGGTAGGTTTAAGAATAGTTTTTGCTGTACTTTCTATAGTGAATAGAGTTAGGCAGGGA

TATTCACCATTATCGTTTCAGACCCACCTCCCAACCCCGAGGGGACCCTATTCCAGCAC

ATATGAGGCTTGGCGTAACTAGATCTTGAGACAAATGGCAGTATTCATCCACAATTTTA

AAAGAAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTCGGGT

TTATTACAGGGACAGCAGAGATCCACTTTGGGCTCGAGGGGGCCCGGGTGCAAAGATGG

ATAAAGTTTTAAACAGAGAGGAATCTTTGCAGCTAATGGACCTTCTAGGTCTTGAAAGG

AGTGGGAATTGGCTCCGGTGCCCGTCAGTGGGCAGAGCGCACATCGCCCACAGTCCCCG

AGAAGTTGGGGGGAGGGGTCGGCAATTGATCCGGTGCCTAGAGAAGGTGGCGCGGGGTA

AACTGGGAAAGTGATGTCGTGTACTGGCTCCGCCTTTTTCCCGAGGGTGGGGGAGAACC

GTATATAAGTGCAGTAGTCGCCGTGAACGTTCTTTTTCGCAACGGGTTTGCCGCCAGAA

CACAGGTAAGTGCCGTGTGTGGTTCCCGCGGGCCTGGCCTCTTTACGGGTTATGGCCCT

TGCGTGCCTTGAATTACTTCCACCTGGCTGCAGTACGTGATTCTTGATCCCGAGCTTCG

GGTTGGAAGTGGGTGGGAGAGTTCGAGGCCTTGCGCTTAAGGAGCCCCTTCGCCTCGTG

CTTGAGTTGAGGCCTGGCCTGGGCGCTGGGGCCGCCGCGTGCGAATCTGGTGGCACCTT

CGCGCCTGTCTCGCTGCTTTCGATAAGTCTCTAGCCATTTAAAATTTTTGATGACCTGC

TGCGACGCTTTTTTTCTGGCAAGATAGTCTTGTAAATGCGGGCCAAGATCTGCACACTG
```

-continued

GTATTTCGGTTTTTGGGGCCGCGGGCGGCGACGGGGCCCGTGCGTCCCAGCGCACATGT

TCGGCGAGGCGGGGCCTGCGAGCGCGGCCACCGAGAATCGGACGGGGGTAGTCTCAAGC

TGGCCGGCCTGCTCTGGTGCCTGGCCTCGCGCCGCCGTGTATCGCCCCGCCCTGGGCGG

CAAGGCTGGCCCGGTCGGCACCAGTTGCGTGAGCGGAAAGATGGCCGCTTCCCGGCCCT

GCTGCAGGGAGCTCAAAATGGAGGACGCGGCGCTCGGGAGAGCGGGCGGGTGAGTCACC

CACACAAAGGAAAAGGGCCTTTCCGTCCTCAGCCGTCGCTTCATGTGACTCCACGGAGT

ACCGGGCGCCGTCCAGGCACCTCGATTAGTTCTCGAGCTTTTGGAGTACGTCGTCTTTA

GGTTGGGGGGAGGGGTTTTATGCGATGGAGTTTCCCCACACTGAGTGGGTGGAGACTGA

AGTTAGGCCAGCTTGGCACTTGATGTAATTCTCCTTGGAATTTGCCCTTTTTGAGTTTG

GATCTTGGTTCATTCTCAAGCCTCAGACAGTGGTTCAAAGTTTTTTTCTTCCATTTCAG

GTGTCGTGAATACCGTCGACTCCGGAATAGCCACCATGCTTCTCCTGGTGACAAGCCTT

CTGCTCTGTGAGTTACCACACCCAGCATTCCTCCTGATCCCAGAGCAGAAACTCATCTC

AGAAGAGGATCTGGACATCCAGATGACACAGACTACATCCTCCCTGTCTGCCTCTCTGG

GAGACAGAGTCACCATCAGTTGCAGGGCAAGTCAGGACATTAGTAAATATTTAAATTGG

TATCAGCAGAAACCAGATGGAACTGTTAAACTCCTGATCTACCATACATCAAGATTACA

CTCAGGAGTCCCATCAAGGTTCAGTGGCAGTGGGTCTGGAACAGATTATTCTCTCACCA

TTAGCAACCTGGAGCAAGAAGATATTGCCACTTACTTTTGCCAACAGGGTAATACGCTT

CCGTACACGTTCGGAGGGGGGACTAAGTTGGAAATAACAGGCTCCACCTCTGGATCCGG

CAAGCCCGGATCTGGCGAGGGATCCACCAAGGGCGAGGTGAAACTGCAGGAGTCAGGAC

CTGGCCTGGTGGCGCCCTCACAGAGCCTGTCCGTCACATGCACTGTCTCAGGGGTCTCA

TTACCCGACTATGGTGTAAGCTGGATTCGCCAGCCTCCACGAAAGGGTCTGGAGTGGCT

GGGAGTAATATGGGGTAGTGAAACCACATACTATAATTCAGCTCTCAAATCCAGACTGA

CCATCATCAAGGACAACTCCAAGAGCCAAGTTTTCTTAAAAATGAACAGTCTGCAAACT

GATGACACAGCCATTTACTACTGTGCCAAACATTATTACTACGGTGGTAGCTATGCTAT

GGACTACTGGGGTCAAGGAACCTCAGTCACaGTCTCCTCAGCGGCCGCAATTGAAGTTA

TGTATCCTCCTCCTTACCTAGACAATGAGAAGAGCAATGGAACCATTATCCATGTGAAA

GGGAAACACCTTTGTCCAAGTCCCCTATTTCCCGGACCTTCTAAGCCCTTTTGGGTGCT

GGTGGTGGTTGGGGGAGTCCTGGCTTGCTATAGCTTGCTAGTAACAGTGGCCTTTATTA

TTTTCTGGGTGAGGAGTAAGAGGAGCAGGCTCCTGCACAGTGACTACATGAACATGACT

CCTAGAAGGCCTGGACCCACCCGCAAGCATTACCAGCCCTATGCCCCACCACGCGACTT

CGCAGCCTATCGCTCCAGAGTGAAGTTCAGCAGGAGCGCAGACGCCCCCGCGTACCAGC

AGGGCCAGAACCAGCTCTATAACGAGCTCAATCTAGGACGAAGAGAGGAGTACGATGTT

TTGGACAAGAGgCGTGGCCGGGACCCTGAGATGGGGGGAAAGCCGAGAAGGAAGAACCC

TCAGGAAGGCCTGTACAATGAACTGCAGAAAGATAAGATGGCGGAGGCCTACAGTGAGA

TTGGGATGAAAGGCGAGCGCCGGAGGGGCAAGGGGCACGATGGCCTTTACCAGGGTCTC

AGTACAGCCACCAAGGACACCTACGACGCCCTTCACATGCAGGCCCTGCCCCCTCGCTC

CGGATTCAATGTCTTAATGGTTCATAAGCGAAGCCATACTGGTGAACGCCCATTGCAGT

GCGAAATATGCGGCTTTACCTGCCGCCAGAAAGGTAACCTCCTCCGCCACATTAAACTG

CACACAGGGGAAAAACCTTTTAAGTGTCACCTCTGCAACTATGCATGCCAAAGAAGAGA

TGCGCTCCGCAAAAGACGCGGATCCGGCGAGGGTAGAGGCAGTCTCCTCACATGTGGCG

-continued

ATGTGGAAGAAAACCCAGGCCCCATGGTGAGCAAGGGCGAGGAGGATAACATGGCCATC

ATCAAGGAGTTCATGCGCTTCAAGGTGCACATGGAGGGCTCCGTGAACGGCCACGAGTT

CGAGATCGAGGGCGAGGGCGAGGGCCGCCCCTACGAGGGCACCCAGACCGCCAAGCTGA

AGGTGACCAAGGGTGGCCCCCTGCCCTTCGCCTGGGACATCCTGTCCCCTCAGTTCATG

TACGGCTCCAAGGCCTACGTGAAGCACCCCGCCGACATCCCCGACTACTTGAAGCTGTC

CTTCCCCGAGGGCTTCAAGTGGGAGCGCGTGATGAACTTCGAGGACGGCGGCGTGGTGA

CCGTGACCCAGGACTCCTCCCTGCAGGACGGCGAGTTCATCTACAAGGTGAAGCTGCGC

GGCACCAACTTCCCCTCCGACGGCCCCGTAATGCAGAAGAAGACCATGGGCTGGGAGGC

CTCCTCCGAGCGGATGTACCCCGAGGACGGCGCCCTGAAGGGCGAGATCAAGCAGAGGC

TGAAGCTGAAGGACGGCGGCCACTACGACGCTGAGGTCAAGACCACCTACAAGGCCAAG

AAGCCCGTGCAGCTGCCCGGCGCCTACAACGTCAACATCAAGTTGGACATCACCTCCCA

CAACGAGGACTACACCATCGTGGAACAGTACGAACGCGCCGAGGGCCGCCACTCCACCG

GCGGCATGGACGAGCTGTACAAGtaaATGCATGAGTAACTGAGGATCCAGGGACAGCAG

AGATACGCGTTAAGTCGACAATCAACCTCTGGATTACAAAATTTGTGAAAGATTGACTG

GTATTCTTAACTATGTTGCTCCTTTTACGCTATGTGGATACGCTGCTTTAATGCCTTTG

TATCATGCTATTGCTTCCCGTATGGCTTTCATTTTCTCCTCCTTGTATAAATCCTGGTT

GCTGTCTCTTTATGAGGAGTTGTGGCCCGTTGTCAGGCAACGTGGCGTGGTGTGCACTG

TGTTTGCTGACGCAACCCCCACTGGTTGGGGCATTGCCACCACCTGTCAGCTCCTTTCC

GGGACTTTCGCTTTCCCCCTCCCTATTGCCACGGCGGAACTCATCGCCGCCTGCCTTGC

CCGCTGCTGGACAGGGGCTCGGCTGTTGGGCACTGACAATTCCGTGGTGTTGTCGGGGA

AATCATCGTCCTTTCCTTGGCTGCTCGCCTGTGTTGCCACCTGGATTCTGCGCGGGACG

TCCTTCTGCTACGTCCCTTCGGCCCTCAATCCAGCGGACCTTCCTTCCCGCGGCCTGCT

GCCGGCTCTGCGGCCTCTTCCGCGTCTTCGCCTTCGCCCTCAGACGAGTCGGATCTCCC

TTTGGGCCGCCTCCCCGCGTCGACTTTAAGACCAATGACTTACAAGGCAGCTGTAGATC

TTAGCCACTTTTTAAAAGAAAAGGGGGGACTGGAAGGGCTAATTCACTCCCAACGAAGA

CAAGATCTGCTTTTTGCTTGTACTGGGTCTCTCTGGTTAGACCAGATCTGAGCCTGGGA

GCTCTCTGGCTAACTAGGGAACCCACTGCTTAAGCCTCAATAAAGCTTGCCTTGAGTGC

TTCAAGTAGTGTGTGCCCGTCTGTTGTGTGACTCTGGTAACTAGAGATCCCTCAGACCC

TTTTAGTCAGTGTGGAAAATCTCTAGCAGTACGTATAGTAGTTCATGTCATCTTATTAT

TCAGTATTTATAACTTGCAAAGAAATGAATATCAGAGAGTGAGAGGAACTTGTTTATTG

CAGCTTATAATGGTTACAAATAAAGCAATAGCATCACAAATTTCACAAATAAAGCATTT

TTTTCACTGCATTCTAGTTGTGGTTTGTCCAAACTCATCAATGTATCTTATCATGTCTG

GCTCTAGCTATCCCGCCCCTAACTCCGCCCATCCCGCCCCTAACTCCGCCCAGTTCCGC

CCATTCTCCGCCCCATGGCTGACTAATTTTTTTTATTTATGCAGAGGCCGAGGCCGCCT

CGGCCTCTGAGCTATTCCAGAAGTAGTGAGGAGGCTTTTTTGGAGGCCTAGGGACGTAC

CCAATTCGCCCTATAGTGAGTCGTATTACGCGCGCTCACTGGCCGTCGTTTTACAACGT

CGTGACTGGGAAAACCCTGGCGTTACCCAACTTAATCGCCTTGCAGCACATCCCCCTTT

CGCCAGCTGGCGTAATAGCGAAGAGGCCCGCACCGATCGCCCTTCCCAACAGTTGCGCA

GCCTGAATGGCGAATGGGACGCGCCCTGTAGCGGCGCATTAAGCGCGGCGGGTGTGGTG

GTTACGCGCAGCGTGACCGCTACACTTGCCAGCGCCCTAGCGCCCGCTCCTTTCGCTTT

CTTCCCTTCCTTTCTCGCCACGTTCGCCGGCTTTCCCCGTCAAGCTCTAAATCGGGGGC

-continued

TCCCTTTAGGGTTCCGATTTAGTGCTTTACGGCACCTCGACCCCAAAAAACTTGATTAG

GGTGATGGTTCACGTAGTGGGCCATCGCCCTGATAGACGGTTTTTCGCCCTTTGACGTT

GGAGTCCACGTTCTTTAATAGTGGACTCTTGTTCCAAACTGGAACAACACTCAACCCTA

TCTCGGTCTATTCTTTTGATTTATAAGGGATTTTGCCGATTTCGGCCTATTGGTTAAAA

AATGAGCTGATTTAACAAAAATTTAACGCGAATTTTAACAAAATATTAACGCTTACAAT

TTAGGTGGCACTTTTCGGGGAAATGTGCGCGGAACCCCTATTTGTTTATTTTTCTAAAT

ACATTCAAATATGTATCCGCTCATGAGACAATAACCCTGATAAATGCTTCAATAATATT

GAAAAAGGAAGAGTATGAGTATTCAACATTTCCGTGTCGCCCTTATTCCCTTTTTTGCG

GCATTTTGCCTTCCTGTTTTTGCTCACCCAGAAACGCTGGTGAAAGTAAAAGATGCTGA

AGATCAGTTGGGTGCACGAGTGGGTTACATCGAACTGGATCTCAACAGCGGTAAGATCC

TTGAGAGTTTTCGCCCCGAAGAACGTTTTCCAATGATGAGCACTTTTAAAGTTCTGCTA

TGTGGCGCGGTATTATCCCGTATTGACGCCGGGCAAGAGCAACTCGGTCGCCGCATACA

CTATTCTCAGAATGACTTGGTTGAGTACTCACCAGTCACAGAAAAGCATCTTACGGATG

GCATGACAGTAAGAGAATTATGCAGTGCTGCCATAACCATGAGTGATAACACTGCGGCC

AACTTACTTCTGACAACGATCGGAGGACCGAAGGAGCTAACCGCTT

BigSur-sCARA913 (FMC63-CD28-d913)

(SEQ ID NO: 141)

TTTTGCACAACATGGGGGATCATGTAACTCGCCTTGATCGTTGGGAACCGGAGCTGAAT

GAAGCCATACCAAACGACGAGCGTGACACCACGATGCCTGTAGCAATGGCAACAACGTT

GCGCAAACTATTAACTGGCGAACTACTTACTCTAGCTTCCCGGCAACAATTAATAGACT

GGATGGAGGCGGATAAAGTTGCAGGACCACTTCTGCGCTCGGCCCTTCCGGCTGGCTGG

TTTATTGCTGATAAATCTGGAGCCGGTGAGCGTGGGTCTCGCGGTATCATTGCAGCACT

GGGGCCAGATGGTAAGCCCTCCCGTATCGTAGTTATCTACACGACGGGGAGTCAGGCAA

CTATGGATGAACGAAATAGACAGATCGCTGAGATAGGTGCCTCACTGATTAAGCATTGG

TAACTGTCAGACCAAGTTTACTCATATATACTTTAGATTGATTTAAAACTTCATTTTTA

ATTTAAAAGGATCTAGGTGAAGATCCTTTTTGATAATCTCATGACCAAAATCCCTTAAC

GTGAGTTTTCGTTCCACTGAGCGTCAGACCCCGTAGAAAAGATCAAAGGATCTTCTTGA

GATCCTTTTTTTCTGCGCGTAATCTGCTGCTTGCAAACAAAAAAACCACCGCTACCAGC

GGTGGTTTGTTTGCCGGATCAAGAGCTACCAACTCTTTTTCCGAAGGTAACTGGCTTCA

GCAGAGCGCAGATACCAAATACTGTTCTTCTAGTGTAGCCGTAGTTAGGCCACCACTTC

AAGAACTCTGTAGCACCGCCTACATACCTCGCTCTGCTAATCCTGTTACCAGTGGCTGC

TGCCAGTGGCGATAAGTCGTGTCTTACCGGGTTGGACTCAAGACGATAGTTACCGGATA

AGGCGCAGCGGTCGGGCTGAACGGGGGGTTCGTGCACACAGCCCAGCTTGGAGCGAACG

ACCTACACCGAACTGAGATACCTACAGCGTGAGCTATGAGAAAGCGCCACGCTTCCCGA

AGGGAGAAAGGCGGACAGGTATCCGGTAAGCGGCAGGGTCGGAACAGGAGAGCGCACGA

GGGAGCTTCCAGGGGGAAACGCCTGGTATCTTTATAGTCCTGTCGGGTTTCGCCACCTC

TGACTTGAGCGTCGATTTTTGTGATGCTCGTCAGGGGGGCGGAGCCTATGGAAAAACGC

CAGCAACGCGGCCTTTTTACGGTTCCTGGCCTTTTGCTGGCCTTTTGCTCACATGTTCT

TTCCTGCGTTATCCCCTGATTCTGTGGATAACCGTATTACCGCCTTTGAGTGAGCTGAT

ACCGCTCGCCGCAGCCGAACGACCGAGCGCAGCGAGTCAGTGAGCGAGGAAGCGGAAGA

GCGCCCAATACGCAAACCGCCTCTCCCCGCGCGTTGGCCGATTCATTAATGCAGCTGGC

-continued

ACGACAGGTTTCCCGACTGGAAAGCGGGCAGTGAGCGCAACGCAATTAATGTGAGTTAG

CTCACTCATTAGGCACCCCAGGCTTTACACTTTATGCTTCCGGCTCGTATGTTGTGTGG

AATTGTGAGCGGATAACAATTTCACACAGGAAACAGCTATGACCATGATTACGCCAAGC

GCGCAATTAACCCTCACTAAAGGGAACAAAAGCTGGAGCTGCAAGCTTAATGTAGTCTT

ATGCAATACTCTTGTAGTCTTGCAACATGGTAACGATGAGTTAGCAACATGCCTTACAA

GGAGAGAAAAAGCACCGTGCATGCCGATTGGTGGAAGTAAGGTGGTACGATCGTGCCTT

ATTAGGAAGGCAACAGACGGGTCTGACATGGATTGGACGAACCACTGAATTGCCGCATT

GCAGAGATATTGTATTTAAGTGCCTAGCTCGATACATAAACGGGTCTCTCTGGTTAGAC

CAGATCTGAGCCTGGGAGCTCTCTGGCTAACTAGGGAACCCACTGCTTAAGCCTCAATA

AAGCTTGCCTTGAGTGCTTCAAGTAGTGTGTGCCCGTCTGTTGTGTGACTCTGGTAACT

AGAGATCCCTCAGACCCTTTTAGTCAGTGTGGAAAATCTCTAGCAGTGGCGCCCGAACA

GGGACTTGAAAGCGAAAGGGAAACCAGAGGAGCTCTCTCGACGCAGGACTCGGCTTGCT

GAAGCGCGCACGGCAAGAGGCGAGGGGCGGCGACTGGTGAGTACGCCAAAAATTTTGAC

TAGCGGAGGCTAGAAGGAGAGAGATGGGTGCGAGAGCGTCAGTATTAAGCGGGGGAGAA

TTAGATCGCGATGGGAAAAAATTCGGTTAAGGCCAGGGGGAAAGAAAAAATATAAATTA

AAACATATAGTATGGGCAAGCAGGGAGCTAGAACGATTCGCAGTTAATCCTGGCCTGTT

AGAAACATCAGAAGGCTGTAGACAAATACTGGGACAGCTACAACCATCCCTTCAGACAG

GATCAGAAGAACTTAGATCATTATATAATACAGTAGCAACCCTCTATTGTGTGCATCAA

AGGATAGAGATAAAAGACACCAAGGAAGCTTTAGACAAGATAGAGGAAGAGCAAAACAA

AAGTAAGACCACCGCACAGCAAGCGGCCGCTGATCTTCAGACCTGGAGGAGGAGATATG

AGGGACAATTGGAGAAGTGAATTATATAAATATAAAGTAGTAAAAATTGAACCATTAGG

AGTAGCACCCACCAAGGCAAAGAGAAGAGTGGTGCAGAGAGAAAAAAGAGCAGTGGGAA

TAGGAGCTTTGTTCCTTGGGTTCTTGGGAGCAGCAGGAAGCACTATGGGCGCAGCGTCA

ATGACGCTGACGGTACAGGCCAGACAATTATTGTCTGGTATAGTGCAGCAGCAGAACAA

TTTGCTGAGGGCTATTGAGGCGCAACAGCATCTGTTGCAACTCACAGTCTGGGGCATCA

AGCAGCTCCAGGCAAGAATCCTGGCTGTGGAAAGATACCTAAAGGATCAACAGCTCCTG

GGGATTTGGGGTTGCTCTGGAAAACTCATTTGCACCACTGCTGTGCCTTGGAATGCTAG

TTGGAGTAATAAATCTCTGGAACAGATTTGGAATCACACGACCTGGATGGAGTGGGACA

GAGAAATTAACAATTACACAAGCTTAATACACTCCTTAATTGAAGAATCGCAAAACCAG

CAAGAAAAGAATGAACAAGAATTATTGGAATTAGATAAATGGGCAAGTTTGTGGAATTG

GTTTAACATAACAAATTGGCTGTGGTATATAAAATTATTCATAATGATAGTAGGAGGCT

TGGTAGGTTTAAGAATAGTTTTTGCTGTACTTTCTATAGTGAATAGAGTTAGGCAGGGA

TATTCACCATTATCGTTTCAGACCCACCTCCCAACCCCGAGGGGACCCTATTCCAGCAC

ATATGAGGCTTGGCGTAACTAGATCTTGAGACAAATGGCAGTATTCATCCACAATTTTA

AAAGAAAAGGGGGGATTGGGGGGTACAGTGCAGGGGAAAGAATAGTAGACATAATAGCA

ACAGACATACAAACTAAAGAATTACAAAAACAAATTACAAAAATTCAAAATTTTCGGGT

TTATTACAGGGACAGCAGAGATCCACTTTGGGCTCGAGGGGGCCCGGGTGCAAAGATGG

ATAAAGTTTTAAACAGAGAGGAATCTTTGCAGCTAATGGACCTTCTAGGTCTTGAAAGG

AGTGGGAATTGGCTCCGGTGCCCGTCAGTGGGCAGAGCGCACATCGCCCACAGTCCCCG

AGAAGTTGGGGGGAGGGGTCGGCAATTGATCCGGTGCCTAGAGAAGGTGGCGCGGGGTA

AACTGGGAAAGTGATGTCGTGTACTGGCTCCGCCTTTTTCCCGAGGGTGGGGGAGAACC

-continued

GTATATAAGTGCAGTAGTCGCCGTGAACGTTCTTTTTCGCAACGGGTTTGCCGCCAGAA

CACAGGTAAGTGCCGTGTGTGGTTCCCGCGGGCCTGGCCTCTTTACGGGTTATGGCCCT

TGCGTGCCTTGAATTACTTCCACCTGGCTGCAGTACGTGATTCTTGATCCCGAGCTTCG

GGTTGGAAGTGGGTGGGAGAGTTCGAGGCCTTGCGCTTAAGGAGCCCCTTCGCCTCGTG

CTTGAGTTGAGGCCTGGCCTGGGCGCTGGGGCCGCCGCGTGCGAATCTGGTGGCACCTT

CGCGCCTGTCTCGCTGCTTTCGATAAGTCTCTAGCCATTTAAAATTTTTGATGACCTGC

TGCGACGCTTTTTTTCTGGCAAGATAGTCTTGTAAATGCGGGCCAAGATCTGCACACTG

GTATTTCGGTTTTTGGGGCCGCGGGCGGCGACGGGGCCCGTGCGTCCCAGCGCACATGT

TCGGCGAGGCGGGGCCTGCGAGCGCGGCCACCGAGAATCGGACGGGGGTAGTCTCAAGC

TGGCCGGCCTGCTCTGGTGCCTGGCCTCGCGCCGCCGTGTATCGCCCCGCCCTGGGCGG

CAAGGCTGGCCCGGTCGGCACCAGTTGCGTGAGCGGAAAGATGGCCGCTTCCCGGCCCT

GCTGCAGGGAGCTCAAAATGGAGGACGCGGCGCTCGGGAGAGCGGGCGGGTGAGTCACC

CACACAAAGGAAAAGGGCCTTTCCGTCCTCAGCCGTCGCTTCATGTGACTCCACGGAGT

ACCGGGCGCCGTCCAGGCACCTCGATTAGTTCTCGAGCTTTTGGAGTACGTCGTCTTTA

GGTTGGGGGGAGGGGTTTTATGCGATGGAGTTTCCCCACACTGAGTGGGTGGAGACTGA

AGTTAGGCCAGCTTGGCACTTGATGTAATTCTCCTTGGAATTTGCCCTTTTTGAGTTTG

GATCTTGGTTCATTCTCAAGCCTCAGACAGTGGTTCAAAGTTTTTTTCTTCCATTTCAG

GTGTCGTGAATACCGTCGACTCCGGAATAGCCACCATGCTTCTCCTGGTGACAAGCCTT

CTGCTCTGTGAGTTACCACACCCAGCATTCCTCCTGATCCCAGAGCAGAAACTCATCTC

AGAAGAGGATCTGGACATCCAGATGACACAGACTACATCCTCCCTGTCTGCCTCTCTGG

GAGACAGAGTCACCATCAGTTGCAGGGCAAGTCAGGACATTAGTAAATATTTAAATTGG

TATCAGCAGAAACCAGATGGAACTGTTAAACTCCTGATCTACCATACATCAAGATTACA

CTCAGGAGTCCCATCAAGGTTCAGTGGCAGTGGGTCTGGAACAGATTATTCTCTCACCA

TTAGCAACCTGGAGCAAGAAGATATTGCCACTTACTTTTGCCAACAGGGTAATACGCTT

CCGTACACGTTCGGAGGGGGGACTAAGTTGGAAATAACAGGCTCCACCTCTGGATCCGG

CAAGCCCGGATCTGGCGAGGGATCCACCAAGGGCGAGGTGAAACTGCAGGAGTCAGGAC

CTGGCCTGGTGGCGCCCTCACAGAGCCTGTCCGTCACATGCACTGTCTCAGGGGTCTCA

TTACCCGACTATGGTGTAAGCTGGATTCGCCAGCCTCCACGAAAGGGTCTGGAGTGGCT

GGGAGTAATATGGGGTAGTGAAACCACATACTATAATTCAGCTCTCAAATCCAGACTGA

CCATCATCAAGGACAACTCCAAGAGCCAAGTTTTCTTAAAAATGAACAGTCTGCAAACT

GATGACACAGCCATTTACTACTGTGCCAAACATTATTACTACGGTGGTAGCTATGCTAT

GGACTACTGGGGTCAAGGAACCTCAGTCACaGTCTCCTCAGCGGCCGCAATTGAAGTTA

TGTATCCTCCTCCTTACCTAGACAATGAGAAGAGCAATGGAACCATTATCCATGTGAAA

GGGAAACACCTTTGTCCAAGTCCCCTATTTCCCGGACCTTCTAAGCCCTTTTGGGTGCT

GGTGGTGGTTGGGGGAGTCCTGGCTTGCTATAGCTTGCTAGTAACAGTGGCCTTTATTA

TTTTCTGGGTGAGGAGTcggAGGAGCAGGCTCCTGCACAGTGACTACATGAACATGACT

CCTAGAAGGCCTGGACCCACCCGCcggCATTACCAGCCCTATGCCCCACCACGCGACTT

CGCAGCCTATCGCTCCTCCGGATTCAATGTCTTAATGGTTCATcggCGAAGCCATACTG

GTGAACGCCCATTGCAGTGCGAAATATGCGGCTTTACCTGCCGCCAGcgcGGTAACCTC

CTCCGCCACATTcgtCTGCACACAGGGGAAcggCCTTTTcggTGTCACCTCTGCAACTA

-continued

TGCATGCCAAAGAAGAGATGCGCTCAGAAGGAGACGCGGATCCGGCGAGGGTAGAGGCA
GTCTCCTCACATGTGGCGATGTGGAAGAAAACCCAGGCCCCATGGTGAGCAAGGGCGAG
GAGGATAACATGGCCATCATCAAGGAGTTCATGCGCTTCAAGGTGCACATGGAGGGCTC
CGTGAACGGCCACGAGTTCGAGATCGAGGGCGAGGGCGAGGGCCGCCCCTACGAGGGCA
CCCAGACCGCCAAGCTGAAGGTGACCAAGGGTGGCCCCCTGCCCTTCGCCTGGGACATC
CTGTCCCCTCAGTTCATGTACGGCTCCAAGGCCTACGTGAAGCACCCCGCCGACATCCC
CGACTACTTGAAGCTGTCCTTCCCCGAGGGCTTCAAGTGGGAGCGCGTGATGAACTTCG
AGGACGGCGGCGTGGTGACCGTGACCCAGGACTCCTCCCTGCAGGACGGCGAGTTCATC
TACAAGGTGAAGCTGCGCGGCACCAACTTCCCCTCCGACGGCCCCGTAATGCAGAAGAA
GACCATGGGCTGGGAGGCCTCCTCCGAGCGGATGTACCCCGAGGACGGCGCCCTGAAGG
GCGAGATCAAGCAGAGGCTGAAGCTGAAGGACGGCGGCCACTACGACGCTGAGGTCAAG
ACCACCTACAAGGCCAAGAAGCCCGTGCAGCTGCCCGGCGCCTACAACGTCAACATCAA
GTTGGACATCACCTCCCACAACGAGGACTACACCATCGTGGAACAGTACGAACGCGCCG
AGGGCCGCCACTCCACCGGCGGCATGGACGAGCTGTACAAGtaaATGCATGAGTAACTG
AGGATCCAGGGACAGCAGAGATACGCGTTAAGTCGACAATCAACCTCTGGATTACAAAA
TTTGTGAAAGATTGACTGGTATTCTTAACTATGTTGCTCCTTTTACGCTATGTGGATAC
GCTGCTTTAATGCCTTTGTATCATGCTATTGCTTCCCGTATGGCTTTCATTTTCTCCTC
CTTGTATAAATCCTGGTTGCTGTCTCTTTATGAGGAGTTGTGGCCCGTTGTCAGGCAAC
GTGGCGTGGTGTGCACTGTGTTTGCTGACGCAACCCCCACTGGTTGGGGCATTGCCACC
ACCTGTCAGCTCCTTTCCGGGACTTTCGCTTTCCCCCTCCCTATTGCCACGGCGGAACT
CATCGCCGCCTGCCTTGCCCGCTGCTGGACAGGGGCTCGGCTGTTGGGCACTGACAATT
CCGTGGTGTTGTCGGGGAAATCATCGTCCTTTCCTTGGCTGCTCGCCTGTGTTGCCACC
TGGATTCTGCGCGGGACGTCCTTCTGCTACGTCCCTTCGGCCCTCAATCCAGCGGACCT
TCCTTCCCGCGGCCTGCTGCCGGCTCTGCGGCCTCTTCCGCGTCTTCGCCTTCGCCCTC
AGACGAGTCGGATCTCCCTTTGGGCCGCCTCCCCGCGTCGACTTTAAGACCAATGACTT
ACAAGGCAGCTGTAGATCTTAGCCACTTTTTAAAAGAAAAGGGGGGACTGGAAGGGCTA
ATTCACTCCCAACGAAGACAAGATCTGCTTTTTGCTTGTACTGGGTCTCTCTGGTTAGA
CCAGATCTGAGCCTGGGAGCTCTCTGGCTAACTAGGGAACCCACTGCTTAAGCCTCAAT
AAAGCTTGCCTTGAGTGCTTCAAGTAGTGTGTGCCCGTCTGTTGTGTGACTCTGGTAAC
TAGAGATCCCTCAGACCCTTTTAGTCAGTGTGGAAAATCTCTAGCAGTACGTATAGTAG
TTCATGTCATCTTATTATTCAGTATTTATAACTTGCAAAGAAATGAATATCAGAGAGTG
AGAGGAACTTGTTTATTGCAGCTTATAATGGTTACAAATAAAGCAATAGCATCACAAAT
TTCACAAATAAAGCATTTTTTTCACTGCATTCTAGTTGTGGTTTGTCCAAACTCATCAA
TGTATCTTATCATGTCTGGCTCTAGCTATCCCGCCCCTAACTCCGCCCATCCCGCCCCT
AACTCCGCCCAGTTCCGCCCATTCTCCGCCCCATGGCTGACTAATTTTTTTTATTTATG
CAGAGGCCGAGGCCGCCTCGGCCTCTGAGCTATTCCAGAAGTAGTGAGGAGGCTTTTTT
GGAGGCCTAGGGACGTACCCAATTCGCCCTATAGTGAGTCGTATTACGCGCGCTCACTG
GCCGTCGTTTTACAACGTCGTGACTGGGAAAACCCTGGCGTTACCCAACTTAATCGCCT
TGCAGCACATCCCCCTTTCGCCAGCTGGCGTAATAGCGAAGAGGCCCGCACCGATCGCC
CTTCCCAACAGTTGCGCAGCCTGAATGGCGAATGGGACGCGCCCTGTAGCGGCGCATTA
AGCGCGGCGGGTGTGGTGGTTACGCGCAGCGTGACCGCTACACTTGCCAGCGCCCTAGC -continued

GCCCGCTCCTTTCGCTTTCTTCCCTTCCTTTCTCGCCACGTTCGCCGGCTTTCCCCGTC

AAGCTCTAAATCGGGGGCTCCCTTTAGGGTTCCGATTTAGTGCTTTACGGCACCTCGAC

CCCAAAAAACTTGATTAGGGTGATGGTTCACGTAGTGGGCCATCGCCCTGATAGACGGT

TTTTCGCCCTTTGACGTTGGAGTCCACGTTCTTTAATAGTGGACTCTTGTTCCAAACTG

GAACAACACTCAACCCTATCTCGGTCTATTCTTTTGATTTATAAGGGATTTTGCCGATT

TCGGCCTATTGGTTAAAAAATGAGCTGATTTAACAAAAATTTAACGCGAATTTTAACAA

AATATTAACGCTTACAATTTAGGTGGCACTTTTCGGGGAAATGTGCGCGGAACCCCTAT

TTGTTTATTTTTCTAAATACATTCAAATATGTATCCGCTCATGAGACAATAACCCTGAT

AAATGCTTCAATAATATTGAAAAAGGAAGAGTATGAGTATTCAACATTTCCGTGTCGCC

CTTATTCCCTTTTTTGCGGCATTTTGCCTTCCTGTTTTTGCTCACCCAGAAACGCTGGT

GAAAGTAAAAGATGCTGAAGATCAGTTGGGTGCACGAGTGGGTTACATCGAACTGGATC

TCAACAGCGGTAAGATCCTTGAGAGTTTTCGCCCCGAAGAACGTTTTCCAATGATGAGC

ACTTTTAAAGTTCTGCTATGTGGCGCGGTATTATCCCGTATTGACGCCGGGCAAGAGCA

ACTCGGTCGCCGCATACACTATTCTCAGAATGACTTGGTTGAGTACTCACCAGTCACAG

AAAAGCATCTTACGGATGGCATGACAGTAAGAGAATTATGCAGTGCTGCCATAACCATG

AGTGATAACACTGCGGCCAACTTACTTCTGACAACGATCGGAGGACCGAAGGAGCTAAC

CGCTT

In another aspect, a nucleic acid is provided (or multiple nucleic acids are provided) that encodes a split CAR system in which a first polypeptide has an extracellular ligand binding domain, a transmembrane domain, and a cytoplasmic domain having one of two heterodimer components, and a second polypeptide has at least one intracellular signaling domain and the second of two heterodimer components, where both heterodimer components are capable of being bound by an FDA-approved agent and where either or both the first and the second polypeptide include one or more co-stimulatory domains, and optionally the second polypeptide is membrane-attached/tethered.

In order to assess the expression of a CAR polypeptide or portion thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the hosT-cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

The cell expressing the CAR or split CAR system of the present disclosure is a cell in which the nucleic acid encoding a CAR or split CAR system described above is introduced and expressed by the cell. The cell of the present disclosure binds to a specific antigen via the CAR, and then a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and a macrophage. In order to confirm the presence of the recombinant DNA sequence in the cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

In certain aspects, a method of modulating the activity of a cell expressing the CARs (or split CAR system) of the present disclosure is provided that includes administering (or withdrawal of administration) to a subject administered the CAR (or split CAR system) expressing cell an FDA-approved agent.

Other aspects of the disclosure include polynucleotide sequences, plasmids, and vectors encoding the CARs (and/or split CAR system) of the present disclosure, and T-cells expressing the CARs (and/or split CAR system) of the present disclosure.

Additional aspects include methods of modulating T lymphocyte or natural killer (NK) cell activity in a patient and treating the patient suffering from cancer by introducing into the individual a T lymphocyte or NK cell that includes a CAR (and/or split CAR system) of the present disclosure, and subsequently administering to (or withdrawing administration from) the subject an FDA-approved agent of the disclosure, thereby activating, inactivating and/or degrading the CAR and/or split CAR system (depending upon whether ON-switch or OFF-switch modalities are employed). These aspects particularly include the treatment of renal cell carcinoma, cervical carcinoma, osteosarcoma, glioblastoma, lung cancer, melanoma, breast cancer, prostate cancer, bladder cancer, salivary gland cancer, endometrial cancer, colon cancer, renal cell carcinoma, ovarian cancer, neuroblastoma, rhabdomyosarcoma, leukemia, and lymphoma. Examples of cancer targets for use with the present disclosure are cancers of B cell origin, particularly including acute lymphoblastic leukemia, B-cell chronic lymphocytic leukemia and B-cell non-Hodgkin's lymphoma.

In one embodiment, a method is provided that includes at least the steps of:

(i) removing immune effector cells, for example T-cells, from a patient with a disorder of diseased cells that can be treated by increasing the ability of the patient's T-cells to recognize and bind to the diseased cells;

(ii) transforming the T-cells ex vivo by inserting a gene or genes encoding a CAR or split CAR system having at least a sequence targeting a diseased cell surface antigen and either a drug-responsive degron amino acid sequence or a drug-responsive heterodimer sequence capable of activating the split CAR system presenting such heterodimer;

(iii) administering to the patient the autologous CAR T-cells; and then (iv) administering to the patient, as needed, an FDA-approved drug which either (in OFF-switch aspects) promotes CAR degradation (thereby minimizing any side effects observed) or (in ON-switch aspects) activates the CAR-T cell therapy, subject to withdrawal of the FDA-approved drug halting CAR-T cell activity in the subject, to minimize or prevent any deleterious side effects that might occur in the presence of activated CAR T-cells in the subject.

An immune effector cell such as lymphocytes including but not limited to cytotoxic lymphocytes, T-cells, cytotoxic T-cells, T helper cells, Thl7 T-cells, natural killer (NK) cells, natural killer T (NKT) cells, mast cells, dendritic cells, killer dendritic cells, or B cells derived from a mammal, for example, a human cell, or a cell derived from a non-human mammal such as a monkey, a mouse, a rat, a pig, a horse, or a dog can be used. For example, a cell collected, isolated, purified or induced from a body fluid, a tissue or an organ such as blood (peripheral blood, umbilical cord blood etc.) or bone marrow can be used. A peripheral blood mononuclear cell (PBMC), an immune cell (a dendritic cell, a B cell, a hematopoietic stem cell, a macrophage, a monocyte, a NK cell or a hematopoietic cell (a neutrophil, a basophil)), an umbilical cord blood mononuclear cell, a fibroblast, a precursor adipocyte, a hepatocyte, a skin keratinocyte, a mesenchymal stem cell, an adipose stem cell, various cancer cell strains, or a neural stem cell can be used. In the present disclosure, particularly, use of a T-cell, a precursor cell of a T-cell (a hematopoietic stem cell, a lymphocyte precursor cell etc.) or a cell population containing them is contemplated. Examples of the T-cell include a CD8-positive T-cell, a CD4-positive T-cell, a regulatory T-cell, a cytotoxic T-cell, and a tumor infiltrating lymphocyte. The cell population containing a T-cell and a precursor cell of a T-cell includes a PBMC. The aforementioned cells may be collected from a living body, obtained by expansion culture of a cell collected from a living body, or established as a cell strain. When transplantation of the produced CAR-expressing cell or a cell differentiated from the produced CAR-expressing cell into a living body is desired, it is preferable to introduce the nucleic acid into a cell collected from the living body itself or a conspecific living body thereof.

In one embodiment, the CAR expressing cell is a T-cell isolated from a subject for autologous therapy. Typically, prior to expansion and genetic modification of the T-cells of the disclosure, a source of T-cells is obtained from a subject. T-cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T-cell lines available in the art, may be used. In certain embodiments of the present disclosure, T-cells can be obtained from a unit of blood collected from a subject using any number of techniques known to the skilled artisan, such as Ficoll™ separation. In one embodiment, cells from the circulating blood of an individual are obtained by apheresis. The apheresis product typically contains lymphocytes, including T-cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the disclosure, the cells are washed with phosphate buffered saline (PBS). In an alternative embodiment, the wash solution lacks calcium and may lack magnesium or may lack many if not all divalent cations. Initial activation steps in the absence of calcium may lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

In another embodiment, T-cells are isolated from peripheral blood lymphocytes by lysing the red blood cells and depleting the monocytes, for example, by centrifugation through a PERCOLL™ gradient or by counterflow centrifugal elutriation. A specific subpopulation of T-cells, such as CD3+, CD28+, CD4+, CD8+, CD45RA+, and CD45RO+ T-cells, can be further isolated by positive or negative selection techniques. For example, in one embodiment, T-cells are isolated by incubation with anti-CD3/anti-CD28 (i.e., 3×28)-conjugated beads, such as DYNABEADS® M-450 CD3/CD28 T, for a time period sufficient for positive selection of the desired T-cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. For isolation of T-cells from patients with leukemia, use of longer incubation times, such as 24 hours, can increase cell yield. Longer incubation times may be used to isolate T-cells in any situation where there are few T-cells as compared to other cell types, such in isolating tumor infiltrating lymphocytes (TIL) from tumor tissue or from immune-compromised individuals. Further, use of longer incubation times can increase the efficiency of capture of CD8+ T-cells. Thus, by simply shortening or lengthening the time T-cells are allowed to bind to the CD3/CD28 beads and/or by increasing or decreasing the ratio of beads to T-cells, subpopulations of T-cells can be preferentially selected for or against at culture initiation or at other time points during the process. Additionally, by increasing or decreasing the ratio of anti-CD3 and/or anti-CD28 antibodies on the beads or other surface, subpopulations of T-cells can be preferentially selected for or against at culture initiation or at other desired time points. The skilled artisan would recognize that multiple rounds of selection can also be used in the context of this disclosure. In certain embodiments, it may be desirable to perform the selection procedure and use the "unselected" cells in the activation and expansion process. "Unselected" cells can also be subjected to further rounds of selection.

Enrichment of a T-cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11 b, CD16, HLA-DR, and CD8. In certain embodiments, it may be desirable to enrich for or positively select for regulatory T-cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T-cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T-cells that normally have weaker CD28 expression.

In a related embodiment, it may be desirable to use lower concentrations of cells. By significantly diluting the mixture of T-cells and surface (e.g., particles such as beads), interactions between the particles and cells is minimized. This selects for cells that express high amounts of desired antigens to be bound to the particles. For example, CD4+ T-cells express higher levels of CD28 and are more efficiently captured than CD8+ T-cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T-cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen. In certain embodiments, cryopreserved cells are thawed and washed as described herein and allowed to rest for one hour at room temperature prior to activation using the methods of the present disclosure.

Also contemplated in the context of the disclosure is the collection of blood samples or apheresis product from a subject at a time period prior to when the expanded cells as described herein might be needed. As such, the source of the cells to be expanded can be collected at any time point necessary, and desired cells, such as T-cells, isolated and frozen for later use in T-cell therapy for any number of diseases or conditions that would benefit from T-cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T-cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66 (1991):807-815; Henderson et al., Immun 73 (1991):316-321; Bierer et al., Curr. Opin. Immun 5 (1993):763-773). In a further embodiment, the cells are isolated for a patient and frozen for later use in conjunction with (e.g., before, simultaneously or following) bone marrow or stem cell transplantation, T-cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present disclosure, T-cells are obtained from a patient directly following treatment. In this regard, it has been observed that following certain cancer treatments, in particular treatments with drugs that damage the immune system, shortly after treatment during the period when patients would normally be recovering from the treatment, the quality of T-cells obtained may be optimal or improved for their ability to expand ex vivo. Likewise, following ex vivo manipulation using the methods described herein, these cells may be in a state for enhanced engraftment and in vivo expansion. Thus, it is contemplated within the context of the present disclosure to collect blood cells, including T-cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T-cells, B cells, dendritic cells, and other cells of the immune system.

Whether prior to or after genetic modification of the T-cells to express a desirable CAR (e.g., CAR with degron, split CAR system with FDA-responsive heterodimer, etc.), the T-cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T-cells of the disclosure are expanded by contact with a surface having attached thereto an agent that stimulates a CD3/TCR complex associated signal and a ligand that stimulates a co-stimulatory molecule on the surface of the T-cells. In particular, T-cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of T-cells can be contacted with an anti-CD3 antibody and an anti-CD28 antibody, under conditions appropriate for stimulating proliferation of the T-cells.

To stimulate proliferation of either CD4+ T-cells or CD8+ T-cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berge et al., Transplant Proc. 30(8) (1998):3975-3977; Haanen et al., J. Exp. Med. 190(9) (1999):1319-1328, 1999; and Garland et al., J. Immunol Meth. 227(1-2) (1999):53-63).

The cell expressing the CAR (e.g., CAR with drug-responsive degron, split CAR system with drug-responsive heterodimer, etc.) can be used as a therapeutic agent for a disease. The therapeutic agent can be the cell expressing the CAR as an active ingredient, and may further include a suitable excipient. The disease against which the cell expressing the CAR is administered is not limited as long as the disease shows sensitivity to the cell. Examples of the disease include a cancer (blood cancer (leukemia), solid tumor etc.), an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis. The cell expressing the CAR of the present disclosure that binds to an antigen possessed by a cell that is desired to be decreased or eliminated for treatment of the aforementioned diseases, that is, a tumor antigen, a viral antigen, a bacterial antigen or the like is administered for treatment of these diseases. The cell of the present disclosure can also be utilized for prevention of an infectious disease after bone marrow transplantation or exposure to radiation, donor lymphocyte transfusion for the purpose of remission of recurrent leukemia, and the like. The therapeutic agent comprising the cell expressing the CAR as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

In a particular embodiment, the CAR expressing cell is an autologous T-cell from a subject with cancer. Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the disclosure include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Other hematological cancers include T-cell or NK-cell lymphoma, for example, but not limited to: peripheral T-cell lymphoma; anaplastic large cell lymphoma, for example anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In one embodiment, the CAR expressing cells can be used in an effective amount to treat a host, for example a human, with a lymphoma or lymphocytic or myelocytic proliferation disorder or abnormality. For example, the CAR expressing cells as described herein can be administered to a host suffering from a Hodgkin Lymphoma or a Non-Hodgkin Lymphoma. For example, the host can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); Chronic Lymphocytic Leukemia/Small Lymphocytic Lymphoma; Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral T-Cell Lymphomas; Primary Central Nervous System Lymphoma; T-Cell Leukemias; Transformed Lymphomas; Treatment-Related T-Cell Lymphomas; or Waldenstrom's Macroglobulinemia.

Alternatively, CAR expressing cells disclosed herein can be used in an effective amount to treat a host, for example a human, with a Hodgkin Lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

Alternatively, CAR expressing cells disclosed herein can be used in an effective amount to treat a host, for example a human with a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T-cell/histiocyte rich large B-cell lymphoma; DLBCL associated with chronic inflammation; Epstein-Barr virus (EBV)+DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In one embodiment, CAR expressing cells disclosed herein can be used in an effective amount to treat a host, for example a human with leukemia. For example, the host may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); large granular lymphocytic leukemia; or Adult T-cell chronic leukemia. In one embodiment, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

In one embodiment, CAR expressing cells disclosed herein can be used in an effective amount to treat a host, for example a human with a solid tumor. Examples include, but are not limited to, but are not limited to: estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, adenocarcinoma of the colon, adenocarcinoma of the rectum, central nervous system germ cell tumors, teratomas, estrogen receptor-negative breast cancer, estrogen receptor-positive breast cancer, familial testicular germ cell tumors, HER2-negative breast cancer, HER2-positive breast cancer, male breast cancer, ovarian immature teratomas, ovarian mature teratoma, ovarian monodermal and highly specialized teratomas, progesterone receptor-negative breast cancer, progesterone receptor-positive breast cancer, recurrent breast cancer, recurrent colon cancer, recurrent extragonadal germ cell tumors, recurrent extragonadal non-seminomatous germ cell tumor, recurrent extragonadal seminomas, recurrent malignant testicular germ cell tumors, recurrent melanomas, recurrent ovarian germ cell tumors, recurrent rectal cancer, stage III extragonadal non-seminomatous germ cell tumors, stage III extragonadal seminomas, stage III malignant testicular germ cell tumors, stage III ovarian germ cell tumors, stage IV breast cancers, stage IV colon cancers, stage IV extragonadal non-seminomatous germ cell tumors, stage IV extragonadal seminoma, stage IV melanomas, stage IV ovarian germ cell tumors, stage IV rectal cancers, testicular immature teratomas, testicular mature teratomas, estrogen-receptor positive, HER2-negative advanced breast cancer, late-line metastatic breast cancer, liposarcoma, non-small cell lung cancer, liver cancer, ovarian cancer, glioblastoma, refractory solid tumors, retinoblastoma positive breast cancer as well as retinoblastoma positive endometrial, vaginal and ovarian cancers and lung and bronchial cancers, metastatic colorectal cancer, metastatic melanoma, or cisplatin-refractory, unresectable germ cell tumors, carcinoma, sarcoma, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, fibrosarcoma, myxosarcoma, chondrosarcoma, osteosarcoma, chordoma, malignant fibrous histiocytoma, hemangiosarcoma, angiosarcoma, lymphangiosarcoma. Mesothelioma, leiomyosarcoma, rhabdomyosarcoma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, IsleT-cell carcinoma, malignant carcinoid, malignant paraganglioma, melanoma, Merkel cell neoplasm, cystosarcoma phylloide, salivary cancers, thymic carcinomas, bladder cancer, and Wilms tumor, a blood disorder or a hematologic malignancy, including, but not limited to, myeloid disorder, lymphoid disorder, leukemia, lymphoma, myelodysplastic syndrome (MDS), myeloproliferative disease (MPD), masT-cell disorder, and myeloma (e.g., multiple myeloma).

In another embodiment, a CAR expressing cell disclosed herein can be used in an effective amount to treat a host, for example a human with an autoimmune disorder. Examples include, but are not limited to: Acute disseminated encephalomyelitis (ADEM); Addison's disease; Agammaglobulinemia; Alopecia areata; Amyotrophic lateral sclerosis (Also Lou Gehrig's disease; Motor Neuron Disease); Ankylosing Spondylitis; Antiphospholipid syndrome; Antisynthetase syndrome; Atopic allergy; Atopic dermatitis; Autoimmune aplastic anemia; Autoimmune arthritis; Autoimmune cardiomyopathy; Autoimmune enteropathy; Autoimmune granulocytopenia; Autoimmune hemolytic anemia; Autoimmune hepatitis; Autoimmune hypoparathyroidism; Autoimmune inner ear disease; Autoimmune lymphoproliferative syndrome; Autoimmune myocarditis; Autoimmune pancreatitis; Autoimmune peripheral neuropathy; Autoimmune ovarian failure; Autoimmune polyendocrine syndrome; Autoimmune progesterone dermatitis; Autoimmune thrombocytopenic purpura; Autoimmune thyroid disorders; Autoimmune urticarial; Autoimmune uveitis; Autoimmune vasculitis; Balo disease/Balo concentric sclerosis; Behçet's disease; Berger's disease; Bickerstaffs encephalitis; Blau syndrome; Bullous pemphigoid; Cancer; Castleman's disease; Celiac disease; Chagas disease; Chronic inflammatory demyelinating polyneuropathy; Chronic inflammatory demyelinating polyneuropathy; Chronic obstructive pulmonary disease; Chronic recurrent multifocal osteomyelitis; Churg-Strauss syndrome; Cicatricial pemphigoid; Cogan syndrome; Cold agglutinin disease; Complement component 2 deficiency; Contact dermatitis; Cranial arteritis; CREST syndrome; Crohn's disease; Cushing's Syndrome; Cutaneous leukocytoclastic angiitis; Dego's disease; Dercum's disease; Dermatitis herpetiformis; Dermatomyositis; Diabetes mellitus type 1; Diffuse cutaneous systemic sclerosis; Discoid lupus erythematosus; Dressler's syndrome; Drug-induced lupus; Eczema; Endometriosis; Enthesitis-related arthritis; Eosinophilic fasciitis; Eosinophilic gastroenteritis; Eosinophilic pneumonia; Epidermolysis bullosa acquisita; Erythema nodosum; Erythroblastosis fetalis; Essential mixed cryoglobulinemia; Evan's syndrome; Extrinsic and intrinsic reactive airways disease (asthma); Fibrodysplasia ossificans progressive; Fibrosing alveolitis (or Idiopathic pulmonary fibrosis); Gastritis; Gastrointestinal pemphigoid; Glomerulonephritis; Goodpasture's syndrome; Graves' disease; Guillain-Barré syndrome (GBS); Hashimoto's encephalopathy; Hashimoto's thyroiditis; Hemolytic anemia; Henoch-Schonlein purpura; Herpes gestationis (Gestational Pemphigoid); Hidradenitis suppurativa; Hughes-Stovin syndrome; Hypogammaglobulinemia; Idiopathic inflammatory demyelinating diseases; Idiopathic pulmonary fibrosis; Idiopathic thrombocytopenic purpura; IgA nephropathy; Immune glomerulonephritis; Immune nephritis; Immune pneumonitis; Inclusion body myositis; inflammatory bowel disease; Interstitial cystitis; Juvenile idiopathic arthritis aka Juvenile rheumatoid arthritis; Kawasaki's disease; Lambert-Eaton myasthenic syndrome; Leukocytoclastic vasculitis; Lichen planus; Lichen sclerosus; Linear IgA disease (LAD); Lupoid hepatitis aka Autoimmune hepatitis; Lupus erythematosus; Majeed syndrome; microscopic polyangiitis; Miller-Fisher syndrome; mixed connective tissue disease; Morphea; Mucha-Habermann disease aka *Pityriasis lichenoides* et varioliformis *acuta*; Multiple sclerosis; Myasthenia gravis; Myositis; Ménière's disease; Narcolepsy; Neuromyelitis optica (also Devic's disease); Neuromyotonia; Occular cicatricial pemphigoid; Opsoclonus myoclonus syndrome; Ord's thyroiditis; Palindromic rheumatism; PANDAS (pediatric autoimmune neuropsychiatric disorders associated with *streptococcus*); Paraneoplastic cerebellar degeneration; Paroxysmal nocturnal hemoglobinuria (PNH); Parry Romberg syndrome; Pars planitis; Parsonage-Turner syndrome; Pemphigus vulgaris; Perivenous encephalomyelitis; Pernicious anaemia; POEMS syndrome; Polyarteritis nodosa; Polymyalgia rheumatic; Polymyositis; Primary biliary cirrhosis; Primary sclerosing cholangitis; Progressive inflammatory neuropathy; Psoriasis; Psoriatic arthritis; pure red cell aplasia; Pyoderma gangrenosum; Rasmussen's encephalitis; Raynaud phenomenon; Reiter's syndrome; relapsing polychondritis; restless leg syndrome; retroperitoneal fibrosis; rheumatic fever; rheumatoid arthritis; Sarcoidosis; Schizophrenia; Schmidt syndrome; Schnitzler syndrome; Scleritis; Scleroderma; Sclerosing cholangitis; serum sickness; Sjögren's syndrome; Spondyloarthropathy; Stiff person syndrome; Still's disease; Subacute bacterial endocarditis (SBE); Susac's syndrome;

Sweet's syndrome; Sydenham chorea; sympathetic ophthalmia; systemic lupus erythematosus; Takayasu's arteritis; temporal arteritis (also known as "gianT-cell arteritis"); thrombocytopenia; Tolosa-Hunt syndrome; transverse myelitis; ulcerative colitis; undifferentiated connective tissue disease; undifferentiated spondyloarthropathy; urticarial vasculitis; vasculitis; vitiligo; viral diseases such as Epstein Barr Virus (EBV), Hepatitis B, Hepatitis C, HIV, HTLV 1, Varicella-Zoster Virus (VZV) and Human Papilloma Virus (HPV); or Wegener's granulomatosis. In some embodiments, the autoimmune disease is an allergic condition, including those from asthma, food allergies, atopic dermatitis, and rhinitis.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In one embodiment, the antigen binding moiety portion of the CAR of the disclosure is designed to treat a particular cancer. For example, a CAR designed to target CD19 can be used to treat cancers and disorders including but are not limited to pre-B ALL (pediatric indication), adult ALL, mantle cell lymphoma, diffuse large B-cell lymphoma, salvage post allogenic bone marrow transplantation, and the like.

In another embodiment, the CAR can be designed to target CD22 to treat diffuse large B-cell lymphoma.

In one embodiment, cancers and disorders include but are not limited to pre-B ALL (pediatric indication), adult ALL, mantle cell lymphoma, diffuse large B-cell lymphoma, salvage post allogenic bone marrow transplantation, and the like can be treated using a combination of CARs that target CD19, CD20, CD22, and ROR1.

In one embodiment, the CAR can be designed to target mesothelin to treat mesothelioma, pancreatic cancer, ovarian cancer, and the like.

In one embodiment, the CAR can be designed to target CD33/IL3Ra to treat acute myelogenous leukemia and the like.

In one embodiment, the CAR can be designed to target CD30 to treat lymphoma, for example Hodgkin lymphoma, and the like.

In one embodiment, the CAR can be designed to target c-Met to treat triple negative breast cancer, non-small cell lung cancer, and the like.

In one embodiment, the CAR can be designed to target PSMA to treat prostate cancer and the like.

In one embodiment, the CAR can be designed to target Glycolipid F77 to treat prostate cancer and the like.

In one embodiment, the CAR can be designed to target EGFRvIII to treat gliobastoma and the like.

In one embodiment, the CAR can be designed to target GD-2 to treat neuroblastoma, melanoma, and the like.

In one embodiment, the CAR can be designed to target NY-ESO-1 TCR to treat myeloma, sarcoma, melanoma, and the like.

In one embodiment, the CAR can be designed to target MAGE A3 TCR to treat myeloma, sarcoma, melanoma, and the like.

In one embodiment, the CAR can be designed to target CEA to treat colorectal cancer and the like.

In one embodiment, the CAR can be designed to target erb-B2, erb-B3, and/or erb-B4 to treat breast cancer, and the like.

In one embodiment, the CAR can be designed to target IL-13R-a2 to treat glioma, glioblastoma, or medulloblastoma, and the like.

However, the disclosure should not be construed to be limited to solely to the antigen targets and diseases disclosed herein. Rather, the disclosure should be construed to include any antigenic or ligand target that is associated with a disease where a CAR or split CAR system having an element (e.g., degron, heterodimer, etc.) that is responsive to a FDA-approved drug can be used to treat the disease or disorder.

The CAR-expressing cells of the disclosure may also serve as a type of vaccine for ex vivo immunization and/or in vivo therapy in a mammal. Optionally, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

The CAR-expressing cells of the present disclosure can be administered either alone, or as a pharmaceutical composition in combination with diluents and/or with other components such as IL-2 or other cytokines or cell populations. Briefly, pharmaceutical compositions of the present disclosure may comprise a target T-cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are optionally formulated for intravenous administration.

Pharmaceutical Compositions, Kits, and Administration

Pharmaceutical compositions of CAR expressing cells of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an antitumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can generally be stated that a pharmaceutical composition comprising the T-cells described herein may be administered at a dosage of $10^4$ to $10^9$ cells/kg body weight, preferably $10^5$ to $10^6$ cells/kg body weight, including all integer values within those ranges. T-cell compositions may also be administered multiple times at these dosages. The cells can be administered by using infusion techniques that are commonly known in immunotherapy (see, e.g., Rosenberg et al., New Eng. J. of Med. 319 (1988):1676).

The optimal dosage and treatment regime for a particular patient can readily be determined by one skilled in the art of medicine by monitoring the patient for signs of disease and adjusting the treatment accordingly.

The administration of the CAR expressing cells may be carried out in any convenient manner, including by aerosol inhalation, injection, ingestion, transfusion, implantation or transplantation. The CAR expressing cells described herein may be administered to a patient subcutaneously, intradermally, intratumorally, intranodally, intramedullary, intramuscularly, by intravenous (i.v.) injection, or intraperitoneally. In one embodiment, the CAR expressing cells of the present disclosure are administered to a patient by intradermal or subcutaneous injection. In another embodiment, the CAR expressing cells of the present disclosure are optionally administered by i.v. injection. The CAR expressing cells may be injected directly into a tumor, lymph node, or site of infection.

The dosage of the above treatments to be administered to a patient will vary with the precise nature of the condition being treated and the recipient of the treatment. The scaling of dosages for human administration can be performed according to art-accepted practices.

Certain aspects of the present application provide pharmaceutical compositions which comprise, e.g., the FDA-approved drugs described herein (or a prodrug, pharmaceutically acceptable salt or other pharmaceutically acceptable derivative thereof), and optionally comprise a pharmaceutically acceptable carrier, optionally also including CAR and/or split CAR nucleic acid vectors of the disclosure and/or CAR- and/or split CAR system-containing cells of the disclosure. It will also be appreciated that certain of the FDA-approved compounds of the present application can exist in free form for treatment, or where appropriate, as a pharmaceutically acceptable derivative thereof. According to the present application, a pharmaceutically acceptable derivative includes, but is not limited to, pharmaceutically acceptable salts, esters, salts of such esters, or a pro-drug or other adduct or derivative of a compound of this application which upon administration to a patient in need is capable of providing, directly or indirectly, an FDA-approved compound possessing qualities (i.e., CAR modulatory properties) as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences 66 (1977):1-19, incorporated herein by reference. The salts can be prepared in situ during the final isolation and purification of the FDA-approved compounds of the application, or separately by reacting a free base or free acid function with a suitable reagent, as described generally below. For example, a free base function can be reacted with a suitable acid. Furthermore, where the FDA-approved compounds of the application carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Additionally, as used herein, the term "pharmaceutically acceptable ester" refers to esters that hydrolyze in vivo and include those that break down readily in the human body to leave the parent FDA-approved compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the FDA-approved compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, (1987), both of which are incorporated herein by reference.

In general, methods of using the FDA-approved compounds for modulating the activity of a CAR expressing cell as described in the present application comprise administering to a subject in need thereof a therapeutically effective amount of a FDA-approved compound of the present application, wherein the FDA-approved compound is administered in an amount sufficient to activate the CAR system (ON-switch) or induce degradation of the CAR (OFF-switch).

In certain embodiments, FDA-approved drugs are useful to modulate or downregulate the activation of the CAR expressing cell, for example a CAR T-cell, for example by degrading the intracellular signaling pathway of the CAR and thus reducing, for example, the release of cytokines by the CAR T-cell due to its activated state. In certain embodiments, according to the methods of treatment of the present application, levels of the CAR in the CAR expressing cell are modulated by contacting CAR expressing cells with a FDA-approved drug, as described herein.

Thus, in another aspect of the application, methods for the modulating of the activity of a CAR expressing cell, for example a CAR T-cell, are provided comprising administering a therapeutically effective amount of a FDA-approved drug to a subject in need thereof. In certain embodiments, a method for the modulation of a CAR expressing cell, for example a CAR T-cell, is provided comprising administering a therapeutically effective amount of FDA-approved compound, or a pharmaceutical composition comprising FDA-approved drug to a subject in need thereof, in such amounts and for such time as is necessary to achieve the desired result. Preferably, the FDA-approved compound is administered orally or intravenously. In certain embodiments of the present application a "therapeutically effective amount" of the FDA-approved drug is that amount effective for reducing the activity of a CAR expressing cell so that an adverse inflammatory or immune response is modulated or reduced. The FDA-approved drug, according to the method of the present application, may be administered using any amount and any route of administration effective for modulating the activity of a CAR expressing cell. The exact amount required will vary from subject to subject, depending on the species, age, and general condition of the subject, the activity of the CAR expressing cell, the particular CAR expressing cell, and the like. In certain embodiments of the present application a "therapeutically effective amount" of the FDA-approved drug is that amount effective for reducing the levels of CARs in a CAR expressing cell. In other embodiments of the present application, a "therapeutically effective amount" of the FDA-approved drug is that amount effective for activating a CAR T-cell therapy in a subject.

An effective amount of an agent of the instant disclosure may vary from about 0.001 mg/kg to about 1000 mg/kg or more in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In certain embodiments, the effective amount is an amount effective to selectively enhance T cell-mediated killing of target cells displaying a targeted (e.g., tumor) antigen by at least about 10%, at least about 20%, at least about 30%, at least about 40%, at least about 50%, at least about 60%, at least about 70%, at least about 80%, at least about 90%, at least about 100%, at least about 200%, at least about 300%, at least about 500%, or at least about 1000%. In certain embodiments, the effective amount is an amount effective for inhibiting T cell-mediated killing of target cells displaying a targeted (e.g., tumor) antigen (or inhibiting an observed side effect of CAR T-cell therapy) by at least about by at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, or at least about 99%.

Pharmaceutical compositions described herein can be prepared by any method known in the art of pharmacology. In general, such preparatory methods include the steps of bringing the agent or compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof.

Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of an agent (e.g., an IMiD) described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

FDA-approved drugs provided herein are typically formulated in dosage unit form for ease of administration and uniformity of dosage. It will be understood, however, that the total daily usage of the agents described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent (e.g., an IMiD) described herein.

As noted elsewhere herein, a drug or CAR T-cell agent of the instant disclosure may be administered via a number of routes of administration, including but not limited to: subcutaneous, intravenous, intrathecal, intramuscular, intranasal, oral, transepidermal, parenteral, by inhalation, or intracerebroventricular.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

In some embodiments of the present disclosure, a formulation as herein defined is administered to the subject by bolus administration.

The modulatory cell therapy or FDA-approved drug is administered to the subject in an amount sufficient to achieve a desired effect at a desired site (e.g., enhanced T cell-mediated killing of target cells, inhibited side-effects observed upon administration/activation of CAR T-cell treatment, etc.) determined by a skilled clinician to be effective. In some embodiments of the disclosure, the agent is administered at least once a year. In other embodiments of the disclosure, the agent is administered at least once a day. In other embodiments of the disclosure, the agent is administered at least once a week. In some embodiments of the disclosure, the agent is administered at least once a month.

Exemplary doses for administration of an agent of the disclosure to a subject include, but are not limited to, the following: 1-20 mg/kg/day, 2-15 mg/kg/day, 5-12 mg/kg/day, 10 mg/kg/day, 1-500 mg/kg/day, 2-250 mg/kg/day, 5-150 mg/kg/day, 20-125 mg/kg/day, 50-120 mg/kg/day, 100 mg/kg/day, at least 10 μg/kg/day, at least 100 μg/kg/day, at least 250 μg/kg/day, at least 500 μg/kg/day, at least 1 mg/kg/day, at least 2 mg/kg/day, at least 5 mg/kg/day, at least 10 mg/kg/day, at least 20 mg/kg/day, at least 50 mg/kg/day, at least 75 mg/kg/day, at least 100 mg/kg/day, at least 200 mg/kg/day, at least 500 mg/kg/day, at least 1 g/kg/day, and an imaging and/or therapeutically effective dose that is less than 500 mg/kg/day, less than 200 mg/kg/day, less than 100 mg/kg/day, less than 50 mg/kg/day, less than 20 mg/kg/day, less than 10 mg/kg/day, less than 5 mg/kg/day, less than 2 mg/kg/day, less than 1 mg/kg/day, less than 500 μg/kg/day, and less than 500 μg/kg/day.

In certain embodiments, when multiple doses are administered to a subject or applied to a tissue or cell, the frequency of administering the multiple doses to, the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent (e.g., an IMiD) described herein. In certain embodiments, a dose described herein includes independently between 1 mg and 3 mg, inclusive, of an agent (e.g., an IMiD) described herein. In certain embodiments, a dose described herein includes independently between 3 mg and 10 mg, inclusive, of an agent (e.g., an IMiD) described herein. In certain embodiments, a dose described herein includes independently between 10 mg and 30 mg, inclusive, of an agent (e.g., an IMiD) described herein. In certain embodiments, a dose described herein includes independently between 30 mg and 100 mg, inclusive, of an agent (e.g., an IMiD) described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that an agent (e.g., an IMiD) or composition, as described herein, can be administered in combination with one or more additional pharmaceutical agents (e.g., therapeutically and/or prophylactically active agents), which are different from the agent or composition and may be useful as, e.g., combination therapies. The agents or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk of developing a disease in a subject in need thereof, in inhibiting the replication of a virus, in killing a virus, etc. a subject or cell. In certain embodiments, a pharmaceutical composition described herein including an agent (e.g., an IMiD) described herein and an additional pharmaceutical agent shows a synergistic effect that is absent in a pharmaceutical composition including one of the agent and the additional pharmaceutical agent, but not both.

In some embodiments of the disclosure, a therapeutic agent distinct from a drug-responsive system of the disclosure is administered prior to, in combination with, at the same time, or after administration of the drug and/or drug-responsive system of the disclosure. In some embodiments, the second therapeutic agent is selected from the group consisting of a chemotherapeutic, an antioxidant, an antiinflammatory agent, an antimicrobial, a steroid, etc.

The agent or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, immunomodulatory agents, anti-cancer agents, anti-proliferative agents, cytotoxic agents, anti-angiogenesis agents, antiinflammatory agents, immunosuppressants, antibacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the agents described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or agent described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or agent described herein. In some embodiments, the pharmaceutical composition or agent described herein provided in the first container and the second container are combined to form one unit dosage form.

Thus, in one aspect, provided are kits including a first container comprising an agent (e.g., an FDA-approved IMiD) described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the kits are useful for treating and/or preventing a disease described herein in a subject in need thereof. In certain embodiments, the kits are useful for treating a disease described herein in a subject in need thereof. In certain embodiments, the kits are useful for preventing a disease described herein in a subject in need thereof. In certain embodiments, the kits are useful for reducing the risk of developing a disease described herein in a subject in need thereof. In certain embodiments, the kits are useful for male contraception. In certain embodiments, the kits are useful for inhibiting sperm formation. In certain embodiments, the kits are useful for in inhibiting the replication of a virus. In certain embodiments, the kits are useful for killing a virus. In certain embodiments, the kits are useful for enhancing the activity (e.g., activating CAR T cell-mediated target cell killing) in a subject or cell. In certain embodiments, the kits are useful for inhibiting the activity (e.g., halting CAR T cell-mediated target cell killing) of CAR T cells in a subject or cell, optionally to minimize or abolish a side-effect of CAR T-cell therapy.

In certain embodiments, the kits are useful for screening a library of agents to identify an agent that is useful in a method of the disclosure.

In certain embodiments, a kit described herein further includes instructions for using the kit, such as instructions for using the kit in a method of the disclosure (e.g., instructions for administering an agent (e.g., an IMiD) or pharmaceutical composition described herein to a subject). A kit described herein may also include information as required by a regulatory agency such as the U.S. Food and Drug Administration (FDA). In certain embodiments, the information included in the kits is prescribing information. In certain embodiments, the kits and instructions provide for treating and/or preventing a disease described herein in a subject in need thereof. In certain embodiments, the kits and instructions provide for treating a disease described herein in a subject in need thereof. In certain embodiments, the kits and instructions provide for preventing a disease described herein in a subject in need thereof. In certain embodiments, the kits and instructions provide for reducing the risk of developing a disease described herein in a subject in need thereof. In certain embodiments, the kits and instructions provide for male contraception. In certain embodiments, the kits and instructions provide for inhibiting the replication of a virus. In certain embodiments, the kits and instructions provide for killing a virus. In certain embodiments, the kits and instructions provide for inducing apoptosis of an in vitro cell. In certain embodiments, the kits and instructions provide for inducing apoptosis of a cell in a subject. In certain embodiments, the kits and instructions provide for inducing G1 arrest in a subject or cell. In certain embodiments, the kits and instructions provide for screening a library of agents to identify an agent (e.g., an IMiD) that is useful in a method of the disclosure. A kit described herein may include one or more additional pharmaceutical agents described herein as a separate composition.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (Danio rerio), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

Constructs

For targeted protein degradation experiments, IKZF3 degron derivatives were synthesized as gene fragments (IDT) and cloned into the Artichoke lentiviral expression marker (pSFFV-insert-linker-eGFP-IRES-mCherry-cppt-EF1a-Puro-WPRE; FIG. 9). For BRET dimerization experiments, IKZF3 degron derivatives were cloned into pFC14K (pCMV-insert-HaloTag) and CRBNderivatives were cloned into pFC32K (pCMV-insert-Nanoluciferase) per manufacturer's instructions (Promega™)

Cell Lines 293T and Jurkat human cell lines were used. 293T cells were maintained in DMEM (Invitrogen) supplemented with 10% FBS, 2 mM L-glutamine, 100 µg/mL penicillin and 100 U/mL streptomycin. Jurkat cells were maintained in RPMI (Invitrogen) supplemented with 10% FBS, 2 mM L-glutamine, 100 µg/mL penicillin and 100 U/mL streptomycin.

Lentivirus Production and Transduction

Lentiviral packaging was performed by co-transfection of expression, psPAX2, and VSV-G plasmids into 293T cells with TransIT-LT1 (MirusBio™) per manufacturer's instructions. 24 hours after transfection, cell culture supernatant containing lentivirus were flash frozen to −80° C. Jurkat, 293T cells, and single cell 293T cell clones with biallelic CRISPR/CAS9-mediated frameshift disruption of CRBN exon 5 (293T-CRBNJe5) and confirmed by Sanger sequencing and Western blotting for CRBN were performed to a target transduction efficiency of 20-50%.

GFP/mCherry Reporter Assay for Protein Degradation and Internalization

Transduced cells were incubated with a range of Pomalidomide concentrations or DMSO for 20 hours. Cells were analyzed by flow cytometry for eGFP and mCherry fluorescence. 1000 mCherry+ cells were analyzed per sample, and the geometric mean of the per-cell eGFP/mCherry ratio was calculated in Flowjo. In Pomalidomide dose titration studies, the EC50 was calculated by non-linear regression in Prism. Experiments were performed in triplicate. In some cases cell surface protein expression was assayed in parallel with the above reporter assay; cells were stained with anti-CD28-BV421 antibody (BD Biosciences 562613) at a 1:50 dilution in FACS buffer (PBS+2% FCS+2 mM EDTA) for 10 minutes on ice. Cells were washed with FACS buffer and analyzed by flow cytometry.

Bioluminescence Resonance Energy Transfer (BRET) Assay for Protein-Protein Interaction 293T cells were co-transfected with pFC14K and pFC32K plasmids expressing IKZF3-HaloTag and CRBN-Nanoluciferase fusion proteins and incubated overnight. Cells were then trypsinized and seeded into 96 well plates, at 40,000 cells per well. The BRET assay was performed per manufacturer's instructions (Promega™). In brief, cells were incubated for 2 hours with varying concentrations of Pomalidomide or DMSO, 10 μM MG132, and 100 nM HaloTag NanoBRET 618 Ligand. NanoBRET Nano-Glo substrate was added and donor (460 nm) and acceptor (618 nm) emission were measured within 10 minutes (EnVision, Perkin Elmer). Mean corrected milliBRET units (mBU) was calculated.

Jurkat/Target Cell Co-Culture Assay

Jurkat T cells lentivirally transduced with the genetic components described herein were co-cultured for 24 hours with K562 cells (human blast crisis Chronic Myeloid Leukemia cell line) lentivirally transduced with an expression vector encoding CD19 (referred to as K562-CD19) (G&P Biosciences LTV-CD19) or isogenic K562 cells lacking the target antigen. Both K562-CD19 and K562 cell lines were engineered to express homogenous high level mCherry expression via transduction with the Jenner lentivirus, allowing discrimination of K562 and Jurkat cells by flow cytometry. Unless otherwise specified, 50,000 Jurkat cells were co-cultured with 10,000 K562 cells in 110 ul of RPMI supplemented with Pen/Strep and 10% fetal calf serum for 24 hours. The supernatant was then harvested for cytokine secretion assays and IL2 concentration in the supernatant was performed according to manufacturer specifications (BD Biosciences 555190). The cells were analyzed by flow cytometry. Expression of the early activation marker CD69 (BioLegend 310910), myc tagged cell surface proteins (Cell Signaling Technologies 2233S), and fluorescent protein markers were assessed.

Primary Human T Cell Experiments

Primary human T cells from normal donors were expanded with CD3/CD28 Dynabead stimulation for 7 days. On day 1, the T cells were transduced with lentivirus encoding chimeric antigen receptors. Flow cytometry for eGFP or mCherry was used to assess transduction efficiency. On day 10, the CAR-T cells were used in functional assays or viably frozen.

Killing Assay

Target tumor cell lines engineered to express Click Beetle Green (CBG) Luciferase were co-cultured with CAR-T cells for 18 hours. Tumor cell killing was determined from endpoint CBG Luciferase signal in surviving cells (Promega BioGlo Luciferase Assay).

Live Cell Imaging

Adherent target tumor cell lines were seeded in 6-well plates, after which CAR-T cells were added and co-cultured for 24 hours. Fluorescence (eGFP and mCherry) live-cell imaging was performed throughout this time course (Incucyte S3).

Example 2: Basis for Molecular Switch Integration into CAR T Cell Design

CAR-T cells can act to kill targeted tumor cells, but can also elicit negative effects that are capable of propagating in an unchecked manner. As noted above, conventional CAR-T design uses a single polypeptide that includes tumor antigen-binding domains (e.g., an scFv), a transmembrane domain, a costimulatory domain and a CD3ζ domain (TCR ITAMs), with this single polypeptide therefore capable of both specifically binding a tumor antigen and propagating an activated T cell response. Chimeric antigen receptors (CARs) are recombinant receptor constructs composed of an extracellular single-chain variable fragment (scFv) derived from an antibody, joined to a hinge/spacer peptide and a transmembrane domain, which is further linked to the intracellular T cell signaling domains of the T cell receptor. CAR T cells combine the specificity of an antibody with the cytotoxic and memory functions of T cells. The specific domains of a CAR construct include: (1) the target element, which is the single-chain variable fragment (scFv) expressed on the surface of a CAR T cell, which confers antigen specificity (the scFv is derived from the portion of an antibody that specifically recognizes a target protein; (2) the spacer domain, which connects the extracellular targeting element to the transmembrane domain (TMD) and affects CAR function and scFv flexibility; (3) the TMD, which traverses the cell membrane and anchors the CAR to the cell surface, also thereby connecting the extracellular domain to the intracellular signaling domain, thereby impacting expression of the CAR on the cell surface; (4) the costimulatory domain, which is derived from the intracellular signaling domains of costimulatory proteins, such as CD28 and 4-1BB, which enhances cytokine production; and (5) the signaling domain, i.e., the CD3ζ domain, which is derived from the intracellular signaling portion of the T cell receptor, which mediates downstream signaling during T cell activation. To control the potentially negative effects of CAR T cell signaling observed in certain instances, it was contemplated that small molecule-responsive switches might be designed and introduced into CAR constructs, thereby enabling greater control over CAR T cell activities than heretofore available.

Example 3: Clinically Useful Molecular ON-Switch Design and Implementation

Figure 1:
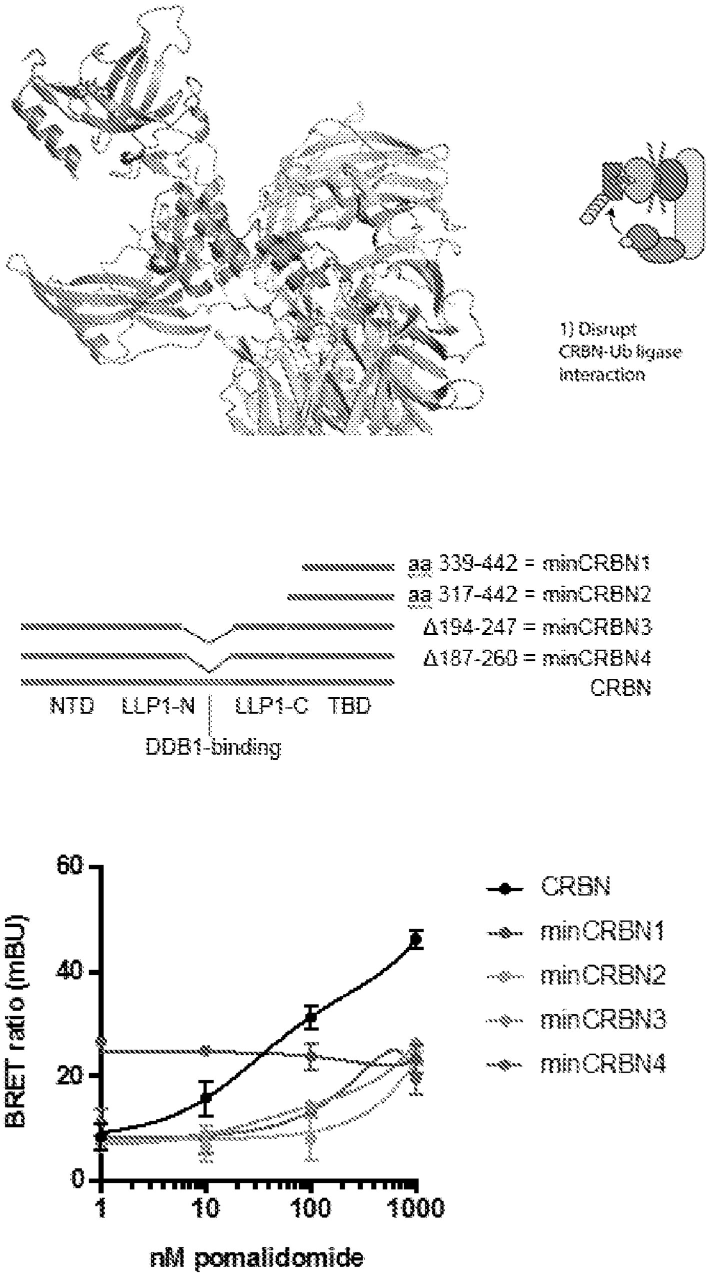
FIG. 1 shows a structural schematic that displays the binding of an IMiD glutarimide ring to the tri-TRP binding pocket of CRBN, further shows a schematic of a split-receptor design, and additionally documents the design and demonstrated efficacy of certain IMiD-responsive ON switches. Particularly shown is an IMiD-responsive (here, pomalidomide) ON-switch that brings together split receptor elements upon IMiD-induced binding between IKZF3 degron and minimal CRBN polypeptide. Specifically, CRBN deletion variants were engineered to retain binding to Pom/IKZF3 but not DDB1/CUL4. Four deletion variants were generated in CRBN that removed the DDB1-binding domain, as shown in the middle image (NTD is the N-terminal domain; LLP1 is Lon-like protease domain 1 (split into LLP1-N and LLP1-C regions); TBD is the Thalidomide binding domain). At middle, BRET assays were performed upon 293T cells harboring bialleleic CRISPR/Cas9 disruption of endogenous CRBN (293T-CRBNΔe5), to assess dimerization between IKZF3aa130-189 and CRBN or minCRBN variants (dose-response data shown are CRBN, minCRBN1, minCRBN2, minCRBN3 and minCRBN4). Effective concentrations for dimerization were identified in various cellular assays—apparent Kd values for CRBN and minCRBN3 were 30 nM, whereas Kd values were not determined for minCRBN1 and minCRBN2. Pomalidomide-dependent dimerization was observed between IKZF3aa130-189-HaloTag and CRBN-Nanoluciferase (NLuc) or minCRBN2-4-NLuc. The bottom plot shows the results of co-transfection of minCRBN1-4 and IKZF3 degron-GFP-IRES-mCherry expression vectors in 293T-CRBNΔe5 cells. 1 day after transfection, cells were exposed to 1 μM pomalidomide for the number of hours indicated and GFP and mCherry fluorescence was measured by flow cytometry (eGFPmCherry levels were detected as 0.5 or less for the CRBN trace). (Kd values for various split receptor designs were further determined to be around 100 nM, with a much higher saturation value; using different transformation conditions, Kd eff for iK0 split receptor was observed to be 50 nM, while Kd eff for a K+ split receptor was observed to be 67 nM.)
Figure 1:
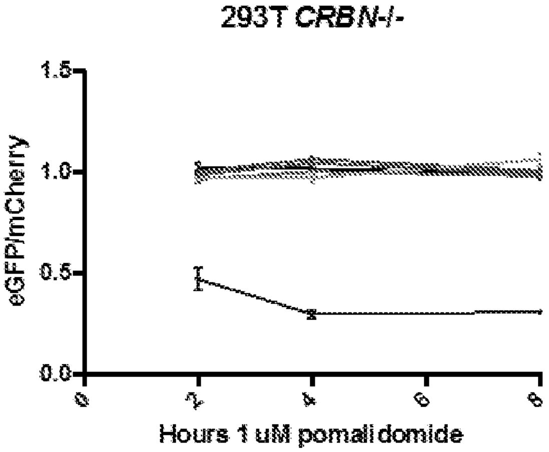

It was herein contemplated that small molecule gating could enable custom tuning, increased safety and expanded applicability of CAR-T cells, as specifically shown in FIG. 1 for an "ON"-switch applied to CAR-T cells. The exemplified ON-switch CAR of the instant disclosure is a split CAR system that requires small molecule-inducible dimerization of domain A and domain B for activation, which can allow oncologists to tune the activity of CAR-T cells along individualized risk/benefit criteria. Prior to the instant disclosure, while a rapamycin-induced dimerization system had been described (see, e.g., Hubbard et al. *Front. Physiol.* 5: 478, which shows the structural basis for rapamycin-induced dimerization of FRB and FKBP as the canonical example of chemically-induced dimerization), a clinically valid drug-inducible heterodimerization system had not yet been disclosed.

In view of the FDA-approved status of thalidomide analog immunomodulatory drugs (IMiDs), and noting the recently described structural basis for lenalidomide-induced CRBN-IKZF3 degron interaction (see Petzold et al. *Nature* 532: 127-130, which shows the structural basis for lenalidomide-induced CRBN-IKZF3 degron interaction, further showing thalidomide analog immunomodulatory drug (IMiD)-dependent binding between CRBN and substrates), it was specifically contemplated that CRBN-IKZF3 degron interaction could be repurposed as a chemically-inducible dimerization (CID) system, through the engineering of multiple novel properties into CRBN- and IKZF3-derived polypeptides. Conserved design features of CID systems include: (1) specific drug-dependent interaction (confirmed for CRBN-IKZF3 degron interaction); (2) modular domain structures (confirmed for CRBN-IKZF3 degron interaction); (3) minimal dimerization domains (identified herein for CRBN-IKZF3 degron interaction and under continuing investigation); and (4) minimal interaction with endogenous proteins (CRBN-IKZF3 degron interaction has been adapted herein to avoid certain endogenous protein interactions; however, such attributes also remain under continuing investigation).

It was contemplated that additional requirements for clinical use of a small molecule-responsive heterodimeric system could also be met by an engineered CRBN-IKZF3 degron system of the instant disclosure, including (1) non-toxicity, e.g., non-immunosuppressive and non-immunogenic attributes (with the caveat that IMiDs, while FDA-approved molecules, remain teratogenic, which would likely limit medical applications of the presently-described heterodimerization system to highly morbid clinical indications such as cancer and severe autoimmunity); (2) availability, including both pharmacodynamics and pharmacokinetic availability; and (3) freedom from regulatory impediment, i.e., the IMiD modulatory agent(s) of the instant disclosure are FDA-approved.

To make an optimized ON-switch that employed the recently characterized IMiD-responsive (CID) CRBN-IKZF3 system, it was specifically identified that such a CRBN-IKZF3-derived CID system would need to have minimal drug-dependent heterodimerization domains, would also need to be disrupted for recruitment of the CRBN-dependent E3 ubiquitin ligase (E3UL)—to thereby effect adaptation of what would otherwise be an OFF-switch to an ON-switch configuration, might further need to disrupt endogenous CRBN-dependent degradation of the IKZF3-derived dimer pair (IKZF3$^{orthogonal}$), yet would also need to retain heterodimerization between the IKZF3$^{orthogonal}$ and CRBN-derived dimer pair (thereby retaining the IMiD-responsiveness of the heterodimer).

Engineering of a CRBN-IKZF3-derived CID system was commenced in a CAR T-cell system. As shown in FIG. 2, minimal heterodimerization domains of CRBN and a CRBN substrate (here, an IKZF3 degron comprising amino acids 130-189 of IKZF3) were engineered to associate in IMiD-dependent fashion, thereby bringing together a scFv- and CD28 co-stimulatory domain-containing first polypeptide with a second polypeptide containing a CD28 co-stimulatory domain and a CD3ζ domain. In the FIG. 2 schematic, the IMiD used was pomalidomide ("Pom") and the second polypeptide comprised a transmembrane domain (TMD). The function of this CRBN-IKZF3-derived CID system within a CAR T-cell context is further shown in FIG. 3, where the scFv of an IKZF3 degron-presenting CAR binds a tumor cell-presented antigen, effecting CAR-T cell activation in the form of cytokine and cytotoxic granule release and T cell proliferation, resulting in tumor cell killing. Withdrawal of the IMiD can then be used to turn off T cell activation, thereby reducing and/or preventing any toxicity that might have otherwise been induced during the (prolonged) activated CAR-T cell response.

Having identified an IKZF3 degron comprising amino acids 130-189 of IKZF3 as functional for pomalidomide-mediated interaction with CRBN, variant forms of CRBN polypeptide were now examined, with the goal of identifying a variant form of CRBN that retained pomalidomide-mediated heterodimerization with IKZF3 degron while also disrupting the mechanism by which native CRBN can interact with and promote ubiquitin-mediated degradation of CRBN substrates (e.g., IKZF3) in the presence of IMiD. As shown in FIG. 1, minimal CRBN polypeptide variants for an ON-switch of the instant disclosure were designed that retained binding to IMiD (pomalidomide as exemplified herein) and the CRBN substrate (here, IKZF3 degron polypeptide) but were also engineered to remove/disrupt the wild-type CRBN domain that binds DDB1/CUL4 (where DDB1/CUL4 binding of wild-type CRBN mediates ubiquitination and degradation of CRBN substrates, via a molecular mechanism also involving ROC and E2). Design/assembly of such a functional cell surface split receptor as exemplified involved introduction of compound that was modeled to bring together a heterodimer that included an antigen-binding scFv-TMD-costimulatory domain-compound-binding component #1 on a first polypeptide and compound-binding component #2 fused to a CD3ζ domain on a second polypeptide. Such a split configuration was modeled to achieve a T cell response only upon both antigen and compound (small molecule) binding. Connection of the exemplified ON-switch system to the wild-type CRBN/DDB1/CUL4A/ROC1/E2/Ubiquitin-mediated system of IMiD (e.g., lenalidomide) substrate degradation was broken, e.g., by use of minimal CRBN polypeptides, thereby removing such a system, when activated, from proteasomal degradation of ubiquitinated substrate that would otherwise have been mediated via CRBN in the presence of the IMiD. Specifically, the ON-switch of the current disclosure has importantly removed IMiD-mediated binding between CRBN and a CRBN substrate from the threat of attack by the native ubiquitin/proteasome pathway, via engineering and use of minimal substrate-binding forms of CRBN from which DDB1/CUL4A binding elements have been removed.

To assess the extent and dose-responsiveness of interactions between various minimal forms of CRBN and the IKZF3 degron, Bioluminescence Resonance Energy Transfer (BRET) was employed (FIG. 1). BRET was specifically used to detect energy transfer from a minimal CRBN polypeptide to the IKZF3 degron. Tested forms of minimal CRBN included minCRBN1, minCRBN2, minCRBN3 and minCRBN4, each of which were aligned against the wild-type CRBN (FIG. 1; all tested minCRBNs lacked the DDB1-binding domain—minCRBN1 comprised amino acids 339-442 of CRBN (including the TBD); minCRBN2 comprised amino acids 317-442 of CRBN (including TBD and an N-terminal extended sequence relative to minCRBN1); minCRBN3 included all CRBN sequence other than amino acids 194-207 (deletion of the DDB1-binding domain); and minCRBN4 included all sequences other than amino acids 187-260 (deletion of the DDB1-binding domain)). BRET assays that tested associations between minCRBN polypeptides and the IKZF3 degron (FIG. 1, where milliBRET units (mBU) were detected) revealed pomalidomide-dependent interactions between IKZF3 degron and any of minCRBN2, minCRBN3 and minCRBN4, as well as between the IKZF3 degron and wild-type CRBN (positive control). Among minCRBN polypeptides tested, pomalidomide dose-dependence was only not observed for the interaction between minCRBN1 and the IKZF3 degron (FIG. 1).

To employ the minCRBN-IKZF3 degron IMiD-responsive engineered system in cells without confronting confounding (i.e., degradative) effects of native CRBN, CRISPR/Cas9 was used to disrupt CRBN in mammalian cells (via introduction of a biallelic CRBNΔe5 disruption of native CRBN, which is described in greater detail below), into which the minCRBN-IKZF3 degron system was also introduced. As shown in FIG. 1, while 293T cells possessing a biallelic CRBN disruption (biallelic CRBNJe5) to which a wild-type CRBN-IKZF3 degron system was added successfully promoted degradation of the IKZF3 degron in the presence of 1 μM pomalidomide (as tracked by assessing the eGFP/mCherry ratio in these cells), the eGFP/mCherry ratio remained unitary and stable over time for all minCRBNs-presenting systems tested (minCBRN1-4), indicating that none of minCRBN1-4 polypeptides were capable of rescuing IMiD-responsive degradation of the IKZF3 degron (consistent with each of minCRBN1-4 lacking the DDB1-binding domain believed to be critical for activation of the ubiquitination pathway). Thus, minimal heterodimerization domains associated in human cells and did not recruit $CRL4^{CRBN}$.

The importance of cell surface localization of non-scFv-presenting polypeptides of the minCRBN-IKZF3 degron CAR system was then examined. As shown in FIG. 2, the IMiD-responsive ON-switch was modified such that different forms of tethering the minCRBN-presenting polypeptide (minCRBN3 polypeptide as depicted and exemplified herein) to the plasma membrane were assessed for IKZF3 degron interaction capability, as compared to an untethered minCRBN3. Specific minCRBN-presenting polypeptide tethers to the plasma membrane that were tested included: (1) a CD8/CD28 system in which about 36 amino acids of TMD and cytosolic sequence connected to the co-stimulatory/minCRBN domains of the thereby membrane-tethered polypeptide; (2) a PD1 Y F ITAM/ITSM construct, in which minCRBN was tethered to the plasma membrane via a TMD and cytosolic domain of approximately 100 amino acids in length; and (3) a LYN-CD28 construct, in which membrane tethering was achieved via myristoyl/palmitoylation. Cytosolic minCRBN (untethered) interacted in a pomalidomide-dependent manner with IKZF3 degron (as assessed via BRET assay, as above) to a significantly lesser extent than any of the various plasma membrane-tethered versions of minCRBN-presenting polypeptide. Strikingly, little difference was observed among the various membrane-tethered forms of minCRBN-presenting polypeptides (all three membrane-tethered minCRBN formats displayed similar levels of IKZF3 degron interaction in the presence of pomalidomide). Cell surface localization of IKZF3 degron and minCRBN3 therefore decreased the observed Kd of pomalidomide-dependent dimerization.

It was next examined whether the IZKF3 degron of the minCRBN-IKZF3 degron system could be further stabilized against ubiquitin pathway-mediated degradation via removal of potential sites of ubiquitination (i.e., lysine residues) within the IKZF3 degron polypeptide sequence. As shown in FIG. 3, five lysine-to-arginine (K to R) substitutions within the IKZF3 polypeptide sequence were performed upon the original ("wild-type") scFv-TMD-CD28-IKZF3 degron polypeptide, to produce an "iK0" polypeptide lacking these sites of potential ubiquitination. When tested by BRET assay for minCRBN3-IKZF3 degron interaction (FIG. 3), the iK0 split receptor demonstrated decreased pomalidomide-dependent Kd and increased Bmax relative to the original ("wild-type") split receptor system. The iK0 split receptor system also exhibited increased BRET signal retention over prolonged exposures to pomalidomide (FIG. 3). Thus additional stabilization of the IKZF3 degron was achieved via elimination of six lysine residues within the IKZF3 degron polypeptide sequence.

While disruption of native CRBN within a cell presenting the IMiD-responsive minCRBN-CRBN substrate system of the instant disclosure was shown to shield the instant CRBN substrate degron from native CRBN-mediated degradation (see above), the prospect was also contemplated of shielding a minCRBN-CRBN system of the instant disclosure from effects mediated by native CRBN by altering the respective IMiD binding pocket residues of both the CRBN substrate of the system (here, IKZF3 degron) and the minCRBN employed by the system, such that a heterodimer of residue-substituted minCRBN and residue-substituted CRBN substrate (e.g., residue substituted IKZF3 degron) associates with one another in IMiD-dependent fashion, yet binding of the residue-substituted CRBN substrate with native forms of CRBN is dramatically reduced or eliminated (thereby possibly even removing the need to perform a disruption of native CRBN within cells that utilize a minCRBN-CRBN substrate system of the instant disclosure). As shown in FIG. 4, strategic residue substitutions were made respectively within the IMiD (pomalidomide) binding pocket of the IKZF3 degron and a minCRBN polypeptide of the instant system. As noted above, such alterations could be used to make the IKZF3 degron less responsive and/or effectively non-responsive to pomalidomide-dependent degradation by native forms of CRBN polypeptide, while it was reasoned that "offsetting" substituted forms of CRBN polypeptide could also be identified that restored pomalidomide-dependent association to the substituted IKZF3 degron-substituted CRBN interaction (thereby effectively freeing this substituted IKZF3 degron-substituted CRBN dimerization from the potential degradative impacts of wild-type CRBN, where present, thus reducing or eliminating the need for genomic disruption of native CRBN in candidate therapeutic cells that employ such a substituted IKZF3 degron-substituted CRBN dimer system). Initially, various substitutions made within the IKZF3 degron at the A153 site (which was shown by crystal structure to interact with IMiD/pomalidomide) were identified that disrupted the pomalidomide-dependent, wild-type CRBN-mediated degradation of the IKZF3 degron in wtCRBN-expressing cells (refer to dose-response curves of the middle panel of FIG. 4). Among all forms of substituted IKZF3 degron tested, the A153D substitution was identified as the most effective at disrupting pomalidomide-dependent IKZF3 degron degradation.

As shown in the lower panels of FIG. 4, an A153M-substituted form of the IKZF3 degron was then examined for whether crystal structure-implicated CRBN substitutions at residues 371 and 388 of CRBN could restore pomalidomide-dependent binding between the newly-substituted CRBN polypeptide and the A153M-substituted form of the IKZF3 degron. It was strikingly identified that the CRBN V388A substitution elicited the greatest restoration of pomalidomide-dependent binding between the newly-substituted CRBN polypeptide and the A153M-substituted form of the IKZF3 degron, as initially assessed by BRET assay at 1 μM pomalidomide, and, as then shown in the dose-response curves at lower right of FIG. 4, pomalidomide dose-responsiveness was also enhanced/restored to interactions with the A153M-substituted form of the IKZF3 degron by the CRBN V388A substituted polypeptide, as compared to the significantly less robust interaction of the A153M-substituted form of the IKZF3 degron with wtCRBN, as assessed by BRET assay across a range of pomalidomide concentrations.

Example 4: Clinically Useful Molecular OFF-Switch Design and Implementation

The above-described IMiD-responsive IKZF3 degron was also utilized to engineer an exemplary IMiD-responsive "OFF"-switch in a CAR-T cell system. As shown in FIG. 13 an OFF-switch CAR construct was designed that presents an engineered element capable of causing intracellular degradation of the CAR in a precise, input-responsive manner. The input-responsive element is referred to as an "engineered degron," and the input to which the degron responds in certain aspects of the instant disclosure is an IMiD (e.g., pomalidomide). In the absence of IMiD administration, the OFF-switch CAR construct comprising the engineered degron is active (thereby recognizing tumor cell antigen and propagating signaling to produce cytokines, cytotoxic granules, T cell proliferation, etc.—see FIG. 13 at right). In contrast, when IMiD is administered to a T cell containing the CAR construct comprising the engineered degron, degradation of the CAR construct is triggered, and T cell activation is thereby terminated. The viability of IMiD-responsive IKZF3 degron-mediated degradation of a polypeptide was first tested in the context of IKZF3 degron inclusion within a GFP-tagged CD28 fusion protein. As shown in FIG. 7, when cell surface and total protein expression were assessed after 20h treatment with or without the IMiD pomalidomide, a CD28-degron-GFP fusion polypeptide (where the degron was an IMiD-responsive IKZF3 polypeptide comprising amino acids 130-189 of IKZF3) showed degradation-responsiveness to the IMiD pomalidomide, within cells expressing wild-type CRBN. Deletion of native CRBN in such cells demonstrated that such degron-mediated degradation was CRBN-dependent (as no pomalidomide-responsive degradation was observed in cells deleted for the native CRBN locus). In particular, the CD28-degron-GFP construct was observed to be internalized upon treatment with pomalidomide in a CRBN-dependent manner (FIG. 7 middle panel), while a dramatic degradation effect (as assessed by reduced normalized GFP signal) was observed at 10 μM pomalidomide for 293T cells expressing the CD28-degron-GFP construct (FIG. 7 right panel). Such pomalidomide-responsive degradation was rescued via disruption of CRBN in these cells—in particular, as shown in the histograms of the right panel of FIG. 7, a biallelic disruption of CRBN exon 5, CRBNde5, when integrated into these cells, resulted in no significant decline in normalized GFP levels in the presence of 10 μM pomalidomide, as contrasted with the highly pomalidomide-responsive degradation observed for 293T cells expressing wild-type CRBN.

Consistent with the above results observed for the CD28-degron-GFP construct, the IKZF3 degron (comprising amino acids 130-189 of IKZF3) also functioned as a highly pomalidomide-responsive OFF-switch when integrated into the context of a CAR construct (FIG. 8). As shown in FIG. 8, an ideal drug-OFF-switch would function by dramatically decreasing signal (e.g., CAR T signal) when an IMiD (e.g., pomalidomide) is administered, yet would revert to previously observed levels of activity/signal following removal of the IMiD. Indicative of such function, the IKZF3 degron mediated particularly robust pomalidomide-responsive degradation of CAR-like polypeptide constructs comprising transmembrane domains (TMDs), as compared to a cytosolic, untethered form of the IKZF3 degron (see lower panel of FIG. 8). Specifically, a cytosolic, untethered form of the IKZF3 degron exhibited an EC50 of 0.4 nM pomalidomide, whereas a CD28-degron construct and a CD28-CD3ζ-degron construct exhibited EC50 values of 24 nM and 8 nM pomalidomide, respectively.

Example 5: Identification of a ZFP91/IKZF3 Hybrid Degron as an Apparently Enhanced Degron A hybrid sequence of two distinct CRBN substrates, IKZF3 and ZFP91, was constructed and examined for activity within an "OFF-switch" system of the instant disclosure. In such experiments, reporter constructs containing zinc finger sequences were expressed in HEK239T cells via lentiviral transduction, after which the cells were treated with a titration of (IMiD) drug concentrations for 20 h. Flow cytometry was used to measure the EGFP/mCherry ratio normalized to the average of three DMSO treated controls. Data shown in FIG. 10 are representative of two experimental replicates (technical replicates=0, experimental replications=2). As shown in FIG. 10, a ZFP91/IKZF3 hybrid sequence (SEQ ID NO: 32) showed greater IMiD sensitivity than either the ZFP91 degron sequence alone or the IKZF3 degron sequence alone. Notably, the "reverse hybrid" configuration of IKZF3/ZFP91 showed minimal IMiD sensitivity/responsiveness, further underscoring that the ZFP91/IKZF3 hybrid sequence configuration was especially active/responsive.

Example 6: Degron-Based Switches were Highly Responsive to Both IMiD Treatment and Withdrawal To examine the kinetics of IMiD responsiveness of a degron-based system of the instant disclosure, an OFF-switch system as employed for FIG. 8 was examined. As for the FIG. 8 OFF-switch system, the CD28-CD3ζ-degron protein differed from the anti-CD19 CAR sequence published previously (PMID 19561539) in two ways. First, the FMC63 anti-CD19 scFv was exchanged for the CD28 Ig-like V-type extracellular domain. Second, the protein was fused in-frame at its C-terminus with the degron IKZF3aa130-189 that was shown to mediate lenalidomide-dependent degradation by $CRL4^{CRBN}$ (PMID 24292625). Jurkat T cells were transduced with lentivirus encoding the three degron-eGFP fusion proteins (pSFFV-insert-linker-eGFP-IRES-mCherry), where mCherry expression served as an internal control for transgene expression.

As shown in FIG. 11, transmembrane protein internalization and degradation of the exemplary OFF-switch CAR design occurred rapidly upon addition of pomalidomide. In particular, degradation of the presently exemplified degron-eGFP protein was measured at the specified times after addition of 1 μM pomalidomide (the experiment was performed in triplicate). The cytoplasmic IKZF3-derived degron was rapidly cleared, approaching 90% degradation by 1 hour after addition of pomalidomide. The CD28-CD3ζ-IKZF3aa130-189 polypeptide was degraded slightly less quickly, yet approached 80% degradation by 3 hours after drug addition. Thus, all polypeptides harboring the OFF-switch degron system were rapidly internalized and degraded in an IMiD-responsive manner.

As shown in FIG. 12, re-synthesis of the exemplified transmembrane degron-tagged protein after washout of pomalidomide also occurred with kinetics that resembled those of the IKZF3 degron alone. In particular, cells with the degron-eGFP fusion proteins were cultured with 1 μM pomalidomide for 16 hours. Cells were then washed with media three times and resuspended for culture in media lacking pomalidomide, after which the return of degron-eGFP was compared to untreated cells at 2 h, 4 h, 8 h and 10 h time points (the experiment was performed in triplicate). After pomalidomide washout, resynthesis of both degron-tagged proteins (the tagged CD28-CD3ζ-IKZF3aa130-189 polypeptide or the tagged IKZF3aa130-189 degron) regenerated >50% of protein levels in less than 8 hours. The exemplified OFF-switch was therefore responsive to removal of IMiD.

A highly effective IMiD-responsive OFF-switch degron format was identified, construction of which employed modification of the non-IKZF3 C2H2 zinc finger degron amino acids 400-410 with N-terminal and C-terminal additions of IKZF3 sequences (IKZF3 amino acids 130-145 were joined at the N-terminus, while IKZF3 amino acids 157-189 were joined at the C-terminus), thereby forming a "d913" hybrid degron sequence (a "K0" form of the d913 degron sequence was also produced, as described elsewhere herein). A d913 degron-tagged fusion protein was demonstrated to turn off the tumor cell killing of primary human T cells engineered to express degron-tagged CARs (FIGS. 13-20. More broadly, it was demonstrated that modification of any given non-IKZF3 C2H2 zinc finger degron sequence via addition of IKZF3 amino acids 130-145 to the N-terminus and IKZF3 amino acids 169-189 to the C-terminus, to generate an approximately 60 amino acid hybrid zinc finger could provide more sensitive/deep drug-induced protein degradation (noting that such longer hybrid degrons resulted in lower protein abundance).

Example 7: Additional Functional, Drug-Inducible ON-Switch and OFF-Switch Formats The IMiD-responsiveness of a split CAR ON-switch configuration was also further validated (including validating CAR-mediated signaling responsiveness to drug administration), as shown in FIGS. 21-27.

As shown in FIG. 28, a degron of the instant disclosure can be fused to an inhibitor of CAR, thereby producing a Chimeric Degradable Inhibitor (CDI), which functions as an ON-switch upon drug administration. The drug-responsiveness of such a CDI was validated, as shown in FIGS. 29-31.

Additional nucleic acid vectors/constructs used in the above experiments are also depicted schematically in FIGS. 32-35.

Further CAR degron constructs were made in the current study, including 1928z-dIKZF3 aka dCAR IKZF3 and 1928z-d913 aka dCAR 913 (FIG. 36).

As demonstrated above, a clinically applicable drug-inducible ON-switch peptide logic gate was generated by engineering heterodimerization domains that can regulate molecular assembly (i.e., split CAR design) to control the function of engineered proteins (see Examples 1-3 above).

In addition, a clinically applicable drug-inducible OFF-switch peptide tag that recruits the $CRL4^{CRBN}$ E3 ubiquitin ligase to degrade engineered proteins was also generated and employed, as specifically exemplified in the context of CAR-T cells (see Examples 1 and 4 above).

Additional formats of both drug-inducible ON-switches and OFF-switches were also described and validated (see Example 7 above).

Each of these synthetic biology tools possesses clinical applications for enhancing the safety of CAR T cell therapy, as well as other engineered cell therapies.

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein.

The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The present disclosure teaches one skilled in the art to test various combinations and/or substitutions of chemical modifications described herein toward generating conjugates possessing improved contrast, diagnostic and/or imaging activity. Therefore, the specific embodiments described herein are not limiting and one skilled in the art can readily appreciate that specific combinations of the modifications described herein can be tested without undue experimentation toward identifying conjugates possessing improved contrast, diagnostic and/or imaging activity.

The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A drug-responsive chimeric antigen receptor (CAR) comprising:
   - an extracellular antigen-binding domain,
   - a transmembrane domain (TMD),
   - a co-stimulatory domain,
   - a signaling domain and
   - a cereblon (CRBN) polypeptide substrate domain capable of binding CRBN in response to drug, thereby promoting ubiquitin pathway-mediated degradation of the drug-responsive CAR, wherein the CRBN polypeptide substrate domain comprises a hybrid fusion polypeptide comprised of ten or more residues of a non-IKZF3 C2H2 zinc finger degron sequence flanked by an N-terminal IKZF3 degron sequence and a C-terminal IKZF3 degron sequence.

2. The drug-responsive CAR of claim 1 further comprising the drug.

3. The drug-responsive CAR of claim 1, wherein the drug is a small molecule drug.

4. The drug-responsive CAR of claim 1, wherein the drug is an FDA-approved drug.

5. The drug-responsive CAR of claim 1, wherein the drug can be administered to a human subject in a clinical setting.

6. The drug-responsive CAR of claim 1, wherein the drug is an immunomodulatory drug (IMiD).

7. The drug-responsive CAR of claim 1, wherein the drug is selected from the group consisting of thalidomide, lenalidomide and pomalidomide.

8. The drug-responsive CAR of claim 1, wherein the N-terminal IKZF3 degron sequence comprises SEQ ID NO: 97 or SEQ ID NO: 100.

9. The drug-responsive CAR of claim 1, wherein the signaling domain is selected from the group consisting of a CD3ζ domain, a CD3 gamma domain, a CD3 delta domain, a CD3 epsilon domain, a FcR gamma domain, a FcR beta domain, a CD5 domain, a CD79a domain, a CD79b domain, a CD66d domain, a CD4 domain, a CD8 domain, a Dap10 domain and a Dap-12 domain.

10. The drug-responsive CAR of claim 1, wherein the co-stimulatory domain is selected from the group consisting of a CD28 co-stimulatory domain, a 4-1BB co-stimulatory domain, and an additional co-stimulatory domain selected from the group consisting of CD27, OX40, CD30, CD40, ICOS, LFA-1, CD2, CD7, NKG2C, and B7-H3.

11. The drug-responsive CAR of claim 1, wherein the extracellular antigen-binding domain comprises a scFv.

12. The drug-responsive CAR of claim 1, wherein the extracellular antigen-binding domain comprises a sequence selected from the group consisting of an anti-CD19/BCMA scFv; a scFv targeting a protein selected from the group consisting of CD19, CD20, CD22, BCMA, CD138, CD38, SLAMF7, kappa light chain, lambda light chain, CD123, CD33, CD45, CD30, CD40, CD70, ErbB2, EGFR, EpCAM, EGFRvIII, mesothelin, ROR1, LeY, PSMA, PSCA, CD34, CD90, TIM3, CD99, CD3, CD4, CD8, and CD52; and a TCR recognizing WT1.

13. The drug-responsive CAR of claim 1, wherein the C-terminal IKZF3 degron sequence comprises SEQ ID NO: 102 or SEQ ID NO: 103.

14. The drug-responsive CAR of claim 1, wherein the non-IKZF3 C2H2 zinc finger degron sequence is a E3 ubiquitin-protein ligase sequence.

15. The drug-responsive CAR of claim 1, wherein the CRBN polypeptide substrate domain comprises the IKZF3/ZFP91/IKZF3 polypeptide of SEQ ID NO: 95.

16. The drug-responsive CAR of claim 10, wherein the co-stimulatory domain comprises K→R residue substitutions selected from the group consisting of K→R residue substitutions at positions 182 and 204 of a CD28 co-stimulatory domain sequence, wherein amino acid positions 180-220 of the CD28 co-stimulatory domain sequence are N-RSKRSRLLHSDYMNMTPRRPGPTRKHYQPYAP-PRDFAAYRS-C(SEQ ID NO: 142); and K→R residue substitutions as shown in any of SEQ ID NOs: 46-69.

* * * * *

```
                         SEQUENCE LISTING


<160> NUMBER OF SEQ ID NOS: 141

<210> SEQ ID NO 1
<211> LENGTH: 104
<212> TYPE: PRT
<213> ORGANISM: Artificial
<220> FEATURE:
<223> OTHER INFORMATION: Synthetic

<400> SEQUENCE: 1

Ser Leu Ser Leu Cys Gly Pro Met Ala Ala Tyr Val Asn Pro His Gly
1               5                   10                  15

Tyr Val His Glu Thr Leu Thr Val Tyr Lys Ala Cys Asn Leu Asn Leu
            20                  25                  30

Ile Gly Arg Pro Ser Thr Glu His Ser Trp Phe Pro Gly Tyr Ala Trp
        35                  40                  45

Thr Val Ala Gln Cys Lys Ile Cys Ala Ser His Ile Gly Trp Lys Phe
    50                  55                  60

Thr Ala Thr Lys Lys Asp Met Ser Pro Gln Lys Phe Trp Gly Leu Thr
65                  70                  75                  80

Arg Ser Ala Leu Leu Pro Thr Ile Pro Asp Thr Glu Asp Glu Ile Ser
                85                  90                  95

Pro Asp Lys Val Ile Leu Cys Leu
            100


<210> SEQ ID NO 2
<211> LENGTH: 125
<212> TYPE: PRT
<213> ORGANISM: Artificial
<220> FEATURE:
<223> OTHER INFORMATION: Synthetic

<400> SEQUENCE: 2

Cys Thr Ser Leu Cys Cys Lys Gln Cys Gln Glu Thr Glu Ile Thr Thr
1               5                   10                  15

Lys Asn Glu Ile Phe Ser Leu Ser Leu Cys Gly Pro Met Ala Ala Tyr
            20                  25                  30

Val Asn Pro His Gly Tyr Val His Glu Thr Leu Thr Val Tyr Lys Ala
        35                  40                  45

Cys Asn Leu Asn Leu Ile Gly Arg Pro Ser Thr Glu His Ser Trp Phe
    50                  55                  60

Pro Gly Tyr Ala Trp Thr Val Ala Gln Cys Lys Ile Cys Ala Ser His
65                  70                  75                  80

Ile Gly Trp Lys Phe Thr Ala Thr Lys Lys Asp Met Ser Pro Gln Lys
                85                  90                  95

Phe Trp Gly Leu Thr Arg Ser Ala Leu Leu Pro Thr Ile Pro Asp Thr
            100                 105                 110

Glu Asp Glu Ile Ser Pro Asp Lys Val Ile Leu Cys Leu
        115                 120                 125
```

<210> SEQ ID NO 3
<211> LENGTH: 386
<212> TYPE: PRT
<213> ORGANISM: Artificial
<220> FEATURE:
<223> OTHER INFORMATION: Synthetic

<400> SEQUENCE: 3

```
Ala Gly Glu Gly Asp Gln Gln Asp Ala Ala His Asn Met Gly Asn His
1               5                   10                  15

Leu Pro Leu Leu Pro Glu Ser Glu Glu Glu Asp Glu Met Glu Val Glu
            20                  25                  30

Asp Gln Asp Ser Lys Glu Ala Lys Lys Pro Asn Ile Ile Asn Phe Asp
        35                  40                  45

Thr Ser Leu Pro Thr Ser His Thr Tyr Leu Gly Ala Asp Met Glu Glu
    50                  55                  60

Phe His Gly Arg Thr Leu His Asp Asp Asp Ser Cys Gln Val Ile Pro
65                  70                  75                  80

Val Leu Pro Gln Val Met Met Ile Leu Ile Pro Gly Gln Thr Leu Pro
                85                  90                  95

Leu Gln Leu Phe His Pro Gln Glu Val Ser Met Val Arg Asn Leu Ile
            100                 105                 110

Gln Lys Asp Arg Thr Phe Ala Val Leu Ala Tyr Ser Asn Val Gln Glu
        115                 120                 125

Arg Glu Ala Gln Phe Gly Thr Thr Ala Glu Ile Tyr Ala Tyr Arg Glu
    130                 135                 140

Glu Gln Asp Phe Gly Ile Glu Ile Val Lys Val Lys Ala Ile Gly Arg
145                 150                 155                 160

Gln Arg Phe Lys Val Leu Glu Leu Arg Thr Gln Ser Asp Gly Ile Gln
                165                 170                 175

Gln Ala Lys Val Gln Ile Leu Pro Glu Cys Val Leu Pro Ser Thr Tyr
            180                 185                 190

Asp Ala Glu Thr Leu Met Asp Arg Ile Lys Lys Gln Leu Arg Glu Trp
        195                 200                 205

Asp Glu Asn Leu Lys Asp Asp Ser Leu Pro Ser Asn Pro Ile Asp Phe
    210                 215                 220

Ser Tyr Arg Val Ala Ala Cys Leu Pro Ile Asp Asp Val Leu Arg Ile
225                 230                 235                 240

Gln Leu Leu Lys Ile Gly Ser Ala Ile Gln Arg Leu Arg Cys Glu Leu
                245                 250                 255

Asp Ile Met Asn Lys Cys Thr Ser Leu Cys Cys Lys Gln Cys Gln Glu
            260                 265                 270

Thr Glu Ile Thr Thr Lys Asn Glu Ile Phe Ser Leu Ser Leu Cys Gly
        275                 280                 285

Pro Met Ala Ala Tyr Val Asn Pro His Gly Tyr Val His Glu Thr Leu
    290                 295                 300

Thr Val Tyr Lys Ala Cys Asn Leu Asn Leu Ile Gly Arg Pro Ser Thr
305                 310                 315                 320

Glu His Ser Trp Phe Pro Gly Tyr Ala Trp Thr Val Ala Gln Cys Lys
                325                 330                 335

Ile Cys Ala Ser His Ile Gly Trp Lys Phe Thr Ala Thr Lys Lys Asp
            340                 345                 350

Met Ser Pro Gln Lys Phe Trp Gly Leu Thr Arg Ser Ala Leu Leu Pro
        355                 360                 365
```

-continued

```
Thr Ile Pro Asp Thr Glu Asp Glu Ile Ser Pro Asp Lys Val Ile Leu
    370                 375                 380

Cys Leu
385


<210> SEQ ID NO 4
<211> LENGTH: 367
<212> TYPE: PRT
<213> ORGANISM: Artificial
<220> FEATURE:
<223> OTHER INFORMATION: Synthetic

<400> SEQUENCE: 4

Met Ala Gly Glu Gly Asp Gln Gln Asp Ala Ala His Asn Met Gly Asn
1               5                   10                  15

His Leu Pro Leu Leu Pro Glu Ser Glu Glu Glu Asp Glu Met Glu Val
            20                  25                  30

Glu Asp Gln Asp Ser Lys Glu Ala Lys Lys Pro Asn Ile Ile Asn Phe
        35                  40                  45

Asp Thr Ser Leu Pro Thr Ser His Thr Tyr Leu Gly Ala Asp Met Glu
    50                  55                  60

Glu Phe His Gly Arg Thr Leu His Asp Asp Asp Ser Cys Gln Val Ile
65                  70                  75                  80

Pro Val Leu Pro Gln Val Met Met Ile Leu Ile Pro Gly Gln Thr Leu
                85                  90                  95

Pro Leu Gln Leu Phe His Pro Gln Glu Val Ser Met Val Arg Asn Leu
            100                 105                 110

Ile Gln Lys Asp Arg Thr Phe Ala Val Leu Ala Tyr Ser Asn Val Gln
        115                 120                 125

Glu Arg Glu Ala Gln Phe Gly Thr Thr Ala Glu Ile Tyr Ala Tyr Arg
    130                 135                 140

Glu Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
                165                 170                 175

Gln Gln Ala Lys Val Gln Ile Leu Pro Leu Arg Glu Trp Asp Glu Asn
            180                 185                 190

Leu Lys Asp Asp Ser Leu Pro Ser Asn Pro Ile Asp Phe Ser Tyr Arg
        195                 200                 205

Val Ala Ala Cys Leu Pro Ile Asp Asp Val Leu Arg Ile Gln Leu Leu
    210                 215                 220

Lys Ile Gly Ser Ala Ile Gln Arg Leu Arg Cys Glu Leu Asp Ile Met
225                 230                 235                 240

Asn Lys Cys Thr Ser Leu Cys Cys Lys Gln Cys Gln Glu Thr Glu Ile
                245                 250                 255

Thr Thr Lys Asn Glu Ile Phe Ser Leu Ser Leu Cys Gly Pro Met Ala
            260                 265                 270

Ala Tyr Val Asn Pro His Gly Tyr Val His Glu Thr Leu Thr Val Tyr
        275                 280                 285

Lys Ala Cys Asn Leu Asn Leu Ile Gly Arg Pro Ser Thr Glu His Ser
    290                 295                 300

Trp Phe Pro Gly Tyr Ala Trp Thr Val Ala Gln Cys Lys Ile Cys Ala
305                 310                 315                 320

Ser His Ile Gly Trp Lys Phe Thr Ala Thr Lys Lys Asp Met Ser Pro
                325                 330                 335
```

Gln Lys Phe Trp Gly Leu Thr Arg Ser Ala Leu Leu Pro Thr Ile Pro
340 345 350

Asp Thr Glu Asp Glu Ile Ser Pro Asp Lys Val Ile Leu Cys Leu
355 360 365

<210> SEQ ID NO 5
<211> LENGTH: 60
<212> TYPE: PRT
<213> ORGANISM: Artificial
<220> FEATURE:
<223> OTHER INFORMATION: Synthetic

<400> SEQUENCE: 5

Phe Asn Val Leu Met Val His Lys Arg Ser His Thr Gly Glu Arg Pro
1 5 10 15

Phe Gln Cys Asn Gln Cys Gly Ala Ser Phe Thr Gln Lys Gly Asn Leu
20 25 30

Leu Arg His Ile Lys Leu His Thr Gly Glu Lys Pro Phe Lys Cys His
35 40 45

Leu Cys Asn Tyr Ala Cys Gln Arg Arg Asp Ala Leu
50 55 60

<210> SEQ ID NO 6
<211> LENGTH: 442
<212> TYPE: PRT
<213> ORGANISM: Homo sapiens

<400> SEQUENCE: 6

Met Ala Gly Glu Gly Asp Gln Gln Asp Ala Ala His Asn Met Gly Asn
1 5 10 15

His Leu Pro Leu Leu Pro Ala Glu Ser Glu Glu Glu Asp Glu Met Glu
20 25 30

Val Glu Asp Gln Asp Ser Lys Glu Ala Lys Lys Pro Asn Ile Ile Asn
35 40 45

Phe Asp Thr Ser Leu Pro Thr Ser His Thr Tyr Leu Gly Ala Asp Met
50 55 60

Glu Glu Phe His Gly Arg Thr Leu His Asp Asp Asp Ser Cys Gln Val
65 70 75 80

Ile Pro Val Leu Pro Gln Val Met Met Ile Leu Ile Pro Gly Gln Thr
85 90 95

Leu Pro Leu Gln Leu Phe His Pro Gln Glu Val Ser Met Val Arg Asn
100 105 110

Leu Ile Gln Lys Asp Arg Thr Phe Ala Val Leu Ala Tyr Ser Asn Val
115 120 125

Gln Glu Arg Glu Ala Gln Phe Gly Thr Thr Ala Glu Ile Tyr Ala Tyr
130 135 140

Arg Glu Glu Gln Asp Phe Gly Ile Glu Ile Val Lys Val Lys Ala Ile
145 150 155 160

Gly Arg Gln Arg Phe Lys Val Leu Glu Leu Arg Thr Gln Ser Asp Gly
165 170 175

Ile Gln Gln Ala Lys Val Gln Ile Leu Pro Glu Cys Val Leu Pro Ser
180 185 190

Thr Met Ser Ala Val Gln Leu Glu Ser Leu Asn Lys Cys Gln Ile Phe
195 200 205

Pro Ser Lys Pro Val Ser Arg Glu Asp Gln Cys Ser Tyr Lys Trp Trp
210 215 220

```
Gln Lys Tyr Gln Lys Arg Lys Phe His Cys Ala Asn Leu Thr Ser Trp
225                 230                 235                 240

Pro Arg Trp Leu Tyr Ser Leu Tyr Asp Ala Glu Thr Leu Met Asp Arg
                245                 250                 255

Ile Lys Lys Gln Leu Arg Glu Trp Asp Glu Asn Leu Lys Asp Asp Ser
            260                 265                 270

Leu Pro Ser Asn Pro Ile Asp Phe Ser Tyr Arg Val Ala Ala Cys Leu
        275                 280                 285

Pro Ile Asp Asp Val Leu Arg Ile Gln Leu Leu Lys Ile Gly Ser Ala
    290                 295                 300

Ile Gln Arg Leu Arg Cys Glu Leu Asp Ile Met Asn Lys Cys Thr Ser
305                 310                 315                 320

Leu Cys Cys Lys Gln Cys Gln Glu Thr Glu Ile Thr Thr Lys Asn Glu
                325                 330                 335

Ile Phe Ser Leu Ser Leu Cys Gly Pro Met Ala Ala Tyr Val Asn Pro
            340                 345                 350

His Gly Tyr Val His Glu Thr Leu Thr Val Tyr Lys Ala Cys Asn Leu
        355                 360                 365

Asn Leu Ile Gly Arg Pro Ser Thr Glu His Ser Trp Phe Pro Gly Tyr
    370                 375                 380

Ala Trp Thr Val Ala Gln Cys Lys Ile Cys Ala Ser His Ile Gly Trp
385                 390                 395                 400

Lys Phe Thr Ala Thr Lys Lys Asp Met Ser Pro Gln Lys Phe Trp Gly
                405                 410                 415

Leu Thr Arg Ser Ala Leu Leu Pro Thr Ile Pro Asp Thr Glu Asp Glu
            420                 425                 430

Ile Ser Pro Asp Lys Val Ile Leu Cys Leu
        435                 440


<210> SEQ ID NO 7
<211> LENGTH: 386
<212> TYPE: PRT
<213> ORGANISM: Artificial
<220> FEATURE:
<223> OTHER INFORMATION: Synthetic

<400> SEQUENCE: 7

Ala Gly Glu Gly Asp Gln Gln Asp Ala Ala His Asn Met Gly Asn His
1               5                   10                  15

Leu Pro Leu Leu Pro Glu Ser Glu Glu Glu Asp Glu Met Glu Val Glu
            20                  25                  30

Asp Gln Asp Ser Lys Glu Ala Lys Lys Pro Asn Ile Ile Asn Phe Asp
        35                  40                  45

Thr Ser Leu Pro Thr Ser His Thr Tyr Leu Gly Ala Asp Met Glu Glu
    50                  55                  60

Phe His Gly Arg Thr Leu His Asp Asp Asp Ser Cys Gln Val Ile Pro
65                  70                  75                  80

Val Leu Pro Gln Val Met Met Ile Leu Ile Pro Gly Gln Thr Leu Pro
                85                  90                  95

Leu Gln Leu Phe His Pro Gln Glu Val Ser Met Val Arg Asn Leu Ile
            100                 105                 110

Gln Lys Asp Arg Thr Phe Ala Val Leu Ala Tyr Ser Asn Val Gln Glu
        115                 120                 125

Arg Glu Ala Gln Phe Gly Thr Thr Ala Glu Ile Tyr Ala Tyr Arg Glu
    130                 135                 140
```

```
Glu Gln Asp Phe Gly Ile Glu Ile Val Lys Val Lys Ala Ile Gly Arg
145                 150                 155                 160

Gln Arg Phe Lys Val Leu Glu Leu Arg Thr Gln Ser Asp Gly Ile Gln
                165                 170                 175

Gln Ala Lys Val Gln Ile Leu Pro Glu Cys Val Leu Pro Ser Thr Tyr
            180                 185                 190

Asp Ala Glu Thr Leu Met Asp Arg Ile Lys Lys Gln Leu Arg Glu Trp
        195                 200                 205

Asp Glu Asn Leu Lys Asp Asp Ser Leu Pro Ser Asn Pro Ile Asp Phe
    210                 215                 220

Ser Tyr Arg Val Ala Ala Cys Leu Pro Ile Asp Asp Val Leu Arg Ile
225                 230                 235                 240

Gln Leu Leu Lys Ile Gly Ser Ala Ile Gln Arg Leu Arg Cys Glu Leu
                245                 250                 255

Asp Ile Met Asn Lys Cys Thr Ser Leu Cys Cys Lys Gln Cys Gln Glu
            260                 265                 270

Thr Glu Ile Thr Thr Lys Asn Glu Ile Phe Ser Leu Ser Leu Cys Gly
        275                 280                 285

Pro Met Ala Ala Tyr Val Asn Pro His Gly Tyr Val His Glu Thr Leu
    290                 295                 300

Thr Val Tyr Lys Ala Cys Asn Leu Asn Leu Ala Gly Arg Pro Ser Thr
305                 310                 315                 320

Glu His Ser Trp Phe Pro Gly Tyr Ala Trp Thr Val Ala Gln Cys Lys
                325                 330                 335

Ile Cys Ala Ser His Ile Gly Trp Lys Phe Thr Ala Thr Lys Lys Asp
            340                 345                 350

Met Ser Pro Gln Lys Phe Trp Gly Leu Thr Arg Ser Ala Leu Leu Pro
        355                 360                 365

Thr Ile Pro Asp Thr Glu Asp Glu Ile Ser Pro Asp Lys Val Ile Leu
    370                 375                 380

Cys Leu
385
```

<210> SEQ ID NO 8
<211> LENGTH: 386
<212> TYPE: PRT
<213> ORGANISM: Artificial
<220> FEATURE:
<223> OTHER INFORMATION: Synthetic

<400> SEQUENCE: 8

```
Ala Gly Glu Gly Asp Gln Gln Asp Ala Ala His Asn Met Gly Asn His
1               5                   10                  15

Leu Pro Leu Leu Pro Glu Ser Glu Glu Glu Asp Glu Met Glu Val Glu
            20                  25                  30

Asp Gln Asp Ser Lys Glu Ala Lys Lys Pro Asn Ile Ile Asn Phe Asp
        35                  40                  45

Thr Ser Leu Pro Thr Ser His Thr Tyr Leu Gly Ala Asp Met Glu Glu
    50                  55                  60

Phe His Gly Arg Thr Leu His Asp Asp Asp Ser Cys Gln Val Ile Pro
65                  70                  75                  80

Val Leu Pro Gln Val Met Met Ile Leu Ile Pro Gly Gln Thr Leu Pro
                85                  90                  95

Leu Gln Leu Phe His Pro Gln Glu Val Ser Met Val Arg Asn Leu Ile
            100                 105                 110
```

-continued

```
Gln Lys Asp Arg Thr Phe Ala Val Leu Ala Tyr Ser Asn Val Gln Glu
        115                 120                 125

Arg Glu Ala Gln Phe Gly Thr Thr Ala Glu Ile Tyr Ala Tyr Arg Glu
    130                 135                 140

Glu Gln Asp Phe Gly Ile Glu Ile Val Lys Val Lys Ala Ile Gly Arg
145                 150                 155                 160

Gln Arg Phe Lys Val Leu Glu Leu Arg Thr Gln Ser Asp Gly Ile Gln
                165                 170                 175

Gln Ala Lys Val Gln Ile Leu Pro Glu Cys Val Leu Pro Ser Thr Tyr
            180                 185                 190

Asp Ala Glu Thr Leu Met Asp Arg Ile Lys Lys Gln Leu Arg Glu Trp
        195                 200                 205

Asp Glu Asn Leu Lys Asp Asp Ser Leu Pro Ser Asn Pro Ile Asp Phe
    210                 215                 220

Ser Tyr Arg Val Ala Ala Cys Leu Pro Ile Asp Asp Val Leu Arg Ile
225                 230                 235                 240

Gln Leu Leu Lys Ile Gly Ser Ala Ile Gln Arg Leu Arg Cys Glu Leu
                245                 250                 255

Asp Ile Met Asn Lys Cys Thr Ser Leu Cys Cys Lys Gln Cys Gln Glu
            260                 265                 270

Thr Glu Ile Thr Thr Lys Asn Glu Ile Phe Ser Leu Ser Leu Cys Gly
        275                 280                 285

Pro Met Ala Ala Tyr Val Asn Pro His Gly Tyr Val His Glu Thr Leu
    290                 295                 300

Thr Val Tyr Lys Ala Cys Asn Leu Asn Leu Gly Gly Arg Pro Ser Thr
305                 310                 315                 320

Glu His Ser Trp Phe Pro Gly Tyr Ala Trp Thr Val Ala Gln Cys Lys
                325                 330                 335

Ile Cys Ala Ser His Ile Gly Trp Lys Phe Thr Ala Thr Lys Lys Asp
            340                 345                 350

Met Ser Pro Gln Lys Phe Trp Gly Leu Thr Arg Ser Ala Leu Leu Pro
        355                 360                 365

Thr Ile Pro Asp Thr Glu Asp Glu Ile Ser Pro Asp Lys Val Ile Leu
    370                 375                 380

Cys Leu
385


<210> SEQ ID NO 9
<211> LENGTH: 386
<212> TYPE: PRT
<213> ORGANISM: Artificial
<220> FEATURE:
<223> OTHER INFORMATION: Synthetic

<400> SEQUENCE: 9

Ala Gly Glu Gly Asp Gln Gln Asp Ala Ala His Asn Met Gly Asn His
1               5                   10                  15

Leu Pro Leu Leu Pro Glu Ser Glu Glu Glu Asp Glu Met Glu Val Glu
            20                  25                  30

Asp Gln Asp Ser Lys Glu Ala Lys Lys Pro Asn Ile Ile Asn Phe Asp
        35                  40                  45

Thr Ser Leu Pro Thr Ser His Thr Tyr Leu Gly Ala Asp Met Glu Glu
    50                  55                  60

Phe His Gly Arg Thr Leu His Asp Asp Asp Ser Cys Gln Val Ile Pro
65                  70                  75                  80
```

-continued

```
Val Leu Pro Gln Val Met Met Ile Leu Ile Pro Gly Gln Thr Leu Pro
                85                  90                  95

Leu Gln Leu Phe His Pro Gln Glu Val Ser Met Val Arg Asn Leu Ile
            100                 105                 110

Gln Lys Asp Arg Thr Phe Ala Val Leu Ala Tyr Ser Asn Val Gln Glu
        115                 120                 125

Arg Glu Ala Gln Phe Gly Thr Thr Ala Glu Ile Tyr Ala Tyr Arg Glu
    130                 135                 140

Glu Gln Asp Phe Gly Ile Glu Ile Val Lys Val Lys Ala Ile Gly Arg
145                 150                 155                 160

Gln Arg Phe Lys Val Leu Glu Leu Arg Thr Gln Ser Asp Gly Ile Gln
                165                 170                 175

Gln Ala Lys Val Gln Ile Leu Pro Glu Cys Val Leu Pro Ser Thr Tyr
            180                 185                 190

Asp Ala Glu Thr Leu Met Asp Arg Ile Lys Lys Gln Leu Arg Glu Trp
        195                 200                 205

Asp Glu Asn Leu Lys Asp Asp Ser Leu Pro Ser Asn Pro Ile Asp Phe
    210                 215                 220

Ser Tyr Arg Val Ala Ala Cys Leu Pro Ile Asp Asp Val Leu Arg Ile
225                 230                 235                 240

Gln Leu Leu Lys Ile Gly Ser Ala Ile Gln Arg Leu Arg Cys Glu Leu
                245                 250                 255

Asp Ile Met Asn Lys Cys Thr Ser Leu Cys Cys Lys Gln Cys Gln Glu
            260                 265                 270

Thr Glu Ile Thr Thr Lys Asn Glu Ile Phe Ser Leu Ser Leu Cys Gly
        275                 280                 285

Pro Met Ala Ala Tyr Val Asn Pro His Gly Tyr Val His Glu Thr Leu
    290                 295                 300

Thr Val Tyr Lys Ala Cys Asn Leu Asn Leu Ile Gly Arg Pro Ser Thr
305                 310                 315                 320

Glu His Ser Trp Phe Pro Gly Tyr Ala Trp Thr Ala Ala Gln Cys Lys
                325                 330                 335

Ile Cys Ala Ser His Ile Gly Trp Lys Phe Thr Ala Thr Lys Lys Asp
            340                 345                 350

Met Ser Pro Gln Lys Phe Trp Gly Leu Thr Arg Ser Ala Leu Leu Pro
        355                 360                 365

Thr Ile Pro Asp Thr Glu Asp Glu Ile Ser Pro Asp Lys Val Ile Leu
    370                 375                 380

Cys Leu
385


<210> SEQ ID NO 10
<211> LENGTH: 386
<212> TYPE: PRT
<213> ORGANISM: Artificial
<220> FEATURE:
<223> OTHER INFORMATION: Synthetic

<400> SEQUENCE: 10

Ala Gly Glu Gly Asp Gln Gln Asp Ala Ala His Asn Met Gly Asn His
1               5                   10                  15

Leu Pro Leu Leu Pro Glu Ser Glu Glu Glu Asp Glu Met Glu Val Glu
            20                  25                  30

Asp Gln Asp Ser Lys Glu Ala Lys Lys Pro Asn Ile Ile Asn Phe Asp
        35                  40                  45
```

-continued

```
Thr Ser Leu Pro Thr Ser His Thr Tyr Leu Gly Ala Asp Met Glu Glu
    50                  55                  60

Phe His Gly Arg Thr Leu His Asp Asp Asp Ser Cys Gln Val Ile Pro
65                  70                  75                  80

Val Leu Pro Gln Val Met Met Ile Leu Ile Pro Gly Gln Thr Leu Pro
                85                  90                  95

Leu Gln Leu Phe His Pro Gln Glu Val Ser Met Val Arg Asn Leu Ile
            100                 105                 110

Gln Lys Asp Arg Thr Phe Ala Val Leu Ala Tyr Ser Asn Val Gln Glu
        115                 120                 125

Arg Glu Ala Gln Phe Gly Thr Thr Ala Glu Ile Tyr Ala Tyr Arg Glu
    130                 135                 140

Glu Gln Asp Phe Gly Ile Glu Ile Val Lys Val Lys Ala Ile Gly Arg
145                 150                 155                 160

Gln Arg Phe Lys Val Leu Glu Leu Arg Thr Gln Ser Asp Gly Ile Gln
                165                 170                 175

Gln Ala Lys Val Gln Ile Leu Pro Glu Cys Val Leu Pro Ser Thr Tyr
            180                 185                 190

Asp Ala Glu Thr Leu Met Asp Arg Ile Lys Lys Gln Leu Arg Glu Trp
        195                 200                 205

Asp Glu Asn Leu Lys Asp Asp Ser Leu Pro Ser Asn Pro Ile Asp Phe
    210                 215                 220

Ser Tyr Arg Val Ala Ala Cys Leu Pro Ile Asp Asp Val Leu Arg Ile
225                 230                 235                 240

Gln Leu Leu Lys Ile Gly Ser Ala Ile Gln Arg Leu Arg Cys Glu Leu
                245                 250                 255

Asp Ile Met Asn Lys Cys Thr Ser Leu Cys Cys Lys Gln Cys Gln Glu
            260                 265                 270

Thr Glu Ile Thr Thr Lys Asn Glu Ile Phe Ser Leu Ser Leu Cys Gly
        275                 280                 285

Pro Met Ala Ala Tyr Val Asn Pro His Gly Tyr Val His Glu Thr Leu
    290                 295                 300

Thr Val Tyr Lys Ala Cys Asn Leu Asn Leu Ile Gly Arg Pro Ser Thr
305                 310                 315                 320

Glu His Ser Trp Phe Pro Gly Tyr Ala Trp Thr Gly Ala Gln Cys Lys
                325                 330                 335

Ile Cys Ala Ser His Ile Gly Trp Lys Phe Thr Ala Thr Lys Lys Asp
            340                 345                 350

Met Ser Pro Gln Lys Phe Trp Gly Leu Thr Arg Ser Ala Leu Leu Pro
        355                 360                 365

Thr Ile Pro Asp Thr Glu Asp Glu Ile Ser Pro Asp Lys Val Ile Leu
    370                 375                 380

Cys Leu
385


<210> SEQ ID NO 11
<211> LENGTH: 477
<212> TYPE: PRT
<213> ORGANISM: Homo sapiens

<400> SEQUENCE: 11

Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30
```

```
Ile Pro Glu Asp Leu Ser Thr Thr Ser Gly Gly Gln Gln Ser Ser Lys
        35                  40                  45

Ser Asp Arg Val Val Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Ile Cys Ile Gly
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Ile Lys Glu Glu Thr Asn His Ser Glu Met Ala
        195                 200                 205

Glu Asp Leu Cys Lys Ile Gly Ser Glu Arg Ser Leu Val Leu Asp Arg
    210                 215                 220

Leu Ala Ser Asn Val Ala Lys Arg Lys Ser Ser Met Pro Gln Lys Phe
225                 230                 235                 240

Leu Gly Asp Lys Gly Leu Ser Asp Thr Pro Tyr Asp Ser Ser Ala Ser
                245                 250                 255

Tyr Glu Lys Glu Asn Glu Met Met Lys Ser His Val Met Asp Gln Ala
            260                 265                 270

Ile Asn Asn Ala Ile Asn Tyr Leu Gly Ala Glu Ser Leu Arg Pro Leu
        275                 280                 285

Val Gln Thr Pro Pro Gly Gly Ser Glu Val Val Pro Val Ile Ser Pro
    290                 295                 300

Met Tyr Gln Leu His Lys Pro Leu Ala Glu Gly Thr Pro Arg Ser Asn
305                 310                 315                 320

His Ser Ala Gln Asp Ser Ala Val Glu Asn Leu Leu Leu Leu Ser Lys
                325                 330                 335

Ala Lys Leu Val Pro Ser Glu Arg Glu Ala Ser Pro Ser Asn Ser Cys
            340                 345                 350

Gln Asp Ser Thr Asp Thr Glu Ser Asn Asn Glu Glu Gln Arg Ser Gly
        355                 360                 365

Leu Ile Tyr Leu Thr Asn His Ile Ala Pro His Ala Arg Asn Gly Leu
    370                 375                 380

Ser Leu Lys Glu Glu His Arg Ala Tyr Asp Leu Leu Arg Ala Ala Ser
385                 390                 395                 400

Glu Asn Ser Gln Asp Ala Leu Arg Val Val Ser Thr Ser Gly Glu Gln
                405                 410                 415

Met Lys Val Tyr Lys Cys Glu His Cys Arg Val Leu Phe Leu Asp His
            420                 425                 430

Val Met Tyr Thr Ile His Met Gly Cys His Gly Phe Arg Asp Pro Phe
        435                 440                 445
```

Glu Cys Asn Met Cys Gly Tyr His Ser Gln Asp Arg Tyr Glu Phe Ser
    450                 455                 460

Ser His Ile Thr Arg Gly Glu His Arg Phe His Met Ser
465                 470                 475

<210> SEQ ID NO 12
<211> LENGTH: 262
<212> TYPE: PRT
<213> ORGANISM: Homo sapiens

<400> SEQUENCE: 12

Met Gly Ser Glu Arg Ala Leu Val Leu Asp Arg Leu Ala Ser Asn Val
1               5                   10                  15

Ala Lys Arg Lys Ser Ser Met Pro Gln Lys Phe Ile Gly Glu Lys Arg
            20                  25                  30

His Cys Phe Asp Val Asn Tyr Asn Ser Ser Tyr Met Tyr Glu Lys Glu
        35                  40                  45

Ser Glu Leu Ile Gln Thr Arg Met Met Asp Gln Ala Ile Asn Asn Ala
    50                  55                  60

Ile Ser Tyr Leu Gly Ala Glu Ala Leu Arg Pro Leu Val Gln Thr Pro
65                  70                  75                  80

Pro Ala Pro Thr Ser Glu Met Val Pro Val Ile Ser Ser Met Tyr Pro
                85                  90                  95

Ile Ala Leu Thr Arg Ala Glu Met Ser Asn Gly Ala Pro Gln Glu Leu
            100                 105                 110

Glu Lys Lys Ser Ile His Leu Pro Glu Lys Ser Val Pro Ser Glu Arg
        115                 120                 125

Gly Leu Ser Pro Asn Asn Ser Gly His Asp Ser Thr Asp Thr Asp Ser
    130                 135                 140

Asn His Glu Glu Arg Gln Asn His Ile Tyr Gln Gln Asn His Met Val
145                 150                 155                 160

Leu Ser Arg Ala Arg Asn Gly Met Pro Leu Leu Lys Glu Val Pro Arg
                165                 170                 175

Ser Tyr Glu Leu Leu Lys Pro Pro Pro Ile Cys Pro Arg Asp Ser Val
            180                 185                 190

Lys Val Ile Asn Lys Glu Gly Glu Val Met Asp Val Tyr Arg Cys Asp
        195                 200                 205

His Cys Arg Val Leu Phe Leu Asp Tyr Val Met Phe Thr Ile His Met
    210                 215                 220

Gly Cys His Gly Phe Arg Asp Pro Phe Glu Cys Asn Met Cys Gly Tyr
225                 230                 235                 240

Arg Ser His Asp Arg Tyr Glu Phe Ser Ser His Ile Ala Arg Gly Glu
                245                 250                 255

His Arg Ala Leu Leu Lys
            260

<210> SEQ ID NO 13
<211> LENGTH: 337
<212> TYPE: PRT
<213> ORGANISM: Homo sapiens

<400> SEQUENCE: 13

Met Ala Ser Ser Ser Gly Ser Lys Ala Glu Phe Ile Val Gly Gly Lys
1               5                   10                  15

Tyr Lys Leu Val Arg Lys Ile Gly Ser Gly Ser Phe Gly Asp Ile Tyr
            20                  25                  30

```
Leu Ala Ile Asn Ile Thr Asn Gly Glu Glu Val Ala Val Lys Leu Glu
        35                  40                  45

Ser Gln Lys Ala Arg His Pro Gln Leu Leu Tyr Glu Ser Lys Leu Tyr
    50                  55                  60

Lys Ile Leu Gln Gly Gly Val Gly Ile Pro His Ile Arg Trp Tyr Gly
65                  70                  75                  80

Gln Glu Lys Asp Tyr Asn Val Leu Val Met Asp Leu Leu Gly Pro Ser
                85                  90                  95

Leu Glu Asp Leu Phe Asn Phe Cys Ser Arg Arg Phe Thr Met Lys Thr
            100                 105                 110

Val Leu Met Leu Ala Asp Gln Met Ile Ser Arg Ile Glu Tyr Val His
        115                 120                 125

Thr Lys Asn Phe Ile His Arg Asp Ile Lys Pro Asp Asn Phe Leu Met
    130                 135                 140

Gly Ile Gly Arg His Cys Asn Lys Leu Phe Leu Ile Asp Phe Gly Leu
145                 150                 155                 160

Ala Lys Lys Tyr Arg Asp Asn Arg Thr Arg Gln His Ile Pro Tyr Arg
                165                 170                 175

Glu Asp Lys Asn Leu Thr Gly Thr Ala Arg Tyr Ala Ser Ile Asn Ala
            180                 185                 190

His Leu Gly Ile Glu Gln Ser Arg Arg Asp Asp Met Glu Ser Leu Gly
        195                 200                 205

Tyr Val Leu Met Tyr Phe Asn Arg Thr Ser Leu Pro Trp Gln Gly Leu
    210                 215                 220

Lys Ala Ala Thr Lys Lys Gln Lys Tyr Glu Lys Ile Ser Glu Lys Lys
225                 230                 235                 240

Met Ser Thr Pro Val Glu Val Leu Cys Lys Gly Phe Pro Ala Glu Phe
                245                 250                 255

Ala Met Tyr Leu Asn Tyr Cys Arg Gly Leu Arg Phe Glu Glu Ala Pro
            260                 265                 270

Asp Tyr Met Tyr Leu Arg Gln Leu Phe Arg Ile Leu Phe Arg Thr Leu
        275                 280                 285

Asn His Gln Tyr Asp Tyr Thr Phe Asp Trp Thr Met Leu Lys Gln Lys
    290                 295                 300

Ala Ala Gln Gln Ala Ala Ser Ser Ser Gly Gln Gly Gln Gln Ala Gln
305                 310                 315                 320

Thr Pro Thr Gly Lys Gln Thr Asp Lys Thr Lys Ser Asn Met Lys Gly
                325                 330                 335

Phe


<210> SEQ ID NO 14
<211> LENGTH: 570
<212> TYPE: PRT
<213> ORGANISM: Homo sapiens

<400> SEQUENCE: 14

Met Pro Gly Glu Thr Glu Glu Pro Arg Pro Pro Glu Gln Gln Asp Gln
1               5                   10                  15

Glu Gly Gly Glu Ala Ala Lys Ala Ala Pro Glu Glu Pro Gln Gln Arg
            20                  25                  30

Pro Pro Glu Ala Val Ala Ala Ala Pro Ala Gly Thr Thr Ser Ser Arg
        35                  40                  45

Val Leu Arg Gly Gly Arg Asp Arg Gly Arg Ala Ala Ala Ala Ala Ala
    50                  55                  60
```

```
Ala Ala Ala Val Ser Arg Arg Arg Lys Ala Glu Tyr Pro Arg Arg Arg
65                  70                  75                  80

Arg Ser Ser Pro Ser Ala Arg Pro Pro Asp Val Pro Gly Gln Gln Pro
                85                  90                  95

Gln Ala Ala Lys Ser Pro Ser Pro Val Gln Gly Lys Lys Ser Pro Arg
            100                 105                 110

Leu Leu Cys Ile Glu Lys Val Thr Thr Asp Lys Asp Pro Lys Glu Glu
        115                 120                 125

Lys Glu Glu Glu Asp Asp Ser Ala Leu Pro Gln Glu Val Ser Ile Ala
    130                 135                 140

Ala Ser Arg Pro Ser Arg Gly Trp Arg Ser Ser Arg Thr Ser Val Ser
145                 150                 155                 160

Arg His Arg Asp Thr Glu Asn Thr Arg Ser Ser Arg Ser Lys Thr Gly
                165                 170                 175

Ser Leu Gln Leu Ile Cys Lys Ser Glu Pro Asn Thr Asp Gln Leu Asp
            180                 185                 190

Tyr Asp Val Gly Glu Glu His Gln Ser Pro Gly Gly Ile Ser Ser Glu
        195                 200                 205

Glu Glu Glu Glu Glu Glu Glu Glu Met Leu Ile Ser Glu Glu Glu Ile
    210                 215                 220

Pro Phe Lys Asp Asp Pro Arg Asp Glu Thr Tyr Lys Pro His Leu Glu
225                 230                 235                 240

Arg Glu Thr Pro Lys Pro Arg Arg Lys Ser Gly Lys Val Lys Glu Glu
                245                 250                 255

Lys Glu Lys Lys Glu Ile Lys Val Glu Val Glu Val Glu Val Lys Glu
            260                 265                 270

Glu Glu Asn Glu Ile Arg Glu Asp Glu Glu Pro Pro Arg Lys Arg Gly
        275                 280                 285

Arg Arg Arg Lys Asp Asp Lys Ser Pro Arg Leu Pro Lys Arg Arg Lys
    290                 295                 300

Lys Pro Pro Ile Gln Tyr Val Arg Cys Glu Met Glu Gly Cys Gly Thr
305                 310                 315                 320

Val Leu Ala His Pro Arg Tyr Leu Gln His His Ile Lys Tyr Gln His
                325                 330                 335

Leu Leu Lys Lys Lys Tyr Val Cys Pro His Pro Ser Cys Gly Arg Leu
            340                 345                 350

Phe Arg Leu Gln Lys Gln Leu Leu Arg His Ala Lys His His Thr Asp
        355                 360                 365

Gln Arg Asp Tyr Ile Cys Glu Tyr Cys Ala Arg Ala Phe Lys Ser Ser
    370                 375                 380

His Asn Leu Ala Val His Arg Met Ile His Thr Gly Glu Lys Pro Leu
385                 390                 395                 400

Gln Cys Glu Ile Cys Gly Phe Thr Cys Arg Gln Lys Ala Ser Leu Asn
                405                 410                 415

Trp His Met Lys Lys His Asp Ala Asp Ser Phe Tyr Gln Phe Ser Cys
            420                 425                 430

Asn Ile Cys Gly Lys Lys Phe Glu Lys Lys Asp Ser Val Val Ala His
        435                 440                 445

Lys Ala Lys Ser His Pro Glu Val Leu Ile Ala Glu Ala Leu Ala Ala
    450                 455                 460

Asn Ala Gly Ala Leu Ile Thr Ser Thr Asp Ile Leu Gly Thr Asn Pro
465                 470                 475                 480

Glu Ser Leu Thr Gln Pro Ser Asp Gly Gln Gly Leu Pro Leu Leu Pro
```

```
                485                 490                 495

Glu Pro Leu Gly Asn Ser Thr Ser Gly Glu Cys Leu Leu Leu Glu Ala
            500                 505                 510

Glu Gly Met Ser Lys Ser Tyr Cys Ser Gly Thr Glu Arg Val Ser Leu
        515                 520                 525

Met Ala Asp Gly Lys Ile Phe Val Gly Ser Gly Ser Ser Gly Gly Thr
    530                 535                 540

Glu Gly Leu Val Met Asn Ser Asp Ile Leu Gly Ala Thr Thr Glu Val
545                 550                 555                 560

Leu Ile Glu Asp Ser Asp Ser Ala Gly Pro
                565                 570


<210> SEQ ID NO 15
<211> LENGTH: 633
<212> TYPE: PRT
<213> ORGANISM: Homo sapiens

<400> SEQUENCE: 15

Met Asp Pro Gly Ser Gly Gly Gly Gly Gly Gly Gly Gly Ser Ser Ser
1               5                   10                  15

Gly Ser Ser Ser Ser Asp Ser Ala Pro Asp Cys Trp Asp Gln Ala Asp
            20                  25                  30

Met Glu Ala Pro Gly Pro Gly Pro Cys Gly Gly Gly Gly Ser Leu Ala
        35                  40                  45

Ala Ala Ala Glu Ala Gln Arg Glu Asn Leu Ser Ala Ala Phe Ser Arg
    50                  55                  60

Gln Leu Asn Val Asn Ala Lys Pro Phe Val Pro Asn Val His Ala Ala
65                  70                  75                  80

Glu Phe Val Pro Ser Phe Leu Arg Cys Pro Ala Ala Pro Pro Pro Pro
                85                  90                  95

Ala Gly Gly Ala Ala Asn Asn His Gly Ala Gly Ser Gly Ala Gly Gly
            100                 105                 110

Arg Ala Ala Pro Val Glu Ser Ser Gln Glu Glu Gln Ser Leu Cys Glu
        115                 120                 125

Gly Ser Asn Ser Ala Val Ser Met Glu Leu Ser Glu Pro Ile Glu Asn
    130                 135                 140

Gly Glu Thr Glu Met Ser Pro Glu Glu Ser Trp Glu His Lys Glu Glu
145                 150                 155                 160

Ile Ser Glu Ala Glu Pro Gly Gly Gly Ser Leu Gly Asp Gly Arg Pro
                165                 170                 175

Pro Glu Glu Ser Ala His Glu Met Met Glu Glu Glu Glu Glu Ile Pro
            180                 185                 190

Lys Pro Lys Ser Val Val Ala Pro Pro Gly Ala Pro Lys Lys Glu His
        195                 200                 205

Val Asn Val Val Phe Ile Gly His Val Asp Ala Gly Lys Ser Thr Ile
    210                 215                 220

Gly Gly Gln Ile Met Tyr Leu Thr Gly Met Val Asp Lys Arg Thr Leu
225                 230                 235                 240

Glu Lys Tyr Glu Arg Glu Ala Lys Glu Lys Asn Arg Glu Thr Trp Tyr
                245                 250                 255

Leu Ser Trp Ala Leu Asp Thr Asn Gln Glu Glu Arg Asp Lys Gly Lys
            260                 265                 270

Thr Val Glu Val Gly Arg Ala Tyr Phe Glu Thr Glu Lys Lys His Phe
        275                 280                 285
```

Thr Ile Leu Asp Ala Pro Gly His Lys Ser Phe Val Pro Asn Met Ile
    290                 295                 300

Gly Gly Ala Ser Gln Ala Asp Leu Ala Val Leu Val Ile Ser Ala Arg
305                 310                 315                 320

Lys Gly Glu Phe Glu Thr Gly Phe Glu Lys Gly Gly Gln Thr Arg Glu
                325                 330                 335

His Ala Met Leu Ala Lys Thr Ala Gly Val Lys His Leu Ile Val Leu
            340                 345                 350

Ile Asn Lys Met Asp Asp Pro Thr Val Asn Trp Ser Asn Glu Arg Tyr
        355                 360                 365

Glu Glu Cys Lys Glu Lys Leu Val Pro Phe Leu Lys Lys Val Gly Phe
    370                 375                 380

Asn Pro Lys Lys Asp Ile His Phe Met Pro Cys Ser Gly Leu Thr Gly
385                 390                 395                 400

Ala Asn Leu Lys Glu Gln Ser Asp Phe Cys Pro Trp Tyr Ile Gly Leu
                405                 410                 415

Pro Phe Ile Pro Tyr Leu Asp Asn Leu Pro Asn Phe Asn Arg Ser Val
            420                 425                 430

Asp Gly Pro Ile Arg Leu Pro Ile Val Asp Lys Tyr Lys Asp Met Gly
        435                 440                 445

Thr Val Val Leu Gly Lys Leu Glu Ser Gly Ser Ile Cys Lys Gly Gln
    450                 455                 460

Gln Leu Val Met Met Pro Asn Lys His Asn Val Glu Val Leu Gly Ile
465                 470                 475                 480

Leu Ser Asp Asp Val Glu Thr Asp Thr Val Ala Pro Gly Glu Asn Leu
                485                 490                 495

Lys Ile Arg Leu Lys Gly Ile Glu Glu Glu Glu Ile Leu Pro Gly Phe
            500                 505                 510

Ile Leu Cys Asp Pro Asn Asn Leu Cys His Ser Gly Arg Thr Phe Asp
        515                 520                 525

Ala Gln Ile Val Ile Ile Glu His Lys Ser Ile Ile Cys Pro Gly Tyr
    530                 535                 540

Asn Ala Val Leu His Ile His Thr Cys Ile Glu Glu Val Glu Ile Thr
545                 550                 555                 560

Ala Leu Ile Cys Leu Val Asp Lys Lys Ser Gly Glu Lys Ser Lys Thr
                565                 570                 575

Arg Pro Arg Phe Val Lys Gln Asp Gln Val Cys Ile Ala Arg Leu Arg
            580                 585                 590

Thr Ala Gly Thr Ile Cys Leu Glu Thr Phe Lys Asp Phe Pro Gln Met
        595                 600                 605

Gly Arg Phe Thr Leu Arg Asp Glu Gly Lys Thr Ile Ala Ile Gly Lys
    610                 615                 620

Val Leu Lys Leu Val Pro Glu Lys Asp
625                 630

<210> SEQ ID NO 16
<211> LENGTH: 474
<212> TYPE: PRT
<213> ORGANISM: Homo sapiens

<400> SEQUENCE: 16

Met Ala Thr Asn Trp Gly Ser Leu Leu Gln Asp Lys Gln Gln Leu Glu
1               5                   10                  15

Glu Leu Ala Arg Gln Ala Val Asp Arg Ala Leu Ala Glu Gly Val Leu
            20                  25                  30

```
Leu Arg Thr Ser Gln Glu Pro Thr Ser Ser Glu Val Val Ser Tyr Ala
        35                  40                  45

Pro Phe Thr Leu Phe Pro Ser Leu Val Pro Ser Ala Leu Leu Glu Gln
    50                  55                  60

Ala Tyr Ala Val Gln Met Asp Phe Asn Leu Leu Val Asp Ala Val Ser
65                  70                  75                  80

Gln Asn Ala Ala Phe Leu Glu Gln Thr Leu Ser Ser Thr Ile Lys Gln
                85                  90                  95

Asp Asp Phe Thr Ala Arg Leu Phe Asp Ile His Lys Gln Val Leu Lys
            100                 105                 110

Glu Gly Ile Ala Gln Thr Val Phe Leu Gly Leu Asn Arg Ser Asp Tyr
        115                 120                 125

Met Phe Gln Arg Ser Ala Asp Gly Ser Pro Ala Leu Lys Gln Ile Glu
    130                 135                 140

Ile Asn Thr Ile Ser Ala Ser Phe Gly Gly Leu Ala Ser Arg Thr Pro
145                 150                 155                 160

Ala Val His Arg His Val Leu Ser Val Leu Ser Lys Thr Lys Glu Ala
                165                 170                 175

Gly Lys Ile Leu Ser Asn Asn Pro Ser Lys Gly Leu Ala Leu Gly Ile
            180                 185                 190

Ala Lys Ala Trp Glu Leu Tyr Gly Ser Pro Asn Ala Leu Val Leu Leu
        195                 200                 205

Ile Ala Gln Glu Lys Glu Arg Asn Ile Phe Asp Gln Arg Ala Ile Glu
    210                 215                 220

Asn Glu Leu Leu Ala Arg Asn Ile His Val Ile Arg Arg Thr Phe Glu
225                 230                 235                 240

Asp Ile Ser Glu Lys Gly Ser Leu Asp Gln Asp Arg Arg Leu Phe Val
                245                 250                 255

Asp Gly Gln Glu Ile Ala Val Val Tyr Phe Arg Asp Gly Tyr Met Pro
            260                 265                 270

Arg Gln Tyr Ser Leu Gln Asn Trp Glu Ala Arg Leu Leu Leu Glu Arg
        275                 280                 285

Ser His Ala Ala Lys Cys Pro Asp Ile Ala Thr Gln Leu Ala Gly Thr
    290                 295                 300

Lys Lys Val Gln Gln Glu Leu Ser Arg Pro Gly Met Leu Glu Met Leu
305                 310                 315                 320

Leu Pro Gly Gln Pro Glu Ala Val Ala Arg Leu Arg Ala Thr Phe Ala
                325                 330                 335

Gly Leu Tyr Ser Leu Asp Val Gly Glu Glu Gly Asp Gln Ala Ile Ala
            340                 345                 350

Glu Ala Leu Ala Ala Pro Ser Arg Phe Val Leu Lys Pro Gln Arg Glu
        355                 360                 365

Gly Gly Gly Asn Asn Leu Tyr Gly Glu Glu Met Val Gln Ala Leu Lys
    370                 375                 380

Gln Leu Lys Asp Ser Glu Glu Arg Ala Ser Tyr Ile Leu Met Glu Lys
385                 390                 395                 400

Ile Glu Pro Glu Pro Phe Glu Asn Cys Leu Leu Arg Pro Gly Ser Pro
                405                 410                 415

Ala Arg Val Val Gln Cys Ile Ser Glu Leu Gly Ile Phe Gly Val Tyr
            420                 425                 430

Val Arg Gln Glu Lys Thr Leu Val Met Asn Lys His Val Gly His Leu
        435                 440                 445
```

```
Leu Arg Thr Lys Ala Ile Glu His Ala Asp Gly Gly Val Ala Ala Gly
    450                 455                 460

Val Ala Val Leu Asp Asn Pro Tyr Pro Val
465                 470


<210> SEQ ID NO 17
<211> LENGTH: 401
<212> TYPE: PRT
<213> ORGANISM: Homo sapiens

<400> SEQUENCE: 17

Met Ala Gln Arg Tyr Asp Glu Leu Pro His Tyr Gly Gly Met Asp Gly
1               5                   10                  15

Val Gly Val Pro Ala Ser Met Tyr Gly Asp Pro His Ala Pro Arg Pro
            20                  25                  30

Ile Pro Pro Val His His Leu Asn His Gly Pro Pro Leu His Ala Thr
        35                  40                  45

Gln His Tyr Gly Ala His Ala Pro His Pro Asn Val Met Pro Ala Ser
    50                  55                  60

Met Gly Ser Ala Val Asn Asp Ala Leu Lys Arg Asp Lys Asp Ala Ile
65                  70                  75                  80

Tyr Gly His Pro Leu Phe Pro Leu Leu Ala Leu Val Phe Glu Lys Cys
                85                  90                  95

Glu Leu Ala Thr Cys Thr Pro Arg Glu Pro Gly Val Ala Gly Gly Asp
            100                 105                 110

Val Cys Ser Ser Asp Ser Phe Asn Glu Asp Ile Ala Val Phe Ala Lys
        115                 120                 125

Gln Val Arg Ala Glu Lys Pro Leu Phe Ser Ser Asn Pro Glu Leu Asp
    130                 135                 140

Asn Leu Met Ile Gln Ala Ile Gln Val Leu Arg Phe His Leu Leu Glu
145                 150                 155                 160

Leu Glu Lys Val His Glu Leu Cys Asp Asn Phe Cys His Arg Tyr Ile
                165                 170                 175

Ser Cys Leu Lys Gly Lys Met Pro Ile Asp Leu Val Ile Asp Glu Arg
            180                 185                 190

Asp Gly Ser Ser Lys Ser Asp His Glu Glu Leu Ser Gly Ser Ser Thr
        195                 200                 205

Asn Leu Ala Asp His Asn Pro Ser Ser Trp Arg Asp His Asp Asp Ala
    210                 215                 220

Thr Ser Thr His Ser Ala Gly Thr Pro Gly Pro Ser Ser Gly Gly His
225                 230                 235                 240

Ala Ser Gln Ser Gly Asp Asn Ser Ser Glu Gln Gly Asp Gly Leu Asp
                245                 250                 255

Asn Ser Val Ala Ser Pro Gly Thr Gly Asp Asp Asp Asp Pro Asp Lys
            260                 265                 270

Asp Lys Lys Arg Gln Lys Lys Arg Gly Ile Phe Pro Lys Val Ala Thr
        275                 280                 285

Asn Ile Met Arg Ala Trp Leu Phe Gln His Leu Thr His Pro Tyr Pro
    290                 295                 300

Ser Glu Glu Gln Lys Lys Gln Leu Ala Gln Asp Thr Gly Leu Thr Ile
305                 310                 315                 320

Leu Gln Val Asn Asn Trp Phe Ile Asn Ala Arg Arg Arg Ile Val Gln
                325                 330                 335

Pro Met Ile Asp Gln Ser Asn Arg Ala Gly Phe Leu Leu Asp Pro Ser
            340                 345                 350
```

```
Val Ser Gln Gly Ala Ala Tyr Ser Pro Glu Gly Gln Pro Met Gly Ser
        355                 360                 365

Phe Val Leu Asp Gly Gln Gln His Met Gly Ile Arg Pro Ala Gly Pro
    370                 375                 380

Met Ser Gly Met Gly Met Asn Met Gly Met Asp Gly Gln Trp His Tyr
385                 390                 395                 400

Met


<210> SEQ ID NO 18
<211> LENGTH: 524
<212> TYPE: PRT
<213> ORGANISM: Homo sapiens

<400> SEQUENCE: 18

Met Pro Leu Val His Met Ala Ser Ser Pro Ala Val Asp Val Ser Cys
1               5                   10                  15

Arg Arg Arg Glu Lys Arg Arg Gln Leu Asp Ala Arg Arg Ser Lys Cys
            20                  25                  30

Arg Ile Arg Leu Gly Gly His Met Glu Gln Trp Cys Leu Leu Lys Glu
        35                  40                  45

Arg Leu Gly Phe Ser Leu His Ser Gln Leu Ala Lys Phe Leu Leu Asp
    50                  55                  60

Arg Tyr Thr Ser Ser Gly Cys Val Leu Cys Ala Gly Pro Glu Pro Leu
65                  70                  75                  80

Pro Pro Lys Gly Leu Gln Tyr Leu Val Leu Leu Ser His Ala His Ser
                85                  90                  95

Arg Glu Cys Ser Leu Val Pro Gly Leu Arg Gly Pro Gly Gly Gln Asp
            100                 105                 110

Gly Gly Leu Val Trp Glu Cys Ser Ala Gly His Thr Phe Ser Trp Gly
        115                 120                 125

Pro Ser Leu Ser Pro Thr Pro Ser Glu Ala Pro Lys Pro Ala Ser Leu
    130                 135                 140

Pro His Thr Thr Arg Arg Ser Trp Cys Ser Glu Ala Thr Ser Gly Gln
145                 150                 155                 160

Glu Leu Ala Asp Leu Glu Ser Glu His Asp Glu Arg Thr Gln Glu Ala
                165                 170                 175

Arg Leu Pro Arg Arg Val Gly Pro Pro Pro Glu Thr Phe Pro Pro Pro
            180                 185                 190

Gly Glu Glu Glu Gly Glu Glu Glu Glu Asp Asn Asp Glu Asp Glu Glu
        195                 200                 205

Glu Met Leu Ser Asp Ala Ser Leu Trp Thr Tyr Ser Ser Ser Pro Asp
    210                 215                 220

Asp Ser Glu Pro Asp Ala Pro Arg Leu Leu Pro Ser Pro Val Thr Cys
225                 230                 235                 240

Thr Pro Lys Glu Gly Glu Thr Pro Pro Ala Pro Ala Ala Leu Ser Ser
                245                 250                 255

Pro Leu Ala Val Pro Ala Leu Ser Ala Ser Ser Leu Ser Ser Arg Ala
            260                 265                 270

Pro Pro Pro Ala Glu Val Arg Val Gln Pro Gln Leu Ser Arg Thr Pro
        275                 280                 285

Gln Ala Ala Gln Gln Thr Glu Ala Leu Ala Ser Thr Gly Ser Gln Ala
    290                 295                 300

Gln Ser Ala Pro Thr Pro Ala Trp Asp Glu Asp Thr Ala Gln Ile Gly
305                 310                 315                 320
```

```
Pro Lys Arg Ile Arg Lys Ala Ala Lys Arg Glu Leu Met Pro Cys Asp
                325                 330                 335

Phe Pro Gly Cys Gly Arg Ile Phe Ser Asn Arg Gln Tyr Leu Asn His
            340                 345                 350

His Lys Lys Tyr Gln His Ile His Gln Lys Ser Phe Ser Cys Pro Glu
        355                 360                 365

Pro Ala Cys Gly Lys Ser Phe Asn Phe Lys Lys His Leu Lys Glu His
    370                 375                 380

Met Lys Leu His Ser Asp Thr Arg Asp Tyr Ile Cys Glu Phe Cys Ala
385                 390                 395                 400

Arg Ser Phe Arg Thr Ser Ser Asn Leu Val Ile His Arg Arg Ile His
                405                 410                 415

Thr Gly Glu Lys Pro Leu Gln Cys Glu Ile Cys Gly Phe Thr Cys Arg
            420                 425                 430

Gln Lys Ala Ser Leu Asn Trp His Gln Arg Lys His Ala Glu Thr Val
        435                 440                 445

Ala Ala Leu Arg Phe Pro Cys Glu Phe Cys Gly Lys Arg Phe Glu Lys
    450                 455                 460

Pro Asp Ser Val Ala Ala His Arg Ser Lys Ser His Pro Ala Leu Leu
465                 470                 475                 480

Leu Ala Pro Gln Glu Ser Pro Ser Gly Pro Leu Glu Pro Cys Pro Ser
                485                 490                 495

Ile Ser Ala Pro Gly Pro Leu Gly Ser Ser Glu Gly Ser Arg Pro Ser
            500                 505                 510

Ala Ser Pro Gln Ala Pro Thr Leu Leu Pro Gln Gln
        515                 520


<210> SEQ ID NO 19
<211> LENGTH: 23
<212> TYPE: PRT
<213> ORGANISM: Artificial
<220> FEATURE:
<223> OTHER INFORMATION: Synthetic

<400> SEQUENCE: 19

Phe Gln Cys Asn Gln Cys Gly Ala Ser Phe Thr Gln Lys Gly Asn Leu
1               5                   10                  15

Leu Arg His Ile Lys Leu His
            20


<210> SEQ ID NO 20
<211> LENGTH: 23
<212> TYPE: PRT
<213> ORGANISM: Artificial
<220> FEATURE:
<223> OTHER INFORMATION: Synthetic

<400> SEQUENCE: 20

Leu Gln Cys Glu Ile Cys Gly Phe Thr Cys Arg Gln Lys Ala Ser Leu
1               5                   10                  15

Asn Trp His Met Lys Lys His
            20


<210> SEQ ID NO 21
<211> LENGTH: 23
<212> TYPE: PRT
<213> ORGANISM: Artificial
<220> FEATURE:
<223> OTHER INFORMATION: Synthetic
```

<400> SEQUENCE: 21

Phe Gln Cys Asn Gln Cys Gly Ala Ser Phe Thr Gln Lys Gly Asn Leu
1               5                   10                  15

Leu Arg His Ile Lys Leu His
            20

<210> SEQ ID NO 22
<211> LENGTH: 60
<212> TYPE: PRT
<213> ORGANISM: Artificial
<220> FEATURE:
<223> OTHER INFORMATION: Synthetic

<400> SEQUENCE: 22

Pro Asn Val Leu Met Val His Lys Arg Ser His Thr Gly Glu Arg Pro
1               5                   10                  15

Phe Gln Cys Asn Gln Cys Gly Ala Ser Phe Thr Gln Lys Gly Asn Leu
            20                  25                  30

Leu Arg His Ile Lys Leu His Ser Gly Glu Lys Pro Phe Lys Cys His
        35                  40                  45

Leu Cys Asn Tyr Ala Cys Arg Arg Arg Asp Ala Leu
    50                  55                  60

<210> SEQ ID NO 23
<211> LENGTH: 23
<212> TYPE: PRT
<213> ORGANISM: Artificial
<220> FEATURE:
<223> OTHER INFORMATION: Synthetic

<400> SEQUENCE: 23

His Glu Cys Lys Leu Cys Gly Ala Ser Phe Arg Thr Lys Gly Ser Leu
1               5                   10                  15

Ile Arg His His Arg Arg His
            20

<210> SEQ ID NO 24
<211> LENGTH: 23
<212> TYPE: PRT
<213> ORGANISM: Artificial
<220> FEATURE:
<223> OTHER INFORMATION: Synthetic

<400> SEQUENCE: 24

Leu Gln Cys Glu Val Cys Gly Phe Gln Cys Arg Gln Arg Ala Ser Leu
1               5                   10                  15

Lys Tyr His Met Thr Lys His
            20

<210> SEQ ID NO 25
<211> LENGTH: 23
<212> TYPE: PRT
<213> ORGANISM: Artificial
<220> FEATURE:
<223> OTHER INFORMATION: Synthetic

<400> SEQUENCE: 25

Tyr Arg Cys Arg Ala Cys Gly Arg Ala Cys Ser Arg Leu Ser Thr Leu
1               5                   10                  15

Ile Gln His Gln Lys Val His
            20

<210> SEQ ID NO 26
<211> LENGTH: 23
<212> TYPE: PRT
<213> ORGANISM: Artificial
<220> FEATURE:
<223> OTHER INFORMATION: Synthetic

<400> SEQUENCE: 26

```
Tyr Gln Cys Lys Val Cys Gly Arg Ala Phe Lys Arg Val Ser His Leu
1               5                   10                  15

Thr Val His Tyr Arg Ile His
            20
```

<210> SEQ ID NO 27
<211> LENGTH: 23
<212> TYPE: PRT
<213> ORGANISM: Artificial
<220> FEATURE:
<223> OTHER INFORMATION: Synthetic

<400> SEQUENCE: 27

```
Leu Gln Cys Glu Ile Cys Gly Tyr Gln Cys Arg Gln Arg Ala Ser Leu
1               5                   10                  15

Asn Trp His Met Lys Lys His
            20
```

<210> SEQ ID NO 28
<211> LENGTH: 23
<212> TYPE: PRT
<213> ORGANISM: Artificial
<220> FEATURE:
<223> OTHER INFORMATION: Synthetic

<400> SEQUENCE: 28

```
Phe Ala Cys Val Ile Cys Gly Arg Lys Phe Arg Asn Arg Gly Leu Met
1               5                   10                  15

Gln Lys His Leu Lys Asn His
            20
```

<210> SEQ ID NO 29
<211> LENGTH: 23
<212> TYPE: PRT
<213> ORGANISM: Artificial
<220> FEATURE:
<223> OTHER INFORMATION: Synthetic

<400> SEQUENCE: 29

```
Leu Gln Cys Glu Ile Cys Gly Phe Thr Cys Arg Gln Lys Ala Ser Leu
1               5                   10                  15

Asn Trp His Gln Arg Lys His
            20
```

<210> SEQ ID NO 30
<211> LENGTH: 23
<212> TYPE: PRT
<213> ORGANISM: Artificial
<220> FEATURE:
<223> OTHER INFORMATION: Synthetic

<400> SEQUENCE: 30

```
Phe Val Cys Pro Arg Cys Gly Arg Gly Phe Ser Gln Pro Lys Ser Leu
1               5                   10                  15

Ala Arg His Leu Arg Leu His
            20
```

<210> SEQ ID NO 31
<211> LENGTH: 23
<212> TYPE: PRT
<213> ORGANISM: Artificial
<220> FEATURE:
<223> OTHER INFORMATION: Synthetic

<400> SEQUENCE: 31

```
Phe Gln Cys Pro Ile Cys Gly Leu Val Ile Lys Arg Lys Ser Tyr Trp
1               5                   10                  15

Lys Arg His Met Val Ile His
            20
```

<210> SEQ ID NO 32
<211> LENGTH: 23
<212> TYPE: PRT
<213> ORGANISM: Artificial
<220> FEATURE:
<223> OTHER INFORMATION: Synthetic

<400> SEQUENCE: 32

```
Leu Gln Cys Glu Ile Cys Gly Phe Thr Cys Arg Gln Lys Gly Asn Leu
1               5                   10                  15

Leu Arg His Ile Lys Leu His
            20
```

<210> SEQ ID NO 33
<211> LENGTH: 23
<212> TYPE: PRT
<213> ORGANISM: Artificial
<220> FEATURE:
<223> OTHER INFORMATION: Synthetic

<400> SEQUENCE: 33

```
Phe Gln Cys Asn Gln Cys Gly Ala Ser Phe Thr Gln Lys Ala Ser Leu
1               5                   10                  15

Asn Trp His Met Lys Lys His
            20
```

<210> SEQ ID NO 34
<211> LENGTH: 60
<212> TYPE: PRT
<213> ORGANISM: Artificial
<220> FEATURE:
<223> OTHER INFORMATION: Synthetic

<400> SEQUENCE: 34

```
Phe Asn Val Leu Met Val His Lys Arg Ser His Thr Gly Glu Arg Pro
1               5                   10                  15

Leu Gln Cys Glu Ile Cys Gly Phe Thr Cys Arg Gln Lys Gly Asn Leu
            20                  25                  30

Leu Arg His Ile Lys Leu His Thr Gly Glu Lys Pro Phe Lys Cys His
        35                  40                  45

Leu Cys Asn Tyr Ala Cys Gln Arg Arg Asp Ala Leu
    50                  55                  60
```

<210> SEQ ID NO 35
<211> LENGTH: 60
<212> TYPE: PRT
<213> ORGANISM: Artificial
<220> FEATURE:
<223> OTHER INFORMATION: Synthetic

<400> SEQUENCE: 35

Phe Asn Val Leu Met Val His Lys Arg Ser His Thr Gly Glu Arg Pro
1               5                   10                  15

Phe Gln Cys Asn Gln Cys Gly Ile Ser Phe Thr Gln Lys Gly Asn Leu
            20                  25                  30

Leu Arg His Ile Lys Leu His Thr Gly Glu Lys Pro Phe Lys Cys His
        35                  40                  45

Leu Cys Asn Tyr Ala Cys Gln Arg Arg Asp Ala Leu
    50                  55                  60

<210> SEQ ID NO 36
<211> LENGTH: 60
<212> TYPE: PRT
<213> ORGANISM: Artificial
<220> FEATURE:
<223> OTHER INFORMATION: Synthetic

<400> SEQUENCE: 36

Phe Asn Val Leu Met Val His Lys Arg Ser His Thr Gly Glu Arg Pro
1               5                   10                  15

Phe Gln Cys Asn Gln Cys Gly Met Ser Phe Thr Gln Lys Gly Asn Leu
            20                  25                  30

Leu Arg His Ile Lys Leu His Thr Gly Glu Lys Pro Phe Lys Cys His
        35                  40                  45

Leu Cys Asn Tyr Ala Cys Gln Arg Arg Asp Ala Leu
    50                  55                  60

<210> SEQ ID NO 37
<211> LENGTH: 60
<212> TYPE: PRT
<213> ORGANISM: Artificial
<220> FEATURE:
<223> OTHER INFORMATION: Synthetic

<400> SEQUENCE: 37

Phe Asn Val Leu Met Val His Lys Arg Ser His Thr Gly Glu Arg Pro
1               5                   10                  15

Phe Gln Cys Asn Gln Cys Gly Thr Ser Phe Thr Gln Lys Gly Asn Leu
            20                  25                  30

Leu Arg His Ile Lys Leu His Thr Gly Glu Lys Pro Phe Lys Cys His
        35                  40                  45

Leu Cys Asn Tyr Ala Cys Gln Arg Arg Asp Ala Leu
    50                  55                  60

<210> SEQ ID NO 38
<211> LENGTH: 60
<212> TYPE: PRT
<213> ORGANISM: Artificial
<220> FEATURE:
<223> OTHER INFORMATION: Synthetic

<400> SEQUENCE: 38

Phe Asn Val Leu Met Val His Lys Arg Ser His Thr Gly Glu Arg Pro
1               5                   10                  15

Phe Gln Cys Asn Gln Cys Gly Asn Ser Phe Thr Gln Lys Gly Asn Leu
            20                  25                  30

Leu Arg His Ile Lys Leu His Thr Gly Glu Lys Pro Phe Lys Cys His
        35                  40                  45

Leu Cys Asn Tyr Ala Cys Gln Arg Arg Asp Ala Leu
    50                  55                  60

<210> SEQ ID NO 39
<211> LENGTH: 60
<212> TYPE: PRT
<213> ORGANISM: Artificial
<220> FEATURE:
<223> OTHER INFORMATION: Synthetic

<400> SEQUENCE: 39

```
Phe Asn Val Leu Met Val His Lys Arg Ser His Thr Gly Glu Arg Pro
1               5                   10                  15

Phe Gln Cys Asn Gln Cys Gly Gln Ser Phe Thr Gln Lys Gly Asn Leu
            20                  25                  30

Leu Arg His Ile Lys Leu His Thr Gly Glu Lys Pro Phe Lys Cys His
        35                  40                  45

Leu Cys Asn Tyr Ala Cys Gln Arg Arg Asp Ala Leu
    50                  55                  60
```

<210> SEQ ID NO 40
<211> LENGTH: 60
<212> TYPE: PRT
<213> ORGANISM: Artificial
<220> FEATURE:
<223> OTHER INFORMATION: Synthetic

<400> SEQUENCE: 40

```
Phe Asn Val Leu Met Val His Lys Arg Ser His Thr Gly Glu Arg Pro
1               5                   10                  15

Phe Gln Cys Asn Gln Cys Gly Arg Ser Phe Thr Gln Lys Gly Asn Leu
            20                  25                  30

Leu Arg His Ile Lys Leu His Thr Gly Glu Lys Pro Phe Lys Cys His
        35                  40                  45

Leu Cys Asn Tyr Ala Cys Gln Arg Arg Asp Ala Leu
    50                  55                  60
```

<210> SEQ ID NO 41
<211> LENGTH: 60
<212> TYPE: PRT
<213> ORGANISM: Artificial
<220> FEATURE:
<223> OTHER INFORMATION: Synthetic

<400> SEQUENCE: 41

```
Phe Asn Val Leu Met Val His Lys Arg Ser His Thr Gly Glu Arg Pro
1               5                   10                  15

Phe Gln Cys Asn Gln Cys Gly His Ser Phe Thr Gln Lys Gly Asn Leu
            20                  25                  30

Leu Arg His Ile Lys Leu His Thr Gly Glu Lys Pro Phe Lys Cys His
        35                  40                  45

Leu Cys Asn Tyr Ala Cys Gln Arg Arg Asp Ala Leu
    50                  55                  60
```

<210> SEQ ID NO 42
<211> LENGTH: 60
<212> TYPE: PRT
<213> ORGANISM: Artificial
<220> FEATURE:
<223> OTHER INFORMATION: Synthetic

<400> SEQUENCE: 42

```
Phe Asn Val Leu Met Val His Lys Arg Ser His Thr Gly Glu Arg Pro
1               5                   10                  15
```

Phe Gln Cys Asn Gln Cys Gly Lys Ser Phe Thr Gln Lys Gly Asn Leu
20 25 30

Leu Arg His Ile Lys Leu His Thr Gly Glu Lys Pro Phe Lys Cys His
35 40 45

Leu Cys Asn Tyr Ala Cys Gln Arg Arg Asp Ala Leu
50 55 60

<210> SEQ ID NO 43
<211> LENGTH: 60
<212> TYPE: PRT
<213> ORGANISM: Artificial
<220> FEATURE:
<223> OTHER INFORMATION: Synthetic

<400> SEQUENCE: 43

Phe Asn Val Leu Met Val His Lys Arg Ser His Thr Gly Glu Arg Pro
1 5 10 15

Phe Gln Cys Asn Gln Cys Gly Asp Ser Phe Thr Gln Lys Gly Asn Leu
20 25 30

Leu Arg His Ile Lys Leu His Thr Gly Glu Lys Pro Phe Lys Cys His
35 40 45

Leu Cys Asn Tyr Ala Cys Gln Arg Arg Asp Ala Leu
50 55 60

<210> SEQ ID NO 44
<211> LENGTH: 60
<212> TYPE: PRT
<213> ORGANISM: Artificial
<220> FEATURE:
<223> OTHER INFORMATION: Synthetic

<400> SEQUENCE: 44

Phe Asn Val Leu Met Val His Lys Arg Ser His Thr Gly Glu Arg Pro
1 5 10 15

Phe Gln Cys Asn Gln Cys Gly Glu Ser Phe Thr Gln Lys Gly Asn Leu
20 25 30

Leu Arg His Ile Lys Leu His Thr Gly Glu Lys Pro Phe Lys Cys His
35 40 45

Leu Cys Asn Tyr Ala Cys Gln Arg Arg Asp Ala Leu
50 55 60

<210> SEQ ID NO 45
<211> LENGTH: 60
<212> TYPE: PRT
<213> ORGANISM: Artificial
<220> FEATURE:
<223> OTHER INFORMATION: Synthetic

<400> SEQUENCE: 45

Phe Asn Val Leu Met Val His Lys Arg Ser His Thr Gly Glu Arg Pro
1 5 10 15

Phe Gln Cys Asn Gln Cys Gly Cys Ser Phe Thr Gln Lys Gly Asn Leu
20 25 30

Leu Arg His Ile Lys Leu His Thr Gly Glu Lys Pro Phe Lys Cys His
35 40 45

Leu Cys Asn Tyr Ala Cys Gln Arg Arg Asp Ala Leu
50 55 60

<210> SEQ ID NO 46
<211> LENGTH: 60

<212> TYPE: PRT
<213> ORGANISM: Artificial
<220> FEATURE:
<223> OTHER INFORMATION: Synthetic

<400> SEQUENCE: 46

```
Phe Asn Val Leu Met Val His Arg Arg Ser His Thr Gly Glu Arg Pro
1               5                   10                  15

Phe Gln Cys Asn Gln Cys Gly Ala Ser Phe Thr Gln Arg Gly Asn Leu
            20                  25                  30

Leu Arg His Ile Arg Leu His Thr Gly Glu Arg Pro Phe Arg Cys His
        35                  40                  45

Leu Cys Asn Tyr Ala Cys Gln Arg Arg Asp Ala Leu
    50                  55                  60
```

<210> SEQ ID NO 47
<211> LENGTH: 23
<212> TYPE: PRT
<213> ORGANISM: Artificial
<220> FEATURE:
<223> OTHER INFORMATION: Synthetic

<400> SEQUENCE: 47

```
Phe Gln Cys Asn Gln Cys Gly Ala Ser Phe Thr Gln Arg Gly Asn Leu
1               5                   10                  15

Leu Arg His Ile Arg Leu His
            20
```

<210> SEQ ID NO 48
<211> LENGTH: 23
<212> TYPE: PRT
<213> ORGANISM: Artificial
<220> FEATURE:
<223> OTHER INFORMATION: Synthetic

<400> SEQUENCE: 48

```
Leu Gln Cys Glu Ile Cys Gly Phe Thr Cys Arg Gln Arg Ala Ser Leu
1               5                   10                  15

Asn Trp His Met Arg Arg His
            20
```

<210> SEQ ID NO 49
<211> LENGTH: 23
<212> TYPE: PRT
<213> ORGANISM: Artificial
<220> FEATURE:
<223> OTHER INFORMATION: Synthetic

<400> SEQUENCE: 49

```
Phe Gln Cys Asn Gln Cys Gly Ala Ser Phe Thr Gln Arg Gly Asn Leu
1               5                   10                  15

Leu Arg His Ile Arg Leu His
            20
```

<210> SEQ ID NO 50
<211> LENGTH: 60
<212> TYPE: PRT
<213> ORGANISM: Artificial
<220> FEATURE:
<223> OTHER INFORMATION: Synthetic

<400> SEQUENCE: 50

```
Pro Asn Val Leu Met Val His Arg Arg Ser His Thr Gly Glu Arg Pro
1               5                   10                  15
```

```
Phe Gln Cys Asn Gln Cys Gly Ala Ser Phe Thr Gln Arg Gly Asn Leu
            20                  25                  30

Leu Arg His Ile Arg Leu His Ser Gly Glu Arg Pro Phe Arg Cys His
        35                  40                  45

Leu Cys Asn Tyr Ala Cys Arg Arg Arg Asp Ala Leu
    50                  55                  60


<210> SEQ ID NO 51
<211> LENGTH: 23
<212> TYPE: PRT
<213> ORGANISM: Artificial
<220> FEATURE:
<223> OTHER INFORMATION: Synthetic

<400> SEQUENCE: 51

His Glu Cys Arg Leu Cys Gly Ala Ser Phe Arg Thr Arg Gly Ser Leu
1               5                   10                  15

Ile Arg His His Arg Arg His
            20


<210> SEQ ID NO 52
<211> LENGTH: 23
<212> TYPE: PRT
<213> ORGANISM: Artificial
<220> FEATURE:
<223> OTHER INFORMATION: Synthetic

<400> SEQUENCE: 52

Leu Gln Cys Glu Val Cys Gly Phe Gln Cys Arg Gln Arg Ala Ser Leu
1               5                   10                  15

Arg Tyr His Met Thr Arg His
            20


<210> SEQ ID NO 53
<211> LENGTH: 23
<212> TYPE: PRT
<213> ORGANISM: Artificial
<220> FEATURE:
<223> OTHER INFORMATION: Synthetic

<400> SEQUENCE: 53

Tyr Arg Cys Arg Ala Cys Gly Arg Ala Cys Ser Arg Leu Ser Thr Leu
1               5                   10                  15

Ile Gln His Gln Arg Val His
            20


<210> SEQ ID NO 54
<211> LENGTH: 23
<212> TYPE: PRT
<213> ORGANISM: Artificial
<220> FEATURE:
<223> OTHER INFORMATION: Synthetic

<400> SEQUENCE: 54

Tyr Gln Cys Arg Val Cys Gly Arg Ala Phe Arg Arg Val Ser His Leu
1               5                   10                  15

Thr Val His Tyr Arg Ile His
            20


<210> SEQ ID NO 55
<211> LENGTH: 23
<212> TYPE: PRT
<213> ORGANISM: Artificial
```

<220> FEATURE:
<223> OTHER INFORMATION: Synthetic

<400> SEQUENCE: 55

Leu Gln Cys Glu Ile Cys Gly Tyr Gln Cys Arg Gln Arg Ala Ser Leu
1 5 10 15

Asn Trp His Met Arg Arg His
20

<210> SEQ ID NO 56
<211> LENGTH: 23
<212> TYPE: PRT
<213> ORGANISM: Artificial
<220> FEATURE:
<223> OTHER INFORMATION: Synthetic

<400> SEQUENCE: 56

Phe Ala Cys Val Ile Cys Gly Arg Arg Phe Arg Asn Arg Gly Leu Met
1 5 10 15

Gln Arg His Leu Arg Asn His
20

<210> SEQ ID NO 57
<211> LENGTH: 23
<212> TYPE: PRT
<213> ORGANISM: Artificial
<220> FEATURE:
<223> OTHER INFORMATION: Synthetic

<400> SEQUENCE: 57

Leu Gln Cys Glu Ile Cys Gly Phe Thr Cys Arg Gln Arg Ala Ser Leu
1 5 10 15

Asn Trp His Gln Arg Arg His
20

<210> SEQ ID NO 58
<211> LENGTH: 23
<212> TYPE: PRT
<213> ORGANISM: Artificial
<220> FEATURE:
<223> OTHER INFORMATION: Synthetic

<400> SEQUENCE: 58

Phe Val Cys Pro Arg Cys Gly Arg Gly Phe Ser Gln Pro Arg Ser Leu
1 5 10 15

Ala Arg His Leu Arg Leu His
20

<210> SEQ ID NO 59
<211> LENGTH: 23
<212> TYPE: PRT
<213> ORGANISM: Artificial
<220> FEATURE:
<223> OTHER INFORMATION: Synthetic

<400> SEQUENCE: 59

Phe Gln Cys Pro Ile Cys Gly Leu Val Ile Arg Arg Arg Ser Tyr Trp
1 5 10 15

Arg Arg His Met Val Ile His
20

<210> SEQ ID NO 60
<211> LENGTH: 23
<212> TYPE: PRT

<213> ORGANISM: Artificial
<220> FEATURE:
<223> OTHER INFORMATION: Synthetic

<400> SEQUENCE: 60

Leu Gln Cys Glu Ile Cys Gly Phe Thr Cys Arg Gln Arg Gly Asn Leu
1 5 10 15

Leu Arg His Ile Arg Leu His
20

<210> SEQ ID NO 61
<211> LENGTH: 23
<212> TYPE: PRT
<213> ORGANISM: Artificial
<220> FEATURE:
<223> OTHER INFORMATION: Synthetic

<400> SEQUENCE: 61

Phe Gln Cys Asn Gln Cys Gly Ala Ser Phe Thr Gln Arg Ala Ser Leu
1 5 10 15

Asn Trp His Met Arg Arg His
20

<210> SEQ ID NO 62
<211> LENGTH: 60
<212> TYPE: PRT
<213> ORGANISM: Artificial
<220> FEATURE:
<223> OTHER INFORMATION: Synthetic

<400> SEQUENCE: 62

Phe Asn Val Leu Met Val His Arg Arg Ser His Thr Gly Glu Arg Pro
1 5 10 15

Leu Gln Cys Glu Ile Cys Gly Phe Thr Cys Arg Gln Arg Gly Asn Leu
20 25 30

Leu Arg His Ile Arg Leu His Thr Gly Glu Arg Pro Phe Arg Cys His
35 40 45

Leu Cys Asn Tyr Ala Cys Gln Arg Arg Asp Ala Leu
50 55 60

<210> SEQ ID NO 63
<211> LENGTH: 477
<212> TYPE: PRT
<213> ORGANISM: Homo sapiens

<400> SEQUENCE: 63

Met Asp Ala Asp Glu Gly Gln Asp Met Ser Gln Val Ser Gly Arg Glu
1 5 10 15

Ser Pro Pro Val Ser Asp Thr Pro Asp Glu Gly Asp Glu Pro Met Pro
20 25 30

Ile Pro Glu Asp Leu Ser Thr Thr Ser Gly Gly Gln Gln Ser Ser Arg
35 40 45

Ser Asp Arg Val Val Ala Ser Asn Val Arg Val Glu Thr Gln Ser Asp
50 55 60

Glu Glu Asn Gly Arg Ala Cys Glu Met Asn Gly Glu Glu Cys Ala Glu
65 70 75 80

Asp Leu Arg Met Leu Asp Ala Ser Gly Glu Arg Met Asn Gly Ser His
85 90 95

Arg Asp Gln Gly Ser Ser Ala Leu Ser Gly Val Gly Gly Ile Arg Leu
100 105 110

-continued

```
Pro Asn Gly Arg Leu Arg Cys Asp Ile Cys Gly Ile Ile Cys Ile Gly
        115                 120                 125

Pro Asn Val Leu Met Val His Arg Arg Ser His Thr Gly Glu Arg Pro
    130                 135                 140

Phe Gln Cys Asn Gln Cys Gly Ala Ser Phe Thr Gln Arg Gly Asn Leu
145                 150                 155                 160

Leu Arg His Ile Arg Leu His Ser Gly Glu Arg Pro Phe Arg Cys His
                165                 170                 175

Leu Cys Asn Tyr Ala Cys Arg Arg Arg Asp Ala Leu Thr Gly His Leu
            180                 185                 190

Arg Thr His Ser Val Ile Arg Glu Glu Thr Asn His Ser Glu Met Ala
        195                 200                 205

Glu Asp Leu Cys Arg Ile Gly Ser Glu Arg Ser Leu Val Leu Asp Arg
    210                 215                 220

Leu Ala Ser Asn Val Ala Arg Arg Arg Ser Ser Met Pro Gln Arg Phe
225                 230                 235                 240

Leu Gly Asp Arg Gly Leu Ser Asp Thr Pro Tyr Asp Ser Ser Ala Ser
                245                 250                 255

Tyr Glu Arg Glu Asn Glu Met Met Arg Ser His Val Met Asp Gln Ala
            260                 265                 270

Ile Asn Asn Ala Ile Asn Tyr Leu Gly Ala Glu Ser Leu Arg Pro Leu
        275                 280                 285

Val Gln Thr Pro Pro Gly Gly Ser Glu Val Val Pro Val Ile Ser Pro
    290                 295                 300

Met Tyr Gln Leu His Arg Pro Leu Ala Glu Gly Thr Pro Arg Ser Asn
305                 310                 315                 320

His Ser Ala Gln Asp Ser Ala Val Glu Asn Leu Leu Leu Leu Ser Arg
                325                 330                 335

Ala Arg Leu Val Pro Ser Glu Arg Glu Ala Ser Pro Ser Asn Ser Cys
            340                 345                 350

Gln Asp Ser Thr Asp Thr Glu Ser Asn Asn Glu Glu Gln Arg Ser Gly
        355                 360                 365

Leu Ile Tyr Leu Thr Asn His Ile Ala Pro His Ala Arg Asn Gly Leu
    370                 375                 380

Ser Leu Arg Glu Glu His Arg Ala Tyr Asp Leu Leu Arg Ala Ala Ser
385                 390                 395                 400

Glu Asn Ser Gln Asp Ala Leu Arg Val Val Ser Thr Ser Gly Glu Gln
                405                 410                 415

Met Arg Val Tyr Arg Cys Glu His Cys Arg Val Leu Phe Leu Asp His
            420                 425                 430

Val Met Tyr Thr Ile His Met Gly Cys His Gly Phe Arg Asp Pro Phe
        435                 440                 445

Glu Cys Asn Met Cys Gly Tyr His Ser Gln Asp Arg Tyr Glu Phe Ser
    450                 455                 460

Ser His Ile Thr Arg Gly Glu His Arg Phe His Met Ser
465                 470                 475
```

<210> SEQ ID NO 64
<211> LENGTH: 262
<212> TYPE: PRT
<213> ORGANISM: Homo sapiens

<400> SEQUENCE: 64

```
Met Gly Ser Glu Arg Ala Leu Val Leu Asp Arg Leu Ala Ser Asn Val
1               5                   10                  15
```

```
Ala Arg Arg Arg Ser Ser Met Pro Gln Arg Phe Ile Gly Glu Arg Arg
            20                  25                  30

His Cys Phe Asp Val Asn Tyr Asn Ser Ser Tyr Met Tyr Glu Arg Glu
        35                  40                  45

Ser Glu Leu Ile Gln Thr Arg Met Met Asp Gln Ala Ile Asn Asn Ala
    50                  55                  60

Ile Ser Tyr Leu Gly Ala Glu Ala Leu Arg Pro Leu Val Gln Thr Pro
65                  70                  75                  80

Pro Ala Pro Thr Ser Glu Met Val Pro Val Ile Ser Ser Met Tyr Pro
                85                  90                  95

Ile Ala Leu Thr Arg Ala Glu Met Ser Asn Gly Ala Pro Gln Glu Leu
            100                 105                 110

Glu Arg Arg Ser Ile His Leu Pro Glu Arg Ser Val Pro Ser Glu Arg
        115                 120                 125

Gly Leu Ser Pro Asn Asn Ser Gly His Asp Ser Thr Asp Thr Asp Ser
    130                 135                 140

Asn His Glu Glu Arg Gln Asn His Ile Tyr Gln Gln Asn His Met Val
145                 150                 155                 160

Leu Ser Arg Ala Arg Asn Gly Met Pro Leu Leu Arg Glu Val Pro Arg
                165                 170                 175

Ser Tyr Glu Leu Leu Arg Pro Pro Pro Ile Cys Pro Arg Asp Ser Val
            180                 185                 190

Arg Val Ile Asn Arg Glu Gly Glu Val Met Asp Val Tyr Arg Cys Asp
        195                 200                 205

His Cys Arg Val Leu Phe Leu Asp Tyr Val Met Phe Thr Ile His Met
    210                 215                 220

Gly Cys His Gly Phe Arg Asp Pro Phe Glu Cys Asn Met Cys Gly Tyr
225                 230                 235                 240

Arg Ser His Asp Arg Tyr Glu Phe Ser Ser His Ile Ala Arg Gly Glu
                245                 250                 255

His Arg Ala Leu Leu Arg
            260
```

<210> SEQ ID NO 65
<211> LENGTH: 365
<212> TYPE: PRT
<213> ORGANISM: Homo sapiens

<400> SEQUENCE: 65

```
Met Ala Ser Ser Ser Gly Ser Arg Ala Glu Phe Ile Val Gly Gly Arg
1               5                   10                  15

Tyr Arg Leu Val Arg Arg Ile Gly Ser Gly Ser Phe Gly Asp Ile Tyr
            20                  25                  30

Leu Ala Ile Asn Ile Thr Asn Gly Glu Glu Val Ala Val Arg Leu Glu
        35                  40                  45

Ser Gln Arg Ala Arg His Pro Gln Leu Leu Tyr Glu Ser Arg Leu Tyr
    50                  55                  60

Arg Ile Leu Gln Gly Gly Val Gly Ile Pro His Ile Arg Trp Tyr Gly
65                  70                  75                  80

Gln Glu Arg Asp Tyr Asn Val Leu Val Met Asp Leu Leu Gly Pro Ser
                85                  90                  95

Leu Glu Asp Leu Phe Asn Phe Cys Ser Arg Arg Phe Thr Met Arg Thr
            100                 105                 110

Val Leu Met Leu Ala Asp Gln Met Ile Ser Arg Ile Glu Tyr Val His
```

```
        115                 120                 125

Thr Arg Asn Phe Ile His Arg Asp Ile Arg Pro Asp Asn Phe Leu Met
    130                 135                 140

Gly Ile Gly Arg His Cys Asn Arg Cys Leu Glu Ser Pro Val Gly Arg
145                 150                 155                 160

Arg Arg Arg Ser Met Thr Val Ser Thr Ser Gln Asp Pro Ser Phe Ser
                165                 170                 175

Gly Leu Asn Gln Leu Phe Leu Ile Asp Phe Gly Leu Ala Arg Arg Tyr
            180                 185                 190

Arg Asp Asn Arg Thr Arg Gln His Ile Pro Tyr Arg Glu Asp Arg Asn
        195                 200                 205

Leu Thr Gly Thr Ala Arg Tyr Ala Ser Ile Asn Ala His Leu Gly Ile
    210                 215                 220

Glu Gln Ser Arg Arg Asp Asp Met Glu Ser Leu Gly Tyr Val Leu Met
225                 230                 235                 240

Tyr Phe Asn Arg Thr Ser Leu Pro Trp Gln Gly Leu Arg Ala Ala Thr
                245                 250                 255

Arg Arg Gln Arg Tyr Glu Arg Ile Ser Glu Arg Arg Met Ser Thr Pro
            260                 265                 270

Val Glu Val Leu Cys Arg Gly Phe Pro Ala Glu Phe Ala Met Tyr Leu
        275                 280                 285

Asn Tyr Cys Arg Gly Leu Arg Phe Glu Glu Ala Pro Asp Tyr Met Tyr
    290                 295                 300

Leu Arg Gln Leu Phe Arg Ile Leu Phe Arg Thr Leu Asn His Gln Tyr
305                 310                 315                 320

Asp Tyr Thr Phe Asp Trp Thr Met Leu Arg Gln Arg Ala Ala Gln Gln
                325                 330                 335

Ala Ala Ser Ser Ser Gly Gln Gly Gln Gln Ala Gln Thr Pro Thr Gly
            340                 345                 350

Arg Gln Thr Asp Arg Thr Arg Ser Asn Met Arg Gly Phe
        355                 360                 365


<210> SEQ ID NO 66
<211> LENGTH: 570
<212> TYPE: PRT
<213> ORGANISM: Homo sapiens

<400> SEQUENCE: 66

Met Pro Gly Glu Thr Glu Glu Pro Arg Pro Pro Glu Gln Gln Asp Gln
1               5                   10                  15

Glu Gly Gly Glu Ala Ala Arg Ala Ala Pro Glu Glu Pro Gln Gln Arg
            20                  25                  30

Pro Pro Glu Ala Val Ala Ala Ala Pro Ala Gly Thr Thr Ser Ser Arg
        35                  40                  45

Val Leu Arg Gly Gly Arg Asp Arg Gly Arg Ala Ala Ala Ala Ala Ala
    50                  55                  60

Ala Ala Ala Val Ser Arg Arg Arg Arg Ala Glu Tyr Pro Arg Arg Arg
65                  70                  75                  80

Arg Ser Ser Pro Ser Ala Arg Pro Pro Asp Val Pro Gly Gln Gln Pro
                85                  90                  95

Gln Ala Ala Arg Ser Pro Ser Pro Val Gln Gly Arg Arg Ser Pro Arg
            100                 105                 110

Leu Leu Cys Ile Glu Arg Val Thr Thr Asp Arg Asp Pro Arg Glu Glu
        115                 120                 125
```

```
Arg Glu Glu Glu Asp Asp Ser Ala Leu Pro Gln Glu Val Ser Ile Ala
    130                 135                 140

Ala Ser Arg Pro Ser Arg Gly Trp Arg Ser Ser Arg Thr Ser Val Ser
145                 150                 155                 160

Arg His Arg Asp Thr Glu Asn Thr Arg Ser Ser Arg Ser Arg Thr Gly
                165                 170                 175

Ser Leu Gln Leu Ile Cys Arg Ser Glu Pro Asn Thr Asp Gln Leu Asp
            180                 185                 190

Tyr Asp Val Gly Glu Glu His Gln Ser Pro Gly Gly Ile Ser Ser Glu
        195                 200                 205

Glu Glu Glu Glu Glu Glu Glu Glu Met Leu Ile Ser Glu Glu Glu Ile
    210                 215                 220

Pro Phe Arg Asp Asp Pro Arg Asp Glu Thr Tyr Arg Pro His Leu Glu
225                 230                 235                 240

Arg Glu Thr Pro Arg Pro Arg Arg Arg Ser Gly Arg Val Arg Glu Glu
                245                 250                 255

Arg Glu Arg Arg Glu Ile Arg Val Glu Val Glu Val Glu Val Arg Glu
            260                 265                 270

Glu Glu Asn Glu Ile Arg Glu Asp Glu Glu Pro Pro Arg Arg Arg Gly
        275                 280                 285

Arg Arg Arg Arg Asp Asp Arg Ser Pro Arg Leu Pro Arg Arg Arg Arg
    290                 295                 300

Arg Pro Pro Ile Gln Tyr Val Arg Cys Glu Met Glu Gly Cys Gly Thr
305                 310                 315                 320

Val Leu Ala His Pro Arg Tyr Leu Gln His His Ile Arg Tyr Gln His
                325                 330                 335

Leu Leu Arg Arg Arg Tyr Val Cys Pro His Pro Ser Cys Gly Arg Leu
            340                 345                 350

Phe Arg Leu Gln Arg Gln Leu Leu Arg His Ala Arg His His Thr Asp
        355                 360                 365

Gln Arg Asp Tyr Ile Cys Glu Tyr Cys Ala Arg Ala Phe Arg Ser Ser
    370                 375                 380

His Asn Leu Ala Val His Arg Met Ile His Thr Gly Glu Arg Pro Leu
385                 390                 395                 400

Gln Cys Glu Ile Cys Gly Phe Thr Cys Arg Gln Arg Ala Ser Leu Asn
                405                 410                 415

Trp His Met Arg Arg His Asp Ala Asp Ser Phe Tyr Gln Phe Ser Cys
            420                 425                 430

Asn Ile Cys Gly Arg Arg Phe Glu Arg Arg Asp Ser Val Val Ala His
        435                 440                 445

Arg Ala Arg Ser His Pro Glu Val Leu Ile Ala Glu Ala Leu Ala Ala
    450                 455                 460

Asn Ala Gly Ala Leu Ile Thr Ser Thr Asp Ile Leu Gly Thr Asn Pro
465                 470                 475                 480

Glu Ser Leu Thr Gln Pro Ser Asp Gly Gln Gly Leu Pro Leu Leu Pro
                485                 490                 495

Glu Pro Leu Gly Asn Ser Thr Ser Gly Glu Cys Leu Leu Leu Glu Ala
            500                 505                 510

Glu Gly Met Ser Arg Ser Tyr Cys Ser Gly Thr Glu Arg Val Ser Leu
        515                 520                 525

Met Ala Asp Gly Arg Ile Phe Val Gly Ser Gly Ser Ser Gly Gly Thr
    530                 535                 540

Glu Gly Leu Val Met Asn Ser Asp Ile Leu Gly Ala Thr Thr Glu Val
```

-continued

```
545                 550                 555                 560

Leu Ile Glu Asp Ser Asp Ser Ala Gly Pro
                565                 570


<210> SEQ ID NO 67
<211> LENGTH: 633
<212> TYPE: PRT
<213> ORGANISM: Homo sapiens

<400> SEQUENCE: 67

Met Asp Pro Gly Ser Gly Gly Gly Gly Gly Gly Gly Gly Ser Ser Ser
1               5                   10                  15

Gly Ser Ser Ser Ser Asp Ser Ala Pro Asp Cys Trp Asp Gln Ala Asp
            20                  25                  30

Met Glu Ala Pro Gly Pro Gly Pro Cys Gly Gly Gly Gly Ser Leu Ala
        35                  40                  45

Ala Ala Ala Glu Ala Gln Arg Glu Asn Leu Ser Ala Ala Phe Ser Arg
    50                  55                  60

Gln Leu Asn Val Asn Ala Arg Pro Phe Val Pro Asn Val His Ala Ala
65                  70                  75                  80

Glu Phe Val Pro Ser Phe Leu Arg Cys Pro Ala Ala Pro Pro Pro Pro
                85                  90                  95

Ala Gly Gly Ala Ala Asn Asn His Gly Ala Gly Ser Gly Ala Gly Gly
            100                 105                 110

Arg Ala Ala Pro Val Glu Ser Ser Gln Glu Glu Gln Ser Leu Cys Glu
        115                 120                 125

Gly Ser Asn Ser Ala Val Ser Met Glu Leu Ser Glu Pro Ile Glu Asn
    130                 135                 140

Gly Glu Thr Glu Met Ser Pro Glu Glu Ser Trp Glu His Arg Glu Glu
145                 150                 155                 160

Ile Ser Glu Ala Glu Pro Gly Gly Gly Ser Leu Gly Asp Gly Arg Pro
                165                 170                 175

Pro Glu Glu Ser Ala His Glu Met Met Glu Glu Glu Glu Glu Ile Pro
            180                 185                 190

Arg Pro Arg Ser Val Val Ala Pro Pro Gly Ala Pro Arg Arg Glu His
        195                 200                 205

Val Asn Val Val Phe Ile Gly His Val Asp Ala Gly Arg Ser Thr Ile
    210                 215                 220

Gly Gly Gln Ile Met Tyr Leu Thr Gly Met Val Asp Arg Arg Thr Leu
225                 230                 235                 240

Glu Arg Tyr Glu Arg Glu Ala Arg Glu Arg Asn Arg Glu Thr Trp Tyr
                245                 250                 255

Leu Ser Trp Ala Leu Asp Thr Asn Gln Glu Glu Arg Asp Arg Gly Arg
            260                 265                 270

Thr Val Glu Val Gly Arg Ala Tyr Phe Glu Thr Glu Arg Arg His Phe
        275                 280                 285

Thr Ile Leu Asp Ala Pro Gly His Arg Ser Phe Val Pro Asn Met Ile
    290                 295                 300

Gly Gly Ala Ser Gln Ala Asp Leu Ala Val Leu Val Ile Ser Ala Arg
305                 310                 315                 320

Arg Gly Glu Phe Glu Thr Gly Phe Glu Arg Gly Gly Gln Thr Arg Glu
                325                 330                 335

His Ala Met Leu Ala Arg Thr Ala Gly Val Arg His Leu Ile Val Leu
            340                 345                 350
```

```
Ile Asn Arg Met Asp Asp Pro Thr Val Asn Trp Ser Asn Glu Arg Tyr
        355                 360                 365

Glu Glu Cys Arg Glu Arg Leu Val Pro Phe Leu Arg Arg Val Gly Phe
    370                 375                 380

Asn Pro Arg Arg Asp Ile His Phe Met Pro Cys Ser Gly Leu Thr Gly
385                 390                 395                 400

Ala Asn Leu Arg Glu Gln Ser Asp Phe Cys Pro Trp Tyr Ile Gly Leu
                405                 410                 415

Pro Phe Ile Pro Tyr Leu Asp Asn Leu Pro Asn Phe Asn Arg Ser Val
            420                 425                 430

Asp Gly Pro Ile Arg Leu Pro Ile Val Asp Arg Tyr Arg Asp Met Gly
        435                 440                 445

Thr Val Val Leu Gly Arg Leu Glu Ser Gly Ser Ile Cys Arg Gly Gln
    450                 455                 460

Gln Leu Val Met Met Pro Asn Arg His Asn Val Glu Val Leu Gly Ile
465                 470                 475                 480

Leu Ser Asp Asp Val Glu Thr Asp Thr Val Ala Pro Gly Glu Asn Leu
                485                 490                 495

Arg Ile Arg Leu Arg Gly Ile Glu Glu Glu Glu Ile Leu Pro Gly Phe
            500                 505                 510

Ile Leu Cys Asp Pro Asn Asn Leu Cys His Ser Gly Arg Thr Phe Asp
        515                 520                 525

Ala Gln Ile Val Ile Ile Glu His Arg Ser Ile Ile Cys Pro Gly Tyr
    530                 535                 540

Asn Ala Val Leu His Ile His Thr Cys Ile Glu Glu Val Glu Ile Thr
545                 550                 555                 560

Ala Leu Ile Cys Leu Val Asp Arg Arg Ser Gly Glu Arg Ser Arg Thr
                565                 570                 575

Arg Pro Arg Phe Val Arg Gln Asp Gln Val Cys Ile Ala Arg Leu Arg
            580                 585                 590

Thr Ala Gly Thr Ile Cys Leu Glu Thr Phe Arg Asp Phe Pro Gln Met
        595                 600                 605

Gly Arg Phe Thr Leu Arg Asp Glu Gly Arg Thr Ile Ala Ile Gly Arg
    610                 615                 620

Val Leu Arg Leu Val Pro Glu Arg Asp
625                 630


<210> SEQ ID NO 68
<211> LENGTH: 474
<212> TYPE: PRT
<213> ORGANISM: Homo sapiens

<400> SEQUENCE: 68

Met Ala Thr Asn Trp Gly Ser Leu Leu Gln Asp Arg Gln Gln Leu Glu
1               5                   10                  15

Glu Leu Ala Arg Gln Ala Val Asp Arg Ala Leu Ala Glu Gly Val Leu
            20                  25                  30

Leu Arg Thr Ser Gln Glu Pro Thr Ser Ser Glu Val Val Ser Tyr Ala
        35                  40                  45

Pro Phe Thr Leu Phe Pro Ser Leu Val Pro Ser Ala Leu Leu Glu Gln
    50                  55                  60

Ala Tyr Ala Val Gln Met Asp Phe Asn Leu Leu Val Asp Ala Val Ser
65                  70                  75                  80

Gln Asn Ala Ala Phe Leu Glu Gln Thr Leu Ser Ser Thr Ile Arg Gln
                85                  90                  95
```

```
Asp Asp Phe Thr Ala Arg Leu Phe Asp Ile His Arg Gln Val Leu Arg
            100                 105                 110

Glu Gly Ile Ala Gln Thr Val Phe Leu Gly Leu Asn Arg Ser Asp Tyr
        115                 120                 125

Met Phe Gln Arg Ser Ala Asp Gly Ser Pro Ala Leu Arg Gln Ile Glu
    130                 135                 140

Ile Asn Thr Ile Ser Ala Ser Phe Gly Gly Leu Ala Ser Arg Thr Pro
145                 150                 155                 160

Ala Val His Arg His Val Leu Ser Val Leu Ser Arg Thr Arg Glu Ala
                165                 170                 175

Gly Arg Ile Leu Ser Asn Asn Pro Ser Arg Gly Leu Ala Leu Gly Ile
            180                 185                 190

Ala Arg Ala Trp Glu Leu Tyr Gly Ser Pro Asn Ala Leu Val Leu Leu
        195                 200                 205

Ile Ala Gln Glu Arg Glu Arg Asn Ile Phe Asp Gln Arg Ala Ile Glu
    210                 215                 220

Asn Glu Leu Leu Ala Arg Asn Ile His Val Ile Arg Arg Thr Phe Glu
225                 230                 235                 240

Asp Ile Ser Glu Arg Gly Ser Leu Asp Gln Asp Arg Arg Leu Phe Val
                245                 250                 255

Asp Gly Gln Glu Ile Ala Val Val Tyr Phe Arg Asp Gly Tyr Met Pro
            260                 265                 270

Arg Gln Tyr Ser Leu Gln Asn Trp Glu Ala Arg Leu Leu Leu Glu Arg
        275                 280                 285

Ser His Ala Ala Arg Cys Pro Asp Ile Ala Thr Gln Leu Ala Gly Thr
    290                 295                 300

Arg Arg Val Gln Gln Glu Leu Ser Arg Pro Gly Met Leu Glu Met Leu
305                 310                 315                 320

Leu Pro Gly Gln Pro Glu Ala Val Ala Arg Leu Arg Ala Thr Phe Ala
                325                 330                 335

Gly Leu Tyr Ser Leu Asp Val Gly Glu Glu Gly Asp Gln Ala Ile Ala
            340                 345                 350

Glu Ala Leu Ala Ala Pro Ser Arg Phe Val Leu Arg Pro Gln Arg Glu
        355                 360                 365

Gly Gly Gly Asn Asn Leu Tyr Gly Glu Glu Met Val Gln Ala Leu Arg
    370                 375                 380

Gln Leu Arg Asp Ser Glu Glu Arg Ala Ser Tyr Ile Leu Met Glu Arg
385                 390                 395                 400

Ile Glu Pro Glu Pro Phe Glu Asn Cys Leu Leu Arg Pro Gly Ser Pro
                405                 410                 415

Ala Arg Val Val Gln Cys Ile Ser Glu Leu Gly Ile Phe Gly Val Tyr
            420                 425                 430

Val Arg Gln Glu Arg Thr Leu Val Met Asn Arg His Val Gly His Leu
        435                 440                 445

Leu Arg Thr Arg Ala Ile Glu His Ala Asp Gly Gly Val Ala Ala Gly
    450                 455                 460

Val Ala Val Leu Asp Asn Pro Tyr Pro Val
465                 470
```

<210> SEQ ID NO 69
<211> LENGTH: 401
<212> TYPE: PRT
<213> ORGANISM: Homo sapiens

<400> SEQUENCE: 69

Met Ala Gln Arg Tyr Asp Glu Leu Pro His Tyr Gly Gly Met Asp Gly
1 5 10 15

Val Gly Val Pro Ala Ser Met Tyr Gly Asp Pro His Ala Pro Arg Pro
20 25 30

Ile Pro Pro Val His His Leu Asn His Gly Pro Pro Leu His Ala Thr
35 40 45

Gln His Tyr Gly Ala His Ala Pro His Pro Asn Val Met Pro Ala Ser
50 55 60

Met Gly Ser Ala Val Asn Asp Ala Leu Arg Arg Asp Arg Asp Ala Ile
65 70 75 80

Tyr Gly His Pro Leu Phe Pro Leu Leu Ala Leu Val Phe Glu Arg Cys
85 90 95

Glu Leu Ala Thr Cys Thr Pro Arg Glu Pro Gly Val Ala Gly Gly Asp
100 105 110

Val Cys Ser Ser Asp Ser Phe Asn Glu Asp Ile Ala Val Phe Ala Arg
115 120 125

Gln Val Arg Ala Glu Arg Pro Leu Phe Ser Ser Asn Pro Glu Leu Asp
130 135 140

Asn Leu Met Ile Gln Ala Ile Gln Val Leu Arg Phe His Leu Leu Glu
145 150 155 160

Leu Glu Arg Val His Glu Leu Cys Asp Asn Phe Cys His Arg Tyr Ile
165 170 175

Ser Cys Leu Arg Gly Arg Met Pro Ile Asp Leu Val Ile Asp Glu Arg
180 185 190

Asp Gly Ser Ser Arg Ser Asp His Glu Glu Leu Ser Gly Ser Ser Thr
195 200 205

Asn Leu Ala Asp His Asn Pro Ser Ser Trp Arg Asp His Asp Asp Ala
210 215 220

Thr Ser Thr His Ser Ala Gly Thr Pro Gly Pro Ser Ser Gly Gly His
225 230 235 240

Ala Ser Gln Ser Gly Asp Asn Ser Ser Glu Gln Gly Asp Gly Leu Asp
245 250 255

Asn Ser Val Ala Ser Pro Gly Thr Gly Asp Asp Asp Asp Pro Asp Arg
260 265 270

Asp Arg Arg Arg Gln Arg Arg Arg Gly Ile Phe Pro Arg Val Ala Thr
275 280 285

Asn Ile Met Arg Ala Trp Leu Phe Gln His Leu Thr His Pro Tyr Pro
290 295 300

Ser Glu Glu Gln Arg Arg Gln Leu Ala Gln Asp Thr Gly Leu Thr Ile
305 310 315 320

Leu Gln Val Asn Asn Trp Phe Ile Asn Ala Arg Arg Arg Ile Val Gln
325 330 335

Pro Met Ile Asp Gln Ser Asn Arg Ala Gly Phe Leu Leu Asp Pro Ser
340 345 350

Val Ser Gln Gly Ala Ala Tyr Ser Pro Glu Gly Gln Pro Met Gly Ser
355 360 365

Phe Val Leu Asp Gly Gln Gln His Met Gly Ile Arg Pro Ala Gly Pro
370 375 380

Met Ser Gly Met Gly Met Asn Met Gly Met Asp Gly Gln Trp His Tyr
385 390 395 400

Met

<210> SEQ ID NO 70
<211> LENGTH: 10568
<212> TYPE: DNA
<213> ORGANISM: Artificial
<220> FEATURE:
<223> OTHER INFORMATION: Synthetic

<400> SEQUENCE: 70
cgaacgaccg agcgcagcga gtcagtgagc gaggaagcgg aagagcgccc aatacgcaaa 60
ccgcctctcc ccgcgcgttg gccgattcat taatgcagct ggcacgacag gtttcccgac 120
tggaaagcgg gcagtgagcg caacgcaatt aatgtgagtt agctcactca ttaggcaccc 180
caggctttac actttatgct tccggctcgt atgttgtgtg gaattgtgag cggataacaa 240
tttcacacag gaaacagcta tgaccatgat tacgccaagc gcgcaattaa ccctcactaa 300
agggaacaaa agctggagct gcaagcttaa tgtagtctta tgcaatactc ttgtagtctt 360
gcaacatggt aacgatgagt tagcaacatg ccttacaagg agagaaaaag caccgtgcat 420
gccgattggt ggaagtaagg tggtacgatc gtgccttatt aggaaggcaa cagacgggtc 480
tgacatggat tggacgaacc actgaattgc cgcattgcag agatattgta tttaagtgcc 540
tagctcgata cataaacggg tctctctggt tagaccagat ctgagcctgg gagctctctg 600
gctaactagg gaacccactg cttaagcctc aataaagctt gccttgagtg cttcaagtag 660
tgtgtgcccg tctgttgtgt gactctggta actagagatc cctcagaccc ttttagtcag 720
tgtggaaaat ctctagcagt ggcgcccgaa cagggacttg aaagcgaaag ggaaaccaga 780
ggagctctct cgacgcagga ctcggcttgc tgaagcgcgc acggcaagag gcgaggggcg 840
gcgactggtg agtacgccaa aaattttgac tagcggaggc tagaaggaga gagatgggtg 900
cgagagcgtc agtattaagc gggggagaat tagatcgcga tgggaaaaaa ttcggttaag 960
gccaggggga aagaaaaaat ataaattaaa acatatagta tgggcaagca gggagctaga 1020
acgattcgca gttaatcctg gcctgttaga aacatcagaa ggctgtagac aaatactggg 1080
acagctacaa ccatcccttc agacaggatc agaagaactt agatcattat ataatacagt 1140
agcaaccctc tattgtgtgc atcaaaggat agagataaaa gacaccaagg aagctttaga 1200
caagatagag gaagagcaaa acaaaagtaa gaccaccgca cagcaagcgg ccgctgatct 1260
tcagacctgg aggaggagat atgagggaca attggagaag tgaattatat aaatataaag 1320
tagtaaaaat tgaaccatta ggagtagcac ccaccaaggc aaagagaaga gtggtgcaga 1380
gagaaaaaag agcagtggga ataggagctt tgttccttgg gttcttggga gcagcaggaa 1440
gcactatggg cgcagcgtca atgacgctga cggtacaggc cagacaatta ttgtctggta 1500
tagtgcagca gcagaacaat ttgctgaggg ctattgaggc gcaacagcat ctgttgcaac 1560
tcacagtctg gggcatcaag cagctccagg caagaatcct ggctgtggaa agatacctaa 1620
aggatcaaca gctcctgggg atttggggtt gctctggaaa actcatttgc accactgctg 1680
tgccttggaa tgctagttgg agtaataaat ctctggaaca gatttggaat cacacgacct 1740
ggatggagtg ggacagagaa attaacaatt acacaagctt aatacactcc ttaattgaag 1800
aatcgcaaaa ccagcaagaa aagaatgaac aagaattatt ggaattagat aaatgggcaa 1860
gtttgtggaa ttggtttaac ataacaaatt ggctgtggta tataaaatta ttcataatga 1920
tagtaggagg cttggtaggt ttaagaatag tttttgctgt actttctata gtgaatagag 1980
ttaggcaggg atattcacca ttatcgtttc agacccacct cccaaccccg aggggaccct 2040
attccagcac atatgagcta gctgcagtaa cgccattttg caaggcatgg aaaaatacca 2100

```
aaccaagaat agagaagttc agatcaaggg cgggtacatg aaaatagcta acgttgggcc   2160
aaacaggata tctgcggtga gcagtttcgg ccccggcccg gggccaagaa cagatggtca   2220
ccgcagtttc ggccccggcc cgaggccaag aacagatggt ccccagatat ggcccaaccc   2280
tcagcagttt cttaagaccc atcagatgtt tccaggctcc cccaaggacc tgaaatgacc   2340
ctgcgcctta tttgaattaa ccaatcagcc tgcttctcgc ttctgttcgc gcgcttctgc   2400
ttcccgagct ctataaaaga gctcacaacc cctcactcgg cgcgccagtc ctccgacaga   2460
ctgagtcggc cggtcgaatc aagcttatcg ataccgtcga ctccggaata gccaccatgg   2520
agacggacgt ctcagctgaa gctgctgcaa aggaagctgc agctaaggag gctgcagcta   2580
aggctgtgag caagggcgag gagctgttca ccggggtggt gcccatcctg gtcgagctgg   2640
acggcgacgt aaacggccac aagttcagcg tgtccggcga gggcgagggc gatgccacct   2700
acggcaagct gaccctgaag ttcatctgca ccaccggcaa gctgcccgtg ccctggccca   2760
ccctcgtgac caccctgacc tacggcgtgc agtgcttcag ccgctacccc gaccacatga   2820
agcagcacga cttcttcaag tccgccatgc ccgaaggcta cgtccaggag cgcaccatct   2880
tcttcaagga cgacggcaac tacaagaccc gcgccgaggt gaagttcgag ggcgacaccc   2940
tggtgaaccg catcgagctg aagggcatcg acttcaagga ggacggcaac atcctggggc   3000
acaagctgga gtacaactac aacagccaca acgtctatat catggccgac aagcagaaga   3060
acggcatcaa ggtgaacttc aagatccgcc acaacatcga ggacggcagc gtgcagctcg   3120
ccgaccacta ccagcagaac acccccatcg gcgacggccc cgtgctgctg cccgacaacc   3180
actacctgag cacccagtcc gccctgagca aagaccccaa cgagaagcgc gatcacatgg   3240
tcctgctgga gttcgtgacc gccgccggga tcactctcgg catggacgag ctgtacaagt   3300
aaatgcatga gtaactgagg atccgcccct ctccctcccc cccccctaac gttactggcc   3360
gaagccgctt ggaataaggc cggtgtgcgt ttgtctatat gttattttcc accatattgc   3420
cgtcttttgg caatgtgagg gcccggaaac ctggccctgt cttcttgacg agcattccta   3480
ggggtctttc ccctctcgcc aaaggaatgc aaggtctgtt gaatgtcgtg aaggaagcag   3540
ttcctctgga agcttcttga agacaaacaa cgtctgtagc gaccctttgc aggcagcgga   3600
accccccacc tggcgacagg tgcctctgcg gccaaaagcc acgtgtataa gatacacctg   3660
caaaggcggc acaaccccag tgccacgttg tgagttggat agttgtggaa agagtcaaat   3720
ggctctcctc aagcgtattc aacaaggggc tgaaggatgc ccagaaggta ccccattgta   3780
tgggatctga tctggggcct cggtacacat gctttacatg tgtttagtcg aggttaaaaa   3840
aacgtctagg ccccccgaac cacggggacg tggttttcct ttgaaaaaca cgatgataat   3900
atggccacaa ccctggaatt cgccaccatg gtgagcaagg gcgaggagga taacatggcc   3960
atcatcaagg agttcatgcg cttcaaggtg cacatggagg gctccgtgaa cggccacgag   4020
ttcgagatcg agggcgaggg cgagggccgc ccctacgagg gcacccagac cgccaagctg   4080
aaggtgacca agggtggccc cctgcccttc gcctgggaca tcctgtcccc tcagttcatg   4140
tacggctcca aggcctacgt gaagcacccc gccgacatcc ccgactactt gaagctgtcc   4200
ttccccgagg gcttcaagtg ggagcgcgtg atgaacttcg aggacggcgg cgtggtgacc   4260
gtgacccagg actcctccct gcaggacggc gagttcatct acaaggtgaa gctgcgcggc   4320
accaacttcc cctccgacgg ccccgtaatg cagaagaaga ccatgggctg ggaggcctcc   4380
tccgagcgga tgtaccccga ggacggcgcc ctgaagggcg agatcaagca gaggctgaag   4440
```

-continued ctgaaggacg gcggccacta cgacgctgag gtcaagacca cctacaaggc caagaagccc 4500
gtgcagctgc ccggcgccta caacgtcaac atcaagttgg acatcacctc ccacaacgag 4560
gactacacca tcgtggaaca gtacgaacgc gccgagggcc gccactccac cggcggcatg 4620
gacgagctgt acaagtaaac tagtaagctt ggcgtaacta gatcttgaga caaatggcag 4680
tattcatcca caattttaaa agaaaagggg ggattggggg gtacagtgca ggggaaagaa 4740
tagtagacat aatagcaaca gacatacaaa ctaaagaatt acaaaaacaa attacaaaaa 4800
ttcaaaattt tcgggtttat tacagggaca gcagagatcc actttgggct cgagggggcc 4860
cgggtgcaaa gatggataaa gttttaaaca gagaggaatc tttgcagcta atggaccttc 4920
taggtcttga aaggagtggg aattggctcc ggtgcccgtc agtgggcaga gcgcacatcg 4980
cccacagtcc ccgagaagtt ggggggaggg gtcggcaatt gatccggtgc ctagagaagg 5040
tggcgcgggg taaactggga aagtgatgtc gtgtactggc tccgcctttt tcccgagggt 5100
gggggagaac cgtatataag tgcagtagtc gccgtgaacg ttcttttttcg caacgggttt 5160 gccgccagaa cacaggtaag tgccgtgtgt ggttcccgcg ggcctggcct ctttacgggt 5220
tatggccctt gcgtgccttg aattacttcc acctggctgc agtacgtgat tcttgatccc 5280
gagcttcggg ttggaagtgg gtgggagagt tcgaggcctt gcgcttaagg agccccttcg 5340
cctcgtgctt gagttgaggc ctggcctggg cgctggggcc gccgcgtgcg aatctggtgg 5400
caccttcgcg cctgtctcgc tgctttcgat aagtctctag ccatttaaaa tttttgatga 5460
cctgctgcga cgcttttttt ctggcaagat agtcttgtaa atgcgggcca agatctgcac 5520
actggtattt cggtttttgg ggccgcgggc ggcgacgggg cccgtgcgtc ccagcgcaca 5580
tgttcggcga ggcggggcct gcgagcgcgg ccaccgagaa tcggacgggg gtagtctcaa 5640
gctggccggc ctgctctggt gcctggcctc gcgccgccgt gtatcgcccc gccctgggcg 5700
gcaaggctgg cccggtcggc accagttgcg tgagcggaaa gatggccgct tcccggccct 5760
gctgcaggga gctcaaaatg gaggacgcgg cgctcgggag agcgggcggg tgagtcaccc 5820
acacaaagga aaagggcctt tccgtcctca gccgtcgctt catgtgactc cacggagtac 5880
cgggcgccgt ccaggcacct cgattagttc tcgagctttt ggagtacgtc gtctttaggt 5940
tggggggagg ggttttatgc gatggagttt ccccacactg agtgggtgga gactgaagtt 6000
aggccagctt ggcacttgat gtaattctcc ttggaatttg ccctttttga gtttggatct 6060
tggttcattc tcaagcctca gacagtggtt caaagttttt ttcttccatt tcaggtgtcg 6120
tgacgtacgg ccaccatgac cgagtacaag cccacggtgc gcctcgccac ccgcgacgac 6180
gtccccaggg ccgtacgcac cctcgccgcc gcgttcgccg actaccccgc cacgcgccac 6240
accgtcgatc cggaccgcca catcgagcgg gtcaccgagc tgcaagaact cttcctcacg 6300
cgcgtcgggc tcgacatcgg caaggtgtgg gtcgcggacg acggcgccgc cgtggcggtc 6360
tggaccacgc cggagagcgt cgaagcgggg gcggtgttcg ccgagatcgg cccgcgcatg 6420
gccgagttga gcggttcccg gctggccgcg cagcaacaga tggaaggcct cctggcgccg 6480
caccggccca aggagcccgc gtggttcctg gccaccgtcg gagtctcgcc cgaccaccag 6540
ggcaagggtc tgggcagcgc cgtcgtgctc cccggagtgg aggcggccga gcgcgccggg 6600
gtgcccgcct tcctggagac ctccgcgccc cgcaacctcc ccttctacga gcggctcggc 6660
ttcaccgtca ccgccgacgt cgaggtgccc gaaggaccgc gcacctggtg catgacccgc 6720
aagcccggtg cctgaacgcg ttaagtcgac aatcaacctc tggattacaa aatttgtgaa 6780
agattgactg gtattcttaa ctatgttgct ccttttacgc tatgtggata cgctgcttta 6840
atgcctttgt atcatgctat tgcttcccgt atggctttca ttttctcctc cttgtataaa 6900
tcctggttgc tgtctcttta tgaggagttg tggcccgttg tcaggcaacg tggcgtggtg 6960
tgcactgtgt ttgctgacgc aacccccact ggttggggca ttgccaccac ctgtcagctc 7020
ctttccggga ctttcgcttt ccccctccct attgccacgg cggaactcat cgccgcctgc 7080
cttgcccgct gctggacagg ggctcggctg ttgggcactg acaattccgt ggtgttgtcg 7140
gggaaatcat cgtcctttcc ttggctgctc gcctgtgttg ccacctggat tctgcgcggg 7200
acgtccttct gctacgtccc ttcggccctc aatccagcgg accttccttc ccgcggcctg 7260
ctgccggctc tgcggcctct tccgcgtctt cgccttcgcc ctcagacgag tcggatctcc 7320
ctttgggccg cctccccgcg tcgactttaa gaccaatgac ttacaaggca gctgtagatc 7380
ttagccactt tttaaaagaa aaggggggac tggaagggct aattcactcc caacgaagac 7440
aagatctgct ttttgcttgt actgggtctc tctggttaga ccagatctga gcctgggagc 7500
tctctggcta actagggaac ccactgctta agcctcaata aagcttgcct tgagtgcttc 7560
aagtagtgtg tgcccgtctg ttgtgtgact ctggtaacta gagatccctc agaccctttt 7620
agtcagtgtg gaaaatctct agcagtacgt atagtagttc atgtcatctt attattcagt 7680
atttataact tgcaaagaaa tgaatatcag agagtgagag gaacttgttt attgcagctt 7740
ataatggtta caaataaagc aatagcatca caaatttcac aaataaagca tttttttcac 7800
tgcattctag ttgtggtttg tccaaactca tcaatgtatc ttatcatgtc tggctctagc 7860
tatcccgccc ctaactccgc ccatcccgcc cctaactccg cccagttccg cccattctcc 7920
gccccatggc tgactaattt tttttattta tgcagaggcc gaggccgcct cggcctctga 7980
gctattccag aagtagtgag gaggcttttt tggaggccta gggacgtacc caattcgccc 8040
tatagtgagt cgtattacgc gcgctcactg gccgtcgttt tacaacgtcg tgactgggaa 8100
aaccctggcg ttacccaact taatcgcctt gcagcacatc cccctttcgc cagctggcgt 8160
aatagcgaag aggcccgcac cgatcgccct tcccaacagt tgcgcagcct gaatggcgaa 8220
tgggacgcgc cctgtagcgg cgcattaagc gcggcgggtg tggtggttac gcgcagcgtg 8280
accgctacac ttgccagcgc cctagcgccc gctcctttcg ctttcttccc ttcctttctc 8340
gccacgttcg ccggctttcc ccgtcaagct ctaaatcggg ggctcccttt agggttccga 8400
tttagtgctt tacggcacct cgaccccaaa aaacttgatt agggtgatgg ttcacgtagt 8460
gggccatcgc cctgatagac ggtttttcgc cctttgacgt tggagtccac gttctttaat 8520
agtggactct tgttccaaac tggaacaaca ctcaacccta tctcggtcta ttcttttgat 8580
ttataaggga ttttgccgat ttcggcctat tggttaaaaa atgagctgat ttaacaaaaa 8640
tttaacgcga attttaacaa aatattaacg cttacaattt aggtggcact tttcggggaa 8700
atgtgcgcgg aacccctatt tgtttatttt tctaaataca ttcaaatatg tatccgctca 8760
tgagacaata accctgataa atgcttcaat aatattgaaa aaggaagagt atgagtattc 8820
aacatttccg tgtcgccctt attccctttt ttgcggcatt ttgccttcct gtttttgctc 8880
acccagaaac gctggtgaaa gtaaaagatg ctgaagatca gttgggtgca cgagtgggtt 8940
acatcgaact ggatctcaac agcggtaaga tccttgagag ttttcgcccc gaagaacgtt 9000
ttccaatgat gagcactttt aaagttctgc tatgtggcgc ggtattatcc cgtattgacg 9060
ccgggcaaga gcaactcggt cgccgcatac actattctca gaatgacttg gttgagtact 9120
caccagtcac agaaaagcat cttacggatg gcatgacagt aagagaatta tgcagtgctg 9180
ccataaccat gagtgataac actgcggcca acttacttct gacaacgatc ggaggaccga 9240
aggagctaac cgcttttttg cacaacatgg gggatcatgt aactcgcctt gatcgttggg 9300
aaccggagct gaatgaagcc ataccaaacg acgagcgtga caccacgatg cctgtagcaa 9360
tggcaacaac gttgcgcaaa ctattaactg gcgaactact tactctagct tcccggcaac 9420
aattaataga ctggatggag gcggataaag ttgcaggacc acttctgcgc tcggcccttc 9480
cggctggctg gtttattgct gataaatctg gagccggtga gcgtgggtct cgcggtatca 9540
ttgcagcact ggggccagat ggtaagccct cccgtatcgt agttatctac acgacgggga 9600
gtcaggcaac tatggatgaa cgaaatagac agatcgctga gataggtgcc tcactgatta 9660
agcattggta actgtcagac caagtttact catatatact ttagattgat ttaaaacttc 9720
atttttaatt taaaaggatc taggtgaaga tcctttttga taatctcatg accaaaatcc 9780
cttaacgtga gttttcgttc cactgagcgt cagaccccgt agaaaagatc aaaggatctt 9840
cttgagatcc tttttttctg cgcgtaatct gctgcttgca aacaaaaaaa ccaccgctac 9900
cagcggtggt ttgtttgccg gatcaagagc taccaactct ttttccgaag gtaactggct 9960
tcagcagagc gcagatacca aatactgttc ttctagtgta gccgtagtta ggccaccact 10020
tcaagaactc tgtagcaccg cctacatacc tcgctctgct aatcctgtta ccagtggctg 10080
ctgccagtgg cgataagtcg tgtcttaccg ggttggactc aagacgatag ttaccggata 10140
aggcgcagcg gtcgggctga acggggggtt cgtgcacaca gcccagcttg gagcgaacga 10200
cctacaccga actgagatac ctacagcgtg agctatgaga aagcgccacg cttcccgaag 10260
ggagaaaggc ggacaggtat ccggtaagcg gcagggtcgg aacaggagag cgcacgaggg 10320
agcttccagg gggaaacgcc tggtatcttt atagtcctgt cgggtttcgc cacctctgac 10380
ttgagcgtcg atttttgtga tgctcgtcag gggggcggag cctatggaaa aacgccagca 10440
acgcggcctt tttacggttc ctggcctttt gctggccttt tgctcacatg ttctttcctg 10500
cgttatcccc tgattctgtg gataaccgta ttaccgcctt tgagtgagct gataccgctc 10560
gccgcagc 10568

<210> SEQ ID NO 71
<211> LENGTH: 5051
<212> TYPE: DNA
<213> ORGANISM: Artificial
<220> FEATURE:
<223> OTHER INFORMATION: Synthetic

<400> SEQUENCE: 71
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gactagttat taatagtaat caattacggg 180
gtcattagtt catagcccat atatggagtt ccgcgttaca taacttacgg taaatggccc 240
gcctggctga ccgcccaacg acccccgccc attgacgtca ataatgacgt atgttcccat 300
agtaacgcca atagggactt tccattgacg tcaatgggtg gagtatttac ggtaaactgc 360
ccacttggca gtacatcaag tgtatcatat gccaagtccg ccccctattg acgtcaatga 420
cggtaaatgg cccgcctggc attatgccca gtacatgacc ttacgggact ttcctacttg 480
gcagtacatc tacgtattag tcatcgctat taccatggtg atgcggtttt ggcagtacac 540
caatgggcgt ggatagcggt ttgactcacg gggatttcca agtctccacc ccattgacgt 600
caatgggagt ttgttttggc accaaaatca acgggacttt ccaaaatgtc gtaataaccc 660

```
cgccccgttg acgcaaatgg gcggtaggcg tgtacggtgg gaggtctata taagcagagc    720
tggtttagtg aaccgtcaga tcactagaag ctttattgcg gtagtttatc acagttaaat    780
tgctaacgca gtcagtgctt ctgacacaac agtctcgaac ttaagctgca gaagttggtc    840
gtgaggcact gggcaggtaa gtatcaaggt tacaagacag gtttaaggag accaatagaa    900
actgggcttg tcgagacaga gaagactctt gcgtttctga taggcaccta ttggtcttac    960
tgacatccac tttgcctttc tctccacagg tgtccactcc cagttcaatt acagctctta   1020
aggctagagt attaatacga ctcactatag ggctagcgat cgccatggaa taagtaagga   1080
atccacatgg cacaggttat caacacgttt gacggggttg cggattatct tcagacatat   1140
cataagctac ctgataatta cattacaaaa tcagaagcac aagccctcgg ctgggtggca   1200
tcaaaaggga accttgcaga cgtcgctccg ggaaaagca tcggcggaga catcttctca    1260
aacagggaag gcaaactccc gggcaaaagc ggacgaacat ggcgtgaagc ggatattaac   1320
tatacatcag gcttcagaaa ttcagaccgg attctttact caagcgactg gctgatttac   1380
aaaacaacgg accattatca gacctttaca aaaatcagat aatgtttaat gaccccgtgt   1440
cgagctctcg agccaaccac tgaggatctg tactttcaga gcgataacga tggatccgaa   1500
atcggtactg gctttccatt cgaccccat tatgtggaag tcctgggcga gcgcatgcac    1560
tacgtcgatg ttggtccgcg cgatggcacc cctgtgctgt tcctgcacgg taacccgacc   1620
tcctcctacg tgtggcgcaa catcatcccg catgttgcac cgacccatcg ctgcattgct   1680
ccagacctga tcggtatggg caaatccgac aaaccagacc tgggttattt cttcgacgac   1740
cacgtccgct tcatggatgc cttcatcgaa gccctgggtc tggaagaggt cgtcctggtc   1800
attcacgact ggggctccgc tctgggtttc cactgggcca agcgcaatcc agagcgcgtc   1860
aaaggtattg catttatgga gttcatccgc cctatcccga cctgggacga atggccagaa   1920
tttgcccgcg agaccttcca ggccttccgc accaccgacg tcggccgcaa gctgatcatc   1980
gatcagaacg tttttatcga gggtacgctg ccgatgggtg tcgtccgccc gctgactgaa   2040
gtcgagatgg accattaccg cgagccgttc ctgaatcctg ttgaccgcga gccactgtgg   2100
cgcttcccaa acgagctgcc aatcgccggt gagccagcga acatcgtcgc gctggtcgaa   2160
gaatacatgg actggctgca ccagtcccct gtcccgaagc tgctgttctg gggcacccca   2220
ggcgttctga tcccaccggc cgaagccgct cgcctggcca aaagcctgcc taactgcaag   2280
gctgtggaca tcggcccggg tctgaatctg ctgcaagaag acaacccgga cctgatcggc   2340
agcgagatcg cgcgctggct gtctactctg gagatttccg gttaatagaa ttctagagtc   2400
gacctgcagg catgcaagct gatccggctg ctaacaaagc ccgaaaggaa gctgagttgg   2460
ctgctgccac cgctgagcaa taactagcat aaccccttgg ggcggccgct tcgagcagac   2520
atgataagat acattgatga gtttggacaa accacaacta gaatgcagtg aaaaaaatgc   2580
tttatttgtg aaatttgtga tgctattgct ttatttgtaa ccattataag ctgcaataaa   2640
caagttaaca acaacaattg cattcatttt atgtttcagg ttcaggggga gatgtgggag   2700
gtttttttaa gcaagtaaaa cctctacaaa tgtggtaaaa tcgaattcta atggatcctc   2760
tttgcgcttg cgttttccct tgtccagata gcccagtagc tgacattcat ccggggtcag   2820
caccgtttct gcggactggc tttctacgtg ttccgcttcc tttagcagcc cttgcgccct   2880
gagtgcttgc ggcagcgtga gcttcaaaag aattgccagc tggggcgccc tctggtaagg   2940
ttgggaagcc ctgcaaagta aactggatgg ctttcttgcc gccaaggatc tgatggcgca   3000
```

-continued

```
ggggatcaag atctgatcaa gagacaggat gacggtcgtt tcgcatgctt gaacaagatg   3060

gattgcacgc aggttctccg gccgcttggg tggagaggct attcggctat gactgggcac   3120

aacagacaat cggctgctct gatgccgccg tgttccggct gtcagcgcag gggcgcccgg   3180

ttctttttgt caagaccgac ctgtccggtg ccctgaatga actgcaggac gaggcagcgc   3240

ggctatcgtg gctggccacg acgggcgttc cttgcgcagc tgtgctcgac gttgtcactg   3300

aagcgggaag ggactggctg ctattgggcg aagtgccggg gcaggatctc ctgtcatctc   3360

accttgctcc tgccgagaaa gtatccatca tggctgatgc aatgcggcgg ctgcatacgc   3420

ttgatccggc tacctgccca ttcgaccacc aagcgaaaca tcgcatcgag cgagcacgca   3480

ctcggatgga agccggtctt gtcgatcagg atgatctgga cgaagagcat caggggctcg   3540

cgccagccga actgttcgcc aggctcaagg cgcgtatgcc ggatggtgag gatctcgtcg   3600

tgactcatgg cgatgcctgc ttgccgaata tcatggtgga aaatggccgc ttttctggat   3660

tcatcgactg tggccggctg ggtgtggcgg accgctatca ggacatagcg ttggctaccc   3720

gtgatattgc tgaagagctt ggcggcgaat gggctgaccg cttcctcgtg ctttacggta   3780

tcgccgctcc cgattcgcag cgcatcgcct tctatcgcct tcttgacgag ttcttctgag   3840

cgggactctg gggttcgaaa tgaccgacca agcgacgccc aaccggtatc agctcactca   3900

aaggcggtaa tacggttatc cacagaatca ggggataacg caggaaagaa catgtgagca   3960

aaaggccagc aaaaggccag gaaccgtaaa aaggccgcgt tgctggcgtt tttccatagg   4020

ctccgccccc ctgacgagca tcacaaaaat cgacgctcaa gtcagaggtg gcgaaacccg   4080

acaggactat aaagatacca ggcgtttccc cctggaagct ccctcgtgcg ctctcctgtt   4140

ccgaccctgc cgcttaccgg atacctgtcc gcctttctcc cttcgggaag cgtggcgctt   4200

tctcatagct cacgctgtag gtatctcagt tcggtgtagg tcgttcgctc caagctgggc   4260

tgtgtgcacg aaccccccgt tcagcccgac cgctgcgcct tatccggtaa ctatcgtctt   4320

gagtccaacc cggtaagaca cgacttatcg ccactggcag cagccactgg taacaggatt   4380

agcagagcga ggtatgtagg cggtgctaca gagttcttga agtggtggcc taactacggc   4440

tacactagaa ggacagtatt tggtatctgc gctctgctga agccagttac cttcggaaaa   4500

agagttggta gctcttgatc cggcaaacaa accaccgctg gtagcggtgg tttttttgtt   4560

tgcaagcagc agattacgcg cagaaaaaaa ggatttcaag aagatccttt gatcttttct   4620

acggggtctg acgctcagtg gaacgaaaac tcacgttaag ggattttggt catgagatta   4680

tcaaaaagga tcttcaccta gatcctttta tagtccggaa atacaggaac gcacgctgga   4740

tggcccttcg ctgggatggt gaaaccatga aaaatggcag cttcagtgga ttaagtgggg   4800

gtaatgtggc ctgtaccctc tggttgcata ggtattcata cggttaaaat ttatcaggcg   4860

cgattgcggc agtttttcgg gtggtttgtt gccattttta cctgtctgct gccgtgatcg   4920

cgctgaacgc gttttagcgg tgcgtacaat taagggatta tggtaaatcc acttactgtc   4980

tgccctcgta gccatcgaga taaaccgcag tactccggcc acgatgcgtc cggcgtagag   5040

gatcgagatc t                                                        5051
```

<210> SEQ ID NO 72
<211> LENGTH: 5119
<212> TYPE: DNA
<213> ORGANISM: Artificial
<220> FEATURE:
<223> OTHER INFORMATION: Synthetic

<400> SEQUENCE: 72

-continued

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg ccccctattg acgtcaatga    420
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaataaccc    660
cgccccgttg acgcaaatgg gcggtaggcg tgtacggtgg gaggtctata taagcagagc    720
tggtttagtg aaccgtcaga tcactagaag ctttattgcg gtagtttatc acagttaaat    780
tgctaacgca gtcagtgctt ctgacacaac agtctcgaac ttaagctgca gaagttggtc    840
gtgaggcact gggcaggtaa gtatcaaggt tacaagacag gtttaaggag accaatagaa    900
actgggcttg tcgagacaga gaagactctt gcgtttctga taggcaccta ttggtcttac    960
tgacatccac tttgcctttc tctccacagg tgtccactcc cagttcaatt acagctctta   1020
aggctagagt attaatacga ctcactatag ggctagcgat cgccatggaa taagtaagga   1080
atccacatgg cacaggttat caacacgttt gacggggttg cggattatct tcagacatat   1140
cataagctac ctgataatta cattacaaaa tcagaagcac aagccctcgg ctgggtggca   1200
tcaaaaggga accttgcaga cgtcgctccg ggaaaaagca tcggcggaga catcttctca   1260
aacagggaag gcaaactccc gggcaaaagc ggacgaacat ggcgtgaagc ggatattaac   1320
tatacatcag gcttcagaaa ttcagaccgg attctttact caagcgactg gctgatttac   1380
aaaacaacgg accattatca gacctttaca aaaatcagat aatgtttaat gaccccgtgt   1440
cgagctctcg gctcgagcgg cgtcttcaca ctcgaagatt tcgttgggga ctggcgacag   1500
acagccggct acaacctgga ccaagtcctt gaacagggag gtgtgtccag tttgtttcag   1560
aatctcgggg tgtccgtaac tccgatccaa aggattgtcc tgagcggtga aaatgggctg   1620
aagatcgaca tccatgtcat catcccgtat gaaggtctga gcggcgacca aatgggccag   1680
atcgaaaaaa tttttaaggt ggtgtaccct gtggatgatc atcactttaa ggtgatcctg   1740
cactatggca cactggtaat cgacggggtt acgccgaaca tgatcgacta tttcggacgg   1800
ccgtatgaag gcatcgccgt gttcgacggc aaaaagatca ctgtaacagg gaccctgtgg   1860
aacggcaaca aaattatcga cgagcgcctg atcaaccccg acggctccct gctgttccga   1920
gtaaccatca acggagtgac cggctggcgg ctgtgcgaac gcattctggc gtaaggccgc   1980
gactctagag tcgacctgca ggcatgcaag ctgatccggc tgctaacaaa gcccgaaagg   2040
aagctgagtt ggctgctgcc accgctgagc aataactagc ataacccctt ggggcggccg   2100
cttcgagcag acatgataag atacattgat gagtttggac aaaccacaac tagaatgcag   2160
tgaaaaaaat gctttatttg tgaaatttgt gatgctattg ctttatttgt aaccattata   2220
agctgcaata aacaagttaa caacaacaat tgcattcatt ttatgtttca ggttcagggg   2280
gagatgtggg aggtttttt aagcaagtaa aacctctaca aatgtggtaa aatcgaattt   2340
```

-continued

```
taacaaaata ttaacgctta caatttcctg atgcggtatt ttctccttac gcatctgtgc   2400
ggtatttcac accgcatacg cggatctgcg cagcaccatg gcctgaaata acctctgaaa   2460
gaggaacttg gttaggtacc ttctgaggcg gaaagaacca gctgtggaat gtgtgtcagt   2520
tagggtgtgg aaagtcccca ggctccccag caggcagaag tatgcaaagc atgcatctca   2580
attagtcagc aaccaggtgt ggaaagtccc caggctcccc agcaggcaga agtatgcaaa   2640
gcatgcatct caattagtca gcaaccatag tcccgcccct aactccgccc atcccgcccc   2700
taactccgcc cagttccgcc cattctccgc cccatggctg actaattttt tttatttatg   2760
cagaggccga ggccgcctcg gcctctgagc tattccagaa gtagtgagga ggcttttttg   2820
gaggcctagg cttttgcaaa aagcttaatt aactgttgac aattaatcat cggcatagta   2880
tatcggcata gtataatacg acaaggtgag gaactaaacc caggaggcag atcatgattg   2940
aacaagatgg attgcacgca ggttctccgg ccgcttgggt ggagaggcta ttcggctatg   3000
actgggcaca acagacaatc ggctgctctg atgccgccgt gttccggctg tcagcgcagg   3060
ggcgcccggt tctttttgtc aagaccgacc tgtccggtgc cctgaatgaa ctgcaggacg   3120
aggcagcgcg gctatcgtgg ctggccacga cgggcgttcc ttgcgcagct gtgctcgacg   3180
ttgtcactga agcgggaagg gactggctgc tattgggcga agtgccgggg caggatctcc   3240
tgtcatctca ccttgctcct gccgagaaag tatccatcat ggctgatgca atgcggcggc   3300
tgcatacgct tgatccggct acctgcccat tcgaccacca agcgaaacat cgcatcgagc   3360
gagcacgtac tcggatggaa gccggtcttg tcgatcagga tgatctggac gaagagcatc   3420
aggggctcgc gccagccgaa ctgttcgcca ggctcaaggc gcgcatgccc gacggcgagg   3480
atctcgtcgt gacccatggc gatgcctgct tgccgaatat catggtggaa aatggccgct   3540
tttctggatt catcgactgt ggccggctgg gtgtggcgga ccgctatcag gacatagcgt   3600
tggctacccg tgatattgct gaagagcttg gcggcgaatg ggctgaccgc ttcctcgtgc   3660
tttacggtat cgccgctccc gattcgcagc gcatcgcctt ctatcgcctt cttgacgagt   3720
tcttctgagc gggactctgg ggttcgaaat gaccgaccaa gcgacgccca acctgccatc   3780
acgatggccg caataaaata tctttatttt cattacatct gtgtgttggt tttttgtgtg   3840
aatcgatagc gataaggatc ctctttgcgc ttgcgttttc ccttgtccag atagcccagt   3900
agctgacatt catccggggt cagcaccgtt tctgcggact ggctttctac ccggtatcag   3960
ctcactcaaa ggcggtaata cggttatcca cagaatcagg ggataacgca ggaaagaaca   4020
tgtgagcaaa aggccagcaa aaggccagga accgtaaaaa ggccgcgttg ctggcgtttt   4080
tccataggct ccgcccccct gacgagcatc acaaaaatcg acgctcaagt cagaggtggc   4140
gaaacccgac aggactataa agataccagg cgtttccccc tggaagctcc ctcgtgcgct   4200
ctcctgttcc gaccctgccg cttaccggat acctgtccgc ctttctccct tcgggaagcg   4260
tggcgctttc tcatagctca cgctgtaggt atctcagttc ggtgtaggtc gttcgctcca   4320
agctgggctg tgtgcacgaa ccccccgttc agcccgaccg ctgcgcctta tccggtaact   4380
atcgtcttga gtccaacccg gtaagacacg acttatcgcc actggcagca gccactggta   4440
acaggattag cagagcgagg tatgtaggcg gtgctacaga gttcttgaag tggtggccta   4500
actacggcta cactagaagg acagtatttg gtatctgcgc tctgctgaag ccagttacct   4560
tcggaaaaag agttggtagc tcttgatccg gcaaacaaac caccgctggt agcggtggtt   4620
tttttgtttg caagcagcag attacgcgca gaaaaaaagg atttcaagaa gatcctttga   4680
tcttttctac ggggtctgac gctcagtgga acgaaaactc acgttaaggg attttggtca   4740
```

```
tgagattatc aaaaaggatc ttcacctaga tccttttata gtccggaaat acaggaacgc   4800

acgctggatg gcccttcgct gggatggtga aaccatgaaa aatggcagct tcagtggatt   4860

aagtgggggt aatgtggcct gtaccctctg gttgcatagg tattcatacg gttaaaattt   4920

atcaggcgcg attgcggcag tttttcgggt ggtttgttgc catttttacc tgtctgctgc   4980

cgtgatcgcg ctgaacgcgt tttagcggtg cgtacaatta agggattatg gtaaatccac   5040

ttactgtctg ccctcgtagc catcgagata aaccgcagta ctccggccac gatgcgtccg   5100

gcgtagagga tcgagatct                                                5119


<210> SEQ ID NO 73
<211> LENGTH: 439
<212> TYPE: PRT
<213> ORGANISM: Artificial
<220> FEATURE:
<223> OTHER INFORMATION: Synthetic

<400> SEQUENCE: 73

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Ile Glu
            260                 265                 270

Val Met Tyr Pro Pro Pro Tyr Leu Asp Asn Glu Lys Ser Asn Gly Thr
        275                 280                 285
```

-continued

```
Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Ser Gly Phe Asn Val Leu Met
    370                 375                 380

Val His Lys Arg Ser His Thr Gly Glu Arg Pro Phe Gln Cys Asn Gln
385                 390                 395                 400

Cys Gly Ala Ser Phe Thr Gln Lys Gly Asn Leu Leu Arg His Ile Lys
                405                 410                 415

Leu His Thr Gly Glu Lys Pro Phe Lys Cys His Leu Cys Asn Tyr Ala
            420                 425                 430

Cys Gln Arg Arg Asp Ala Leu
        435


<210> SEQ ID NO 74
<211> LENGTH: 439
<212> TYPE: PRT
<213> ORGANISM: Artificial
<220> FEATURE:
<223> OTHER INFORMATION: Synthetic

<400> SEQUENCE: 74

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205
```

```
Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Ile Glu
            260                 265                 270

Val Met Tyr Pro Pro Pro Tyr Leu Asp Asn Glu Lys Ser Asn Gly Thr
        275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Arg Arg Ser Arg Leu Leu His Ser Asp Tyr Met Asn Met Thr
            340                 345                 350

Pro Arg Arg Pro Gly Pro Thr Arg Arg His Tyr Gln Pro Tyr Ala Pro
        355                 360                 365

Pro Arg Asp Phe Ala Ala Tyr Arg Ser Ser Gly Phe Asn Val Leu Met
    370                 375                 380

Val His Arg Arg Ser His Thr Gly Glu Arg Pro Phe Gln Cys Asn Gln
385                 390                 395                 400

Cys Gly Ala Ser Phe Thr Gln Arg Gly Asn Leu Leu Arg His Ile Arg
                405                 410                 415

Leu His Thr Gly Glu Arg Pro Phe Arg Cys His Leu Cys Asn Tyr Ala
            420                 425                 430

Cys Gln Arg Arg Asp Ala Leu
        435


<210> SEQ ID NO 75
<211> LENGTH: 522
<212> TYPE: PRT
<213> ORGANISM: Artificial
<220> FEATURE:
<223> OTHER INFORMATION: Synthetic

<400> SEQUENCE: 75

Met Ala Leu Pro Val Thr Ala Leu Leu Leu Pro Leu Ala Leu Leu Leu
1               5                   10                  15

His Ala Ala Arg Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Phe Ala
    50                  55                  60

Cys Asp Ile Tyr Ile Trp Ala Pro Leu Ala Gly Thr Cys Gly Val Leu
65                  70                  75                  80

Leu Leu Ser Leu Val Ile Thr Leu Tyr Cys Arg Ser Lys Arg Ser Arg
                85                  90                  95

Leu Leu His Ser Asp Tyr Met Asn Met Thr Pro Arg Arg Pro Gly Pro
            100                 105                 110

Thr Arg Lys His Tyr Gln Pro Tyr Ala Pro Pro Arg Asp Phe Ala Ala
        115                 120                 125
```

Tyr Arg Ser Gly Gly Gly Gly Ser Ala Gly Glu Gly Asp Gln Gln Asp
130 135 140

Ala Ala His Asn Met Gly Asn His Leu Pro Leu Leu Pro Glu Ser Glu
145 150 155 160

Glu Glu Asp Glu Met Glu Val Glu Asp Gln Asp Ser Lys Glu Ala Lys
165 170 175

Lys Pro Asn Ile Ile Asn Phe Asp Thr Ser Leu Pro Thr Ser His Thr
180 185 190

Tyr Leu Gly Ala Asp Met Glu Glu Phe His Gly Arg Thr Leu His Asp
195 200 205

Asp Asp Ser Cys Gln Val Ile Pro Val Leu Pro Gln Val Met Met Ile
210 215 220

Leu Ile Pro Gly Gln Thr Leu Pro Leu Gln Leu Phe His Pro Gln Glu
225 230 235 240

Val Ser Met Val Arg Asn Leu Ile Gln Lys Asp Arg Thr Phe Ala Val
245 250 255

Leu Ala Tyr Ser Asn Val Gln Glu Arg Glu Ala Gln Phe Gly Thr Thr
260 265 270

Ala Glu Ile Tyr Ala Tyr Arg Glu Glu Gln Asp Phe Gly Ile Glu Ile
275 280 285

Val Lys Val Lys Ala Ile Gly Arg Gln Arg Phe Lys Val Leu Glu Leu
290 295 300

Arg Thr Gln Ser Asp Gly Ile Gln Gln Ala Lys Val Gln Ile Leu Pro
305 310 315 320

Glu Cys Val Leu Pro Ser Thr Tyr Asp Ala Glu Thr Leu Met Asp Arg
325 330 335

Ile Lys Lys Gln Leu Arg Glu Trp Asp Glu Asn Leu Lys Asp Asp Ser
340 345 350

Leu Pro Ser Asn Pro Ile Asp Phe Ser Tyr Arg Val Ala Ala Cys Leu
355 360 365

Pro Ile Asp Asp Val Leu Arg Ile Gln Leu Leu Lys Ile Gly Ser Ala
370 375 380

Ile Gln Arg Leu Arg Cys Glu Leu Asp Ile Met Asn Lys Cys Thr Ser
385 390 395 400

Leu Cys Cys Lys Gln Cys Gln Glu Thr Glu Ile Thr Thr Lys Asn Glu
405 410 415

Ile Phe Ser Leu Ser Leu Cys Gly Pro Met Ala Ala Tyr Val Asn Pro
420 425 430

His Gly Tyr Val His Glu Thr Leu Thr Val Tyr Lys Ala Cys Asn Leu
435 440 445

Asn Leu Ile Gly Arg Pro Ser Thr Glu His Ser Trp Phe Pro Gly Tyr
450 455 460

Ala Trp Thr Val Ala Gln Cys Lys Ile Cys Ala Ser His Ile Gly Trp
465 470 475 480

Lys Phe Thr Ala Thr Lys Lys Asp Met Ser Pro Gln Lys Phe Trp Gly
485 490 495

Leu Thr Arg Ser Ala Leu Leu Pro Thr Ile Pro Asp Thr Glu Asp Glu
500 505 510

Ile Ser Pro Asp Lys Val Ile Leu Cys Leu
515 520

<210> SEQ ID NO 76
<211> LENGTH: 453
<212> TYPE: PRT

<213> ORGANISM: Artificial
<220> FEATURE:
<223> OTHER INFORMATION: Synthetic

<400> SEQUENCE: 76

```
Met Gly Cys Ile Lys Ser Lys Arg Lys Asp Asn Leu Asn Asp Asp Gly
1               5                   10                  15

Val Asp Met Lys Thr Arg Ser Lys Arg Ser Arg Leu Leu His Ser Asp
            20                  25                  30

Tyr Met Asn Met Thr Pro Arg Arg Pro Gly Pro Thr Arg Lys His Tyr
        35                  40                  45

Gln Pro Tyr Ala Pro Pro Arg Asp Phe Ala Ala Tyr Arg Ser Gly Gly
    50                  55                  60

Gly Gly Ser Ala Gly Glu Gly Asp Gln Gln Asp Ala Ala His Asn Met
65                  70                  75                  80

Gly Asn His Leu Pro Leu Leu Pro Glu Ser Glu Glu Glu Asp Glu Met
                85                  90                  95

Glu Val Glu Asp Gln Asp Ser Lys Glu Ala Lys Lys Pro Asn Ile Ile
            100                 105                 110

Asn Phe Asp Thr Ser Leu Pro Thr Ser His Thr Tyr Leu Gly Ala Asp
        115                 120                 125

Met Glu Glu Phe His Gly Arg Thr Leu His Asp Asp Asp Ser Cys Gln
    130                 135                 140

Val Ile Pro Val Leu Pro Gln Val Met Met Ile Leu Ile Pro Gly Gln
145                 150                 155                 160

Thr Leu Pro Leu Gln Leu Phe His Pro Gln Glu Val Ser Met Val Arg
                165                 170                 175

Asn Leu Ile Gln Lys Asp Arg Thr Phe Ala Val Leu Ala Tyr Ser Asn
            180                 185                 190

Val Gln Glu Arg Glu Ala Gln Phe Gly Thr Thr Ala Glu Ile Tyr Ala
        195                 200                 205

Tyr Arg Glu Glu Gln Asp Phe Gly Ile Glu Ile Val Lys Val Lys Ala
    210                 215                 220

Ile Gly Arg Gln Arg Phe Lys Val Leu Glu Leu Arg Thr Gln Ser Asp
225                 230                 235                 240

Gly Ile Gln Gln Ala Lys Val Gln Ile Leu Pro Glu Cys Val Leu Pro
                245                 250                 255

Ser Thr Tyr Asp Ala Glu Thr Leu Met Asp Arg Ile Lys Lys Gln Leu
            260                 265                 270

Arg Glu Trp Asp Glu Asn Leu Lys Asp Asp Ser Leu Pro Ser Asn Pro
        275                 280                 285

Ile Asp Phe Ser Tyr Arg Val Ala Ala Cys Leu Pro Ile Asp Asp Val
    290                 295                 300

Leu Arg Ile Gln Leu Leu Lys Ile Gly Ser Ala Ile Gln Arg Leu Arg
305                 310                 315                 320

Cys Glu Leu Asp Ile Met Asn Lys Cys Thr Ser Leu Cys Cys Lys Gln
                325                 330                 335

Cys Gln Glu Thr Glu Ile Thr Thr Lys Asn Glu Ile Phe Ser Leu Ser
            340                 345                 350

Leu Cys Gly Pro Met Ala Ala Tyr Val Asn Pro His Gly Tyr Val His
        355                 360                 365

Glu Thr Leu Thr Val Tyr Lys Ala Cys Asn Leu Asn Leu Ile Gly Arg
    370                 375                 380

Pro Ser Thr Glu His Ser Trp Phe Pro Gly Tyr Ala Trp Thr Val Ala
```

-continued

```
385                 390                 395                 400

Gln Cys Lys Ile Cys Ala Ser His Ile Gly Trp Lys Phe Thr Ala Thr
                405                 410                 415

Lys Lys Asp Met Ser Pro Gln Lys Phe Trp Gly Leu Thr Arg Ser Ala
            420                 425                 430

Leu Leu Pro Thr Ile Pro Asp Thr Glu Asp Glu Ile Ser Pro Asp Lys
        435                 440                 445

Val Ile Leu Cys Leu
    450


<210> SEQ ID NO 77
<211> LENGTH: 555
<212> TYPE: PRT
<213> ORGANISM: Artificial
<220> FEATURE:
<223> OTHER INFORMATION: Synthetic

<400> SEQUENCE: 77

Met Ala Leu Pro Val Thr Ala Leu Leu Leu Pro Leu Ala Leu Leu Leu
1               5                   10                  15

His Ala Ala Arg Pro Glu Arg Arg Ala Glu Val Pro Thr Ala His Pro
            20                  25                  30

Ser Pro Ser Pro Arg Pro Ala Gly Gln Phe Gln Thr Leu Val Val Gly
        35                  40                  45

Val Val Gly Gly Leu Leu Gly Ser Leu Val Leu Leu Val Trp Val Leu
    50                  55                  60

Ala Val Ile Cys Ser Arg Ala Ala Arg Gly Thr Ile Gly Ala Arg Arg
65                  70                  75                  80

Thr Gly Gln Pro Leu Lys Glu Asp Pro Ser Ala Val Pro Val Phe Ser
                85                  90                  95

Val Asp Phe Gly Glu Leu Asp Phe Gln Trp Arg Glu Lys Thr Pro Glu
            100                 105                 110

Pro Pro Val Pro Cys Val Pro Glu Gln Thr Glu Phe Ala Thr Ile Val
        115                 120                 125

Phe Pro Ser Gly Met Gly Thr Ser Ser Pro Ala Arg Arg Gly Ser Ala
    130                 135                 140

Asp Gly Pro Arg Ser Ala Gln Pro Leu Arg Pro Glu Asp Gly His Cys
145                 150                 155                 160

Ser Trp Pro Leu Gly Gly Gly Gly Ser Ala Gly Glu Gly Asp Gln Gln
                165                 170                 175

Asp Ala Ala His Asn Met Gly Asn His Leu Pro Leu Leu Pro Glu Ser
            180                 185                 190

Glu Glu Glu Asp Glu Met Glu Val Glu Asp Gln Asp Ser Lys Glu Ala
        195                 200                 205

Lys Lys Pro Asn Ile Ile Asn Phe Asp Thr Ser Leu Pro Thr Ser His
    210                 215                 220

Thr Tyr Leu Gly Ala Asp Met Glu Glu Phe His Gly Arg Thr Leu His
225                 230                 235                 240

Asp Asp Asp Ser Cys Gln Val Ile Pro Val Leu Pro Gln Val Met Met
                245                 250                 255

Ile Leu Ile Pro Gly Gln Thr Leu Pro Leu Gln Leu Phe His Pro Gln
            260                 265                 270

Glu Val Ser Met Val Arg Asn Leu Ile Gln Lys Asp Arg Thr Phe Ala
        275                 280                 285

Val Leu Ala Tyr Ser Asn Val Gln Glu Arg Glu Ala Gln Phe Gly Thr
```

```
    290                 295                 300

Thr Ala Glu Ile Tyr Ala Tyr Arg Glu Glu Gln Asp Phe Gly Ile Glu
305                 310                 315                 320

Ile Val Lys Val Lys Ala Ile Gly Arg Gln Arg Phe Lys Val Leu Glu
                325                 330                 335

Leu Arg Thr Gln Ser Asp Gly Ile Gln Gln Ala Lys Val Gln Ile Leu
            340                 345                 350

Pro Glu Cys Val Leu Pro Ser Thr Tyr Asp Ala Glu Thr Leu Met Asp
        355                 360                 365

Arg Ile Lys Lys Gln Leu Arg Glu Trp Asp Glu Asn Leu Lys Asp Asp
    370                 375                 380

Ser Leu Pro Ser Asn Pro Ile Asp Phe Ser Tyr Arg Val Ala Ala Cys
385                 390                 395                 400

Leu Pro Ile Asp Asp Val Leu Arg Ile Gln Leu Leu Lys Ile Gly Ser
                405                 410                 415

Ala Ile Gln Arg Leu Arg Cys Glu Leu Asp Ile Met Asn Lys Cys Thr
            420                 425                 430

Ser Leu Cys Cys Lys Gln Cys Gln Glu Thr Glu Ile Thr Thr Lys Asn
        435                 440                 445

Glu Ile Phe Ser Leu Ser Leu Cys Gly Pro Met Ala Ala Tyr Val Asn
    450                 455                 460

Pro His Gly Tyr Val His Glu Thr Leu Thr Val Tyr Lys Ala Cys Asn
465                 470                 475                 480

Leu Asn Leu Ile Gly Arg Pro Ser Thr Glu His Ser Trp Phe Pro Gly
                485                 490                 495

Tyr Ala Trp Thr Val Ala Gln Cys Lys Ile Cys Ala Ser His Ile Gly
            500                 505                 510

Trp Lys Phe Thr Ala Thr Lys Lys Asp Met Ser Pro Gln Lys Phe Trp
        515                 520                 525

Gly Leu Thr Arg Ser Ala Leu Leu Pro Thr Ile Pro Asp Thr Glu Asp
    530                 535                 540

Glu Ile Ser Pro Asp Lys Val Ile Leu Cys Leu
545                 550                 555


<210> SEQ ID NO 78
<211> LENGTH: 635
<212> TYPE: PRT
<213> ORGANISM: Artificial
<220> FEATURE:
<223> OTHER INFORMATION: Synthetic

<400> SEQUENCE: 78

Met Ala Leu Pro Val Thr Ala Leu Leu Leu Pro Leu Ala Leu Leu Leu
1               5                   10                  15

His Ala Ala Arg Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Phe Ala
    50                  55                  60

Cys Asp Ile Tyr Ile Trp Ala Pro Leu Ala Gly Thr Cys Gly Val Leu
65                  70                  75                  80

Leu Leu Ser Leu Val Ile Thr Leu Tyr Cys Arg Ser Lys Arg Ser Arg
                85                  90                  95

Leu Leu His Ser Asp Tyr Met Asn Met Thr Pro Arg Arg Pro Gly Pro
```

-continued

```
            100                 105                 110

Thr Arg Lys His Tyr Gln Pro Tyr Ala Pro Pro Arg Asp Phe Ala Ala
        115                 120                 125

Tyr Arg Ser Gly Gly Gly Gly Ser Ala Gly Glu Gly Asp Gln Gln Asp
    130                 135                 140

Ala Ala His Asn Met Gly Asn His Leu Pro Leu Leu Pro Glu Ser Glu
145                 150                 155                 160

Glu Glu Asp Glu Met Glu Val Glu Asp Gln Asp Ser Lys Glu Ala Lys
                165                 170                 175

Lys Pro Asn Ile Ile Asn Phe Asp Thr Ser Leu Pro Thr Ser His Thr
            180                 185                 190

Tyr Leu Gly Ala Asp Met Glu Glu Phe His Gly Arg Thr Leu His Asp
        195                 200                 205

Asp Asp Ser Cys Gln Val Ile Pro Val Leu Pro Gln Val Met Met Ile
    210                 215                 220

Leu Ile Pro Gly Gln Thr Leu Pro Leu Gln Leu Phe His Pro Gln Glu
225                 230                 235                 240

Val Ser Met Val Arg Asn Leu Ile Gln Lys Asp Arg Thr Phe Ala Val
                245                 250                 255

Leu Ala Tyr Ser Asn Val Gln Glu Arg Glu Ala Gln Phe Gly Thr Thr
            260                 265                 270

Ala Glu Ile Tyr Ala Tyr Arg Glu Glu Gln Asp Phe Gly Ile Glu Ile
        275                 280                 285

Val Lys Val Lys Ala Ile Gly Arg Gln Arg Phe Lys Val Leu Glu Leu
    290                 295                 300

Arg Thr Gln Ser Asp Gly Ile Gln Gln Ala Lys Val Gln Ile Leu Pro
305                 310                 315                 320

Glu Cys Val Leu Pro Ser Thr Tyr Asp Ala Glu Thr Leu Met Asp Arg
                325                 330                 335

Ile Lys Lys Gln Leu Arg Glu Trp Asp Glu Asn Leu Lys Asp Asp Ser
            340                 345                 350

Leu Pro Ser Asn Pro Ile Asp Phe Ser Tyr Arg Val Ala Ala Cys Leu
        355                 360                 365

Pro Ile Asp Asp Val Leu Arg Ile Gln Leu Leu Lys Ile Gly Ser Ala
    370                 375                 380

Ile Gln Arg Leu Arg Cys Glu Leu Asp Ile Met Asn Lys Cys Thr Ser
385                 390                 395                 400

Leu Cys Cys Lys Gln Cys Gln Glu Thr Glu Ile Thr Thr Lys Asn Glu
                405                 410                 415

Ile Phe Ser Leu Ser Leu Cys Gly Pro Met Ala Ala Tyr Val Asn Pro
            420                 425                 430

His Gly Tyr Val His Glu Thr Leu Thr Val Tyr Lys Ala Cys Asn Leu
        435                 440                 445

Asn Leu Ile Gly Arg Pro Ser Thr Glu His Ser Trp Phe Pro Gly Tyr
    450                 455                 460

Ala Trp Thr Val Ala Gln Cys Lys Ile Cys Ala Ser His Ile Gly Trp
465                 470                 475                 480

Lys Phe Thr Ala Thr Lys Lys Asp Met Ser Pro Gln Lys Phe Trp Gly
                485                 490                 495

Leu Thr Arg Ser Ala Leu Leu Pro Thr Ile Pro Asp Thr Glu Asp Glu
            500                 505                 510

Ile Ser Pro Asp Lys Val Ile Leu Cys Leu Ser Leu Gly Phe Ser Arg
        515                 520                 525
```

```
Ser Ala Asp Ala Pro Ala Tyr Gln Gln Gly Gln Asn Gln Leu Tyr Asn
    530                 535                 540

Glu Leu Asn Leu Gly Arg Arg Glu Glu Tyr Asp Val Leu Asp Lys Arg
545                 550                 555                 560

Arg Gly Arg Asp Pro Glu Met Gly Gly Lys Pro Gln Arg Arg Lys Asn
                565                 570                 575

Pro Gln Glu Gly Leu Tyr Asn Glu Leu Gln Lys Asp Lys Met Ala Glu
            580                 585                 590

Ala Tyr Ser Glu Ile Gly Met Lys Gly Glu Arg Arg Arg Gly Lys Gly
        595                 600                 605

His Asp Gly Leu Tyr Gln Gly Leu Ser Thr Ala Thr Lys Asp Thr Tyr
    610                 615                 620

Asp Ala Leu His Met Gln Ala Leu Pro Pro Arg
625                 630                 635


<210> SEQ ID NO 79
<211> LENGTH: 566
<212> TYPE: PRT
<213> ORGANISM: Artificial
<220> FEATURE:
<223> OTHER INFORMATION: Synthetic

<400> SEQUENCE: 79

Met Gly Cys Ile Lys Ser Lys Arg Lys Asp Asn Leu Asn Asp Asp Gly
1               5                   10                  15

Val Asp Met Lys Thr Arg Ser Lys Arg Ser Arg Leu Leu His Ser Asp
            20                  25                  30

Tyr Met Asn Met Thr Pro Arg Arg Pro Gly Pro Thr Arg Lys His Tyr
        35                  40                  45

Gln Pro Tyr Ala Pro Pro Arg Asp Phe Ala Ala Tyr Arg Ser Gly Gly
    50                  55                  60

Gly Gly Ser Ala Gly Glu Gly Asp Gln Gln Asp Ala Ala His Asn Met
65                  70                  75                  80

Gly Asn His Leu Pro Leu Leu Pro Glu Ser Glu Glu Glu Asp Glu Met
                85                  90                  95

Glu Val Glu Asp Gln Asp Ser Lys Glu Ala Lys Lys Pro Asn Ile Ile
            100                 105                 110

Asn Phe Asp Thr Ser Leu Pro Thr Ser His Thr Tyr Leu Gly Ala Asp
        115                 120                 125

Met Glu Glu Phe His Gly Arg Thr Leu His Asp Asp Asp Ser Cys Gln
    130                 135                 140

Val Ile Pro Val Leu Pro Gln Val Met Met Ile Leu Ile Pro Gly Gln
145                 150                 155                 160

Thr Leu Pro Leu Gln Leu Phe His Pro Gln Glu Val Ser Met Val Arg
                165                 170                 175

Asn Leu Ile Gln Lys Asp Arg Thr Phe Ala Val Leu Ala Tyr Ser Asn
            180                 185                 190

Val Gln Glu Arg Glu Ala Gln Phe Gly Thr Thr Ala Glu Ile Tyr Ala
        195                 200                 205

Tyr Arg Glu Glu Gln Asp Phe Gly Ile Glu Ile Val Lys Val Lys Ala
    210                 215                 220

Ile Gly Arg Gln Arg Phe Lys Val Leu Glu Leu Arg Thr Gln Ser Asp
225                 230                 235                 240

Gly Ile Gln Gln Ala Lys Val Gln Ile Leu Pro Glu Cys Val Leu Pro
                245                 250                 255
```

```
Ser Thr Tyr Asp Ala Glu Thr Leu Met Asp Arg Ile Lys Lys Gln Leu
            260                 265                 270

Arg Glu Trp Asp Glu Asn Leu Lys Asp Asp Ser Leu Pro Ser Asn Pro
        275                 280                 285

Ile Asp Phe Ser Tyr Arg Val Ala Ala Cys Leu Pro Ile Asp Asp Val
    290                 295                 300

Leu Arg Ile Gln Leu Leu Lys Ile Gly Ser Ala Ile Gln Arg Leu Arg
305                 310                 315                 320

Cys Glu Leu Asp Ile Met Asn Lys Cys Thr Ser Leu Cys Cys Lys Gln
                325                 330                 335

Cys Gln Glu Thr Glu Ile Thr Thr Lys Asn Glu Ile Phe Ser Leu Ser
            340                 345                 350

Leu Cys Gly Pro Met Ala Ala Tyr Val Asn Pro His Gly Tyr Val His
        355                 360                 365

Glu Thr Leu Thr Val Tyr Lys Ala Cys Asn Leu Asn Leu Ile Gly Arg
    370                 375                 380

Pro Ser Thr Glu His Ser Trp Phe Pro Gly Tyr Ala Trp Thr Val Ala
385                 390                 395                 400

Gln Cys Lys Ile Cys Ala Ser His Ile Gly Trp Lys Phe Thr Ala Thr
                405                 410                 415

Lys Lys Asp Met Ser Pro Gln Lys Phe Trp Gly Leu Thr Arg Ser Ala
            420                 425                 430

Leu Leu Pro Thr Ile Pro Asp Thr Glu Asp Glu Ile Ser Pro Asp Lys
        435                 440                 445

Val Ile Leu Cys Leu Ser Leu Gly Phe Ser Arg Ser Ala Asp Ala Pro
    450                 455                 460

Ala Tyr Gln Gln Gly Gln Asn Gln Leu Tyr Asn Glu Leu Asn Leu Gly
465                 470                 475                 480

Arg Arg Glu Glu Tyr Asp Val Leu Asp Lys Arg Arg Gly Arg Asp Pro
                485                 490                 495

Glu Met Gly Gly Lys Pro Gln Arg Arg Lys Asn Pro Gln Glu Gly Leu
            500                 505                 510

Tyr Asn Glu Leu Gln Lys Asp Lys Met Ala Glu Ala Tyr Ser Glu Ile
        515                 520                 525

Gly Met Lys Gly Glu Arg Arg Arg Gly Lys Gly His Asp Gly Leu Tyr
    530                 535                 540

Gln Gly Leu Ser Thr Ala Thr Lys Asp Thr Tyr Asp Ala Leu His Met
545                 550                 555                 560

Gln Ala Leu Pro Pro Arg
                565


<210> SEQ ID NO 80
<211> LENGTH: 668
<212> TYPE: PRT
<213> ORGANISM: Artificial
<220> FEATURE:
<223> OTHER INFORMATION: Synthetic

<400> SEQUENCE: 80

Met Ala Leu Pro Val Thr Ala Leu Leu Leu Pro Leu Ala Leu Leu Leu
1               5                   10                  15

His Ala Ala Arg Pro Glu Arg Arg Ala Glu Val Pro Thr Ala His Pro
            20                  25                  30

Ser Pro Ser Pro Arg Pro Ala Gly Gln Phe Gln Thr Leu Val Val Gly
        35                  40                  45
```

-continued

```
Val Val Gly Gly Leu Leu Gly Ser Leu Val Leu Leu Val Trp Val Leu
    50                  55                  60

Ala Val Ile Cys Ser Arg Ala Ala Arg Gly Thr Ile Gly Ala Arg Arg
65                  70                  75                  80

Thr Gly Gln Pro Leu Lys Glu Asp Pro Ser Ala Val Pro Val Phe Ser
                85                  90                  95

Val Asp Phe Gly Glu Leu Asp Phe Gln Trp Arg Glu Lys Thr Pro Glu
            100                 105                 110

Pro Pro Val Pro Cys Val Pro Glu Gln Thr Glu Phe Ala Thr Ile Val
        115                 120                 125

Phe Pro Ser Gly Met Gly Thr Ser Ser Pro Ala Arg Arg Gly Ser Ala
    130                 135                 140

Asp Gly Pro Arg Ser Ala Gln Pro Leu Arg Pro Glu Asp Gly His Cys
145                 150                 155                 160

Ser Trp Pro Leu Gly Gly Gly Gly Ser Ala Gly Glu Gly Asp Gln Gln
                165                 170                 175

Asp Ala Ala His Asn Met Gly Asn His Leu Pro Leu Leu Pro Glu Ser
            180                 185                 190

Glu Glu Glu Asp Glu Met Glu Val Glu Asp Gln Asp Ser Lys Glu Ala
        195                 200                 205

Lys Lys Pro Asn Ile Ile Asn Phe Asp Thr Ser Leu Pro Thr Ser His
    210                 215                 220

Thr Tyr Leu Gly Ala Asp Met Glu Glu Phe His Gly Arg Thr Leu His
225                 230                 235                 240

Asp Asp Asp Ser Cys Gln Val Ile Pro Val Leu Pro Gln Val Met Met
                245                 250                 255

Ile Leu Ile Pro Gly Gln Thr Leu Pro Leu Gln Leu Phe His Pro Gln
            260                 265                 270

Glu Val Ser Met Val Arg Asn Leu Ile Gln Lys Asp Arg Thr Phe Ala
        275                 280                 285

Val Leu Ala Tyr Ser Asn Val Gln Glu Arg Glu Ala Gln Phe Gly Thr
    290                 295                 300

Thr Ala Glu Ile Tyr Ala Tyr Arg Glu Glu Gln Asp Phe Gly Ile Glu
305                 310                 315                 320

Ile Val Lys Val Lys Ala Ile Gly Arg Gln Arg Phe Lys Val Leu Glu
                325                 330                 335

Leu Arg Thr Gln Ser Asp Gly Ile Gln Gln Ala Lys Val Gln Ile Leu
            340                 345                 350

Pro Glu Cys Val Leu Pro Ser Thr Tyr Asp Ala Glu Thr Leu Met Asp
        355                 360                 365

Arg Ile Lys Lys Gln Leu Arg Glu Trp Asp Glu Asn Leu Lys Asp Asp
    370                 375                 380

Ser Leu Pro Ser Asn Pro Ile Asp Phe Ser Tyr Arg Val Ala Ala Cys
385                 390                 395                 400

Leu Pro Ile Asp Asp Val Leu Arg Ile Gln Leu Leu Lys Ile Gly Ser
                405                 410                 415

Ala Ile Gln Arg Leu Arg Cys Glu Leu Asp Ile Met Asn Lys Cys Thr
            420                 425                 430

Ser Leu Cys Cys Lys Gln Cys Gln Glu Thr Glu Ile Thr Thr Lys Asn
        435                 440                 445

Glu Ile Phe Ser Leu Ser Leu Cys Gly Pro Met Ala Ala Tyr Val Asn
    450                 455                 460
```

```
Pro His Gly Tyr Val His Glu Thr Leu Thr Val Tyr Lys Ala Cys Asn
465                 470                 475                 480

Leu Asn Leu Ile Gly Arg Pro Ser Thr Glu His Ser Trp Phe Pro Gly
                485                 490                 495

Tyr Ala Trp Thr Val Ala Gln Cys Lys Ile Cys Ala Ser His Ile Gly
            500                 505                 510

Trp Lys Phe Thr Ala Thr Lys Lys Asp Met Ser Pro Gln Lys Phe Trp
        515                 520                 525

Gly Leu Thr Arg Ser Ala Leu Leu Pro Thr Ile Pro Asp Thr Glu Asp
    530                 535                 540

Glu Ile Ser Pro Asp Lys Val Ile Leu Cys Leu Ser Leu Gly Phe Ser
545                 550                 555                 560

Arg Ser Ala Asp Ala Pro Ala Tyr Gln Gln Gly Gln Asn Gln Leu Tyr
                565                 570                 575

Asn Glu Leu Asn Leu Gly Arg Arg Glu Glu Tyr Asp Val Leu Asp Lys
            580                 585                 590

Arg Arg Gly Arg Asp Pro Glu Met Gly Gly Lys Pro Gln Arg Arg Lys
        595                 600                 605

Asn Pro Gln Glu Gly Leu Tyr Asn Glu Leu Gln Lys Asp Lys Met Ala
    610                 615                 620

Glu Ala Tyr Ser Glu Ile Gly Met Lys Gly Glu Arg Arg Arg Gly Lys
625                 630                 635                 640

Gly His Asp Gly Leu Tyr Gln Gly Leu Ser Thr Ala Thr Lys Asp Thr
                645                 650                 655

Tyr Asp Ala Leu His Met Gln Ala Leu Pro Pro Arg
            660                 665


<210> SEQ ID NO 81
<211> LENGTH: 561
<212> TYPE: PRT
<213> ORGANISM: Artificial
<220> FEATURE:
<223> OTHER INFORMATION: Synthetic

<400> SEQUENCE: 81

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

Asp Ile Gln Met Thr Gln Thr Thr Ser Ser Leu Ser Ala Ser Leu Gly
        35                  40                  45

Asp Arg Val Thr Ile Ser Cys Arg Ala Ser Gln Asp Ile Ser Lys Tyr
    50                  55                  60

Leu Asn Trp Tyr Gln Gln Lys Pro Asp Gly Thr Val Lys Leu Leu Ile
65                  70                  75                  80

Tyr His Thr Ser Arg Leu His Ser Gly Val Pro Ser Arg Phe Ser Gly
                85                  90                  95

Ser Gly Ser Gly Thr Asp Tyr Ser Leu Thr Ile Ser Asn Leu Glu Gln
            100                 105                 110

Glu Asp Ile Ala Thr Tyr Phe Cys Gln Gln Gly Asn Thr Leu Pro Tyr
        115                 120                 125

Thr Phe Gly Gly Gly Thr Lys Leu Glu Ile Thr Gly Ser Thr Ser Gly
    130                 135                 140

Ser Gly Lys Pro Gly Ser Gly Glu Gly Ser Thr Lys Gly Glu Val Lys
145                 150                 155                 160
```

```
Leu Gln Glu Ser Gly Pro Gly Leu Val Ala Pro Ser Gln Ser Leu Ser
                165                 170                 175

Val Thr Cys Thr Val Ser Gly Val Ser Leu Pro Asp Tyr Gly Val Ser
            180                 185                 190

Trp Ile Arg Gln Pro Pro Arg Lys Gly Leu Glu Trp Leu Gly Val Ile
        195                 200                 205

Trp Gly Ser Glu Thr Thr Tyr Tyr Asn Ser Ala Leu Lys Ser Arg Leu
    210                 215                 220

Thr Ile Ile Lys Asp Asn Ser Lys Ser Gln Val Phe Leu Lys Met Asn
225                 230                 235                 240

Ser Leu Gln Thr Asp Asp Thr Ala Ile Tyr Tyr Cys Ala Lys His Tyr
                245                 250                 255

Tyr Tyr Gly Gly Ser Tyr Ala Met Asp Tyr Trp Gly Gln Gly Thr Ser
            260                 265                 270

Val Thr Val Ser Ser Ala Ala Ala Ile Glu Val Met Tyr Pro Pro Pro
        275                 280                 285

Tyr Leu Asp Asn Glu Lys Ser Asn Gly Thr Ile Ile His Val Lys Gly
    290                 295                 300

Lys His Leu Cys Pro Ser Pro Leu Phe Pro Gly Pro Ser Lys Pro Phe
305                 310                 315                 320

Trp Val Leu Val Val Val Gly Gly Val Leu Ala Cys Tyr Ser Leu Leu
                325                 330                 335

Val Thr Val Ala Phe Ile Ile Phe Trp Val Arg Ser Lys Arg Ser Arg
            340                 345                 350

Leu Leu His Ser Asp Tyr Met Asn Met Thr Pro Arg Arg Pro Gly Pro
        355                 360                 365

Thr Arg Lys His Tyr Gln Pro Tyr Ala Pro Pro Arg Asp Phe Ala Ala
    370                 375                 380

Tyr Arg Ser Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Ser Gly Phe Asn Val Leu Met Val His Lys Arg Ser His
            500                 505                 510

Thr Gly Glu Arg Pro Phe Gln Cys Asn Gln Cys Gly Ala Ser Phe Thr
        515                 520                 525

Gln Lys Gly Asn Leu Leu Arg His Ile Lys Leu His Thr Gly Glu Lys
    530                 535                 540

Pro Phe Lys Cys His Leu Cys Asn Tyr Ala Cys Gln Arg Arg Asp Ala
545                 550                 555                 560

Leu
```

<210> SEQ ID NO 82

-continued

<211> LENGTH: 282
<212> TYPE: PRT
<213> ORGANISM: Artificial
<220> FEATURE:
<223> OTHER INFORMATION: Synthetic

<400> SEQUENCE: 82

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser Ser Gly Phe Asn
    210                 215                 220

Val Leu Met Val His Lys Arg Ser His Thr Gly Glu Arg Pro Phe Gln
225                 230                 235                 240

Cys Asn Gln Cys Gly Ala Ser Phe Thr Gln Lys Gly Asn Leu Leu Arg
                245                 250                 255

His Ile Lys Leu His Thr Gly Glu Lys Pro Phe Lys Cys His Leu Cys
            260                 265                 270

Asn Tyr Ala Cys Gln Arg Arg Asp Ala Leu
        275                 280

<210> SEQ ID NO 83
<211> LENGTH: 392
<212> TYPE: PRT
<213> ORGANISM: Artificial
<220> FEATURE:
<223> OTHER INFORMATION: Synthetic

<400> SEQUENCE: 83

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser

-continued

```
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser Phe Ser Arg Ser
    210                 215                 220

Ala Asp Ala Pro Ala Tyr Gln Gln Gly Gln Asn Gln Leu Tyr Asn Glu
225                 230                 235                 240

Leu Asn Leu Gly Arg Arg Glu Glu Tyr Asp Val Leu Asp Lys Arg Arg
                245                 250                 255

Gly Arg Asp Pro Glu Met Gly Gly Lys Pro Gln Arg Arg Lys Asn Pro
            260                 265                 270

Gln Glu Gly Leu Tyr Asn Glu Leu Gln Lys Asp Lys Met Ala Glu Ala
        275                 280                 285

Tyr Ser Glu Ile Gly Met Lys Gly Glu Arg Arg Arg Gly Lys Gly His
    290                 295                 300

Asp Gly Leu Tyr Gln Gly Leu Ser Thr Ala Thr Lys Asp Thr Tyr Asp
305                 310                 315                 320

Ala Leu His Met Gln Ala Leu Pro Pro Arg Ser Gly Phe Asn Val Leu
                325                 330                 335

Met Val His Lys Arg Ser His Thr Gly Glu Arg Pro Phe Gln Cys Asn
            340                 345                 350

Gln Cys Gly Ala Ser Phe Thr Gln Lys Gly Asn Leu Leu Arg His Ile
        355                 360                 365

Lys Leu His Thr Gly Glu Lys Pro Phe Lys Cys His Leu Cys Asn Tyr
    370                 375                 380

Ala Cys Gln Arg Arg Asp Ala Leu
385                 390
```

<210> SEQ ID NO 84
<211> LENGTH: 1635
<212> TYPE: DNA
<213> ORGANISM: Artificial
<220> FEATURE:
<223> OTHER INFORMATION: Synthetic

<400> SEQUENCE: 84
atggaggagg ccatcctggt cccctgcgtg ctggggctcc tgctgctgcc catcctggcc 60
atgttgatgg cactgtgtgt gcactgccac agactgccaa tgtcagcaat acaggccgcc 120
tggccatccg gtacagaatg tattgccaag tacaacttcc acggcactgc cgagcaggac 180
ctgcccttct gcaaagggga cgtgctcacc attgtggccg tcaccaagga ccccaactgg 240
tacaaagcca aaaacaaggt gggccgtgag ggcatcatcc cagccaacta cgtccagaag 300
cgggagggcg tgaaggcggg taccaaactc agcctcatgc cttggttcca cggcaagatc 360
acacgggagc aggctgagcg gcttctgtac ccgccggaga caggcctgtt cctggtgcgg 420
gagagcacca actaccccgg agactacacg ctgtgcgtga gctgcgacgg caaggtggag 480
cactaccgca tcatgtacca tgccagcaag ctcagcatcg acgaggaggt gtactttgag 540
aacctcatgc agctggtgga gcactacacc tcagacgcag atggactctg tacgcgcctc 600
attaaaccaa aggtcatgga gggcacagtg gcggcccagg atgagttcta ccgcagcggc 660
tgggccctga acatgaagga gctgaagctg ctgcagacca tcgggaaggg ggagttcggg 720
gacgtgatgc tgggcgatta ccgagggaac aaagtcgccg tcaagtgcat taagaacgac 780
gccactgccc aggccttcct ggctgaagcc tcagtcatga cgcaactgcg gcatagcaac 840
ctggtgcagc tcctgggcgt gatcgtggag gagaagggcg ggctctacat cgtcactgag 900
tacatggcca aggggagcct tgtggactac ctgcggtcta ggggtcggtc agtgctgggc 960
ggagactgtc tcctcaagtt ctcgctagat gtctgcgagg ccatggaata cctggagggc 1020
aacaatttcg tgcatcgaga cctggctgcc cgcaatgtgc tggtgtctga ggacaacgtg 1080
gccaaggtca gcgactttgg tctcaccaag gaggcgtcca gcacccagga cacgggcaag 1140
ctgccagtca agtggacagc ccctgaggcc ctgagagaga agaaattctc cactaagtct 1200
gacgtgtgga gtttcggaat ccttctctgg gaaatctact cctttgggcg agtgccttat 1260
ccaagaattc ccctgaagga cgtcgtccct cgggtggaga agggctacaa gatggatgcc 1320
cccgacggct gcccgcccgc agtctatgaa gtcatgaaga actgctggca cctggacgcc 1380
gccatgcggc cctccttcct acagctccga gagcagcttg agcacatcaa aacccacgag 1440
ctgcacctgt ccggattcaa tgtcttaatg gttcataagc gaagccatac tggtgaacgc 1500
ccattccagt gtaatcagtg tggggcatct tttactcaga aaggtaacct cctccgccac 1560
attaaactgc acacagggga aaaacctttt aagtgtcacc tctgcaacta tgcatgccaa 1620
agaagagatg cgctc 1635

<210> SEQ ID NO 85
<211> LENGTH: 1635
<212> TYPE: DNA
<213> ORGANISM: Artificial
<220> FEATURE:
<223> OTHER INFORMATION: Synthetic

<400> SEQUENCE: 85
atggaggagg ccatcctggt cccctgcgtg ctggggctcc tgctgctgcc catcctggcc 60
atgttgatgg cactgtgtgt gcactgccac agactgccaa tgtcagcaat acaggccgcc 120
tggccatccg gtacagaatg tattgccaag tacaacttcc acggcactgc cgagcaggac 180
ctgcccttct gcaaagggga cgtgctcacc attgtggccg tcaccaagga ccccaactgg 240
tacaaagcca aaaacaaggt gggccgtgag ggcatcatcc cagccaacta cgtccagaag 300
cgggagggcg tgaaggcggg taccaaactc agcctcatgc cttggttcca cggcaagatc 360
acacgggagc aggctgagcg gcttctgtac ccgccggaga caggcctgtt cctggtgcgg 420

```
gagagcacca actaccccgg agactacacg ctgtgcgtga gctgcgacgg caaggtggag    480

cactaccgca tcatgtacca tgccagcaag ctcagcatcg acgaggaggt gtactttgag    540

aacctcatgc agctggtggc gcactacacc tcagacgcag atggactctg tacgcgcctc    600

attaaaccaa aggtcatgga gggcacagtg gcggcccagg atgagttcta ccgcagcggc    660

tgggccctga acatgaagga gctgaagctg ctgcagacca tcgggaaggg ggagttcggg    720

gacgtgatgc tgggcgatta ccgagggaac aaagtcgccg tcaagtgcat taagaacgac    780

gccactgccc aggccttcct ggctgaagcc tcagtcatga cgcaactgcg gcatagcaac    840

ctggtgcagc tcctgggcgt gatcgtggag gagaagggcg ggctctacat cgtcactgag    900

tacatggcca aggggagcct tgtggactac ctgcggtcta ggggtcggtc agtgctgggc    960

ggagactgtc tcctcaagtt ctcgctagat gtctgcgagg ccatggaata cctggagggc   1020

aacaatttcg tgcatcgaga cctggctgcc cgcaatgtgc tggtgtctga ggacaacgtg   1080

gccaaggtca gcgactttgg tctcaccaag gaggcgtcca gcacccagga cacgggcaag   1140

ctgccagtca agtggacagc ccctgaggcc ctgagagaga agaaattctc cactaagtct   1200

gacgtgtgga gtttcggaat ccttctctgg gaaatctact cctttgggcg agtgccttat   1260

ccaagaattc ccctgaagga cgtcgtccct cgggtggaga agggctacaa gatggatgcc   1320

cccgacggct gcccgcccgc agtctatgaa gtcatgaaga actgctggca cctggacgcc   1380

gccatgcggc cctccttcct acagctccga gagcagcttg agcacatcaa aacccacgag   1440

ctgcacctgt ccggattcaa tgtcttaatg gttcataagc gaagccatac tggtgaacgc   1500

ccattccagt gtaatcagtg tggggcatct tttactcaga aaggtaacct cctccgccac   1560

attaaactgc acacagggga aaaacctttt aagtgtcacc tctgcaacta tgcatgccaa   1620

agaagagatg cgctc                                                     1635
```

<210> SEQ ID NO 86
<211> LENGTH: 1635
<212> TYPE: DNA
<213> ORGANISM: Artificial
<220> FEATURE:
<223> OTHER INFORMATION: Synthetic

<400> SEQUENCE: 86

```
atggaggagg ccatcctggt cccctgcgtg ctggggctcc tgctgctgcc catcctggcc     60

atgttgatgg cactgtgtgt gcactgccac agactgccaa tgtcagcaat acaggccgcc    120

tggccatccg gtacagaatg tattgccaag tacaacttcc acggcactgc cgagcaggac    180

ctgcccttct gcaaagggga cgtgctcacc attgtggccg tcaccaagga ccccaacgcg    240

tacaaagcca aaaacaaggt gggccgtgag ggcatcatcc cagccaacta cgtccagaag    300

cgggagggcg tgaaggcggg taccaaactc agcctcatgc cttggttcca cggcaagatc    360

acacgggagc aggctgagcg gcttctgtac ccgccggaga caggcctgtt cctggtgaag    420

gagagcacca actaccccgg agactacacg ctgtgcgtga gctgcgacgg caaggtggag    480

cactaccgca tcatgtacca tgccagcaag ctcagcatcg acgaggaggt gtactttgag    540

aacctcatgc agctggtggc gcactacacc tcagacgcag atggactctg tacgcgcctc    600

attaaaccaa aggtcatgga gggcacagtg gcggcccagg atgagttcta ccgcagcggc    660

tgggccctga acatgaagga gctgaagctg ctgcagacca tcgggaaggg ggagttcggg    720

gacgtgatgc tgggcgatta ccgagggaac aaagtcgccg tcaagtgcat taagaacgac    780

gccactgccc aggccttcct ggctgaagcc tcagtcatga cgcaactgcg gcatagcaac    840
```

```
ctggtgcagc tcctgggcgt gatcgtggag gagaagggcg ggctctacat cgtcactgag     900
tacatggcca aggggagcct tgtggactac ctgcggtcta ggggtcggtc agtgctgggc     960
ggagactgtc tcctcaagtt ctcgctagat gtctgcgagg ccatggaata cctggagggc    1020
aacaatttcg tgcatcgaga cctggctgcc cgcaatgtgc tggtgtctga ggacaacgtg    1080
gccaaggtca gcgactttgg tctcaccaag gaggcgtcca gcacccagga cacgggcaag    1140
ctgccagtca agtggacagc ccctgaggcc ctgagagaga agaaattctc cactaagtct    1200
gacgtgtgga gtttcggaat ccttctctgg gaaatctact cctttgggcg agtgccttat    1260
ccaagaattc ccctgaagga cgtcgtccct cgggtggaga agggctacaa gatggatgcc    1320
cccgacggct gcccgcccgc agtctatgaa gtcatgaaga actgctggca cctggacgcc    1380
gccatgcggc cctccttcct acagctccga gagcagcttg agcacatcaa aacccacgag    1440
ctgcacctgt ccggattcaa tgtcttaatg gttcataagc gaagccatac tggtgaacgc    1500
ccattccagt gtaatcagtg tggggcatct tttactcaga aaggtaacct cctccgccac    1560
attaaactgc acacagggga aaaacctttt aagtgtcacc tctgcaacta tgcatgccaa    1620
agaagagatg cgctc                                                     1635
```

```
<210> SEQ ID NO 87
<211> LENGTH: 1464
<212> TYPE: DNA
<213> ORGANISM: Artificial
<220> FEATURE:
<223> OTHER INFORMATION: Synthetic

<400> SEQUENCE: 87

atggaggagg ccatcctggt cccctgcgtg ctggggctcc tgctgctgcc catcctggcc      60
atgttgatgg cactgtgtgt gcactgccac agactgccat caggcgcctt tgtctacctg     120
cggcagccgt actatgccac gagggtgaat gcggctgaca ttgagaaccg agtgttggaa     180
ctgaacaaga agcaggagtc cgaggataca gccaaggctg gcttctggga ggagtttgag     240
agtttgcaga agcaggaggt gaagaacttg caccagcgtc tggaagggca gcggccagag     300
aacaagggca agaaccgcta caagaacatt ctcccctttg accacagccg agtgatcctg     360
cagggacggg acagtaacat ccccgggtcc gactacatca atgccaacta catcaagaac     420
cagctgctag gccctgatga gaacgctaag acctacatcg ccagccaggg ctgtctggag     480
gccacggtca atgacttctg gcagatggcg tggcaggaga acagccgtgt catcgtcatg     540
accacccgag aggtggagaa aggccggaac aaatgcgtcc catactggcc cgaggtgggc     600
atgcagcgtg cttatgggcc ctactctgtg accaactgcg gggagcatga cacaaccgaa     660
tacaaactcc gtaccttaca ggtctccccg ctggacaatg gagacctgat tcgggagatc     720
tggcattacc agtacctgag ctggcccgac catggggtcc ccagtgagcc tgggggtgtc     780
ctcagcttcc tggaccagat caaccagcgg caggaaagtc tgcctcacgc agggcccatc     840
atcgtgcact gcagcgccgg catcggccgc acaggcacca tcattgtcat cgacatgctc     900
atggagaaca tctccaccaa gggcctggac tgtgacattg acatccagaa gaccatccag     960
atggtgcggg cgcagcgctc gggcatggtg cagacggagg cgcagtacaa gttcatctac    1020
gtggccatcg cccagttcat tgaaaccact aagaagaagc tggaggtcct gcagtcgcag    1080
aagggccagg agtcggagta cgggaacatc acctatcccc cagccatgaa gaatgcccat    1140
gccaaggcct cccgcacctc gtccaaacac aaggaggatg tgtatgagaa cctgcacact    1200
```

aagaacaaga gggaggagaa agtgaagaag cagcggtcag cagacaagga gaagagcaag 1260
ggttccctca agaggaagtc cggattcaat gtcttaatgg ttcataagcg aagccatact 1320
ggtgaacgcc cattccagtg taatcagtgt ggggcatctt ttactcagaa aggtaacctc 1380
ctccgccaca ttaaactgca cacaggggaa aaacctttta agtgtcacct ctgcaactat 1440
gcatgccaaa gaagagatgc gctc 1464

<210> SEQ ID NO 88
<211> LENGTH: 1122
<212> TYPE: DNA
<213> ORGANISM: Artificial
<220> FEATURE:
<223> OTHER INFORMATION: Synthetic

<400> SEQUENCE: 88
atggcgctcc cagtcactgc cctgcttttg cccctggcac ttcttcttca cgctgccaga 60
cccacaacga ccccagctcc acgcccgccg actcccgcgc caactatagc cagtcagccc 120
ctgtcactgc ggccggaggc gtgtcgccct gcagcggggg gagccgtcca cacacgaggt 180
cttgacttcg cctgtgacat ctatatctgg gcgcctctgg ccggtacatg cggcgtgttg 240
ttgcttagcc tcgtgataac actctattgc aggagtaaga ggagcaggct cctgcacagt 300
gactacatga acatgactcc tagaaggcct ggacccaccc gcaagcatta ccagccctat 360
gccccaccac gcgacttcgc agcctatcgc tccggagggg gtggttcttg tacttccctt 420
tgctgtaaac aatgtcaaga aacagaaata acaaccaaaa atgaaatatt cagtttatcc 480
ttatgtgggc cgatggcagc ttatgtgaat cctcatggat atgtgcatga gacacttact 540
gtgtataagg cttgcaactt gaatctgata ggccggcctt ctacagaaca cagctggttt 600
cctgggtatg cctggactgt tgcccagtgt aagatctgtg caagccatat tggatggaag 660
tttacggcca ccaaaaaaga catgtcacct caaaaatttt ggggcttaac gcgatctgct 720
ctgttgccca cgatcccaga cactgaagat gaaataagtc cagacaaagt aatactttgc 780
ttgtctctcg gcttcagtcg atcagcagat gctccagcgt accagcaagg ccagaaccaa 840
ctttataatg aactgaattt gggccgacgc gaggaatacg acgttcttga caagcggagg 900
ggccgcgatc cagaaatggg ggggaaaccg caacgaagaa agaatcccca ggaggggctc 960
tacaatgaac ttcaaaagga taaaatggca gaggcctata gcgaaatcgg tatgaagggg 1020
gagcgaaggc gaggtaaggg gcatgatggg ttgtatcaag gcctgtccac ggcgaccaag 1080
gatacctatg acgctcttca catgcaagca ttgcctccta ga 1122

<210> SEQ ID NO 89
<211> LENGTH: 8216
<212> TYPE: DNA
<213> ORGANISM: Artificial
<220> FEATURE:
<223> OTHER INFORMATION: Synthetic

<400> SEQUENCE: 89
ttttgcacaa catgggggat catgtaactc gccttgatcg ttgggaaccg gagctgaatg 60
aagccatacc aaacgacgag cgtgacacca cgatgcctgt agcaatggca acaacgttgc 120
gcaaactatt aactggcgaa ctacttactc tagcttcccg gcaacaatta atagactgga 180
tggaggcgga taaagttgca ggaccacttc tgcgctcggc ccttccggct ggctggttta 240
ttgctgataa atctggagcc ggtgagcgtg ggtctcgcgg tatcattgca gcactggggc 300
cagatggtaa gccctcccgt atcgtagtta tctacacgac ggggagtcag gcaactatgg 360

-continued

```
atgaacgaaa tagacagatc gctgagatag gtgcctcact gattaagcat tggtaactgt    420
cagaccaagt ttactcatat atactttaga ttgatttaaa acttcatttt taatttaaaa    480
ggatctaggt gaagatcctt tttgataatc tcatgaccaa aatcccttaa cgtgagtttt    540
cgttccactg agcgtcagac cccgtagaaa agatcaaagg atcttcttga gatccttttt    600
ttctgcgcgt aatctgctgc ttgcaaacaa aaaaaccacc gctaccagcg gtggtttgtt    660
tgccggatca agagctacca actctttttc cgaaggtaac tggcttcagc agagcgcaga    720
taccaaatac tgttcttcta gtgtagccgt agttaggcca ccacttcaag aactctgtag    780
caccgcctac atacctcgct ctgctaatcc tgttaccagt ggctgctgcc agtggcgata    840
agtcgtgtct taccgggttg gactcaagac gatagttacc ggataaggcg cagcggtcgg    900
gctgaacggg gggttcgtgc acacagccca gcttggagcg aacgacctac accgaactga    960
gatacctaca gcgtgagcta tgagaaagcg ccacgcttcc cgaagggaga aaggcggaca   1020
ggtatccggt aagcggcagg gtcggaacag gagagcgcac gagggagctt ccagggggaa   1080
acgcctggta tctttatagt cctgtcgggt ttcgccacct ctgacttgag cgtcgatttt   1140
tgtgatgctc gtcagggggg cggagcctat ggaaaaacgc cagcaacgcg gcctttttac   1200
ggttcctggc cttttgctgg ccttttgctc acatgttctt tcctgcgtta tcccctgatt   1260
ctgtggataa ccgtattacc gcctttgagt gagctgatac cgctcgccgc agccgaacga   1320
ccgagcgcag cgagtcagtg agcgaggaag cggaagagcg cccaatacgc aaaccgcctc   1380
tccccgcgcg ttggccgatt cattaatgca gctggcacga caggtttccc gactggaaag   1440
cgggcagtga gcgcaacgca attaatgtga gttagctcac tcattaggca ccccaggctt   1500
tacactttat gcttccggct cgtatgttgt gtggaattgt gagcggataa caatttcaca   1560
caggaaacag ctatgaccat gattacgcca agcgcgcaat taaccctcac taaagggaac   1620
aaaagctgga gctgcaagct taatgtagtc ttatgcaata ctcttgtagt cttgcaacat   1680
ggtaacgatg agttagcaac atgccttaca aggagagaaa aagcaccgtg catgccgatt   1740
ggtggaagta aggtggtacg atcgtgcctt attaggaagg caacagacgg gtctgacatg   1800
gattggacga accactgaat tgccgcattg cagagatatt gtatttaagt gcctagctcg   1860
atacataaac gggtctctct ggttagacca gatctgagcc tgggagctct ctggctaact   1920
agggaaccca ctgcttaagc ctcaataaag cttgccttga gtgcttcaag tagtgtgtgc   1980
ccgtctgttg tgtgactctg gtaactagag atccctcaga cccttttagt cagtgtggaa   2040
aatctctagc agtggcgccc gaacagggac ttgaaagcga aagggaaacc agaggagctc   2100
tctcgacgca ggactcggct tgctgaagcg cgcacggcaa gaggcgaggg gcggcgactg   2160
gtgagtacgc caaaaatttt gactagcgga ggctagaagg agagagatgg gtgcgagagc   2220
gtcagtatta agcgggggag aattagatcg cgatgggaaa aaattcggtt aaggccaggg   2280
ggaaagaaaa aatataaatt aaaacatata gtatgggcaa gcagggagct agaacgattc   2340
gcagttaatc ctggcctgtt agaaacatca gaaggctgta gacaaatact gggacagcta   2400
caaccatccc ttcagacagg atcagaagaa cttagatcat tatataatac agtagcaacc   2460
ctctattgtg tgcatcaaag gatagagata aaagacacca aggaagcttt agacaagata   2520
gaggaagagc aaaacaaaag taagaccacc gcacagcaag cggccgctga tcttcagacc   2580
tggaggagga gatatgaggg acaattggag aagtgaatta tataaatata aagtagtaaa   2640
aattgaacca ttaggagtag cacccaccaa ggcaaagaga agagtggtgc agagagaaaa   2700
```

-continued

```
aagagcagtg ggaataggag ctttgttcct tgggttcttg ggagcagcag gaagcactat   2760
gggcgcagcg tcaatgacgc tgacggtaca ggccagacaa ttattgtctg gtatagtgca   2820
gcagcagaac aatttgctga gggctattga ggcgcaacag catctgttgc aactcacagt   2880
ctggggcatc aagcagctcc aggcaagaat cctggctgtg gaaagatacc taaaggatca   2940
acagctcctg gggatttggg gttgctctgg aaaactcatt tgcaccactg ctgtgccttg   3000
gaatgctagt tggagtaata aatctctgga acagatttgg aatcacacga cctggatgga   3060
gtgggacaga gaaattaaca attacacaag cttaatacac tccttaattg aagaatcgca   3120
aaaccagcaa gaaaagaatg aacaagaatt attggaatta gataaatggg caagtttgtg   3180
gaattggttt aacataacaa attggctgtg gtatataaaa ttattcataa tgatagtagg   3240
aggcttggta ggtttaagaa tagtttttgc tgtactttct atagtgaata gagttaggca   3300
gggatattca ccattatcgt ttcagaccca cctcccaacc ccgaggggac cctattccag   3360
cacatatgag gcttggcgta actagatctt gagacaaatg gcagtattca tccacaattt   3420
taaaagaaaa ggggggattg gggggtacag tgcaggggaa agaatagtag acataatagc   3480
aacagacata caaactaaag aattacaaaa acaaattaca aaaattcaaa attttcgggt   3540
ttattacagg gacagcagag atccactttg ggctcgaggg ggcccgggtg caaagatgga   3600
taaagtttta aacagagagg aatctttgca gctaatggac cttctaggtc ttgaaaggag   3660
tgggaattgg ctccggtgcc cgtcagtggg cagagcgcac atcgcccaca gtccccgaga   3720
agttgggggg aggggtcggc aattgatccg gtgcctagag aaggtggcgc ggggtaaact   3780
gggaaagtga tgtcgtgtac tggctccgcc tttttcccga gggtggggga gaaccgtata   3840
taagtgcagt agtcgccgtg aacgttcttt ttcgcaacgg gtttgccgcc agaacacagg   3900
taagtgccgt gtgtggttcc cgcgggcctg gcctctttac gggttatggc ccttgcgtgc   3960
cttgaattac ttccacctgg ctgcagtacg tgattcttga tcccgagctt cgggttggaa   4020
gtgggtggga gagttcgagg ccttgcgctt aaggagcccc ttcgcctcgt gcttgagttg   4080
aggcctggcc tgggcgctgg ggccgccgcg tgcgaatctg gtggcacctt cgcgcctgtc   4140
tcgctgcttt cgataagtct ctagccattt aaaatttttg atgacctgct gcgacgcttt   4200
ttttctggca agatagtctt gtaaatgcgg gccaagatct gcacactggt atttcggttt   4260
ttggggccgc gggcggcgac ggggcccgtg cgtcccagcg cacatgttcg gcgaggcggg   4320
gcctgcgagc gcggccaccg agaatcggac gggggtagtc tcaagctggc cggcctgctc   4380
tggtgcctgg cctcgcgccg ccgtgtatcg ccccgccctg ggcggcaagg ctggcccggt   4440
cggcaccagt tgcgtgagcg gaaagatggc cgcttcccgg ccctgctgca gggagctcaa   4500
aatggaggac gcggcgctcg ggagagcggg cgggtgagtc acccacacaa aggaaaaggg   4560
cctttccgtc ctcagccgtc gcttcatgtg actccacgga gtaccgggcg ccgtccaggc   4620
acctcgatta gttctcgagc ttttggagta cgtcgtcttt aggttggggg gaggggtttt   4680
atgcgatgga gtttccccac actgagtggg tggagactga agttaggcca gcttggcact   4740
tgatgtaatt ctccttggaa tttgcccttt ttgagtttgg atcttggttc attctcaagc   4800
ctcagacagt ggttcaaagt ttttttcttc catttcaggt gtcgtgaata ccgtcgactc   4860
cggaatagcc accatggaga cggacgtctc agctgaagct gctgcaaagg aagctgcagc   4920
taaggaggct gcagctaagg ctgtgagcaa gggcgaggag ctgttcaccg gggtggtgcc   4980
catcctggtc gagctggacg gcgacgtaaa cggccacaag ttcagcgtgt ccggcgaggg   5040
cgagggcgat gccacctacg gcaagctgac cctgaagttc atctgcacca ccggcaagct   5100
```

-continued

```
gcccgtgccc tggcccaccc tcgtgaccac cctgacctac ggcgtgcagt gcttcagccg   5160
ctaccccgac cacatgaagc agcacgactt cttcaagtcc gccatgcccg aaggctacgt   5220
ccaggagcgc accatcttct tcaaggacga cggcaactac aagacccgcg ccgaggtgaa   5280
gttcgagggc gacaccctgg tgaaccgcat cgagctgaag ggcatcgact tcaaggagga   5340
cggcaacatc ctggggcaca agctggagta caactacaac agccacaacg tctatatcat   5400
ggccgacaag cagaagaacg gcatcaaggt gaacttcaag atccgccaca acatcgagga   5460
cggcagcgtg cagctcgccg accactacca gcagaacacc cccatcggcg acggccccgt   5520
gctgctgccc gacaaccact acctgagcac ccagtccgcc ctgagcaaag accccaacga   5580
gaagcgcgat cacatggtcc tgctggagtt cgtgaccgcc gccgggatca ctctcggcat   5640
ggacgagctg tacaagtaaa tgcatgagta actgaggatc cagggacagc agagatacgc   5700
gttaagtcga caatcaacct ctggattaca aaatttgtga aagattgact ggtattctta   5760
actatgttgc tccttttacg ctatgtggat acgctgcttt aatgcctttg tatcatgcta   5820
ttgcttcccg tatggctttc attttctcct ccttgtataa atcctggttg ctgtctcttt   5880
atgaggagtt gtggcccgtt gtcaggcaac gtggcgtggt gtgcactgtg tttgctgacg   5940
caacccccac tggttggggc attgccacca cctgtcagct cctttccggg actttcgctt   6000
tccccctccc tattgccacg gcggaactca tcgccgcctg ccttgcccgc tgctggacag   6060
gggctcggct gttgggcact gacaattccg tggtgttgtc ggggaaatca tcgtcctttc   6120
cttggctgct cgcctgtgtt gccacctgga ttctgcgcgg gacgtccttc tgctacgtcc   6180
cttcggccct caatccagcg gaccttcctt cccgcggcct gctgccggct ctgcggcctc   6240
ttccgcgtct tcgccttcgc cctcagacga gtcggatctc cctttgggcc gcctccccgc   6300
gtcgacttta agaccaatga cttacaaggc agctgtagat cttagccact tttaaaaga    6360
aaagggggga ctggaagggc taattcactc ccaacgaaga caagatctgc tttttgcttg   6420
tactgggtct ctctggttag accagatctg agcctgggag ctctctggct aactagggaa   6480
cccactgctt aagcctcaat aaagcttgcc ttgagtgctt caagtagtgt gtgcccgtct   6540
gttgtgtgac tctggtaact agagatccct cagacccttt tagtcagtgt ggaaaatctc   6600
tagcagtacg tatagtagtt catgtcatct tattattcag tatttataac ttgcaaagaa   6660
atgaatatca gagagtgaga ggaacttgtt tattgcagct tataatggtt acaaataaag   6720
caatagcatc acaaatttca caaataaagc atttttttca ctgcattcta gttgtggttt   6780
gtccaaactc atcaatgtat cttatcatgt ctggctctag ctatcccgcc cctaactccg   6840
cccatcccgc ccctaactcc gcccagttcc gcccattctc cgccccatgg ctgactaatt   6900
ttttttattt atgcagaggc cgaggccgcc tcggcctctg agctattcca gaagtagtga   6960
ggaggctttt ttggaggcct agggacgtac ccaattcgcc ctatagtgag tcgtattacg   7020
cgcgctcact ggccgtcgtt ttacaacgtc gtgactggga aaaccctggc gttacccaac   7080
ttaatcgcct tgcagcacat ccccctttcg ccagctggcg taatagcgaa gaggcccgca   7140
ccgatcgccc ttcccaacag ttgcgcagcc tgaatggcga atgggacgcg ccctgtagcg   7200
gcgcattaag cgcggcgggt gtggtggtta cgcgcagcgt gaccgctaca cttgccagcg   7260
ccctagcgcc cgctcctttc gctttcttcc cttcctttct cgccacgttc gccggctttc   7320
cccgtcaagc tctaaatcgg gggctccctt tagggttccg atttagtgct ttacggcacc   7380
tcgaccccaa aaaacttgat tagggtgatg gttcacgtag tgggccatcg ccctgataga   7440
```

cggtttttcg ccctttgacg ttggagtcca cgttctttaa tagtggactc ttgttccaaa 7500
ctggaacaac actcaaccct atctcggtct attcttttga tttataaggg attttgccga 7560
tttcggccta ttggttaaaa aatgagctga tttaacaaaa atttaacgcg aattttaaca 7620
aaatattaac gcttacaatt taggtggcac ttttcgggga aatgtgcgcg gaacccctat 7680
ttgtttattt ttctaaatac attcaaatat gtatccgctc atgagacaat aaccctgata 7740
aatgcttcaa taatattgaa aaaggaagag tatgagtatt caacatttcc gtgtcgccct 7800
tattcccttt tttgcggcat tttgccttcc tgtttttgct cacccagaaa cgctggtgaa 7860
agtaaaagat gctgaagatc agttgggtgc acgagtgggt tacatcgaac tggatctcaa 7920
cagcggtaag atccttgaga gttttcgccc cgaagaacgt tttccaatga tgagcacttt 7980
taaagttctg ctatgtggcg cggtattatc ccgtattgac gccgggcaag agcaactcgg 8040
tcgccgcata cactattctc agaatgactt ggttgagtac tcaccagtca cagaaaagca 8100
tcttacggat ggcatgacag taagagaatt atgcagtgct gccataacca tgagtgataa 8160
cactgcggcc aacttacttc tgacaacgat cggaggaccg aaggagctaa ccgctt 8216

<210> SEQ ID NO 90
<211> LENGTH: 8185
<212> TYPE: DNA
<213> ORGANISM: Artificial
<220> FEATURE:
<223> OTHER INFORMATION: Synthetic

<400> SEQUENCE: 90
ctgtcagacc aagtttactc atatatactt tagattgatt taaaacttca tttttaattt 60
aaaaggatct aggtgaagat cctttttgat aatctcatga ccaaaatccc ttaacgtgag 120
ttttcgttcc actgagcgtc agaccccgta gaaaagatca aaggatcttc ttgagatcct 180 tttttctgc gcgtaatctg ctgcttgcaa acaaaaaaac caccgctacc agcggtggtt 240
tgtttgccgg atcaagagct accaactctt tttccgaagg taactggctt cagcagagcg 300
cagataccaa atactgttct tctagtgtag ccgtagttag gccaccactt caagaactct 360
gtagcaccgc ctacatacct cgctctgcta atcctgttac cagtggctgc tgccagtggc 420
gataagtcgt gtcttaccgg gttggactca agacgatagt taccggataa ggcgcagcgg 480
tcgggctgaa cggggggttc gtgcacacag cccagcttgg agcgaacgac ctacaccgaa 540
ctgagatacc tacagcgtga gctatgagaa agcgccacgc ttcccgaagg gagaaaggcg 600
gacaggtatc cggtaagcgg cagggtcgga acaggagagc gcacgaggga gcttccaggg 660
ggaaacgcct ggtatcttta tagtcctgtc gggtttcgcc acctctgact tgagcgtcga 720
tttttgtgat gctcgtcagg ggggcggagc ctatggaaaa acgccagcaa cgcggccttt 780
ttacggttcc tggccttttg ctggcctttt gctcacatgt tctttcctgc gttatcccct 840
gattctgtgg ataaccgtat taccgccttt gagtgagctg ataccgctcg ccgcagccga 900
acgaccgagc gcagcgagtc agtgagcgag gaagcggaag agcgcccaat acgcaaaccg 960
cctctccccg cgcgttggcc gattcattaa tgcagctggc acgacaggtt tcccgactgg 1020
aaagcgggca gtgagcgcaa cgcaattaat gtgagttagc tcactcatta ggcaccccag 1080
gctttacact ttatgcttcc ggctcgtatg ttgtgtggaa ttgtgagcgg ataacaattt 1140
cacacaggaa acagctatga ccatgattac gccaagcgcg caattaaccc tcactaaagg 1200
gaacaaaagc tggagctgca agcttaatgt agtcttatgc aatactcttg tagtcttgca 1260
acatggtaac gatgagttag caacatgcct tacaaggaga gaaaaagcac cgtgcatgcc 1320

```
gattggtgga agtaaggtgg tacgatcgtg ccttattagg aaggcaacag acgggtctga   1380
catggattgg acgaaccact gaattgccgc attgcagaga tattgtattt aagtgcctag   1440
ctcgatacat aaacgggtct ctctggttag accagatctg agcctgggag ctctctggct   1500
aactagggaa cccactgctt aagcctcaat aaagcttgcc ttgagtgctt caagtagtgt   1560
gtgcccgtct gttgtgtgac tctggtaact agagatccct cagacccttt tagtcagtgt   1620
ggaaaatctc tagcagtggc gcccgaacag ggacttgaaa gcgaaaggga aaccagagga   1680
gctctctcga cgcaggactc ggcttgctga agcgcgcacg gcaagaggcg aggggcggcg   1740
actggtgagt acgccaaaaa ttttgactag cggaggctag aaggagagag atgggtgcga   1800
gagcgtcagt attaagcggg ggagaattag atcgcgatgg gaaaaaattc ggttaaggcc   1860
agggggaaag aaaaaatata aattaaaaca tatagtatgg gcaagcaggg agctagaacg   1920
attcgcagtt aatcctggcc tgttagaaac atcagaaggc tgtagacaaa tactgggaca   1980
gctacaacca tcccttcaga caggatcaga agaacttaga tcattatata atacagtagc   2040
aaccctctat tgtgtgcatc aaaggataga gataaaagac accaaggaag ctttagacaa   2100
gatagaggaa gagcaaaaca aaagtaagac caccgcacag caagcggccg ctgatcttca   2160
gacctggagg aggagatatg agggacaatt ggagaagtga attatataaa tataaagtag   2220
taaaaattga accattagga gtagcaccca ccaaggcaaa gagaagagtg gtgcagagag   2280
aaaaaagagc agtgggaata ggagctttgt tccttgggtt cttgggagca gcaggaagca   2340
ctatgggcgc agcgtcaatg acgctgacgg tacaggccag acaattattg tctggtatag   2400
tgcagcagca gaacaatttg ctgagggcta ttgaggcgca acagcatctg ttgcaactca   2460
cagtctgggg catcaagcag ctccaggcaa gaatcctggc tgtggaaaga tacctaaagg   2520
atcaacagct cctggggatt tggggttgct ctggaaaact catttgcacc actgctgtgc   2580
cttggaatgc tagttggagt aataaatctc tggaacagat ttggaatcac acgacctgga   2640
tggagtggga cagagaaatt aacaattaca caagcttaat acactcctta attgaagaat   2700
cgcaaaacca gcaagaaaag aatgaacaag aattattgga attagataaa tgggcaagtt   2760
tgtggaattg gtttaacata acaaattggc tgtggtatat aaaattattc ataatgatag   2820
taggaggctt ggtaggttta agaatagttt ttgctgtact ttctatagtg aatagagtta   2880
ggcagggata ttcaccatta tcgtttcaga cccacctccc aaccccgagg ggacccctatt  2940
ccagcacata tgaggcttgg cgtaactaga tcttgagaca aatggcagta ttcatccaca   3000
attttaaaag aaaagggggg attggggggt acagtgcagg ggaaagaata gtagacataa   3060
tagcaacaga catacaaact aaagaattac aaaaacaaat tacaaaaatt caaaattttc   3120
gggtttatta cagggacagc agagatccac tttgggctcg aggggggcccg ggtgcaaaga   3180
tggataaagt tttaaacaga gaggaatctt tgcagctaat ggaccttcta ggtcttgaaa   3240
ggagtgggaa ttggctccgg tgcccgtcag tgggcagagc gcacatcgcc cacagtcccc   3300
gagaagttgg ggggaggggt cggcaattga tccggtgcct agagaaggtg gcgcggggta   3360
aactgggaaa gtgatgtcgt gtactggctc cgcctttttc ccgagggtgg gggagaaccg   3420
tatataagtg cagtagtcgc cgtgaacgtt ctttttcgca acgggtttgc cgccagaaca   3480
caggtaagtg ccgtgtgtgg ttcccgcggg cctggcctct ttacgggtta tggcccttgc   3540
gtgccttgaa ttacttccac ctggctgcag tacgtgattc ttgatcccga gcttcgggtt   3600
ggaagtgggt gggagagttc gaggccttgc gcttaaggag ccccttcgcc tcgtgcttga   3660
```

-continued

```
gttgaggcct ggcctgggcg ctggggccgc cgcgtgcgaa tctggtggca ccttcgcgcc   3720
tgtctcgctg ctttcgataa gtctctagcc atttaaaatt tttgatgacc tgctgcgacg   3780
ctttttttct ggcaagatag tcttgtaaat gcgggccaag atctgcacac tggtatttcg   3840
gtttttgggg ccgcgggcgg cgacggggcc cgtgcgtccc agcgcacatg ttcggcgagg   3900
cggggcctgc gagcgcggcc accgagaatc ggacgggggt agtctcaagc tggccggcct   3960
gctctggtgc ctggcctcgc gccgccgtgt atcgccccgc cctgggcggc aaggctggcc   4020
cggtcggcac cagttgcgtg agcggaaaga tggccgcttc ccggccctgc tgcagggagc   4080
tcaaaatgga ggacgcggcg ctcgggagag cgggcgggtg agtcacccac acaaaggaaa   4140
agggcctttc cgtcctcagc cgtcgcttca tgtgactcca cggagtaccg ggcgccgtcc   4200
aggcacctcg attagttctc gagcttttgg agtacgtcgt ctttaggttg gggggagggg   4260
ttttatgcga tggagtttcc ccacactgag tgggtggaga ctgaagttag gccagcttgg   4320
cacttgatgt aattctcctt ggaatttgcc ctttttgagt ttggatcttg gttcattctc   4380
aagcctcaga cagtggttca aagttttttt cttccatttc aggtgtcgtg aggatctacc   4440
ggtcgccacc atggagacgg acgtctcagc tgaagctgct gcaaaggaag ctgcagctaa   4500
ggaggctgca gctaaggcta tggtgtctaa gggcgaagag ctgattaagg agaacatgca   4560
catgaagctg tacatggagg gcaccgtgga caaccatcac ttcaagtgca catccgaggg   4620
cgaaggcaag ccctacgagg gcacccagac catgagaatc aaggtggtcg agggcggccc   4680
tctccccttc gccttcgaca tcctggctac tagcttcctc tacggcagca agaccttcat   4740
caaccacacc cagggcatcc ccgacttctt caagcagtcc ttccctgagg gcttcacatg   4800
ggagagagtc accacatacg aagacggggg cgtgctgacc gctacccagg acaccagcct   4860
ccaggacggc tgcctcatct acaacgtcaa gatcagaggg gtgaacttca catccaacgg   4920
ccctgtgatg cagaagaaaa cactcggctg ggaggccttc accgagaccc tgtaccccgc   4980
tgacggcggc ctggaaggca gaaacgacat ggccctgaag ctcgtgggcg ggagccatct   5040
gatcgcaaac gccaagacca catatagatc caagaaaccc gctaagaacc tcaagatgcc   5100
tggcgtctac tatgtggact acagactgga aagaatcaag gaggccaaca acgagaccta   5160
cgtcgagcag cacgaggtgg cagtggccag atactgcgac ctccctagca aactggggca   5220
caagcttaat taacagggac agcagagata cgcgttaagt cgacaatcaa cctctggatt   5280
acaaaatttg tgaaagattg actggtattc ttaactatgt tgctcctttt acgctatgtg   5340
gatacgctgc tttaatgcct ttgtatcatg ctattgcttc ccgtatggct ttcattttct   5400
cctccttgta taaatcctgg ttgctgtctc tttatgagga gttgtggccc gttgtcaggc   5460
aacgtggcgt ggtgtgcact gtgtttgctg acgcaacccc cactggttgg ggcattgcca   5520
ccacctgtca gctcctttcc gggactttcg ctttccccct ccctattgcc acggcggaac   5580
tcatcgccgc ctgccttgcc cgctgctgga caggggctcg gctgttgggc actgacaatt   5640
ccgtggtgtt gtcggggaaa tcatcgtcct ttccttggct gctcgcctgt gttgccacct   5700
ggattctgcg cgggacgtcc ttctgctacg tcccttcggc cctcaatcca gcggaccttc   5760
cttcccgcgg cctgctgccg gctctgcggc ctcttccgcg tcttcgcctt cgccctcaga   5820
cgagtcggat ctccctttgg gccgcctccc cgcgtcgact ttaagaccaa tgacttacaa   5880
ggcagctgta gatcttagcc actttttaaa agaaaagggg ggactggaag ggctaattca   5940
ctcccaacga agacaagatc tgctttttgc ttgtactggg tctctctggt tagaccagat   6000
ctgagcctgg gagctctctg gctaactagg gaacccactg cttaagcctc aataaagctt   6060
```

gccttgagtg cttcaagtag tgtgtgcccg tctgttgtgt gactctggta actagagatc 6120
cctcagaccc ttttagtcag tgtggaaaat ctctagcagt acgtatagta gttcatgtca 6180
tcttattatt cagtatttat aacttgcaaa gaaatgaata tcagagagtg agaggaactt 6240
gtttattgca gcttataatg gttacaaata aagcaatagc atcacaaatt tcacaaataa 6300
agcatttttt tcactgcatt ctagttgtgg tttgtccaaa ctcatcaatg tatcttatca 6360
tgtctggctc tagctatccc gcccctaact ccgcccatcc cgcccctaac tccgcccagt 6420
tccgcccatt ctccgcccca tggctgacta attttttta tttatgcaga ggccgaggcc 6480
gcctcggcct ctgagctatt ccagaagtag tgaggaggct tttttggagg cctagggacg 6540
tacccaattc gccctatagt gagtcgtatt acgcgcgctc actggccgtc gttttacaac 6600
gtcgtgactg ggaaaaccct ggcgttaccc aacttaatcg ccttgcagca catccccctt 6660
tcgccagctg gcgtaatagc gaagaggccc gcaccgatcg cccttcccaa cagttgcgca 6720
gcctgaatgg cgaatgggac gcgccctgta gcggcgcatt aagcgcggcg ggtgtggtgg 6780
ttacgcgcag cgtgaccgct acacttgcca gcgccctagc gcccgctcct ttcgctttct 6840
tcccttcctt tctcgccacg ttcgccggct ttccccgtca agctctaaat cgggggctcc 6900
ctttagggtt ccgatttagt gctttacggc acctcgaccc caaaaaactt gattagggtg 6960
atggttcacg tagtgggcca tcgccctgat agacggtttt tcgccctttg acgttggagt 7020
ccacgttctt taatagtgga ctcttgttcc aaactggaac aacactcaac cctatctcgg 7080
tctattcttt tgatttataa gggattttgc cgatttcggc ctattggtta aaaaatgagc 7140
tgatttaaca aaaatttaac gcgaatttta acaaaatatt aacgcttaca atttaggtgg 7200
cacttttcgg ggaaatgtgc gcggaacccc tatttgttta tttttctaaa tacattcaaa 7260
tatgtatccg ctcatgagac aataaccctg ataaatgctt caataatatt gaaaaaggaa 7320
gagtatgagt attcaacatt tccgtgtcgc ccttattccc ttttttgcgg cattttgcct 7380
tcctgttttt gctcacccag aaacgctggt gaaagtaaaa gatgctgaag atcagttggg 7440
tgcacgagtg ggttacatcg aactggatct caacagcggt aagatccttg agagttttcg 7500
ccccgaagaa cgttttccaa tgatgagcac ttttaaagtt ctgctatgtg gcgcggtatt 7560
atcccgtatt gacgccgggc aagagcaact cggtcgccgc atacactatt ctcagaatga 7620
cttggttgag tactcaccag tcacagaaaa gcatcttacg gatggcatga cagtaagaga 7680
attatgcagt gctgccataa ccatgagtga taacactgcg gccaacttac ttctgacaac 7740
gatcggagga ccgaaggagc taaccgcttt tttgcacaac atgggggatc atgtaactcg 7800
ccttgatcgt tgggaaccgg agctgaatga agccatacca aacgacgagc gtgacaccac 7860
gatgcctgta gcaatggcaa caacgttgcg caaactatta actggcgaac tacttactct 7920
agcttcccgg caacaattaa tagactggat ggaggcggat aaagttgcag gaccacttct 7980
gcgctcggcc cttccggctg gctggtttat tgctgataaa tctggagccg gtgagcgtgg 8040
gtctcgcggt atcattgcag cactggggcc agatggtaag ccctcccgta tcgtagttat 8100
ctacacgacg gggagtcagg caactatgga tgaacgaaat agacagatcg ctgagatagg 8160
tgcctcactg attaagcatt ggtaa 8185

<210> SEQ ID NO 91
<211> LENGTH: 8693
<212> TYPE: DNA
<213> ORGANISM: Artificial
<220> FEATURE:

-continued

<223> OTHER INFORMATION: Synthetic

<400> SEQUENCE: 91
ttttgcacaa catgggggat catgtaactc gccttgatcg ttgggaaccg gagctgaatg 60
aagccatacc aaacgacgag cgtgacacca cgatgcctgt agcaatggca acaacgttgc 120
gcaaactatt aactggcgaa ctacttactc tagcttcccg gcaacaatta atagactgga 180
tggaggcgga taaagttgca ggaccacttc tgcgctcggc ccttccggct ggctggttta 240
ttgctgataa atctggagcc ggtgagcgtg ggtctcgcgg tatcattgca gcactggggc 300
cagatggtaa gccctcccgt atcgtagtta tctacacgac ggggagtcag gcaactatgg 360
atgaacgaaa tagacagatc gctgagatag gtgcctcact gattaagcat tggtaactgt 420
cagaccaagt ttactcatat atactttaga ttgatttaaa acttcatttt taatttaaaa 480
ggatctaggt gaagatcctt tttgataatc tcatgaccaa aatcccttaa cgtgagtttt 540
cgttccactg agcgtcagac cccgtagaaa agatcaaagg atcttcttga gatccttttt 600
ttctgcgcgt aatctgctgc ttgcaaacaa aaaaaccacc gctaccagcg gtggtttgtt 660
tgccggatca agagctacca actctttttc cgaaggtaac tggcttcagc agagcgcaga 720
taccaaatac tgttcttcta gtgtagccgt agttaggcca ccacttcaag aactctgtag 780
caccgcctac atacctcgct ctgctaatcc tgttaccagt ggctgctgcc agtggcgata 840
agtcgtgtct taccgggttg gactcaagac gatagttacc ggataaggcg cagcggtcgg 900
gctgaacggg gggttcgtgc acacagccca gcttggagcg aacgacctac accgaactga 960
gatacctaca gcgtgagcta tgagaaagcg ccacgcttcc cgaagggaga aaggcggaca 1020
ggtatccggt aagcggcagg gtcggaacag gagagcgcac gagggagctt ccagggggaa 1080
acgcctggta tctttatagt cctgtcgggt ttcgccacct ctgacttgag cgtcgatttt 1140
tgtgatgctc gtcagggggg cggagcctat ggaaaaacgc cagcaacgcg gcctttttac 1200
ggttcctggc cttttgctgg ccttttgctc acatgttctt tcctgcgtta tcccctgatt 1260
ctgtggataa ccgtattacc gcctttgagt gagctgatac cgctcgccgc agccgaacga 1320
ccgagcgcag cgagtcagtg agcgaggaag cggaagagcg cccaatacgc aaaccgcctc 1380
tccccgcgcg ttggccgatt cattaatgca gctggcacga caggtttccc gactggaaag 1440
cgggcagtga gcgcaacgca attaatgtga gttagctcac tcattaggca ccccaggctt 1500
tacactttat gcttccggct cgtatgttgt gtggaattgt gagcggataa caatttcaca 1560
caggaaacag ctatgaccat gattacgcca agcgcgcaat taaccctcac taaagggaac 1620
aaaagctgga gctgcaagct taatgtagtc ttatgcaata ctcttgtagt cttgcaacat 1680
ggtaacgatg agttagcaac atgccttaca aggagagaaa aagcaccgtg catgccgatt 1740
ggtggaagta aggtggtacg atcgtgcctt attaggaagg caacagacgg gtctgacatg 1800
gattggacga accactgaat tgccgcattg cagagatatt gtatttaagt gcctagctcg 1860
atacataaac gggtctctct ggttagacca gatctgagcc tgggagctct ctggctaact 1920
agggaaccca ctgcttaagc ctcaataaag cttgccttga gtgcttcaag tagtgtgtgc 1980
ccgtctgttg tgtgactctg gtaactagag atccctcaga cccttttagt cagtgtggaa 2040
aatctctagc agtggcgccc gaacagggac ttgaaagcga aagggaaacc agaggagctc 2100
tctcgacgca ggactcggct tgctgaagcg cgcacggcaa gaggcgaggg gcggcgactg 2160
gtgagtacgc caaaaatttt gactagcgga ggctagaagg agagagatgg gtgcgagagc 2220
gtcagtatta agcgggggag aattagatcg cgatgggaaa aaattcggtt aaggccaggg 2280

-continued

```
ggaaagaaaa aatataaatt aaaacatata gtatgggcaa gcagggagct agaacgattc   2340
gcagttaatc ctggcctgtt agaaacatca gaaggctgta gacaaatact gggacagcta   2400
caaccatccc ttcagacagg atcagaagaa cttagatcat tatataatac agtagcaacc   2460
ctctattgtg tgcatcaaag gatagagata aaagacacca aggaagcttt agacaagata   2520
gaggaagagc aaaacaaaag taagaccacc gcacagcaag cggccgctga tcttcagacc   2580
tggaggagga gatatgaggg acaattggag aagtgaatta tataaatata aagtagtaaa   2640
aattgaacca ttaggagtag cacccaccaa ggcaaagaga agagtggtgc agagagaaaa   2700
aagagcagtg ggaataggag ctttgttcct tgggttcttg ggagcagcag gaagcactat   2760
gggcgcagcg tcaatgacgc tgacggtaca ggccagacaa ttattgtctg gtatagtgca   2820
gcagcagaac aatttgctga gggctattga ggcgcaacag catctgttgc aactcacagt   2880
ctggggcatc aagcagctcc aggcaagaat cctggctgtg gaaagatacc taaaggatca   2940
acagctcctg gggatttggg gttgctctgg aaaactcatt tgcaccactg ctgtgccttg   3000
gaatgctagt tggagtaata aatctctgga acagatttgg aatcacacga cctggatgga   3060
gtgggacaga gaaattaaca attacacaag cttaatacac tccttaattg aagaatcgca   3120
aaaccagcaa gaaaagaatg aacaagaatt attggaatta gataaatggg caagtttgtg   3180
gaattggttt aacataacaa attggctgtg gtatataaaa ttattcataa tgatagtagg   3240
aggcttggta ggtttaagaa tagtttttgc tgtactttct atagtgaata gagttaggca   3300
gggatattca ccattatcgt ttcagaccca cctcccaacc ccgaggggac cctattccag   3360
cacatatgag gcttggcgta actagatctt gagacaaatg gcagtattca tccacaattt   3420
taaaagaaaa ggggggattg gggggtacag tgcaggggaa agaatagtag acataatagc   3480
aacagacata caaactaaag aattacaaaa acaaattaca aaaattcaaa attttcgggt   3540
ttattacagg gacagcagag atccactttg gctcgagggg ggcccgggtg caaagatgga   3600
taaagtttta aacagagagg aatctttgca gctaatggac cttctaggtc ttgaaaggag   3660
tgggaattgg ctccggtgcc cgtcagtggg cagagcgcac atcgcccaca gtccccgaga   3720
agttgggggg aggggtcggc aattgatccg gtgcctagag aaggtggcgc ggggtaaact   3780
gggaaagtga tgtcgtgtac tggctccgcc tttttcccga gggtggggga gaaccgtata   3840
taagtgcagt agtcgccgtg aacgttcttt ttcgcaacgg gtttgccgcc agaacacagg   3900
taagtgccgt gtgtggttcc cgcgggcctg gcctctttac gggttatggc ccttgcgtgc   3960
cttgaattac ttccacctgg ctgcagtacg tgattcttga tcccgagctt cgggttggaa   4020
gtgggtggga gagttcgagg ccttgcgctt aaggagcccc ttcgcctcgt gcttgagttg   4080
aggcctggcc tgggcgctgg ggccgccgcg tgcgaatctg gtggcacctt cgcgcctgtc   4140
tcgctgcttt cgataagtct ctagccattt aaaatttttg atgacctgct gcgacgcttt   4200
ttttctggca agatagtctt gtaaatgcgg gccaagatct gcacactggt atttcggttt   4260
ttggggccgc gggcggcgac ggggcccgtg cgtcccagcg cacatgttcg gcgaggcggg   4320
gcctgcgagc gcggccaccg agaatcggac gggggtagtc tcaagctggc cggcctgctc   4380
tggtgcctgg cctcgcgccg ccgtgtatcg ccccgccctg ggcggcaagg ctggcccggt   4440
cggcaccagt tgcgtgagcg gaaagatggc cgcttcccgg ccctgctgca gggagctcaa   4500
aatggaggac gcggcgctcg ggagagcggg cgggtgagtc acccacacaa aggaaaaggg   4560
cctttccgtc ctcagccgtc gcttcatgtg actccacgga gtaccgggcg ccgtccaggc   4620
```

-continued

```
acctcgatta gttctcgagc ttttggagta cgtcgtcttt aggttggggg gaggggtttt   4680
atgcgatgga gtttccccac actgagtggg tggagactga agttaggcca gcttggcact   4740
tgatgtaatt ctccttggaa tttgcccttt ttgagtttgg atcttggttc attctcaagc   4800
ctcagacagt ggttcaaagt ttttttcttc catttcaggt gtcgtgaata ccgtcgactc   4860
cggaatagcc accatggaga cggacgtctc agctgaagct gctgcaaagg aagctgcagc   4920
taaggaggct gcagctaagg ctatggtgtc taagggcgaa gagctgatta aggagaacat   4980
gcacatgaag ctgtacatgg agggcaccgt ggacaaccat cacttcaagt gcacatccga   5040
gggcgaaggc aagccctacg agggcaccca gaccatgaga atcaaggtgg tcgagggcgg   5100
ccctctcccc ttcgccttcg acatcctggc tactagcttc ctctacggca gcaagacctt   5160
catcaaccac acccagggca tccccgactt cttcaagcag tccttccctg agggcttcac   5220
atgggagaga gtcaccacat acgaagacgg gggcgtgctg accgctaccc aggacaccag   5280
cctccaggac ggctgcctca tctacaacgt caagatcaga ggggtgaact tcacatccaa   5340
cggccctgtg atgcagaaga aaacactcgg ctgggaggcc ttcaccgaga ccctgtaccc   5400
cgctgacggc ggcctggaag gcagaaacga catggccctg aagctcgtgg gcgggagcca   5460
tctgatcgca aacgccaaga ccacatatag atccaagaaa cccgctaaga acctcaagat   5520
gcctggcgtc tactatgtgg actacagact ggaaagaatc aaggaggcca acaacgagac   5580
ctacgtcgag cagcacgagg tggcagtggc cagatactgc gacctcccta gcaaactggg   5640
gcacaagctt aatggactca gagtttgggt aggaagcgga gctactaact tcagcctgct   5700
gaagcaggct ggagatgtgg aggagaaccc tggacctatg gccaagcctt tgtctcaaga   5760
agaatccacc ctcattgaaa gagcaacggc tacaatcaac agcatcccca tctctgaaga   5820
ctacagcgtc gccagcgcag ctctctctag cgacggccgc atcttcactg gtgtcaatgt   5880
atatcatttt actgggggac cttgtgcaga actcgtggtg ctgggcactg ctgctgctgc   5940
ggcagctggc aacctgactt gtatcgtcgc gatcggaaat gagaacaggg gcatcttgag   6000
cccctgcgga cggtgccgac aggtgcttct cgatctgcat cctgggatca aagccatagt   6060
gaaggacagt gatggacagc cgacggcagt tgggattcgt gaattgctgc cctctggtta   6120
tgtgtgggag ggctaaatgc atgagtaact gaggatccag ggacagcaga gatacgcgtt   6180
aagtcgacaa tcaacctctg gattacaaaa tttgtgaaag attgactggt attcttaact   6240
atgttgctcc ttttacgcta tgtggatacg ctgctttaat gcctttgtat catgctattg   6300
cttcccgtat ggctttcatt ttctcctcct tgtataaatc ctggttgctg tctctttatg   6360
aggagttgtg gcccgttgtc aggcaacgtg gcgtggtgtg cactgtgttt gctgacgcaa   6420
cccccactgg ttggggcatt gccaccacct gtcagctcct ttccgggact ttcgctttcc   6480
ccctccctat tgccacggcg gaactcatcg ccgcctgcct tgcccgctgc tggacagggg   6540
ctcggctgtt gggcactgac aattccgtgg tgttgtcggg gaaatcatcg tcctttcctt   6600
ggctgctcgc ctgtgttgcc acctggattc tgcgcgggac gtccttctgc tacgtccctt   6660
cggccctcaa tccagcggac cttccttccc gcggcctgct gccggctctg cggcctcttc   6720
cgcgtcttcg ccttcgccct cagacgagtc ggatctccct ttgggccgcc tccccgcgtc   6780
gactttaaga ccaatgactt acaaggcagc tgtagatctt agccactttt taaaagaaaa   6840
ggggggactg gaagggctaa ttcactccca acgaagacaa gatctgcttt ttgcttgtac   6900
tgggtctctc tggttagacc agatctgagc ctgggagctc tctggctaac tagggaaccc   6960
actgcttaag cctcaataaa gcttgccttg agtgcttcaa gtagtgtgtg cccgtctgtt   7020
```

```
gtgtgactct ggtaactaga gatccctcag accctttag tcagtgtgga aaatctctag   7080

cagtacgtat agtagttcat gtcatcttat tattcagtat ttataacttg caaagaaatg   7140

aatatcagag agtgagagga acttgtttat tgcagcttat aatggttaca aataaagcaa   7200

tagcatcaca aatttcacaa ataaagcatt tttttcactg cattctagtt gtggtttgtc   7260

caaactcatc aatgtatctt atcatgtctg gctctagcta tcccgcccct aactccgccc   7320

atcccgcccc taactccgcc cagttccgcc cattctccgc cccatggctg actaattttt   7380

tttatttatg cagaggccga ggccgcctcg gcctctgagc tattccagaa gtagtgagga   7440

ggcttttttg gaggcctagg gacgtaccca attcgcccta tagtgagtcg tattacgcgc   7500

gctcactggc cgtcgtttta caacgtcgtg actgggaaaa ccctggcgtt acccaactta   7560

atcgccttgc agcacatccc cctttcgcca gctggcgtaa tagcgaagag gcccgcaccg   7620

atcgcccttc ccaacagttg cgcagcctga atggcgaatg ggacgcgccc tgtagcggcg   7680

cattaagcgc ggcgggtgtg gtggttacgc gcagcgtgac cgctacactt gccagcgccc   7740

tagcgcccgc tcctttcgct ttcttccctt cctttctcgc cacgttcgcc ggctttcccc   7800

gtcaagctct aaatcggggg ctccctttag ggttccgatt tagtgcttta cggcacctcg   7860

accccaaaaa acttgattag ggtgatggtt cacgtagtgg gccatcgccc tgatagacgg   7920

tttttcgccc tttgacgttg gagtccacgt tctttaatag tggactcttg ttccaaactg   7980

gaacaacact caaccctatc tcggtctatt cttttgattt ataagggatt ttgccgattt   8040

cggcctattg gttaaaaaat gagctgattt aacaaaaatt taacgcgaat tttaacaaaa   8100

tattaacgct tacaatttag gtggcacttt tcggggaaat gtgcgcggaa cccctatttg   8160

tttatttttc taaatacatt caaatatgta tccgctcatg agacaataac cctgataaat   8220

gcttcaataa tattgaaaaa ggaagagtat gagtattcaa catttccgtg tcgcccttat   8280

tcccttttt gcggcatttt gccttcctgt ttttgctcac ccagaaacgc tggtgaaagt   8340

aaaagatgct gaagatcagt tgggtgcacg agtgggttac atcgaactgg atctcaacag   8400

cggtaagatc cttgagagtt ttcgccccga agaacgtttt ccaatgatga gcacttttaa   8460

agttctgcta tgtggcgcgg tattatcccg tattgacgcc gggcaagagc aactcggtcg   8520

ccgcatacac tattctcaga atgacttggt tgagtactca ccagtcacag aaaagcatct   8580

tacggatggc atgacagtaa gagaattatg cagtgctgcc ataaccatga gtgataacac   8640

tgcggccaac ttacttctga caacgatcgg aggaccgaag gagctaaccg ctt          8693
```

```
<210> SEQ ID NO 92
<211> LENGTH: 9086
<212> TYPE: DNA
<213> ORGANISM: Artificial
<220> FEATURE:
<223> OTHER INFORMATION: Synthetic

<400> SEQUENCE: 92

ttttgcacaa catgggggat catgtaactc gccttgatcg ttgggaaccg gagctgaatg     60

aagccatacc aaacgacgag cgtgacacca cgatgcctgt agcaatggca acaacgttgc    120

gcaaactatt aactggcgaa ctacttactc tagcttcccg gcaacaatta atagactgga    180

tggaggcgga taaagttgca ggaccacttc tgcgctcggc ccttccggct ggctggttta    240

ttgctgataa atctggagcc ggtgagcgtg ggtctcgcgg tatcattgca gcactggggc    300

cagatggtaa gccctcccgt atcgtagtta tctacacgac ggggagtcag gcaactatgg    360
```

```
atgaacgaaa tagacagatc gctgagatag gtgcctcact gattaagcat tggtaactgt    420
cagaccaagt ttactcatat atactttaga ttgatttaaa acttcatttt taatttaaaa    480
ggatctaggt gaagatcctt tttgataatc tcatgaccaa aatcccttaa cgtgagtttt    540
cgttccactg agcgtcagac cccgtagaaa agatcaaagg atcttcttga gatccttttt    600
ttctgcgcgt aatctgctgc ttgcaaacaa aaaaaccacc gctaccagcg gtggtttgtt    660
tgccggatca agagctacca actctttttc cgaaggtaac tggcttcagc agagcgcaga    720
taccaaatac tgttcttcta gtgtagccgt agttaggcca ccacttcaag aactctgtag    780
caccgcctac atacctcgct ctgctaatcc tgttaccagt ggctgctgcc agtggcgata    840
agtcgtgtct taccgggttg gactcaagac gatagttacc ggataaggcg cagcggtcgg    900
gctgaacggg gggttcgtgc acacagccca gcttggagcg aacgacctac accgaactga    960
gatacctaca gcgtgagcta tgagaaagcg ccacgcttcc cgaagggaga aaggcggaca   1020
ggtatccggt aagcggcagg gtcggaacag gagagcgcac gagggagctt ccagggggaa   1080
acgcctggta tctttatagt cctgtcgggt ttcgccacct ctgacttgag cgtcgatttt   1140
tgtgatgctc gtcagggggg cggagcctat ggaaaaacgc cagcaacgcg gcctttttac   1200
ggttcctggc cttttgctgg ccttttgctc acatgttctt tcctgcgtta tcccctgatt   1260
ctgtggataa ccgtattacc gcctttgagt gagctgatac cgctcgccgc agccgaacga   1320
ccgagcgcag cgagtcagtg agcgaggaag cggaagagcg cccaatacgc aaaccgcctc   1380
tccccgcgcg ttggccgatt cattaatgca gctggcacga caggtttccc gactggaaag   1440
cgggcagtga gcgcaacgca attaatgtga gttagctcac tcattaggca ccccaggctt   1500
tacactttat gcttccggct cgtatgttgt gtggaattgt gagcggataa caatttcaca   1560
caggaaacag ctatgaccat gattacgcca agcgcgcaat taaccctcac taaagggaac   1620
aaaagctgga gctgcaagct taatgtagtc ttatgcaata ctcttgtagt cttgcaacat   1680
ggtaacgatg agttagcaac atgccttaca aggagagaaa aagcaccgtg catgccgatt   1740
ggtggaagta aggtggtacg atcgtgcctt attaggaagg caacagacgg gtctgacatg   1800
gattggacga accactgaat tgccgcattg cagagatatt gtatttaagt gcctagctcg   1860
atacataaac gggtctctct ggttagacca gatctgagcc tgggagctct ctggctaact   1920
agggaaccca ctgcttaagc ctcaataaag cttgccttga gtgcttcaag tagtgtgtgc   1980
ccgtctgttg tgtgactctg gtaactagag atccctcaga cccttttagt cagtgtggaa   2040
aatctctagc agtggcgccc gaacagggac ttgaaagcga aagggaaacc agaggagctc   2100
tctcgacgca ggactcggct tgctgaagcg cgcacggcaa gaggcgaggg gcggcgactg   2160
gtgagtacgc caaaaatttt gactagcgga ggctagaagg agagagatgg gtgcgagagc   2220
gtcagtatta agcgggggag aattagatcg cgatgggaaa aaattcggtt aaggccaggg   2280
ggaaagaaaa aatataaatt aaaacatata gtatgggcaa gcagggagct agaacgattc   2340
gcagttaatc ctggcctgtt agaaacatca gaaggctgta gacaaatact gggacagcta   2400
caaccatccc ttcagacagg atcagaagaa cttagatcat tatataatac agtagcaacc   2460
ctctattgtg tgcatcaaag gatagagata aaagacacca aggaagcttt agacaagata   2520
gaggaagagc aaaacaaaag taagaccacc gcacagcaag cggccgctga tcttcagacc   2580
tggaggagga gatatgaggg acaattggag aagtgaatta tataaatata aagtagtaaa   2640
aattgaacca ttaggagtag cacccaccaa ggcaaagaga agagtggtgc agagagaaaa   2700
aagagcagtg ggaataggag ctttgttcct tgggttcttg ggagcagcag gaagcactat   2760
```

-continued

```
gggcgcagcg tcaatgacgc tgacggtaca ggccagacaa ttattgtctg gtatagtgca   2820
gcagcagaac aatttgctga gggctattga ggcgcaacag catctgttgc aactcacagt   2880
ctggggcatc aagcagctcc aggcaagaat cctggctgtg gaaagatacc taaaggatca   2940
acagctcctg gggatttggg gttgctctgg aaaactcatt tgcaccactg ctgtgccttg   3000
gaatgctagt tggagtaata aatctctgga acagatttgg aatcacacga cctggatgga   3060
gtgggacaga gaaattaaca attacacaag cttaatacac tccttaattg aagaatcgca   3120
aaaccagcaa gaaaagaatg aacaagaatt attggaatta gataaatggg caagtttgtg   3180
gaattggttt aacataacaa attggctgtg gtatataaaa ttattcataa tgatagtagg   3240
aggcttggta ggtttaagaa tagtttttgc tgtactttct atagtgaata gagttaggca   3300
gggatattca ccattatcgt ttcagaccca cctcccaacc ccgaggggac cctattccag   3360
cacatatgag gcttggcgta actagatctt gagacaaatg gcagtattca tccacaattt   3420
taaaagaaaa ggggggattg gggggtacag tgcaggggaa agaatagtag acataatagc   3480
aacagacata caaactaaag aattacaaaa acaaattaca aaaattcaaa attttcgggt   3540
ttattacagg gacagcagag atccactttg ggctcgaggg ggcccgggtg caaagatgga   3600
taaagtttta aacagagagg aatctttgca gctaatggac cttctaggtc ttgaaaggag   3660
tgggaattgg ctccggtgcc cgtcagtggg cagagcgcac atcgcccaca gtccccgaga   3720
agttgggggg aggggtcggc aattgatccg gtgcctagag aaggtggcgc ggggtaaact   3780
gggaaagtga tgtcgtgtac tggctccgcc tttttcccga gggtggggga gaaccgtata   3840
taagtgcagt agtcgccgtg aacgttcttt ttcgcaacgg gtttgccgcc agaacacagg   3900
taagtgccgt gtgtggttcc cgcgggcctg gcctctttac gggttatggc ccttgcgtgc   3960
cttgaattac ttccacctgg ctgcagtacg tgattcttga tcccgagctt cgggttggaa   4020
gtgggtggga gagttcgagg ccttgcgctt aaggagcccc ttcgcctcgt gcttgagttg   4080
aggcctggcc tgggcgctgg ggccgccgcg tgcgaatctg gtggcacctt cgcgcctgtc   4140
tcgctgcttt cgataagtct ctagccattt aaaatttttg atgacctgct gcgacgcttt   4200
ttttctggca agatagtctt gtaaatgcgg gccaagatct gcacactggt atttcggttt   4260
ttggggccgc gggcggcgac ggggcccgtg cgtcccagcg cacatgttcg gcgaggcggg   4320
gcctgcgagc gcggccaccg agaatcggac gggggtagtc tcaagctggc cggcctgctc   4380
tggtgcctgg cctcgcgccg ccgtgtatcg ccccgccctg ggcggcaagg ctggcccggt   4440
cggcaccagt tgcgtgagcg gaaagatggc cgcttcccgg ccctgctgca gggagctcaa   4500
aatggaggac gcggcgctcg ggagagcggg cgggtgagtc acccacacaa aggaaaaggg   4560
cctttccgtc ctcagccgtc gcttcatgtg actccacgga gtaccgggcg ccgtccaggc   4620
acctcgatta gttctcgagc ttttggagta cgtcgtcttt aggttggggg gaggggtttt   4680
atgcgatgga gtttccccac actgagtggg tggagactga agttaggcca gcttggcact   4740
tgatgtaatt ctccttggaa tttgcccttt ttgagtttgg atcttggttc attctcaagc   4800
ctcagacagt ggttcaaagt ttttttcttc catttcaggt gtcgtgaata ccgtcgactc   4860
cggaatagcc accatggaga cggacgtctc agctgaagct gctgcaaagg aagctgcagc   4920
taaggaggct gcagctaagg ctatggtgag caagggcgag gaggataaca tggccatcat   4980
caaggagttc atgcgcttca aggtgcacat ggagggctcc gtgaacggcc acgagttcga   5040
gatcgagggc gagggcgagg gccgccccta cgagggcacc cagaccgcca agctgaaggt   5100
```

-continued

```
gaccaagggt ggccccctgc ccttcgcctg ggacatcctg tcccctcagt tcatgtacgg   5160
ctccaaggcc tacgtgaagc accccgccga catccccgac tacttgaagc tgtccttccc   5220
cgagggcttc aagtgggagc gcgtgatgaa cttcgaggac ggcggcgtgg tgaccgtgac   5280
ccaggactcc tccctgcagg acggcgagtt catctacaag gtgaagctgc gcggcaccaa   5340
cttcccctcc gacggccccg taatgcagaa gaagaccatg ggctgggagg cctcctccga   5400
gcggatgtac cccgaggacg gcgccctgaa gggcgagatc aagcagaggc tgaagctgaa   5460
ggacggcggc cactacgacg ctgaggtcaa gaccacctac aaggccaaga agcccgtgca   5520
gctgcccggc gcctacaacg tcaacatcaa gttggacatc acctcccaca acgaggacta   5580
caccatcgtg gaacagtacg aacgcgccga gggccgccac tccaccggcg gcatggacga   5640
gctgtacaag ggactcagag tttgggtagg aagcggagct actaacttca gcctgctgaa   5700
gcaggctgga gatgtggagg agaaccctgg acctatgatt gaacaagatg gattgcacgc   5760
aggttctccg gccgcttggg tggagaggct attcggctat gactgggcac aacagacaat   5820
cggctgctct gatgccgccg tgttccggct gtcagcgcag gggcgcccgg ttctttttgt   5880
caagaccgac ctgtccggtg ccctgaatga actgcaggac gaggcagcgc ggctatcgtg   5940
gctggccacg acgggcgttc cttgcgcagc tgtgctcgac gttgtcactg aagcgggaag   6000
ggactggctg ctattgggcg aagtgccggg gcaggatctc ctgtcatctc accttgctcc   6060
tgccgagaaa gtatccatca tggctgatgc aatgcggcgg ctgcatacgc ttgatccggc   6120
tacctgccca ttcgaccacc aagcgaaaca tcgcatcgag cgagcacgta ctcggatgga   6180
agccggtctt gtcgatcagg atgatctgga cgaagagcat caggggctcg cgccagccga   6240
actgttcgcc aggctcaagg cgcgcatgcc cgacggcgag gatctcgtcg tgacccatgg   6300
cgatgcctgc ttgccgaata tcatggtgga aaatggccgc ttttctggat tcatcgactg   6360
tggccggctg ggtgtggccg accgctatca ggacatagcg ttggctaccc gtgatattgc   6420
tgaagagctt ggcggcgaat gggctgaccg cttcctcgtg ctttacggta tcgccgctcc   6480
cgattcgcag cgcatcgcct tctatcgcct tcttgacgag ttcttctgaa tgcatgagta   6540
actgaggatc cagggacagc agagatacgc gttaagtcga caatcaacct ctggattaca   6600
aaatttgtga aagattgact ggtattctta actatgttgc tccttttacg ctatgtggat   6660
acgctgcttt aatgcctttg tatcatgcta ttgcttcccg tatggctttc attttctcct   6720
ccttgtataa atcctggttg ctgtctcttt atgaggagtt gtggcccgtt gtcaggcaac   6780
gtggcgtggt gtgcactgtg tttgctgacg caacccccac tggttggggc attgccacca   6840
cctgtcagct cctttccggg actttcgctt tccccctccc tattgccacg gcggaactca   6900
tcgccgcctg ccttgcccgc tgctggacag gggctcggct gttgggcact gacaattccg   6960
tggtgttgtc ggggaaatca tcgtcctttc cttggctgct cgcctgtgtt gccacctgga   7020
ttctgcgcgg gacgtccttc tgctacgtcc cttcggccct caatccagcg gaccttcctt   7080
cccgcggcct gctgccggct ctgcggcctc ttccgcgtct tcgccttcgc cctcagacga   7140
gtcggatctc cctttgggcc gcctccccgc gtcgacttta agaccaatga cttacaaggc   7200
agctgtagat cttagccact ttttaaaaga aaaggggga ctggaagggc taattcactc   7260
ccaacgaaga caagatctgc tttttgcttg tactgggtct ctctggttag accagatctg   7320
agcctgggag ctctctggct aactagggaa cccactgctt aagcctcaat aaagcttgcc   7380
ttgagtgctt caagtagtgt gtgcccgtct gttgtgtgac tctggtaact agagatccct   7440
cagacccttt tagtcagtgt ggaaaatctc tagcagtacg tatagtagtt catgtcatct   7500
```

```
tattattcag tatttataac ttgcaaagaa atgaatatca gagagtgaga ggaacttgtt   7560

tattgcagct tataatggtt acaaataaag caatagcatc acaaatttca caaataaagc   7620

atttttttca ctgcattcta gttgtggttt gtccaaactc atcaatgtat cttatcatgt   7680

ctggctctag ctatcccgcc cctaactccg cccatcccgc ccctaactcc gcccagttcc   7740

gcccattctc cgccccatgg ctgactaatt ttttttattt atgcagaggc cgaggccgcc   7800

tcggcctctg agctattcca gaagtagtga ggaggctttt ttggaggcct agggacgtac   7860

ccaattcgcc ctatagtgag tcgtattacg cgcgctcact ggccgtcgtt ttacaacgtc   7920

gtgactggga aaaccctggc gttacccaac ttaatcgcct tgcagcacat ccccctttcg   7980

ccagctggcg taatagcgaa gaggcccgca ccgatcgccc ttcccaacag ttgcgcagcc   8040

tgaatggcga atgggacgcg ccctgtagcg gcgcattaag cgcggcgggt gtggtggtta   8100

cgcgcagcgt gaccgctaca cttgccagcg ccctagcgcc cgctcctttc gctttcttcc   8160

cttcctttct cgccacgttc gccggctttc cccgtcaagc tctaaatcgg gggctccctt   8220

tagggttccg atttagtgct ttacggcacc tcgaccccaa aaaacttgat tagggtgatg   8280

gttcacgtag tgggccatcg ccctgataga cggtttttcg ccctttgacg ttggagtcca   8340

cgttctttaa tagtggactc ttgttccaaa ctggaacaac actcaaccct atctcggtct   8400

attcttttga tttataaggg attttgccga tttcggccta ttggttaaaa aatgagctga   8460

tttaacaaaa atttaacgcg aattttaaca aaatattaac gcttacaatt taggtggcac   8520

ttttcgggga aatgtgcgcg gaacccctat ttgtttattt ttctaaatac attcaaatat   8580

gtatccgctc atgagacaat aaccctgata aatgcttcaa taatattgaa aaaggaagag   8640

tatgagtatt caacatttcc gtgtcgccct tattcccttt tttgcggcat tttgccttcc   8700

tgtttttgct cacccagaaa cgctggtgaa agtaaaagat gctgaagatc agttgggtgc   8760

acgagtgggt tacatcgaac tggatctcaa cagcggtaag atccttgaga gttttcgccc   8820

cgaagaacgt tttccaatga tgagcacttt taaagttctg ctatgtggcg cggtattatc   8880

ccgtattgac gccgggcaag agcaactcgg tcgccgcata cactattctc agaatgactt   8940

ggttgagtac tcaccagtca cagaaaagca tcttacggat ggcatgacag taagagaatt   9000

atgcagtgct gccataacca tgagtgataa cactgcggcc aacttacttc tgacaacgat   9060

cggaggaccg aaggagctaa ccgctt                                        9086
```

<210> SEQ ID NO 93
<211> LENGTH: 10
<212> TYPE: PRT
<213> ORGANISM: Artificial
<220> FEATURE:
<223> OTHER INFORMATION: Synthetic

<400> SEQUENCE: 93

```
Gly Gly Gly Gly Ser Gly Gly Gly Gly Ser
1               5                   10
```

<210> SEQ ID NO 94
<211> LENGTH: 17
<212> TYPE: PRT
<213> ORGANISM: Artificial
<220> FEATURE:
<223> OTHER INFORMATION: Synthetic

<400> SEQUENCE: 94

```
Ala Glu Ala Ala Ala Lys Glu Ala Ala Ala Lys Glu Ala Ala Ala Lys
```

1 5 10 15

Ala

<210> SEQ ID NO 95
<211> LENGTH: 60
<212> TYPE: PRT
<213> ORGANISM: Artificial
<220> FEATURE:
<223> OTHER INFORMATION: Synthetic

<400> SEQUENCE: 95

Phe Asn Val Leu Met Val His Lys Arg Ser His Thr Gly Glu Arg Pro
1 5 10 15

Leu Gln Cys Glu Ile Cys Gly Phe Thr Cys Arg Gln Lys Gly Asn Leu
20 25 30

Leu Arg His Ile Lys Leu His Thr Gly Glu Lys Pro Phe Lys Cys His
35 40 45

Leu Cys Asn Tyr Ala Cys Gln Arg Arg Asp Ala Leu
50 55 60

<210> SEQ ID NO 96
<211> LENGTH: 60
<212> TYPE: PRT
<213> ORGANISM: Artificial
<220> FEATURE:
<223> OTHER INFORMATION: Synthetic

<400> SEQUENCE: 96

Phe Asn Val Leu Met Val His Arg Arg Ser His Thr Gly Glu Arg Pro
1 5 10 15

Leu Gln Cys Glu Ile Cys Gly Phe Thr Cys Arg Gln Arg Gly Asn Leu
20 25 30

Leu Arg His Ile Arg Leu His Thr Gly Glu Arg Pro Phe Arg Cys His
35 40 45

Leu Cys Asn Tyr Ala Cys Gln Arg Arg Asp Ala Leu
50 55 60

<210> SEQ ID NO 97
<211> LENGTH: 16
<212> TYPE: PRT
<213> ORGANISM: Artificial
<220> FEATURE:
<223> OTHER INFORMATION: Synthetic

<400> SEQUENCE: 97

Phe Asn Val Leu Met Val His Lys Arg Ser His Thr Gly Glu Arg Pro
1 5 10 15

<210> SEQ ID NO 98
<211> LENGTH: 11
<212> TYPE: PRT
<213> ORGANISM: Artificial
<220> FEATURE:
<223> OTHER INFORMATION: Synthetic

<400> SEQUENCE: 98

Leu Gln Cys Glu Ile Cys Gly Phe Thr Cys Arg
1 5 10

<210> SEQ ID NO 99
<211> LENGTH: 33
<212> TYPE: PRT
<213> ORGANISM: Artificial

<220> FEATURE:
<223> OTHER INFORMATION: Synthetic

<400> SEQUENCE: 99

Gln Lys Gly Asn Leu Leu Arg His Ile Lys Leu His Thr Gly Glu Lys
1 5 10 15

Pro Phe Lys Cys His Leu Cys Asn Tyr Ala Cys Gln Arg Arg Asp Ala
20 25 30

Leu

<210> SEQ ID NO 100
<211> LENGTH: 16
<212> TYPE: PRT
<213> ORGANISM: Artificial
<220> FEATURE:
<223> OTHER INFORMATION: Synthetic

<400> SEQUENCE: 100

Phe Asn Val Leu Met Val His Arg Arg Ser His Thr Gly Glu Arg Pro
1 5 10 15

<210> SEQ ID NO 101
<211> LENGTH: 33
<212> TYPE: PRT
<213> ORGANISM: Artificial
<220> FEATURE:
<223> OTHER INFORMATION: Synthetic

<400> SEQUENCE: 101

Gln Arg Gly Asn Leu Leu Arg His Ile Arg Leu His Thr Gly Glu Arg
1 5 10 15

Pro Phe Arg Cys His Leu Cys Asn Tyr Ala Cys Gln Arg Arg Asp Ala
20 25 30

Leu

<210> SEQ ID NO 102
<211> LENGTH: 21
<212> TYPE: PRT
<213> ORGANISM: Artificial
<220> FEATURE:
<223> OTHER INFORMATION: Synthetic

<400> SEQUENCE: 102

Thr Gly Glu Lys Pro Phe Lys Cys His Leu Cys Asn Tyr Ala Cys Gln
1 5 10 15

Arg Arg Asp Ala Leu
20

<210> SEQ ID NO 103
<211> LENGTH: 21
<212> TYPE: PRT
<213> ORGANISM: Artificial
<220> FEATURE:
<223> OTHER INFORMATION: Synthetic

<400> SEQUENCE: 103

Thr Gly Glu Arg Pro Phe Arg Cys His Leu Cys Asn Tyr Ala Cys Gln
1 5 10 15

Arg Arg Asp Ala Leu
20

<210> SEQ ID NO 104
<211> LENGTH: 23

<212> TYPE: PRT
<213> ORGANISM: Artificial
<220> FEATURE:
<223> OTHER INFORMATION: Synthetic

<400> SEQUENCE: 104

His Glu Cys Lys Leu Cys Gly Ala Ser Phe Arg Thr Lys Gly Ser Leu
1 5 10 15

Ile Arg His His Arg Arg His
20

<210> SEQ ID NO 105
<211> LENGTH: 23
<212> TYPE: PRT
<213> ORGANISM: Artificial
<220> FEATURE:
<223> OTHER INFORMATION: Synthetic

<400> SEQUENCE: 105

Leu Gln Cys Glu Val Cys Gly Phe Gln Cys Arg Gln Arg Ala Ser Leu
1 5 10 15

Lys Tyr His Met Thr Lys His
20

<210> SEQ ID NO 106
<211> LENGTH: 23
<212> TYPE: PRT
<213> ORGANISM: Artificial
<220> FEATURE:
<223> OTHER INFORMATION: Synthetic

<400> SEQUENCE: 106

Tyr Arg Cys Arg Ala Cys Gly Arg Ala Cys Ser Arg Leu Ser Thr Leu
1 5 10 15

Ile Gln His Gln Lys Val His
20

<210> SEQ ID NO 107
<211> LENGTH: 23
<212> TYPE: PRT
<213> ORGANISM: Artificial
<220> FEATURE:
<223> OTHER INFORMATION: Synthetic

<400> SEQUENCE: 107

Tyr Gln Cys Lys Val Cys Gly Arg Ala Phe Lys Arg Val Ser His Leu
1 5 10 15

Thr Val His Tyr Arg Ile His
20

<210> SEQ ID NO 108
<211> LENGTH: 23
<212> TYPE: PRT
<213> ORGANISM: Artificial
<220> FEATURE:
<223> OTHER INFORMATION: Synthetic

<400> SEQUENCE: 108

Leu Gln Cys Glu Ile Cys Gly Tyr Gln Cys Arg Gln Arg Ala Ser Leu
1 5 10 15

Asn Trp His Met Lys Lys His
20

<210> SEQ ID NO 109

<211> LENGTH: 23
<212> TYPE: PRT
<213> ORGANISM: Artificial
<220> FEATURE:
<223> OTHER INFORMATION: Synthetic

<400> SEQUENCE: 109

Phe Ala Cys Val Ile Cys Gly Arg Lys Phe Arg Asn Arg Gly Leu Met
1 5 10 15

Gln Lys His Leu Lys Asn His
20

<210> SEQ ID NO 110
<211> LENGTH: 23
<212> TYPE: PRT
<213> ORGANISM: Artificial
<220> FEATURE:
<223> OTHER INFORMATION: Synthetic

<400> SEQUENCE: 110

Leu Gln Cys Glu Ile Cys Gly Phe Thr Cys Arg Gln Lys Ala Ser Leu
1 5 10 15

Asn Trp His Gln Arg Lys His
20

<210> SEQ ID NO 111
<211> LENGTH: 23
<212> TYPE: PRT
<213> ORGANISM: Artificial
<220> FEATURE:
<223> OTHER INFORMATION: Synthetic

<400> SEQUENCE: 111

Phe Val Cys Pro Arg Cys Gly Arg Gly Phe Ser Gln Pro Lys Ser Leu
1 5 10 15

Ala Arg His Leu Arg Leu His
20

<210> SEQ ID NO 112
<211> LENGTH: 23
<212> TYPE: PRT
<213> ORGANISM: Artificial
<220> FEATURE:
<223> OTHER INFORMATION: Synthetic

<400> SEQUENCE: 112

Phe Gln Cys Pro Ile Cys Gly Leu Val Ile Lys Arg Lys Ser Tyr Trp
1 5 10 15

Lys Arg His Met Val Ile His
20

<210> SEQ ID NO 113
<211> LENGTH: 23
<212> TYPE: PRT
<213> ORGANISM: Artificial
<220> FEATURE:
<223> OTHER INFORMATION: Synthetic

<400> SEQUENCE: 113

Leu Gln Cys Glu Ile Cys Gly Phe Thr Cys Arg Gln Lys Ala Ser Leu
1 5 10 15

Asn Trp His Met Lys Lys His
20

<210> SEQ ID NO 114
<211> LENGTH: 74
<212> TYPE: PRT
<213> ORGANISM: Artificial
<220> FEATURE:
<223> OTHER INFORMATION: Synthetic

<400> SEQUENCE: 114

Ala Gly Ser Gly Gly Ser Gly Gly Ser Gly Gly Ser Pro Val Pro Ser
1 5 10 15

Thr Pro Pro Thr Asn Ser Ser Ser Thr Pro Pro Thr Pro Ser Pro Ser
20 25 30

Pro Val Pro Ser Thr Pro Pro Thr Asn Ser Ser Ser Thr Pro Pro Thr
35 40 45

Pro Ser Pro Ser Pro Val Pro Ser Thr Pro Pro Thr Asn Ser Ser Ser
50 55 60

Thr Pro Pro Thr Pro Ser Pro Ser Ala Ser
65 70

<210> SEQ ID NO 115
<211> LENGTH: 74
<212> TYPE: PRT
<213> ORGANISM: Artificial
<220> FEATURE:
<223> OTHER INFORMATION: Synthetic

<400> SEQUENCE: 115

Ala Gly Ser Gly Gly Ser Gly Gly Ser Gly Gly Ser Pro Val Pro Ser
1 5 10 15

Thr Pro Pro Thr Pro Ser Pro Ser Thr Pro Pro Thr Pro Ser Pro Ser
20 25 30

Pro Val Pro Ser Thr Pro Pro Thr Asn Ser Ser Ser Thr Pro Pro Thr
35 40 45

Pro Ser Pro Ser Pro Val Pro Ser Thr Pro Pro Thr Pro Ser Pro Ser
50 55 60

Thr Pro Pro Thr Pro Ser Pro Ser Ala Ser
65 70

<210> SEQ ID NO 116
<211> LENGTH: 66
<212> TYPE: PRT
<213> ORGANISM: Artificial
<220> FEATURE:
<223> OTHER INFORMATION: Synthetic

<400> SEQUENCE: 116

Ala Gly Ser Gly Gly Ser Gly Gly Ser Gly Gly Ser Pro Val Pro Ser
1 5 10 15

Thr Pro Pro Thr Pro Ser Pro Ser Thr Pro Pro Thr Pro Ser Pro Ser
20 25 30

Gly Gly Ser Gly Asn Ser Ser Gly Ser Gly Gly Ser Pro Val Pro Ser
35 40 45

Thr Pro Pro Thr Pro Ser Pro Ser Thr Pro Pro Thr Pro Ser Pro Ser
50 55 60

Ala Ser
65

<210> SEQ ID NO 117
<211> LENGTH: 74
<212> TYPE: PRT
<213> ORGANISM: Artificial

<220> FEATURE:
<223> OTHER INFORMATION: Synthetic

<400> SEQUENCE: 117

Ala Gly Ser Gly Gly Ser Gly Gly Ser Gly Gly Ser Pro Val Pro Ser
1               5                   10                  15

Thr Pro Pro Thr Pro Ser Pro Ser Thr Pro Pro Thr Pro Ser Pro Ser
            20                  25                  30

Pro Val Pro Ser Thr Pro Pro Thr Pro Ser Pro Ser Thr Pro Pro Thr
        35                  40                  45

Pro Ser Pro Ser Pro Val Pro Ser Thr Pro Pro Thr Pro Ser Pro Ser
    50                  55                  60

Thr Pro Pro Thr Pro Ser Pro Ser Ala Ser
65                  70

<210> SEQ ID NO 118
<211> LENGTH: 152
<212> TYPE: PRT
<213> ORGANISM: Artificial
<220> FEATURE:
<223> OTHER INFORMATION: Synthetic

<400> SEQUENCE: 118

Ala Gly Ser Gly Gly Ser Gly Gly Ser Gly Gly Ser Pro Val Pro Ser
1               5                   10                  15

Thr Pro Pro Thr Pro Ser Pro Ser Thr Pro Pro Thr Pro Ser Pro Ser
            20                  25                  30

Ile Gln Arg Thr Pro Lys Ile Gln Val Tyr Ser Arg His Pro Ala Glu
        35                  40                  45

Asn Gly Lys Ser Asn Phe Leu Asn Cys Tyr Val Ser Gly Phe His Pro
    50                  55                  60

Ser Asp Ile Glu Val Asp Leu Leu Lys Asn Gly Glu Arg Ile Glu Lys
65                  70                  75                  80

Val Glu His Ser Asp Leu Ser Phe Ser Lys Asp Trp Ser Phe Tyr Leu
                85                  90                  95

Leu Tyr Tyr Thr Glu Phe Thr Pro Thr Glu Lys Asp Glu Tyr Ala Cys
            100                 105                 110

Arg Val Asn His Val Thr Leu Ser Gln Pro Lys Ile Val Lys Trp Asp
        115                 120                 125

Arg Asp Pro Val Pro Ser Thr Pro Pro Thr Pro Ser Pro Ser Thr Pro
    130                 135                 140

Pro Thr Pro Ser Pro Ser Ala Ser
145                 150

<210> SEQ ID NO 119
<211> LENGTH: 144
<212> TYPE: PRT
<213> ORGANISM: Artificial
<220> FEATURE:
<223> OTHER INFORMATION: Synthetic

<400> SEQUENCE: 119

Ala Gly Ser Gly Gly Ser Gly Gly Ser Gly Gly Ser Pro Val Pro Ser
1               5                   10                  15

Thr Pro Pro Thr Pro Ser Pro Ser Thr Pro Pro Thr Pro Ser Pro Ser
            20                  25                  30

Ile Gln Arg Thr Pro Lys Ile Gln Val Tyr Ser Arg His Pro Ala Glu
        35                  40                  45

```
Asn Gly Lys Ser Asn Phe Leu Asn Cys Tyr Val Ser Gly Phe His Pro
    50                  55                  60

Ser Asp Ile Glu Val Asp Leu Leu Lys Asn Gly Glu Arg Ile Glu Lys
65                  70                  75                  80

Val Glu His Ser Asp Leu Ser Phe Ser Lys Asp Trp Ser Phe Tyr Leu
                85                  90                  95

Leu Tyr Tyr Thr Glu Phe Thr Pro Thr Glu Lys Asp Glu Tyr Ala Cys
            100                 105                 110

Arg Val Asn His Val Thr Leu Ser Gln Pro Lys Ile Val Lys Trp Asp
        115                 120                 125

Arg Asp Gly Gly Ser Gly Gly Ser Gly Gly Ser Gly Gly Ser Ala Ser
    130                 135                 140


<210> SEQ ID NO 120
<211> LENGTH: 242
<212> TYPE: PRT
<213> ORGANISM: Artificial
<220> FEATURE:
<223> OTHER INFORMATION: Synthetic

<400> SEQUENCE: 120

Ala Gly Pro Val Pro Ser Thr Pro Pro Thr Pro Ser Pro Ser Thr Pro
1               5                   10                  15

Pro Thr Pro Ser Pro Ser Ile Gln Arg Thr Pro Lys Ile Gln Val Tyr
            20                  25                  30

Ser Arg His Pro Ala Glu Asn Gly Lys Ser Asn Phe Leu Asn Cys Tyr
        35                  40                  45

Val Ser Gly Phe His Pro Ser Asp Ile Glu Val Asp Leu Leu Lys Asn
    50                  55                  60

Gly Glu Arg Ile Glu Lys Val Glu His Ser Asp Leu Ser Phe Ser Lys
65                  70                  75                  80

Asp Trp Ser Phe Tyr Leu Leu Tyr Tyr Thr Glu Phe Thr Pro Thr Glu
                85                  90                  95

Lys Asp Glu Tyr Ala Cys Arg Val Asn His Val Thr Leu Ser Gln Pro
            100                 105                 110

Lys Ile Val Lys Trp Asp Arg Asp Gly Gly Ser Gly Gly Ser Gly Gly
        115                 120                 125

Ser Gly Gly Ser Ile Gln Arg Thr Pro Lys Ile Gln Val Tyr Ser Arg
    130                 135                 140

His Pro Ala Glu Asn Gly Lys Ser Asn Phe Leu Asn Cys Tyr Val Ser
145                 150                 155                 160

Gly Phe His Pro Ser Asp Ile Glu Val Asp Leu Leu Lys Asn Gly Glu
                165                 170                 175

Arg Ile Glu Lys Val Glu His Ser Asp Leu Ser Phe Ser Lys Asp Trp
            180                 185                 190

Ser Phe Tyr Leu Leu Tyr Tyr Thr Glu Phe Thr Pro Thr Glu Lys Asp
        195                 200                 205

Glu Tyr Ala Cys Arg Val Asn His Val Thr Leu Ser Gln Pro Lys Ile
    210                 215                 220

Val Lys Trp Asp Arg Asp Gly Gly Ser Gly Gly Ser Gly Gly Ser Gly
225                 230                 235                 240

Ala Ser


<210> SEQ ID NO 121
<211> LENGTH: 262
<212> TYPE: PRT
```

<213> ORGANISM: Artificial
<220> FEATURE:
<223> OTHER INFORMATION: Synthetic

<400> SEQUENCE: 121

Ala Gly Ser Gly Gly Ser Gly Gly Ser Gly Gly Ser Pro Val Pro Ser
1 5 10 15

Thr Pro Pro Thr Pro Ser Pro Ser Thr Pro Pro Thr Pro Ser Pro Ser
20 25 30

Ile Gln Arg Thr Pro Lys Ile Gln Val Tyr Ser Arg His Pro Ala Glu
35 40 45

Asn Gly Lys Ser Asn Phe Leu Asn Cys Tyr Val Ser Gly Phe His Pro
50 55 60

Ser Asp Ile Glu Val Asp Leu Leu Lys Asn Gly Glu Arg Ile Glu Lys
65 70 75 80

Val Glu His Ser Asp Leu Ser Phe Ser Lys Asp Trp Ser Phe Tyr Leu
85 90 95

Leu Tyr Tyr Thr Glu Phe Thr Pro Thr Glu Lys Asp Glu Tyr Ala Cys
100 105 110

Arg Val Asn His Val Thr Leu Ser Gln Pro Lys Ile Val Lys Trp Asp
115 120 125

Arg Asp Gly Gly Ser Gly Gly Ser Gly Gly Ser Gly Gly Ser Ile Gln
130 135 140

Arg Thr Pro Lys Ile Gln Val Tyr Ser Arg His Pro Ala Glu Asn Gly
145 150 155 160

Lys Ser Asn Phe Leu Asn Cys Tyr Val Ser Gly Phe His Pro Ser Asp
165 170 175

Ile Glu Val Asp Leu Leu Lys Asn Gly Glu Arg Ile Glu Lys Val Glu
180 185 190

His Ser Asp Leu Ser Phe Ser Lys Asp Trp Ser Phe Tyr Leu Leu Tyr
195 200 205

Tyr Thr Glu Phe Thr Pro Thr Glu Lys Asp Glu Tyr Ala Cys Arg Val
210 215 220

Asn His Val Thr Leu Ser Gln Pro Lys Ile Val Lys Trp Asp Arg Asp
225 230 235 240

Pro Val Pro Ser Thr Pro Pro Thr Pro Ser Pro Ser Thr Pro Pro Thr
245 250 255

Pro Ser Pro Ser Ala Ser
260

<210> SEQ ID NO 122
<211> LENGTH: 121
<212> TYPE: PRT
<213> ORGANISM: Artificial
<220> FEATURE:
<223> OTHER INFORMATION: Synthetic

<400> SEQUENCE: 122

Ala Gly Ser Gly Gly Ser Gly Gly Ser Gly Gly Ser Pro Val Pro Ser
1 5 10 15

Thr Pro Pro Thr Pro Ser Pro Ser Thr Pro Pro Thr Pro Ser Pro Ser
20 25 30

Gln Ile Phe Val Lys Thr Leu Thr Gly Lys Thr Ile Thr Leu Glu Val
35 40 45

Glu Pro Ser Asp Thr Ile Glu Asn Val Lys Ala Lys Ile Gln Asp Lys
50 55 60

```
Glu Gly Ile Pro Pro Asp Gln Gln Arg Leu Ile Phe Ala Gly Lys Gln
65                  70                  75                  80

Leu Glu Asp Gly Arg Thr Leu Ser Asp Tyr Asn Ile Gln Lys Glu Ser
                85                  90                  95

Thr Leu His Leu Val Leu Arg Leu Arg Gly Gly Gly Gly Ser Gly Gly
            100                 105                 110

Ser Gly Gly Ser Gly Gly Ser Ala Ser
        115                 120


<210> SEQ ID NO 123
<211> LENGTH: 326
<212> TYPE: PRT
<213> ORGANISM: Artificial
<220> FEATURE:
<223> OTHER INFORMATION: Synthetic

<400> SEQUENCE: 123

Ala Gly Ser Gly Gly Ser Gly Gly Ser Gly Gly Ser Pro Val Pro Ser
1               5                   10                  15

Thr Pro Pro Thr Pro Ser Pro Ser Thr Pro Pro Thr Pro Ser Pro Ser
            20                  25                  30

Asp Gly Arg Tyr Ser Leu Thr Tyr Ile Tyr Thr Gly Leu Ser Lys His
        35                  40                  45

Val Glu Asp Val Pro Ala Phe Gln Ala Leu Gly Ser Leu Asn Asp Leu
    50                  55                  60

Gln Phe Phe Arg Tyr Asn Ser Lys Asp Arg Lys Ser Gln Pro Met Gly
65                  70                  75                  80

Leu Trp Arg Gln Val Glu Gly Met Glu Asp Trp Lys Gln Asp Ser Gln
                85                  90                  95

Leu Gln Lys Ala Arg Glu Asp Ile Phe Met Glu Thr Leu Lys Asp Ile
            100                 105                 110

Val Glu Tyr Tyr Asn Asp Ser Asn Gly Ser His Val Leu Gln Gly Arg
        115                 120                 125

Phe Gly Cys Glu Ile Glu Asn Asn Arg Ser Ser Gly Ala Phe Trp Lys
    130                 135                 140

Tyr Tyr Tyr Asp Gly Lys Asp Tyr Ile Glu Phe Asn Lys Glu Ile Pro
145                 150                 155                 160

Ala Trp Val Pro Phe Asp Pro Ala Ala Gln Ile Thr Lys Gln Lys Trp
                165                 170                 175

Glu Ala Glu Pro Val Tyr Val Gln Arg Ala Lys Ala Tyr Leu Glu Glu
            180                 185                 190

Glu Cys Pro Ala Thr Leu Arg Lys Tyr Leu Lys Tyr Ser Lys Asn Ile
        195                 200                 205

Leu Asp Arg Gln Asp Pro Pro Ser Val Val Val Thr Ser His Gln Ala
    210                 215                 220

Pro Gly Glu Lys Lys Lys Leu Lys Cys Leu Ala Tyr Asp Phe Tyr Pro
225                 230                 235                 240

Gly Lys Ile Asp Val His Trp Thr Arg Ala Gly Glu Val Gln Glu Pro
                245                 250                 255

Glu Leu Arg Gly Asp Val Leu His Asn Gly Asn Gly Thr Tyr Gln Ser
            260                 265                 270

Trp Val Val Val Ala Val Pro Pro Gln Asp Thr Ala Pro Tyr Ser Cys
        275                 280                 285

His Val Gln His Ser Ser Leu Ala Gln Pro Leu Val Val Pro Trp Glu
    290                 295                 300
```

```
Ala Ser Pro Val Pro Ser Thr Pro Pro Thr Pro Ser Pro Ser Thr Pro
305                 310                 315                 320

Pro Thr Pro Ser Ala Ser
                325


<210> SEQ ID NO 124
<211> LENGTH: 606
<212> TYPE: PRT
<213> ORGANISM: Artificial
<220> FEATURE:
<223> OTHER INFORMATION: Synthetic

<400> SEQUENCE: 124

Ala Gly Ser Gly Gly Ser Gly Gly Ser Gly Gly Ser Gly Gly Ser Gly
1               5                   10                  15

Gly Ser Gly Gly Ser Gly Gly Ser Asp Gly Arg Tyr Ser Leu Thr Tyr
            20                  25                  30

Ile Tyr Thr Gly Leu Ser Lys His Val Glu Asp Val Pro Ala Phe Gln
        35                  40                  45

Ala Leu Gly Ser Leu Asn Asp Leu Gln Phe Phe Arg Tyr Asn Ser Lys
    50                  55                  60

Asp Arg Lys Ser Gln Pro Met Gly Leu Trp Arg Gln Val Glu Gly Met
65                  70                  75                  80

Glu Asp Trp Lys Gln Asp Ser Gln Leu Gln Lys Ala Arg Glu Asp Ile
                85                  90                  95

Phe Met Glu Thr Leu Lys Asp Ile Val Glu Tyr Tyr Asn Asp Ser Asn
            100                 105                 110

Gly Ser His Val Leu Gln Gly Arg Phe Gly Cys Glu Ile Glu Asn Asn
        115                 120                 125

Arg Ser Ser Gly Ala Phe Trp Lys Tyr Tyr Tyr Asp Gly Lys Asp Tyr
    130                 135                 140

Ile Glu Phe Asn Lys Glu Ile Pro Ala Trp Val Pro Phe Asp Pro Ala
145                 150                 155                 160

Ala Gln Ile Thr Lys Gln Lys Trp Glu Ala Glu Pro Val Tyr Val Gln
                165                 170                 175

Arg Ala Lys Ala Tyr Leu Glu Glu Glu Cys Pro Ala Thr Leu Arg Lys
            180                 185                 190

Tyr Leu Lys Tyr Ser Lys Asn Ile Leu Asp Arg Gln Asp Pro Pro Ser
        195                 200                 205

Val Val Val Thr Ser His Gln Ala Pro Gly Glu Lys Lys Lys Leu Lys
    210                 215                 220

Cys Leu Ala Tyr Asp Phe Tyr Pro Gly Lys Ile Asp Val His Trp Thr
225                 230                 235                 240

Arg Ala Gly Glu Val Gln Glu Pro Glu Leu Arg Gly Asp Val Leu His
                245                 250                 255

Asn Gly Asn Gly Thr Tyr Gln Ser Trp Val Val Val Ala Val Pro Pro
            260                 265                 270

Gln Asp Thr Ala Pro Tyr Ser Cys His Val Gln His Ser Ser Leu Ala
        275                 280                 285

Gln Pro Leu Val Val Pro Trp Glu Ala Ser Gly Gly Ser Gly Gly Ser
    290                 295                 300

Gly Gly Ser Gly Gly Ser Asp Gly Arg Tyr Ser Leu Thr Tyr Ile Tyr
305                 310                 315                 320

Thr Gly Leu Ser Lys His Val Glu Asp Val Pro Ala Phe Gln Ala Leu
                325                 330                 335
```

Gly Ser Leu Asn Asp Leu Gln Phe Phe Arg Tyr Asn Ser Lys Asp Arg
340 345 350

Lys Ser Gln Pro Met Gly Leu Trp Arg Gln Val Glu Gly Met Glu Asp
355 360 365

Trp Lys Gln Asp Ser Gln Leu Gln Lys Ala Arg Glu Asp Ile Phe Met
370 375 380

Glu Thr Leu Lys Asp Ile Val Glu Tyr Tyr Asn Asp Ser Asn Gly Ser
385 390 395 400

His Val Leu Gln Gly Arg Phe Gly Cys Glu Ile Glu Asn Asn Arg Ser
405 410 415

Ser Gly Ala Phe Trp Lys Tyr Tyr Tyr Asp Gly Lys Asp Tyr Ile Glu
420 425 430

Phe Asn Lys Glu Ile Pro Ala Trp Val Pro Phe Asp Pro Ala Ala Gln
435 440 445

Ile Thr Lys Gln Lys Trp Glu Ala Glu Pro Val Tyr Val Gln Arg Ala
450 455 460

Lys Ala Tyr Leu Glu Glu Glu Cys Pro Ala Thr Leu Arg Lys Tyr Leu
465 470 475 480

Lys Tyr Ser Lys Asn Ile Leu Asp Arg Gln Asp Pro Pro Ser Val Val
485 490 495

Val Thr Ser His Gln Ala Pro Gly Glu Lys Lys Lys Leu Lys Cys Leu
500 505 510

Ala Tyr Asp Phe Tyr Pro Gly Lys Ile Asp Val His Trp Thr Arg Ala
515 520 525

Gly Glu Val Gln Glu Pro Glu Leu Arg Gly Asp Val Leu His Asn Gly
530 535 540

Asn Gly Thr Tyr Gln Ser Trp Val Val Val Ala Val Pro Pro Gln Asp
545 550 555 560

Thr Ala Pro Tyr Ser Cys His Val Gln His Ser Ser Leu Ala Gln Pro
565 570 575

Leu Val Val Pro Trp Glu Ala Ser Pro Val Pro Ser Thr Pro Pro Thr
580 585 590

Pro Ser Pro Ser Thr Pro Pro Thr Pro Ser Pro Ser Ala Ser
595 600 605

<210> SEQ ID NO 125
<211> LENGTH: 46
<212> TYPE: PRT
<213> ORGANISM: Artificial
<220> FEATURE:
<223> OTHER INFORMATION: Synthetic

<400> SEQUENCE: 125

Ala Gly Ser Gly Asn Ser Ser Gly Ser Gly Gly Ser Gly Gly Ser Gly
1 5 10 15

Asn Ser Ser Gly Ser Gly Gly Ser Pro Val Pro Ser Thr Pro Pro Thr
20 25 30

Pro Ser Pro Ser Thr Pro Pro Thr Pro Ser Pro Ser Ala Ser
35 40 45

<210> SEQ ID NO 126
<211> LENGTH: 141
<212> TYPE: PRT
<213> ORGANISM: Artificial
<220> FEATURE:
<223> OTHER INFORMATION: Synthetic

<400> SEQUENCE: 126

```
Lys Leu Ser Gly Gly Gly Gly Ser Gly Gly Gly Gly Ser Gly Gly Gly
1               5                   10                  15

Gly Ser Ala Glu Ala Trp Tyr Asn Leu Gly Asn Ala Tyr Tyr Lys Gln
            20                  25                  30

Gly Asp Tyr Gln Lys Ala Ile Glu Tyr Tyr Gln Lys Ala Leu Glu Leu
        35                  40                  45

Asp Pro Asn Asn Ala Glu Ala Trp Tyr Asn Leu Gly Asn Ala Tyr Tyr
    50                  55                  60

Lys Gln Gly Asp Tyr Gln Lys Ala Ile Glu Tyr Tyr Gln Lys Ala Leu
65                  70                  75                  80

Glu Leu Asp Pro Asn Asn Ala Glu Ala Trp Tyr Asn Leu Gly Asn Ala
                85                  90                  95

Tyr Tyr Lys Gln Gly Asp Tyr Gln Lys Ala Ile Glu Asp Tyr Gln Lys
            100                 105                 110

Ala Leu Glu Leu Asp Pro Asn Asn Leu Gln Arg Ser Ala Gly Gly Gly
        115                 120                 125

Gly Ser Gly Gly Gly Gly Ser Gly Gly Gly Gly Ala Ser
    130                 135                 140


<210> SEQ ID NO 127
<211> LENGTH: 245
<212> TYPE: PRT
<213> ORGANISM: Artificial
<220> FEATURE:
<223> OTHER INFORMATION: Synthetic

<400> SEQUENCE: 127

Lys Leu Ser Gly Gly Gly Gly Ser Gly Gly Gly Gly Ser Gly Gly Gly
1               5                   10                  15

Gly Ser Ala Glu Ala Trp Tyr Asn Leu Gly Asn Ala Tyr Tyr Lys Gln
            20                  25                  30

Gly Asp Tyr Gln Lys Ala Ile Glu Tyr Tyr Gln Lys Ala Leu Glu Leu
        35                  40                  45

Asp Pro Asn Asn Ala Glu Ala Trp Tyr Asn Leu Gly Asn Ala Tyr Tyr
    50                  55                  60

Lys Gln Gly Asp Tyr Gln Lys Ala Ile Glu Tyr Tyr Gln Lys Ala Leu
65                  70                  75                  80

Glu Leu Asp Pro Asn Asn Ala Glu Ala Trp Tyr Asn Leu Gly Asn Ala
                85                  90                  95

Tyr Tyr Lys Gln Gly Asp Tyr Gln Lys Ala Ile Glu Asp Tyr Gln Lys
            100                 105                 110

Ala Leu Glu Leu Asp Pro Asn Asn Leu Gln Ala Glu Ala Trp Lys Asn
        115                 120                 125

Leu Gly Asn Ala Tyr Tyr Lys Gln Gly Asp Tyr Gln Lys Ala Ile Glu
    130                 135                 140

Tyr Tyr Gln Lys Ala Leu Glu Leu Asp Pro Asn Asn Ala Ser Ala Trp
145                 150                 155                 160

Tyr Asn Leu Gly Asn Ala Tyr Tyr Lys Gln Gly Asp Tyr Gln Lys Ala
                165                 170                 175

Ile Glu Tyr Tyr Gln Lys Ala Leu Glu Leu Asp Pro Asn Asn Ala Lys
            180                 185                 190

Ala Trp Tyr Arg Arg Gly Asn Ala Tyr Tyr Lys Gln Gly Asp Tyr Gln
        195                 200                 205

Lys Ala Ile Glu Asp Tyr Gln Lys Ala Leu Glu Leu Asp Pro Asn Asn
    210                 215                 220
```

```
Arg Ser Arg Ser Ala Gly Gly Gly Gly Ser Gly Gly Gly Gly Ser Gly
225                 230                 235                 240

Gly Gly Gly Ala Ser
                245


<210> SEQ ID NO 128
<211> LENGTH: 431
<212> TYPE: PRT
<213> ORGANISM: Artificial
<220> FEATURE:
<223> OTHER INFORMATION: Synthetic

<400> SEQUENCE: 128

Lys Leu Ser Gly Gly Gly Gly Ser Gly Gly Gly Gly Ser Gly Gly Gly
1               5                   10                  15

Gly Ser Ala Glu Ala Trp Tyr Asn Leu Gly Asn Ala Tyr Tyr Lys Gln
            20                  25                  30

Gly Asp Tyr Gln Lys Ala Ile Glu Tyr Tyr Gln Lys Ala Leu Glu Leu
        35                  40                  45

Asp Pro Asn Asn Ala Glu Ala Trp Tyr Asn Leu Gly Asn Ala Tyr Tyr
    50                  55                  60

Lys Gln Gly Asp Tyr Gln Lys Ala Ile Glu Tyr Tyr Gln Lys Ala Leu
65                  70                  75                  80

Glu Leu Asp Pro Asn Asn Ala Glu Ala Trp Tyr Asn Leu Gly Asn Ala
                85                  90                  95

Tyr Tyr Lys Gln Gly Asp Tyr Gln Lys Ala Ile Glu Asp Tyr Gln Lys
            100                 105                 110

Ala Leu Glu Leu Asp Pro Asn Asn Leu Gln Ala Glu Ala Trp Lys Asn
        115                 120                 125

Leu Gly Asn Ala Tyr Tyr Lys Gln Gly Asp Tyr Gln Lys Ala Ile Glu
    130                 135                 140

Tyr Tyr Gln Lys Ala Leu Glu Leu Asp Pro Asn Asn Ala Ser Ala Trp
145                 150                 155                 160

Tyr Asn Leu Gly Asn Ala Tyr Tyr Lys Gln Gly Asp Tyr Gln Lys Ala
                165                 170                 175

Ile Glu Tyr Tyr Gln Lys Ala Leu Glu Leu Asp Pro Asn Asn Ala Lys
            180                 185                 190

Ala Trp Tyr Arg Arg Gly Asn Ala Tyr Tyr Lys Gln Gly Asp Tyr Gln
        195                 200                 205

Lys Ala Ile Glu Asp Tyr Gln Lys Ala Leu Glu Leu Asp Pro Asn Asn
    210                 215                 220

Arg Ser Ala Glu Ala Trp Tyr Asn Leu Gly Asn Ala Tyr Tyr Lys Gln
225                 230                 235                 240

Gly Asp Tyr Gln Lys Ala Ile Glu Tyr Tyr Gln Lys Ala Leu Glu Leu
                245                 250                 255

Asp Pro Asn Asn Ala Glu Ala Trp Tyr Asn Leu Gly Asn Ala Tyr Tyr
            260                 265                 270

Lys Gln Gly Asp Tyr Gln Lys Ala Ile Glu Tyr Tyr Gln Lys Ala Leu
        275                 280                 285

Glu Leu Asp Pro Asn Asn Ala Glu Ala Trp Tyr Asn Leu Gly Asn Ala
    290                 295                 300

Tyr Tyr Lys Gln Gly Asp Tyr Gln Lys Ala Ile Glu Asp Tyr Gln Lys
305                 310                 315                 320

Ala Leu Glu Leu Asp Pro Asn Ala Ile Glu Tyr Tyr Gln Lys Ala Leu
                325                 330                 335
```

Glu Leu Asp Pro Asn Asn Ala Glu Ala Trp Tyr Asn Leu Gly Asn Ala
340 345 350

Tyr Tyr Lys Gln Gly Asp Tyr Gln Lys Ala Ile Glu Tyr Tyr Gln Lys
355 360 365

Ala Leu Glu Leu Asp Pro Asn Asn Ala Glu Ala Trp Tyr Asn Leu Gly
370 375 380

Asn Ala Tyr Tyr Lys Gln Gly Asp Tyr Gln Lys Ala Ile Glu Asp Tyr
385 390 395 400

Gln Lys Ala Leu Glu Leu Asp Pro Asn Asn Leu Gln Arg Ser Ala Gly
405 410 415

Gly Gly Gly Ser Gly Gly Gly Gly Ser Gly Gly Gly Gly Ala Ser
420 425 430

<210> SEQ ID NO 129
<211> LENGTH: 451
<212> TYPE: PRT
<213> ORGANISM: Artificial
<220> FEATURE:
<223> OTHER INFORMATION: Synthetic

<400> SEQUENCE: 129

Lys Leu Ser Gly Gly Gly Gly Ser Gly Gly Gly Gly Ser Gly Gly Gly
1 5 10 15

Gly Ser Ala Glu Ala Trp Tyr Asn Leu Gly Asn Ala Tyr Tyr Lys Gln
20 25 30

Gly Asp Tyr Gln Lys Ala Ile Glu Tyr Tyr Gln Lys Ala Leu Glu Leu
35 40 45

Asp Pro Asn Asn Ala Glu Ala Trp Tyr Asn Leu Gly Asn Ala Tyr Tyr
50 55 60

Lys Gln Gly Asp Tyr Gln Lys Ala Ile Glu Tyr Tyr Gln Lys Ala Leu
65 70 75 80

Glu Leu Asp Pro Asn Asn Ala Glu Ala Trp Tyr Asn Leu Gly Asn Ala
85 90 95

Tyr Tyr Lys Gln Gly Asp Tyr Gln Lys Ala Ile Glu Asp Tyr Gln Lys
100 105 110

Ala Leu Glu Leu Asp Pro Asn Asn Leu Gln Ala Glu Ala Trp Lys Asn
115 120 125

Leu Gly Asn Ala Tyr Tyr Lys Gln Gly Asp Tyr Gln Lys Ala Ile Glu
130 135 140

Tyr Tyr Gln Lys Ala Leu Glu Leu Asp Pro Asn Asn Ala Ser Ala Trp
145 150 155 160

Tyr Asn Leu Gly Asn Ala Tyr Tyr Lys Gln Gly Asp Tyr Gln Lys Ala
165 170 175

Ile Glu Tyr Tyr Gln Lys Ala Leu Glu Leu Asp Pro Asn Asn Ala Lys
180 185 190

Ala Trp Tyr Arg Arg Gly Asn Ala Tyr Tyr Lys Gln Gly Asp Tyr Gln
195 200 205

Lys Ala Ile Glu Asp Tyr Gln Lys Ala Leu Glu Leu Asp Pro Asn Asn
210 215 220

Arg Ser Ala Glu Ala Trp Tyr Asn Leu Gly Asn Ala Tyr Tyr Lys Gln
225 230 235 240

Gly Asp Tyr Gln Lys Ala Ile Glu Tyr Tyr Gln Lys Ala Leu Glu Leu
245 250 255

Asp Pro Asn Asn Ala Glu Ala Trp Tyr Asn Leu Gly Asn Ala Tyr Tyr
260 265 270

Lys Gln Gly Asp Tyr Gln Lys Ala Ile Glu Tyr Tyr Gln Lys Ala Leu
        275                 280                 285

Glu Leu Asp Pro Asn Asn Ala Glu Ala Trp Tyr Asn Leu Gly Asn Ala
    290                 295                 300

Tyr Tyr Lys Gln Gly Asp Tyr Gln Lys Ala Ile Glu Asp Tyr Gln Lys
305                 310                 315                 320

Ala Leu Glu Leu Asp Pro Asn Asn Leu Gln Ala Glu Ala Trp Lys Asn
                325                 330                 335

Leu Gly Asn Ala Tyr Tyr Lys Gln Gly Asp Tyr Gln Lys Ala Ile Glu
            340                 345                 350

Tyr Tyr Gln Lys Ala Leu Glu Leu Asp Pro Asn Asn Ala Ser Ala Trp
        355                 360                 365

Tyr Asn Leu Gly Asn Ala Tyr Tyr Lys Gln Gly Asp Tyr Gln Lys Ala
    370                 375                 380

Ile Glu Tyr Tyr Gln Lys Ala Leu Glu Leu Asp Pro Asn Asn Ala Lys
385                 390                 395                 400

Ala Trp Tyr Arg Arg Gly Asn Ala Tyr Tyr Lys Gln Gly Asp Tyr Gln
                405                 410                 415

Lys Ala Ile Glu Asp Tyr Gln Lys Ala Leu Glu Leu Asp Pro Asn Asn
            420                 425                 430

Arg Ser Ala Gly Gly Gly Gly Ser Gly Gly Gly Gly Ser Gly Gly Gly
        435                 440                 445

Gly Ala Ser
    450

<210> SEQ ID NO 130
<211> LENGTH: 7
<212> TYPE: PRT
<213> ORGANISM: Artificial
<220> FEATURE:
<223> OTHER INFORMATION: Synthetic

<400> SEQUENCE: 130

Gly Gly Gly Gly Ser Ala Ser
1               5

<210> SEQ ID NO 131
<211> LENGTH: 12
<212> TYPE: PRT
<213> ORGANISM: Artificial
<220> FEATURE:
<223> OTHER INFORMATION: Synthetic

<400> SEQUENCE: 131

Gly Gly Gly Gly Ser Gly Gly Gly Gly Ser Ala Ser
1               5                   10

<210> SEQ ID NO 132
<211> LENGTH: 17
<212> TYPE: PRT
<213> ORGANISM: Artificial
<220> FEATURE:
<223> OTHER INFORMATION: Synthetic

<400> SEQUENCE: 132

Gly Gly Gly Gly Ser Gly Gly Gly Gly Ser Gly Gly Gly Gly Ser Ala
1               5                   10                  15

Ser

```
<210> SEQ ID NO 133
<211> LENGTH: 27
<212> TYPE: PRT
<213> ORGANISM: Artificial
<220> FEATURE:
<223> OTHER INFORMATION: Synthetic

<400> SEQUENCE: 133

Gly Gly Gly Gly Ser Gly Gly Gly Gly Ser Gly Gly Gly Gly Ser Gly
1               5                   10                  15

Gly Gly Gly Ser Gly Gly Gly Gly Ser Ala Ser
            20                  25


<210> SEQ ID NO 134
<211> LENGTH: 32
<212> TYPE: PRT
<213> ORGANISM: Artificial
<220> FEATURE:
<223> OTHER INFORMATION: Synthetic

<400> SEQUENCE: 134

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Ala Ser
            20                  25                  30


<210> SEQ ID NO 135
<211> LENGTH: 37
<212> TYPE: PRT
<213> ORGANISM: Artificial
<220> FEATURE:
<223> OTHER INFORMATION: Synthetic

<400> SEQUENCE: 135

Ala Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Ala Ser
        35


<210> SEQ ID NO 136
<211> LENGTH: 42
<212> TYPE: PRT
<213> ORGANISM: Artificial
<220> FEATURE:
<223> OTHER INFORMATION: Synthetic

<400> SEQUENCE: 136

Ala Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Ala Ser
        35                  40


<210> SEQ ID NO 137
<211> LENGTH: 47
<212> TYPE: PRT
<213> ORGANISM: Artificial
<220> FEATURE:
<223> OTHER INFORMATION: Synthetic

<400> SEQUENCE: 137
```

```
Ala Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Ala Ser
        35                  40                  45


<210> SEQ ID NO 138
<211> LENGTH: 561
<212> TYPE: PRT
<213> ORGANISM: Artificial
<220> FEATURE:
<223> OTHER INFORMATION: Synthetic

<400> SEQUENCE: 138

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

Asp Ile Gln Met Thr Gln Thr Thr Ser Ser Leu Ser Ala Ser Leu Gly
        35                  40                  45

Asp Arg Val Thr Ile Ser Cys Arg Ala Ser Gln Asp Ile Ser Lys Tyr
    50                  55                  60

Leu Asn Trp Tyr Gln Gln Lys Pro Asp Gly Thr Val Lys Leu Leu Ile
65                  70                  75                  80

Tyr His Thr Ser Arg Leu His Ser Gly Val Pro Ser Arg Phe Ser Gly
                85                  90                  95

Ser Gly Ser Gly Thr Asp Tyr Ser Leu Thr Ile Ser Asn Leu Glu Gln
            100                 105                 110

Glu Asp Ile Ala Thr Tyr Phe Cys Gln Gln Gly Asn Thr Leu Pro Tyr
        115                 120                 125

Thr Phe Gly Gly Gly Thr Lys Leu Glu Ile Thr Gly Ser Thr Ser Gly
    130                 135                 140

Ser Gly Lys Pro Gly Ser Gly Glu Gly Ser Thr Lys Gly Glu Val Lys
145                 150                 155                 160

Leu Gln Glu Ser Gly Pro Gly Leu Val Ala Pro Ser Gln Ser Leu Ser
                165                 170                 175

Val Thr Cys Thr Val Ser Gly Val Ser Leu Pro Asp Tyr Gly Val Ser
            180                 185                 190

Trp Ile Arg Gln Pro Pro Arg Lys Gly Leu Glu Trp Leu Gly Val Ile
        195                 200                 205

Trp Gly Ser Glu Thr Thr Tyr Tyr Asn Ser Ala Leu Lys Ser Arg Leu
    210                 215                 220

Thr Ile Ile Lys Asp Asn Ser Lys Ser Gln Val Phe Leu Lys Met Asn
225                 230                 235                 240

Ser Leu Gln Thr Asp Asp Thr Ala Ile Tyr Tyr Cys Ala Lys His Tyr
                245                 250                 255

Tyr Tyr Gly Gly Ser Tyr Ala Met Asp Tyr Trp Gly Gln Gly Thr Ser
            260                 265                 270

Val Thr Val Ser Ser Ala Ala Ala Ile Glu Val Met Tyr Pro Pro Pro
        275                 280                 285

Tyr Leu Asp Asn Glu Lys Ser Asn Gly Thr Ile Ile His Val Lys Gly
    290                 295                 300

Lys His Leu Cys Pro Ser Pro Leu Phe Pro Gly Pro Ser Lys Pro Phe
305                 310                 315                 320
```

```
Trp Val Leu Val Val Val Gly Gly Val Leu Ala Cys Tyr Ser Leu Leu
                325                 330                 335

Val Thr Val Ala Phe Ile Ile Phe Trp Val Arg Ser Lys Arg Ser Arg
            340                 345                 350

Leu Leu His Ser Asp Tyr Met Asn Met Thr Pro Arg Arg Pro Gly Pro
        355                 360                 365

Thr Arg Lys His Tyr Gln Pro Tyr Ala Pro Pro Arg Asp Phe Ala Ala
    370                 375                 380

Tyr Arg Ser Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Ser Gly Phe Asn Val Leu Met Val His Lys Arg Ser His
            500                 505                 510

Thr Gly Glu Arg Pro Leu Gln Cys Glu Ile Cys Gly Phe Thr Cys Arg
        515                 520                 525

Gln Lys Gly Asn Leu Leu Arg His Ile Lys Leu His Thr Gly Glu Lys
    530                 535                 540

Pro Phe Lys Cys His Leu Cys Asn Tyr Ala Cys Gln Arg Arg Asp Ala
545                 550                 555                 560

Leu


<210> SEQ ID NO 139
<211> LENGTH: 449
<212> TYPE: PRT
<213> ORGANISM: Artificial
<220> FEATURE:
<223> OTHER INFORMATION: Synthetic

<400> SEQUENCE: 139

Met Leu Leu Leu Val Thr Ser Leu Leu Leu Cys Glu Leu Pro His Pro
1               5                   10                  15

Ala Phe Leu Leu Ile Pro Glu Gln Lys Leu Ile Ser Glu Glu Asp Leu
            20                  25                  30

Asp Ile Gln Met Thr Gln Thr Thr Ser Ser Leu Ser Ala Ser Leu Gly
        35                  40                  45

Asp Arg Val Thr Ile Ser Cys Arg Ala Ser Gln Asp Ile Ser Lys Tyr
    50                  55                  60

Leu Asn Trp Tyr Gln Gln Lys Pro Asp Gly Thr Val Lys Leu Leu Ile
65                  70                  75                  80

Tyr His Thr Ser Arg Leu His Ser Gly Val Pro Ser Arg Phe Ser Gly
                85                  90                  95

Ser Gly Ser Gly Thr Asp Tyr Ser Leu Thr Ile Ser Asn Leu Glu Gln
            100                 105                 110

Glu Asp Ile Ala Thr Tyr Phe Cys Gln Gln Gly Asn Thr Leu Pro Tyr
```

```
        115                 120                 125

Thr Phe Gly Gly Gly Thr Lys Leu Glu Ile Thr Gly Ser Thr Ser Gly
    130                 135                 140

Ser Gly Lys Pro Gly Ser Gly Glu Gly Ser Thr Lys Gly Glu Val Lys
145                 150                 155                 160

Leu Gln Glu Ser Gly Pro Gly Leu Val Ala Pro Ser Gln Ser Leu Ser
                165                 170                 175

Val Thr Cys Thr Val Ser Gly Val Ser Leu Pro Asp Tyr Gly Val Ser
            180                 185                 190

Trp Ile Arg Gln Pro Pro Arg Lys Gly Leu Glu Trp Leu Gly Val Ile
        195                 200                 205

Trp Gly Ser Glu Thr Thr Tyr Tyr Asn Ser Ala Leu Lys Ser Arg Leu
    210                 215                 220

Thr Ile Ile Lys Asp Asn Ser Lys Ser Gln Val Phe Leu Lys Met Asn
225                 230                 235                 240

Ser Leu Gln Thr Asp Asp Thr Ala Ile Tyr Tyr Cys Ala Lys His Tyr
                245                 250                 255

Tyr Tyr Gly Gly Ser Tyr Ala Met Asp Tyr Trp Gly Gln Gly Thr Ser
            260                 265                 270

Val Thr Val Ser Ser Ala Ala Ala Ile Glu Val Met Tyr Pro Pro Pro
        275                 280                 285

Tyr Leu Asp Asn Glu Lys Ser Asn Gly Thr Ile Ile His Val Lys Gly
    290                 295                 300

Lys His Leu Cys Pro Ser Pro Leu Phe Pro Gly Pro Ser Lys Pro Phe
305                 310                 315                 320

Trp Val Leu Val Val Val Gly Gly Val Leu Ala Cys Tyr Ser Leu Leu
                325                 330                 335

Val Thr Val Ala Phe Ile Ile Phe Trp Val Arg Ser Arg Arg Ser Arg
            340                 345                 350

Leu Leu His Ser Asp Tyr Met Asn Met Thr Pro Arg Arg Pro Gly Pro
        355                 360                 365

Thr Arg Arg His Tyr Gln Pro Tyr Ala Pro Pro Arg Asp Phe Ala Ala
    370                 375                 380

Tyr Arg Ser Ser Gly Phe Asn Val Leu Met Val His Arg Arg Ser His
385                 390                 395                 400

Thr Gly Glu Arg Pro Leu Gln Cys Glu Ile Cys Gly Phe Thr Cys Arg
                405                 410                 415

Gln Arg Gly Asn Leu Leu Arg His Ile Arg Leu His Thr Gly Glu Arg
            420                 425                 430

Pro Phe Arg Cys His Leu Cys Asn Tyr Ala Cys Gln Arg Arg Asp Ala
        435                 440                 445

Leu
```

<210> SEQ ID NO 140
<211> LENGTH: 9899
<212> TYPE: DNA
<213> ORGANISM: Artificial
<220> FEATURE:
<223> OTHER INFORMATION: Synthetic

<400> SEQUENCE: 140

```
ttttgcacaa catgggggat catgtaactc gccttgatcg ttgggaaccg gagctgaatg      60

aagccatacc aaacgacgag cgtgacacca cgatgcctgt agcaatggca acaacgttgc     120

gcaaactatt aactggcgaa ctacttactc tagcttcccg gcaacaatta atagactgga     180
```

-continued

```
tggaggcgga taaagttgca ggaccacttc tgcgctcggc ccttccggct ggctggttta    240
ttgctgataa atctggagcc ggtgagcgtg ggtctcgcgg tatcattgca gcactggggc    300
cagatggtaa gccctcccgt atcgtagtta tctacacgac ggggagtcag gcaactatgg    360
atgaacgaaa tagacagatc gctgagatag gtgcctcact gattaagcat tggtaactgt    420
cagaccaagt ttactcatat atactttaga ttgatttaaa acttcatttt taatttaaaa    480
ggatctaggt gaagatcctt tttgataatc tcatgaccaa aatcccttaa cgtgagtttt    540
cgttccactg agcgtcagac cccgtagaaa agatcaaagg atcttcttga gatccttttt    600
ttctgcgcgt aatctgctgc ttgcaaacaa aaaaaccacc gctaccagcg gtggtttgtt    660
tgccggatca agagctacca actctttttc cgaaggtaac tggcttcagc agagcgcaga    720
taccaaatac tgttcttcta gtgtagccgt agttaggcca ccacttcaag aactctgtag    780
caccgcctac atacctcgct ctgctaatcc tgttaccagt ggctgctgcc agtggcgata    840
agtcgtgtct taccgggttg gactcaagac gatagttacc ggataaggcg cagcggtcgg    900
gctgaacggg gggttcgtgc acacagccca gcttggagcg aacgacctac accgaactga    960
gatacctaca gcgtgagcta tgagaaagcg ccacgcttcc cgaagggaga aaggcggaca   1020
ggtatccggt aagcggcagg gtcggaacag gagagcgcac gagggagctt ccagggggaa   1080
acgcctggta tctttatagt cctgtcgggt ttcgccacct ctgacttgag cgtcgatttt   1140
tgtgatgctc gtcagggggg cggagcctat ggaaaaacgc cagcaacgcg gcctttttac   1200
ggttcctggc cttttgctgg ccttttgctc acatgttctt tcctgcgtta tcccctgatt   1260
ctgtggataa ccgtattacc gcctttgagt gagctgatac cgctcgccgc agccgaacga   1320
ccgagcgcag cgagtcagtg agcgaggaag cggaagagcg cccaatacgc aaaccgcctc   1380
tccccgcgcg ttggccgatt cattaatgca gctggcacga caggtttccc gactggaaag   1440
cgggcagtga gcgcaacgca attaatgtga gttagctcac tcattaggca ccccaggctt   1500
tacactttat gcttccggct cgtatgttgt gtggaattgt gagcggataa caatttcaca   1560
caggaaacag ctatgaccat gattacgcca agcgcgcaat taaccctcac taaagggaac   1620
aaaagctgga gctgcaagct taatgtagtc ttatgcaata ctcttgtagt cttgcaacat   1680
ggtaacgatg agttagcaac atgccttaca aggagagaaa aagcaccgtg catgccgatt   1740
ggtggaagta aggtggtacg atcgtgcctt attaggaagg caacagacgg gtctgacatg   1800
gattggacga accactgaat tgccgcattg cagagatatt gtatttaagt gcctagctcg   1860
atacataaac gggtctctct ggttagacca gatctgagcc tgggagctct ctggctaact   1920
agggaaccca ctgcttaagc ctcaataaag cttgccttga gtgcttcaag tagtgtgtgc   1980
ccgtctgttg tgtgactctg gtaactagag atccctcaga cccttttagt cagtgtggaa   2040
aatctctagc agtggcgccc gaacagggac ttgaaagcga aagggaaacc agaggagctc   2100
tctcgacgca ggactcggct tgctgaagcg cgcacggcaa gaggcgaggg gcggcgactg   2160
gtgagtacgc caaaaatttt gactagcgga ggctagaagg agagagatgg gtgcgagagc   2220
gtcagtatta agcgggggag aattagatcg cgatgggaaa aaattcggtt aaggccaggg   2280
ggaaagaaaa aatataaatt aaaacatata gtatgggcaa gcagggagct agaacgattc   2340
gcagttaatc ctggcctgtt agaaacatca gaaggctgta gacaaatact gggacagcta   2400
caaccatccc ttcagacagg atcagaagaa cttagatcat tatataatac agtagcaacc   2460
ctctattgtg tgcatcaaag gatagagata aaagacacca aggaagcttt agacaagata   2520
```

-continued

```
gaggaagagc aaaacaaaag taagaccacc gcacagcaag cggccgctga tcttcagacc   2580
tggaggagga gatatgaggg acaattggag aagtgaatta tataaatata aagtagtaaa   2640
aattgaacca ttaggagtag cacccaccaa ggcaaagaga agagtggtgc agagagaaaa   2700
aagagcagtg ggaataggag ctttgttcct tgggttcttg ggagcagcag gaagcactat   2760
gggcgcagcg tcaatgacgc tgacggtaca ggccagacaa ttattgtctg gtatagtgca   2820
gcagcagaac aatttgctga gggctattga ggcgcaacag catctgttgc aactcacagt   2880
ctggggcatc aagcagctcc aggcaagaat cctggctgtg gaaagatacc taaaggatca   2940
acagctcctg gggatttggg gttgctctgg aaaactcatt tgcaccactg ctgtgccttg   3000
gaatgctagt tggagtaata aatctctgga acagatttgg aatcacacga cctggatgga   3060
gtgggacaga gaaattaaca attacacaag cttaatacac tccttaattg aagaatcgca   3120
aaaccagcaa gaaaagaatg aacaagaatt attggaatta gataaatggg caagtttgtg   3180
gaattggttt aacataacaa attggctgtg gtatataaaa ttattcataa tgatagtagg   3240
aggcttggta ggtttaagaa tagtttttgc tgtactttct atagtgaata gagttaggca   3300
gggatattca ccattatcgt ttcagaccca cctcccaacc ccgaggggac cctattccag   3360
cacatatgag gcttggcgta actagatctt gagacaaatg gcagtattca tccacaattt   3420
taaaagaaaa ggggggattg gggggtacag tgcaggggaa agaatagtag acataatagc   3480
aacagacata caaactaaag aattacaaaa acaaattaca aaaattcaaa attttcgggt   3540
ttattacagg gacagcagag atccactttg ggctcgaggg ggcccgggtg caaagatgga   3600
taaagtttta aacagagagg aatctttgca gctaatggac cttctaggtc ttgaaaggag   3660
tgggaattgg ctccggtgcc cgtcagtggg cagagcgcac atcgcccaca gtccccgaga   3720
agttgggggg aggggtcggc aattgatccg gtgcctagag aaggtggcgc ggggtaaact   3780
gggaaagtga tgtcgtgtac tggctccgcc tttttcccga gggtggggga gaaccgtata   3840
taagtgcagt agtcgccgtg aacgttcttt ttcgcaacgg gtttgccgcc agaacacagg   3900
taagtgccgt gtgtggttcc cgcgggcctg gcctctttac gggttatggc ccttgcgtgc   3960
cttgaattac ttccacctgg ctgcagtacg tgattcttga tcccgagctt cgggttggaa   4020
gtgggtggga gagttcgagg ccttgcgctt aaggagcccc ttcgcctcgt gcttgagttg   4080
aggcctggcc tgggcgctgg ggccgccgcg tgcgaatctg gtggcacctt cgcgcctgtc   4140
tcgctgcttt cgataagtct ctagccattt aaaatttttg atgacctgct gcgacgcttt   4200
ttttctggca agatagtctt gtaaatgcgg gccaagatct gcacactggt atttcggttt   4260
ttggggccgc gggcggcgac ggggcccgtg cgtcccagcg cacatgttcg gcgaggcggg   4320
gcctgcgagc gcggccaccg agaatcggac gggggtagtc tcaagctggc cggcctgctc   4380
tggtgcctgg cctcgcgccg ccgtgtatcg ccccgccctg ggcggcaagg ctggcccggt   4440
cggcaccagt tgcgtgagcg gaaagatggc cgcttcccgg ccctgctgca gggagctcaa   4500
aatggaggac gcggcgctcg ggagagcggg cgggtgagtc acccacacaa aggaaaaggg   4560
cctttccgtc ctcagccgtc gcttcatgtg actccacgga gtaccgggcg ccgtccaggc   4620
acctcgatta gttctcgagc ttttggagta cgtcgtcttt aggttggggg gaggggtttt   4680
atgcgatgga gtttccccac actgagtggg tggagactga agttaggcca gcttggcact   4740
tgatgtaatt ctccttggaa tttgcccttt ttgagtttgg atcttggttc attctcaagc   4800
ctcagacagt ggttcaaagt ttttttcttc catttcaggt gtcgtgaata ccgtcgactc   4860
cggaatagcc accatgcttc tcctggtgac aagccttctg ctctgtgagt taccacaccc   4920
```

-continued agcattcctc ctgatcccag agcagaaact catctcagaa gaggatctgg acatccagat 4980
gacacagact acatcctccc tgtctgcctc tctgggagac agagtcacca tcagttgcag 5040
ggcaagtcag gacattagta aatatttaaa ttggtatcag cagaaaccag atggaactgt 5100
taaactcctg atctaccata catcaagatt acactcagga gtcccatcaa ggttcagtgg 5160
cagtgggtct ggaacagatt attctctcac cattagcaac ctggagcaag aagatattgc 5220
cacttacttt tgccaacagg gtaatacgct tccgtacacg ttcggagggg ggactaagtt 5280
ggaaataaca ggctccacct ctggatccgg caagcccgga tctggcgagg gatccaccaa 5340
gggcgaggtg aaactgcagg agtcaggacc tggcctggtg gcgccctcac agagcctgtc 5400
cgtcacatgc actgtctcag ggtctcatt acccgactat ggtgtaagct ggattcgcca 5460
gcctccacga aagggtctgg agtggctggg agtaatatgg ggtagtgaaa ccacatacta 5520
taattcagct ctcaaatcca gactgaccat catcaaggac aactccaaga gccaagtttt 5580
cttaaaaatg aacagtctgc aaactgatga cacagccatt tactactgtg ccaaacatta 5640
ttactacggt ggtagctatg ctatggacta ctggggtcaa ggaacctcag tcacagtctc 5700
ctcagcggcc gcaattgaag ttatgtatcc tcctccttac ctagacaatg agaagagcaa 5760
tggaaccatt atccatgtga aagggaaaca cctttgtcca agtcccctat ttcccggacc 5820
ttctaagccc ttttgggtgc tggtggtggt tgggggagtc ctggcttgct atagcttgct 5880
agtaacagtg gcctttatta ttttctgggt gaggagtaag aggagcaggc tcctgcacag 5940
tgactacatg aacatgactc ctagaaggcc tggacccacc cgcaagcatt accagcccta 6000
tgccccacca cgcgacttcg cagcctatcg ctccagagtg aagttcagca ggagcgcaga 6060
cgcccccgcg taccagcagg gccagaacca gctctataac gagctcaatc taggacgaag 6120
agaggagtac gatgttttgg acaagaggcg tggccgggac cctgagatgg ggggaaagcc 6180
gagaaggaag aaccctcagg aaggcctgta caatgaactg cagaaagata agatggcgga 6240
ggcctacagt gagattggga tgaaaggcga gcgccggagg ggcaaggggc acgatggcct 6300
ttaccagggt ctcagtacag ccaccaagga cacctacgac gcccttcaca tgcaggccct 6360
gccccctcgc tccggattca atgtcttaat ggttcataag cgaagccata ctggtgaacg 6420
cccattgcag tgcgaaatat gcggctttac ctgccgccag aaaggtaacc tcctccgcca 6480
cattaaactg cacacagggg aaaaaccttt taagtgtcac ctctgcaact atgcatgcca 6540
aagaagagat gcgctccgca aaagacgcgg atccggcgag ggtagaggca gtctcctcac 6600
atgtggcgat gtggaagaaa acccaggccc catggtgagc aagggcgagg aggataacat 6660
ggccatcatc aaggagttca tgcgcttcaa ggtgcacatg gagggctccg tgaacggcca 6720
cgagttcgag atcgagggcg agggcgaggg ccgcccctac gagggcaccc agaccgccaa 6780
gctgaaggtg accaagggtg gccccctgcc cttcgcctgg gacatcctgt cccctcagtt 6840
catgtacggc tccaaggcct acgtgaagca ccccgccgac atccccgact acttgaagct 6900
gtccttcccc gagggcttca agtgggagcg cgtgatgaac ttcgaggacg gcggcgtggt 6960
gaccgtgacc caggactcct ccctgcagga cggcgagttc atctacaagg tgaagctgcg 7020
cggcaccaac ttcccctccg acggccccgt aatgcagaag aagaccatgg gctgggaggc 7080
ctcctccgag cggatgtacc ccgaggacgg cgccctgaag ggcgagatca agcagaggct 7140
gaagctgaag gacggcggcc actacgacgc tgaggtcaag accacctaca aggccaagaa 7200
gcccgtgcag ctgcccggcg cctacaacgt caacatcaag ttggacatca cctcccacaa 7260
cgaggactac accatcgtgg aacagtacga acgcgccgag ggccgccact ccaccggcgg 7320
catggacgag ctgtacaagt aaatgcatga gtaactgagg atccagggac agcagagata 7380
cgcgttaagt cgacaatcaa cctctggatt acaaaatttg tgaaagattg actggtattc 7440
ttaactatgt tgctcctttt acgctatgtg gatacgctgc tttaatgcct ttgtatcatg 7500
ctattgcttc ccgtatggct ttcattttct cctccttgta taaatcctgg ttgctgtctc 7560
tttatgagga gttgtggccc gttgtcaggc aacgtggcgt ggtgtgcact gtgtttgctg 7620
acgcaacccc cactggttgg ggcattgcca ccacctgtca gctcctttcc gggactttcg 7680
ctttccccct ccctattgcc acggcggaac tcatcgccgc ctgccttgcc cgctgctgga 7740
caggggctcg gctgttgggc actgacaatt ccgtggtgtt gtcggggaaa tcatcgtcct 7800
ttccttggct gctcgcctgt gttgccacct ggattctgcg cgggacgtcc ttctgctacg 7860
tcccttcggc cctcaatcca gcggaccttc cttcccgcgg cctgctgccg gctctgcggc 7920
ctcttccgcg tcttcgcctt cgccctcaga cgagtcggat ctccctttgg gccgcctccc 7980
cgcgtcgact ttaagaccaa tgacttacaa ggcagctgta gatcttagcc actttttaaa 8040
agaaaagggg ggactggaag ggctaattca ctcccaacga agacaagatc tgcttttttgc 8100
ttgtactggg tctctctggt tagaccagat ctgagcctgg gagctctctg gctaactagg 8160
gaacccactg cttaagcctc aataaagctt gccttgagtg cttcaagtag tgtgtgcccg 8220
tctgttgtgt gactctggta actagagatc cctcagaccc ttttagtcag tgtggaaaat 8280
ctctagcagt acgtatagta gttcatgtca tcttattatt cagtatttat aacttgcaaa 8340
gaaatgaata tcagagagtg agaggaactt gtttattgca gcttataatg gttacaaata 8400
aagcaatagc atcacaaatt tcacaaataa agcatttttt tcactgcatt ctagttgtgg 8460
tttgtccaaa ctcatcaatg tatcttatca tgtctggctc tagctatccc gcccctaact 8520
ccgcccatcc cgcccctaac tccgcccagt tccgcccatt ctccgcccca tggctgacta 8580
atttttttta tttatgcaga ggccgaggcc gcctcggcct ctgagctatt ccagaagtag 8640
tgaggaggct tttttggagg cctagggacg tacccaattc gccctatagt gagtcgtatt 8700
acgcgcgctc actggccgtc gttttacaac gtcgtgactg ggaaaaccct ggcgttaccc 8760
aacttaatcg ccttgcagca catccccctt tcgccagctg gcgtaatagc gaagaggccc 8820
gcaccgatcg cccttcccaa cagttgcgca gcctgaatgg cgaatgggac gcgccctgta 8880
gcggcgcatt aagcgcggcg ggtgtggtgg ttacgcgcag cgtgaccgct acacttgcca 8940
gcgccctagc gcccgctcct ttcgctttct tcccttcctt tctcgccacg ttcgccggct 9000
ttccccgtca agctctaaat cgggggctcc ctttagggtt ccgatttagt gctttacggc 9060
acctcgaccc caaaaaactt gattagggtg atggttcacg tagtgggcca tcgccctgat 9120
agacggtttt tcgccctttg acgttggagt ccacgttctt taatagtgga ctcttgttcc 9180
aaactggaac aacactcaac cctatctcgg tctattcttt tgatttataa gggattttgc 9240
cgatttcggc ctattggtta aaaaatgagc tgatttaaca aaaatttaac gcgaatttta 9300
acaaaatatt aacgcttaca atttaggtgg cacttttcgg ggaaatgtgc gcggaacccc 9360
tatttgttta tttttctaaa tacattcaaa tatgtatccg ctcatgagac aataaccctg 9420
ataaatgctt caataatatt gaaaaaggaa gagtatgagt attcaacatt tccgtgtcgc 9480
ccttattccc ttttttgcgg cattttgcct tcctgttttt gctcacccag aaacgctggt 9540
gaaagtaaaa gatgctgaag atcagttggg tgcacgagtg ggttacatcg aactggatct 9600
caacagcggt aagatccttg agagttttcg ccccgaagaa cgttttccaa tgatgagcac 9660
ttttaaagtt ctgctatgtg gcgcggtatt atcccgtatt gacgccgggc aagagcaact 9720
cggtcgccgc atacactatt ctcagaatga cttggttgag tactcaccag tcacagaaaa 9780
gcatcttacg gatggcatga cagtaagaga attatgcagt gctgccataa ccatgagtga 9840
taacactgcg gccaacttac ttctgacaac gatcggagga ccgaaggagc taaccgctt 9899

<210> SEQ ID NO 141
<211> LENGTH: 9563
<212> TYPE: DNA
<213> ORGANISM: Artificial
<220> FEATURE:
<223> OTHER INFORMATION: Synthetic

<400> SEQUENCE: 141
ttttgcacaa catgggggat catgtaactc gccttgatcg ttgggaaccg gagctgaatg 60
aagccatacc aaacgacgag cgtgacacca cgatgcctgt agcaatggca acaacgttgc 120
gcaaactatt aactggcgaa ctacttactc tagcttcccg gcaacaatta atagactgga 180
tggaggcgga taaagttgca ggaccacttc tgcgctcggc ccttccggct ggctggttta 240
ttgctgataa atctggagcc ggtgagcgtg ggtctcgcgg tatcattgca gcactggggc 300
cagatggtaa gccctcccgt atcgtagtta tctacacgac ggggagtcag gcaactatgg 360
atgaacgaaa tagacagatc gctgagatag gtgcctcact gattaagcat tggtaactgt 420
cagaccaagt ttactcatat atactttaga ttgatttaaa acttcatttt taatttaaaa 480
ggatctaggt gaagatcctt tttgataatc tcatgaccaa aatcccttaa cgtgagtttt 540
cgttccactg agcgtcagac cccgtagaaa agatcaaagg atcttcttga gatccttttt 600
ttctgcgcgt aatctgctgc ttgcaaacaa aaaaaccacc gctaccagcg gtggtttgtt 660
tgccggatca agagctacca actctttttc cgaaggtaac tggcttcagc agagcgcaga 720
taccaaatac tgttcttcta gtgtagccgt agttaggcca ccacttcaag aactctgtag 780
caccgcctac atacctcgct ctgctaatcc tgttaccagt ggctgctgcc agtggcgata 840
agtcgtgtct taccgggttg gactcaagac gatagttacc ggataaggcg cagcggtcgg 900
gctgaacggg gggttcgtgc acacagccca gcttggagcg aacgacctac accgaactga 960
gatacctaca gcgtgagcta tgagaaagcg ccacgcttcc cgaagggaga aaggcggaca 1020
ggtatccggt aagcggcagg gtcggaacag gagagcgcac gagggagctt ccagggggaa 1080
acgcctggta tctttatagt cctgtcgggt ttcgccacct ctgacttgag cgtcgatttt 1140
tgtgatgctc gtcagggggg cggagcctat ggaaaaacgc cagcaacgcg gcctttttac 1200
ggttcctggc cttttgctgg ccttttgctc acatgttctt tcctgcgtta tcccctgatt 1260
ctgtggataa ccgtattacc gcctttgagt gagctgatac cgctcgccgc agccgaacga 1320
ccgagcgcag cgagtcagtg agcgaggaag cggaagagcg cccaatacgc aaaccgcctc 1380
tccccgcgcg ttggccgatt cattaatgca gctggcacga caggtttccc gactggaaag 1440
cgggcagtga gcgcaacgca attaatgtga gttagctcac tcattaggca ccccaggctt 1500
tacactttat gcttccggct cgtatgttgt gtggaattgt gagcggataa caatttcaca 1560
caggaaacag ctatgaccat gattacgcca agcgcgcaat taaccctcac taaagggaac 1620
aaaagctgga gctgcaagct taatgtagtc ttatgcaata ctcttgtagt cttgcaacat 1680
ggtaacgatg agttagcaac atgccttaca aggagagaaa aagcaccgtg catgccgatt 1740
ggtggaagta aggtggtacg atcgtgcctt attaggaagg caacagacgg gtctgacatg 1800

-continued

```
gattggacga accactgaat tgccgcattg cagagatatt gtatttaagt gcctagctcg   1860
atacataaac gggtctctct ggttagacca gatctgagcc tgggagctct ctggctaact   1920
agggaaccca ctgcttaagc ctcaataaag cttgccttga gtgcttcaag tagtgtgtgc   1980
ccgtctgttg tgtgactctg gtaactagag atccctcaga cccttttagt cagtgtggaa   2040
aatctctagc agtggcgccc gaacagggac ttgaaagcga aagggaaacc agaggagctc   2100
tctcgacgca ggactcggct tgctgaagcg cgcacggcaa gaggcgaggg gcggcgactg   2160
gtgagtacgc caaaaatttt gactagcgga ggctagaagg agagagatgg gtgcgagagc   2220
gtcagtatta agcgggggag aattagatcg cgatgggaaa aaattcggtt aaggccaggg   2280
ggaaagaaaa aatataaatt aaaacatata gtatgggcaa gcagggagct agaacgattc   2340
gcagttaatc ctggcctgtt agaaacatca gaaggctgta gacaaatact gggacagcta   2400
caaccatccc ttcagacagg atcagaagaa cttagatcat tatataatac agtagcaacc   2460
ctctattgtg tgcatcaaag gatagagata aaagacacca aggaagcttt agacaagata   2520
gaggaagagc aaaacaaaag taagaccacc gcacagcaag cggccgctga tcttcagacc   2580
tggaggagga gatatgaggg acaattggag aagtgaatta tataaatata aagtagtaaa   2640
aattgaacca ttaggagtag cacccaccaa ggcaaagaga agagtggtgc agagagaaaa   2700
aagagcagtg ggaataggag ctttgttcct tgggttcttg ggagcagcag gaagcactat   2760
gggcgcagcg tcaatgacgc tgacggtaca ggccagacaa ttattgtctg gtatagtgca   2820
gcagcagaac aatttgctga gggctattga ggcgcaacag catctgttgc aactcacagt   2880
ctggggcatc aagcagctcc aggcaagaat cctggctgtg gaaagatacc taaaggatca   2940
acagctcctg gggatttggg gttgctctgg aaaactcatt tgcaccactg ctgtgccttg   3000
gaatgctagt tggagtaata aatctctgga acagatttgg aatcacacga cctggatgga   3060
gtgggacaga gaaattaaca attacacaag cttaatacac tccttaattg aagaatcgca   3120
aaaccagcaa gaaaagaatg aacaagaatt attggaatta gataaatggg caagtttgtg   3180
gaattggttt aacataacaa attggctgtg gtatataaaa ttattcataa tgatagtagg   3240
aggcttggta ggtttaagaa tagtttttgc tgtactttct atagtgaata gagttaggca   3300
gggatattca ccattatcgt ttcagaccca cctcccaacc ccgaggggac ccgacaggcc   3360
cacatatgag gcttggcgta actagatctt gagacaaatg gcagtattca tccacaattt   3420
taaaagaaaa ggggggattg gggggtacag tgcaggggaa agaatagtag acataatagc   3480
aacagacata caaactaaag aattacaaaa acaaattaca aaaattcaaa attttcgggt   3540
ttattacagg gacagcagag atccactttg gctcgaggg ggcccgggtg caaagatgga   3600
taaagtttta aacagagagg aatctttgca gctaatggac cttctaggtc ttgaaaggag   3660
tgggaattgg ctccggtgcc cgtcagtggg cagagcgcac atcgcccaca gtccccgaga   3720
agttgggggg aggggtcggc aattgatccg gtgcctagag aaggtggcgc ggggtaaact   3780
gggaaagtga tgtcgtgtac tggctccgcc tttttcccga gggtggggga gaaccgtata   3840
taagtgcagt agtcgccgtg aacgttcttt ttcgcaacgg gtttgccgcc agaacacagg   3900
taagtgccgt gtgtggttcc cgcgggcctg gcctctttac gggttatggc ccttgcgtgc   3960
cttgaattac ttccacctgg ctgcagtacg tgattcttga tcccgagctt cgggttggaa   4020
gtgggtggga gagttcgagg ccttgcgctt aaggagcccc ttcgcctcgt gcttgagttg   4080
aggcctggcc tgggcgctgg ggccgccgcg tgcgaatctg gtggcacctt cgcgcctgtc   4140
tcgctgcttt cgataagtct ctagccattt aaaatttttg atgacctgct gcgacgcttt   4200
```

```
ttttctggca agatagtctt gtaaatgcgg gccaagatct gcacactggt atttcggttt   4260
ttggggccgc gggcggcgac ggggcccgtg cgtcccagcg cacatgttcg gcgaggcggg   4320
gcctgcgagc gcggccaccg agaatcggac gggggtagtc tcaagctggc cggcctgctc   4380
tggtgcctgg cctcgcgccg ccgtgtatcg ccccgccctg ggcggcaagg ctggcccggt   4440
cggcaccagt tgcgtgagcg gaaagatggc cgcttcccgg ccctgctgca gggagctcaa   4500
aatggaggac gcggcgctcg ggagagcggg cgggtgagtc acccacacaa aggaaaaggg   4560
cctttccgtc ctcagccgtc gcttcatgtg actccacgga gtaccgggcg ccgtccaggc   4620
acctcgatta gttctcgagc ttttggagta cgtcgtcttt aggttggggg gaggggtttt   4680
atgcgatgga gtttccccac actgagtggg tggagactga agttaggcca gcttggcact   4740
tgatgtaatt ctccttggaa tttgcccttt ttgagtttgg atcttggttc attctcaagc   4800
ctcagacagt ggttcaaagt ttttttcttc catttcaggt gtcgtgaata ccgtcgactc   4860
cggaatagcc accatgcttc tcctggtgac aagccttctg ctctgtgagt taccacaccc   4920
agcattcctc ctgatcccag agcagaaact catctcagaa gaggatctgg acatccagat   4980
gacacagact acatcctccc tgtctgcctc tctgggagac agagtcacca tcagttgcag   5040
ggcaagtcag gacattagta aatatttaaa ttggtatcag cagaaaccag atggaactgt   5100
taaactcctg atctaccata catcaagatt acactcagga gtcccatcaa ggttcagtgg   5160
cagtgggtct ggaacagatt attctctcac cattagcaac ctggagcaag aagatattgc   5220
cacttacttt tgccaacagg gtaatacgct tccgtacacg ttcggagggg ggactaagtt   5280
ggaaataaca ggctccacct ctggatccgg caagcccgga tctggcgagg gatccaccaa   5340
gggcgaggtg aaactgcagg agtcaggacc tggcctggtg gcgccctcac agagcctgtc   5400
cgtcacatgc actgtctcag gggtctcatt acccgactat ggtgtaagct ggattcgcca   5460
gcctccacga aagggtctgg agtggctggg agtaatatgg ggtagtgaaa ccacatacta   5520
taattcagct ctcaaatcca gactgaccat catcaaggac aactccaaga gccaagtttt   5580
cttaaaaatg aacagtctgc aaactgatga cacagccatt tactactgtg ccaaacatta   5640
ttactacggt ggtagctatg ctatggacta ctggggtcaa ggaacctcag tcacagtctc   5700
ctcagcggcc gcaattgaag ttatgtatcc tcctccttac ctagacaatg agaagagcaa   5760
tggaaccatt atccatgtga aagggaaaca cctttgtcca agtcccctat ttcccggacc   5820
ttctaagccc ttttgggtgc tggtggtggt tgggggagtc ctggcttgct atagcttgct   5880
agtaacagtg gcctttatta ttttctgggt gaggagtcgg aggagcaggc tcctgcacag   5940
tgactacatg aacatgactc ctagaaggcc tggacccacc cgccggcatt accagcccta   6000
tgccccacca cgcgacttcg cagcctatcg ctcctccgga ttcaatgtct taatggttca   6060
tcggcgaagc catactggtg aacgcccatt gcagtgcgaa atatgcggct ttacctgccg   6120
ccagcgcggt aacctcctcc gccacattcg tctgcacaca ggggaacggc cttttcggtg   6180
tcacctctgc aactatgcat gccaaagaag agatgcgctc agaaggagac gcggatccgg   6240
cgagggtaga ggcagtctcc tcacatgtgg cgatgtggaa gaaaacccag gccccatggt   6300
gagcaagggc gaggaggata acatggccat catcaaggag ttcatgcgct tcaaggtgca   6360
catggagggc tccgtgaacg gccacgagtt cgagatcgag ggcgagggcg agggccgccc   6420
ctacgagggc acccagaccg ccaagctgaa ggtgaccaag ggtggccccc tgcccttcgc   6480
ctgggacatc ctgtcccctc agttcatgta cggctccaag gcctacgtga agcaccccgc   6540
```

-continued cgacatcccc gactacttga agctgtcctt ccccgagggc ttcaagtggg agcgcgtgat 6600
gaacttcgag gacggcggcg tggtgaccgt gacccaggac tcctccctgc aggacggcga 6660
gttcatctac aaggtgaagc tgcgcggcac caacttcccc tccgacggcc ccgtaatgca 6720
gaagaagacc atgggctggg aggcctcctc cgagcggatg taccccgagg acggcgccct 6780
gaagggcgag atcaagcaga ggctgaagct gaaggacggc ggccactacg acgctgaggt 6840
caagaccacc tacaaggcca agaagcccgt gcagctgccc ggcgcctaca acgtcaacat 6900
caagttggac atcacctccc acaacgagga ctacaccatc gtggaacagt acgaacgcgc 6960
cgagggccgc cactccaccg gcggcatgga cgagctgtac aagtaaatgc atgagtaact 7020
gaggatccag ggacagcaga gatacgcgtt aagtcgacaa tcaacctctg gattacaaaa 7080
tttgtgaaag attgactggt attcttaact atgttgctcc ttttacgcta tgtggatacg 7140
ctgctttaat gcctttgtat catgctattg cttcccgtat ggctttcatt ttctcctcct 7200
tgtataaatc ctggttgctg tctctttatg aggagttgtg gcccgttgtc aggcaacgtg 7260
gcgtggtgtg cactgtgttt gctgacgcaa cccccactgg ttggggcatt gccaccacct 7320
gtcagctcct ttccgggact ttcgctttcc ccctccctat tgccacggcg gaactcatcg 7380
ccgcctgcct tgcccgctgc tggacagggg ctcggctgtt gggcactgac aattccgtgg 7440
tgttgtcggg gaaatcatcg tcctttcctt ggctgctcgc ctgtgttgcc acctggattc 7500
tgcgcgggac gtccttctgc tacgtccctt cggccctcaa tccagcggac cttccttccc 7560
gcggcctgct gccggctctg cggcctcttc cgcgtcttcg ccttcgccct cagacgagtc 7620
ggatctccct ttgggccgcc tccccgcgtc gactttaaga ccaatgactt acaaggcagc 7680
tgtagatctt agccactttt taaaagaaaa ggggggactg gaagggctaa ttcactccca 7740
acgaagacaa gatctgcttt ttgcttgtac tgggtctctc tggttagacc agatctgagc 7800
ctgggagctc tctggctaac tagggaaccc actgcttaag cctcaataaa gcttgccttg 7860
agtgcttcaa gtagtgtgtg cccgtctgtt gtgtgactct ggtaactaga gatccctcag 7920
acccttttag tcagtgtgga aaatctctag cagtacgtat agtagttcat gtcatcttat 7980
tattcagtat ttataacttg caaagaaatg aatatcagag agtgagagga acttgtttat 8040
tgcagcttat aatggttaca aataaagcaa tagcatcaca aatttcacaa ataaagcatt 8100
tttttcactg cattctagtt gtggtttgtc caaactcatc aatgtatctt atcatgtctg 8160
gctctagcta tcccgcccct aactccgccc atcccgcccc taactccgcc cagttccgcc 8220
cattctccgc cccatggctg actaattttt tttatttatg cagaggccga ggccgcctcg 8280
gcctctgagc tattccagaa gtagtgagga ggcttttttg gaggcctagg gacgtaccca 8340
attcgcccta tagtgagtcg tattacgcgc gctcactggc cgtcgtttta caacgtcgtg 8400
actgggaaaa ccctggcgtt acccaactta atcgccttgc agcacatccc cctttcgcca 8460
gctggcgtaa tagcgaagag gcccgcaccg atcgcccttc ccaacagttg cgcagcctga 8520
atggcgaatg ggacgcgccc tgtagcggcg cattaagcgc ggcgggtgtg gtggttacgc 8580
gcagcgtgac cgctacactt gccagcgccc tagcgcccgc tcctttcgct ttcttccctt 8640
cctttctcgc cacgttcgcc ggctttcccc gtcaagctct aaatcggggg ctccctttag 8700
ggttccgatt tagtgcttta cggcacctcg accccaaaaa acttgattag ggtgatggtt 8760
cacgtagtgg gccatcgccc tgatagacgg tttttcgccc tttgacgttg gagtccacgt 8820
tctttaatag tggactcttg ttccaaactg gaacaacact caaccctatc tcggtctatt 8880
cttttgattt ataagggatt ttgccgattt cggcctattg gttaaaaaat gagctgattt 8940

-continued

```
aacaaaaatt taacgcgaat tttaacaaaa tattaacgct tacaatttag gtggcacttt    9000
tcggggaaat gtgcgcggaa cccctatttg tttatttttc taaatacatt caaatatgta    9060
tccgctcatg agacaataac cctgataaat gcttcaataa tattgaaaaa ggaagagtat    9120
gagtattcaa catttccgtg tcgcccttat tccctttttt gcggcatttt gccttcctgt    9180
ttttgctcac ccagaaacgc tggtgaaagt aaaagatgct gaagatcagt tgggtgcacg    9240
agtgggttac atcgaactgg atctcaacag cggtaagatc cttgagagtt ttcgccccga    9300
agaacgtttt ccaatgatga gcacttttaa agttctgcta tgtggcgcgg tattatcccg    9360
tattgacgcc gggcaagagc aactcggtcg ccgcatacac tattctcaga atgacttggt    9420
tgagtactca ccagtcacag aaaagcatct tacggatggc atgacagtaa gagaattatg    9480
cagtgctgcc ataaccatga gtgataacac tgcggccaac ttacttctga caacgatcgg    9540
aggaccgaag gagctaaccg ctt                                            9563
```